United States Patent
Burkhart et al.

(10) Patent No.: US 11,407,854 B2
(45) Date of Patent: Aug. 9, 2022

(54) MATERIALS FOR ELECTRONIC DEVICES

(71) Applicant: Merck Patent GmbH, Darmstadt (DE)

(72) Inventors: Beate Burkhart, Darmstadt (DE); Katja Scheible, Darmstadt (DE); Nils Koenen, Griesheim (DE); Holger Heil, Frankfurt am Main (DE)

(73) Assignee: MERCK PATENT GMBH, Darmstadt (DE)

( * ) Notice: Subject to any disclaimer, the term of this patent is extended or adjusted under 35 U.S.C. 154(b) by 86 days.

(21) Appl. No.: 16/625,276

(22) PCT Filed: Jun. 18, 2018

(86) PCT No.: PCT/EP2018/066074
§ 371 (c)(1),
(2) Date: Dec. 20, 2019

(87) PCT Pub. No.: WO2018/234220
PCT Pub. Date: Dec. 27, 2018

(65) Prior Publication Data
US 2020/0216605 A1 Jul. 9, 2020

(30) Foreign Application Priority Data
Jun. 21, 2017 (EP) .................................... 17177211

(51) Int. Cl.
*C08G 61/12* (2006.01)
*H01L 51/00* (2006.01)
*H01L 51/50* (2006.01)

(52) U.S. Cl.
CPC .......... *C08G 61/12* (2013.01); *H01L 51/0043* (2013.01); *C08G 2261/12* (2013.01); *C08G 2261/148* (2013.01); *C08G 2261/149* (2013.01); *C08G 2261/1424* (2013.01); *C08G 2261/3162* (2013.01); *C08G 2261/512* (2013.01); *C08G 2261/95* (2013.01); *H01L 51/5012* (2013.01); *H01L 51/5056* (2013.01); *H01L 51/5088* (2013.01); *H01L 51/5096* (2013.01)

(58) Field of Classification Search
CPC ............ C09K 11/06; C09K 2211/1011; C07D 209/86; C07D 307/91; C07D 405/12; H01L 51/06; H01L 51/006; H01L 51/0061; H01L 51/0072; H01L 51/5012; H01L 51/5056; H01L 51/5088; H05B 33/14

See application file for complete search history.

(56) References Cited

U.S. PATENT DOCUMENTS

| | | | |
|---|---|---|---|
| 2011/0042661 A1* | 2/2011 | Endo | H01L 51/0035 257/40 |
| 2015/0069303 A1* | 3/2015 | Eckes | C08G 61/10 252/500 |
| 2015/0076415 A1* | 3/2015 | Heil | C08L 79/02 252/500 |
| 2017/0253795 A1* | 9/2017 | Yoshioka | C08G 73/0266 |
| 2019/0259952 A1* | 8/2019 | Sasada | H01L 51/0072 |
| 2019/0326515 A1* | 10/2019 | Togashi | H01L 51/0043 |

FOREIGN PATENT DOCUMENTS

| | | |
|---|---|---|
| JP | 2005208111 A | 8/2005 |
| JP | 4276959 B2 | 6/2009 |
| JP | 2012188637 A | 10/2012 |
| JP | 2013036023 A | 2/2013 |
| JP | 2013124271 A | 6/2013 |
| JP | 2013155294 A | 8/2013 |
| WO | 2013156130 A1 | 10/2013 |

OTHER PUBLICATIONS

English Translation of International Search Report dated Aug. 6, 2018 in PCT/EP2018/066074.

* cited by examiner

*Primary Examiner* — Shane Fang
(74) *Attorney, Agent, or Firm* — Faegre Drinker Biddle & Reath LLP

(57) ABSTRACT

The present application relates to a polymer containing at least one structural unit of a formula (I). The polymer is suitable for use in an electronic device.

18 Claims, No Drawings

MATERIALS FOR ELECTRONIC DEVICES

RELATED APPLICATIONS

This application is a national stage entry, filed pursuant to 35 U.S.C. § 371, of PCT/EP2018/066074, filed Jun. 18, 2018, which claims the benefit of European Patent Application No. 17177211.4, filed Jun. 21, 2017, which is incorporated herein by reference in its entirety.

The present application relates to a polymer containing at least one structural unit of a formula (I) as defined below. The polymer is suitable for use in an electronic device.

Electronic devices in the context of this application are understood to mean what are called organic electronic devices, which contain organic semiconductor materials as functional materials. More particularly, these are understood to mean OLEDs. The term OLEDs is understood to mean electronic devices which have one or more layers comprising organic compounds and which emit light on application of electrical voltage. The construction and general principle of function of OLEDs are known to those skilled in the art.

In electronic devices, especially OLEDs, there is great interest in improving the performance data, especially lifetime, efficiency and operating voltage. In these aspects, it has not yet been possible to find any entirely satisfactory solution.

There is therefore a continuing search for novel materials, especially polymers, for use in OLEDs.

In the case of OLEDs, two important methods of applying the materials in layer form are known: application from the gas phase, by sublimation, and application from solution. For the latter method, suitable materials include polymers.

For the preparation of polymers of this kind, it is important that the polymers and the monomers used have good solubility, since it is otherwise not possible to obtain polymers having high chain lengths.

When the polymers are applied from solution in the production of the OLEDs, it is important that they have good solubility in the solvents used. It is also important that they dissolve rapidly in the solvents used. It is also important that they have good film-forming properties.

A factor of particular significance in the case of use of polymers in OLEDs is that they bring about a long lifetime and efficiency of the device. This is especially true when polymers are used in the hole-transporting layer of the OLED, in combination with a subsequent emitting layer which is likewise applied from solution.

It is also important that the polymers are of maximum chemical stability and do not break down.

It has now been found that at least one, preferably more than one, of the abovementioned technical problems can be solved by the provision of a novel polymer containing particular structural units as defined below.

The present application thus provides a polymer containing at least one structural unit of the formula (I)

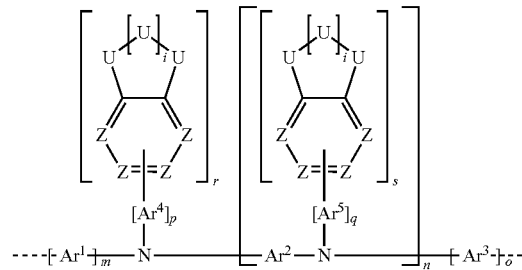

formula (I)

where the variables that occur are as follows:

U is the same or different at each instance and is $C(R^1)_2$, $CR^1=CR^1$, $Si(R^1)_2$, O or S, where groups selected from $CR^1=CR^1$, O and S are not bonded directly to one another;

Z is the same or different at each instance and is N or $CR^2$ when no group is bonded thereto, and is C when a group is bonded thereto;

$Ar^1$, $Ar^2$, $Ar^3$, $Ar^4$ and $Ar^5$ are the same or different and are selected from heteroaromatic ring systems which have 5 to 40 aromatic ring atoms and may be substituted by one or more $R^3$ radicals, and from aromatic ring systems which have 6 to 40 aromatic ring atoms and may be substituted by one or more $R^3$ radicals;

$R^1$ is the same or different at each instance and is selected from H, D, F, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ or $R^2$ or $R^3$ radicals may be joined to one another and may form a ring; where the alkyl, alkoxy, alkenyl and alkynyl groups mentioned and the aromatic ring systems and heteroaromatic ring systems mentioned may each be substituted by one or more $R^4$ radicals; and where one or more $CH_2$ groups in the alkyl, alkoxy, alkenyl and alkynyl groups mentioned may be replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, SO or $SO_2$;

$R^2$, $R^3$ are the same or different at each instance and are selected from H, D, F, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ or $R^2$ or $R^3$ radicals may be joined to one another and may form a ring; where the alkyl, alkoxy, alkenyl and alkynyl groups mentioned and the aromatic ring systems and heteroaromatic ring systems mentioned may each be substituted by one or more $R^4$ radicals; and where one or more $CH_2$ groups in the alkyl, alkoxy, alkenyl and alkynyl groups mentioned may be replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, SO or $SO_2$;

$R^4$ is the same or different at each instance and is selected from H, D, F, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^4$ radicals may be joined to one another and may form a ring; where the alkyl, alkoxy, alkenyl and alkynyl groups mentioned and the aromatic ring systems and heteroaromatic ring systems mentioned may each be substituted by one or more $R^5$ radicals; and where one or more $CH_2$ groups in the alkyl, alkoxy, alkenyl and alkynyl groups mentioned may be replaced by —$R^5C$=$CR^5$—, —C≡C—, $Si(R^5)_2$, C=O, C=$NR^5$, —C(=O)O—, —C(=O)$NR^5$—, $NR^5$, P(=O)($R^5$), —O—, —S—, SO or $SO_2$;

$R^5$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^5$ radicals may be joined to one another and may form a ring; and where the alkyl, alkoxy, alkenyl and alkynyl groups, aromatic ring systems and heteroaromatic ring systems mentioned may be substituted by F or CN;

r is 1, 2 or 3 when p is 1, and is 1 when p is 0;

s is 0, 1, 2 or 3 when q is 1, and is 1 when q is 0;

p is 0 or 1; where, when p is 0, the groups bonded to the unit between square brackets with index p are bonded directly to one another;

q is 0 or 1; where, when q is 0, the groups bonded to the unit between square brackets with index q are bonded directly to one another;

n is 0 or 1, where, when n is 0, the groups bonded to the unit between square brackets with index n are bonded directly to one another;

m is 0 or 1, where, when m is 0, the groups bonded to the unit between square brackets with index m are bonded directly to one another, o is 0 or 1, where, when o is 0, the groups bonded to the unit between square brackets with index o are bonded directly to one another;

i is the same or different at each instance and is 1, 2, 3, 4, 5, 6, 7 or 8;

where at least one U group containing one or more $R^1$ groups selected from straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms is present; where two or more $R^1$ or $R^2$ or $R^3$ radicals may be joined to one another and may form a ring; where the alkyl, alkoxy, alkenyl and alkynyl groups mentioned and the aromatic ring systems and heteroaromatic ring systems mentioned may each be substituted by one or more $R^4$ radicals; and where one or more $CH_2$ groups in the alkyl, alkoxy, alkenyl and alkynyl groups mentioned may be replaced by —$R^4C$=$CR^4$—, —C≡C—, $Si(R^4)_2$, C=O, C=$NR^4$, —C(=O)O—, —C(=O)$NR^4$—, $NR^4$, P(=O)($R^4$), —O—, —S—, SO or $SO_2$.

In the formulae for structural units, the dotted lines indicate the bonds to adjacent structural units of the polymer.

In the present application, the term "polymer" encompasses polymeric compounds, oligomeric compounds and dendrimers. The polymers of the invention have preferably 10 to 10,000, more preferably 10 to 5,000 and most preferably 10 to 2,000 structural units (i.e. repeat units). The oligomeric compounds of the invention preferably have 3 to 9 structural units. The branching factor of the polymers is between 0 (linear polymer, no branching sites) and 1 (fully branched dendrimer).

The polymers of the invention preferably have a molecular weight $M_w$ in the range from 10,000 to 1,000,000 g/mol, more preferably a molecular weight $M_w$ in the range from 20,000 to 500,000 g/mol and most preferably a molecular weight $M_w$ in the range from 25,000 to 200,000 g/mol. The molecular weight $M_w$ is determined by means of GPC (=gel permeation chromatography) against an internal polystyrene standard.

The polymers of the invention are conjugated, semi-conjugated or non-conjugated polymers. Preference is given to conjugated or semi-conjugated polymers.

According to the invention, the structural units of the formula (I) may be incorporated into the main chain or side chain of the polymer. Preferably, however, the structural units of the formula (I) are incorporated into the main chain of the polymer. In the case of incorporation into the side chain of the polymer, the structural units of the formula (I) may either be mono- or bivalent, meaning that they have either one or two bonds to adjacent structural units in the polymer.

"Conjugated polymers" in the context of the present application are polymers containing mainly $sp^2$-hybridized (or else optionally sp-hybridized) carbon atoms in the main chain, which may also be replaced by correspondingly hybridized heteroatoms. In the simplest case, this means the alternating presence of double and single bonds in the main chain, but polymers having units such as a meta-bonded phenylene, for example, should also be regarded as conjugated polymers in the context of this application. "Mainly" means that defects that occur naturally (involuntarily) and lead to interrupted conjugation do not make the term "conjugated polymer" inapplicable. Conjugated polymers are likewise considered to be polymers having a conjugated main chain and non-conjugated side chains.

In addition, the present application likewise refers to conjugation when, for example, arylamine units, arylphosphine units, particular heterocycles (i.e. conjugation via nitrogen, oxygen or sulfur atoms) and/or organometallic complexes (i.e. conjugation by the metal atom) are present in the main chain. The same applies to conjugated dendrimers. In contrast, units such as simple alkyl bridges, (thio) ether, ester, amide or imide linkages, for example, are unambiguously defined as non-conjugated segments.

A semi-conjugated polymer shall be understood in the present application to mean a polymer containing conjugated regions separated from one another by non-conjugated sections, deliberate conjugation breakers (for example spacer groups) or branches, for example in which comparatively long conjugated sections in the main chain are interrupted by non-conjugated sections, or containing comparatively long conjugated sections in the side chains of a polymer non-conjugated in the main chain. Conjugated and semi-conjugated polymers may also contain conjugated, semi-conjugated or non-conjugated dendrimers.

The term "dendrimer" in the present application shall be understood to mean a highly branched compound formed from a multifunctional core to which monomers branched in a regular structure are bonded, such that a tree-like structure is obtained. In this case, both the core and the monomers may assume any desired branched structures consisting both of purely organic units and organometallic compounds or coordination compounds. "Dendrimeric" shall generally be understood here as described, for example, by M. Fischer and F. Vögtle (*Angew. Chem., Int. Ed.* 1999, 38, 885).

The term "structural unit" in the present application is understood to mean a unit that occurs multiple times with the structure specified in the polymer. It may occur more than once in direct succession and/or in isolated form in the polymer. Preferably, a multitude of structural units having the structure specified occur in the polymer, more preferably 10 to 1000, most preferably 50 to 500.

Further preferably, a structural unit in the context of the present application is derived from a monomer used in the polymerization in that the reactive groups of the monomer have reacted in accordance with their chemical reactivity and purpose. For example, in the case of a monomer containing two bromine atoms as reactive groups in a Suzuki polymerization reaction, the structural unit formed in the polymer is characterized in that it corresponds to the monomer structure, except that the bromine atoms are absent and the bonds to the bromine atoms are now bonds to the adjacent structural units. In the case of monomers containing crosslinker groups or precursor groups for crosslinker groups, it is possible here for one or more further reactions of the crosslinker group or of the corresponding precursor groups of the crosslinker group to proceed until the corresponding ultimate structural unit of the polymer is obtained.

An aryl group in the context of this invention contains 6 to 40 aromatic ring atoms of which none is a heteroatom. An aryl group in the context of this invention is understood to mean either a simple aromatic cycle, i.e. benzene, or a fused aromatic polycycle, for example naphthalene, phenanthrene or anthracene. A fused aromatic polycycle in the context of the present application consists of two or more simple aromatic cycles fused to one another. Fusion between cycles is understood here to mean that the cycles share at least one edge with one another.

A heteroaryl group in the context of this invention contains 5 to 40 aromatic ring atoms of which at least one is a heteroatom. The heteroatoms of the heteroaryl group are preferably selected from N, O and S. A heteroaryl group in the context of this invention is understood to mean either a simple heteroaromatic cycle, for example pyridine, pyrimidine or thiophene, or a fused heteroaromatic polycycle, for example quinoline or carbazole. A fused heteroaromatic polycycle in the context of the present application consists of two or more simple heteroaromatic cycles fused to one another. Fusion between cycles is understood here to mean that the cycles share at least one edge with one another.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention contains 6 to 40 carbon atoms in the ring system and does not include any heteroatoms as aromatic ring atoms. An aromatic ring system in the context of this invention therefore does not contain any heteroaryl groups. An aromatic ring system in the context of this invention shall be understood to mean a system which does not necessarily contain only aryl groups but in which it is also possible for a plurality of aryl groups to be bonded by a single bond or by a non-aromatic unit, for example one or more optionally substituted C, Si, N, O or S atoms. In this case, the non-aromatic unit comprises preferably less than 10% of the atoms other than H, based on the total number of atoms other than H in the system. For example, systems such as 9,9'-spirobifluorene, 9,9'-diarylfluorene, triarylamine, diaryl ethers and stilbene are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl groups are joined to one another via single bonds are also regarded as aromatic ring systems in the context of this invention, for example systems such as biphenyl and terphenyl.

Preferably, an aromatic ring system is understood to mean a chemical group in which the aryl groups present therein are conjugated to one another. This means that the aryl groups present must be bonded to one another via single bonds or via connecting units having a free pi electron pair that can take part in the conjugation. Connecting units here are preferably selected from nitrogen atoms, individual C=C units, individual C≡C units, multiple C=C units conjugated to one another and/or C≡C units, —O—, and —S—.

A heteroaromatic ring system in the context of this invention contains 5 to 40 aromatic ring atoms, at least one of which is a heteroatom. The heteroatoms of the heteroaromatic ring system are preferably selected from N, O and/or S. A heteroaromatic ring system corresponds to the abovementioned definition of an aromatic ring system, but has at least one heteroatom as one of the aromatic ring atoms. In this way, it differs from an aromatic ring system in the sense of the definition of the present application, which, according to this definition, cannot contain any heteroatom as aromatic ring atom.

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, I-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyt, heptenyl, cycloheptenyl, octenyl, cyclooctenyl, ethynyl, propynyl, butynyl, pentynyl, hexynyl or octynyl radicals.

Preferred alkyl groups having 1 to 20 carbon atoms are depicted in the following table:

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, I-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentenylthio, hexenylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

Preferably, U is the same or different at each instance and is selected from $C(R^1)_2$, O and S; more preferably, U is $C(R^1)_2$.

Preferably, Z is $CR^2$ when no group is bonded thereto, and it is C when a group is bonded thereto.

Preferably, $Ar^1$, $Ar^2$, $Ar^3$, $Ar^4$ and $Ar^5$ are the same or different at each instance and are selected from aromatic ring systems which have 6 to 25 aromatic ring atoms and may be substituted by one or more $R^1$ radicals, and from heteroaromatic ring systems which have 5 to 25 aromatic ring atoms and may be substituted by one or more $R^2$ radicals. More preferably, $Ar^1$, $Ar^2$, $Ar^3$, $Ar^4$ and $Ar^5$ are the same or different at each instance and are selected from benzene, biphenyl, terphenyl, fluorene, naphthalene, phenanthrene, indenofluorene, spirobifluorene, dibenzofuran, dibenzothiophene, carbazole, indenocarbazole and indolocarbazole, each of which may be substituted by one or more $R^1$ radicals. Even more preferably, $Ar^4$ and $Ar^5$ are benzene which may be substituted by one or more $R^1$ radicals. Even more preferably, $Ar^1$, $Ar^2$ and $Ar^3$ are the same or different at each instance and are selected from benzene, biphenyl, fluorene, phenanthrene, indenofluorene and spirobifluorene, which may be substituted by one or more $R^1$ radicals. Most preferably, $Ar^1$ and $Ar^3$ are selected from benzene which may be substituted by one or more $R^1$ radicals.

Preferred $Ar^1$ to $Ar^5$ groups are selected from the following groups:

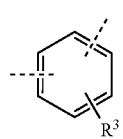
A1

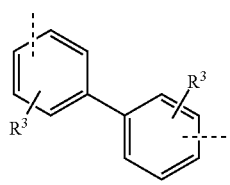
A2

-continued

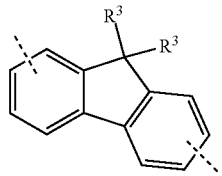
A3

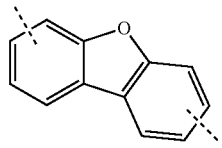
A4

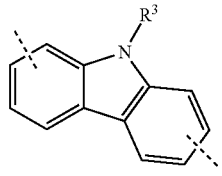
A5

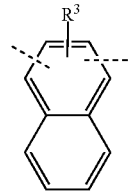
A6

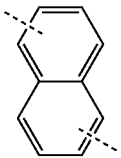
A7

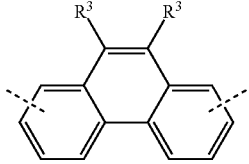
A8

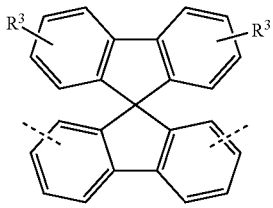
A9

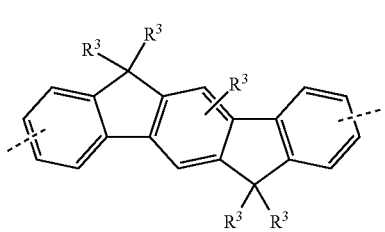
A10 where the dotted lines represent the attachment positions, and
where an $R^3$ group bonded to an aromatic ring in a non-specific manner means that an $R^3$ group may be bonded in each case to the ring in question in any unoccupied position.
Preferred embodiments of the abovementioned A1 to A10 groups are shown below:
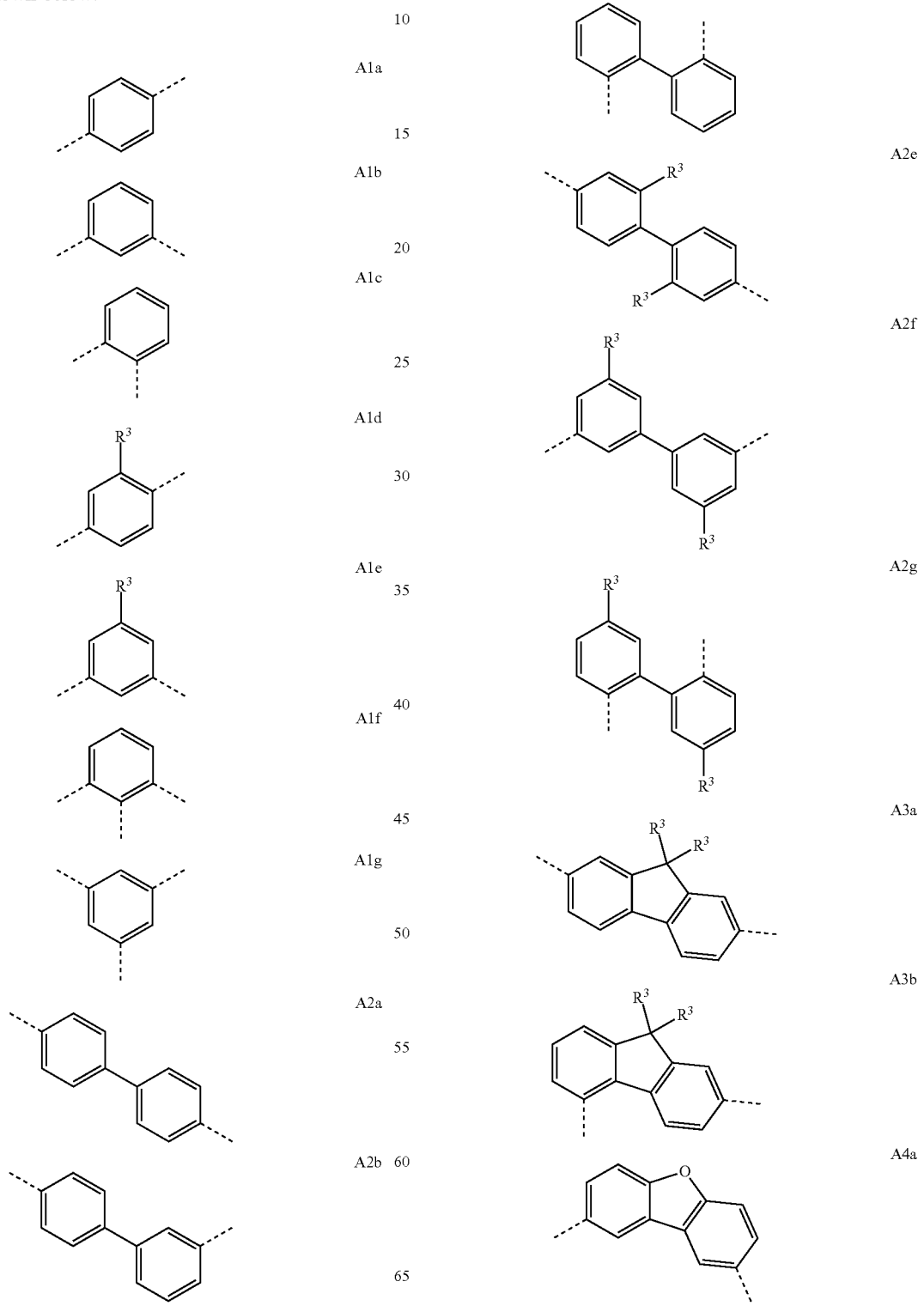

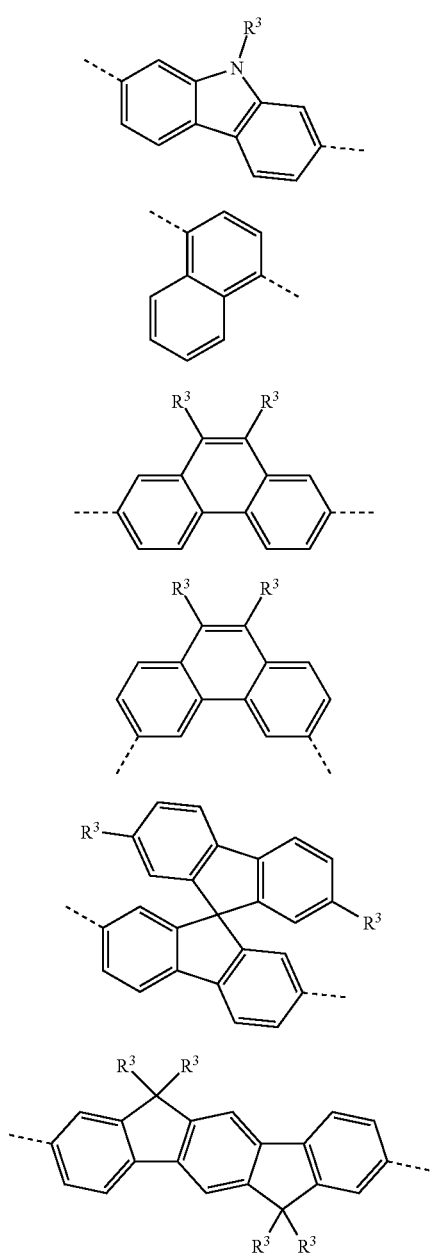

where the dotted lines represent the attachment positions.

R¹ is preferably the same or different at each instance and is selected from H, D, F, CN, Si(R⁴)₃, OR⁴, straight-chain alkyl and alkoxy groups having 1 to 10 carbon atoms, branched or cyclic alkyl and alkoxy groups having 3 to 10 carbon atoms, and aromatic ring systems having 6 to 20 aromatic ring atoms, where two or more R¹ or R² or R³ radicals may be joined to one another and may form a ring; and where the alkyl and alkoxy groups mentioned and the aromatic ring systems mentioned may each be substituted by one or more R⁴ radicals. More preferably, R¹ is the same or different at each instance and is selected from H, D, F, straight-chain alkyl groups having 1 to 10 carbon atoms and branched or cyclic alkyl groups having 3 to 10 carbon atoms. Even more preferably, R¹ is selected from straight-chain alkyl groups having 1 to 10 carbon atoms and branched alkyl groups having 3 to 10 carbon atoms.

It is particularly preferable that those two U groups that are directly adjacent to the bridgehead carbon atom, i.e. are in the benzylic position, bear R¹ radicals that are not H or D, preferably R¹ radicals selected from F, CN, Si(R⁴)₃, OR⁴, straight-chain alkyl and alkoxy groups having 1 to 10 carbon atoms, branched or cyclic alkyl and alkoxy groups having 3 to 10 carbon atoms, and aromatic ring systems having 6 to 20 aromatic ring atoms, where two or more R¹ or R² or R³ radicals may be joined to one another and may form a ring; and where the alkyl and alkoxy groups mentioned and the aromatic ring systems mentioned may each be substituted by one or more R⁴ radicals.

In a preferred embodiment, the structural unit of the formula (I) contains at least one U group having two R¹ groups that are joined to one another and form a ring, such that the U group is a spiro atom. Preferably, the rings formed at a U group by two R¹ groups are selected from cyclopropane, cyclobutane, cyclopentane, cyclohexane, fluorene, dibenzopyran, dihydroacridine and pyran.

Preferred

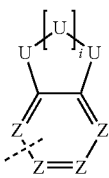

units in the structural unit of the formula (I) are selected from units of the following formula:

E-1

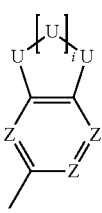

where the free bond is the bond to the rest of the structural unit of the formula (I).

In addition, it is preferable that the abovementioned unit is selected from units of the following formulae:

E-a

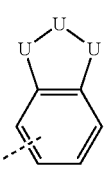

E-b

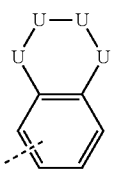

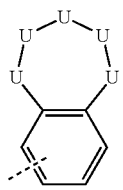
E-c where the corresponding free positions may each be substituted by an $R^2$ radical, and where the dotted line is the bond to the rest of the structural unit of the formula (I).

It is especially preferable that the abovementioned units of the formulae E-a to E-c are selected from the following units:

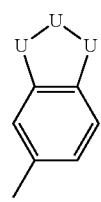
E-a-1

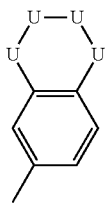
E-b-1

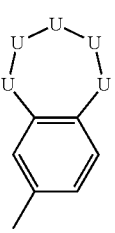
E-c-1 where the free bond is the bond to the rest of the structural unit of the formula (I), and where units E-a-1 and E-b-1 are particularly preferred among the units mentioned, and unit E-a-1 is the most preferred.

Preferred embodiments of the E-a, E-b and E-c units are the following

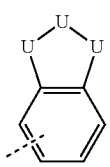
E-a-1

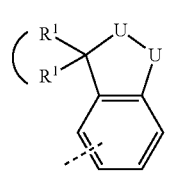
E-a-2

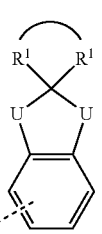
E-a-3

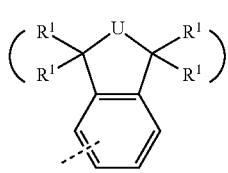
E-a-4

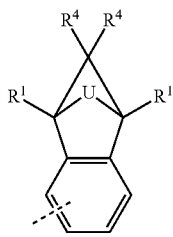
E-a-5

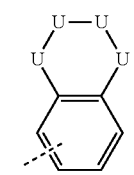
E-b-1

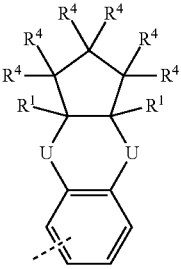
E-b-2

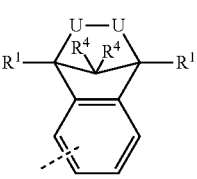
E-b-3

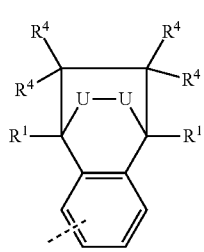
E-b-4

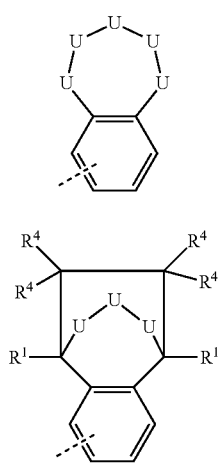
E-c-1
E-c-2
where the dotted line represents the bond to the rest of the structural unit of the formula (I), and where the semicircular bond means that the two R¹ groups involved are joined to one another and form a ring.
Particularly preferred
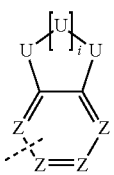
units are selected from the following formulae:
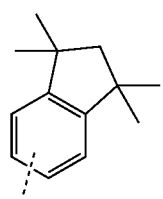
a
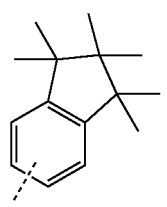
b
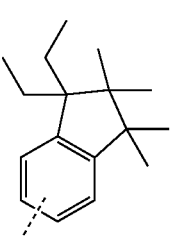
c
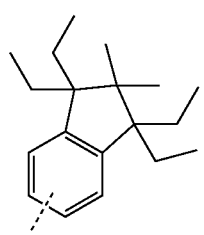
d
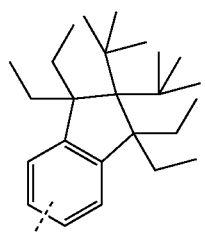
e
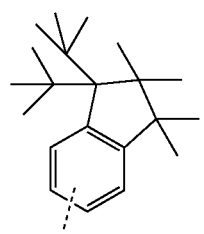
f
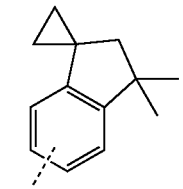
g
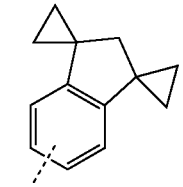
h
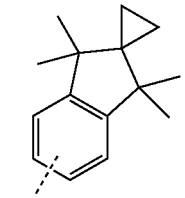
i
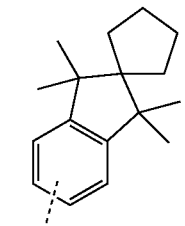
j -continued
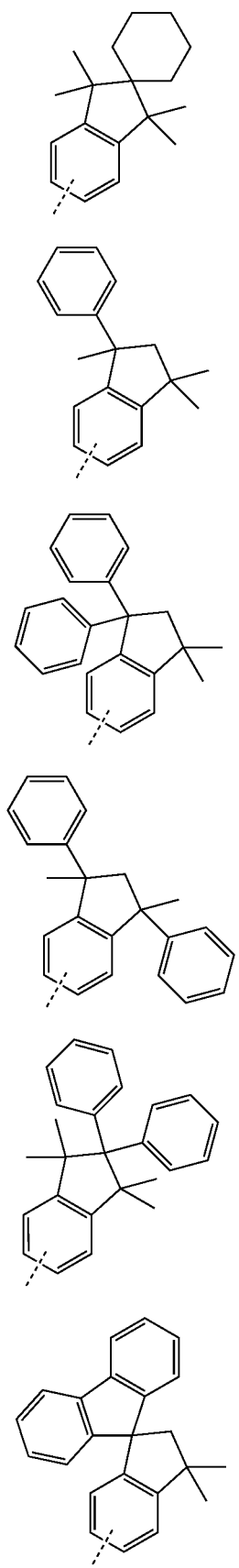
k
l
m
n
o
p
-continued
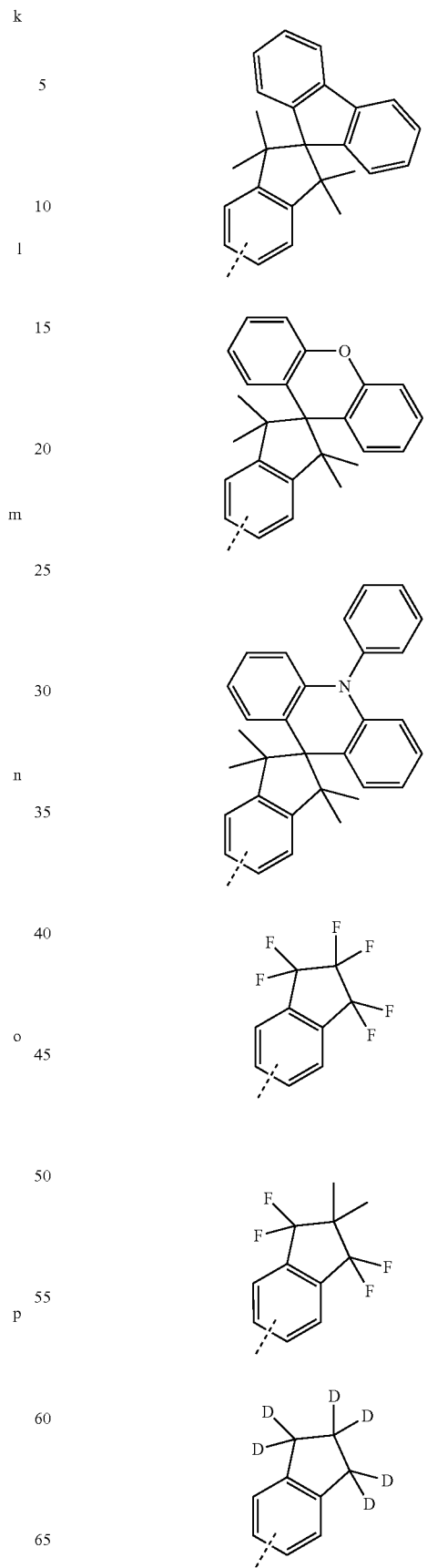
q
r
s
t
u
v -continued
| | |
|---|---|
| 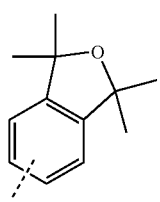 | w |
| 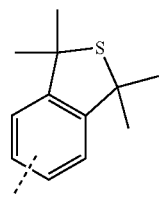 | x |
| 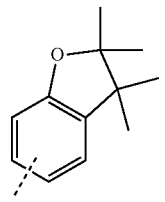 | y |
| 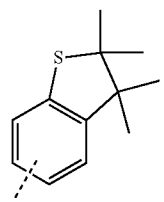 | z |
| 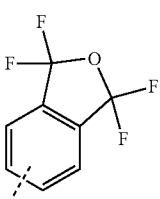 | aa |
| 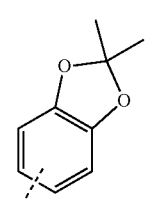 | ab |
| 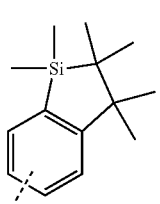 | ac |
| 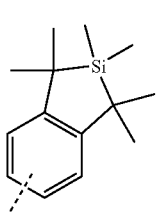 | ad |
-continued
| | |
|---|---|
| 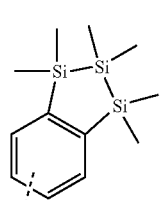 | ae |
| 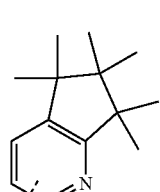 | af |
| 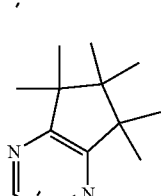 | ag |
| 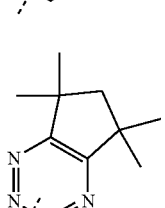 | ah |
| 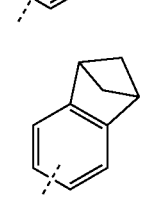 | ai |
| 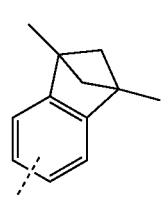 | aj |
| 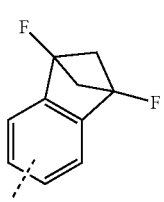 | ak |
| 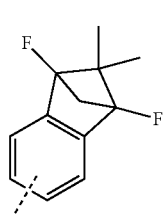 | al |

| | | | |
|---|---|---|---|
| 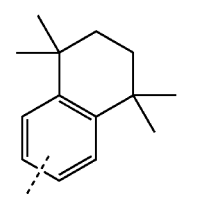 | am | 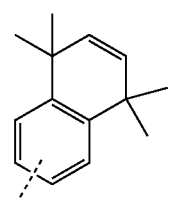 | at |
| 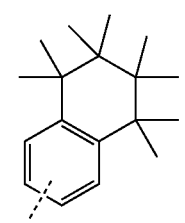 | an | 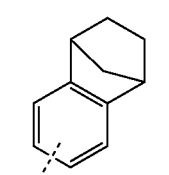 | au |
| 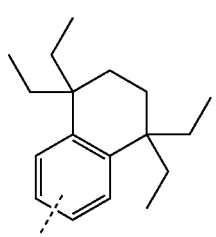 | ao | 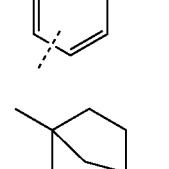 | av |
| 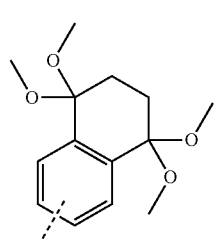 | ap | 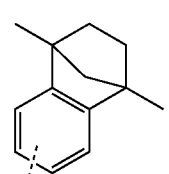 | aw |
| 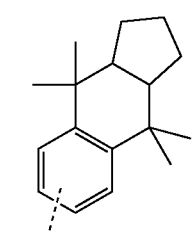 | aq | 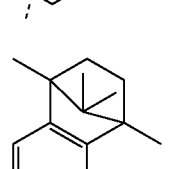 | ax |
| 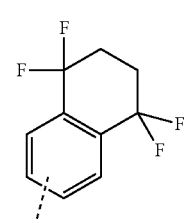 | ar | 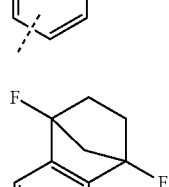 | ay |
| | | 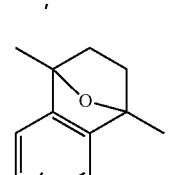 | az |
| 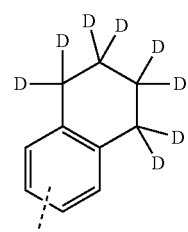 | as | 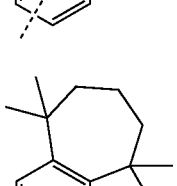 | ba |

-continued bb 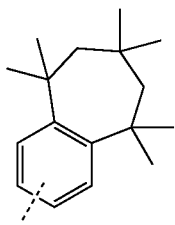

bc 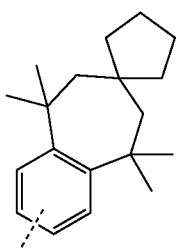

bd 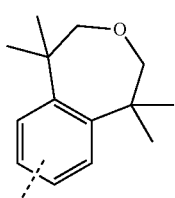

where the dotted line is the bond to the rest of the structural unit of the formula (I). Preferably, in the above-mentioned formulae, the bond to the rest of the structural unit is localized in the position meta and para to the two U groups, as shown in the E-1 unit.

Most preferred among the formulae shown above is formula b.

$R^2$ is preferably the same or different at each instance and is selected from H, D, F, straight-chain alkyl groups having 1 to 10 carbon atoms, branched alkyl groups having 3 to 10 carbon atoms, aromatic ring systems having 6 to 20 aromatic ring atoms, and heteroaromatic ring systems having 5 to 20 aromatic ring atoms, where the alkyl groups, aromatic ring systems and heteroaromatic ring systems mentioned may each be substituted by one or more $R^4$ radicals. More preferably, $R^2$ is the same or different at each instance and is selected from H and straight-chain alkyl groups having 1 to 10 carbon atoms, and branched alkyl groups having 3 to 10 carbon atoms.

$R^3$ is preferably the same or different at each instance and is selected from H, D, F, straight-chain alkyl groups having 1 to 10 carbon atoms, branched alkyl groups having 3 to 10 carbon atoms, aromatic ring systems having 6 to 20 aromatic ring atoms, and heteroaromatic ring systems having 5 to 20 aromatic ring atoms, where the alkyl groups, aromatic ring systems and heteroaromatic ring systems mentioned may each be substituted by one or more $R^4$ radicals. More preferably, $R^3$ is the same or different at each instance and is selected from H and straight-chain alkyl groups having 1 to 10 carbon atoms, and branched alkyl groups having 3 to 10 carbon atoms.

$R^4$ is preferably the same or different at each instance and is selected from H, D, F, CN, $Si(R^5)_3$, $OR^5$, straight-chain alkyl and alkoxy groups having 1 to 10 carbon atoms, branched alkyl and alkoxy groups having 3 to 10 carbon atoms, aromatic ring systems having 6 to 20 aromatic ring atoms, and heteroaromatic ring systems having 5 to 20 aromatic ring atoms, where two or more $R^4$ radicals may be joined to one another and may form a ring; and where the alkyl and alkoxy groups mentioned and the aromatic and heteroaromatic ring systems mentioned may each be substituted by one or more $R^5$ radicals.

Index r is preferably 1 or 2, more preferably 1.
Index s is preferably 1 or 2, more preferably 1.
Index p is preferably 1.
Index q is preferably 1.
Index n is preferably 0.
Index m is preferably 1.
Index o is preferably 1.
Index i is preferably 1, 2 or 3, more preferably 1 or 2, and most preferably 1.

Preferred embodiments of the structural element of the formula (I) are selected from the structural elements of the formulae (I-1) to (I-6)

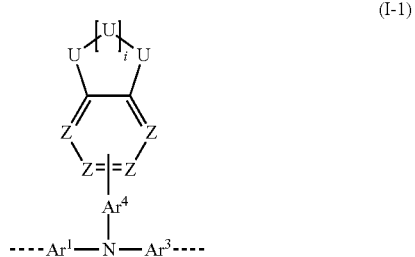 (I-1)

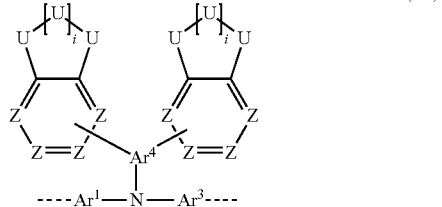 (I-2)

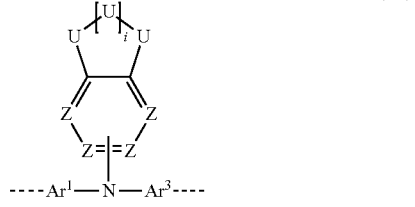 (I-3)

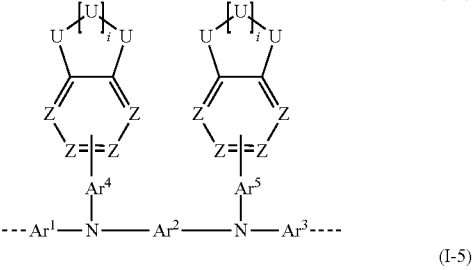 (I-4)

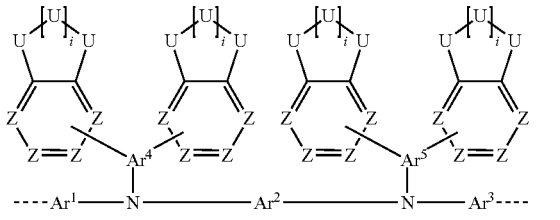 (I-5)

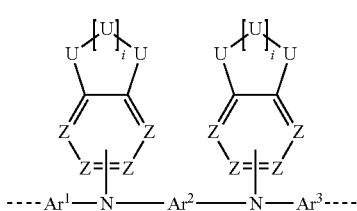 (I-6)

Among the abovementioned formulae, particular preference is given to the formula (I-1).

Preferred structural units of the formula (I) are the structural units shown in the table which follows, in which the variables $Ar^1$ to $Ar^5$, m, n, o, p, q, r and s that occur in formula (I) are selected as shown below, and in which the structural unit

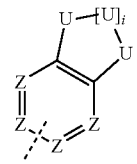

is selected from one of the formulae specified below.

| Structural unit | $Ar^1$ | $Ar^2$ | $Ar^3$ | $Ar^4$ | $Ar^5$ | corresponds to formula 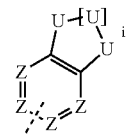 | m | n | o | p | q | r | s |
|---|---|---|---|---|---|---|---|---|---|---|---|---|---|
| M1 | A1 | A1 | | | | a | 1 | 0 | 1 | 0 | 0 | 1 | 0 |
| M2 | A1 | A1 | | | | b | 1 | 0 | 1 | 0 | 0 | 1 | 0 |
| M3 | A1 | A1 | | | | c | 1 | 0 | 1 | 0 | 0 | 1 | 0 |
| M4 | A1 | A1 | | | | d | 1 | 0 | 1 | 0 | 0 | 1 | 0 |
| M5 | A1 | A1 | | | | e | 1 | 0 | 1 | 0 | 0 | 1 | 0 |
| M6 | A1 | A1 | | | | f | 1 | 0 | 1 | 0 | 0 | 1 | 0 |
| M7 | A1 | A1 | | | | g | 1 | 0 | 1 | 0 | 0 | 1 | 0 |
| M8 | A1 | A1 | | | | h | 1 | 0 | 1 | 0 | 0 | 1 | 0 |
| M9 | A1 | A1 | | | | i | 1 | 0 | 1 | 0 | 0 | 1 | 0 |
| M10 | A1 | A1 | | | | j | 1 | 0 | 1 | 0 | 0 | 1 | 0 |
| M11 | A1 | A1 | | | | k | 1 | 0 | 1 | 0 | 0 | 1 | 0 |
| M12 | A1 | A1 | | | | l | 1 | 0 | 1 | 0 | 0 | 1 | 0 |
| M13 | A1 | A1 | | | | m | 1 | 0 | 1 | 0 | 0 | 1 | 0 |
| M14 | A1 | A1 | | | | n | 1 | 0 | 1 | 0 | 0 | 1 | 0 |
| M15 | A1 | A1 | | | | o | 1 | 0 | 1 | 0 | 0 | 1 | 0 |
| M16 | A1 | A1 | | | | p | 1 | 0 | 1 | 0 | 0 | 1 | 0 |
| M17 | A1 | A1 | | | | q | 1 | 0 | 1 | 0 | 0 | 1 | 0 |
| M18 | A1 | A1 | | | | r | 1 | 0 | 1 | 0 | 0 | 1 | 0 |
| M19 | A1 | A1 | | | | s | 1 | 0 | 1 | 0 | 0 | 1 | 0 |
| M20 | A1 | A1 | | | | t | 1 | 0 | 1 | 0 | 0 | 1 | 0 |
| M21 | A1 | A1 | | | | u | 1 | 0 | 1 | 0 | 0 | 1 | 0 |
| M22 | A1 | A1 | | | | v | 1 | 0 | 1 | 0 | 0 | 1 | 0 |
| M23 | A1 | A1 | | | | w | 1 | 0 | 1 | 0 | 0 | 1 | 0 |
| M24 | A1 | A1 | | | | x | 1 | 0 | 1 | 0 | 0 | 1 | 0 |
| M25 | A1 | A1 | | | | y | 1 | 0 | 1 | 0 | 0 | 1 | 0 |
| M26 | A1 | A1 | | | | z | 1 | 0 | 1 | 0 | 0 | 1 | 0 |
| M27 | A1 | A1 | | | | aa | 1 | 0 | 1 | 0 | 0 | 1 | 0 |
| M28 | A1 | A1 | | | | ab | 1 | 0 | 1 | 0 | 0 | 1 | 0 |
| M29 | A1 | A1 | | | | ac | 1 | 0 | 1 | 0 | 0 | 1 | 0 |
| M30 | A1 | A1 | | | | ad | 1 | 0 | 1 | 0 | 0 | 1 | 0 |
| M31 | A1 | A1 | | | | ae | 1 | 0 | 1 | 0 | 0 | 1 | 0 |
| M32 | A1 | A1 | | | | af | 1 | 0 | 1 | 0 | 0 | 1 | 0 |
| M33 | A1 | A1 | | | | ag | 1 | 0 | 1 | 0 | 0 | 1 | 0 |
| M34 | A1 | A1 | | | | ah | 1 | 0 | 1 | 0 | 0 | 1 | 0 |
| M35 | A1 | A1 | | | | ai | 1 | 0 | 1 | 0 | 0 | 1 | 0 |
| M36 | A1 | A1 | | | | aj | 1 | 0 | 1 | 0 | 0 | 1 | 0 |
| M37 | A1 | A1 | | | | ak | 1 | 0 | 1 | 0 | 0 | 1 | 0 |
| M38 | A1 | A1 | | | | al | 1 | 0 | 1 | 0 | 0 | 1 | 0 |
| M39 | A1 | A1 | | | | am | 1 | 0 | 1 | 0 | 0 | 1 | 0 |
| M40 | A1 | A1 | | | | an | 1 | 0 | 1 | 0 | 0 | 1 | 0 |
| M41 | A1 | A1 | | | | ao | 1 | 0 | 1 | 0 | 0 | 1 | 0 |
| M42 | A1 | A1 | | | | ap | 1 | 0 | 1 | 0 | 0 | 1 | 0 |
| M43 | A1 | A1 | | | | aq | 1 | 0 | 1 | 0 | 0 | 1 | 0 |
| M44 | A1 | A1 | | | | ar | 1 | 0 | 1 | 0 | 0 | 1 | 0 |
| M45 | A1 | A1 | | | | as | 1 | 0 | 1 | 0 | 0 | 1 | 0 |
| M46 | A1 | A1 | | | | at | 1 | 0 | 1 | 0 | 0 | 1 | 0 |
| M47 | A1 | A1 | | | | au | 1 | 0 | 1 | 0 | 0 | 1 | 0 |
| M48 | A1 | A1 | | | | av | 1 | 0 | 1 | 0 | 0 | 1 | 0 |
| M49 | A1 | A1 | | | | aw | 1 | 0 | 1 | 0 | 0 | 1 | 0 |
| M50 | A1 | A1 | | | | ax | 1 | 0 | 1 | 0 | 0 | 1 | 0 |
| M51 | A1 | A1 | | | | ay | 1 | 0 | 1 | 0 | 0 | 1 | 0 |

-continued

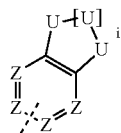

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M52 | A1 | A1 | | | | z | 1 | 0 | 1 | 0 | 0 | 1 | 0 |
| M53 | A1 | A1 | | | | ba | 1 | 0 | 1 | 0 | 0 | 1 | 0 |
| M54 | A1 | A1 | | | | bb | 1 | 0 | 1 | 0 | 0 | 1 | 0 |
| M55 | A1 | A1 | | | | ba | 1 | 0 | 1 | 0 | 0 | 1 | 0 |
| M56 | A1 | A1 | | | | bd | 1 | 0 | 1 | 0 | 0 | 1 | 0 |
| M57 | A2 | A2 | | | | a | 1 | 0 | 1 | 0 | 0 | 1 | 0 |
| M58 | A2 | A2 | | | | b | 1 | 0 | 1 | 0 | 0 | 1 | 0 |
| M59 | A2 | A2 | | | | c | 1 | 0 | 1 | 0 | 0 | 1 | 0 |
| M60 | A2 | A2 | | | | d | 1 | 0 | 1 | 0 | 0 | 1 | 0 |
| M61 | A2 | A2 | | | | e | 1 | 0 | 1 | 0 | 0 | 1 | 0 |
| M62 | A2 | A2 | | | | f | 1 | 0 | 1 | 0 | 0 | 1 | 0 |
| M63 | A2 | A2 | | | | g | 1 | 0 | 1 | 0 | 0 | 1 | 0 |
| M64 | A2 | A2 | | | | h | 1 | 0 | 1 | 0 | 0 | 1 | 0 |
| M65 | A2 | A2 | | | | i | 1 | 0 | 1 | 0 | 0 | 1 | 0 |
| M66 | A2 | A2 | | | | j | 1 | 0 | 1 | 0 | 0 | 1 | 0 |
| M67 | A2 | A2 | | | | k | 1 | 0 | 1 | 0 | 0 | 1 | 0 |
| M68 | A2 | A2 | | | | l | 1 | 0 | 1 | 0 | 0 | 1 | 0 |
| M69 | A2 | A2 | | | | m | 1 | 0 | 1 | 0 | 0 | 1 | 0 |
| M70 | A2 | A2 | | | | n | 1 | 0 | 1 | 0 | 0 | 1 | 0 |
| M71 | A2 | A2 | | | | o | 1 | 0 | 1 | 0 | 0 | 1 | 0 |
| M72 | A2 | A2 | | | | p | 1 | 0 | 1 | 0 | 0 | 1 | 0 |
| M73 | A2 | A2 | | | | q | 1 | 0 | 1 | 0 | 0 | 1 | 0 |
| M74 | A2 | A2 | | | | r | 1 | 0 | 1 | 0 | 0 | 1 | 0 |
| M75 | A2 | A2 | | | | s | 1 | 0 | 1 | 0 | 0 | 1 | 0 |
| M76 | A2 | A2 | | | | t | 1 | 0 | 1 | 0 | 0 | 1 | 0 |
| M77 | A2 | A2 | | | | u | 1 | 0 | 1 | 0 | 0 | 1 | 0 |
| M78 | A2 | A2 | | | | v | 1 | 0 | 1 | 0 | 0 | 1 | 0 |
| M79 | A2 | A2 | | | | w | 1 | 0 | 1 | 0 | 0 | 1 | 0 |
| M80 | A2 | A2 | | | | x | 1 | 0 | 1 | 0 | 0 | 1 | 0 |
| M81 | A2 | A2 | | | | y | 1 | 0 | 1 | 0 | 0 | 1 | 0 |
| M82 | A2 | A2 | | | | z | 1 | 0 | 1 | 0 | 0 | 1 | 0 |
| M83 | A2 | A2 | | | | aa | 1 | 0 | 1 | 0 | 0 | 1 | 0 |
| M84 | A2 | A2 | | | | ab | 1 | 0 | 1 | 0 | 0 | 1 | 0 |
| M85 | A2 | A2 | | | | ac | 1 | 0 | 1 | 0 | 0 | 1 | 0 |
| M86 | A2 | A2 | | | | ad | 1 | 0 | 1 | 0 | 0 | 1 | 0 |
| M87 | A2 | A2 | | | | ae | 1 | 0 | 1 | 0 | 0 | 1 | 0 |
| M88 | A2 | A2 | | | | af | 1 | 0 | 1 | 0 | 0 | 1 | 0 |
| M89 | A2 | A2 | | | | ag | 1 | 0 | 1 | 0 | 0 | 1 | 0 |
| M90 | A2 | A2 | | | | ah | 1 | 0 | 1 | 0 | 0 | 1 | 0 |
| M91 | A2 | A2 | | | | ai | 1 | 0 | 1 | 0 | 0 | 1 | 0 |
| M92 | A2 | A2 | | | | aj | 1 | 0 | 1 | 0 | 0 | 1 | 0 |
| M93 | A2 | A2 | | | | ak | 1 | 0 | 1 | 0 | 0 | 1 | 0 |
| M94 | A2 | A2 | | | | al | 1 | 0 | 1 | 0 | 0 | 1 | 0 |
| M95 | A2 | A2 | | | | am | 1 | 0 | 1 | 0 | 0 | 1 | 0 |
| M96 | A2 | A2 | | | | an | 1 | 0 | 1 | 0 | 0 | 1 | 0 |
| M97 | A2 | A2 | | | | ao | 1 | 0 | 1 | 0 | 0 | 1 | 0 |
| M98 | A2 | A2 | | | | ap | 1 | 0 | 1 | 0 | 0 | 1 | 0 |
| M99 | A2 | A2 | | | | aq | 1 | 0 | 1 | 0 | 0 | 1 | 0 |
| M100 | A2 | A2 | | | | ar | 1 | 0 | 1 | 0 | 0 | 1 | 0 |
| M101 | A2 | A2 | | | | as | 1 | 0 | 1 | 0 | 0 | 1 | 0 |
| M102 | A2 | A2 | | | | at | 1 | 0 | 1 | 0 | 0 | 1 | 0 |
| M103 | A2 | A2 | | | | au | 1 | 0 | 1 | 0 | 0 | 1 | 0 |
| M104 | A2 | A2 | | | | av | 1 | 0 | 1 | 0 | 0 | 1 | 0 |
| M105 | A2 | A2 | | | | aw | 1 | 0 | 1 | 0 | 0 | 1 | 0 |
| M106 | A2 | A2 | | | | ax | 1 | 0 | 1 | 0 | 0 | 1 | 0 |
| M107 | A2 | A2 | | | | ay | 1 | 0 | 1 | 0 | 0 | 1 | 0 |
| M108 | A2 | A2 | | | | z | 1 | 0 | 1 | 0 | 0 | 1 | 0 |
| M109 | A2 | A2 | | | | ba | 1 | 0 | 1 | 0 | 0 | 1 | 0 |
| M110 | A2 | A2 | | | | bb | 1 | 0 | 1 | 0 | 0 | 1 | 0 |
| M111 | A2 | A2 | | | | ba | 1 | 0 | 1 | 0 | 0 | 1 | 0 |
| M112 | A2 | A2 | | | | bd | 1 | 0 | 1 | 0 | 0 | 1 | 0 |
| M113 | A3 | A3 | | | | a | 1 | 0 | 1 | 0 | 0 | 1 | 0 |
| M114 | A3 | A3 | | | | b | 1 | 0 | 1 | 0 | 0 | 1 | 0 |
| M115 | A3 | A3 | | | | c | 1 | 0 | 1 | 0 | 0 | 1 | 0 |
| M116 | A3 | A3 | | | | d | 1 | 0 | 1 | 0 | 0 | 1 | 0 |
| M117 | A3 | A3 | | | | e | 1 | 0 | 1 | 0 | 0 | 1 | 0 |
| M118 | A3 | A3 | | | | f | 1 | 0 | 1 | 0 | 0 | 1 | 0 |
| M119 | A3 | A3 | | | | g | 1 | 0 | 1 | 0 | 0 | 1 | 0 |
| M120 | A3 | A3 | | | | h | 1 | 0 | 1 | 0 | 0 | 1 | 0 |

-continued

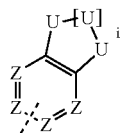

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M121 | A3 | A3 | | | | i | 1 | 0 | 1 | 0 | 0 | 1 | 0 |
| M122 | A3 | A3 | | | | j | 1 | 0 | 1 | 0 | 0 | 1 | 0 |
| M123 | A3 | A3 | | | | k | 1 | 0 | 1 | 0 | 0 | 1 | 0 |
| M124 | A3 | A3 | | | | l | 1 | 0 | 1 | 0 | 0 | 1 | 0 |
| M125 | A3 | A3 | | | | m | 1 | 0 | 1 | 0 | 0 | 1 | 0 |
| M126 | A3 | A3 | | | | n | 1 | 0 | 1 | 0 | 0 | 1 | 0 |
| M127 | A3 | A3 | | | | o | 1 | 0 | 1 | 0 | 0 | 1 | 0 |
| M128 | A3 | A3 | | | | p | 1 | 0 | 1 | 0 | 0 | 1 | 0 |
| M129 | A3 | A3 | | | | q | 1 | 0 | 1 | 0 | 0 | 1 | 0 |
| M130 | A3 | A3 | | | | r | 1 | 0 | 1 | 0 | 0 | 1 | 0 |
| M131 | A3 | A3 | | | | s | 1 | 0 | 1 | 0 | 0 | 1 | 0 |
| M132 | A3 | A3 | | | | t | 1 | 0 | 1 | 0 | 0 | 1 | 0 |
| M133 | A3 | A3 | | | | u | 1 | 0 | 1 | 0 | 0 | 1 | 0 |
| M134 | A3 | A3 | | | | v | 1 | 0 | 1 | 0 | 0 | 1 | 0 |
| M135 | A3 | A3 | | | | w | 1 | 0 | 1 | 0 | 0 | 1 | 0 |
| M136 | A3 | A3 | | | | x | 1 | 0 | 1 | 0 | 0 | 1 | 0 |
| M137 | A3 | A3 | | | | y | 1 | 0 | 1 | 0 | 0 | 1 | 0 |
| M138 | A3 | A3 | | | | z | 1 | 0 | 1 | 0 | 0 | 1 | 0 |
| M139 | A3 | A3 | | | | aa | 1 | 0 | 1 | 0 | 0 | 1 | 0 |
| M140 | A3 | A3 | | | | ab | 1 | 0 | 1 | 0 | 0 | 1 | 0 |
| M141 | A3 | A3 | | | | ac | 1 | 0 | 1 | 0 | 0 | 1 | 0 |
| M142 | A3 | A3 | | | | ad | 1 | 0 | 1 | 0 | 0 | 1 | 0 |
| M143 | A3 | A3 | | | | ae | 1 | 0 | 1 | 0 | 0 | 1 | 0 |
| M144 | A3 | A3 | | | | af | 1 | 0 | 1 | 0 | 0 | 1 | 0 |
| M145 | A3 | A3 | | | | ag | 1 | 0 | 1 | 0 | 0 | 1 | 0 |
| M146 | A3 | A3 | | | | ah | 1 | 0 | 1 | 0 | 0 | 1 | 0 |
| M147 | A3 | A3 | | | | ai | 1 | 0 | 1 | 0 | 0 | 1 | 0 |
| M148 | A3 | A3 | | | | aj | 1 | 0 | 1 | 0 | 0 | 1 | 0 |
| M149 | A3 | A3 | | | | ak | 1 | 0 | 1 | 0 | 0 | 1 | 0 |
| M150 | A3 | A3 | | | | al | 1 | 0 | 1 | 0 | 0 | 1 | 0 |
| M151 | A3 | A3 | | | | am | 1 | 0 | 1 | 0 | 0 | 1 | 0 |
| M152 | A3 | A3 | | | | an | 1 | 0 | 1 | 0 | 0 | 1 | 0 |
| M153 | A3 | A3 | | | | ao | 1 | 0 | 1 | 0 | 0 | 1 | 0 |
| M154 | A3 | A3 | | | | ap | 1 | 0 | 1 | 0 | 0 | 1 | 0 |
| M155 | A3 | A3 | | | | aq | 1 | 0 | 1 | 0 | 0 | 1 | 0 |
| M156 | A3 | A3 | | | | ar | 1 | 0 | 1 | 0 | 0 | 1 | 0 |
| M157 | A3 | A3 | | | | as | 1 | 0 | 1 | 0 | 0 | 1 | 0 |
| M158 | A3 | A3 | | | | at | 1 | 0 | 1 | 0 | 0 | 1 | 0 |
| M159 | A3 | A3 | | | | au | 1 | 0 | 1 | 0 | 0 | 1 | 0 |
| M160 | A3 | A3 | | | | av | 1 | 0 | 1 | 0 | 0 | 1 | 0 |
| M161 | A3 | A3 | | | | aw | 1 | 0 | 1 | 0 | 0 | 1 | 0 |
| M162 | A3 | A3 | | | | ax | 1 | 0 | 1 | 0 | 0 | 1 | 0 |
| M163 | A3 | A3 | | | | ay | 1 | 0 | 1 | 0 | 0 | 1 | 0 |
| M164 | A3 | A3 | | | | z | 1 | 0 | 1 | 0 | 0 | 1 | 0 |
| M165 | A3 | A3 | | | | ba | 1 | 0 | 1 | 0 | 0 | 1 | 0 |
| M166 | A3 | A3 | | | | bb | 1 | 0 | 1 | 0 | 0 | 1 | 0 |
| M167 | A3 | A3 | | | | ba | 1 | 0 | 1 | 0 | 0 | 1 | 0 |
| M168 | A3 | A3 | | | | bd | 1 | 0 | 1 | 0 | 0 | 1 | 0 |
| M169 | A4 | A4 | | | | a | 1 | 0 | 1 | 0 | 0 | 1 | 0 |
| M170 | A4 | A4 | | | | b | 1 | 0 | 1 | 0 | 0 | 1 | 0 |
| M171 | A4 | A4 | | | | c | 1 | 0 | 1 | 0 | 0 | 1 | 0 |
| M172 | A4 | A4 | | | | d | 1 | 0 | 1 | 0 | 0 | 1 | 0 |
| M173 | A4 | A4 | | | | e | 1 | 0 | 1 | 0 | 0 | 1 | 0 |
| M174 | A4 | A4 | | | | f | 1 | 0 | 1 | 0 | 0 | 1 | 0 |
| M175 | A4 | A4 | | | | g | 1 | 0 | 1 | 0 | 0 | 1 | 0 |
| M176 | A4 | A4 | | | | h | 1 | 0 | 1 | 0 | 0 | 1 | 0 |
| M177 | A4 | A4 | | | | i | 1 | 0 | 1 | 0 | 0 | 1 | 0 |
| M178 | A4 | A4 | | | | j | 1 | 0 | 1 | 0 | 0 | 1 | 0 |
| M179 | A4 | A4 | | | | k | 1 | 0 | 1 | 0 | 0 | 1 | 0 |
| M180 | A4 | A4 | | | | l | 1 | 0 | 1 | 0 | 0 | 1 | 0 |
| M181 | A4 | A4 | | | | m | 1 | 0 | 1 | 0 | 0 | 1 | 0 |
| M182 | A4 | A4 | | | | n | 1 | 0 | 1 | 0 | 0 | 1 | 0 |
| M183 | A4 | A4 | | | | o | 1 | 0 | 1 | 0 | 0 | 1 | 0 |
| M184 | A4 | A4 | | | | p | 1 | 0 | 1 | 0 | 0 | 1 | 0 |
| M185 | A4 | A4 | | | | q | 1 | 0 | 1 | 0 | 0 | 1 | 0 |
| M186 | A4 | A4 | | | | r | 1 | 0 | 1 | 0 | 0 | 1 | 0 |
| M187 | A4 | A4 | | | | s | 1 | 0 | 1 | 0 | 0 | 1 | 0 |
| M188 | A4 | A4 | | | | t | 1 | 0 | 1 | 0 | 0 | 1 | 0 |
| M189 | A4 | A4 | | | | u | 1 | 0 | 1 | 0 | 0 | 1 | 0 |

-continued

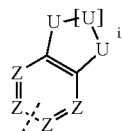

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M190 | A4 | A4 | | | | v | 1 | 0 | 1 | 0 | 0 | 1 | 0 |
| M191 | A4 | A4 | | | | w | 1 | 0 | 1 | 0 | 0 | 1 | 0 |
| M192 | A4 | A4 | | | | x | 1 | 0 | 1 | 0 | 0 | 1 | 0 |
| M193 | A4 | A4 | | | | y | 1 | 0 | 1 | 0 | 0 | 1 | 0 |
| M194 | A4 | A4 | | | | z | 1 | 0 | 1 | 0 | 0 | 1 | 0 |
| M195 | A4 | A4 | | | | aa | 1 | 0 | 1 | 0 | 0 | 1 | 0 |
| M196 | A4 | A4 | | | | ab | 1 | 0 | 1 | 0 | 0 | 1 | 0 |
| M197 | A4 | A4 | | | | ac | 1 | 0 | 1 | 0 | 0 | 1 | 0 |
| M198 | A4 | A4 | | | | ad | 1 | 0 | 1 | 0 | 0 | 1 | 0 |
| M199 | A4 | A4 | | | | ae | 1 | 0 | 1 | 0 | 0 | 1 | 0 |
| M200 | A4 | A4 | | | | af | 1 | 0 | 1 | 0 | 0 | 1 | 0 |
| M201 | A4 | A4 | | | | ag | 1 | 0 | 1 | 0 | 0 | 1 | 0 |
| M202 | A4 | A4 | | | | ah | 1 | 0 | 1 | 0 | 0 | 1 | 0 |
| M203 | A4 | A4 | | | | ai | 1 | 0 | 1 | 0 | 0 | 1 | 0 |
| M204 | A4 | A4 | | | | aj | 1 | 0 | 1 | 0 | 0 | 1 | 0 |
| M205 | A4 | A4 | | | | ak | 1 | 0 | 1 | 0 | 0 | 1 | 0 |
| M206 | A4 | A4 | | | | al | 1 | 0 | 1 | 0 | 0 | 1 | 0 |
| M207 | A4 | A4 | | | | am | 1 | 0 | 1 | 0 | 0 | 1 | 0 |
| M208 | A4 | A4 | | | | an | 1 | 0 | 1 | 0 | 0 | 1 | 0 |
| M209 | A4 | A4 | | | | ao | 1 | 0 | 1 | 0 | 0 | 1 | 0 |
| M210 | A4 | A4 | | | | ap | 1 | 0 | 1 | 0 | 0 | 1 | 0 |
| M211 | A4 | A4 | | | | aq | 1 | 0 | 1 | 0 | 0 | 1 | 0 |
| M212 | A4 | A4 | | | | ar | 1 | 0 | 1 | 0 | 0 | 1 | 0 |
| M213 | A4 | A4 | | | | as | 1 | 0 | 1 | 0 | 0 | 1 | 0 |
| M214 | A4 | A4 | | | | at | 1 | 0 | 1 | 0 | 0 | 1 | 0 |
| M215 | A4 | A4 | | | | au | 1 | 0 | 1 | 0 | 0 | 1 | 0 |
| M216 | A4 | A4 | | | | av | 1 | 0 | 1 | 0 | 0 | 1 | 0 |
| M217 | A4 | A4 | | | | aw | 1 | 0 | 1 | 0 | 0 | 1 | 0 |
| M218 | A4 | A4 | | | | ax | 1 | 0 | 1 | 0 | 0 | 1 | 0 |
| M219 | A4 | A4 | | | | ay | 1 | 0 | 1 | 0 | 0 | 1 | 0 |
| M220 | A4 | A4 | | | | z | 1 | 0 | 1 | 0 | 0 | 1 | 0 |
| M221 | A4 | A4 | | | | ba | 1 | 0 | 1 | 0 | 0 | 1 | 0 |
| M222 | A4 | A4 | | | | bb | 1 | 0 | 1 | 0 | 0 | 1 | 0 |
| M223 | A4 | A4 | | | | ba | 1 | 0 | 1 | 0 | 0 | 1 | 0 |
| M224 | A4 | A4 | | | | bd | 1 | 0 | 1 | 0 | 0 | 1 | 0 |
| M225 | A5 | A5 | | | | a | 1 | 0 | 1 | 0 | 0 | 1 | 0 |
| M226 | A5 | A5 | | | | b | 1 | 0 | 1 | 0 | 0 | 1 | 0 |
| M227 | A5 | A5 | | | | c | 1 | 0 | 1 | 0 | 0 | 1 | 0 |
| M228 | A5 | A5 | | | | d | 1 | 0 | 1 | 0 | 0 | 1 | 0 |
| M229 | A5 | A5 | | | | e | 1 | 0 | 1 | 0 | 0 | 1 | 0 |
| M230 | A5 | A5 | | | | f | 1 | 0 | 1 | 0 | 0 | 1 | 0 |
| M231 | A5 | A5 | | | | g | 1 | 0 | 1 | 0 | 0 | 1 | 0 |
| M232 | A5 | A5 | | | | h | 1 | 0 | 1 | 0 | 0 | 1 | 0 |
| M233 | A5 | A5 | | | | i | 1 | 0 | 1 | 0 | 0 | 1 | 0 |
| M234 | A5 | A5 | | | | j | 1 | 0 | 1 | 0 | 0 | 1 | 0 |
| M235 | A5 | A5 | | | | k | 1 | 0 | 1 | 0 | 0 | 1 | 0 |
| M236 | A5 | A5 | | | | l | 1 | 0 | 1 | 0 | 0 | 1 | 0 |
| M237 | A5 | A5 | | | | m | 1 | 0 | 1 | 0 | 0 | 1 | 0 |
| M238 | A5 | A5 | | | | n | 1 | 0 | 1 | 0 | 0 | 1 | 0 |
| M239 | A5 | A5 | | | | o | 1 | 0 | 1 | 0 | 0 | 1 | 0 |
| M240 | A5 | A5 | | | | p | 1 | 0 | 1 | 0 | 0 | 1 | 0 |
| M241 | A5 | A5 | | | | q | 1 | 0 | 1 | 0 | 0 | 1 | 0 |
| M242 | A5 | A5 | | | | r | 1 | 0 | 1 | 0 | 0 | 1 | 0 |
| M243 | A5 | A5 | | | | s | 1 | 0 | 1 | 0 | 0 | 1 | 0 |
| M244 | A5 | A5 | | | | t | 1 | 0 | 1 | 0 | 0 | 1 | 0 |
| M245 | A5 | A5 | | | | u | 1 | 0 | 1 | 0 | 0 | 1 | 0 |
| M246 | A5 | A5 | | | | v | 1 | 0 | 1 | 0 | 0 | 1 | 0 |
| M247 | A5 | A5 | | | | w | 1 | 0 | 1 | 0 | 0 | 1 | 0 |
| M248 | A5 | A5 | | | | x | 1 | 0 | 1 | 0 | 0 | 1 | 0 |
| M249 | A5 | A5 | | | | y | 1 | 0 | 1 | 0 | 0 | 1 | 0 |
| M250 | A5 | A5 | | | | z | 1 | 0 | 1 | 0 | 0 | 1 | 0 |
| M251 | A5 | A5 | | | | aa | 1 | 0 | 1 | 0 | 0 | 1 | 0 |
| M252 | A5 | A5 | | | | ab | 1 | 0 | 1 | 0 | 0 | 1 | 0 |
| M253 | A5 | A5 | | | | ac | 1 | 0 | 1 | 0 | 0 | 1 | 0 |
| M254 | A5 | A5 | | | | ad | 1 | 0 | 1 | 0 | 0 | 1 | 0 |
| M255 | A5 | A5 | | | | ae | 1 | 0 | 1 | 0 | 0 | 1 | 0 |
| M256 | A5 | A5 | | | | af | 1 | 0 | 1 | 0 | 0 | 1 | 0 |
| M257 | A5 | A5 | | | | ag | 1 | 0 | 1 | 0 | 0 | 1 | 0 |
| M258 | A5 | A5 | | | | ah | 1 | 0 | 1 | 0 | 0 | 1 | 0 |

-continued

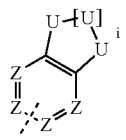

| Structural unit | $Ar^1$ | $Ar^2$ | $Ar^3$ | $Ar^4$ | $Ar^5$ | corresponds to formula | m | n | o | p | q | r | s |
|---|---|---|---|---|---|---|---|---|---|---|---|---|---|
| M259 | A5 | A5 | | | | ai | 1 | 0 | 1 | 0 | 0 | 1 | 0 |
| M260 | A5 | A5 | | | | aj | 1 | 0 | 1 | 0 | 0 | 1 | 0 |
| M261 | A5 | A5 | | | | ak | 1 | 0 | 1 | 0 | 0 | 1 | 0 |
| M262 | A5 | A5 | | | | al | 1 | 0 | 1 | 0 | 0 | 1 | 0 |
| M263 | A5 | A5 | | | | am | 1 | 0 | 1 | 0 | 0 | 1 | 0 |
| M264 | A5 | A5 | | | | an | 1 | 0 | 1 | 0 | 0 | 1 | 0 |
| M265 | A5 | A5 | | | | ao | 1 | 0 | 1 | 0 | 0 | 1 | 0 |
| M266 | A5 | A5 | | | | ap | 1 | 0 | 1 | 0 | 0 | 1 | 0 |
| M267 | A5 | A5 | | | | aq | 1 | 0 | 1 | 0 | 0 | 1 | 0 |
| M268 | A5 | A5 | | | | ar | 1 | 0 | 1 | 0 | 0 | 1 | 0 |
| M269 | A5 | A5 | | | | as | 1 | 0 | 1 | 0 | 0 | 1 | 0 |
| M270 | A5 | A5 | | | | at | 1 | 0 | 1 | 0 | 0 | 1 | 0 |
| M271 | A5 | A5 | | | | au | 1 | 0 | 1 | 0 | 0 | 1 | 0 |
| M272 | A5 | A5 | | | | av | 1 | 0 | 1 | 0 | 0 | 1 | 0 |
| M273 | A5 | A5 | | | | aw | 1 | 0 | 1 | 0 | 0 | 1 | 0 |
| M274 | A5 | A5 | | | | ax | 1 | 0 | 1 | 0 | 0 | 1 | 0 |
| M275 | A5 | A5 | | | | ay | 1 | 0 | 1 | 0 | 0 | 1 | 0 |
| M276 | A5 | A5 | | | | z | 1 | 0 | 1 | 0 | 0 | 1 | 0 |
| M277 | A5 | A5 | | | | ba | 1 | 0 | 1 | 0 | 0 | 1 | 0 |
| M278 | A5 | A5 | | | | bb | 1 | 0 | 1 | 0 | 0 | 1 | 0 |
| M279 | A5 | A5 | | | | ba | 1 | 0 | 1 | 0 | 0 | 1 | 0 |
| M280 | A5 | A5 | | | | bd | 1 | 0 | 1 | 0 | 0 | 1 | 0 |
| M281 | A6 | A6 | | | | a | 1 | 0 | 1 | 0 | 0 | 1 | 0 |
| M282 | A6 | A6 | | | | b | 1 | 0 | 1 | 0 | 0 | 1 | 0 |
| M283 | A6 | A6 | | | | c | 1 | 0 | 1 | 0 | 0 | 1 | 0 |
| M284 | A6 | A6 | | | | d | 1 | 0 | 1 | 0 | 0 | 1 | 0 |
| M285 | A6 | A6 | | | | e | 1 | 0 | 1 | 0 | 0 | 1 | 0 |
| M286 | A6 | A6 | | | | f | 1 | 0 | 1 | 0 | 0 | 1 | 0 |
| M287 | A6 | A6 | | | | g | 1 | 0 | 1 | 0 | 0 | 1 | 0 |
| M288 | A6 | A6 | | | | h | 1 | 0 | 1 | 0 | 0 | 1 | 0 |
| M289 | A6 | A6 | | | | i | 1 | 0 | 1 | 0 | 0 | 1 | 0 |
| M290 | A6 | A6 | | | | j | 1 | 0 | 1 | 0 | 0 | 1 | 0 |
| M291 | A6 | A6 | | | | k | 1 | 0 | 1 | 0 | 0 | 1 | 0 |
| M292 | A6 | A6 | | | | l | 1 | 0 | 1 | 0 | 0 | 1 | 0 |
| M293 | A6 | A6 | | | | m | 1 | 0 | 1 | 0 | 0 | 1 | 0 |
| M294 | A6 | A6 | | | | n | 1 | 0 | 1 | 0 | 0 | 1 | 0 |
| M295 | A6 | A6 | | | | o | 1 | 0 | 1 | 0 | 0 | 1 | 0 |
| M296 | A6 | A6 | | | | p | 1 | 0 | 1 | 0 | 0 | 1 | 0 |
| M297 | A6 | A6 | | | | q | 1 | 0 | 1 | 0 | 0 | 1 | 0 |
| M298 | A6 | A6 | | | | r | 1 | 0 | 1 | 0 | 0 | 1 | 0 |
| M299 | A6 | A6 | | | | s | 1 | 0 | 1 | 0 | 0 | 1 | 0 |
| M300 | A6 | A6 | | | | t | 1 | 0 | 1 | 0 | 0 | 1 | 0 |
| M301 | A6 | A6 | | | | u | 1 | 0 | 1 | 0 | 0 | 1 | 0 |
| M302 | A6 | A6 | | | | v | 1 | 0 | 1 | 0 | 0 | 1 | 0 |
| M303 | A6 | A6 | | | | w | 1 | 0 | 1 | 0 | 0 | 1 | 0 |
| M304 | A6 | A6 | | | | x | 1 | 0 | 1 | 0 | 0 | 1 | 0 |
| M305 | A6 | A6 | | | | y | 1 | 0 | 1 | 0 | 0 | 1 | 0 |
| M306 | A6 | A6 | | | | z | 1 | 0 | 1 | 0 | 0 | 1 | 0 |
| M307 | A6 | A6 | | | | aa | 1 | 0 | 1 | 0 | 0 | 1 | 0 |
| M308 | A6 | A6 | | | | ab | 1 | 0 | 1 | 0 | 0 | 1 | 0 |
| M309 | A6 | A6 | | | | ac | 1 | 0 | 1 | 0 | 0 | 1 | 0 |
| M310 | A6 | A6 | | | | ad | 1 | 0 | 1 | 0 | 0 | 1 | 0 |
| M311 | A6 | A6 | | | | ae | 1 | 0 | 1 | 0 | 0 | 1 | 0 |
| M312 | A6 | A6 | | | | af | 1 | 0 | 1 | 0 | 0 | 1 | 0 |
| M313 | A6 | A6 | | | | ag | 1 | 0 | 1 | 0 | 0 | 1 | 0 |
| M314 | A6 | A6 | | | | ah | 1 | 0 | 1 | 0 | 0 | 1 | 0 |
| M315 | A6 | A6 | | | | ai | 1 | 0 | 1 | 0 | 0 | 1 | 0 |
| M316 | A6 | A6 | | | | aj | 1 | 0 | 1 | 0 | 0 | 1 | 0 |
| M317 | A6 | A6 | | | | ak | 1 | 0 | 1 | 0 | 0 | 1 | 0 |
| M318 | A6 | A6 | | | | al | 1 | 0 | 1 | 0 | 0 | 1 | 0 |
| M319 | A6 | A6 | | | | am | 1 | 0 | 1 | 0 | 0 | 1 | 0 |
| M320 | A6 | A6 | | | | an | 1 | 0 | 1 | 0 | 0 | 1 | 0 |
| M321 | A6 | A6 | | | | ao | 1 | 0 | 1 | 0 | 0 | 1 | 0 |
| M322 | A6 | A6 | | | | ap | 1 | 0 | 1 | 0 | 0 | 1 | 0 |
| M323 | A6 | A6 | | | | aq | 1 | 0 | 1 | 0 | 0 | 1 | 0 |
| M324 | A6 | A6 | | | | ar | 1 | 0 | 1 | 0 | 0 | 1 | 0 |
| M325 | A6 | A6 | | | | as | 1 | 0 | 1 | 0 | 0 | 1 | 0 |
| M326 | A6 | A6 | | | | at | 1 | 0 | 1 | 0 | 0 | 1 | 0 |
| M327 | A6 | A6 | | | | au | 1 | 0 | 1 | 0 | 0 | 1 | 0 |

-continued

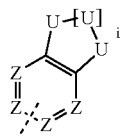

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M328 | A6 | A6 | | | | av | 1 | 0 | 1 | 0 | 0 | 1 | 0 |
| M329 | A6 | A6 | | | | aw | 1 | 0 | 1 | 0 | 0 | 1 | 0 |
| M330 | A6 | A6 | | | | ax | 1 | 0 | 1 | 0 | 0 | 1 | 0 |
| M331 | A6 | A6 | | | | ay | 1 | 0 | 1 | 0 | 0 | 1 | 0 |
| M332 | A6 | A6 | | | | z | 1 | 0 | 1 | 0 | 0 | 1 | 0 |
| M333 | A6 | A6 | | | | ba | 1 | 0 | 1 | 0 | 0 | 1 | 0 |
| M334 | A6 | A6 | | | | bb | 1 | 0 | 1 | 0 | 0 | 1 | 0 |
| M335 | A6 | A6 | | | | ba | 1 | 0 | 1 | 0 | 0 | 1 | 0 |
| M336 | A6 | A6 | | | | bd | 1 | 0 | 1 | 0 | 0 | 1 | 0 |
| M337 | A7 | A7 | | | | a | 1 | 0 | 1 | 0 | 0 | 1 | 0 |
| M338 | A7 | A7 | | | | b | 1 | 0 | 1 | 0 | 0 | 1 | 0 |
| M339 | A7 | A7 | | | | c | 1 | 0 | 1 | 0 | 0 | 1 | 0 |
| M340 | A7 | A7 | | | | d | 1 | 0 | 1 | 0 | 0 | 1 | 0 |
| M341 | A7 | A7 | | | | e | 1 | 0 | 1 | 0 | 0 | 1 | 0 |
| M342 | A7 | A7 | | | | f | 1 | 0 | 1 | 0 | 0 | 1 | 0 |
| M343 | A7 | A7 | | | | g | 1 | 0 | 1 | 0 | 0 | 1 | 0 |
| M344 | A7 | A7 | | | | h | 1 | 0 | 1 | 0 | 0 | 1 | 0 |
| M345 | A7 | A7 | | | | i | 1 | 0 | 1 | 0 | 0 | 1 | 0 |
| M346 | A7 | A7 | | | | j | 1 | 0 | 1 | 0 | 0 | 1 | 0 |
| M347 | A7 | A7 | | | | k | 1 | 0 | 1 | 0 | 0 | 1 | 0 |
| M348 | A7 | A7 | | | | l | 1 | 0 | 1 | 0 | 0 | 1 | 0 |
| M349 | A7 | A7 | | | | m | 1 | 0 | 1 | 0 | 0 | 1 | 0 |
| M350 | A7 | A7 | | | | n | 1 | 0 | 1 | 0 | 0 | 1 | 0 |
| M351 | A7 | A7 | | | | o | 1 | 0 | 1 | 0 | 0 | 1 | 0 |
| M352 | A7 | A7 | | | | p | 1 | 0 | 1 | 0 | 0 | 1 | 0 |
| M353 | A7 | A7 | | | | q | 1 | 0 | 1 | 0 | 0 | 1 | 0 |
| M354 | A7 | A7 | | | | r | 1 | 0 | 1 | 0 | 0 | 1 | 0 |
| M355 | A7 | A7 | | | | s | 1 | 0 | 1 | 0 | 0 | 1 | 0 |
| M356 | A7 | A7 | | | | t | 1 | 0 | 1 | 0 | 0 | 1 | 0 |
| M357 | A7 | A7 | | | | u | 1 | 0 | 1 | 0 | 0 | 1 | 0 |
| M358 | A7 | A7 | | | | v | 1 | 0 | 1 | 0 | 0 | 1 | 0 |
| M359 | A7 | A7 | | | | w | 1 | 0 | 1 | 0 | 0 | 1 | 0 |
| M360 | A7 | A7 | | | | x | 1 | 0 | 1 | 0 | 0 | 1 | 0 |
| M361 | A7 | A7 | | | | y | 1 | 0 | 1 | 0 | 0 | 1 | 0 |
| M362 | A7 | A7 | | | | z | 1 | 0 | 1 | 0 | 0 | 1 | 0 |
| M363 | A7 | A7 | | | | aa | 1 | 0 | 1 | 0 | 0 | 1 | 0 |
| M364 | A7 | A7 | | | | ab | 1 | 0 | 1 | 0 | 0 | 1 | 0 |
| M365 | A7 | A7 | | | | ac | 1 | 0 | 1 | 0 | 0 | 1 | 0 |
| M366 | A7 | A7 | | | | ad | 1 | 0 | 1 | 0 | 0 | 1 | 0 |
| M367 | A7 | A7 | | | | ae | 1 | 0 | 1 | 0 | 0 | 1 | 0 |
| M368 | A7 | A7 | | | | af | 1 | 0 | 1 | 0 | 0 | 1 | 0 |
| M369 | A7 | A7 | | | | ag | 1 | 0 | 1 | 0 | 0 | 1 | 0 |
| M370 | A7 | A7 | | | | ah | 1 | 0 | 1 | 0 | 0 | 1 | 0 |
| M371 | A7 | A7 | | | | ai | 1 | 0 | 1 | 0 | 0 | 1 | 0 |
| M372 | A7 | A7 | | | | aj | 1 | 0 | 1 | 0 | 0 | 1 | 0 |
| M373 | A7 | A7 | | | | ak | 1 | 0 | 1 | 0 | 0 | 1 | 0 |
| M374 | A7 | A7 | | | | al | 1 | 0 | 1 | 0 | 0 | 1 | 0 |
| M375 | A7 | A7 | | | | am | 1 | 0 | 1 | 0 | 0 | 1 | 0 |
| M376 | A7 | A7 | | | | an | 1 | 0 | 1 | 0 | 0 | 1 | 0 |
| M377 | A7 | A7 | | | | ao | 1 | 0 | 1 | 0 | 0 | 1 | 0 |
| M378 | A7 | A7 | | | | ap | 1 | 0 | 1 | 0 | 0 | 1 | 0 |
| M379 | A7 | A7 | | | | aq | 1 | 0 | 1 | 0 | 0 | 1 | 0 |
| M380 | A7 | A7 | | | | ar | 1 | 0 | 1 | 0 | 0 | 1 | 0 |
| M381 | A7 | A7 | | | | as | 1 | 0 | 1 | 0 | 0 | 1 | 0 |
| M382 | A7 | A7 | | | | at | 1 | 0 | 1 | 0 | 0 | 1 | 0 |
| M383 | A7 | A7 | | | | au | 1 | 0 | 1 | 0 | 0 | 1 | 0 |
| M384 | A7 | A7 | | | | av | 1 | 0 | 1 | 0 | 0 | 1 | 0 |
| M385 | A7 | A7 | | | | aw | 1 | 0 | 1 | 0 | 0 | 1 | 0 |
| M386 | A7 | A7 | | | | ax | 1 | 0 | 1 | 0 | 0 | 1 | 0 |
| M387 | A7 | A7 | | | | ay | 1 | 0 | 1 | 0 | 0 | 1 | 0 |
| M388 | A7 | A7 | | | | z | 1 | 0 | 1 | 0 | 0 | 1 | 0 |
| M389 | A7 | A7 | | | | ba | 1 | 0 | 1 | 0 | 0 | 1 | 0 |
| M390 | A7 | A7 | | | | bb | 1 | 0 | 1 | 0 | 0 | 1 | 0 |
| M391 | A7 | A7 | | | | ba | 1 | 0 | 1 | 0 | 0 | 1 | 0 |
| M392 | A7 | A7 | | | | bd | 1 | 0 | 1 | 0 | 0 | 1 | 0 |
| M393 | A8 | A8 | | | | a | 1 | 0 | 1 | 0 | 0 | 1 | 0 |
| M394 | A8 | A8 | | | | b | 1 | 0 | 1 | 0 | 0 | 1 | 0 |
| M395 | A8 | A8 | | | | c | 1 | 0 | 1 | 0 | 0 | 1 | 0 |
| M396 | A8 | A8 | | | | d | 1 | 0 | 1 | 0 | 0 | 1 | 0 |

-continued

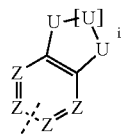

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M397 | A8 | A8 | | | | e | 1 | 0 | 1 | 0 | 0 | 1 | 0 |
| M398 | A8 | A8 | | | | f | 1 | 0 | 1 | 0 | 0 | 1 | 0 |
| M399 | A8 | A8 | | | | g | 1 | 0 | 1 | 0 | 0 | 1 | 0 |
| M400 | A8 | A8 | | | | h | 1 | 0 | 1 | 0 | 0 | 1 | 0 |
| M401 | A8 | A8 | | | | i | 1 | 0 | 1 | 0 | 0 | 1 | 0 |
| M402 | A8 | A8 | | | | j | 1 | 0 | 1 | 0 | 0 | 1 | 0 |
| M403 | A8 | A8 | | | | k | 1 | 0 | 1 | 0 | 0 | 1 | 0 |
| M404 | A8 | A8 | | | | l | 1 | 0 | 1 | 0 | 0 | 1 | 0 |
| M405 | A8 | A8 | | | | m | 1 | 0 | 1 | 0 | 0 | 1 | 0 |
| M406 | A8 | A8 | | | | n | 1 | 0 | 1 | 0 | 0 | 1 | 0 |
| M407 | A8 | A8 | | | | o | 1 | 0 | 1 | 0 | 0 | 1 | 0 |
| M408 | A8 | A8 | | | | p | 1 | 0 | 1 | 0 | 0 | 1 | 0 |
| M409 | A8 | A8 | | | | q | 1 | 0 | 1 | 0 | 0 | 1 | 0 |
| M410 | A8 | A8 | | | | r | 1 | 0 | 1 | 0 | 0 | 1 | 0 |
| M411 | A8 | A8 | | | | s | 1 | 0 | 1 | 0 | 0 | 1 | 0 |
| M412 | A8 | A8 | | | | t | 1 | 0 | 1 | 0 | 0 | 1 | 0 |
| M413 | A8 | A8 | | | | u | 1 | 0 | 1 | 0 | 0 | 1 | 0 |
| M414 | A8 | A8 | | | | v | 1 | 0 | 1 | 0 | 0 | 1 | 0 |
| M415 | A8 | A8 | | | | w | 1 | 0 | 1 | 0 | 0 | 1 | 0 |
| M416 | A8 | A8 | | | | x | 1 | 0 | 1 | 0 | 0 | 1 | 0 |
| M417 | A8 | A8 | | | | y | 1 | 0 | 1 | 0 | 0 | 1 | 0 |
| M418 | A8 | A8 | | | | z | 1 | 0 | 1 | 0 | 0 | 1 | 0 |
| M419 | A8 | A8 | | | | aa | 1 | 0 | 1 | 0 | 0 | 1 | 0 |
| M420 | A8 | A8 | | | | ab | 1 | 0 | 1 | 0 | 0 | 1 | 0 |
| M421 | A8 | A8 | | | | ac | 1 | 0 | 1 | 0 | 0 | 1 | 0 |
| M422 | A8 | A8 | | | | ad | 1 | 0 | 1 | 0 | 0 | 1 | 0 |
| M423 | A8 | A8 | | | | ae | 1 | 0 | 1 | 0 | 0 | 1 | 0 |
| M424 | A8 | A8 | | | | af | 1 | 0 | 1 | 0 | 0 | 1 | 0 |
| M425 | A8 | A8 | | | | ag | 1 | 0 | 1 | 0 | 0 | 1 | 0 |
| M426 | A8 | A8 | | | | ah | 1 | 0 | 1 | 0 | 0 | 1 | 0 |
| M427 | A8 | A8 | | | | ai | 1 | 0 | 1 | 0 | 0 | 1 | 0 |
| M428 | A8 | A8 | | | | aj | 1 | 0 | 1 | 0 | 0 | 1 | 0 |
| M429 | A8 | A8 | | | | ak | 1 | 0 | 1 | 0 | 0 | 1 | 0 |
| M430 | A8 | A8 | | | | al | 1 | 0 | 1 | 0 | 0 | 1 | 0 |
| M431 | A8 | A8 | | | | am | 1 | 0 | 1 | 0 | 0 | 1 | 0 |
| M432 | A8 | A8 | | | | an | 1 | 0 | 1 | 0 | 0 | 1 | 0 |
| M433 | A8 | A8 | | | | ao | 1 | 0 | 1 | 0 | 0 | 1 | 0 |
| M434 | A8 | A8 | | | | ap | 1 | 0 | 1 | 0 | 0 | 1 | 0 |
| M435 | A8 | A8 | | | | aq | 1 | 0 | 1 | 0 | 0 | 1 | 0 |
| M436 | A8 | A8 | | | | ar | 1 | 0 | 1 | 0 | 0 | 1 | 0 |
| M437 | A8 | A8 | | | | as | 1 | 0 | 1 | 0 | 0 | 1 | 0 |
| M438 | A8 | A8 | | | | at | 1 | 0 | 1 | 0 | 0 | 1 | 0 |
| M439 | A8 | A8 | | | | au | 1 | 0 | 1 | 0 | 0 | 1 | 0 |
| M440 | A8 | A8 | | | | av | 1 | 0 | 1 | 0 | 0 | 1 | 0 |
| M441 | A8 | A8 | | | | aw | 1 | 0 | 1 | 0 | 0 | 1 | 0 |
| M442 | A8 | A8 | | | | ax | 1 | 0 | 1 | 0 | 0 | 1 | 0 |
| M443 | A8 | A8 | | | | ay | 1 | 0 | 1 | 0 | 0 | 1 | 0 |
| M444 | A8 | A8 | | | | z | 1 | 0 | 1 | 0 | 0 | 1 | 0 |
| M445 | A8 | A8 | | | | ba | 1 | 0 | 1 | 0 | 0 | 1 | 0 |
| M446 | A8 | A8 | | | | bb | 1 | 0 | 1 | 0 | 0 | 1 | 0 |
| M447 | A8 | A8 | | | | ba | 1 | 0 | 1 | 0 | 0 | 1 | 0 |
| M448 | A8 | A8 | | | | bd | 1 | 0 | 1 | 0 | 0 | 1 | 0 |
| M449 | A9 | A9 | | | | a | 1 | 0 | 1 | 0 | 0 | 1 | 0 |
| M450 | A9 | A9 | | | | b | 1 | 0 | 1 | 0 | 0 | 1 | 0 |
| M451 | A9 | A9 | | | | c | 1 | 0 | 1 | 0 | 0 | 1 | 0 |
| M452 | A9 | A9 | | | | d | 1 | 0 | 1 | 0 | 0 | 1 | 0 |
| M453 | A9 | A9 | | | | e | 1 | 0 | 1 | 0 | 0 | 1 | 0 |
| M454 | A9 | A9 | | | | f | 1 | 0 | 1 | 0 | 0 | 1 | 0 |
| M455 | A9 | A9 | | | | g | 1 | 0 | 1 | 0 | 0 | 1 | 0 |
| M456 | A9 | A9 | | | | h | 1 | 0 | 1 | 0 | 0 | 1 | 0 |
| M457 | A9 | A9 | | | | i | 1 | 0 | 1 | 0 | 0 | 1 | 0 |
| M458 | A9 | A9 | | | | j | 1 | 0 | 1 | 0 | 0 | 1 | 0 |
| M459 | A9 | A9 | | | | k | 1 | 0 | 1 | 0 | 0 | 1 | 0 |
| M460 | A9 | A9 | | | | l | 1 | 0 | 1 | 0 | 0 | 1 | 0 |
| M461 | A9 | A9 | | | | m | 1 | 0 | 1 | 0 | 0 | 1 | 0 |
| M462 | A9 | A9 | | | | n | 1 | 0 | 1 | 0 | 0 | 1 | 0 |
| M463 | A9 | A9 | | | | o | 1 | 0 | 1 | 0 | 0 | 1 | 0 |
| M464 | A9 | A9 | | | | p | 1 | 0 | 1 | 0 | 0 | 1 | 0 |
| M465 | A9 | A9 | | | | q | 1 | 0 | 1 | 0 | 0 | 1 | 0 |

-continued

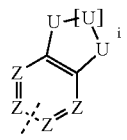

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M466 | A9 | | A9 | | | r | 1 | 0 | 1 | 0 | 0 | 1 | 0 |
| M467 | A9 | | A9 | | | s | 1 | 0 | 1 | 0 | 0 | 1 | 0 |
| M468 | A9 | | A9 | | | t | 1 | 0 | 1 | 0 | 0 | 1 | 0 |
| M469 | A9 | | A9 | | | u | 1 | 0 | 1 | 0 | 0 | 1 | 0 |
| M470 | A9 | | A9 | | | v | 1 | 0 | 1 | 0 | 0 | 1 | 0 |
| M471 | A9 | | A9 | | | w | 1 | 0 | 1 | 0 | 0 | 1 | 0 |
| M472 | A9 | | A9 | | | x | 1 | 0 | 1 | 0 | 0 | 1 | 0 |
| M473 | A9 | | A9 | | | y | 1 | 0 | 1 | 0 | 0 | 1 | 0 |
| M474 | A9 | | A9 | | | z | 1 | 0 | 1 | 0 | 0 | 1 | 0 |
| M475 | A9 | | A9 | | | aa | 1 | 0 | 1 | 0 | 0 | 1 | 0 |
| M476 | A9 | | A9 | | | ab | 1 | 0 | 1 | 0 | 0 | 1 | 0 |
| M477 | A9 | | A9 | | | ac | 1 | 0 | 1 | 0 | 0 | 1 | 0 |
| M478 | A9 | | A9 | | | ad | 1 | 0 | 1 | 0 | 0 | 1 | 0 |
| M479 | A9 | | A9 | | | ae | 1 | 0 | 1 | 0 | 0 | 1 | 0 |
| M480 | A9 | | A9 | | | af | 1 | 0 | 1 | 0 | 0 | 1 | 0 |
| M481 | A9 | | A9 | | | ag | 1 | 0 | 1 | 0 | 0 | 1 | 0 |
| M482 | A9 | | A9 | | | ah | 1 | 0 | 1 | 0 | 0 | 1 | 0 |
| M483 | A9 | | A9 | | | ai | 1 | 0 | 1 | 0 | 0 | 1 | 0 |
| M484 | A9 | | A9 | | | aj | 1 | 0 | 1 | 0 | 0 | 1 | 0 |
| M485 | A9 | | A9 | | | ak | 1 | 0 | 1 | 0 | 0 | 1 | 0 |
| M486 | A9 | | A9 | | | al | 1 | 0 | 1 | 0 | 0 | 1 | 0 |
| M487 | A9 | | A9 | | | am | 1 | 0 | 1 | 0 | 0 | 1 | 0 |
| M488 | A9 | | A9 | | | an | 1 | 0 | 1 | 0 | 0 | 1 | 0 |
| M489 | A9 | | A9 | | | ao | 1 | 0 | 1 | 0 | 0 | 1 | 0 |
| M490 | A9 | | A9 | | | ap | 1 | 0 | 1 | 0 | 0 | 1 | 0 |
| M491 | A9 | | A9 | | | aq | 1 | 0 | 1 | 0 | 0 | 1 | 0 |
| M492 | A9 | | A9 | | | ar | 1 | 0 | 1 | 0 | 0 | 1 | 0 |
| M493 | A9 | | A9 | | | as | 1 | 0 | 1 | 0 | 0 | 1 | 0 |
| M494 | A9 | | A9 | | | at | 1 | 0 | 1 | 0 | 0 | 1 | 0 |
| M495 | A9 | | A9 | | | au | 1 | 0 | 1 | 0 | 0 | 1 | 0 |
| M496 | A9 | | A9 | | | av | 1 | 0 | 1 | 0 | 0 | 1 | 0 |
| M497 | A9 | | A9 | | | aw | 1 | 0 | 1 | 0 | 0 | 1 | 0 |
| M498 | A9 | | A9 | | | ax | 1 | 0 | 1 | 0 | 0 | 1 | 0 |
| M499 | A9 | | A9 | | | ay | 1 | 0 | 1 | 0 | 0 | 1 | 0 |
| M500 | A9 | | A9 | | | z | 1 | 0 | 1 | 0 | 0 | 1 | 0 |
| M501 | A9 | | A9 | | | ba | 1 | 0 | 1 | 0 | 0 | 1 | 0 |
| M502 | A9 | | A9 | | | bb | 1 | 0 | 1 | 0 | 0 | 1 | 0 |
| M503 | A9 | | A9 | | | ba | 1 | 0 | 1 | 0 | 0 | 1 | 0 |
| M504 | A9 | | A9 | | | bd | 1 | 0 | 1 | 0 | 0 | 1 | 0 |
| M505 | A10 | | A10 | | | b | 1 | 0 | 1 | 0 | 0 | 1 | 0 |
| M506 | A1 | | A1 | A1 | | a | 1 | 0 | 1 | 1 | 0 | 1 | 0 |
| M507 | A1 | | A1 | A2 | | a | 1 | 0 | 1 | 1 | 0 | 1 | 0 |
| M508 | A1 | | A1 | A3 | | a | 1 | 0 | 1 | 1 | 0 | 1 | 0 |
| M509 | A1 | | A1 | A4 | | a | 1 | 0 | 1 | 1 | 0 | 1 | 0 |
| M510 | A1 | | A1 | A5 | | a | 1 | 0 | 1 | 1 | 0 | 1 | 0 |
| M511 | A1 | | A1 | A5 | | a | 1 | 0 | 1 | 1 | 0 | 1 | 0 |
| M512 | A1 | | A1 | A6 | | a | 1 | 0 | 1 | 1 | 0 | 1 | 0 |
| M513 | A1 | | A1 | A7 | | a | 1 | 0 | 1 | 1 | 0 | 1 | 0 |
| M514 | A1 | | A1 | A8 | | a | 1 | 0 | 1 | 1 | 0 | 1 | 0 |
| M515 | A1 | | A1 | A9 | | a | 1 | 0 | 1 | 1 | 0 | 1 | 0 |
| M516 | A1 | | A1 | A1 | | b | 1 | 0 | 1 | 1 | 0 | 1 | 0 |
| M517 | A1 | | A1 | A2 | | b | 1 | 0 | 1 | 1 | 0 | 1 | 0 |
| M518 | A1 | | A1 | A3 | | b | 1 | 0 | 1 | 1 | 0 | 1 | 0 |
| M519 | A1 | | A1 | A4 | | b | 1 | 0 | 1 | 1 | 0 | 1 | 0 |
| M520 | A1 | | A1 | A5 | | b | 1 | 0 | 1 | 1 | 0 | 1 | 0 |
| M521 | A1 | | A1 | A5 | | b | 1 | 0 | 1 | 1 | 0 | 1 | 0 |
| M522 | A1 | | A1 | A6 | | b | 1 | 0 | 1 | 1 | 0 | 1 | 0 |
| M523 | A1 | | A1 | A7 | | b | 1 | 0 | 1 | 1 | 0 | 1 | 0 |
| M524 | A1 | | A1 | A8 | | b | 1 | 0 | 1 | 1 | 0 | 1 | 0 |
| M525 | A1 | | A1 | A9 | | b | 1 | 0 | 1 | 1 | 0 | 1 | 0 |
| M526 | A1 | | A1 | A1 | | c | 1 | 0 | 1 | 1 | 0 | 1 | 0 |
| M527 | A1 | | A1 | A2 | | c | 1 | 0 | 1 | 1 | 0 | 1 | 0 |
| M528 | A1 | | A1 | A3 | | c | 1 | 0 | 1 | 1 | 0 | 1 | 0 |
| M529 | A1 | | A1 | A1 | | t | 1 | 0 | 1 | 1 | 0 | 1 | 0 |
| M530 | A1 | | A1 | A2 | | t | 1 | 0 | 1 | 1 | 0 | 1 | 0 |
| M531 | A1 | | A1 | A3 | | t | 1 | 0 | 1 | 1 | 0 | 1 | 0 |
| M532 | A1 | | A1 | A1 | | v | 1 | 0 | 1 | 1 | 0 | 1 | 0 |
| M533 | A1 | | A1 | A2 | | v | 1 | 0 | 1 | 1 | 0 | 1 | 0 |
| M534 | A1 | | A1 | A3 | | v | 1 | 0 | 1 | 1 | 0 | 1 | 0 |

-continued

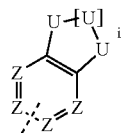

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M535 | A1 | | A1 | A1 | | w | 1 | 0 | 1 | 1 | 0 | 1 | 0 |
| M536 | A1 | | A1 | A2 | | w | 1 | 0 | 1 | 1 | 0 | 1 | 0 |
| M537 | A1 | | A1 | A1 | | af | 1 | 0 | 1 | 1 | 0 | 1 | 0 |
| M538 | A1 | | A1 | A2 | | af | 1 | 0 | 1 | 1 | 0 | 1 | 0 |
| M539 | A1 | | A1 | A1 | | am | 1 | 0 | 1 | 1 | 0 | 1 | 0 |
| M540 | A1 | | A1 | A2 | | am | 1 | 0 | 1 | 1 | 0 | 1 | 0 |
| M541 | A1 | | A1 | A1 | | an | 1 | 0 | 1 | 1 | 0 | 1 | 0 |
| M542 | A1 | | A1 | A2 | | an | 1 | 0 | 1 | 1 | 0 | 1 | 0 |
| M543 | A1 | | A1 | A1 | | ba | 1 | 0 | 1 | 1 | 0 | 1 | 0 |
| M544 | A1 | | A1 | A2 | | ba | 1 | 0 | 1 | 1 | 0 | 1 | 0 |
| M545 | A1 | | A1 | A1 | | bb | 1 | 0 | 1 | 1 | 0 | 1 | 0 |
| M546 | A1 | | A1 | A2 | | bb | 1 | 0 | 1 | 1 | 0 | 1 | 0 |
| M547 | A1 | | A1 | A1 | | b | 1 | 0 | 1 | 1 | 0 | 2 | 0 |
| M548 | A1 | | A1 | A2 | | b | 1 | 0 | 1 | 1 | 0 | 2 | 0 |
| M549 | A1 | | A1 | A3 | | b | 1 | 0 | 1 | 1 | 0 | 2 | 0 |
| M550 | A1 | | A1 | A1 | | b | 1 | 0 | 1 | 1 | 0 | 3 | 0 |
| M551 | A1 | | A1 | A2 | | b | 1 | 0 | 1 | 1 | 0 | 3 | 0 |
| M552 | A1 | | A1 | A1 | | a | 1 | 0 | 1 | 2 | 0 | 1 | 0 |
| M553 | A1 | | A1 | A2 | | a | 1 | 0 | 1 | 2 | 0 | 1 | 0 |
| M554 | A1 | | A1 | A1 | | b | 1 | 0 | 1 | 2 | 0 | 1 | 0 |
| M555 | A1 | | A1 | A2 | | b | 1 | 0 | 1 | 2 | 0 | 1 | 0 |
| M556 | A2 | | A2 | A1 | | a | 1 | 0 | 1 | 1 | 0 | 1 | 0 |
| M557 | A2 | | A2 | A2 | | a | 1 | 0 | 1 | 1 | 0 | 1 | 0 |
| M558 | A2 | | A2 | A3 | | a | 1 | 0 | 1 | 1 | 0 | 1 | 0 |
| M559 | A2 | | A2 | A4 | | a | 1 | 0 | 1 | 1 | 0 | 1 | 0 |
| M560 | A2 | | A2 | A5 | | a | 1 | 0 | 1 | 1 | 0 | 1 | 0 |
| M561 | A2 | | A2 | A5 | | a | 1 | 0 | 1 | 1 | 0 | 1 | 0 |
| M562 | A2 | | A2 | A6 | | a | 1 | 0 | 1 | 1 | 0 | 1 | 0 |
| M563 | A2 | | A2 | A7 | | a | 1 | 0 | 1 | 1 | 0 | 1 | 0 |
| M564 | A2 | | A2 | A8 | | a | 1 | 0 | 1 | 1 | 0 | 1 | 0 |
| M565 | A2 | | A2 | A9 | | a | 1 | 0 | 1 | 1 | 0 | 1 | 0 |
| M566 | A2 | | A2 | A1 | | b | 1 | 0 | 1 | 1 | 0 | 1 | 0 |
| M567 | A2 | | A2 | A2 | | b | 1 | 0 | 1 | 1 | 0 | 1 | 0 |
| M568 | A2 | | A2 | A3 | | b | 1 | 0 | 1 | 1 | 0 | 1 | 0 |
| M569 | A2 | | A2 | A1 | | v | 1 | 0 | 1 | 1 | 0 | 1 | 0 |
| M570 | A2 | | A2 | A2 | | v | 1 | 0 | 1 | 1 | 0 | 1 | 0 |
| M571 | A2 | | A2 | A3 | | v | 1 | 0 | 1 | 1 | 0 | 1 | 0 |
| M572 | A2 | | A2 | A1 | | b | 1 | 0 | 1 | 1 | 0 | 2 | 0 |
| M573 | A2 | | A2 | A2 | | b | 1 | 0 | 1 | 1 | 0 | 2 | 0 |
| M574 | A2 | | A2 | A3 | | b | 1 | 0 | 1 | 1 | 0 | 2 | 0 |
| M575 | A2 | | A2 | A4 | | b | 1 | 0 | 1 | 1 | 0 | 1 | 0 |
| M576 | A2 | | A2 | A5 | | b | 1 | 0 | 1 | 1 | 0 | 1 | 0 |
| M577 | A2 | | A2 | A5 | | b | 1 | 0 | 1 | 1 | 0 | 1 | 0 |
| M578 | A2 | | A2 | A6 | | b | 1 | 0 | 1 | 1 | 0 | 1 | 0 |
| M579 | A2 | | A2 | A7 | | b | 1 | 0 | 1 | 1 | 0 | 1 | 0 |
| M580 | A2 | | A2 | A8 | | b | 1 | 0 | 1 | 1 | 0 | 1 | 0 |
| M581 | A2 | | A2 | A9 | | b | 1 | 0 | 1 | 1 | 0 | 1 | 0 |
| M582 | A3 | | A3 | A1 | | a | 1 | 0 | 1 | 1 | 0 | 1 | 0 |
| M583 | A3 | | A3 | A2 | | a | 1 | 0 | 1 | 1 | 0 | 1 | 0 |
| M584 | A3 | | A3 | A3 | | a | 1 | 0 | 1 | 1 | 0 | 1 | 0 |
| M585 | A3 | | A3 | A4 | | a | 1 | 0 | 1 | 1 | 0 | 1 | 0 |
| M586 | A3 | | A3 | A5 | | a | 1 | 0 | 1 | 1 | 0 | 1 | 0 |
| M587 | A3 | | A3 | A5 | | a | 1 | 0 | 1 | 1 | 0 | 1 | 0 |
| M588 | A3 | | A3 | A6 | | a | 1 | 0 | 1 | 1 | 0 | 1 | 0 |
| M589 | A3 | | A3 | A7 | | a | 1 | 0 | 1 | 1 | 0 | 1 | 0 |
| M590 | A3 | | A3 | A8 | | a | 1 | 0 | 1 | 1 | 0 | 1 | 0 |
| M591 | A3 | | A3 | A9 | | a | 1 | 0 | 1 | 1 | 0 | 1 | 0 |
| M592 | A3 | | A3 | A1 | | b | 1 | 0 | 1 | 1 | 0 | 1 | 0 |
| M593 | A3 | | A3 | A2 | | b | 1 | 0 | 1 | 1 | 0 | 1 | 0 |
| M594 | A3 | | A3 | A3 | | b | 1 | 0 | 1 | 1 | 0 | 1 | 0 |
| M595 | A3 | | A3 | A4 | | b | 1 | 0 | 1 | 1 | 0 | 1 | 0 |
| M596 | A3 | | A3 | A5 | | b | 1 | 0 | 1 | 1 | 0 | 1 | 0 |
| M597 | A3 | | A3 | A5 | | b | 1 | 0 | 1 | 1 | 0 | 1 | 0 |
| M598 | A3 | | A3 | A6 | | b | 1 | 0 | 1 | 1 | 0 | 1 | 0 |
| M599 | A3 | | A3 | A7 | | b | 1 | 0 | 1 | 1 | 0 | 1 | 0 |
| M600 | A3 | | A3 | A8 | | b | 1 | 0 | 1 | 1 | 0 | 1 | 0 |
| M601 | A3 | | A3 | A9 | | b | 1 | 0 | 1 | 1 | 0 | 1 | 0 |
| M602 | A4 | | A4 | A1 | | a | 1 | 0 | 1 | 1 | 0 | 1 | 0 |
| M603 | A4 | | A4 | A2 | | a | 1 | 0 | 1 | 1 | 0 | 1 | 0 |

-continued

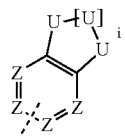

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M604 | A4 | | A4 | A3 | | a | 1 | 0 | 1 | 1 | 0 | 1 | 0 |
| M605 | A4 | | A4 | A4 | | a | 1 | 0 | 1 | 1 | 0 | 1 | 0 |
| M606 | A4 | | A4 | A5 | | a | 1 | 0 | 1 | 1 | 0 | 1 | 0 |
| M607 | A4 | | A4 | A5 | | a | 1 | 0 | 1 | 1 | 0 | 1 | 0 |
| M608 | A4 | | A4 | A6 | | a | 1 | 0 | 1 | 1 | 0 | 1 | 0 |
| M609 | A4 | | A4 | A7 | | a | 1 | 0 | 1 | 1 | 0 | 1 | 0 |
| M610 | A4 | | A4 | A8 | | a | 1 | 0 | 1 | 1 | 0 | 1 | 0 |
| M611 | A4 | | A4 | A9 | | a | 1 | 0 | 1 | 1 | 0 | 1 | 0 |
| M612 | A4 | | A4 | A1 | | b | 1 | 0 | 1 | 1 | 0 | 1 | 0 |
| M613 | A4 | | A4 | A2 | | b | 1 | 0 | 1 | 1 | 0 | 1 | 0 |
| M614 | A4 | | A4 | A3 | | b | 1 | 0 | 1 | 1 | 0 | 1 | 0 |
| M615 | A4 | | A4 | A4 | | b | 1 | 0 | 1 | 1 | 0 | 1 | 0 |
| M616 | A4 | | A4 | A5 | | b | 1 | 0 | 1 | 1 | 0 | 1 | 0 |
| M617 | A4 | | A4 | A5 | | b | 1 | 0 | 1 | 1 | 0 | 1 | 0 |
| M618 | A4 | | A4 | A6 | | b | 1 | 0 | 1 | 1 | 0 | 1 | 0 |
| M619 | A4 | | A4 | A7 | | b | 1 | 0 | 1 | 1 | 0 | 1 | 0 |
| M620 | A4 | | A4 | A8 | | b | 1 | 0 | 1 | 1 | 0 | 1 | 0 |
| M621 | A4 | | A4 | A9 | | b | 1 | 0 | 1 | 1 | 0 | 1 | 0 |
| M622 | A5 | | A5 | A1 | | a | 1 | 0 | 1 | 1 | 0 | 1 | 0 |
| M623 | A5 | | A5 | A2 | | a | 1 | 0 | 1 | 1 | 0 | 1 | 0 |
| M624 | A5 | | A5 | A3 | | a | 1 | 0 | 1 | 1 | 0 | 1 | 0 |
| M625 | A5 | | A5 | A4 | | a | 1 | 0 | 1 | 1 | 0 | 1 | 0 |
| M626 | A5 | | A5 | A5 | | a | 1 | 0 | 1 | 1 | 0 | 1 | 0 |
| M627 | A5 | | A5 | A5 | | a | 1 | 0 | 1 | 1 | 0 | 1 | 0 |
| M628 | A5 | | A5 | A6 | | a | 1 | 0 | 1 | 1 | 0 | 1 | 0 |
| M629 | A5 | | A5 | A7 | | a | 1 | 0 | 1 | 1 | 0 | 1 | 0 |
| M630 | A5 | | A5 | A8 | | a | 1 | 0 | 1 | 1 | 0 | 1 | 0 |
| M631 | A5 | | A5 | A9 | | a | 1 | 0 | 1 | 1 | 0 | 1 | 0 |
| M632 | A5 | | A5 | A1 | | b | 1 | 0 | 1 | 1 | 0 | 1 | 0 |
| M633 | A5 | | A5 | A2 | | b | 1 | 0 | 1 | 1 | 0 | 1 | 0 |
| M634 | A5 | | A5 | A3 | | b | 1 | 0 | 1 | 1 | 0 | 1 | 0 |
| M635 | A5 | | A5 | A4 | | b | 1 | 0 | 1 | 1 | 0 | 1 | 0 |
| M636 | A5 | | A5 | A5 | | b | 1 | 0 | 1 | 1 | 0 | 1 | 0 |
| M637 | A5 | | A5 | A5 | | b | 1 | 0 | 1 | 1 | 0 | 1 | 0 |
| M638 | A5 | | A5 | A6 | | b | 1 | 0 | 1 | 1 | 0 | 1 | 0 |
| M639 | A5 | | A5 | A7 | | b | 1 | 0 | 1 | 1 | 0 | 1 | 0 |
| M640 | A5 | | A5 | A8 | | b | 1 | 0 | 1 | 1 | 0 | 1 | 0 |
| M641 | A5 | | A5 | A9 | | b | 1 | 0 | 1 | 1 | 0 | 1 | 0 |
| M642 | A6 | | A6 | A1 | | a | 1 | 0 | 1 | 1 | 0 | 1 | 0 |
| M643 | A6 | | A6 | A2 | | a | 1 | 0 | 1 | 1 | 0 | 1 | 0 |
| M644 | A6 | | A6 | A3 | | a | 1 | 0 | 1 | 1 | 0 | 1 | 0 |
| M645 | A6 | | A6 | A4 | | a | 1 | 0 | 1 | 1 | 0 | 1 | 0 |
| M646 | A6 | | A6 | A5 | | a | 1 | 0 | 1 | 1 | 0 | 1 | 0 |
| M647 | A6 | | A6 | A5 | | a | 1 | 0 | 1 | 1 | 0 | 1 | 0 |
| M648 | A6 | | A6 | A6 | | a | 1 | 0 | 1 | 1 | 0 | 1 | 0 |
| M649 | A6 | | A6 | A7 | | a | 1 | 0 | 1 | 1 | 0 | 1 | 0 |
| M650 | A6 | | A6 | A8 | | a | 1 | 0 | 1 | 1 | 0 | 1 | 0 |
| M651 | A6 | | A6 | A9 | | a | 1 | 0 | 1 | 1 | 0 | 1 | 0 |
| M652 | A6 | | A6 | A1 | | b | 1 | 0 | 1 | 1 | 0 | 1 | 0 |
| M653 | A6 | | A6 | A2 | | b | 1 | 0 | 1 | 1 | 0 | 1 | 0 |
| M654 | A6 | | A6 | A3 | | b | 1 | 0 | 1 | 1 | 0 | 1 | 0 |
| M655 | A6 | | A6 | A4 | | b | 1 | 0 | 1 | 1 | 0 | 1 | 0 |
| M656 | A6 | | A6 | A5 | | b | 1 | 0 | 1 | 1 | 0 | 1 | 0 |
| M657 | A6 | | A6 | A5 | | b | 1 | 0 | 1 | 1 | 0 | 1 | 0 |
| M658 | A6 | | A6 | A6 | | b | 1 | 0 | 1 | 1 | 0 | 1 | 0 |
| M659 | A6 | | A6 | A7 | | b | 1 | 0 | 1 | 1 | 0 | 1 | 0 |
| M660 | A6 | | A6 | A8 | | b | 1 | 0 | 1 | 1 | 0 | 1 | 0 |
| M661 | A6 | | A6 | A9 | | b | 1 | 0 | 1 | 1 | 0 | 1 | 0 |
| M662 | A7 | | A7 | A1 | | a | 1 | 0 | 1 | 1 | 0 | 1 | 0 |
| M663 | A7 | | A7 | A2 | | a | 1 | 0 | 1 | 1 | 0 | 1 | 0 |
| M664 | A7 | | A7 | A3 | | a | 1 | 0 | 1 | 1 | 0 | 1 | 0 |
| M665 | A7 | | A7 | A4 | | a | 1 | 0 | 1 | 1 | 0 | 1 | 0 |
| M666 | A7 | | A7 | A5 | | a | 1 | 0 | 1 | 1 | 0 | 1 | 0 |
| M667 | A7 | | A7 | A5 | | a | 1 | 0 | 1 | 1 | 0 | 1 | 0 |
| M668 | A7 | | A7 | A6 | | a | 1 | 0 | 1 | 1 | 0 | 1 | 0 |
| M669 | A7 | | A7 | A7 | | a | 1 | 0 | 1 | 1 | 0 | 1 | 0 |
| M670 | A7 | | A7 | A8 | | a | 1 | 0 | 1 | 1 | 0 | 1 | 0 |
| M671 | A7 | | A7 | A9 | | a | 1 | 0 | 1 | 1 | 0 | 1 | 0 |
| M672 | A7 | | A7 | A1 | | b | 1 | 0 | 1 | 1 | 0 | 1 | 0 |

-continued

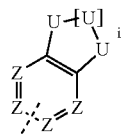

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M673 | A7 | | A7 | A2 | | b | 1 | 0 | 1 | 1 | 0 | 1 | 0 |
| M674 | A7 | | A7 | A3 | | b | 1 | 0 | 1 | 1 | 0 | 1 | 0 |
| M675 | A7 | | A7 | A4 | | b | 1 | 0 | 1 | 1 | 0 | 1 | 0 |
| M676 | A7 | | A7 | A5 | | b | 1 | 0 | 1 | 1 | 0 | 1 | 0 |
| M677 | A7 | | A7 | A5 | | b | 1 | 0 | 1 | 1 | 0 | 1 | 0 |
| M678 | A7 | | A7 | A6 | | b | 1 | 0 | 1 | 1 | 0 | 1 | 0 |
| M679 | A7 | | A7 | A7 | | b | 1 | 0 | 1 | 1 | 0 | 1 | 0 |
| M680 | A7 | | A7 | A8 | | b | 1 | 0 | 1 | 1 | 0 | 1 | 0 |
| M681 | A7 | | A7 | A9 | | b | 1 | 0 | 1 | 1 | 0 | 1 | 0 |
| M682 | A8 | | A8 | A1 | | a | 1 | 0 | 1 | 1 | 0 | 1 | 0 |
| M683 | A8 | | A8 | A2 | | a | 1 | 0 | 1 | 1 | 0 | 1 | 0 |
| M684 | A8 | | A8 | A3 | | a | 1 | 0 | 1 | 1 | 0 | 1 | 0 |
| M685 | A8 | | A8 | A4 | | a | 1 | 0 | 1 | 1 | 0 | 1 | 0 |
| M686 | A8 | | A8 | A5 | | a | 1 | 0 | 1 | 1 | 0 | 1 | 0 |
| M687 | A8 | | A8 | A5 | | a | 1 | 0 | 1 | 1 | 0 | 1 | 0 |
| M688 | A8 | | A8 | A6 | | a | 1 | 0 | 1 | 1 | 0 | 1 | 0 |
| M689 | A8 | | A8 | A7 | | a | 1 | 0 | 1 | 1 | 0 | 1 | 0 |
| M690 | A8 | | A8 | A8 | | a | 1 | 0 | 1 | 1 | 0 | 1 | 0 |
| M691 | A8 | | A8 | A9 | | a | 1 | 0 | 1 | 1 | 0 | 1 | 0 |
| M692 | A8 | | A8 | A1 | | b | 1 | 0 | 1 | 1 | 0 | 1 | 0 |
| M693 | A8 | | A8 | A2 | | b | 1 | 0 | 1 | 1 | 0 | 1 | 0 |
| M694 | A8 | | A8 | A3 | | b | 1 | 0 | 1 | 1 | 0 | 1 | 0 |
| M695 | A8 | | A8 | A4 | | b | 1 | 0 | 1 | 1 | 0 | 1 | 0 |
| M696 | A8 | | A8 | A5 | | b | 1 | 0 | 1 | 1 | 0 | 1 | 0 |
| M697 | A8 | | A8 | A5 | | b | 1 | 0 | 1 | 1 | 0 | 1 | 0 |
| M698 | A8 | | A8 | A6 | | b | 1 | 0 | 1 | 1 | 0 | 1 | 0 |
| M699 | A8 | | A8 | A7 | | b | 1 | 0 | 1 | 1 | 0 | 1 | 0 |
| M700 | A8 | | A8 | A8 | | b | 1 | 0 | 1 | 1 | 0 | 1 | 0 |
| M701 | A8 | | A8 | A9 | | b | 1 | 0 | 1 | 1 | 0 | 1 | 0 |
| M702 | A9 | | A9 | A1 | | a | 1 | 0 | 1 | 1 | 0 | 1 | 0 |
| M703 | A9 | | A9 | A2 | | a | 1 | 0 | 1 | 1 | 0 | 1 | 0 |
| M704 | A9 | | A9 | A3 | | a | 1 | 0 | 1 | 1 | 0 | 1 | 0 |
| M705 | A9 | | A9 | A4 | | a | 1 | 0 | 1 | 1 | 0 | 1 | 0 |
| M706 | A9 | | A9 | A5 | | a | 1 | 0 | 1 | 1 | 0 | 1 | 0 |
| M707 | A9 | | A9 | A5 | | a | 1 | 0 | 1 | 1 | 0 | 1 | 0 |
| M708 | A9 | | A9 | A6 | | a | 1 | 0 | 1 | 1 | 0 | 1 | 0 |
| M709 | A9 | | A9 | A7 | | a | 1 | 0 | 1 | 1 | 0 | 1 | 0 |
| M710 | A9 | | A9 | A8 | | a | 1 | 0 | 1 | 1 | 0 | 1 | 0 |
| M711 | A9 | | A9 | A9 | | a | 1 | 0 | 1 | 1 | 0 | 1 | 0 |
| M712 | A9 | | A9 | A1 | | b | 1 | 0 | 1 | 1 | 0 | 1 | 0 |
| M713 | A9 | | A9 | A2 | | b | 1 | 0 | 1 | 1 | 0 | 1 | 0 |
| M714 | A9 | | A9 | A3 | | b | 1 | 0 | 1 | 1 | 0 | 1 | 0 |
| M715 | A9 | | A9 | A4 | | b | 1 | 0 | 1 | 1 | 0 | 1 | 0 |
| M716 | A9 | | A9 | A5 | | b | 1 | 0 | 1 | 1 | 0 | 1 | 0 |
| M717 | A9 | | A9 | A5 | | b | 1 | 0 | 1 | 1 | 0 | 1 | 0 |
| M718 | A9 | | A9 | A6 | | b | 1 | 0 | 1 | 1 | 0 | 1 | 0 |
| M719 | A9 | | A9 | A7 | | b | 1 | 0 | 1 | 1 | 0 | 1 | 0 |
| M720 | A9 | | A9 | A8 | | b | 1 | 0 | 1 | 1 | 0 | 1 | 0 |
| M721 | A9 | | A9 | A9 | | b | 1 | 0 | 1 | 1 | 0 | 1 | 0 |
| M722 | A10 | | A1 | A10 | | b | 1 | 0 | 1 | 1 | 0 | 1 | 0 |
| M723 | A1 | A1 | A1 | | | a | 1 | 1 | 1 | 0 | 0 | 1 | 1 |
| M724 | A1 | A1 | A1 | | | b | 1 | 1 | 1 | 0 | 0 | 1 | 1 |
| M725 | A1 | A2 | A1 | | | a | 1 | 1 | 1 | 0 | 0 | 1 | 1 |
| M726 | A1 | A2 | A1 | | | b | 1 | 1 | 1 | 0 | 0 | 1 | 1 |
| M727 | A1 | A3 | A1 | | | a | 1 | 1 | 1 | 0 | 0 | 1 | 1 |
| M728 | A1 | A3 | A1 | | | b | 1 | 1 | 1 | 0 | 0 | 1 | 1 |
| M729 | A1 | A3 | A1 | | | t | 1 | 1 | 1 | 0 | 0 | 1 | 1 |
| M730 | A1 | A3 | A1 | | | v | 1 | 1 | 1 | 0 | 0 | 1 | 1 |
| M731 | A1 | A3 | A1 | | | av | 1 | 1 | 1 | 0 | 0 | 1 | 1 |
| M732 | A1 | A4 | A1 | | | a | 1 | 1 | 1 | 0 | 0 | 1 | 1 |
| M733 | A1 | A4 | A1 | | | b | 1 | 1 | 1 | 0 | 0 | 1 | 1 |
| M734 | A1 | A5 | A1 | | | a | 1 | 1 | 1 | 0 | 0 | 1 | 1 |
| M735 | A1 | A5 | A1 | | | b | 1 | 1 | 1 | 0 | 0 | 1 | 1 |
| M736 | A1 | A6 | A1 | | | a | 1 | 1 | 1 | 0 | 0 | 1 | 1 |
| M737 | A1 | A6 | A1 | | | b | 1 | 1 | 1 | 0 | 0 | 1 | 1 |
| M738 | A1 | A7 | A1 | | | a | 1 | 1 | 1 | 0 | 0 | 1 | 1 |
| M739 | A1 | A7 | A1 | | | b | 1 | 1 | 1 | 0 | 0 | 1 | 1 |
| M740 | A1 | A8 | A1 | | | a | 1 | 1 | 1 | 0 | 0 | 1 | 1 |
| M741 | A1 | A8 | A1 | | | b | 1 | 1 | 1 | 0 | 0 | 1 | 1 |

-continued

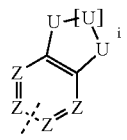

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M742 | A1 | A9 | A1 | | | a | 1 | 1 | 1 | 0 | 0 | 1 | 1 |
| M743 | A1 | A9 | A1 | | | b | 1 | 1 | 1 | 0 | 0 | 1 | 1 |
| M744 | A1 | A10 | A1 | | | a | 1 | 1 | 1 | 0 | 0 | 1 | 1 |
| M745 | A1 | A10 | A1 | | | b | 1 | 1 | 1 | 0 | 0 | 1 | 1 |
| M746 | A1 | A9 | A1 | | | w | 1 | 1 | 1 | 0 | 0 | 1 | 1 |
| M747 | A1 | A9 | A1 | | | ae | 1 | 1 | 1 | 0 | 0 | 1 | 1 |
| M748 | A1 | A9 | A1 | | | c | 1 | 1 | 1 | 0 | 0 | 1 | 1 |
| M749 | A2 | A1 | A2 | | | a | 1 | 1 | 1 | 0 | 0 | 1 | 1 |
| M750 | A2 | A1 | A2 | | | b | 1 | 1 | 1 | 0 | 0 | 1 | 1 |
| M751 | A2 | A2 | A2 | | | a | 1 | 1 | 1 | 0 | 0 | 1 | 1 |
| M752 | A2 | A2 | A2 | | | b | 1 | 1 | 1 | 0 | 0 | 1 | 1 |
| M753 | A2 | A3 | A2 | | | a | 1 | 1 | 1 | 0 | 0 | 1 | 1 |
| M754 | A2 | A3 | A2 | | | b | 1 | 1 | 1 | 0 | 0 | 1 | 1 |
| M755 | A2 | A3 | A2 | | | t | 1 | 1 | 1 | 0 | 0 | 1 | 1 |
| M756 | A2 | A3 | A2 | | | v | 1 | 1 | 1 | 0 | 0 | 1 | 1 |
| M757 | A2 | A3 | A2 | | | d | 1 | 1 | 1 | 0 | 0 | 1 | 1 |
| M758 | A2 | A4 | A2 | | | a | 1 | 1 | 1 | 0 | 0 | 1 | 1 |
| M759 | A2 | A4 | A2 | | | b | 1 | 1 | 1 | 0 | 0 | 1 | 1 |
| M760 | A2 | A5 | A2 | | | a | 1 | 1 | 1 | 0 | 0 | 1 | 1 |
| M761 | A2 | A5 | A2 | | | b | 1 | 1 | 1 | 0 | 0 | 1 | 1 |
| M762 | A2 | A6 | A2 | | | a | 1 | 1 | 1 | 0 | 0 | 1 | 1 |
| M763 | A2 | A6 | A2 | | | b | 1 | 1 | 1 | 0 | 0 | 1 | 1 |
| M764 | A2 | A7 | A2 | | | a | 1 | 1 | 1 | 0 | 0 | 1 | 1 |
| M765 | A2 | A7 | A2 | | | b | 1 | 1 | 1 | 0 | 0 | 1 | 1 |
| M766 | A2 | A8 | A2 | | | ag | 1 | 1 | 1 | 0 | 0 | 1 | 1 |
| M767 | A2 | A8 | A2 | | | b | 1 | 1 | 1 | 0 | 0 | 1 | 1 |
| M768 | A2 | A9 | A2 | | | a | 1 | 1 | 1 | 0 | 0 | 1 | 1 |
| M769 | A2 | A9 | A2 | | | b | 1 | 1 | 1 | 0 | 0 | 1 | 1 |
| M770 | A2 | A9 | A2 | | | w | 1 | 1 | 1 | 0 | 0 | 1 | 1 |
| M771 | A2 | A9 | A2 | | | ae | 1 | 1 | 1 | 0 | 0 | 1 | 1 |
| M772 | A2 | A9 | A2 | | | bb | 1 | 1 | 1 | 0 | 0 | 1 | 1 |
| M773 | A2 | A10 | A2 | | | a | 1 | 1 | 1 | 0 | 0 | 1 | 1 |
| M774 | A2 | A10 | A2 | | | b | 1 | 1 | 1 | 0 | 0 | 1 | 1 |
| M775 | A3 | A1 | A3 | | | a | 1 | 1 | 1 | 0 | 0 | 1 | 1 |
| M776 | A3 | A1 | A3 | | | b | 1 | 1 | 1 | 0 | 0 | 1 | 1 |
| M777 | A3 | A2 | A3 | | | a | 1 | 1 | 1 | 0 | 0 | 1 | 1 |
| M778 | A3 | A2 | A3 | | | b | 1 | 1 | 1 | 0 | 0 | 1 | 1 |
| M779 | A3 | A3 | A3 | | | x | 1 | 1 | 1 | 0 | 0 | 1 | 1 |
| M780 | A3 | A3 | A3 | | | b | 1 | 1 | 1 | 0 | 0 | 1 | 1 |
| M781 | A3 | A3 | A3 | | | t | 1 | 1 | 1 | 0 | 0 | 1 | 1 |
| M782 | A3 | A3 | A3 | | | v | 1 | 1 | 1 | 0 | 0 | 1 | 1 |
| M783 | A3 | A3 | A3 | | | d | 1 | 1 | 1 | 0 | 0 | 1 | 1 |
| M784 | A3 | A4 | A3 | | | a | 1 | 1 | 1 | 0 | 0 | 1 | 1 |
| M785 | A3 | A4 | A3 | | | b | 1 | 1 | 1 | 0 | 0 | 1 | 1 |
| M786 | A3 | A5 | A3 | | | s | 1 | 1 | 1 | 0 | 0 | 1 | 1 |
| M787 | A3 | A5 | A3 | | | b | 1 | 1 | 1 | 0 | 0 | 1 | 1 |
| M788 | A3 | A6 | A3 | | | a | 1 | 1 | 1 | 0 | 0 | 1 | 1 |
| M789 | A3 | A6 | A3 | | | b | 1 | 1 | 1 | 0 | 0 | 1 | 1 |
| M790 | A3 | A7 | A3 | | | a | 1 | 1 | 1 | 0 | 0 | 1 | 1 |
| M791 | A3 | A7 | A3 | | | j | 1 | 1 | 1 | 0 | 0 | 1 | 1 |
| M792 | A3 | A8 | A3 | | | a | 1 | 1 | 1 | 0 | 0 | 1 | 1 |
| M793 | A3 | A8 | A3 | | | b | 1 | 1 | 1 | 0 | 0 | 1 | 1 |
| M794 | A3 | A9 | A3 | | | d | 1 | 1 | 1 | 0 | 0 | 1 | 1 |
| M795 | A3 | A9 | A3 | | | b | 1 | 1 | 1 | 0 | 0 | 1 | 1 |
| M796 | A3 | A9 | A3 | | | w | 1 | 1 | 1 | 0 | 0 | 1 | 1 |
| M797 | A3 | A9 | A3 | | | ae | 1 | 1 | 1 | 0 | 0 | 1 | 1 |
| M798 | A3 | A9 | A3 | | | bb | 1 | 1 | 1 | 0 | 0 | 1 | 1 |
| M799 | A3 | A10 | A3 | | | am | 1 | 1 | 1 | 0 | 0 | 1 | 1 |
| M800 | A3 | A10 | A3 | | | b | 1 | 1 | 1 | 0 | 0 | 1 | 1 |
| M801 | A4 | A1 | A4 | | | an | 1 | 1 | 1 | 0 | 0 | 1 | 1 |
| M802 | A4 | A1 | A4 | | | b | 1 | 1 | 1 | 0 | 0 | 1 | 1 |
| M803 | A4 | A2 | A4 | | | as | 1 | 1 | 1 | 0 | 0 | 1 | 1 |
| M804 | A4 | A2 | A4 | | | b | 1 | 1 | 1 | 0 | 0 | 1 | 1 |
| M805 | A4 | A3 | A4 | | | x | 1 | 1 | 1 | 0 | 0 | 1 | 1 |
| M806 | A4 | A3 | A4 | | | b | 1 | 1 | 1 | 0 | 0 | 1 | 1 |
| M807 | A4 | A3 | A4 | | | t | 1 | 1 | 1 | 0 | 0 | 1 | 1 |
| M808 | A4 | A3 | A4 | | | v | 1 | 1 | 1 | 0 | 0 | 1 | 1 |
| M809 | A4 | A3 | A4 | | | d | 1 | 1 | 1 | 0 | 0 | 1 | 1 |
| M810 | A4 | A4 | A4 | | | au | 1 | 1 | 1 | 0 | 0 | 1 | 1 |

-continued

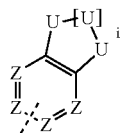

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M811 | A4 | A4 | A4 | | | b | 1 | 1 | 1 | 0 | 0 | 1 | 1 |
| M812 | A4 | A5 | A4 | | | s | 1 | 1 | 1 | 0 | 0 | 1 | 1 |
| M813 | A4 | A5 | A4 | | | b | 1 | 1 | 1 | 0 | 0 | 1 | 1 |
| M814 | A4 | A6 | A4 | | | a | 1 | 1 | 1 | 0 | 0 | 1 | 1 |
| M815 | A4 | A6 | A4 | | | b | 1 | 1 | 1 | 0 | 0 | 1 | 1 |
| M816 | A4 | A7 | A4 | | | a | 1 | 1 | 1 | 0 | 0 | 1 | 1 |
| M817 | A4 | A7 | A4 | | | j | 1 | 1 | 1 | 0 | 0 | 1 | 1 |
| M818 | A4 | A8 | A4 | | | a | 1 | 1 | 1 | 0 | 0 | 1 | 1 |
| M819 | A4 | A8 | A4 | | | b | 1 | 1 | 1 | 0 | 0 | 1 | 1 |
| M820 | A4 | A9 | A4 | | | d | 1 | 1 | 1 | 0 | 0 | 1 | 1 |
| M821 | A4 | A9 | A4 | | | b | 1 | 1 | 1 | 0 | 0 | 1 | 1 |
| M822 | A4 | A9 | A4 | | | w | 1 | 1 | 1 | 0 | 0 | 1 | 1 |
| M823 | A4 | A9 | A4 | | | ae | 1 | 1 | 1 | 0 | 0 | 1 | 1 |
| M824 | A4 | A9 | A4 | | | bb | 1 | 1 | 1 | 0 | 0 | 1 | 1 |
| M825 | A4 | A10 | A4 | | | am | 1 | 1 | 1 | 0 | 0 | 1 | 1 |
| M826 | A4 | A10 | A4 | | | b | 1 | 1 | 1 | 0 | 0 | 1 | 1 |
| M827 | A5 | A1 | A5 | | | an | 1 | 1 | 1 | 0 | 0 | 1 | 1 |
| M828 | A5 | A1 | A5 | | | b | 1 | 1 | 1 | 0 | 0 | 1 | 1 |
| M829 | A5 | A2 | A5 | | | as | 1 | 1 | 1 | 0 | 0 | 1 | 1 |
| M830 | A5 | A2 | A5 | | | b | 1 | 1 | 1 | 0 | 0 | 1 | 1 |
| M831 | A5 | A3 | A5 | | | x | 1 | 1 | 1 | 0 | 0 | 1 | 1 |
| M832 | A5 | A3 | A5 | | | b | 1 | 1 | 1 | 0 | 0 | 1 | 1 |
| M833 | A5 | A3 | A5 | | | t | 1 | 1 | 1 | 0 | 0 | 1 | 1 |
| M834 | A5 | A3 | A5 | | | v | 1 | 1 | 1 | 0 | 0 | 1 | 1 |
| M835 | A5 | A3 | A5 | | | d | 1 | 1 | 1 | 0 | 0 | 1 | 1 |
| M836 | A5 | A4 | A5 | | | au | 1 | 1 | 1 | 0 | 0 | 1 | 1 |
| M837 | A5 | A4 | A5 | | | b | 1 | 1 | 1 | 0 | 0 | 1 | 1 |
| M838 | A5 | A5 | A5 | | | s | 1 | 1 | 1 | 0 | 0 | 1 | 1 |
| M839 | A5 | A5 | A5 | | | b | 1 | 1 | 1 | 0 | 0 | 1 | 1 |
| M840 | A5 | A6 | A5 | | | a | 1 | 1 | 1 | 0 | 0 | 1 | 1 |
| M841 | A5 | A6 | A5 | | | b | 1 | 1 | 1 | 0 | 0 | 1 | 1 |
| M842 | A5 | A7 | A5 | | | a | 1 | 1 | 1 | 0 | 0 | 1 | 1 |
| M843 | A5 | A7 | A5 | | | j | 1 | 1 | 1 | 0 | 0 | 1 | 1 |
| M844 | A5 | A8 | A5 | | | a | 1 | 1 | 1 | 0 | 0 | 1 | 1 |
| M845 | A5 | A8 | A5 | | | b | 1 | 1 | 1 | 0 | 0 | 1 | 1 |
| M846 | A5 | A9 | A5 | | | d | 1 | 1 | 1 | 0 | 0 | 1 | 1 |
| M847 | A5 | A9 | A5 | | | b | 1 | 1 | 1 | 0 | 0 | 1 | 1 |
| M848 | A5 | A9 | A5 | | | w | 1 | 1 | 1 | 0 | 0 | 1 | 1 |
| M849 | A5 | A9 | A5 | | | ae | 1 | 1 | 1 | 0 | 0 | 1 | 1 |
| M850 | A5 | A9 | A5 | | | bb | 1 | 1 | 1 | 0 | 0 | 1 | 1 |
| M851 | A5 | A10 | A5 | | | am | 1 | 1 | 1 | 0 | 0 | 1 | 1 |
| M852 | A5 | A10 | A5 | | | b | 1 | 1 | 1 | 0 | 0 | 1 | 1 |
| M853 | A6 | A1 | A6 | | | an | 1 | 1 | 1 | 0 | 0 | 1 | 1 |
| M854 | A6 | A1 | A6 | | | b | 1 | 1 | 1 | 0 | 0 | 1 | 1 |
| M855 | A6 | A2 | A6 | | | as | 1 | 1 | 1 | 0 | 0 | 1 | 1 |
| M856 | A6 | A2 | A6 | | | b | 1 | 1 | 1 | 0 | 0 | 1 | 1 |
| M857 | A6 | A3 | A6 | | | x | 1 | 1 | 1 | 0 | 0 | 1 | 1 |
| M858 | A6 | A3 | A6 | | | b | 1 | 1 | 1 | 0 | 0 | 1 | 1 |
| M859 | A6 | A3 | A6 | | | t | 1 | 1 | 1 | 0 | 0 | 1 | 1 |
| M860 | A6 | A3 | A6 | | | v | 1 | 1 | 1 | 0 | 0 | 1 | 1 |
| M861 | A6 | A3 | A6 | | | d | 1 | 1 | 1 | 0 | 0 | 1 | 1 |
| M862 | A6 | A4 | A6 | | | au | 1 | 1 | 1 | 0 | 0 | 1 | 1 |
| M863 | A6 | A4 | A6 | | | b | 1 | 1 | 1 | 0 | 0 | 1 | 1 |
| M864 | A6 | A5 | A6 | | | s | 1 | 1 | 1 | 0 | 0 | 1 | 1 |
| M865 | A6 | A5 | A6 | | | b | 1 | 1 | 1 | 0 | 0 | 1 | 1 |
| M866 | A6 | A6 | A6 | | | a | 1 | 1 | 1 | 0 | 0 | 1 | 1 |
| M867 | A6 | A6 | A6 | | | b | 1 | 1 | 1 | 0 | 0 | 1 | 1 |
| M868 | A6 | A7 | A6 | | | a | 1 | 1 | 1 | 0 | 0 | 1 | 1 |
| M869 | A6 | A7 | A6 | | | j | 1 | 1 | 1 | 0 | 0 | 1 | 1 |
| M870 | A6 | A8 | A6 | | | a | 1 | 1 | 1 | 0 | 0 | 1 | 1 |
| M871 | A6 | A8 | A6 | | | b | 1 | 1 | 1 | 0 | 0 | 1 | 1 |
| M872 | A6 | A9 | A6 | | | d | 1 | 1 | 1 | 0 | 0 | 1 | 1 |
| M873 | A6 | A9 | A6 | | | b | 1 | 1 | 1 | 0 | 0 | 1 | 1 |
| M874 | A6 | A9 | A6 | | | w | 1 | 1 | 1 | 0 | 0 | 1 | 1 |
| M875 | A6 | A9 | A6 | | | ae | 1 | 1 | 1 | 0 | 0 | 1 | 1 |
| M876 | A6 | A9 | A6 | | | bb | 1 | 1 | 1 | 0 | 0 | 1 | 1 |
| M877 | A6 | A10 | A6 | | | am | 1 | 1 | 1 | 0 | 0 | 1 | 1 |
| M878 | A6 | A10 | A6 | | | b | 1 | 1 | 1 | 0 | 0 | 1 | 1 |
| M879 | A7 | A1 | A7 | | | c | 1 | 1 | 1 | 0 | 0 | 1 | 1 |

-continued

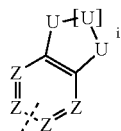

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M880 | A7 | A1 | A7 | | | b | 1 | 1 | 1 | 0 | 0 | 1 | 1 |
| M881 | A7 | A2 | A7 | | | l | 1 | 1 | 1 | 0 | 0 | 1 | 1 |
| M882 | A7 | A2 | A7 | | | b | 1 | 1 | 1 | 0 | 0 | 1 | 1 |
| M883 | A7 | A3 | A7 | | | s | 1 | 1 | 1 | 0 | 0 | 1 | 1 |
| M884 | A7 | A3 | A7 | | | b | 1 | 1 | 1 | 0 | 0 | 1 | 1 |
| M885 | A7 | A3 | A7 | | | r | 1 | 1 | 1 | 0 | 0 | 1 | 1 |
| M886 | A7 | A3 | A7 | | | v | 1 | 1 | 1 | 0 | 0 | 1 | 1 |
| M887 | A7 | A3 | A7 | | | d | 1 | 1 | 1 | 0 | 0 | 1 | 1 |
| M888 | A7 | A4 | A7 | | | aa | 1 | 1 | 1 | 0 | 0 | 1 | 1 |
| M889 | A7 | A4 | A7 | | | b | 1 | 1 | 1 | 0 | 0 | 1 | 1 |
| M890 | A7 | A5 | A7 | | | ad | 1 | 1 | 1 | 0 | 0 | 1 | 1 |
| M891 | A7 | A5 | A7 | | | b | 1 | 1 | 1 | 0 | 0 | 1 | 1 |
| M892 | A7 | A6 | A7 | | | aq | 1 | 1 | 1 | 0 | 0 | 1 | 1 |
| M893 | A7 | A6 | A7 | | | b | 1 | 1 | 1 | 0 | 0 | 1 | 1 |
| M894 | A7 | A7 | A7 | | | a | 1 | 1 | 1 | 0 | 0 | 1 | 1 |
| M895 | A7 | A7 | A7 | | | j | 1 | 1 | 1 | 0 | 0 | 1 | 1 |
| M896 | A7 | A8 | A7 | | | a | 1 | 1 | 1 | 0 | 0 | 1 | 1 |
| M897 | A7 | A8 | A7 | | | b | 1 | 1 | 1 | 0 | 0 | 1 | 1 |
| M898 | A7 | A9 | A7 | | | d | 1 | 1 | 1 | 0 | 0 | 1 | 1 |
| M899 | A7 | A9 | A7 | | | b | 1 | 1 | 1 | 0 | 0 | 1 | 1 |
| M900 | A7 | A9 | A7 | | | w | 1 | 1 | 1 | 0 | 0 | 1 | 1 |
| M901 | A7 | A9 | A7 | | | ae | 1 | 1 | 1 | 0 | 0 | 1 | 1 |
| M902 | A7 | A9 | A7 | | | bb | 1 | 1 | 1 | 0 | 0 | 1 | 1 |
| M903 | A7 | A10 | A7 | | | am | 1 | 1 | 1 | 0 | 0 | 1 | 1 |
| M904 | A7 | A10 | A7 | | | b | 1 | 1 | 1 | 0 | 0 | 1 | 1 |
| M905 | A8 | A1 | A8 | | | av | 1 | 1 | 1 | 0 | 0 | 1 | 1 |
| M906 | A8 | A1 | A8 | | | b | 1 | 1 | 1 | 0 | 0 | 1 | 1 |
| M907 | A8 | A2 | A8 | | | az | 1 | 1 | 1 | 0 | 0 | 1 | 1 |
| M908 | A8 | A2 | A8 | | | b | 1 | 1 | 1 | 0 | 0 | 1 | 1 |
| M909 | A8 | A3 | A8 | | | al | 1 | 1 | 1 | 0 | 0 | 1 | 1 |
| M910 | A8 | A3 | A8 | | | b | 1 | 1 | 1 | 0 | 0 | 1 | 1 |
| M911 | A8 | A3 | A8 | | | t | 1 | 1 | 1 | 0 | 0 | 1 | 1 |
| M912 | A8 | A3 | A8 | | | v | 1 | 1 | 1 | 0 | 0 | 1 | 1 |
| M913 | A8 | A3 | A8 | | | d | 1 | 1 | 1 | 0 | 0 | 1 | 1 |
| M914 | A8 | A4 | A8 | | | au | 1 | 1 | 1 | 0 | 0 | 1 | 1 |
| M915 | A8 | A4 | A8 | | | b | 1 | 1 | 1 | 0 | 0 | 1 | 1 |
| M916 | A8 | A5 | A8 | | | bb | 1 | 1 | 1 | 0 | 0 | 1 | 1 |
| M917 | A8 | A5 | A8 | | | b | 1 | 1 | 1 | 0 | 0 | 1 | 1 |
| M918 | A8 | A6 | A8 | | | bd | 1 | 1 | 1 | 0 | 0 | 1 | 1 |
| M919 | A8 | A6 | A8 | | | b | 1 | 1 | 1 | 0 | 0 | 1 | 1 |
| M920 | A8 | A7 | A8 | | | a | 1 | 1 | 1 | 0 | 0 | 1 | 1 |
| M921 | A8 | A7 | A8 | | | bc | 1 | 1 | 1 | 0 | 0 | 1 | 1 |
| M922 | A8 | A8 | A8 | | | a | 1 | 1 | 1 | 0 | 0 | 1 | 1 |
| M923 | A8 | A8 | A8 | | | b | 1 | 1 | 1 | 0 | 0 | 1 | 1 |
| M924 | A8 | A9 | A8 | | | d | 1 | 1 | 1 | 0 | 0 | 1 | 1 |
| M925 | A8 | A9 | A8 | | | b | 1 | 1 | 1 | 0 | 0 | 1 | 1 |
| M926 | A8 | A9 | A8 | | | w | 1 | 1 | 1 | 0 | 0 | 1 | 1 |
| M927 | A8 | A9 | A8 | | | ae | 1 | 1 | 1 | 0 | 0 | 1 | 1 |
| M928 | A8 | A9 | A8 | | | bb | 1 | 1 | 1 | 0 | 0 | 1 | 1 |
| M929 | A8 | A10 | A8 | | | am | 1 | 1 | 1 | 0 | 0 | 1 | 1 |
| M930 | A8 | A10 | A8 | | | b | 1 | 1 | 1 | 0 | 0 | 1 | 1 |
| M931 | A9 | A1 | A9 | | | an | 1 | 1 | 1 | 0 | 0 | 1 | 1 |
| M932 | A9 | A1 | A9 | | | b | 1 | 1 | 1 | 0 | 0 | 1 | 1 |
| M933 | A9 | A2 | A9 | | | as | 1 | 1 | 1 | 0 | 0 | 1 | 1 |
| M934 | A9 | A2 | A9 | | | b | 1 | 1 | 1 | 0 | 0 | 1 | 1 |
| M935 | A9 | A3 | A9 | | | x | 1 | 1 | 1 | 0 | 0 | 1 | 1 |
| M936 | A9 | A3 | A9 | | | b | 1 | 1 | 1 | 0 | 0 | 1 | 1 |
| M937 | A9 | A3 | A9 | | | t | 1 | 1 | 1 | 0 | 0 | 1 | 1 |
| M938 | A9 | A3 | A9 | | | v | 1 | 1 | 1 | 0 | 0 | 1 | 1 |
| M939 | A9 | A3 | A9 | | | d | 1 | 1 | 1 | 0 | 0 | 1 | 1 |
| M940 | A9 | A4 | A9 | | | au | 1 | 1 | 1 | 0 | 0 | 1 | 1 |
| M941 | A9 | A4 | A9 | | | b | 1 | 1 | 1 | 0 | 0 | 1 | 1 |
| M942 | A9 | A5 | A9 | | | s | 1 | 1 | 1 | 0 | 0 | 1 | 1 |
| M943 | A9 | A5 | A9 | | | b | 1 | 1 | 1 | 0 | 0 | 1 | 1 |
| M944 | A9 | A6 | A9 | | | a | 1 | 1 | 1 | 0 | 0 | 1 | 1 |
| M945 | A9 | A6 | A9 | | | b | 1 | 1 | 1 | 0 | 0 | 1 | 1 |
| M946 | A9 | A7 | A9 | | | a | 1 | 1 | 1 | 0 | 0 | 1 | 1 |
| M947 | A9 | A7 | A9 | | | j | 1 | 1 | 1 | 0 | 0 | 1 | 1 |
| M948 | A9 | A8 | A9 | | | a | 1 | 1 | 1 | 0 | 0 | 1 | 1 |

-continued

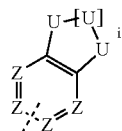

| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M949 | A9 | A8 | A9 | | | b | 1 | 1 | 1 | 0 | 0 | 1 | 1 |
| M950 | A9 | A9 | A9 | | | d | 1 | 1 | 1 | 0 | 0 | 1 | 1 |
| M951 | A9 | A9 | A9 | | | b | 1 | 1 | 1 | 0 | 0 | 1 | 1 |
| M952 | A9 | A9 | A9 | | | w | 1 | 1 | 1 | 0 | 0 | 1 | 1 |
| M953 | A9 | A9 | A9 | | | ae | 1 | 1 | 1 | 0 | 0 | 1 | 1 |
| M954 | A9 | A9 | A9 | | | bb | 1 | 1 | 1 | 0 | 0 | 1 | 1 |
| M955 | A9 | A10 | A9 | | | am | 1 | 1 | 1 | 0 | 0 | 1 | 1 |
| M956 | A9 | A10 | A9 | | | b | 1 | 1 | 1 | 0 | 0 | 1 | 1 |
| M957 | A10 | A1 | A10 | | | b | 1 | 1 | 1 | 0 | 0 | 1 | 1 |
| M958 | A1 | A1 | A2 | | | b | 1 | 1 | 1 | 0 | 0 | 1 | 1 |
| M959 | A2 | A3 | A3 | | | b | 1 | 1 | 1 | 0 | 0 | 1 | 1 |
| M960 | A1 | A3 | A1 | | | b | 2 | 1 | 2 | 0 | 0 | 1 | 1 |
| M961 | A1 | A8 | A1 | | | b | 2 | 1 | 2 | 0 | 0 | 1 | 1 |
| M962 | A1 | A1 | A1 | A1 | A1 | b | 1 | 1 | 1 | 1 | 1 | 1 | 1 |
| M963 | A1 | A2 | A1 | A1 | A1 | b | 1 | 1 | 1 | 1 | 1 | 1 | 1 |
| M964 | A1 | A3 | A1 | A1 | A1 | b | 1 | 1 | 1 | 1 | 1 | 1 | 1 |
| M965 | A1 | A3 | A1 | A1 | A1 | b | 2 | 1 | 2 | 1 | 1 | 1 | 1 |
| M966 | A1 | A3 | A1 | A1 | A1 | v | 1 | 1 | 1 | 1 | 1 | 1 | 1 |
| M967 | A1 | A8 | A1 | A1 | A1 | b | 1 | 1 | 1 | 1 | 1 | 1 | 1 |
| M968 | A1 | A9 | A1 | A1 | A1 | b | 1 | 1 | 1 | 1 | 1 | 1 | 1 |
| M969 | A1 | A1 | A1 | A2 | A2 | b | 1 | 1 | 1 | 1 | 1 | 1 | 1 |
| M970 | A1 | A2 | A1 | A2 | A2 | b | 1 | 1 | 1 | 1 | 1 | 1 | 1 |
| M971 | A1 | A3 | A1 | A2 | A2 | b | 3 | 1 | 3 | 1 | 1 | 1 | 1 |
| M972 | A1 | A3 | A1 | A3 | A3 | b | 1 | 1 | 1 | 1 | 1 | 1 | 1 |
| M973 | A1 | A10 | A1 | A1 | A1 | b | 1 | 1 | 1 | 1 | 1 | 1 | 1 |
| M974 | A1 | A3 | A1 | A1 | A1 | b | 1 | 1 | 1 | 1 | 1 | 2 | 2 |
| M975 | A1 | A3 | A1 | A1 | A1 | t | 1 | 1 | 1 | 1 | 1 | 2 | 2 |
| M976 | A1 | A10 | A1 | A1 | A1 | b | 1 | 1 | 1 | 1 | 1 | 2 | 2 |
| M977 | A2 | A2 | A2 | A2 | A2 | b | 1 | 1 | 1 | 1 | 1 | 1 | 1 |
| M978 | A2 | A1 | A2 | A2 | A2 | b | 1 | 1 | 1 | 1 | 1 | 1 | 1 |
| M979 | A2 | A1 | A2 | A1 | A1 | b | 1 | 1 | 1 | 1 | 1 | 1 | 1 |
| M980 | A2 | A3 | A2 | A1 | A1 | b | 1 | 1 | 1 | 1 | 1 | 1 | 1 |
| M981 | A2 | A8 | A2 | A1 | A1 | b | 1 | 1 | 1 | 1 | 1 | 1 | 1 |
| M982 | A2 | A9 | A2 | A1 | A1 | b | 1 | 1 | 1 | 1 | 1 | 1 | 1 |
| M983 | A2 | A10 | A2 | A1 | A1 | b | 1 | 1 | 1 | 1 | 1 | 1 | 1 |
| M984 | A2 | A3 | A2 | A1 | A1 | b | 1 | 1 | 1 | 1 | 1 | 2 | 2 |
| M985 | A2 | A6 | A2 | A2 | A2 | t | 1 | 1 | 1 | 1 | 1 | 1 | 1 |
| M986 | A3 | A3 | A3 | A3 | A3 | v | 1 | 1 | 1 | 1 | 1 | 1 | 1 |
| M987 | A3 | A2 | A3 | A3 | A3 | b | 1 | 1 | 1 | 1 | 1 | 1 | 1 |
| M988 | A3 | A2 | A3 | A1 | A1 | c | 1 | 1 | 1 | 1 | 1 | 1 | 1 |
| M989 | A3 | A2 | A3 | A3 | A1 | u | 1 | 1 | 1 | 1 | 1 | 1 | 1 |
| M990 | A3 | A2 | A1 | A1 | A1 | b | 1 | 1 | 1 | 1 | 1 | 1 | 1 |
| M991 | A3 | A7 | A3 | A1 | A1 | s | 1 | 1 | 1 | 1 | 1 | 1 | 1 |
| M992 | A3 | A5 | A3 | A1 | A1 | t | 1 | 1 | 1 | 1 | 1 | 1 | 1 |
| M993 | A3 | A10 | A3 | A1 | A1 | b | 1 | 1 | 1 | 1 | 1 | 1 | 1 |
| M994 | A4 | A4 | A4 | A4 | A4 | bc | 1 | 1 | 1 | 1 | 1 | 1 | 1 |
| M995 | A4 | A2 | A4 | A1 | A1 | b | 1 | 1 | 1 | 1 | 1 | 1 | 1 |
| M996 | A6 | A6 | A6 | A6 | A6 | bd | 1 | 1 | 1 | 1 | 1 | 1 | 1 |
| M997 | A6 | A3 | A6 | A1 | A1 | a | 1 | 1 | 1 | 1 | 1 | 2 | 2 |
| M998 | A8 | A2 | A8 | A1 | A1 | b | 1 | 1 | 1 | 1 | 1 | 2 | 2 |
| M999 | A9 | A7 | A9 | A2 | A2 | am | 1 | 1 | 1 | 1 | 1 | 1 | 1 |
| M1000 | A10 | A2 | A1 | A1 | A1 | u | 1 | 1 | 1 | 1 | 1 | 1 | 1 |
| M1001 | | | | A1 | | b | 0 | 0 | 0 | 1 | 0 | 1 | 0 |
| M1002 | | | | A1 | | t | 0 | 0 | 0 | 1 | 0 | 1 | 0 |
| M1003 | | | | A1 | | v | 0 | 0 | 0 | 1 | 0 | 1 | 0 |
| M1004 | | | | A1 | | am | 0 | 0 | 0 | 1 | 0 | 1 | 0 |
| M1005 | | | | A1 | | as | 0 | 0 | 0 | 1 | 0 | 1 | 0 |
| M1006 | | | | A1 | | m | 0 | 0 | 0 | 1 | 0 | 1 | 0 |
| M1007 | | | | A1 | | b | 0 | 0 | 0 | 1 | 0 | 2 | 0 |
| M1008 | | | | A2 | | a | 0 | 0 | 0 | 1 | 0 | 1 | 0 |
| M1009 | | | | A3 | | s | 0 | 0 | 0 | 1 | 0 | 2 | 0 |
| M1010 | | | | A4 | | a | 0 | 0 | 0 | 1 | 0 | 1 | 0 |
| M1011 | | | | A5 | | b | 0 | 0 | 0 | 1 | 0 | 2 | 0 |
| M1012 | | | | A6 | | b | 0 | 0 | 0 | 1 | 0 | 1 | 0 |
| M1013 | | | | A7 | | w | 0 | 0 | 0 | 1 | 0 | 2 | 0 |
| M1014 | | | | A8 | | t | 0 | 0 | 0 | 1 | 0 | 1 | 0 |
| M1015 | | | | A9 | | c | 0 | 0 | 0 | 1 | 0 | 2 | 0 |
| M1016 | | A1 | | A1 | A1 | b | 0 | 1 | 0 | 1 | 1 | 1 | 1 |
| M1017 | | A1 | | A1 | A1 | b | 0 | 1 | 0 | 1 | 1 | 2 | 2 |

-continued
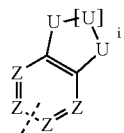
| Structural unit | Ar¹ | Ar² | Ar³ | Ar⁴ | Ar⁵ | corresponds to formula | m | n | o | p | q | r | s |
|---|---|---|---|---|---|---|---|---|---|---|---|---|---|
| M1018 |  | A3 |  | A1 | A1 | b | 0 | 1 | 0 | 1 | 1 | 1 | 1 |
| M1019 |  | A10 |  | A1 | A1 | b | 0 | 1 | 0 | 1 | 1 | 1 | 1 |
| M1020 |  | A3 |  | A2 | A2 | b | 0 | 1 | 0 | 1 | 1 | 1 | 1 |
| M1021 |  | A1 |  |  |  |  | 0 | 1 | 0 | 0 | 0 | 1 | 1 |
| M1022 |  | A2 |  |  |  |  | 0 | 1 | 0 | 0 | 0 | 1 | 1 |
| M1023 |  | A3 |  |  |  |  | 0 | 1 | 0 | 0 | 0 | 1 | 1 |
| M1024 |  | A4 |  |  |  |  | 0 | 1 | 0 | 0 | 0 | 1 | 1 |
| M1025 |  | A5 |  |  |  |  | 0 | 1 | 0 | 0 | 0 | 1 | 1 |
| M1026 |  | A6 |  |  |  |  | 0 | 1 | 0 | 0 | 0 | 1 | 1 |
| M1027 |  | A7 |  |  |  |  | 0 | 1 | 0 | 0 | 0 | 1 | 1 |
| M1028 |  | A8 |  |  |  |  | 0 | 1 | 0 | 0 | 0 | 1 | 1 |
| M1029 |  | A9 |  |  |  |  | 0 | 1 | 0 | 0 | 0 | 1 | 1 |
| M1030 |  | A10 |  |  |  |  | 0 | 1 | 0 | 0 | 0 | 1 | 1 |
Preferred specific embodiments of the structural units of the formula (I) are shown in the following table:
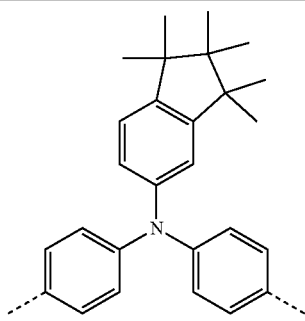
(1)
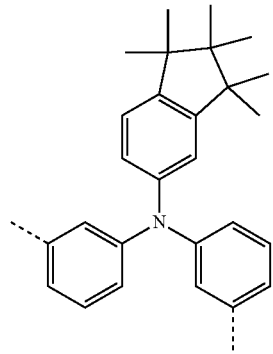
(2)
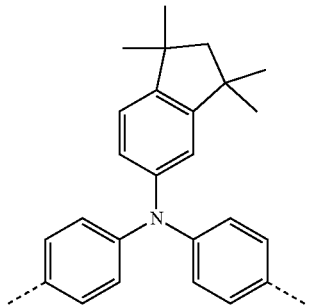
(3)

-continued
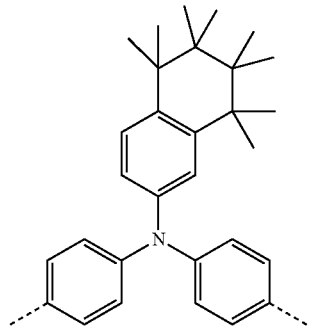
(4)
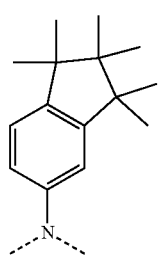
(5)
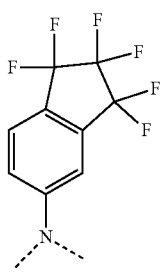
(6)
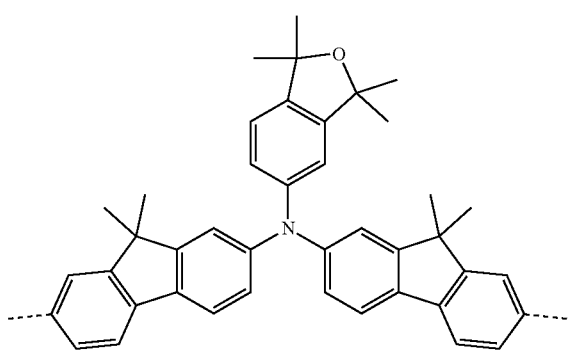
(7)
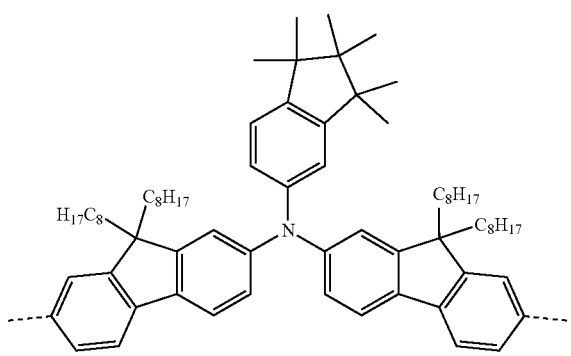
(8)

-continued
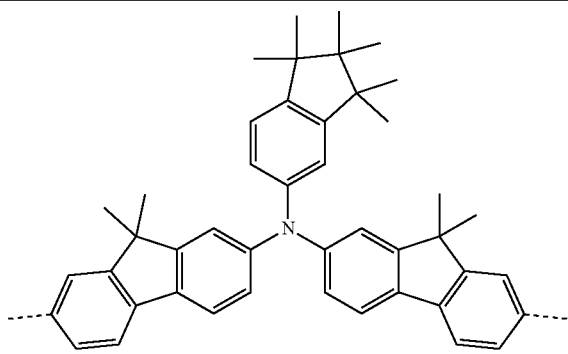
(9)
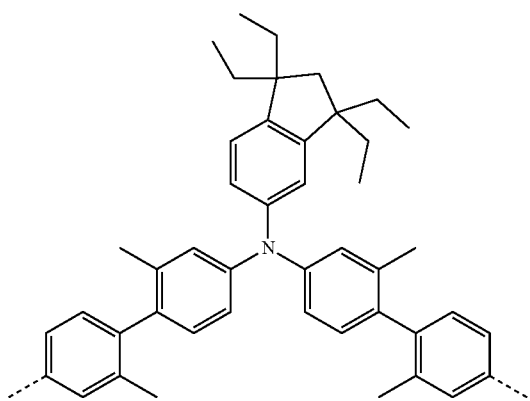
(10)
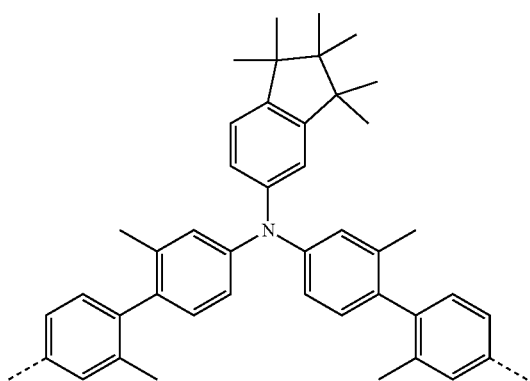
(11)
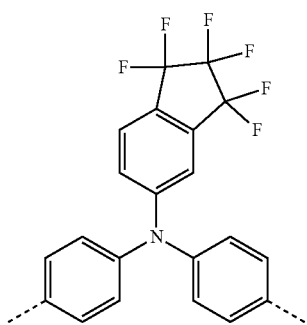
(12)

-continued
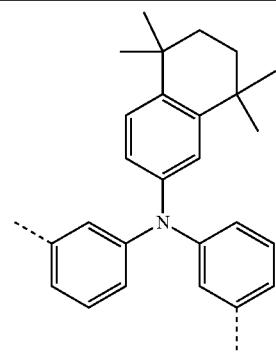
(13)
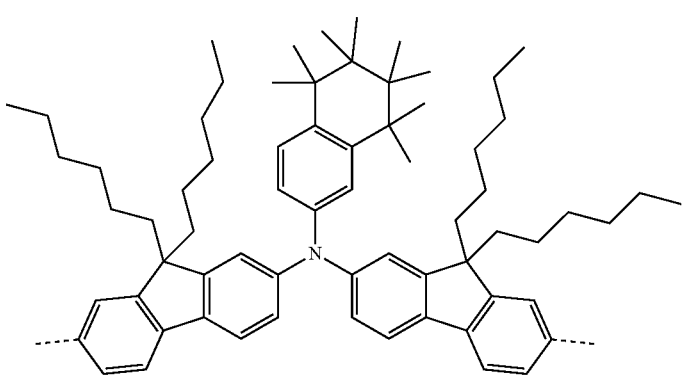
(14)
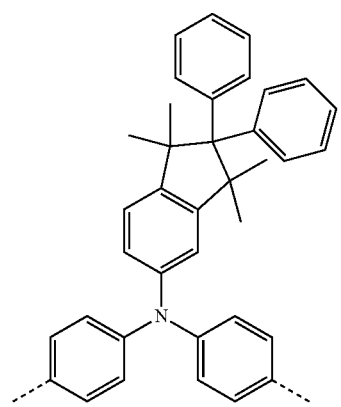
(15)
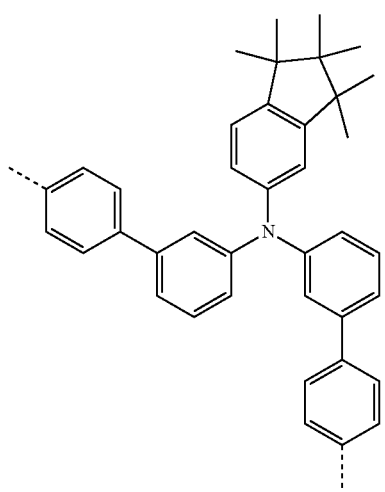
(16)

(17)
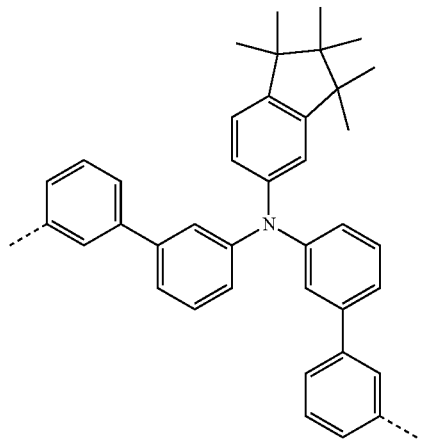
(18)
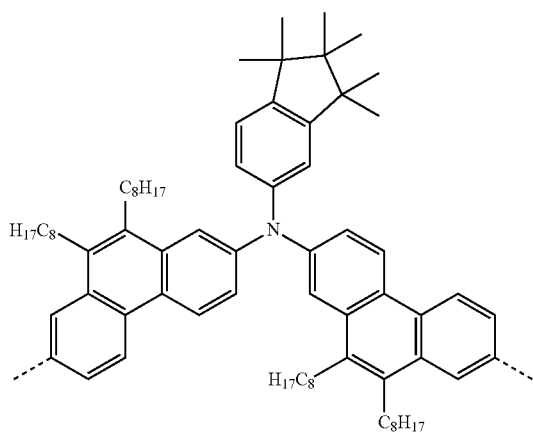
(19)
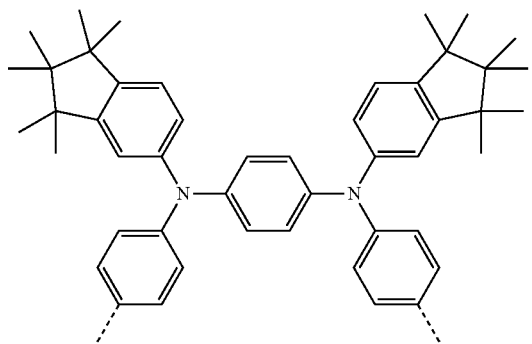
(20)
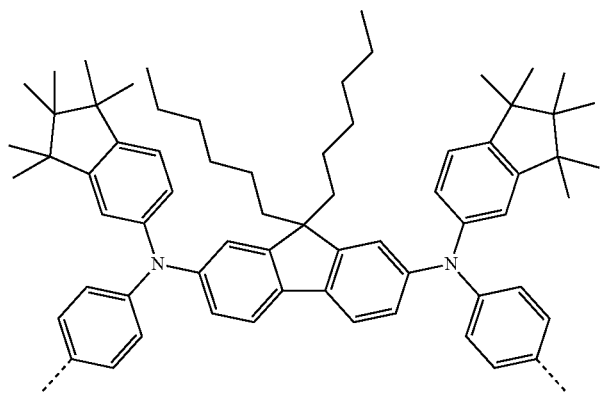

(21)
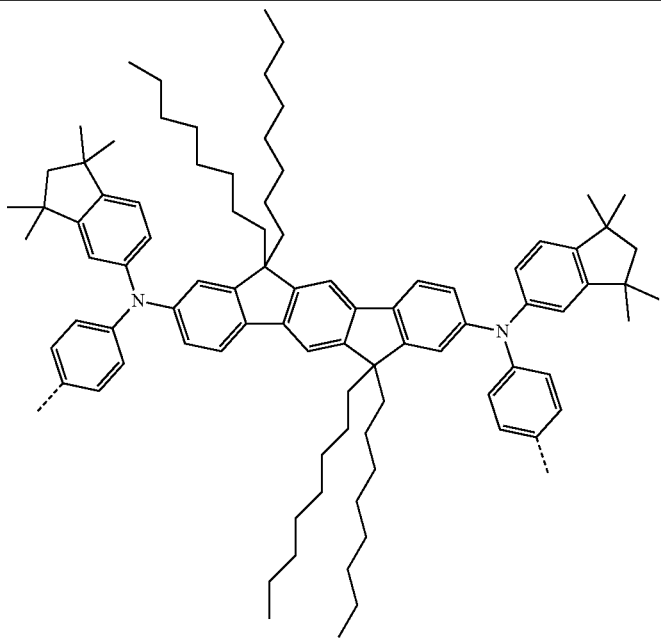
(22)
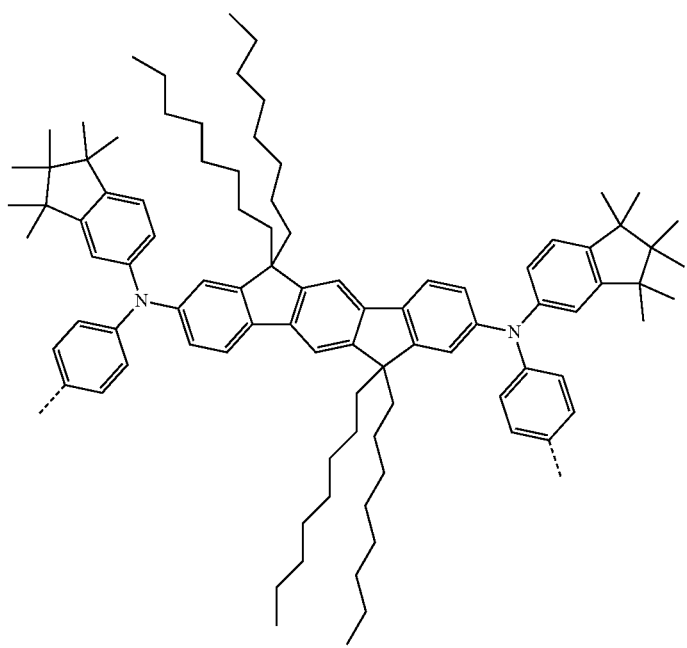

-continued
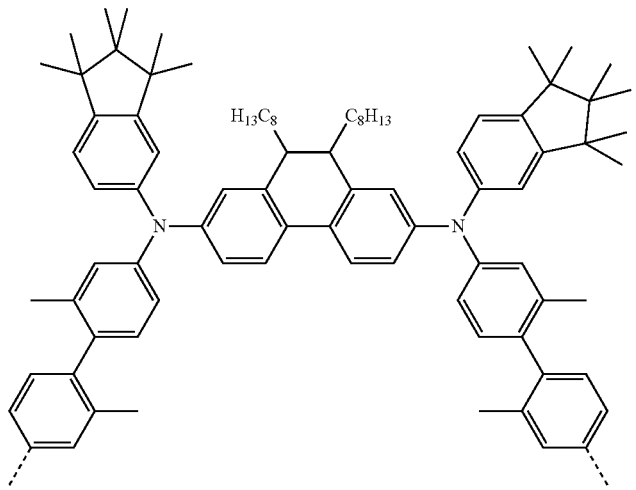
(23)
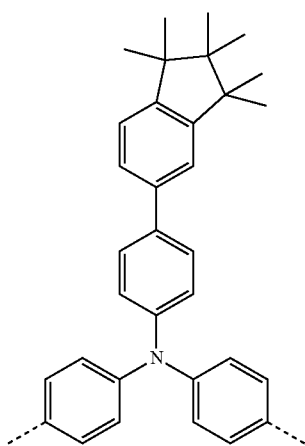
(24)
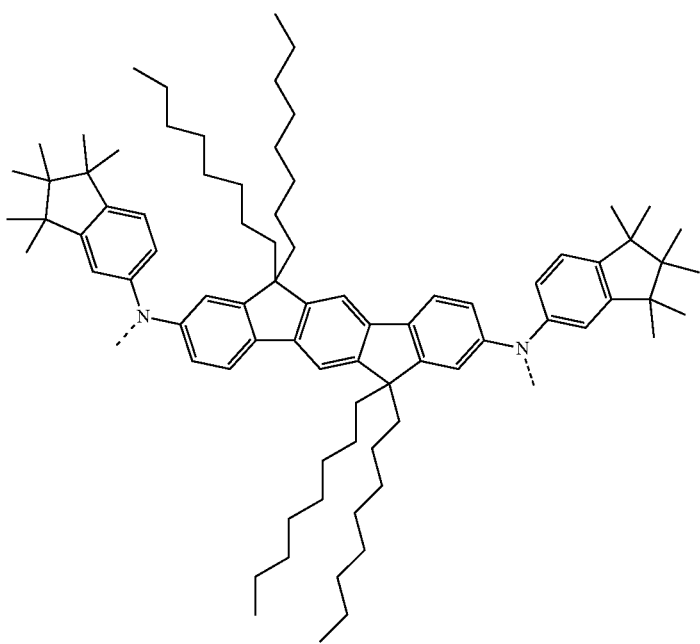
(25)

-continued
(26)
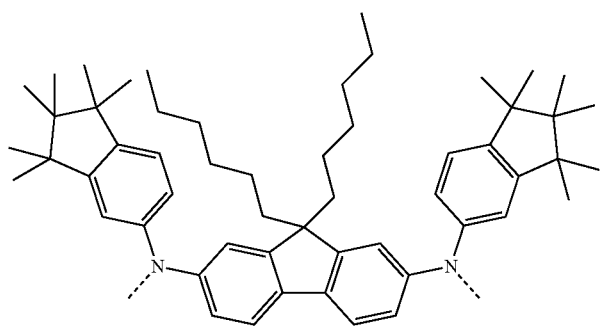
(27)
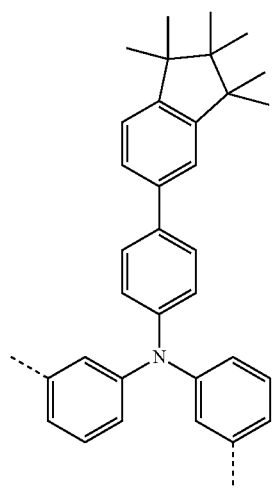
(28)
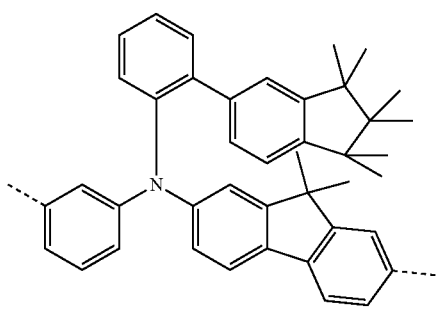
(29)
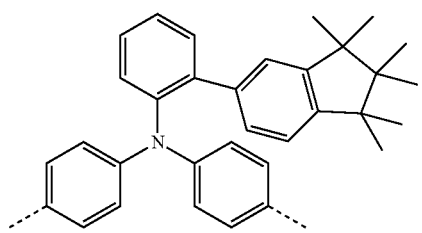

-continued
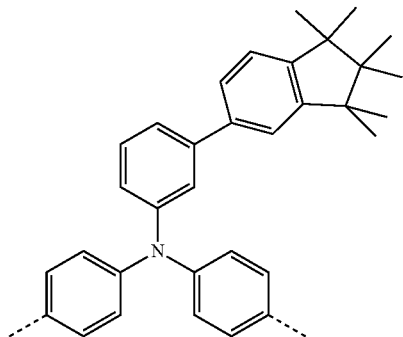
(30)
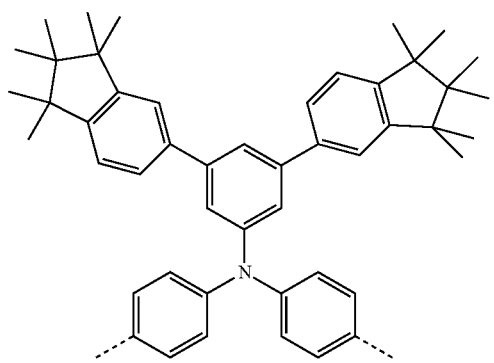
(31)
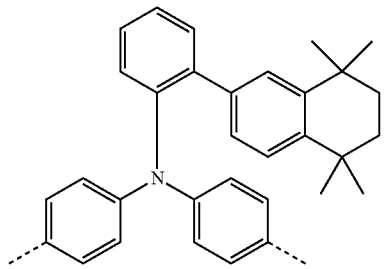
(32)
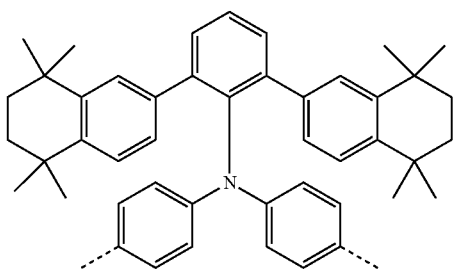
(33)
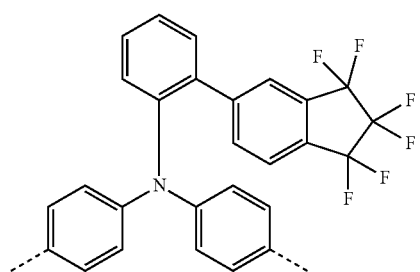
(34)

-continued
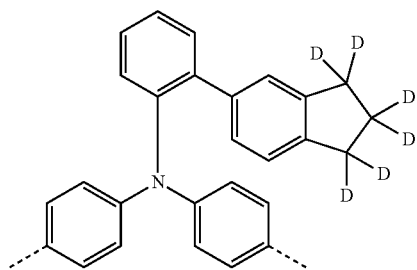
(35)
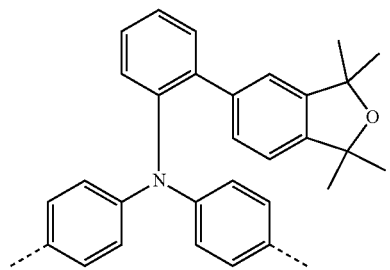
(36)
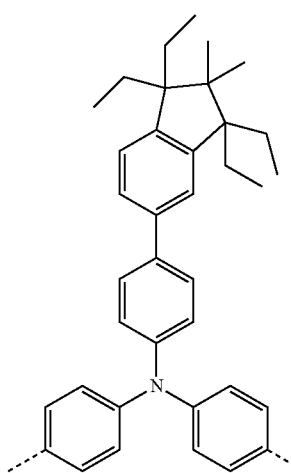
(37)
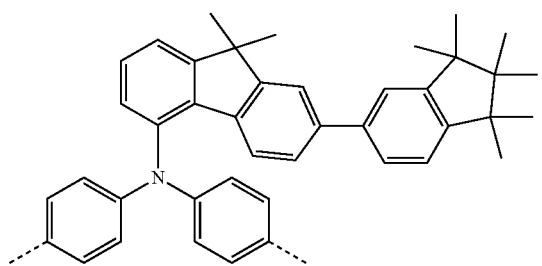
(38)
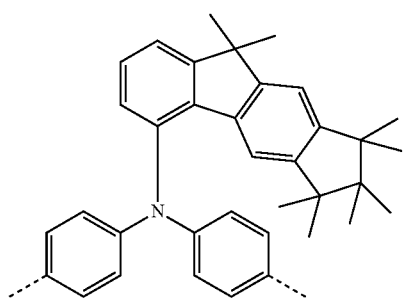
(39)

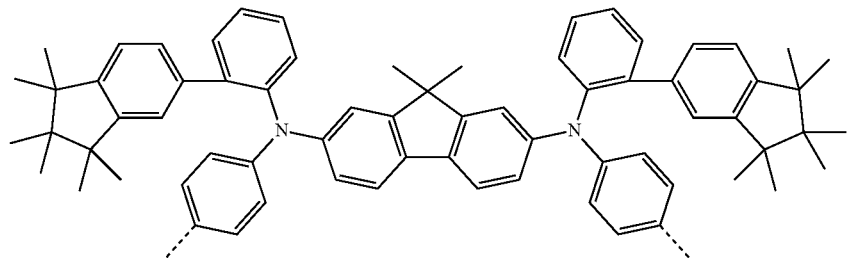

(40)

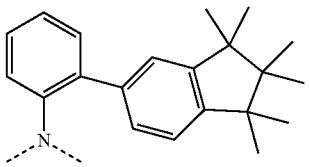

(41)

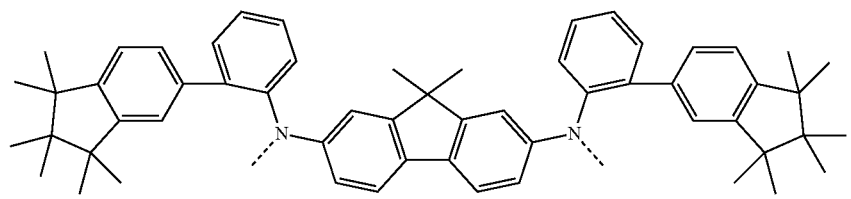

(42)

The proportion of structural units of the formula (I) in the polymer is in the range from 1 to 100 mol %. In a preferred embodiment, the proportion of structural units of the formula (I) in the polymer is in the range from 30 to 70 mol %, more preferably in the range from 40 to 60 mol %, based on 100 mol % of all copolymerizable monomers present as structural units in the polymer, meaning that the polymer of the invention, as well as one or more structural units of the formula (I), also has further structural units different from the structural units of the formula (I).

These structural units different from the structural units of the formula (I) include those as disclosed and listed in WO 2002/077060 A1, in WO 2005/014689 A2 and in WO 2013/156130. These are incorporated by reference into the disclosure of the present patent application. The further structural units may come, for example, from the following classes:
Group 1: units which influence the hole injection and/or hole transport properties of the polymers;
Group 2: units which influence the electron injection and/or electron transport properties of the polymers;
Group 3: units having combinations of individual units of group 1 and group 2;
Group 4: units which alter the emission characteristics in such a way that electrophosphorescence rather than electrofluorescence is obtainable;
Group 5: units which improve the transition from the singlet to the triplet state;
Group 6: units which affect the emission colour of the resulting polymers;
Group 7: units which are typically used as polymer backbone;
Group 8: units which interrupt the delocalization of the π electrons in the polymer and hence shorten the conjugation length in the polymer.

Preferred polymers of the invention are those in which at least one structural unit has charge transport properties, i.e. those which contain the units from groups 1 and/or 2.

Structural units from group 1 having hole injection and/or hole transport properties are, for example, triarylamine, benzidine, tetraaryl-para-phenylenediamine, triarylphosphine, phenothiazine, phenoxazine, dihydrophenazine, thianthrene, dibenzo-para-dioxin, phenoxathine, carbazole, azulene, thiophene, pyrrole and furan derivatives and further O-, S- or N-containing heterocycles.

Structural units from group 2 having electron injection and/or electron transport properties are, for example, pyridine, pyrimidine, pyridazine, pyrazine, oxadiazole, quinoline, quinoxaline, anthracene, benzanthracene, pyrene, perylene, benzimidazole, triazine, ketone, phosphine oxide and phenazine derivatives, but also triarylboranes and further O-, S- or N-containing heterocycles.

It may be preferable when the polymers of the invention contain units from group 3 in which structures which increase hole mobility and which increase electron mobility (i.e. units from group 1 and 2) are bonded directly to one another, or structures which increase both hole mobility and electron mobility are present. Some of these units may serve as emitters and shift the emission colour into the green, yellow or red. The use thereof is thus suitable, for example, for the creation of other emission colours from originally blue-emitting polymers.

Structural units of group 4 are those which can emit light with high efficiency from the triplet state even at room temperature, i.e. exhibit electrophosphorescence rather than electrofluorescence, which frequently brings about an increase in energy efficiency. Suitable for this purpose, first of all, are compounds containing heavy atoms having an atomic number of more than 36. Preferred compounds are those which contain d or f transition metals, which fulfil the abovementioned condition. Particular preference is given here to corresponding structural units containing elements of groups 8 to 10 (Ru, Os, Rh, Ir, Pd, Pt). Useful structural units here for the polymers of the invention include, for example, various complexes as described, for example, in WO 02/068435 A1, WO 02/081488 A1, EP 1239526 A2 and WO 2004/026886 A2. Corresponding monomers are described in WO 02/068435 A1 and in WO 2005/042548 A1.

Structural units of group 5 are those which improve the transition from the singlet to the triplet state and which, used in association with the structural elements of group 4, improve the phosphorescence properties of these structural elements. Useful units for this purpose are especially carbazole and bridged carbazole dimer units, as described, for example, in WO 2004/070772 A2 and WO 2004/113468 A1. Additionally useful for this purpose are ketones, phosphine oxides, sulfoxides, sulfones, silane derivatives and similar compounds, as described, for example, in WO 2005/040302 A1.

Structural units of group 6 are, as well as those mentioned above, those which include at least one further aromatic structure or another conjugated structure which are not among the abovementioned groups, i.e. which have only little effect on the charge carrier mobilities, which are not organometallic complexes or which have no effect on the singlet-triplet transition. Structural elements of this kind can affect the emission colour of the resulting polymers. According to the unit, they can therefore also be used as emitters. Preference is given to aromatic structures having 6 to 40 carbon atoms or else tolane, stilbene or bisstyrylarylene derivatives which may each be substituted by one or more R radicals. Particular preference is given to the incorporation of 1,4- or 9,10-anthrylene, 1,6-, 2,7- or 4,9-pyrenylene, 3,9- or 3,10-perylenylene, 4,4'-tolanylene, 4,4'-stilbenylene, benzothiadiazole and corresponding oxygen derivatives, quinoxaline, phenothiazine, phenoxazine, dihydrophenazine, bis(thiophenyl)arylene, oligo(thiophenylene), phenazine, rubrene, pentacene or perylene derivatives which are preferably substituted, or preferably conjugated push-pull systems (systems substituted by donor and acceptor substituents) or systems such as squarines or quinacridones which are preferably substituted.

Structural units of group 7 are units including aromatic structures having 6 to 40 carbon atoms, which are typically used as the polymer backbone. These are, for example, 4,5-dihydropyrene derivatives, 4,5,9,10-tetrahydropyrene derivatives, fluorene derivatives, 9,9'-spirobifluorene derivatives, phenanthrene derivatives, 9,10-dihydrophenanthrene derivatives, 5,7-dihydrodibenzooxepine derivatives and cis- and trans-indenofluorene derivatives, but also 1,2-, 1,3- or 1,4-phenylene, 1,2-, 1,3- or 1,4-naphthylene, 2,2'-, 3,3'- or 4,4'-biphenylylene, 2,2'-, 3,3- or 4,4'-terphenylylene, 2,2'-, 3,3'- or 4,4'-bi-1,1'-naphthylylene or 2,2'''-, 3,3'''- or 4,4'''-quaterphenylylene derivatives.

Structural units of group 8 are those that have conjugation-interrupting properties, for example via meta bonding, steric hindrance or use of saturated carbon or silicon atoms. Compounds of this kind are disclosed, for example, in WO2006/063852, WO 2012/048778 and WO 2013/093490. The conjugation-interrupting properties of the structural units of group 8 are manifested inter ala by a blue shift in the absorption edge of the polymer.

Preference is given to polymers of the invention which simultaneously contain, as well as structural units of the formula (I), additionally one or more units selected from groups 1 to 8. Particular preference is given to the structural units of groups 1, 7 and 8. It may likewise be preferable when more than one further structural unit from one of the abovementioned groups is present.

If the polymer of the invention contains one or more units selected from groups 1 to 8, one or more of these units, preferably a unit from group 1, may have one or more crosslinkable groups, preferably one crosslinkable group.

The polymers of the invention are either homopolymers composed of structural units of the formula (I) or copolymers. The polymers of the invention may be linear or branched, preferably linear. Copolymers of the invention may, as well as one or more structural units of the formula (I), potentially have one or more further structures from the above-detailed groups 1 to 8.

The copolymers of the invention may have random, alternating or block structures, or else have two or more of these structures in alternation. More preferably, the copolymers of the invention have random or alternating structures. More preferably, the copolymers are random or alternating copolymers. The way in which copolymers having block structures are obtainable and which further structural elements are particularly preferred for the purpose is described in detail, for example, in WO 2005/014688 A2. This is incorporated into the present application by reference. It should likewise be emphasized once again at this point that the polymer may also have dendritic structures.

In a further embodiment of the present invention, the polymers of the invention contain at least one, preferably one, structural unit containing a crosslinkable Q group.

"Crosslinkable Q group" in the context of the present invention means a functional group capable of entering into a reaction and thus forming an insoluble compound. The reaction may be with a further identical Q group, a further different Q group or any other portion of the same or another polymer chain. The crosslinkable group is thus a reactive group. This affords, as a result of the reaction of the crosslinkable group, a correspondingly crosslinked polymer. The chemical reaction can also be conducted in the layer, giving rise to an insoluble layer. The crosslinking can usually be promoted by means of heat or by means of UV radiation, microwave radiation, x-radiation or electron beams, optionally in the presence of an initiator. "insoluble" in the context of the present invention preferably means that the inventive polymer, after the crosslinking reaction, i.e. after the reaction of the crosslinkable groups, has a lower solubility at room temperature in an organic solvent by at least a factor of 3, preferably at least a factor of 10, than that of the corresponding non-crosslinked inventive polymer in the same organic solvent.

The crosslinkable Q group may be introduced into the polymer of the invention as such via a monomer correspondingly substituted by the crosslinkable group. Alternatively and likewise preferably in particular cases, the crosslinkable Q group may be introduced into the polymer via a precursor Q* group which is part of a monomer. In this case, the polymer obtained at first bears the precursor Q* group. In a reaction on the polymer, the Q* group is then converted to the actual crosslinkable Q group. One example of such a precursor Q* group is a terminal aldehyde group, which can be converted to a terminal alkenyl group by a Wittig reaction for example. The latter is then the actual crosslinkable Q group.

The structural unit that bears the crosslinkable Q group may, in a first embodiment, be selected from the structural units of the formula (I).

Preferred structural units correspond to one of the following formulae (I-Q-1) to (I-Q-6):

Formula (I-Q-1)

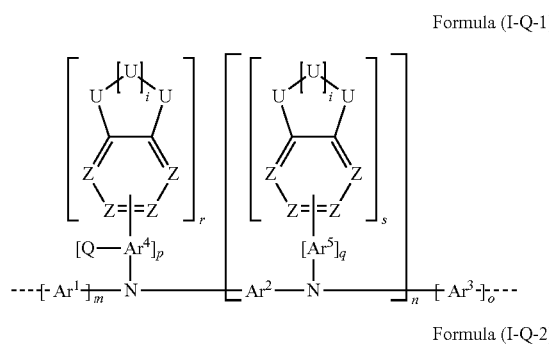

Formula (I-Q-2)

Formula (I-Q-3)

Formula (I-Q-4)

Formula (I-Q-5)

Formula (I-Q-6)

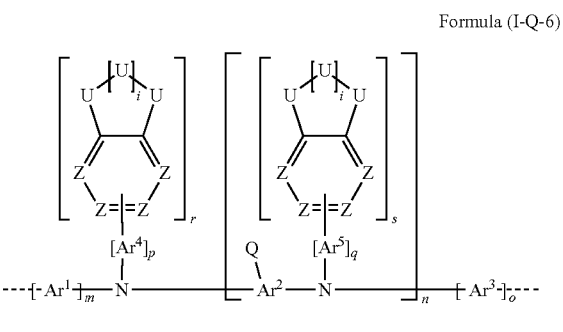

where Q is a crosslinkable group and is preferably as defined in the preferred embodiments specified below, and where the other variables are as defined above.

Particularly preferred structural units of the formula (I) that comprise a crosslinkable Q group are the following structural units:

Formula (I-Q-7)

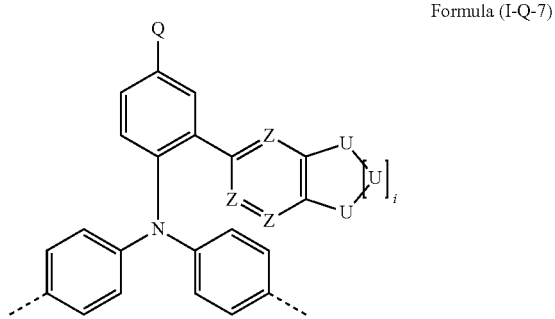

(Formula (I-Q-8))

Formula (I-Q-9)

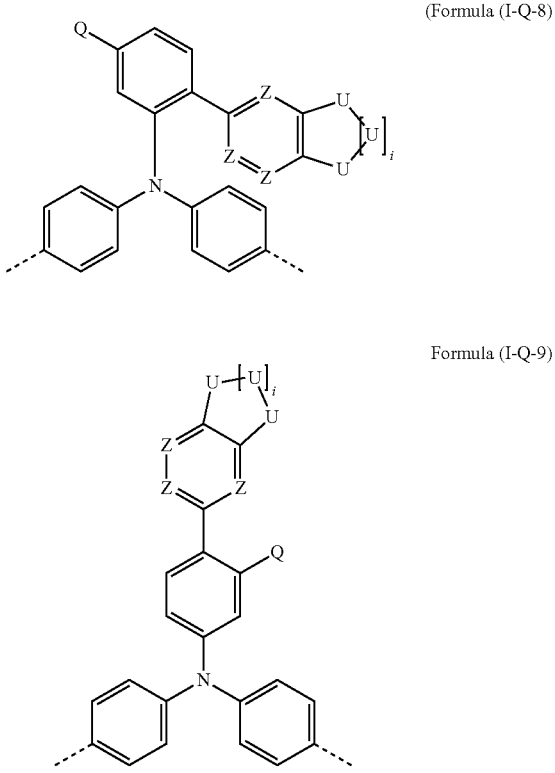

Formula (I-Q-10)
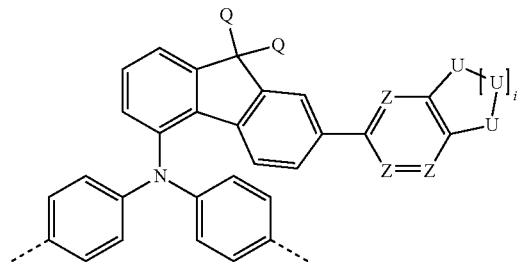
Formula (I-Q-11)
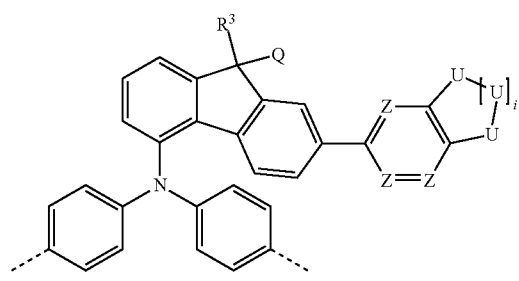
Formula (I-Q-12)
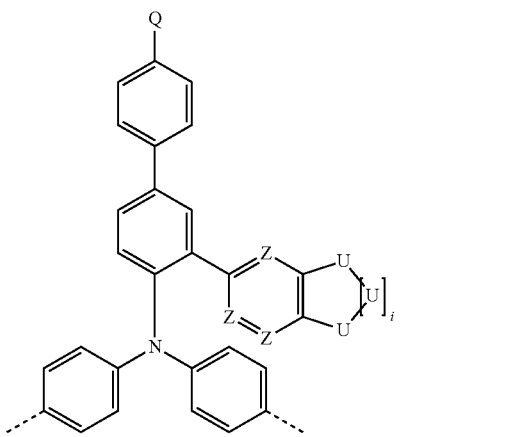
Formula (I-Q-13)
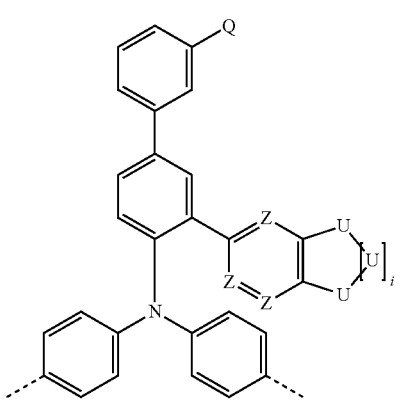
Formula (I-Q-14)
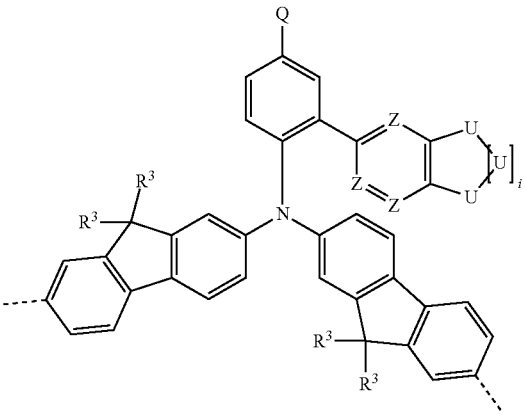
Formula (I-Q-15)
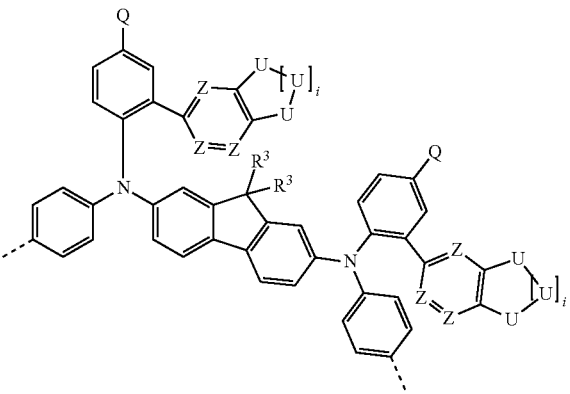
Formula (I-Q-16)
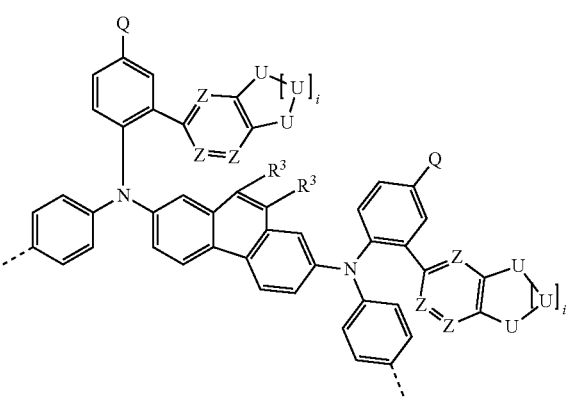

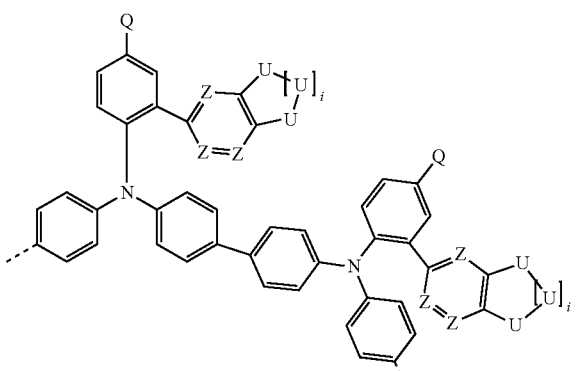

Formula (I-Q-17)

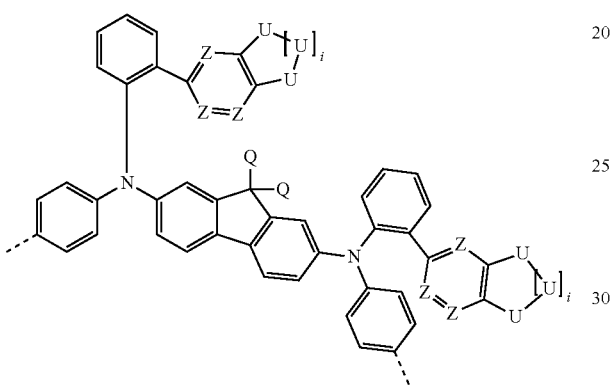

Formula (I-Q-18)

where Q is a crosslinkable group and is preferably as defined in the preferred embodiments specified below, and where the other variables are as defined above.

In an alternative embodiment, the structural unit that bears the Q group is selected from structural units of the abovementioned groups 1 to 8, preferably from structural units of the abovementioned groups 1, 7 and 8, more preferably from structural units of the abovementioned group 1.

Crosslinkable Q groups preferred in accordance with the invention are the following groups:

a) Terminal or Cyclic Alkenyl or Terminal Dienyl and Alkynyl Groups:

Suitable units are those which contain a terminal or cyclic double bond, a terminal dienyl group or a terminal triple bond, especially terminal or cyclic alkenyl, terminal dienyl or terminal alkynyl groups having 2 to 40 carbon atoms, preferably having 2 to 10 carbon atoms, where individual $CH_2$ groups and/or individual hydrogen atoms may also be replaced by the abovementioned R groups.

b) Alkenyloxy, Dienyloxy or Alkynyloxy Groups:

Additionally suitable are alkenyloxy, dienyloxy or alkynyloxy groups, preferably alkenyloxy groups.

c) Acrylic Acid Groups:

Additionally suitable are acrylic acid units in the broadest sense, preferably acrylic esters, acrylamides, methacrylic esters and methacrylamides. Particular preference is given to $C_{1-10}$-alkyl acrylate and $C_{1-10}$-alkyl methacrylate.

The crosslinking reaction of the groups mentioned above under a) to c) can be effected via a free-radical, cationic or anionic mechanism, or else via cycloaddition.

It may be advisable to add an appropriate initiator for the crosslinking reaction. Suitable initiators for the free-radical crosslinking are, for example, dibenzoyl peroxide, AIBN or TEMPO. Suitable initiators for the cationic crosslinking are, for example, $AlCl_3$, $BF_3$, triphenylmethyl perchlorate or tropylium hexachloroantimonate. Suitable initiators for the anionic crosslinking are bases, especially butyllithium.

In a preferred embodiment of the present invention, the crosslinking, however, is conducted without the addition of an initiator and is initiated exclusively by thermal means. The reason for this preference is that the absence of the initiator prevents contamination of the layer which could lead to worsening of the device properties.

d) Oxetanes and Oxiranes:

A further suitable class of crosslinkable Q groups is that of oxetanes and oxiranes which crosslink cationically via ring opening.

It may be advisable to add an appropriate initiator for the crosslinking reaction. Suitable initiators are, for example, $AlCl_3$, $BF_3$, triphenylmethyl perchlorate or tropylium hexachloroantimonate. It is likewise possible to add photoacids as initiators.

e) Silanes:

Additionally suitable as a class of crosslinkable groups are silane groups $SiR_3$ where at least two R groups, preferably all three R groups, are Cl or an alkoxy group having 1 to 20 carbon atoms.

This group reacts in the presence of water to give an oligo- or polysiloxane.

f) Cyclobutane Groups

The crosslinkable Q groups mentioned above under a) to f) are generally known to those skilled in the art, as are the suitable reaction conditions which are used for reaction of these groups.

Preferred crosslinkable Q groups include alkenyl groups of the following formula Q1, dienyl groups of the following formula Q2, alkynyl groups of the following formula Q3, alkenyloxy groups of the following formula Q4, dienyloxy groups of the following formula Q5, alkynyloxy groups of the following formula Q6, acrylic acid groups of the following formulae Q7 and Q8, oxetane groups of the following formulae Q9 and Q10, oxirane groups of the following formula Q11 and cyclobutane groups of the following formulae Q12, Q13 and Q14:

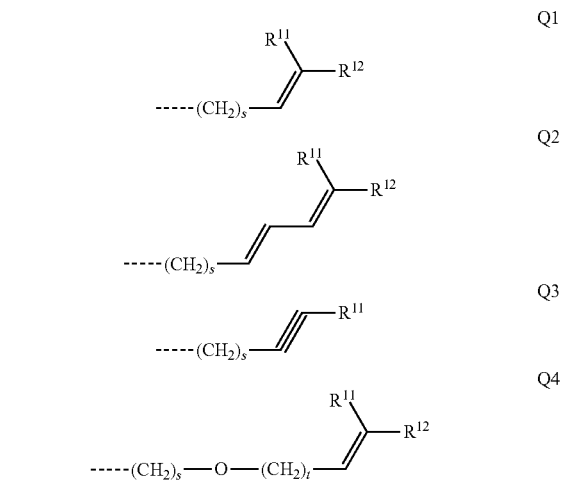

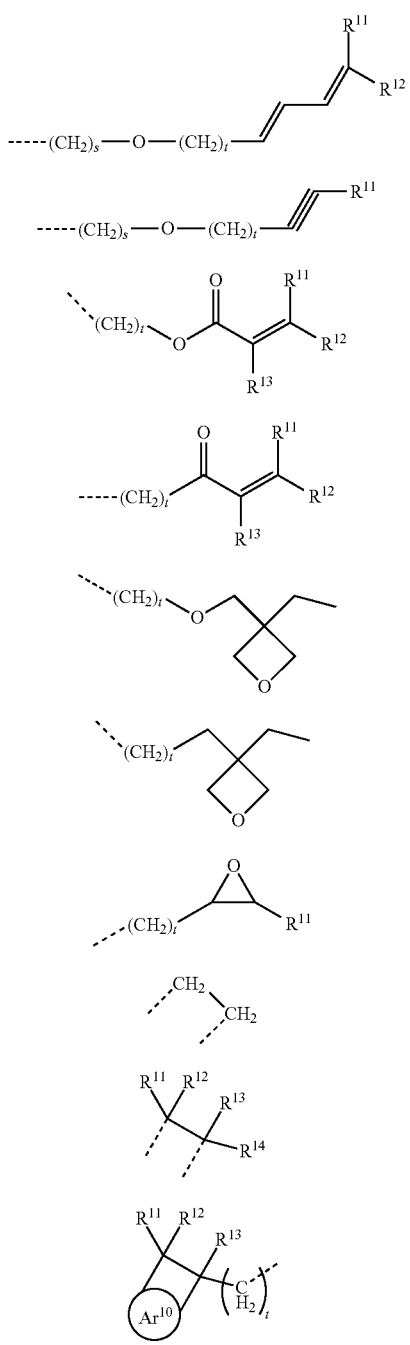

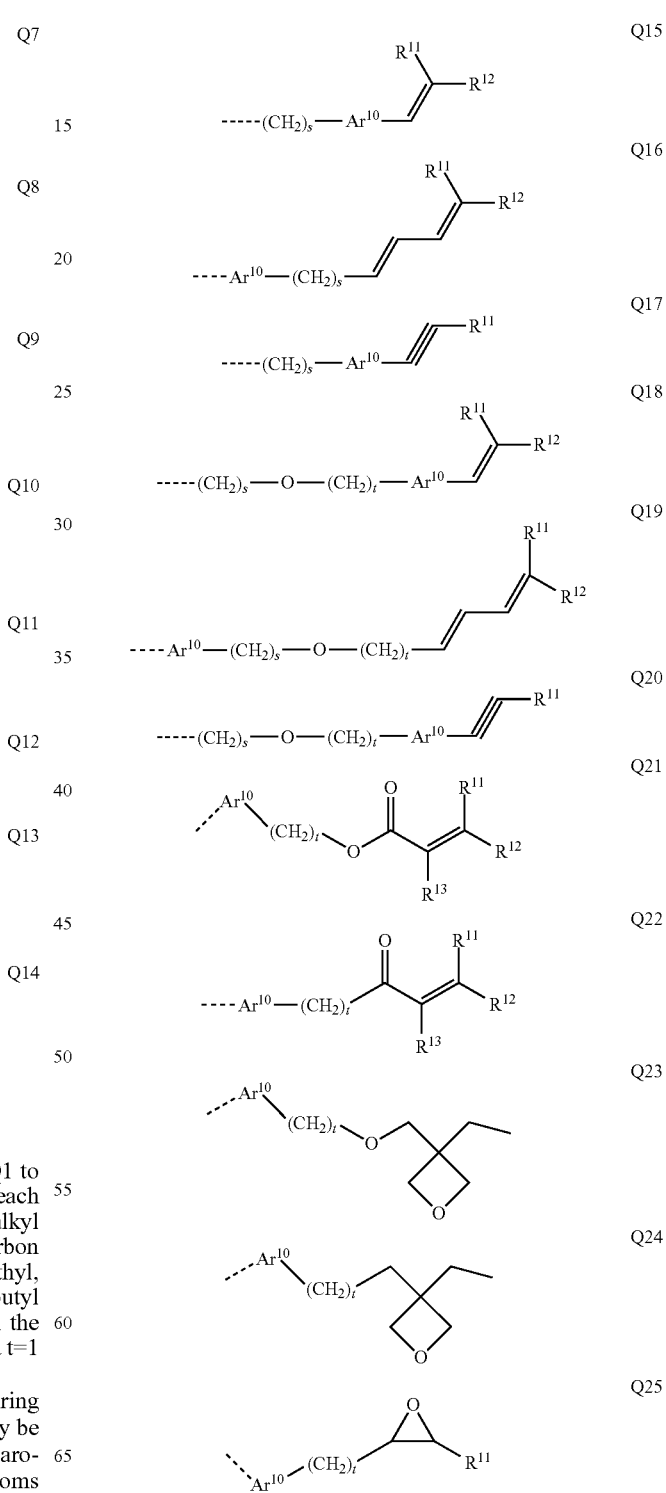

The dotted bond in the formulae Q1 to Q11 and Q14 and the dotted bonds in the formulae Q12 and Q13 represent the linkage of the crosslinkable group to the structural units.

The crosslinkable groups of the formulae Q1 to Q14 may be joined directly to the structural unit, or else indirectly, via a further mono- or polycyclic, aromatic or heteroaromatic ring system $Ar^{10}$, as shown in the following formulae Q15 to Q28:

The $R^{11}$, $R^{12}$, $R^{13}$ and $R^{14}$ radicals in the formulae Q1 to Q8, Q11, Q13 and Q14 are the same or different at each instance and are H or a straight-chain or branched alkyl group having 1 to 6 carbon atoms, preferably 1 to 4 carbon atoms. More preferably, $R^{11}$, $R^{12}$, $R^{13}$ and $R^{14}$ are H, methyl, ethyl, n-propyl, isopropyl, n-butyl, sec-butyl or tert-butyl and most preferably H or methyl. The indices used in the formulae Q1 to Q14 are defined as follows: s=0 to 8; and t=1 to 8.

$Ar^{10}$ in the formula Q14 is selected from aromatic ring systems which have 6 to 40 aromatic ring atoms and may be substituted by one or more $R^{11}$ radicals, and from heteroaromatic ring systems which have 5 to 40 aromatic ring atoms and may be substituted by one or more $R^{11}$ radicals.

-continued

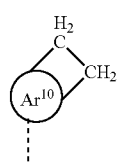 Q26

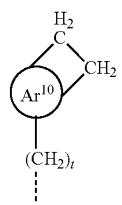 Q27

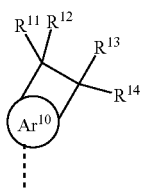 Q28 where $Ar^{10}$ is selected from automatic ring systems which have 6 to 40 aromatic ring atoms and may be substituted by one or more $R^{11}$ radicals, and from heteroaromatic ring systems which have 5 to 40 aromatic ring atoms and may be substituted by one or more $R^{11}$ radicals, and where: The $R^{11}$, $R^{12}$, $R^{13}$ and $R^{14}$ radicals are the same or different at each instance and are H or a straight-chain or branched alkyl group having 1 to 6 carbon atoms, preferably 1 to 4 carbon atoms. More preferably, $R^{11}$, $R^{12}$, $R^{13}$ and $R^{14}$ are H, methyl, ethyl, n-propyl, Isopropyl, n-butyl, sec-butyl or tert-butyl and most preferably H or methyl. The indices used in the formulae Q15 to Q28 are defined as follows: s=0 to 8; and t=1 to 8.

Particularly preferred crosslinkable Q groups are as follows:

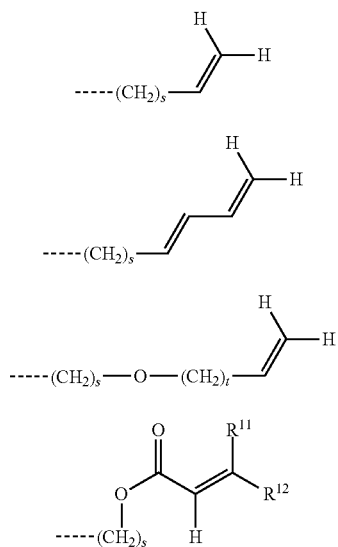

-continued

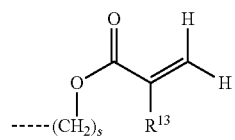 Q7b

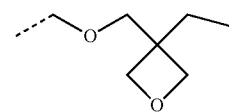 Q9a

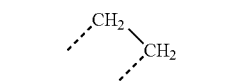 Q12

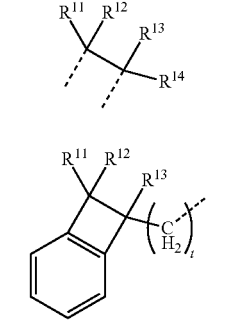 Q13

Q14a

Q15a

Q16a

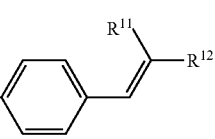 Q18a

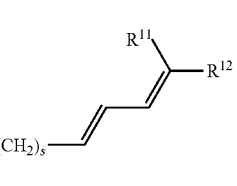 Q21a

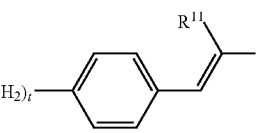 Q21b

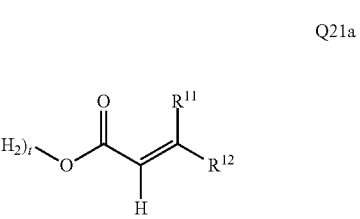

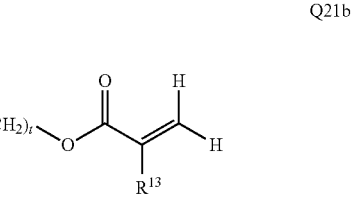

Q23a
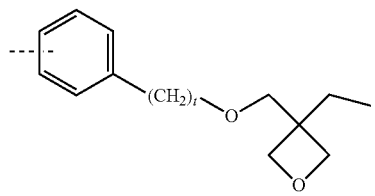

Q26a
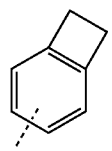

Q27a
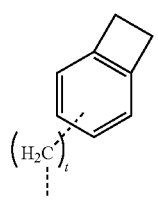

Q28a
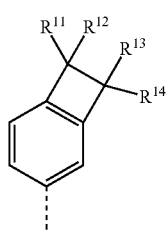

The $R^{11}$, $R^{12}$, $R^{13}$ and $R^{14}$ radicals are the same or different at each instance and are H or a straight-chain or branched alkyl group having 1 to 6 carbon atoms, preferably 1 to 4 carbon atoms. More preferably, the $R^{11}$, $R^{12}$, $R^{13}$ and $R^{14}$ radicals are methyl, ethyl, n-propyl, Isopropyl, n-butyl, sec-butyl or tert-butyl and most preferably methyl.

The indices used in formula Q1a to Q28a are defined as follows: s=0 to 8 and t=1 to 8.

Very particularly preferred crosslinkable 0 groups are as follows:

Q1b
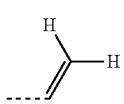

Q1c
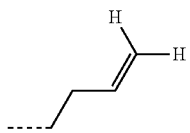

Q2b
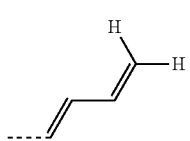

Q2c

Q4b

Q7c

Q7d

Q12b

Q13a

Q14b
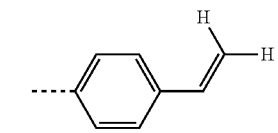

Q15b

Q15c
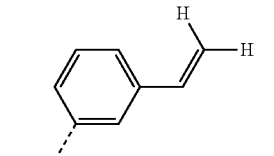

Q15d
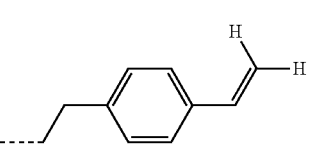

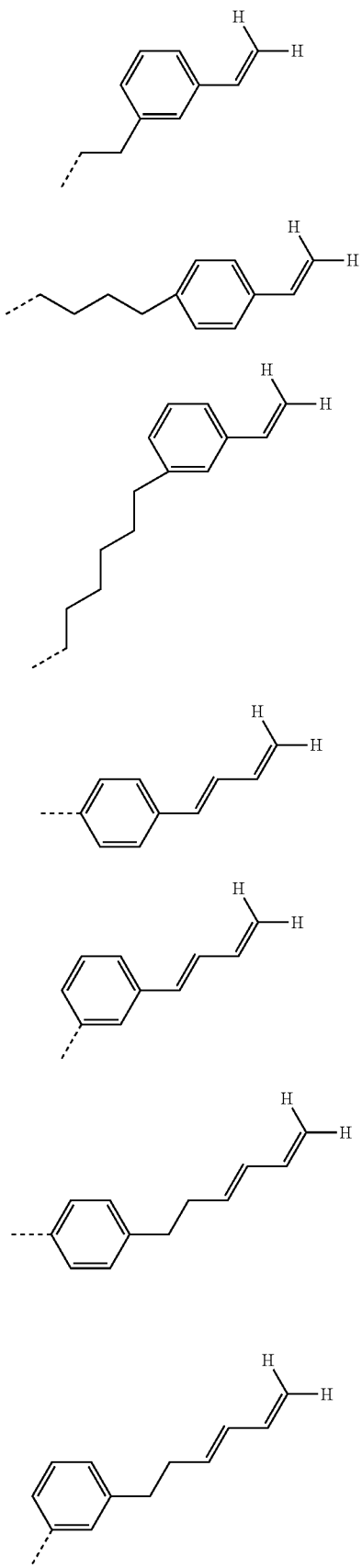
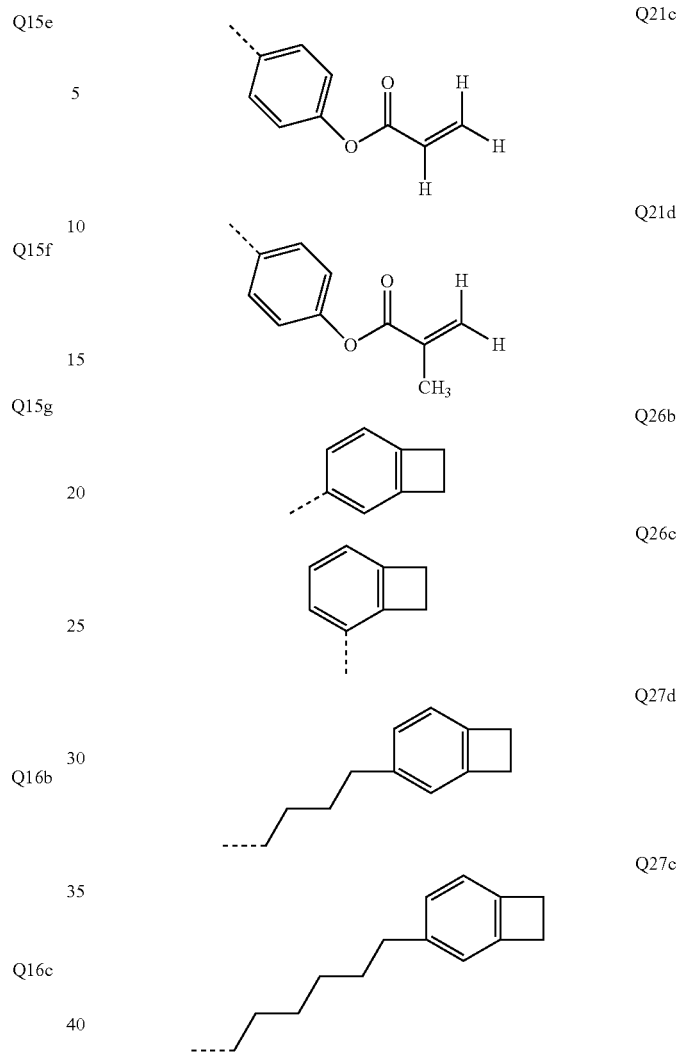

The polymers of the invention containing structural units of the formula (I) are generally prepared by polymerization of one or more monomer types, of which at least one monomer leads to structural units of the formula (I) in the polymer. Suitable polymerization reactions are known to those skilled in the art and are described in the literature. Particularly suitable and preferred polymerization reactions which lead to C—C and C—N couplings are as follows:

(A) SUZUKI polymerization;
(B) YAMAMOTO polymerization;
(C) STILLE polymerization;
(D) HECK polymerization;
(E) NEGISHI polymerization;
(F) SONOGASHIRA polymerization;
(G) HIYAMA polymerization; and
(H) HARTWIG-BUCHWALD polymerization.

How the polymerization can be conducted by these methods and how the polymers can then be separated from the reaction medium and purified is known to those skilled in the art and is described in detail in the literature, for example in WO 03/048225 A2, WO 2004/037887 A2 and WO 2004/037887 A2.

The C—C couplings are preferably selected from the groups of SUZUKI coupling, YAMAMOTO coupling and STILLE coupling; the C—N coupling is preferably a coupling according to HARTWIG-BUCHWALD.

The present invention thus also provides a process for preparing the polymers of the invention, which is characterized in that they are prepared by SUZUKI polymerization, YAMAMOTO polymerization, STILLE polymerization or HARTWIG-BUCHWALD polymerization, more preferably SUZUKI polymerization.

Synthesis of the polymers of the invention requires monomer compounds that introduce structural units of the formula (I) into the polymer.

The invention thus further provides monomers of a formula (M)

formula (M)

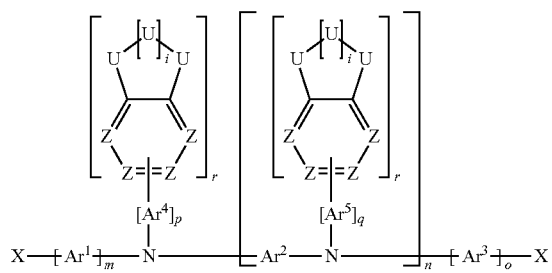

where the variables that occur are as defined above, and where X is the same or different at each instance and is a leaving group suitable for a polymerization reaction.

Preferably, X is the same or different at each instance and is selected from H, D, halogens, preferably chlorine, bromine or iodine, O-tosylates, O-triflates, O-sulfonates, boronic acid, boronic esters, partly fluorinated silyl groups, diazonium groups and organotin compounds. When m is 1, the X group bonded to the left-hand side is more preferably selected from halogens, preferably chlorine, bromine or iodine, boronic acid and boronic esters. When m is 0, the X group bonded to the left-hand side is more preferably H. When o is 1, the X group bonded to the right-hand side is more preferably selected from halogens, preferably chlorine, bromine or iodine, boronic acid and boronic esters. When o is 0, the X group bonded to the right-hand side is more preferably H.

For the other variables that occur, preferred embodiments are the same preferred embodiments as specified above for the structural unit of the formula (I).

The monomers are preferably synthesized using Buchwald coupling reactions, Suzuki coupling reactions and bromination reactions. In a preferred process (Scheme 1), a brominated amine is reacted with a boronic acid derivative of the formula

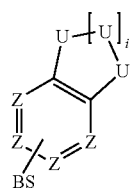

where BS is a boronic acid derivative in a Suzuki coupling reaction. The coupling product obtained is then brominated, which affords a compound of the formula (M) usable as a monomer.

Scheme 1

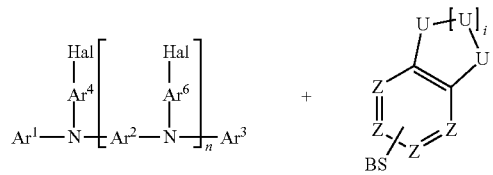

Suzuki coupling

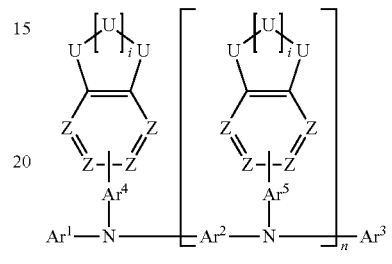

halogenation

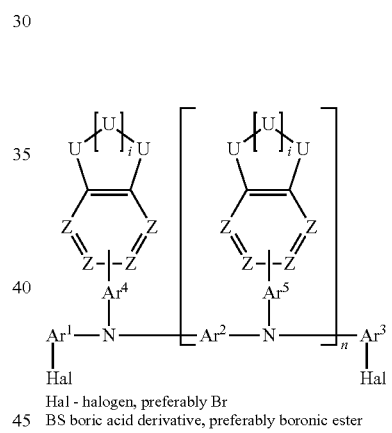

Hal - halogen, preferably Br
BS boric acid derivative, preferably boronic ester

In an alternative preferred process (Scheme 2), an amine is reacted with a halogen-substituted derivative of the following formula:

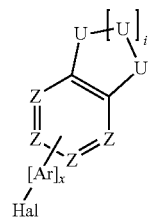

where BS is a boronic acid derivative and Ar is an aromatic or heteroaromatic ring system, and x is 0 or 1, in a Buchwald coupling reaction. The coupling product obtained is then brominated, which affords a compound of the formula (M) usable as a monomer.

Scheme 2

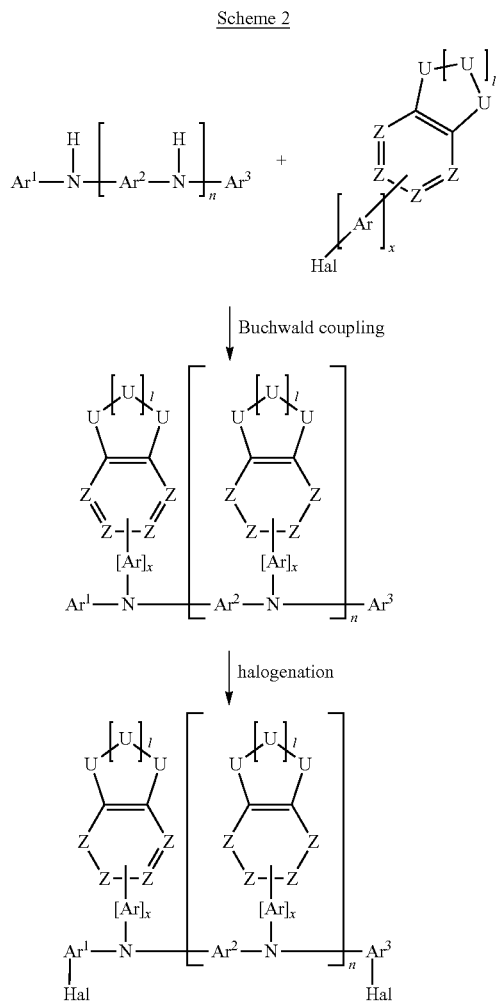

Hal = Halogen, preferably Br  Ar = aromatic or heteroaromatic ring system  x = 0 or 1

Monomers of the formula (M) are used to prepare polymers of the invention containing at least one structural unit of the formula (I) as defined above.

The polymers of the invention can be used as a neat substance, or else as a mixture together with any further polymeric, oligomeric, dendritic or low molecular weight substances. A low molecular weight substance is understood in the present invention to mean compounds having a molecular weight in the range from 100 to 3000 g/mol, preferably 200 to 2000 g/mol. These further substances can, for example, improve the electronic properties or emit themselves. A mixture refers above and below to a mixture comprising at least one polymeric component. In this way, it is possible to produce one or more polymer layers consisting of a mixture (blend) of one or more polymers of the invention having a structural unit of the formula (I) and optionally one or more further polymers with one or more low molecular weight substances.

The present invention thus further provides a polymer blend comprising one or more polymers of the invention, and one or more further polymeric, oligomeric, dendritic and/or low molecular weight substances.

The invention further provides solutions and formulations composed of one or more polymers of the invention or a polymer blend in one or more solvents. The way in which such solutions can be prepared is known to those skilled in the art and is described, for example, in WO 02/072714 A1, WO 03/019694 A2 and the literature cited therein.

These solutions can be used in order to produce thin polymer layers, for example by surface coating methods (e.g. spin-coating) or by printing methods (e.g. inkjet printing).

Polymers containing structural units having a crosslinkable Q group are particularly suitable for producing films or coatings, especially for producing structured coatings, for example by thermal or light-induced in situ polymerization and in situ crosslinking, for example in situ UV photopolymerization or photopatterning. It is possible here to use either corresponding polymers in pure form or else formulations or mixtures of these polymers as described above. These can be used with or without addition of solvents and/or binders. Suitable materials, processes and apparatuses for the above-described methods are described, for example, in WO 2005/083812 A2. Possible binders are, for example, polystyrene, polycarbonate, poly(meth)acrylates, polyacrylates, polyvinyl butyral and similar optoelectronically neutral polymers.

Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention thus further provides for the use of a polymer containing structural units having a crosslinkable Q group for preparation of a crosslinked polymer. The crosslinkable group, which is more preferably a vinyl group or alkenyl group, is preferably incorporated into the polymer by the WITTIG reaction or a WITTIG-like reaction. If the crosslinkable group is a vinyl group or alkenyl group, the crosslinking can take place via free-radical or ionic polymerization, which can be induced thermally or by radiation. Preference is given to free-radical polymerization which is induced thermally, preferably at temperatures of less than 250° C., more preferably at temperatures of less than 230° C.

Optionally, during the crosslinking process, an additional styrene monomer is added in order to achieve a higher degree of crosslinking. Preferably, the proportion of the added styrene monomer is in the range from 0.01 to 50 mol %, more preferably 0.1 to 30 mol %, based on 100 mol % of all the copolymerized monomers present as structural units in the polymer.

The present invention thus also provides a process for preparing a crosslinked polymer, comprising the following steps:
  (a) providing polymers containing structural units having one or more crosslinkable Q groups; and (b) free-radical or ionic crosslinking, preferably free-radical crosslinking, which can be induced either thermally or by radiation, preferably thermally.

The crosslinked polymers prepared by the process of the invention are insoluble in all standard solvents. In this way, it is possible to produce defined layer thicknesses which are not dissolved or partly dissolved again even by the application of subsequent layers.

The present invention thus also relates to a crosslinked polymer obtainable by the aforementioned process. The crosslinked polymer is—as described above—preferably produced in the form of a crosslinked polymer layer. Because of the insolubility of the crosslinked polymer in all solvents, a further layer can be applied from a solvent to the surface of such a crosslinked polymer layer by the above-described techniques.

The polymers of the invention can be used in electronic or optoelectronic devices or for production thereof.

The present application thus further provides for the use of the polymers of the invention in electronic or optoelectronic devices, preferably in organic electroluminescent devices (OLEDs), organic field-effect transistors (OFETs), organic integrated circuits (O—ICs), organic thin-film transistors (TFTs), organic solar cells (O—SCs), organic laser diodes (O-laser), organic photovoltaic (OPV) elements or devices or organic photoreceptors (OPCs), more preferably in organic electroluminescent devices (OLEDs).

The present application further provides a device selected from the abovementioned devices, comprising at least one polymer of the invention. Preferably, the polymer here is present in a hole-transporting layer.

Apart from cathode, anode, emitting layer and hole-transporting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers in the organic electroluminescent device comprising the polymer of the invention is preferably as follows:

anode-hole injection layer-hole transport layer-optionally further hole transport layer(s)-emitting layer-optionally hole blocker layer-electron transport layer-cathode. It is additionally possible for further layers to be present in the OLED.

Preferred embodiments of OLEDs comprising the polymer of the invention are hybrid devices in which one or more layers which are processed from solution and one or more layers which are produced by vapour deposition of low molecular weight substances are present. These are also referred to as combined PLED/SMOLED (polymeric light emitting diode/small molecule organic light-emitting diode) systems. Preferably, in the device of the invention, the layers between the anode and emitting layer and the emitting layer are applied from solution, and the layers between the emitting layer and cathode are preferably applied by a sublimation method.

Layers from solution are preferably produced by spin-coating, or by any printing method, for example screen printing, flexographic printing, nozzle printing or offset printing, more preferably LITI (light-induced thermal imaging, thermal transfer printing) or inkjet printing.

In the case of application of layers by means of sublimation, the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

In an alternative embodiment, one or more layers are applied by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

The way in which OLEDs can be produced is known to those skilled in the art and is described in detail, for example, as a general process in WO 2004/070772 A2, which has to be adapted appropriately to the individual case.

The polymers of the invention are especially suitable for use in a hole-transporting layer of an OLED. A hole-transporting layer is especially understood here to mean a layer that adjoins the emitting layer on the anode side.

However, the polymers of the invention can also be used in a hole injection layer (HIL), In a hole blocker layer (HBL) and in an emitting layer. When the polymers are used in an emitting layer, they preferably function as a matrix material and especially function as a hole-transporting and/or as a wide-bandgap matrix material. A hole injection layer is especially understood to mean a layer which directly adjoins the anode and is arranged between the anode and a hole transport layer. A hole blocker layer is especially understood to mean a layer which directly adjoins the emitting layer on the cathode side and is arranged between the emitting layer and an electron transport layer.

Preferred embodiments of the different functional materials in the electronic device are listed hereinafter.

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups are bonded to the pyrene preferably in the 1 position or 1,6 positions. Further preferred emitting compounds are indenofluoreneamines or -diamines, for example according to WO 2006/108497 or WO 2006/122630, benzoindenofluoreneamines or -diamines, for example according to WO 2008/006449, and dibenzoindenofluoreneamines or -diamines, for example according to WO 2007/140847, and the indenofluorene derivatives having fused aryl groups disclosed in WO 2010/012328. Likewise preferred are the pyrenearylamines disclosed in WO 2012/048780 and in WO 2013/185871. Likewise preferred are the benzoindenofluoreneamines disclosed in WO 2014/037077, the benzofluoreneamines disclosed in WO 2014/106522, the extended benzoindenofluorenes disclosed in WO 2014/111269 and in WO 2017/036574, the phenoxazines disclosed in WO 2017/028940 and WO 2017/028941, and the fluorene derivatives bonded to furan units or to thiophene units that are disclosed in WO 2016/150544.

Particular preference is given to the extended benzoindenofluorenes disclosed in WO 2014/111269 for use as fluorescent emitters in the emitting layer.

Preferred fluorescent emitters for use in the emitting layer of devices comprising the polymers of the invention are shown below:

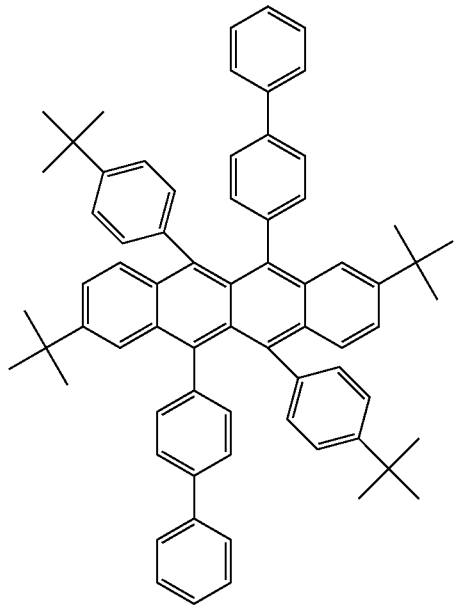

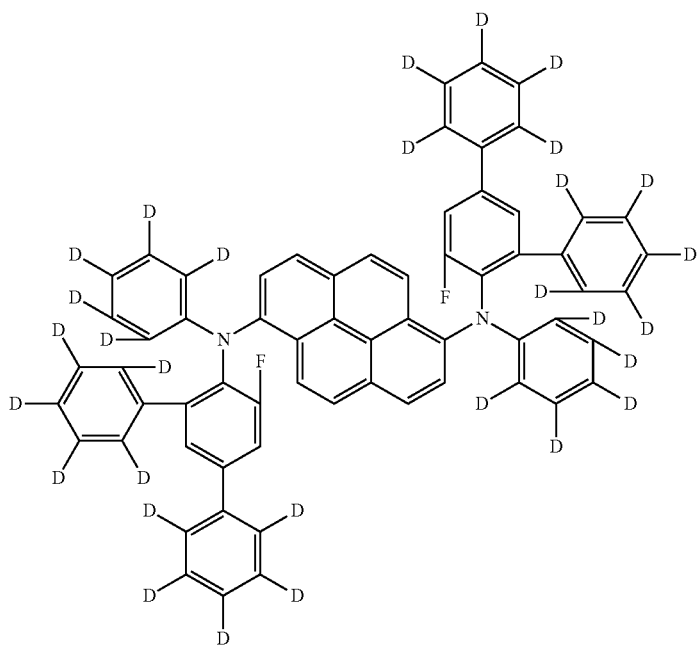

103
-continued
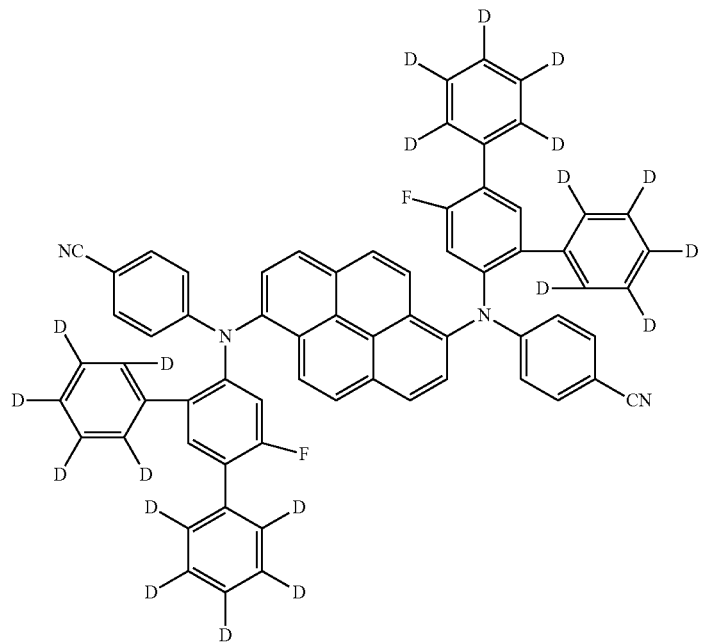
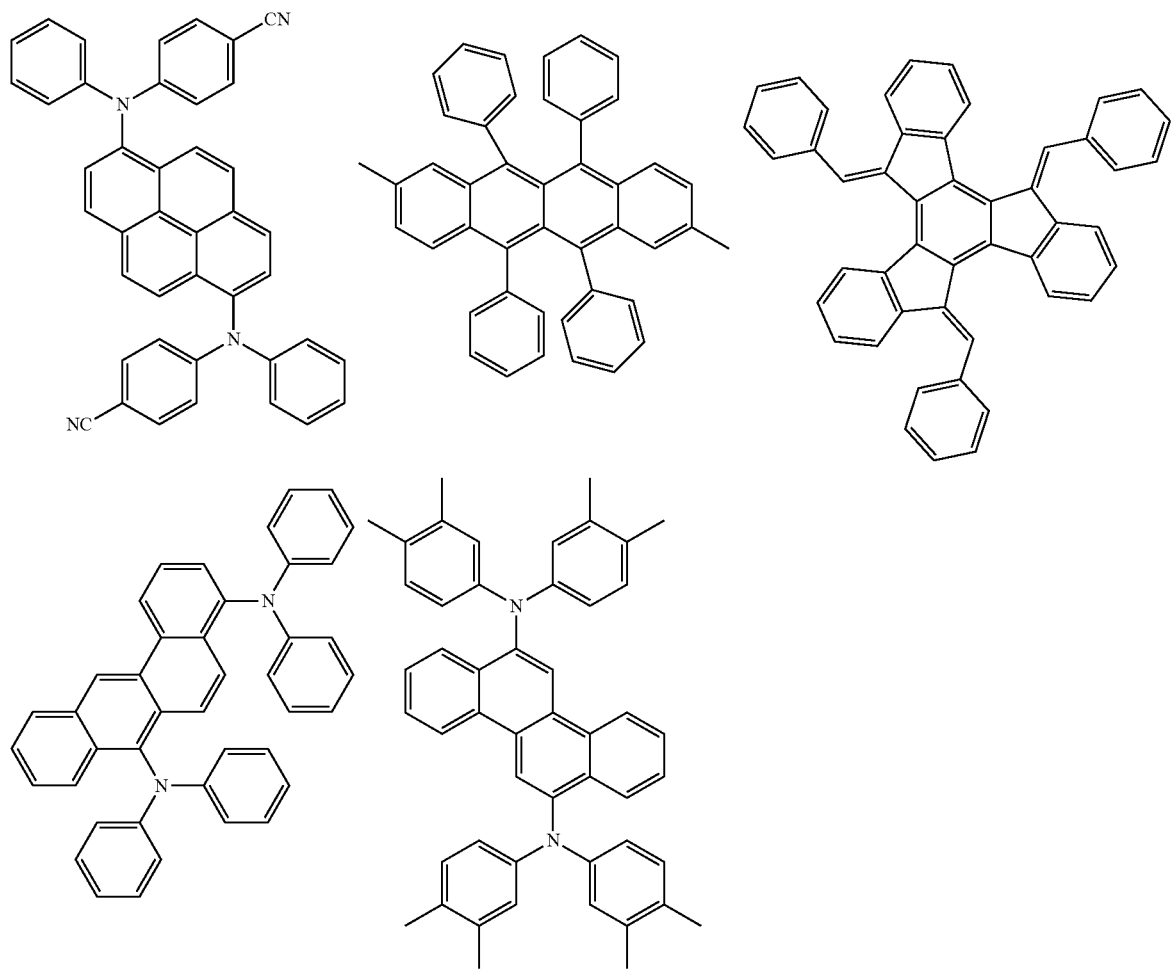

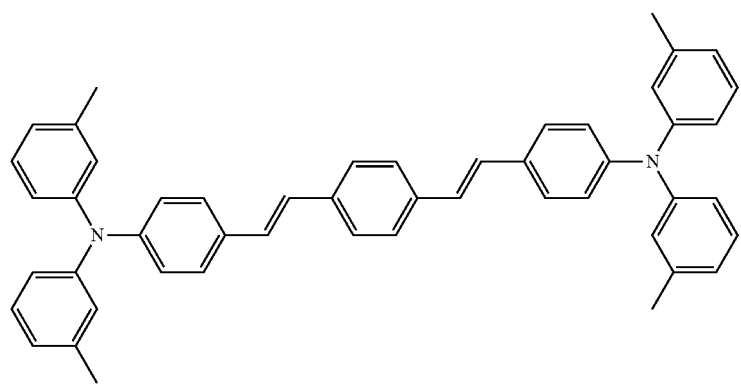
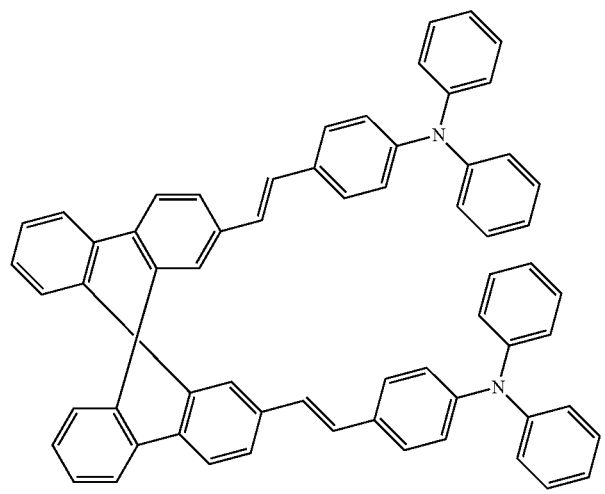
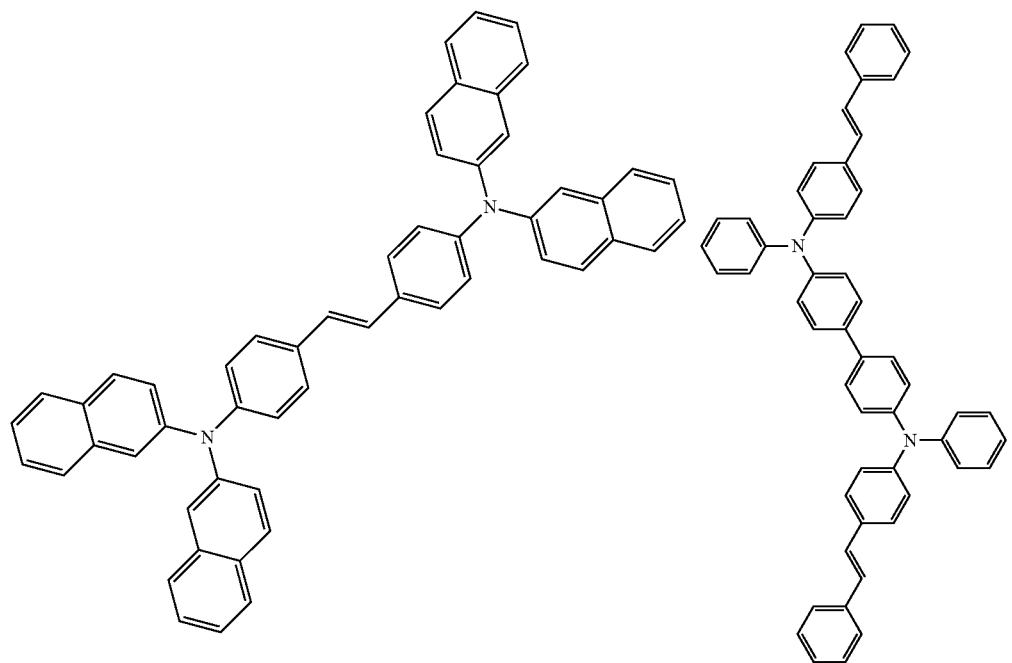

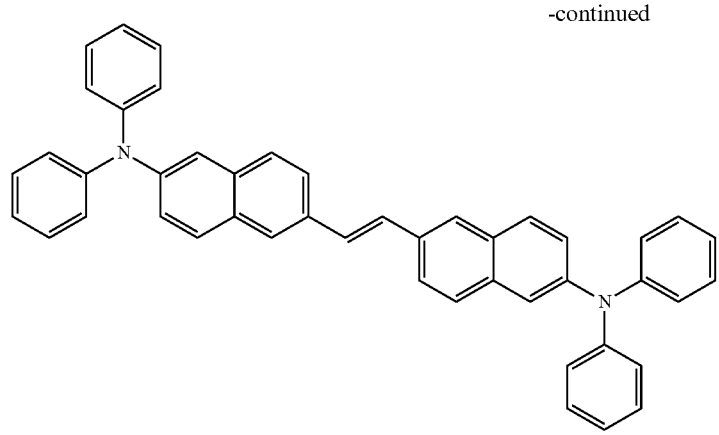
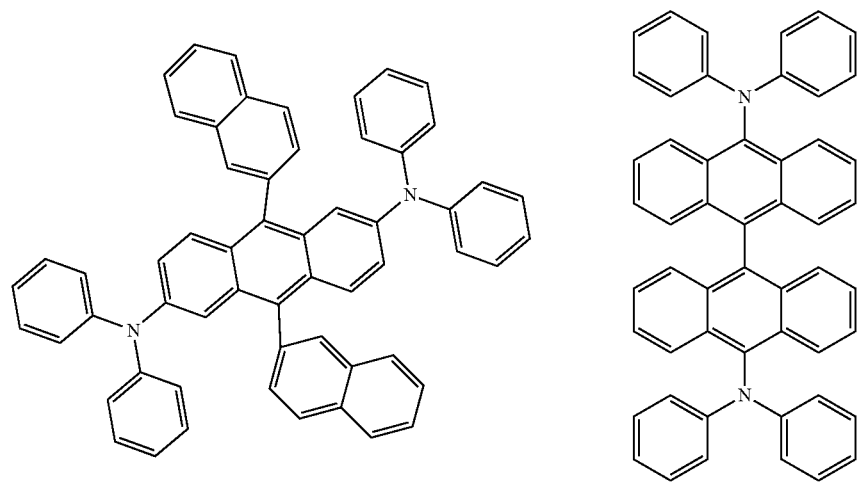
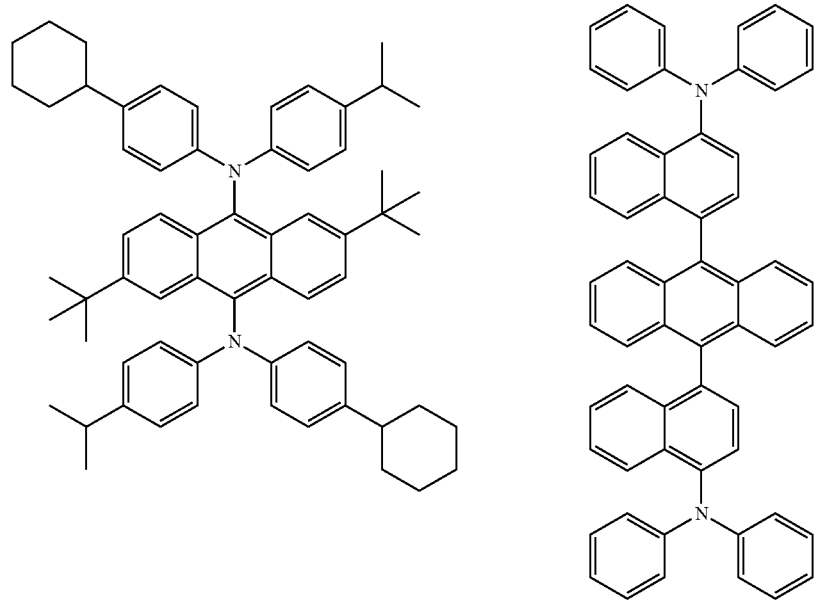

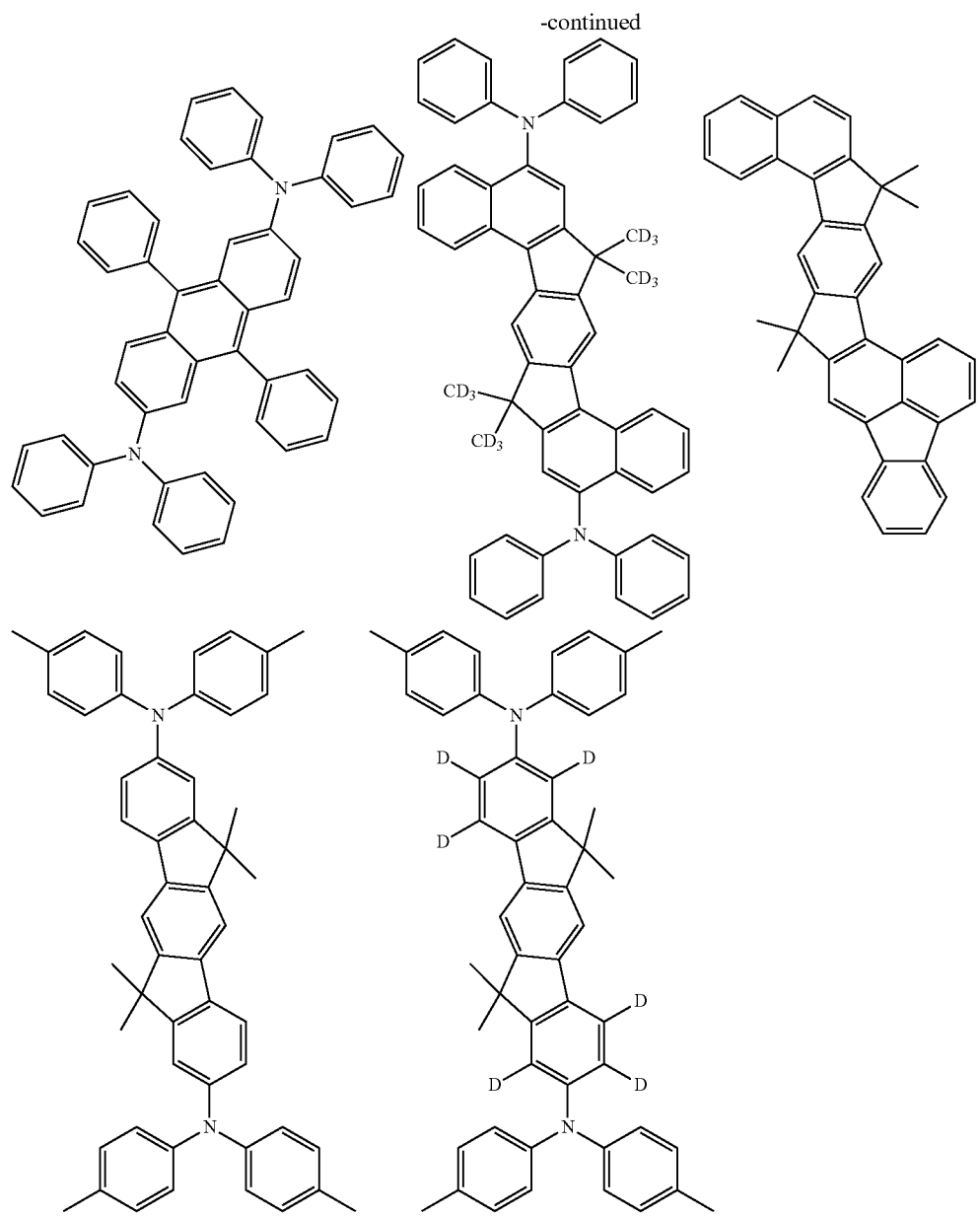
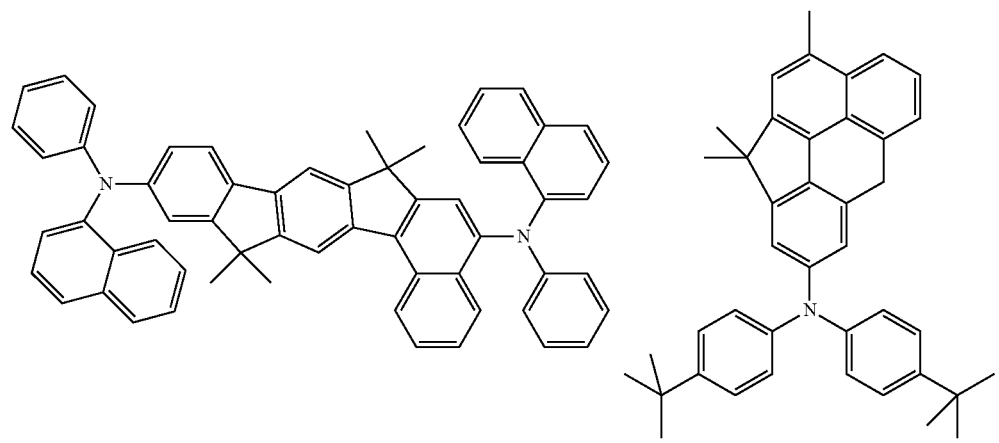

-continued
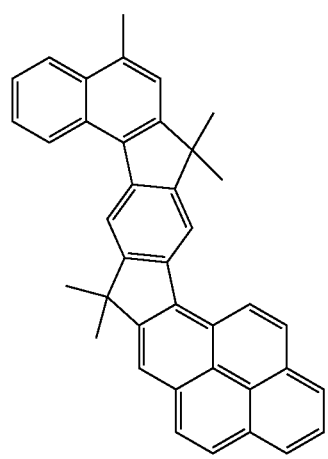
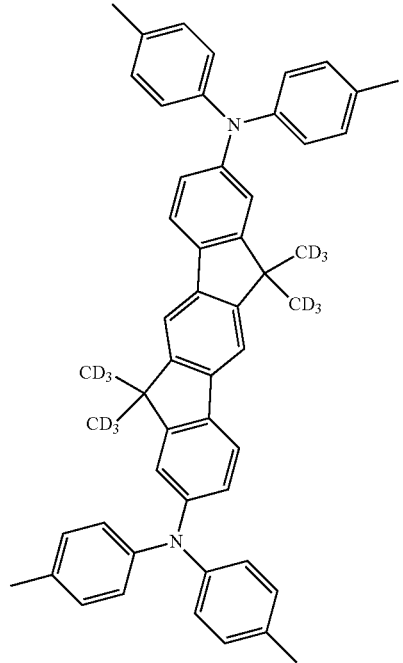
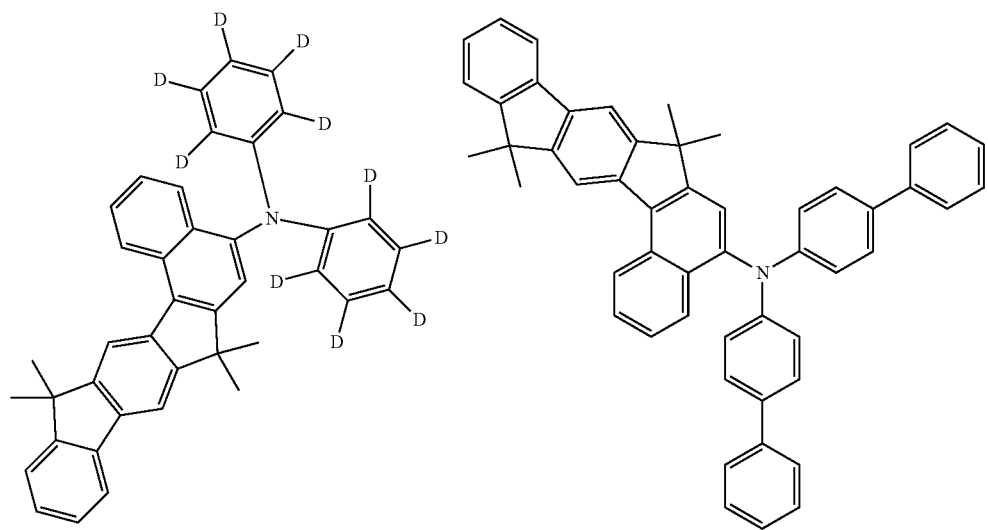

113 114
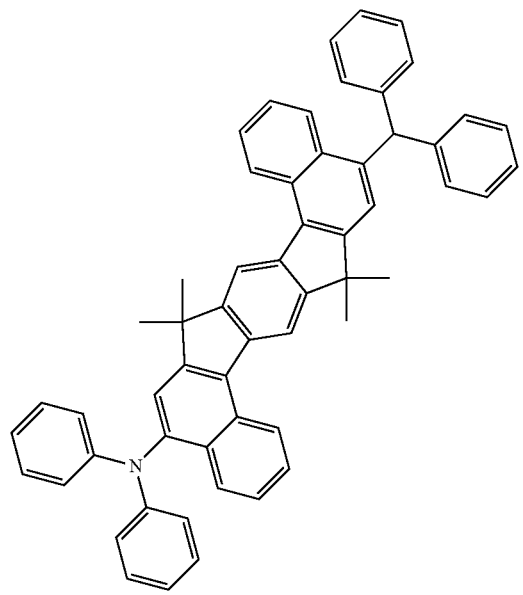
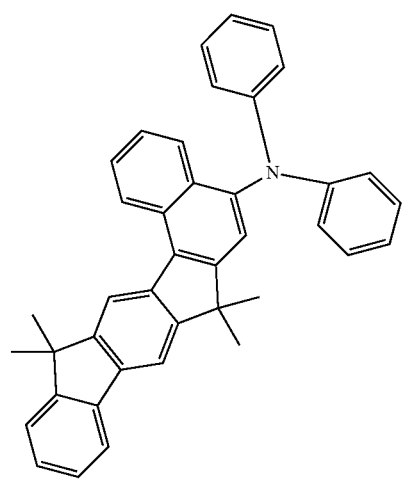
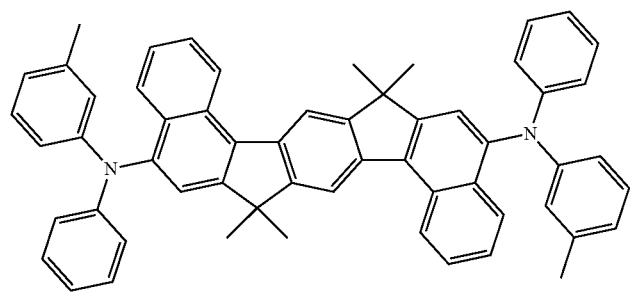
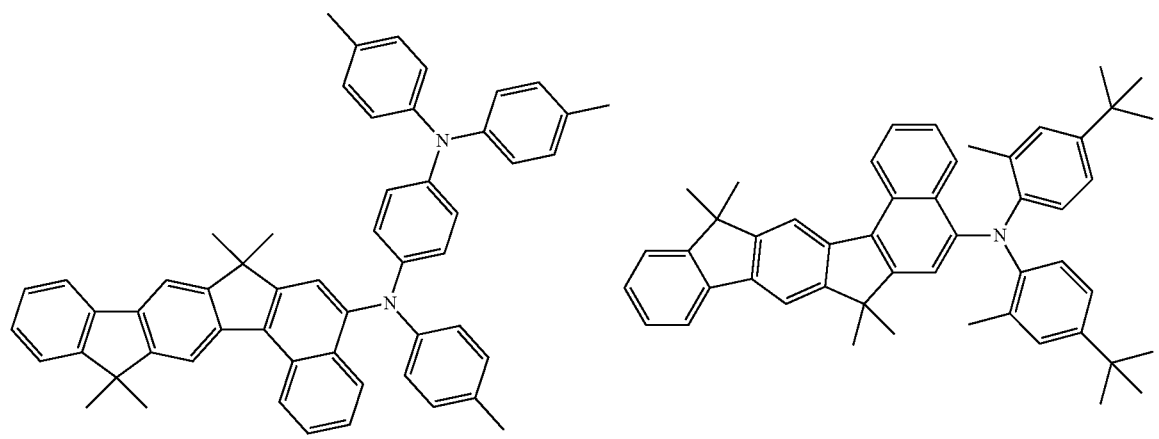

-continued
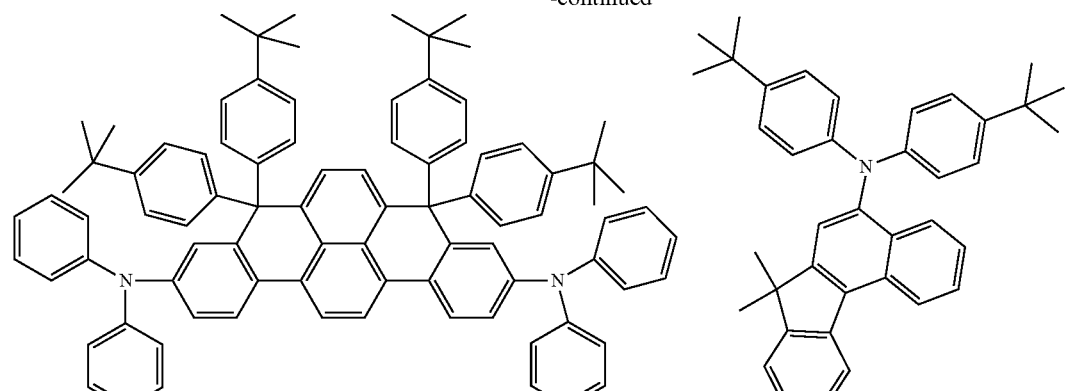
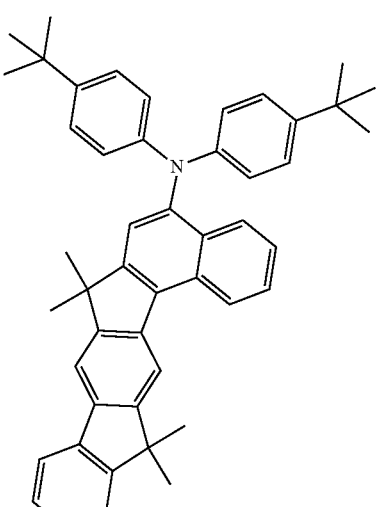
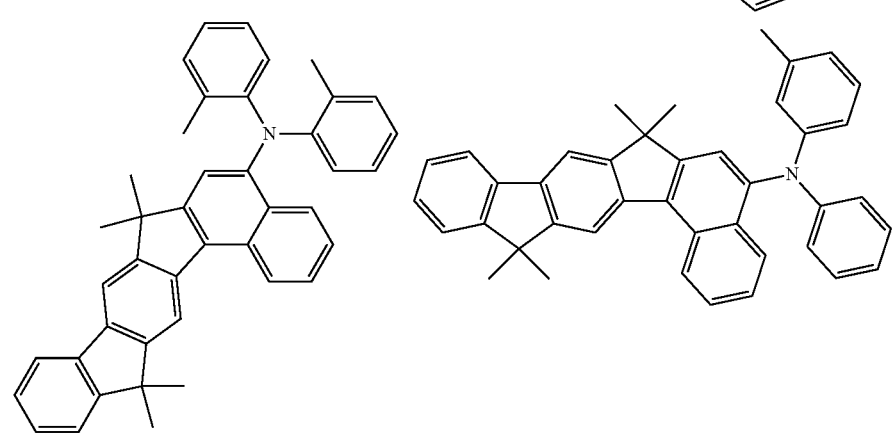
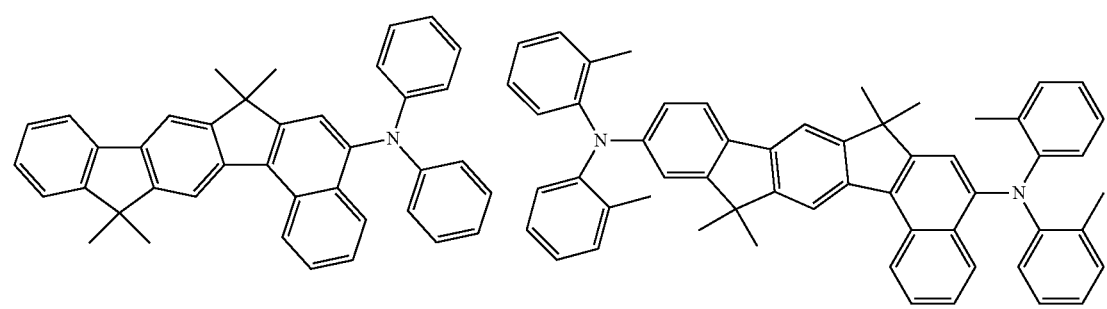
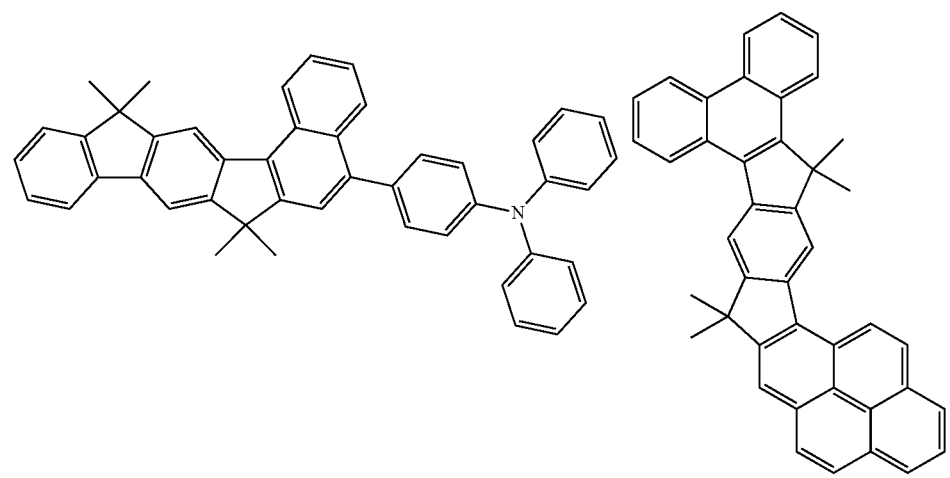

-continued
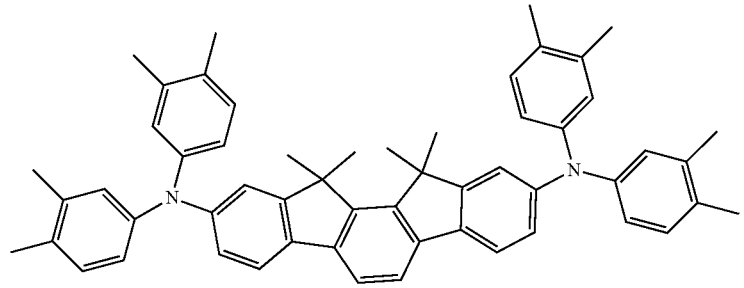
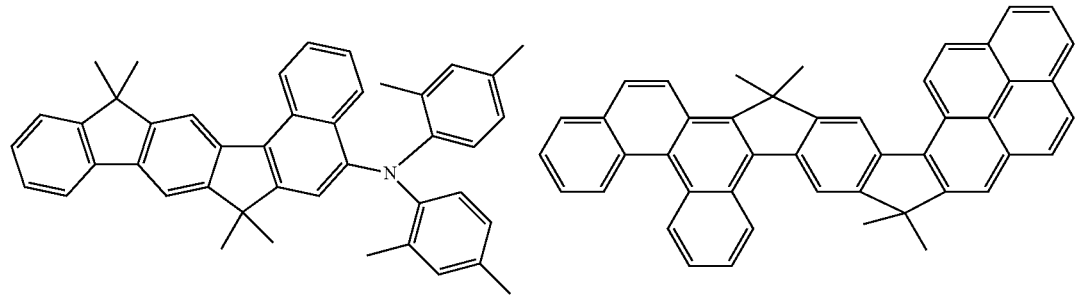
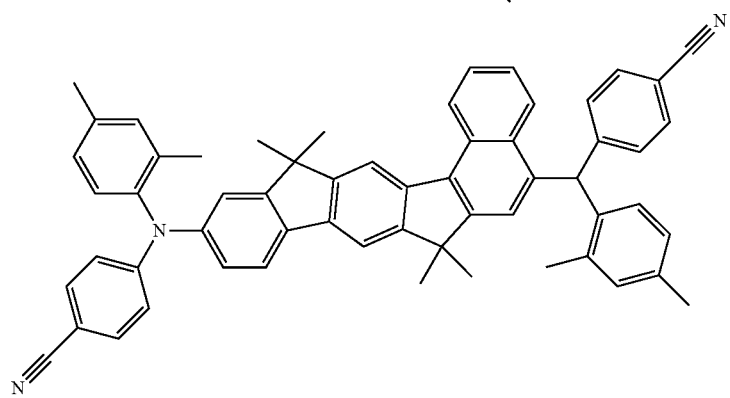
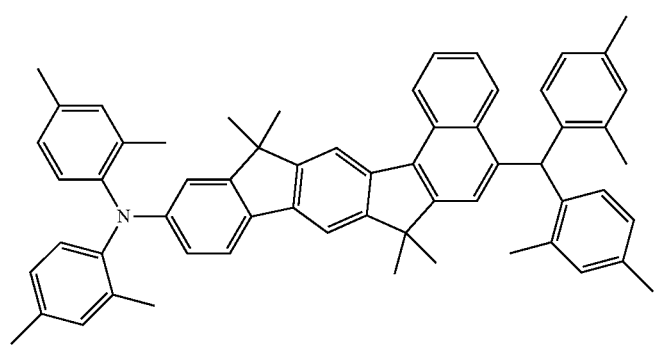
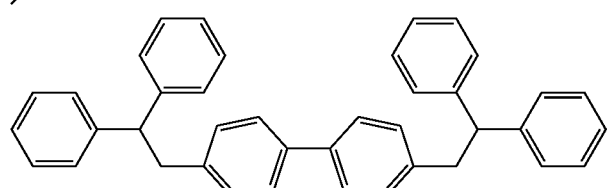
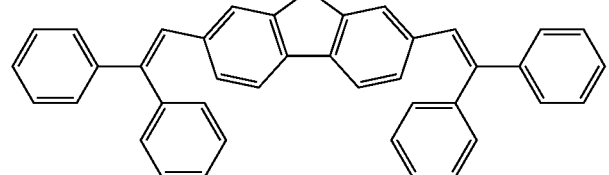

-continued
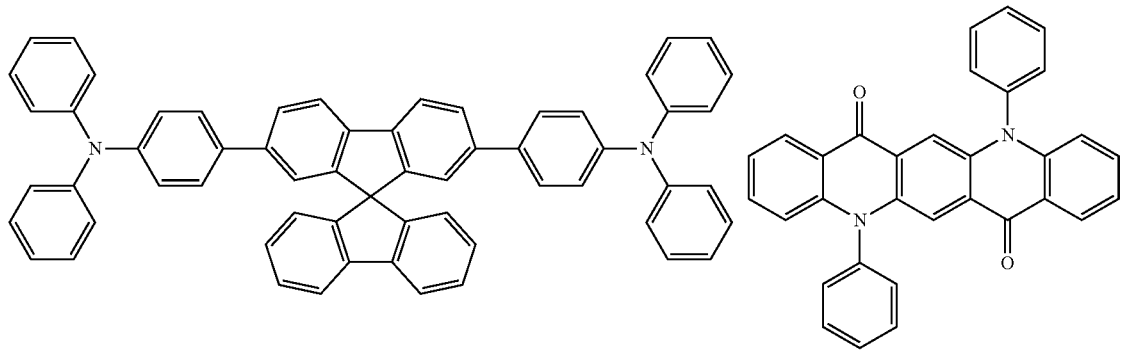
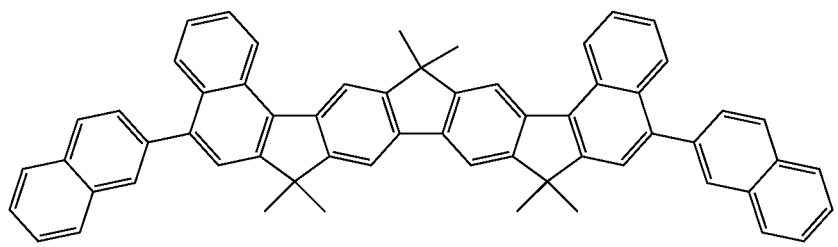
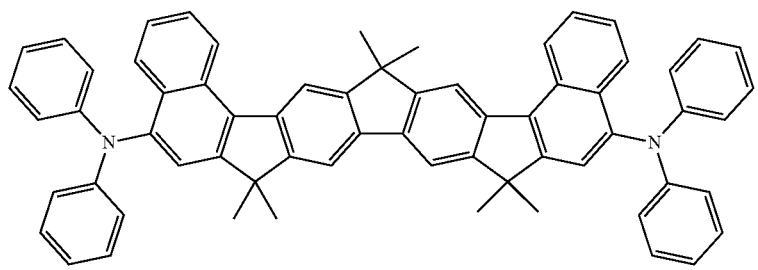
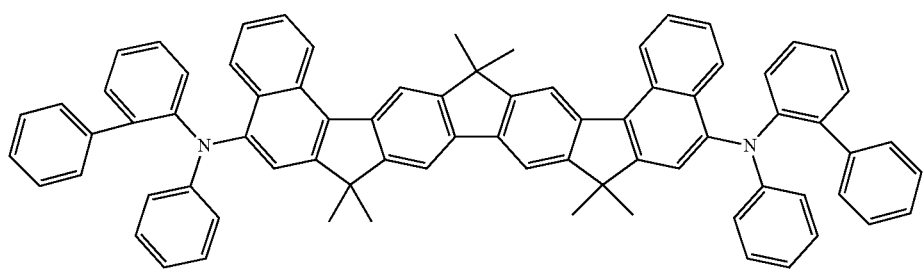
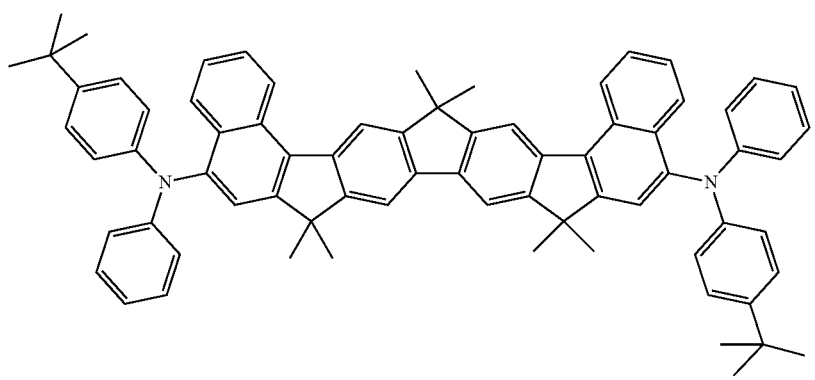

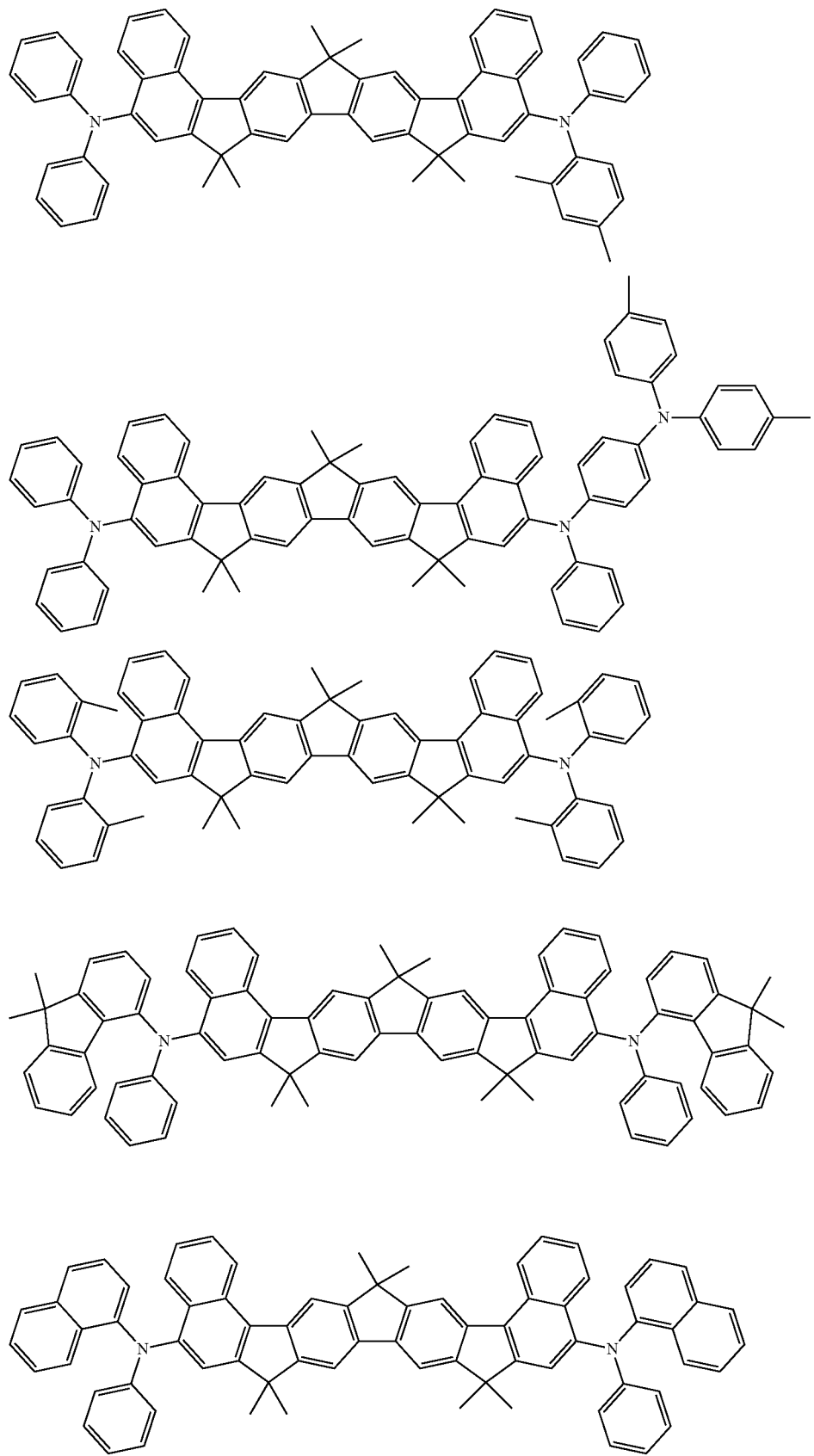

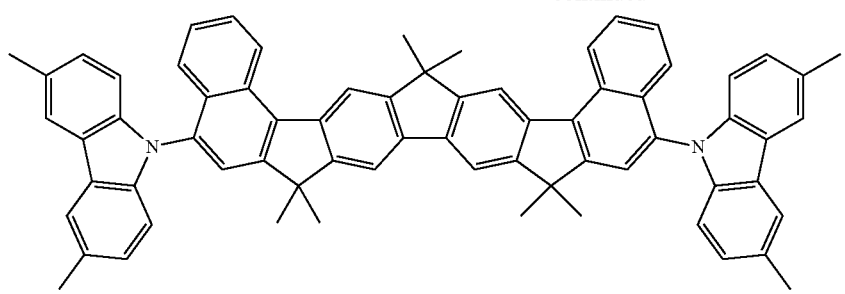
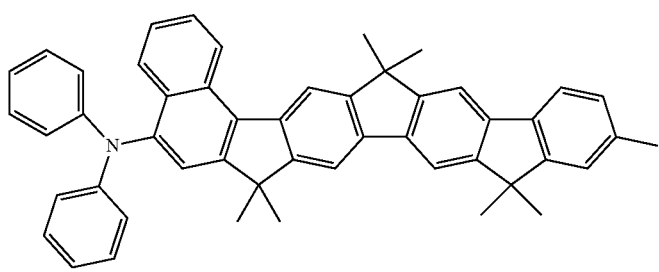
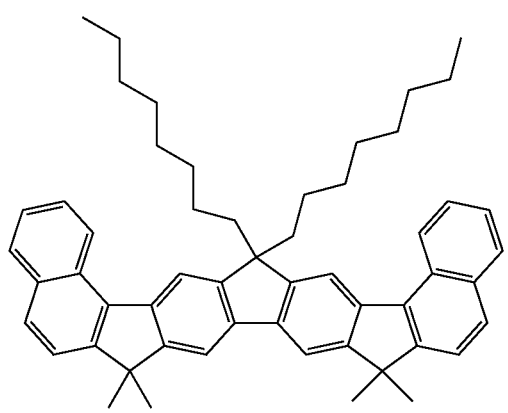
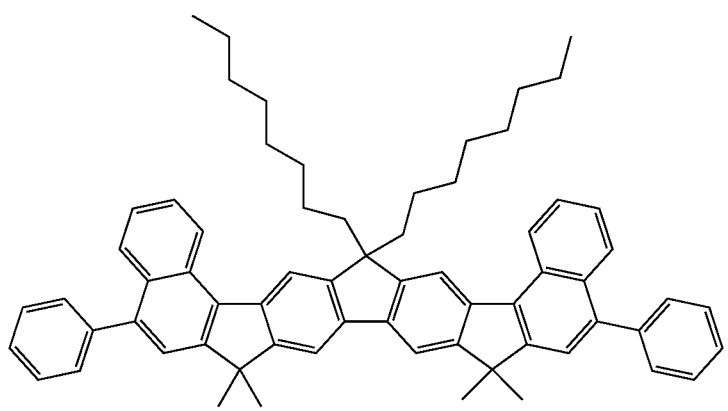

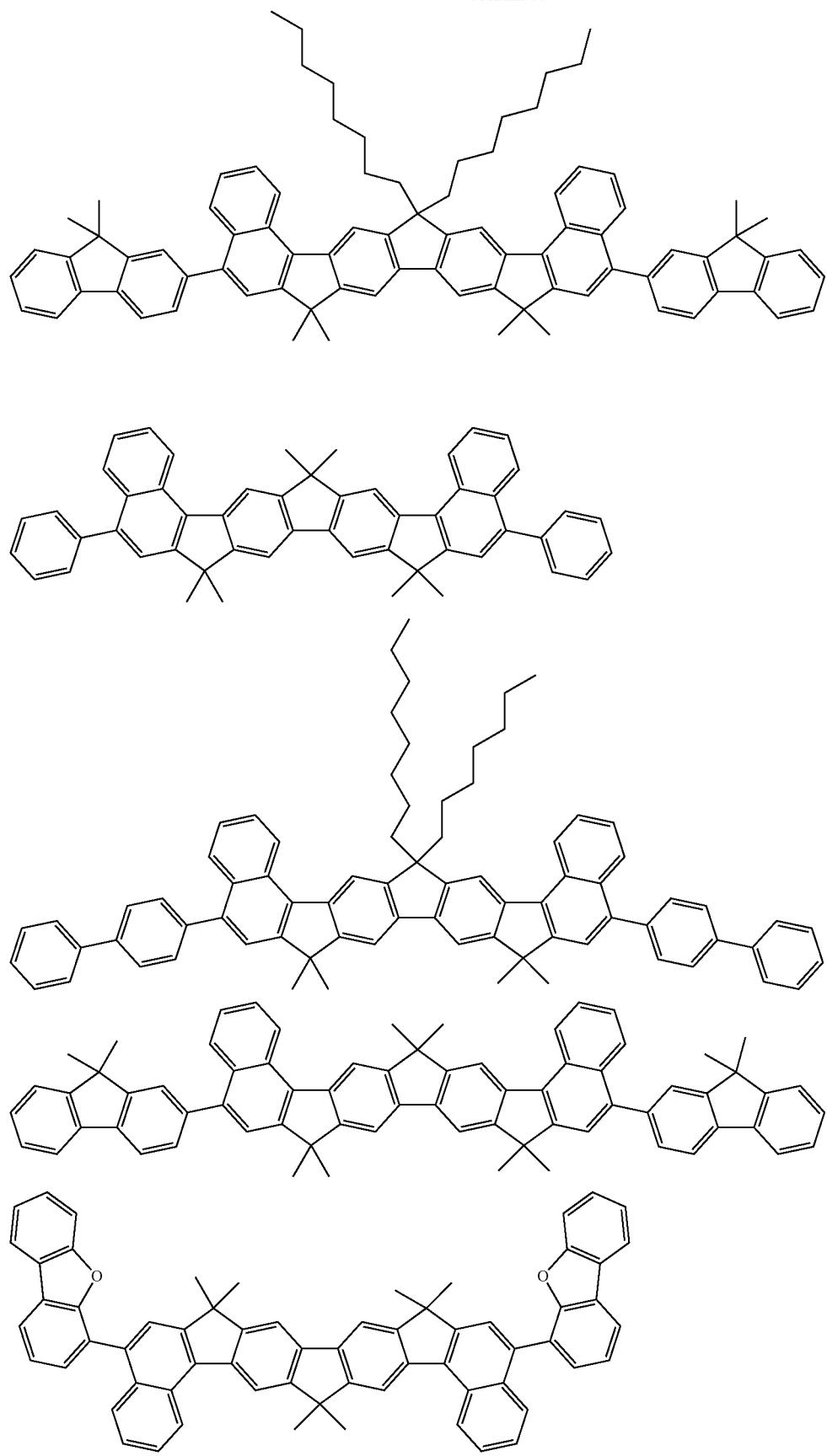

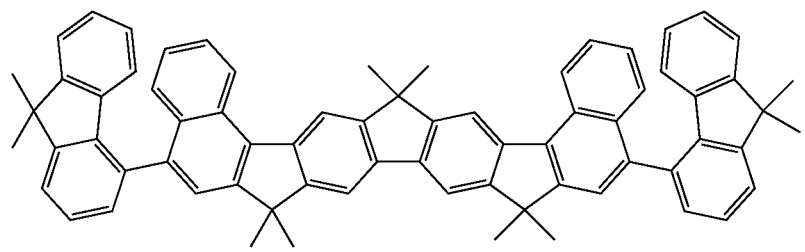
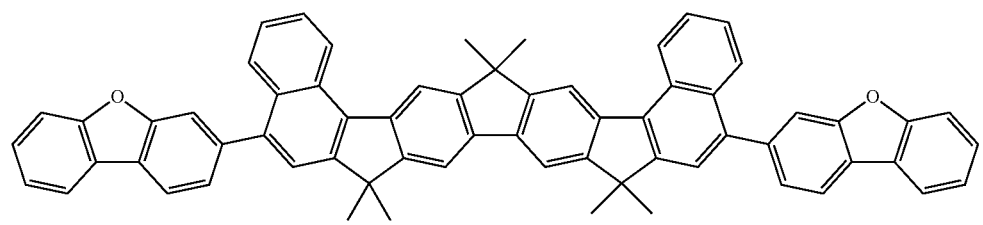
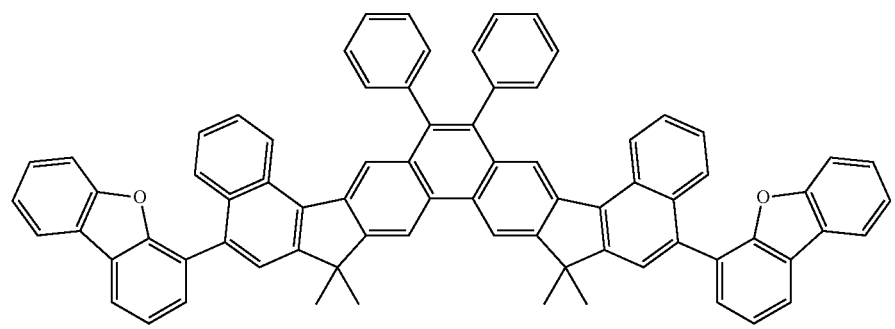
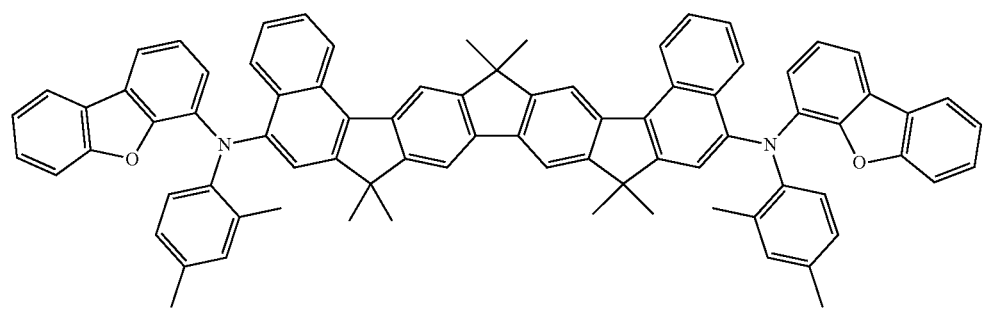
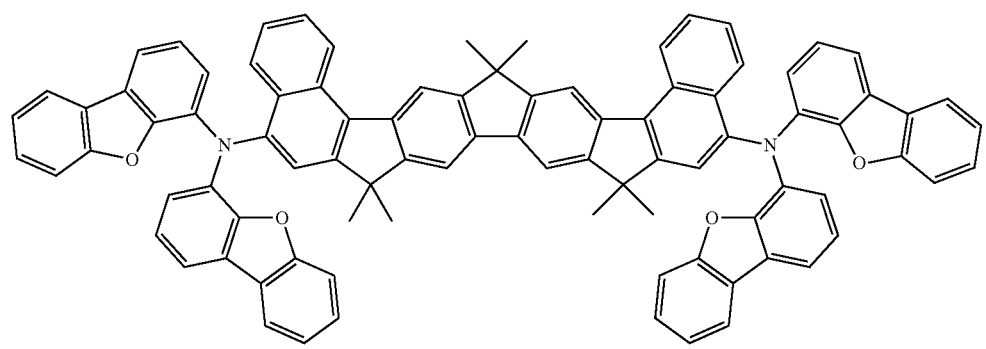

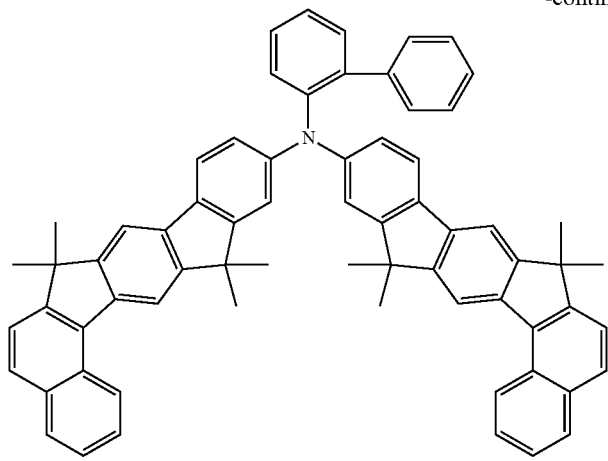

Useful matrix materials, preferably for fluorescent emitting compounds, include materials of various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another. Preference is further given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, the pyrene compounds disclosed in EP 1749809, EP 1905754 and US 2012/0187826, the benzanthracenylanthracene compounds disclosed in WO 2015/158409, the indenobenzofurans disclosed in WO 2017/025165, and the phenanthrylanthracenes disclosed in WO 2017/036573.

Preferred matrix materials for fluorescent emitters for use in the emitting layer of devices comprising the polymers of the invention are shown below:

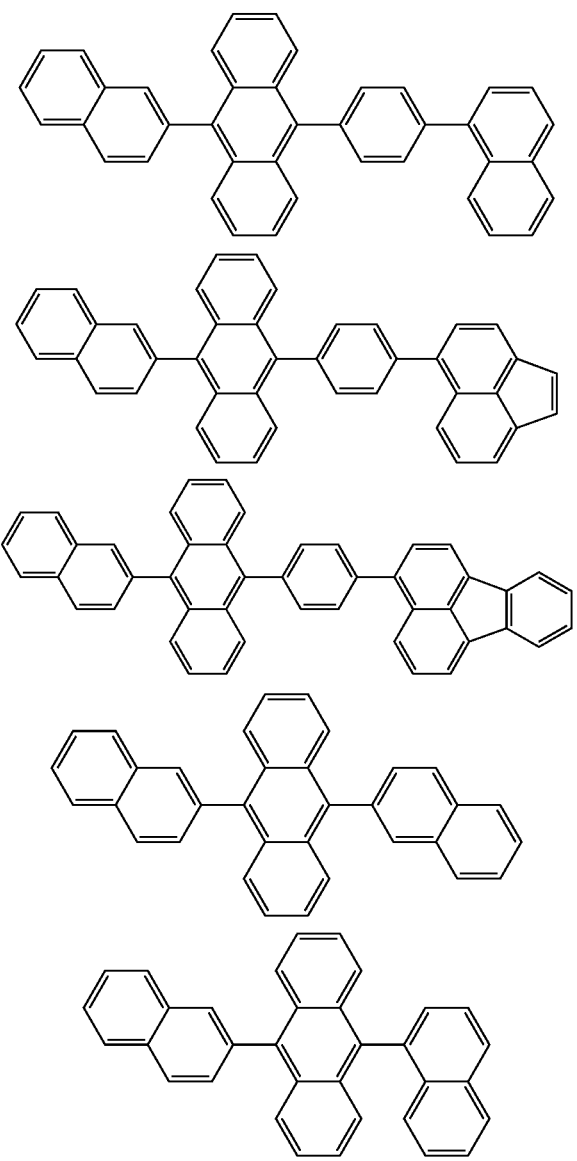

131
-continued
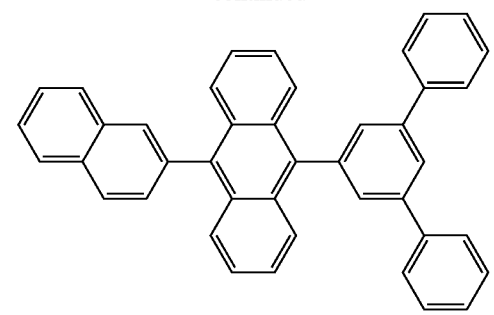
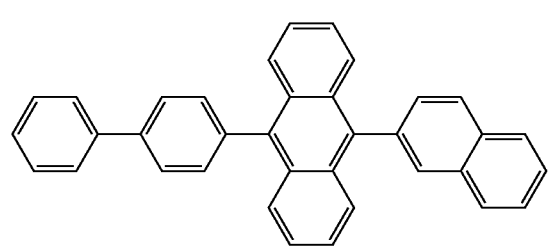
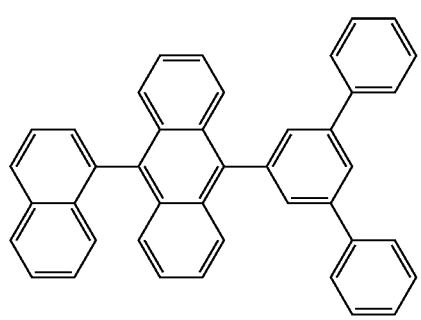
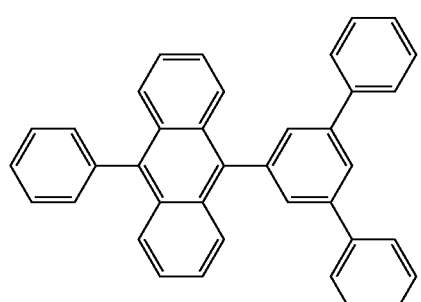
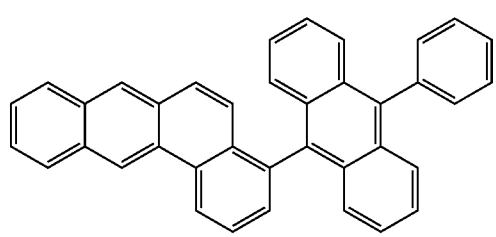
132
-continued
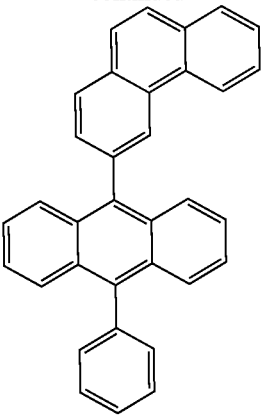
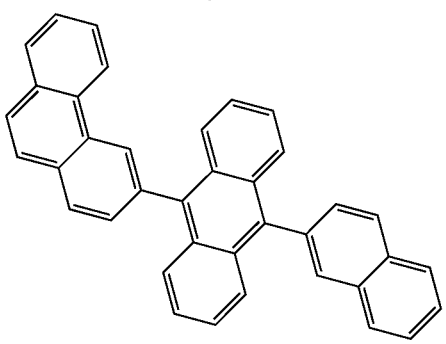
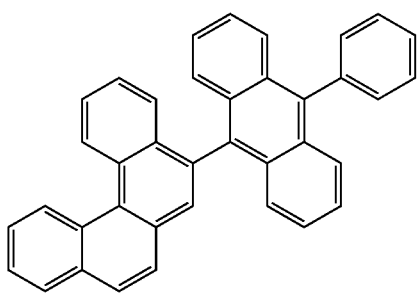
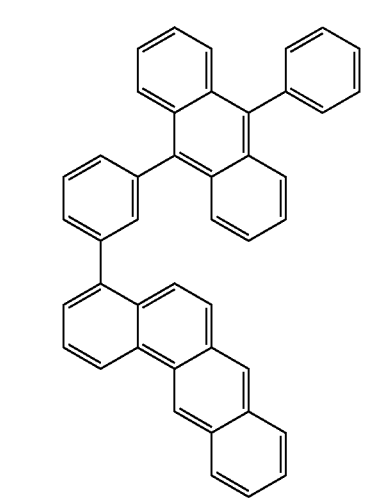

133
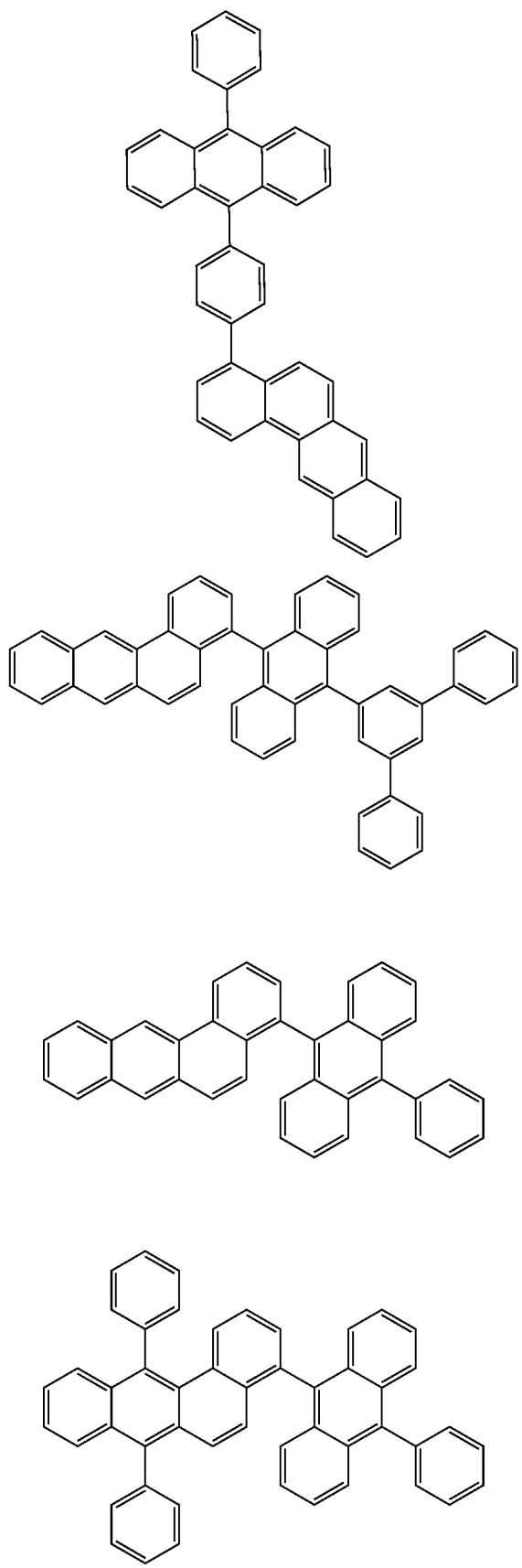
134
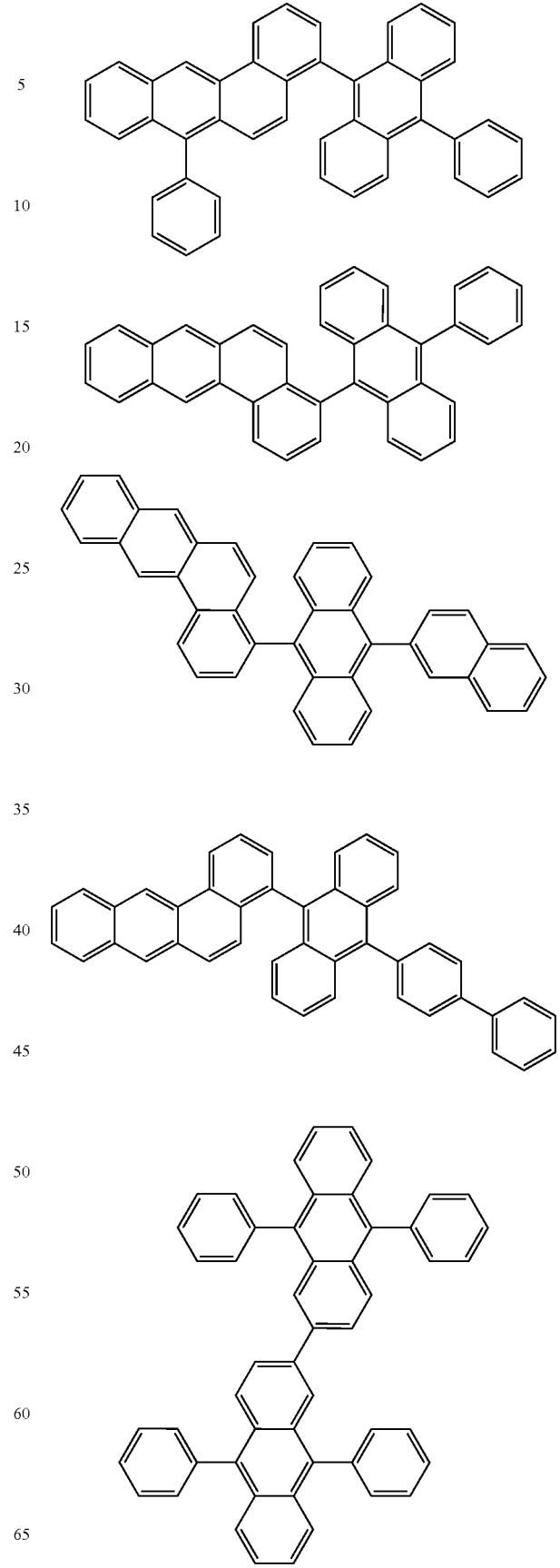

135
-continued
136
-continued
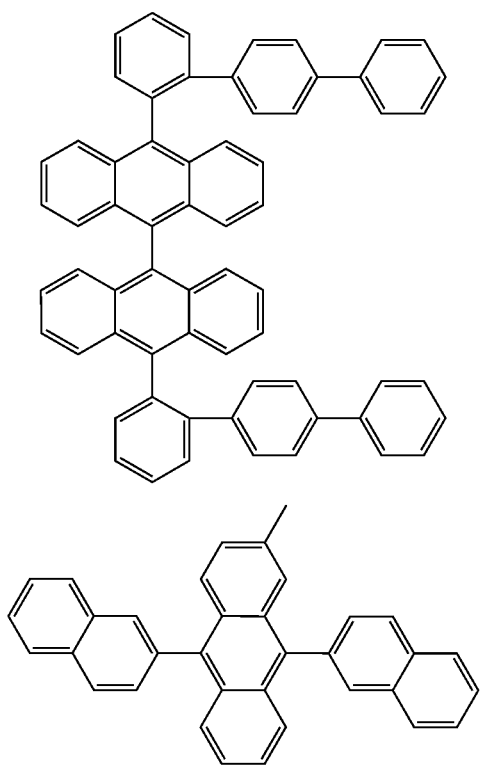
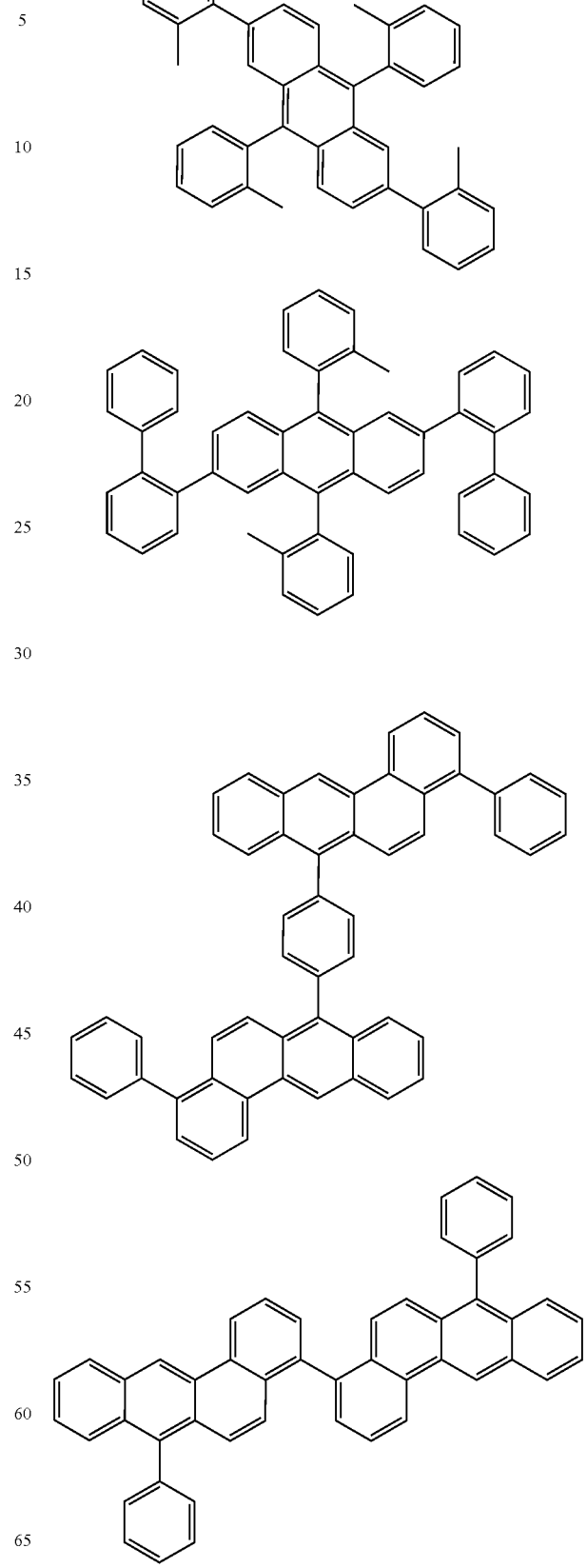

137
-continued
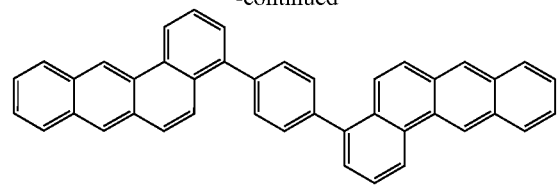
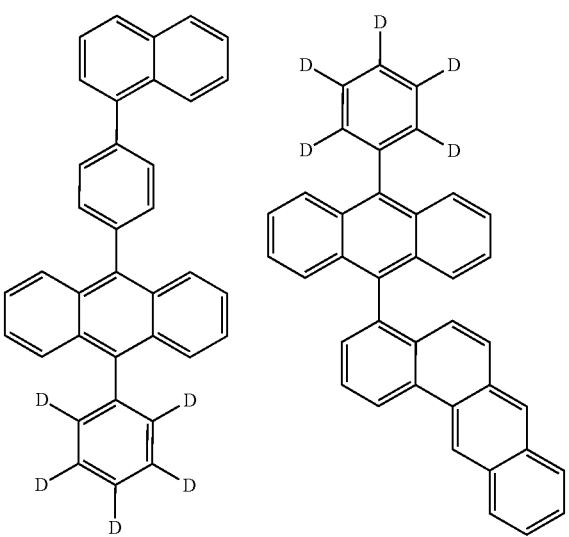
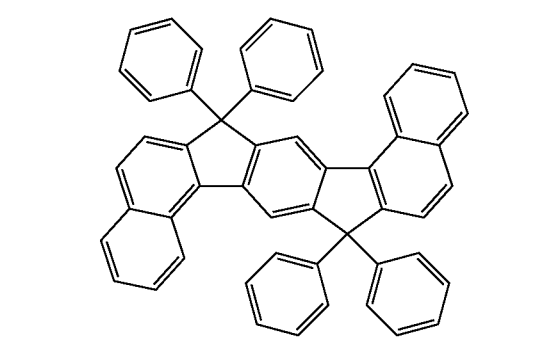
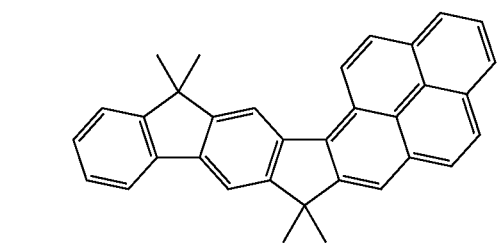
138
-continued
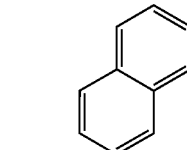
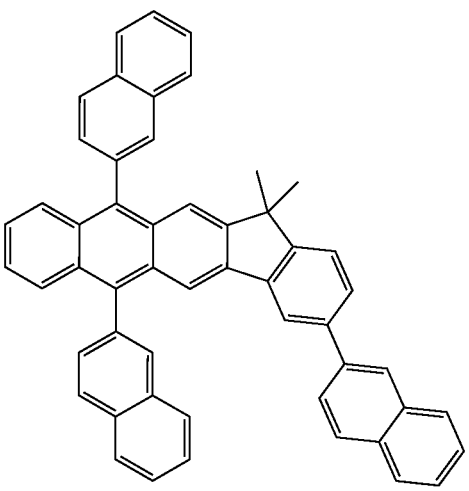
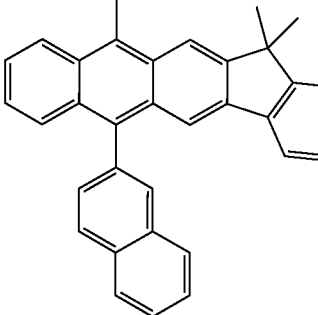
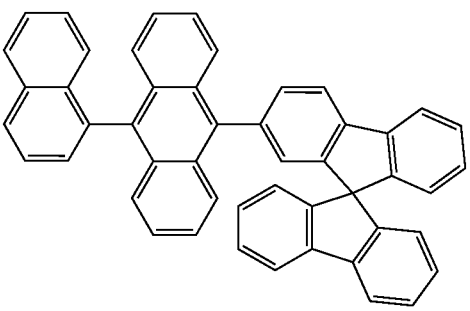
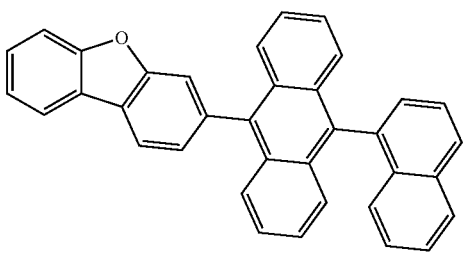
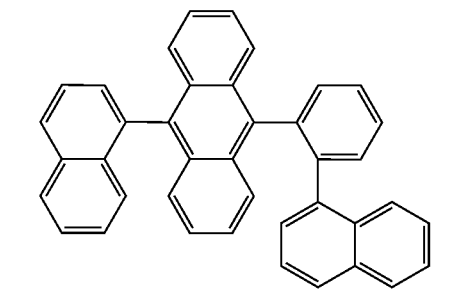
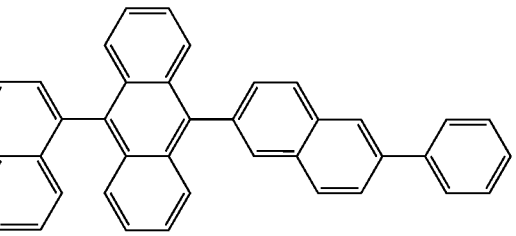

-continued
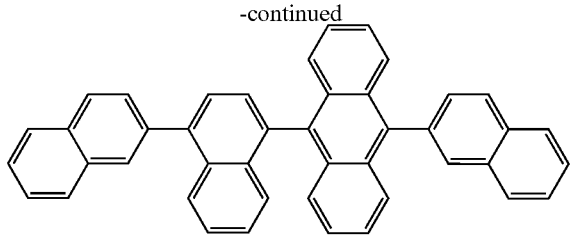
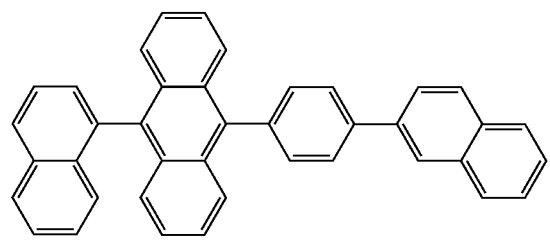
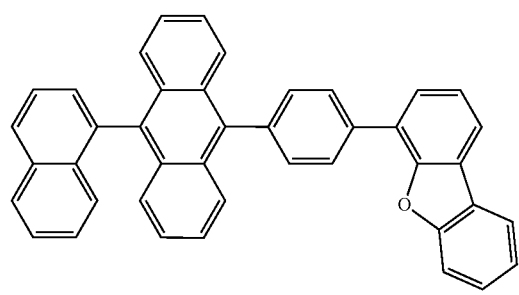
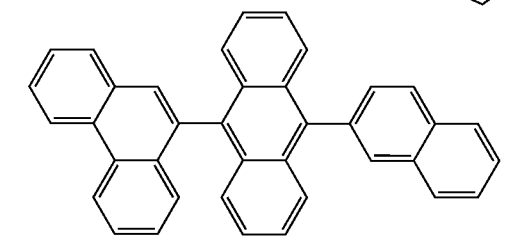
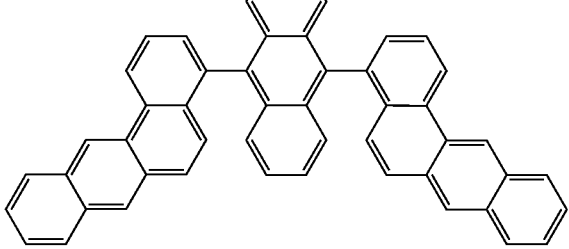
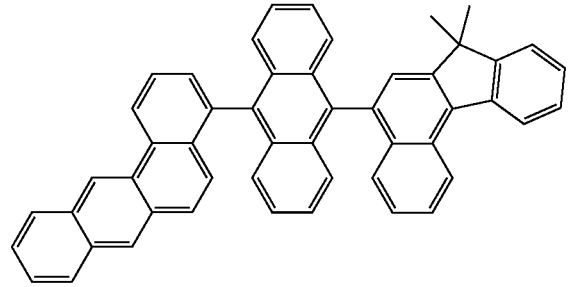
-continued
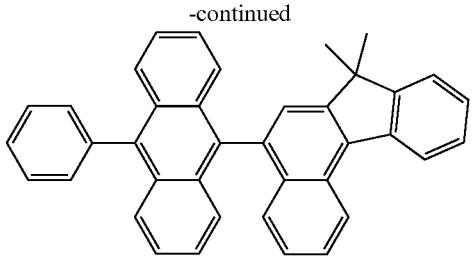
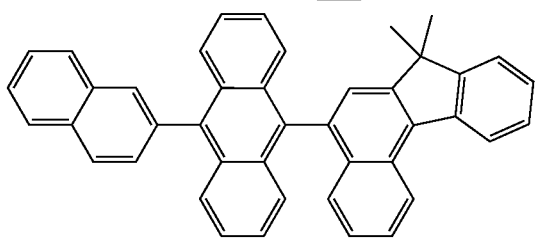
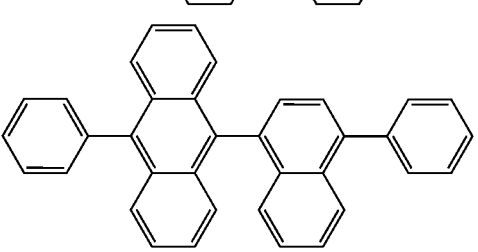
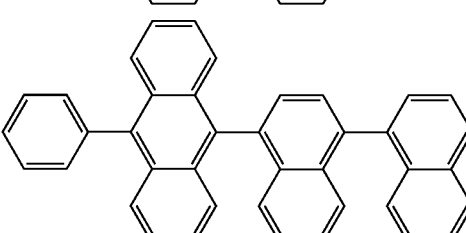
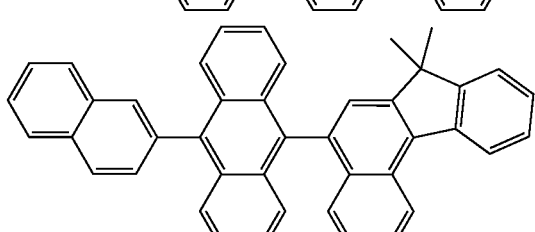
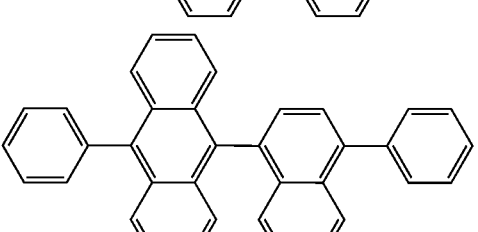
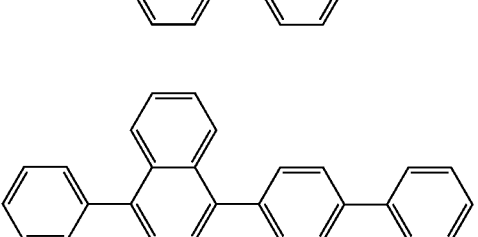

-continued

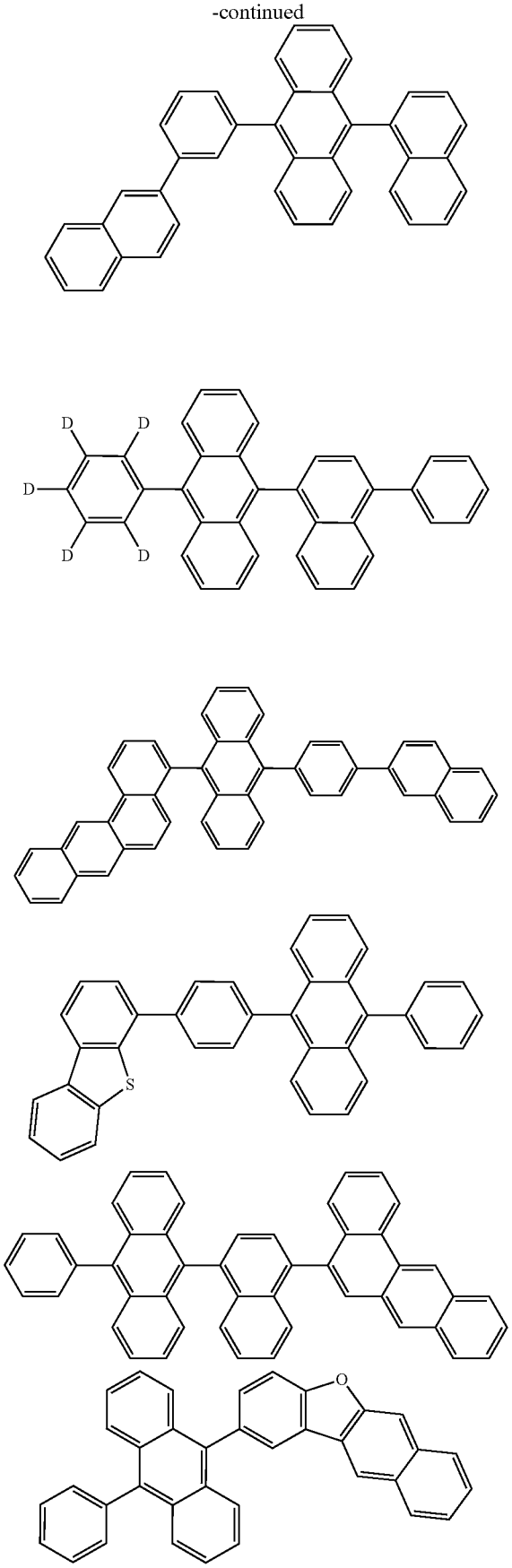

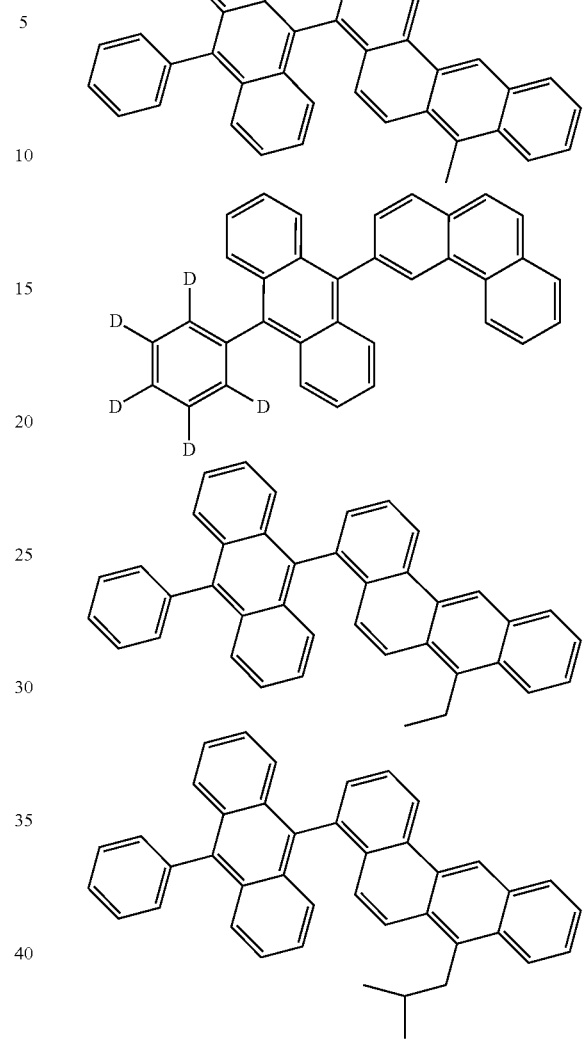

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds.

Examples of the above-described emitting compounds can be found in applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used for phosphorescent OLEDs according to the prior art and as known to those skilled in the art in the field of organic electroluminescent devices are suitable.

Preferred matrix materials for phosphorescent emitting compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109, WO 2011/000455 or WO 2013/041176, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951.

Suitable charge transport materials as usable in the hole injection or hole transport layer or electron blocker layer or in the electron transport layer of the electronic device of the invention are, as well as the polymers of the invention, for example, the compounds disclosed in Y. Shirota et al., Chem. Rev. 2007, 107(4), 953-1010, or other materials as used in these layers according to the prior art.

Materials used for the electron transport layer may, as well as the compounds of the invention, be any materials as used according to the prior art as electron transport materials in the electron transport layer. Especially suitable are aluminium complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the abovementioned compounds as disclosed in JP 2000/053957, WO 2003/060956, WO 2004/028217, WO 2004/080975 and WO 2010/072300.

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LIQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

According to the invention, the electronic devices comprising one or more polymers of the invention can be used in displays, as light sources in lighting applications and as light sources in medical and/or cosmetic applications (e.g. light therapy).

EXAMPLES

A) Synthesis Examples

1) Synthesis of the Monomers of the Invention 1-1) The following building blocks (BB) are used for the synthesis of the monomers for preparation of the polymers of the invention:

a) Tetralin-Analogous Building Blocks

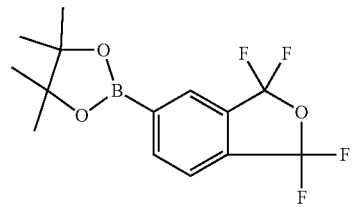

CAS-1562418-39-6
BB-001

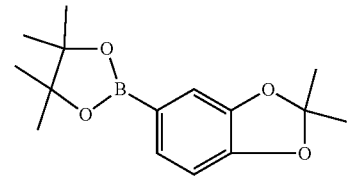

CAS-1562418-43-2
BB-002

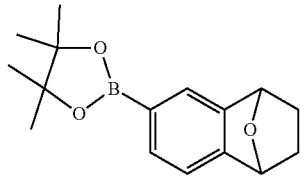

CAS-1562418-44-3
BB-003

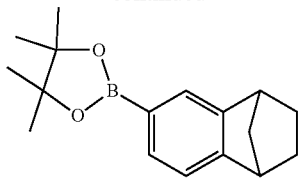
CAS-1562418-27-2
BB-004
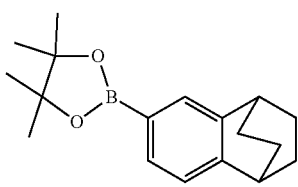
CAS-1801624-60-1
BB-005
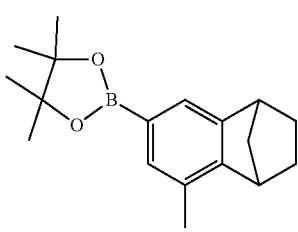
CAS-1562418-29-4
BB-006
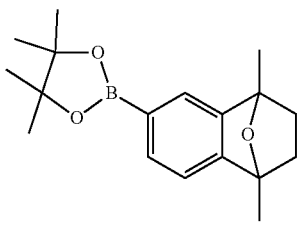
CAS-1562418-47-6
BB-007
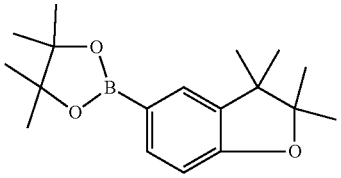
CAS-1562418-41-0
BB-008
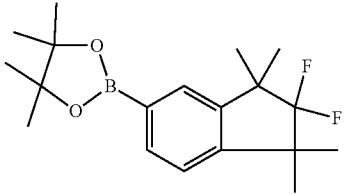
CAS-1562418-25-0
BB-009
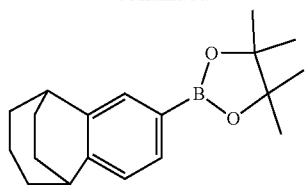
CAS-1801624-62-3
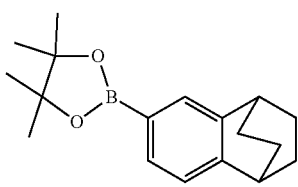
CAS-1562418-31-8
BB-011
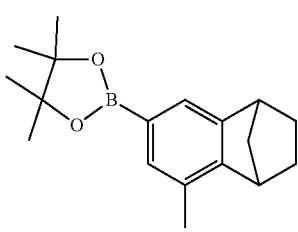
CAS-1312464-73-5
BB-012
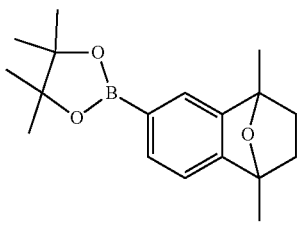
CAS-1562418-49-8
BB-013
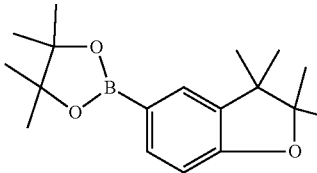
CAS-1801624-61-2
BB-014
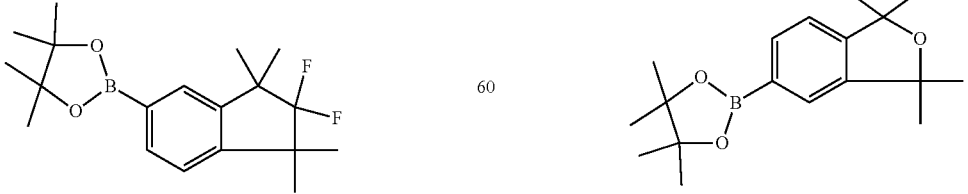
CAS-1562418-37-4
BB-015

147
-continued
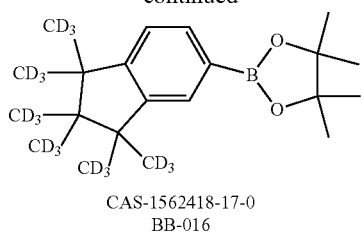
CAS-1562418-17-0
BB-016
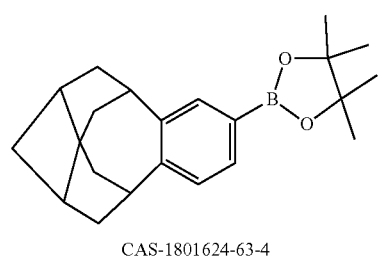
CAS-1801624-63-4
BB-017
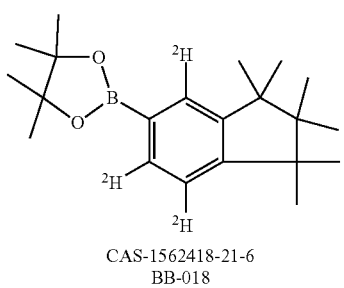
CAS-1562418-21-6
BB-018
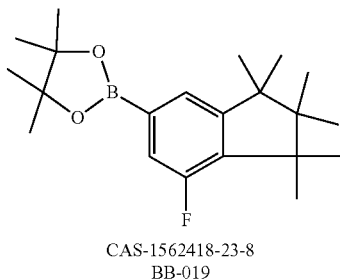
CAS-1562418-23-8
BB-019
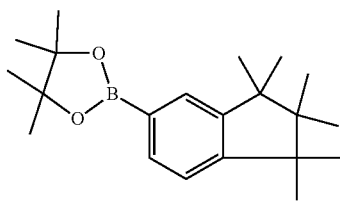
CAS-1562418-16-9
BB-020
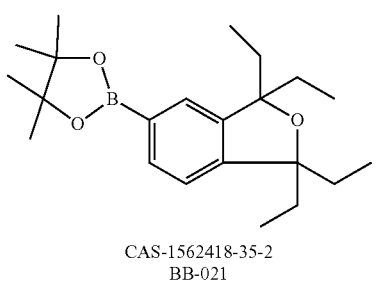
CAS-1562418-35-2
BB-021
148
-continued
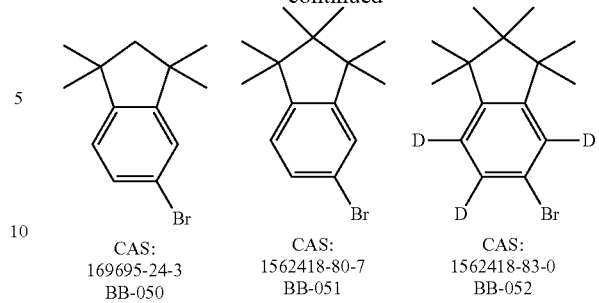
| CAS: 169695-24-3 BB-050 | CAS: 1562418-80-7 BB-051 | CAS: 1562418-83-0 BB-052 |
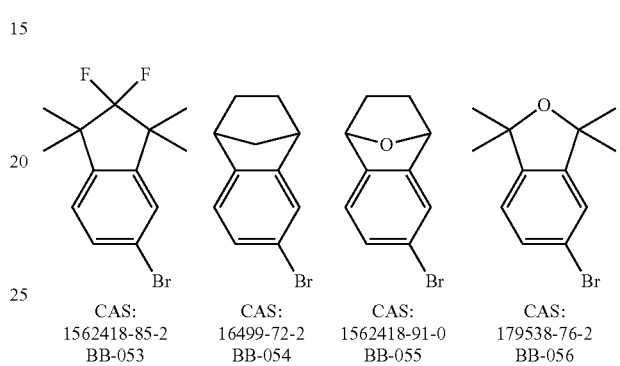
| CAS: 1562418-85-2 BB-053 | CAS: 16499-72-2 BB-054 | CAS: 1562418-91-0 BB-055 | CAS: 179538-76-2 BB-056 |
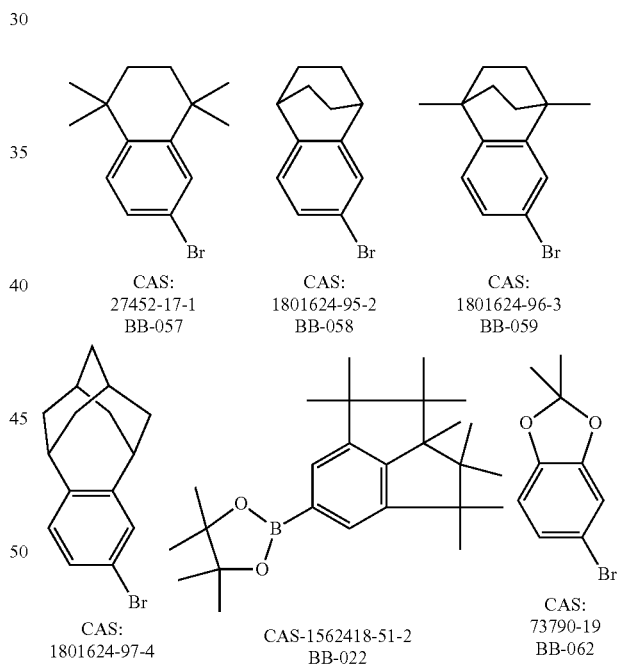
| CAS: 27452-17-1 BB-057 | CAS: 1801624-95-2 BB-058 | CAS: 1801624-96-3 BB-059 |
| CAS: 1801624-97-4 BB-060 | CAS-1562418-51-2 BB-022 | CAS: 73790-19 BB-062 |
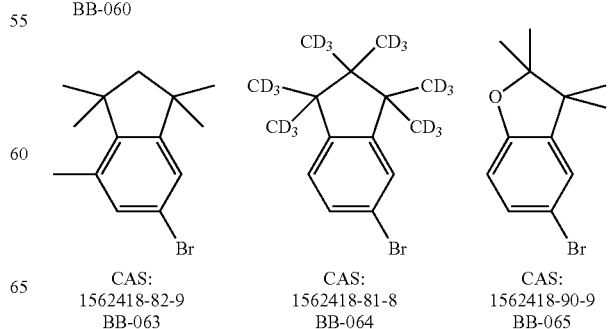
| CAS: 1562418-82-9 BB-063 | CAS: 1562418-81-8 BB-064 | CAS: 1562418-90-9 BB-065 |

-continued
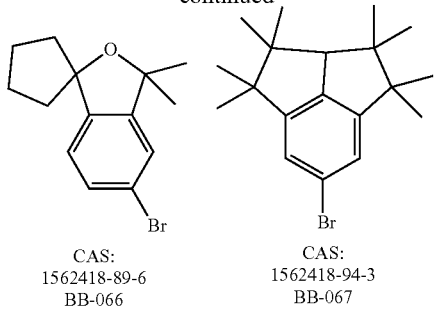
CAS:
1562418-89-6
BB-066
CAS:
1562418-94-3
BB-067
b) Amine Building Blocks
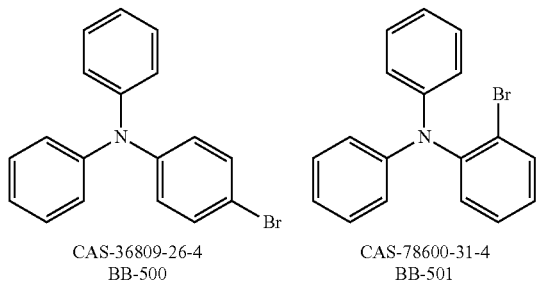
CAS-36809-26-4
BB-500
CAS-78600-31-4
BB-501
CAS-78600-33-6
BB-502
CAS-449153-47-3
BB-503
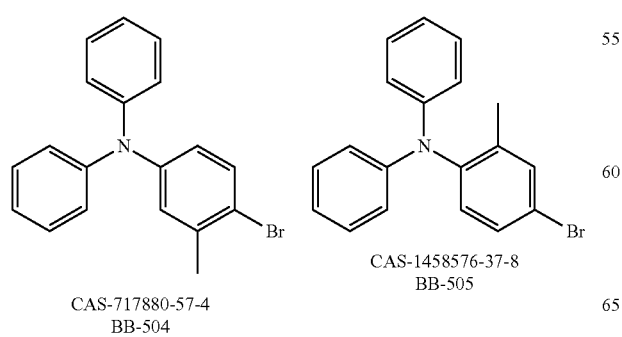
CAS-717880-57-4
BB-504
CAS-1458576-37-8
BB-505
-continued
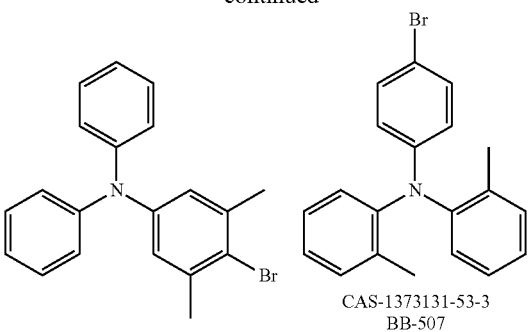
CAS-883550-96-7
BB-506
CAS-1373131-53-3
BB-507
CAS-227314-47-8
BB-508
CAS-1807906-06-4
BB-509
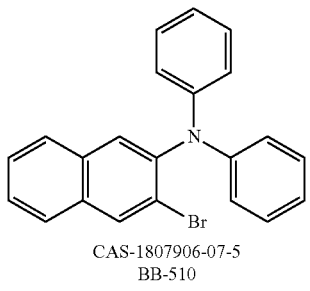
CAS-1807906-07-5
BB-510
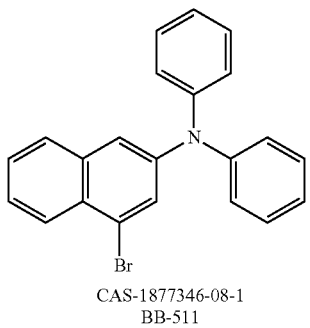
CAS-1877346-08-1
BB-511
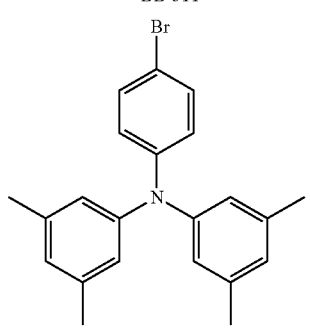
CAS-1372115-87-1
BB-512

-continued
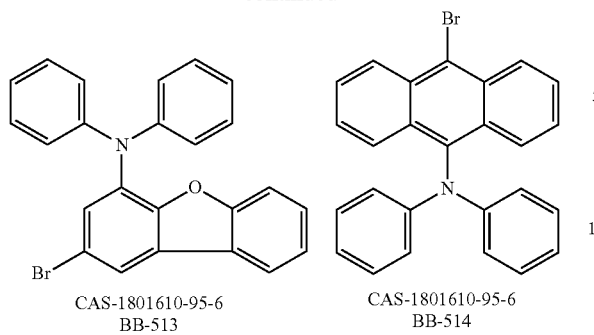
CAS-1801610-95-6
BB-513
CAS-1801610-95-6
BB-514
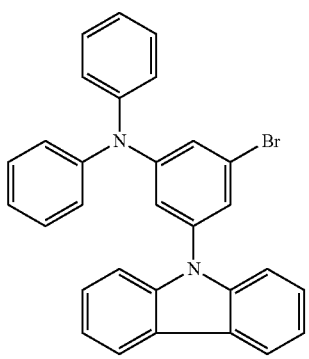
CAS-1686098-89-4
BB-515
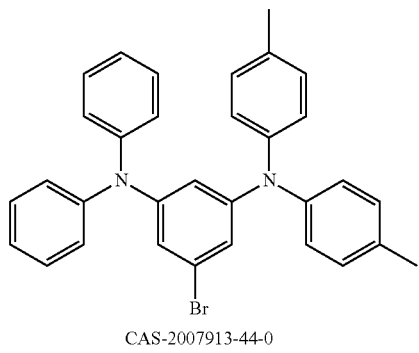
CAS-2007913-44-0
BB-516
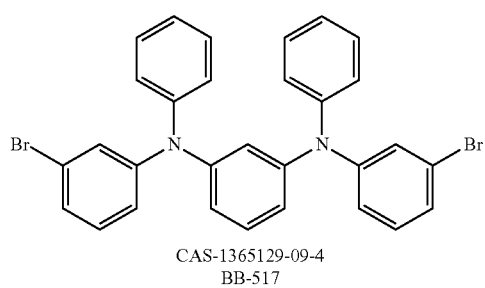
CAS-1365129-09-4
BB-517
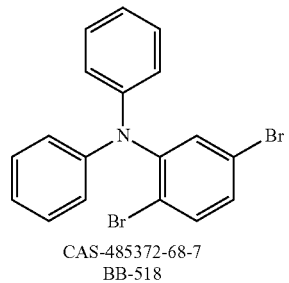
CAS-485372-68-7
BB-518
-continued
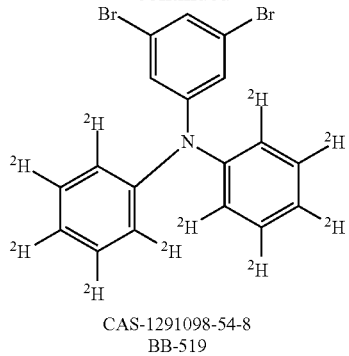
CAS-1291098-54-8
BB-519
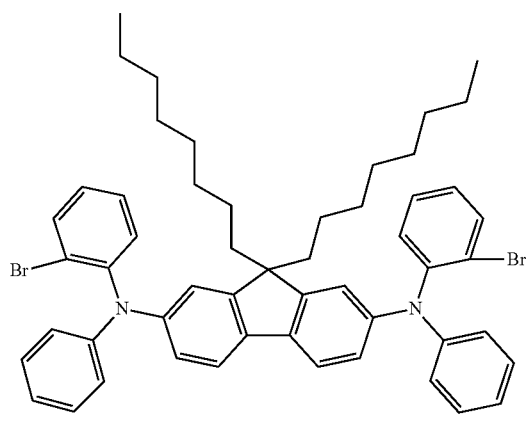
BB-520
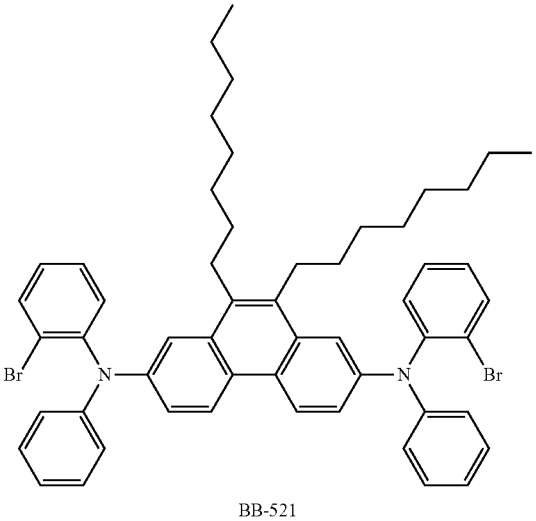
BB-521

-continued

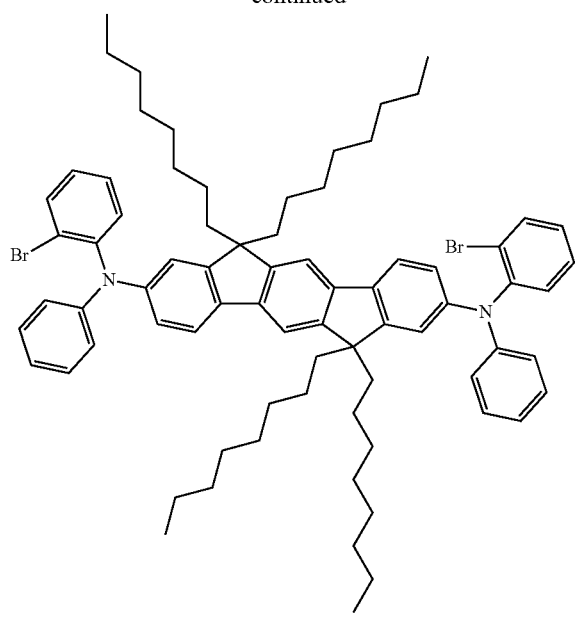

BB-522

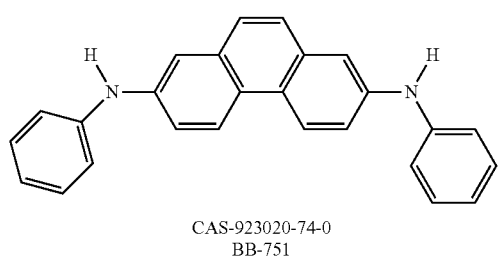

CAS-122-39-4
BB-750

CAS-923020-74-0
BB-751

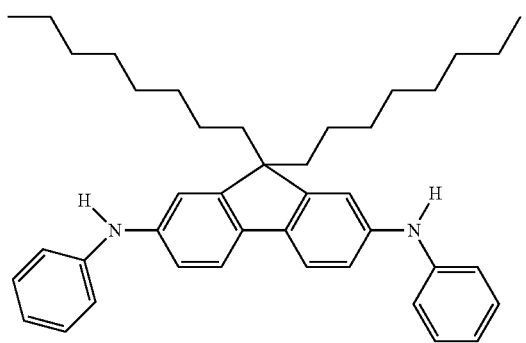

CAS-915031-04-8
BB-752

1-2) Suzuki reaction of the tetralin-analogous building blocks and the amine building blocks to give coupling products Example Reaction

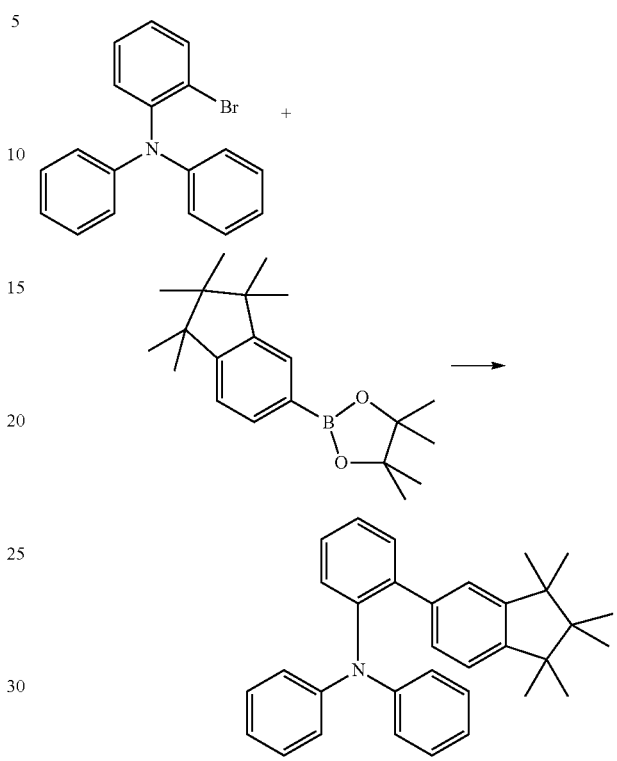

Into a 2 litre four-neck flask with precision glass stirrer, heating bath, reflux condenser and argon connection are weighed 57 g (176 mmol) of BB-501, 57.7 g (176 mmol, 1 eq.) of BB-020, 10.16 g (9 mmol, 0.05 eq) of tetrakis(triphenylphosphine)palladium(0) (CAS: 14221-01-3) and 53.46 g (387 mmol, 2.2 eq) potassium carbonate, and the system is inertized with protective gas. 400 ml of toluene, 250 ml of 1,4-dioxane and 115 ml of water are added, and the reaction mixture is heated under reflux for 24 h. After cooling, the mixture is diluted with water, the organic phase is separated off and the solvent is removed under reduced pressure. The residue is repeatedly recrystallized from heptane and then sublimed. 34.8 g (44.42%, 78 mmol) of the colourless solid DB-1031 are obtained.

The following structures can be obtained by the same method and with similar yields:

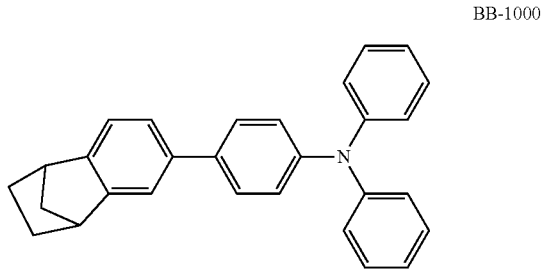

BB-1000

BB-500 + BB-004

BB-1001
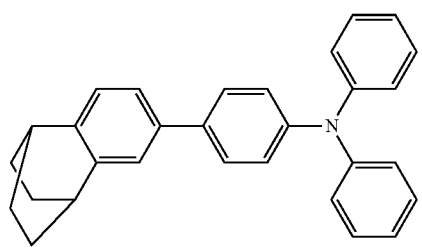
BB-500 + BB-005
BB-1002
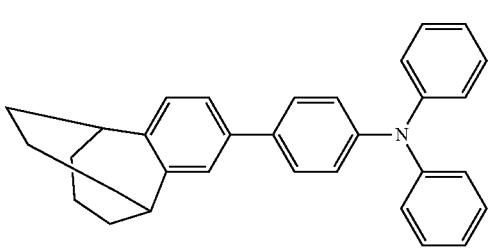
BB-500 + BB-010
BB-1003
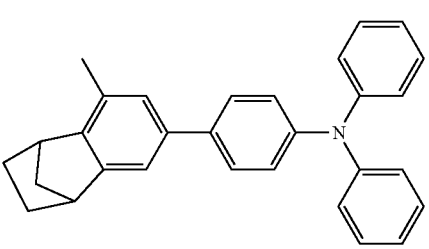
BB-500 + BB-006
BB-1004
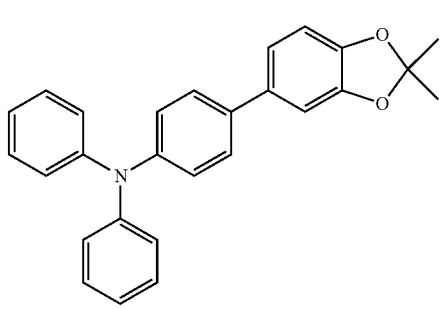
BB-500 + BB-002
BB-1005
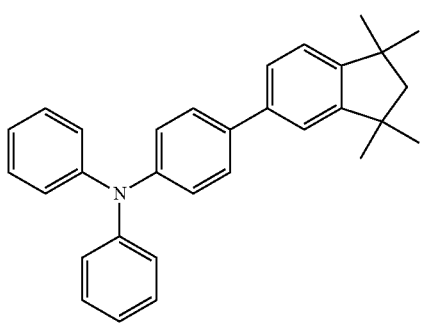
BB-500 + BB-012
BB-1006
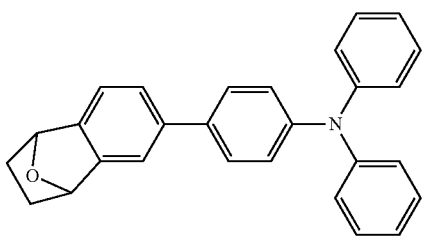
BB-500 + BB-003
BB-1007
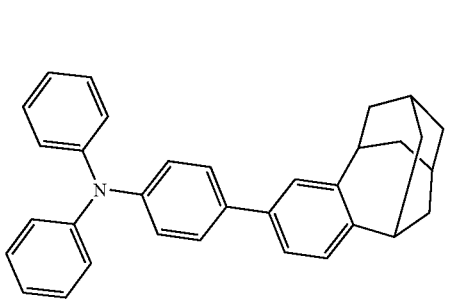
BB-500 + BB-017
BB-1008
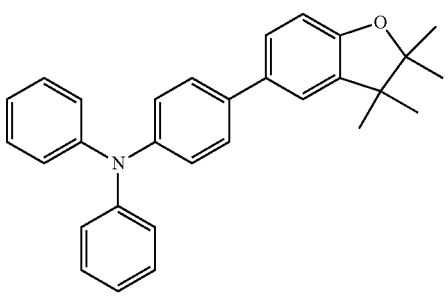
BB-500 + BB-008
BB-1009
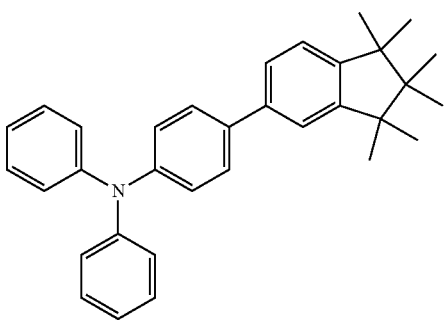
BB-500 + BB-020

-continued
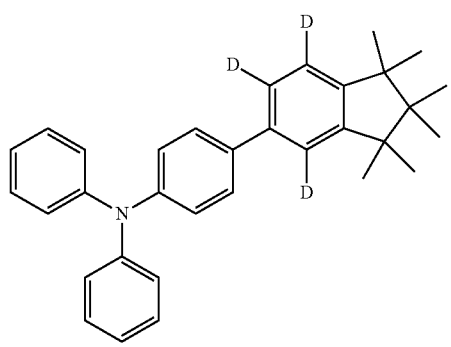
BB-1010
BB-500 + BB0-18
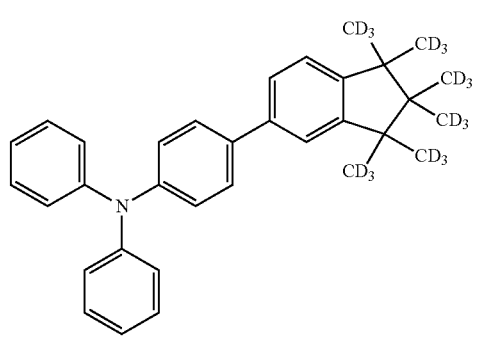
BB-1011
BB-500 + BB-016
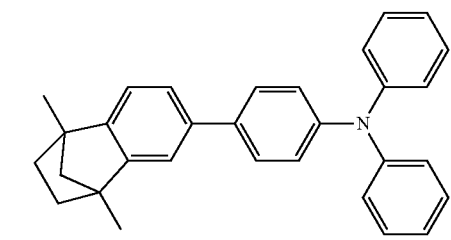
BB-1012
BB-500 + BB-011
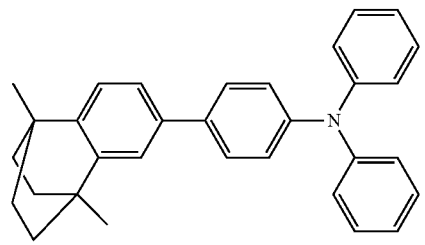
BB-1013
BB-500 + BB-014
-continued
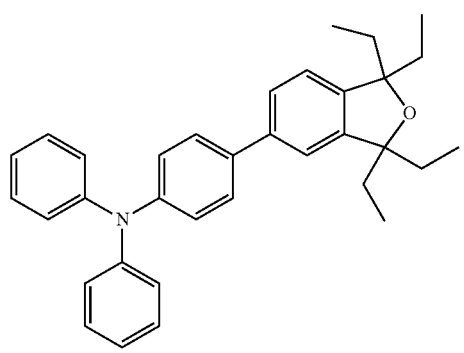
BB-1014
BB-500 + BB-021
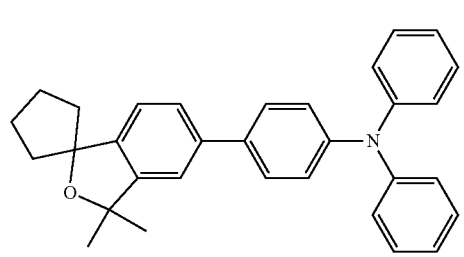
BB-1015
BB-500 + BB-015
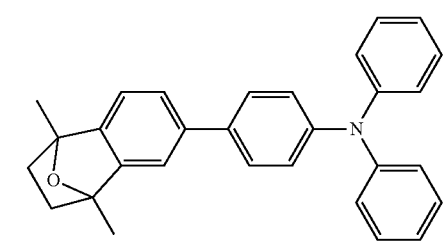
BB-1016
BB-500 + BB-007
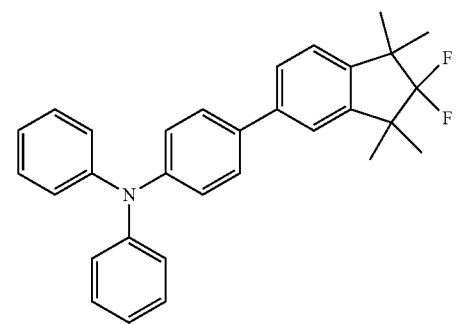
BB-1017
BB-500 + BB-009

-continued
BB-1018
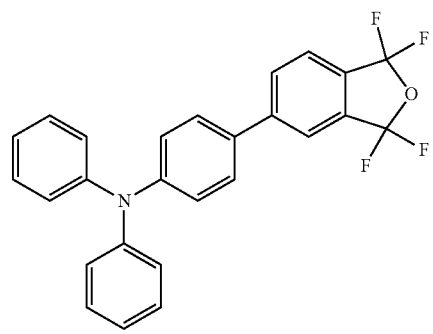
BB-500 + BB-001
BB-1019
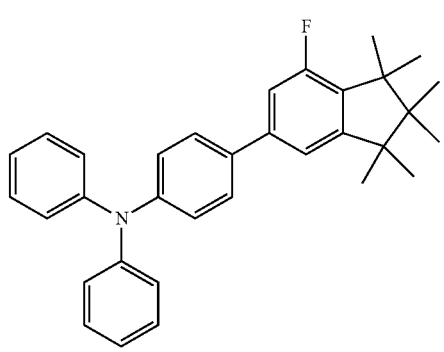
BB-500 + BB-019
BB-1020
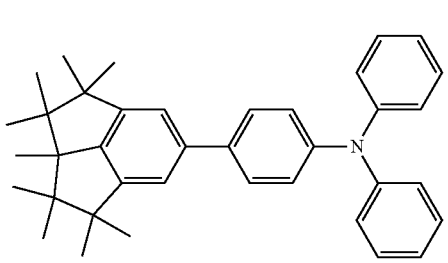
BB-500 + BB-022
BB-1021

BB-500 + BB-013
-continued
BB-1022
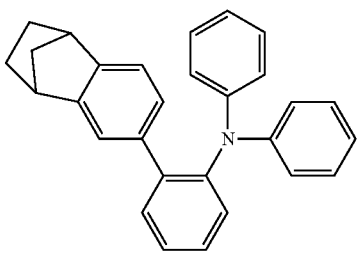
BB-501 + BB-004
BB-1023
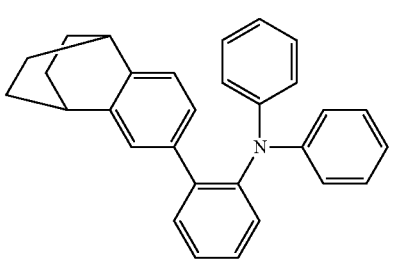
BB-501 + BB-005
BB-1024
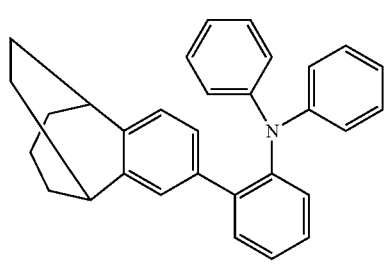
BB-501 + BB-010
BB-1025
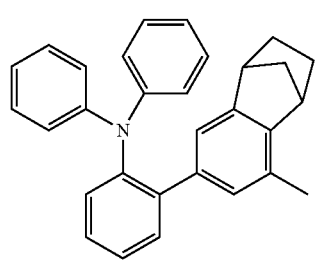
BB-501 + BB-006
BB-1026
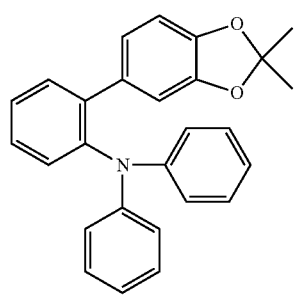
BB-501 + BB-002

BB-1027
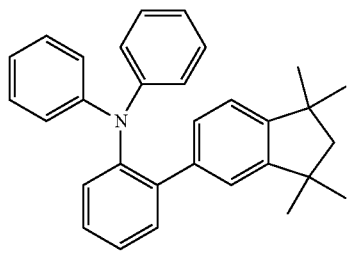
BB-501 + BB-012
BB-1028
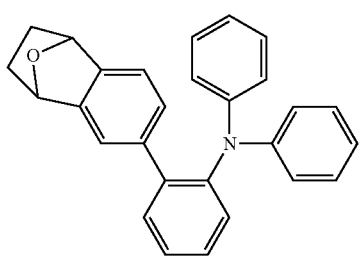
BB-501 + BB-003
BB-1029
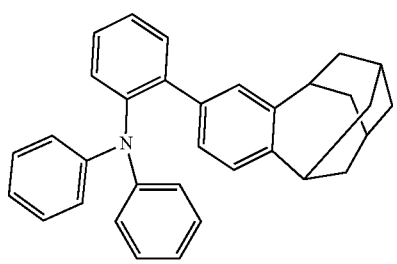
BB-501 + BB-017
BB-1030
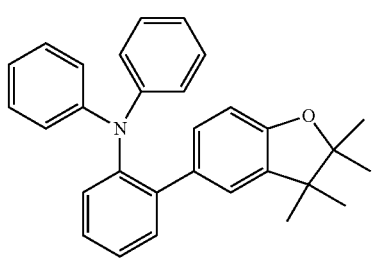
BB-501 + BB-008
BB-1031
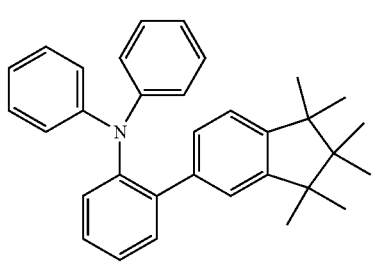
BB-501 + BB-020
BB-1032
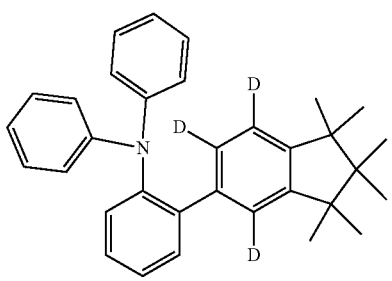
BB-501 + BB-018
BB-1033
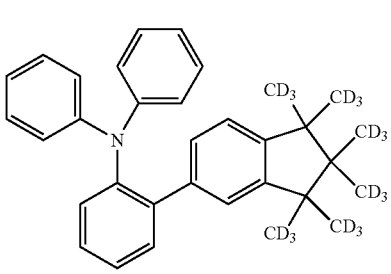
BB-501 + BB-016
BB-1034
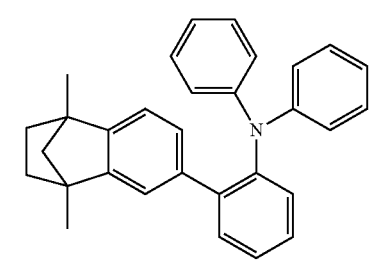
BB-501 + BB-011
BB-1035
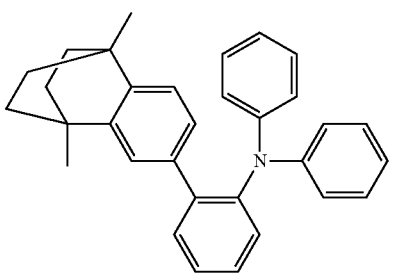
BB-501 + BB-014
BB-1036
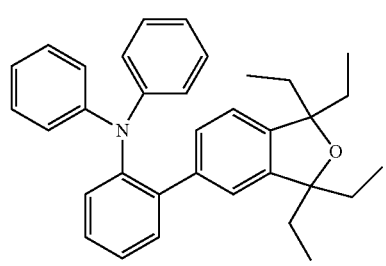
BB-501 + BB-021

-continued
BB-1037
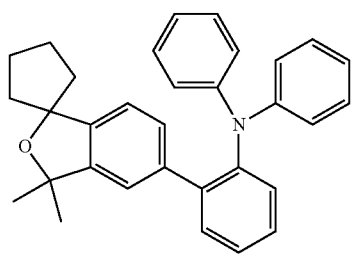
BB-501 + BB-015
BB-1038
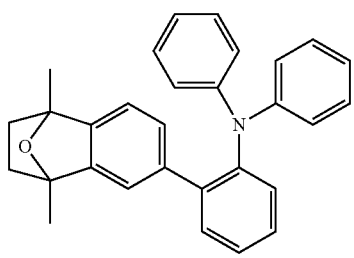
BB-501 + BB-007
BB-1039
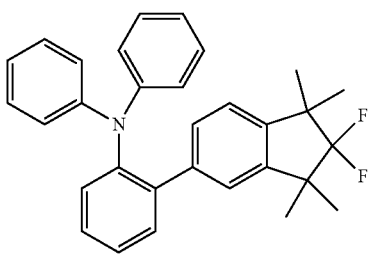
BB-501 + BB-009
BB-1040
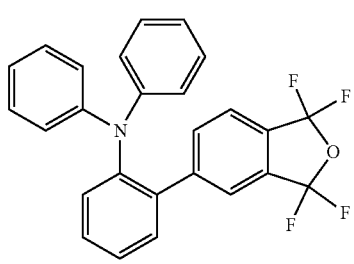
BB-501 + BB-001
BB-1041
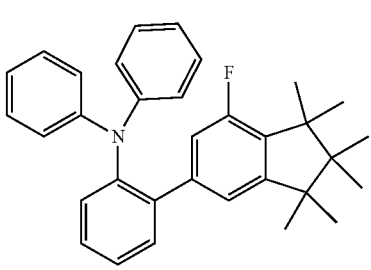
BB-501 + BB-019
-continued
BB-1042
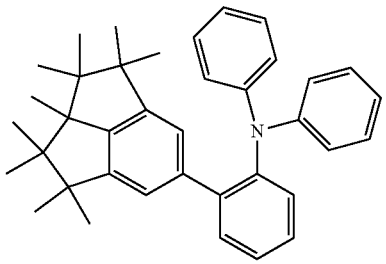
BB-501 + BB-022
BB-1043
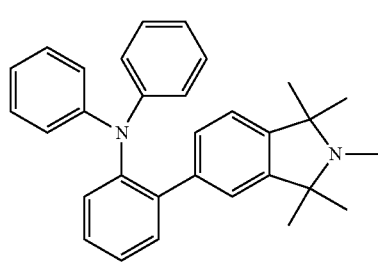
BB-501 + BB-013
BB-1044
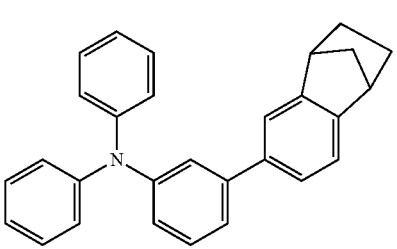
BB-502 + BB-004
BB-1045
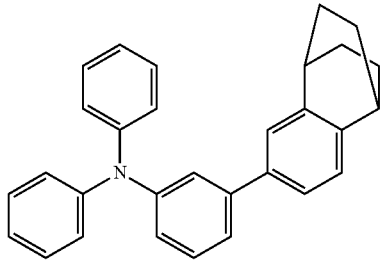
BB-502 + BB-005
BB-1046
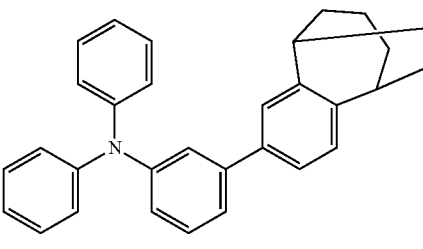
BB-502 + BB-010

-continued
BB-1047
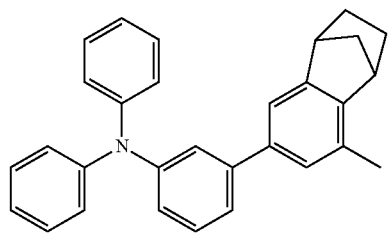
BB-502 + BB-006
BB-1048
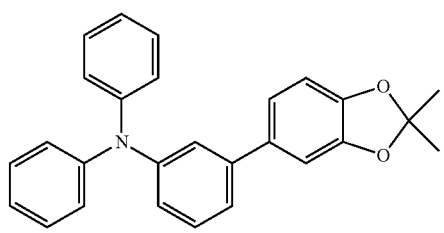
BB-502 + BB-002
BB-1049
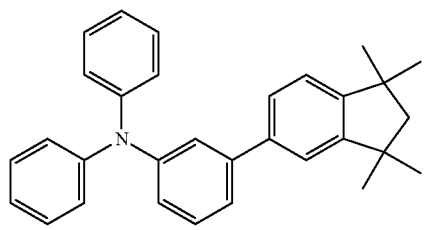
BB-502 + BB-012
BB-1050
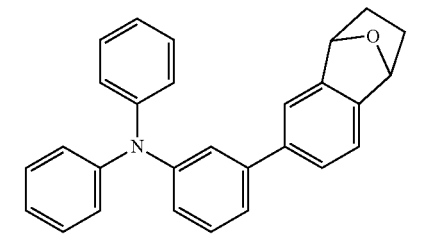
BB-502 + BB-003
BB-1051
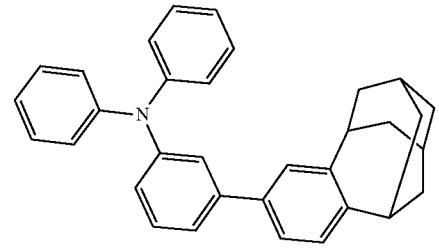
BB-502 + BB-017
-continued
BB-1052
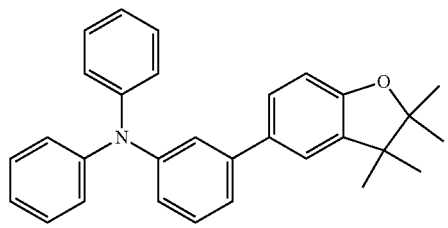
BB-502 + BB-008
BB-1053
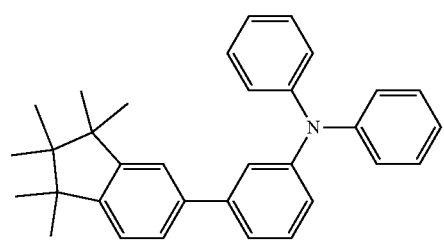
BB-502 + BB-020
BB-1054
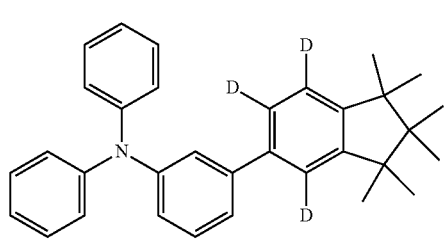
BB-502 + BB-018
BB-1055
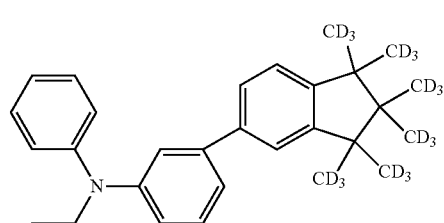
BB-502 + BB-016
BB-1056
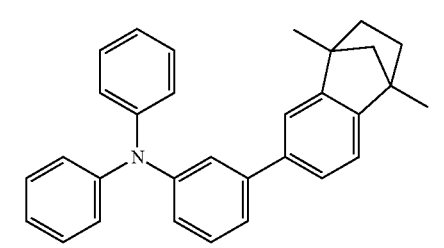
BB-502 + BB-011

BB-1057
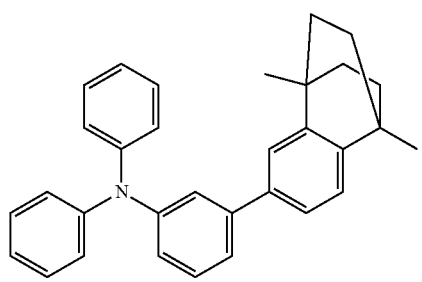
BB-502 + BB-014
BB-1058
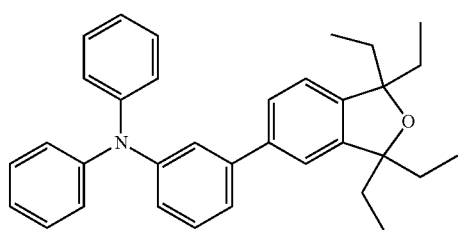
BB-502 + BB-021
BB-1059
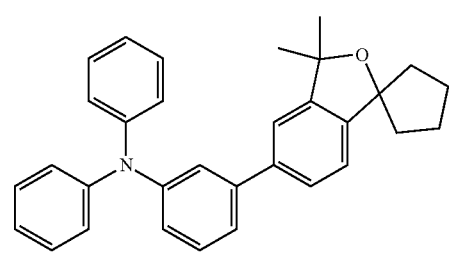
BB-502 + BB-015
BB-1060
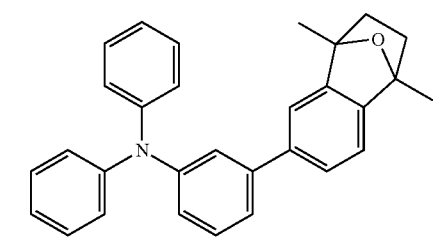
BB-502 + BB-007
BB-1061
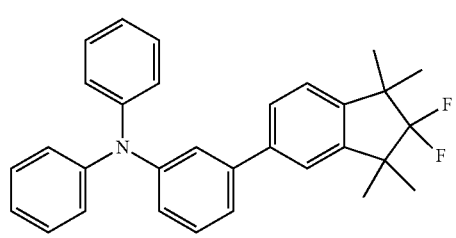
BB-502 + BB-009
BB-1062
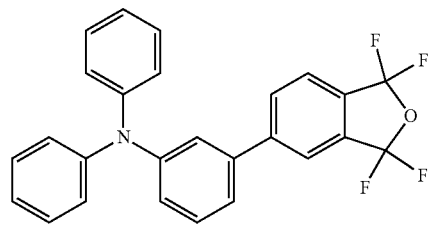
BB-502 + BB-001
BB-1063
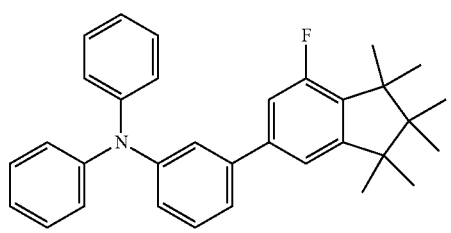
BB-502 + BB-019
BB-1064
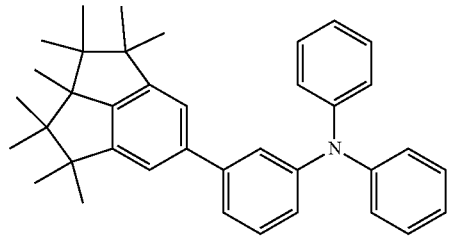
BB-502 + BB-022
BB-1065
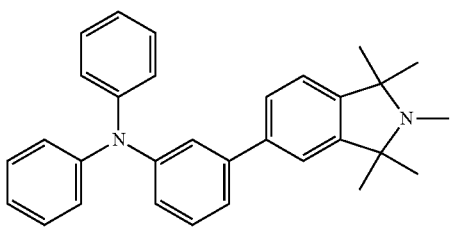
BB-502 + BB-013
BB-1066
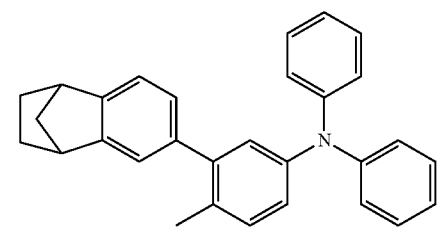
BB-503 + BB-004

-continued
BB-1067
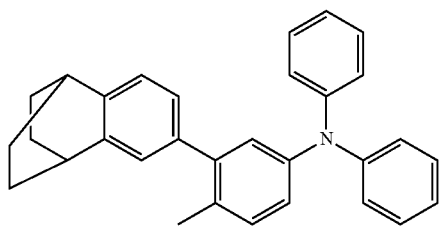
BB-503 + BB-005
BB-1068
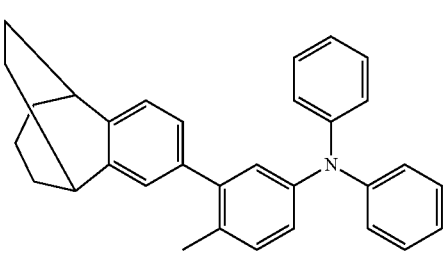
BB-503 + BB-010
BB-1069
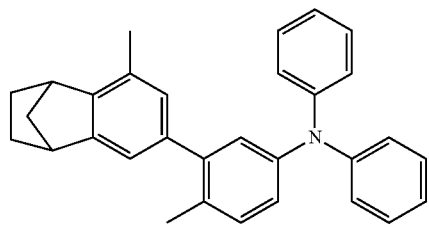
BB-503 + BB-006
BB-1070
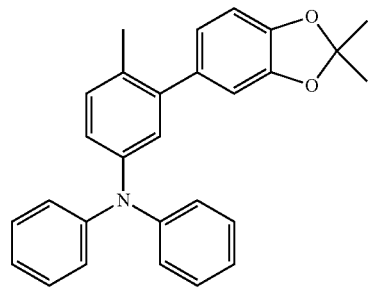
BB-503 + BB-002
BB-1071
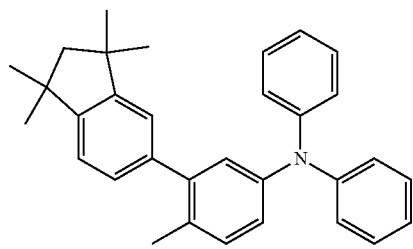
BB-503 + BB-012
-continued
BB-1072
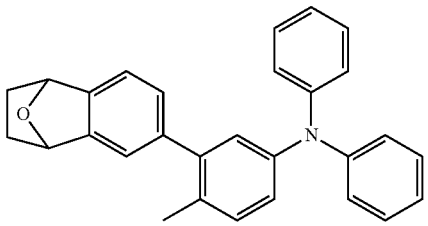
BB-503 + BB-003
BB-1073
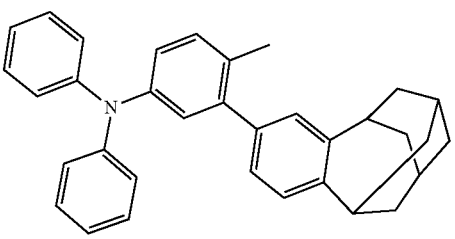
BB-503 + BB-017
BB-1074
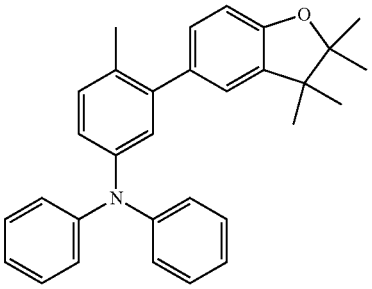
BB-503 + BB-008
BB-1075
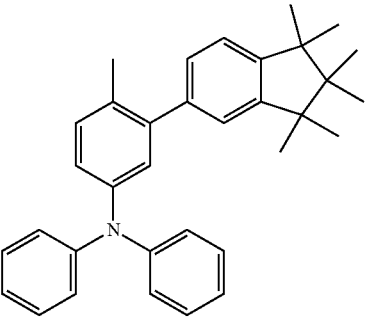
BB-503 + BB-020
BB-1076
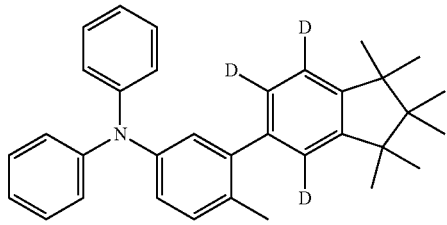
BB-503 + BB-018

BB-1077
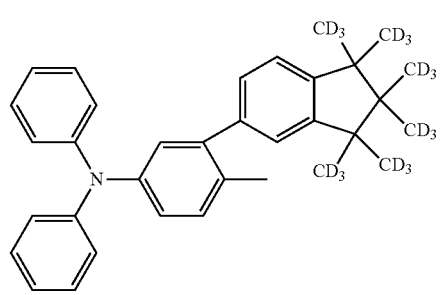
BB-503 + BB-016
BB-1079
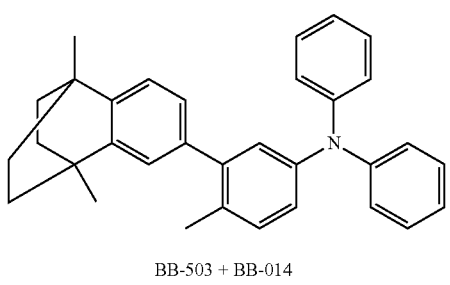
BB-503 + BB-014
BB-1080
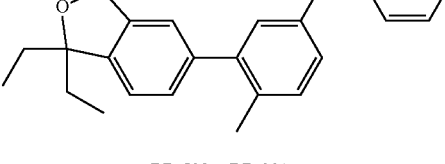
BB-503 + BB-021
BB-1081
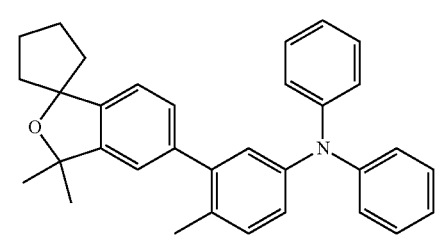
BB-503 + BB-015
BB-1082
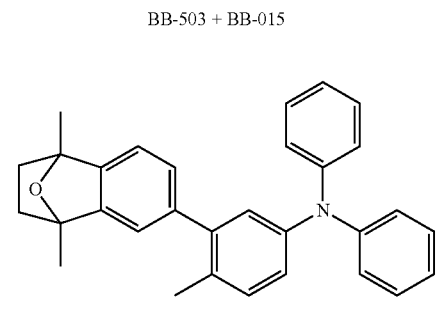
BB-503 + BB-007
BB-1083
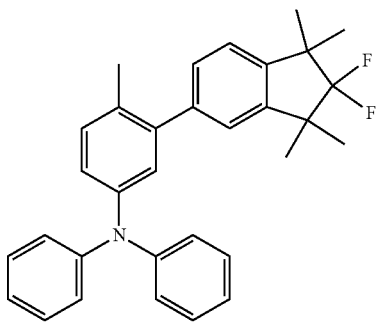
BB-503 + BB-009
BB-1084
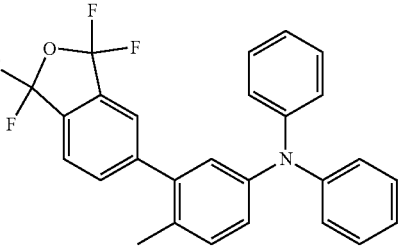
BB-503 + BB-001
BB-1085
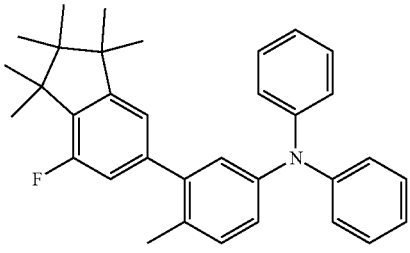
BB-503 + BB-019
BB-1086
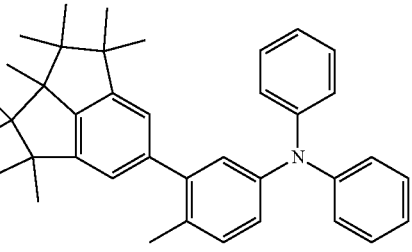
BB-503 + BB-022

-continued
BB-1087
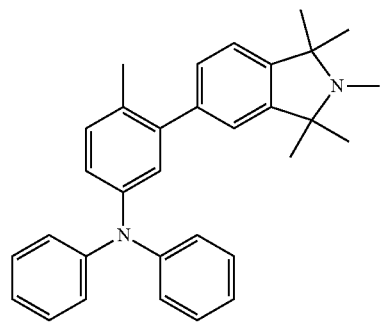
BB-503 + BB-013
BB-1088
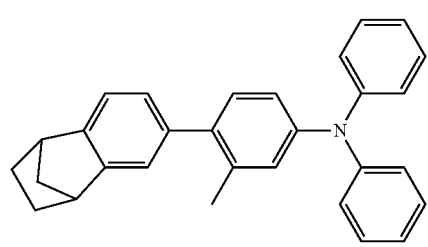
BB-504 + BB-004
BB-1089
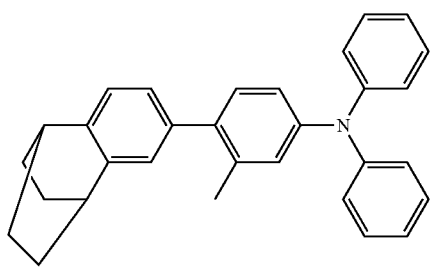
BB-504 + BB-005
BB-1090
BB-504 + BB-010
BB-1091
BB-504 + BB-006
-continued
BB-1092
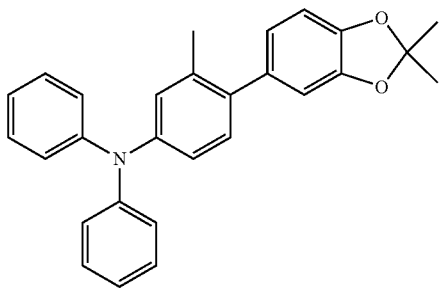
BB-504 + BB-002
BB-1093
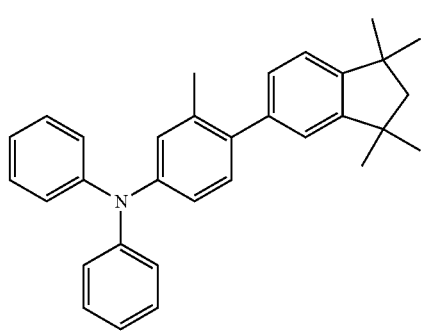
BB-504 + BB-012
BB-1094
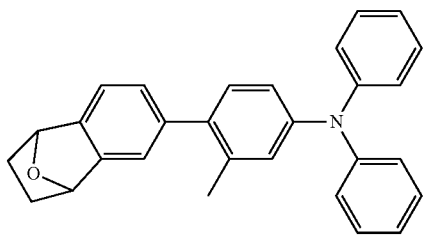
BB-504 + BB-003
BB-1095
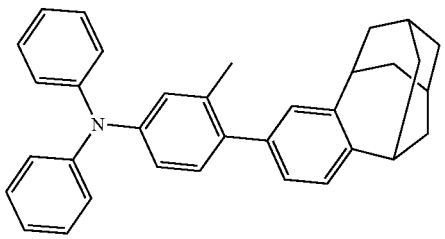
BB-504 + BB-017

-continued
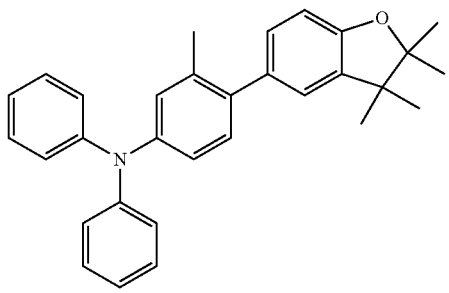
BB-504 + BB-008
BB-1096
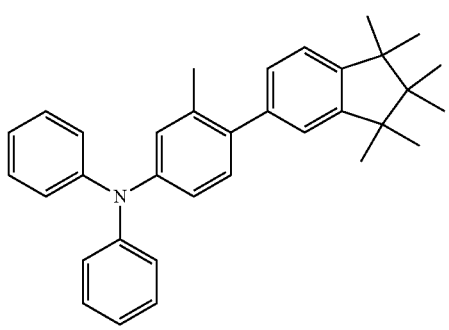
BB-504 + BB-020
BB-1097
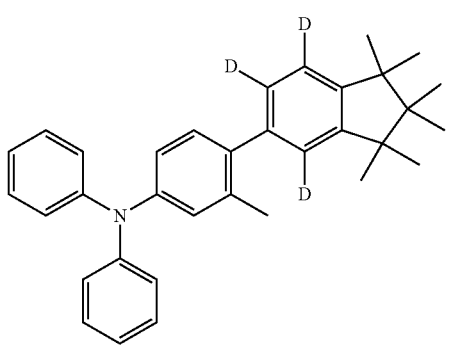
BB-504 + BB-018
BB-1098
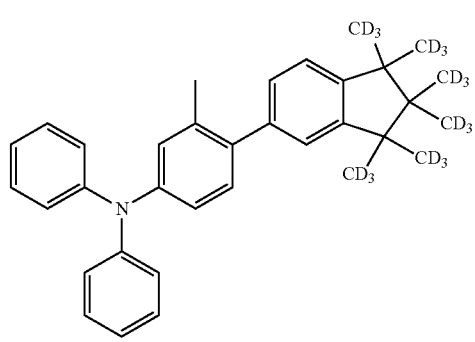
BB-504 + BB-016
BB-1099
-continued
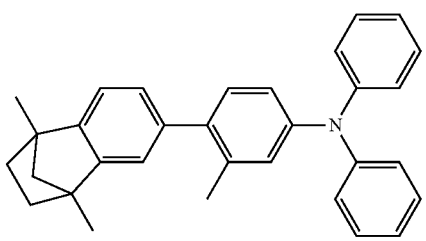
BB-504 + BB-011
BB-1100
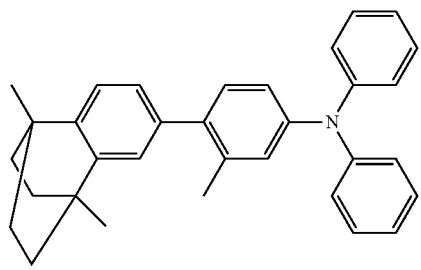
BB-504 + BB-014
BB-1101
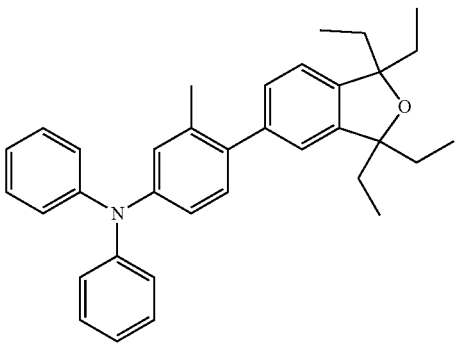
BB-504 + BB-021
BB-1102
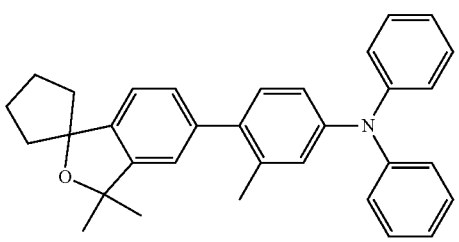
BB-504 + BB-015
BB-1103
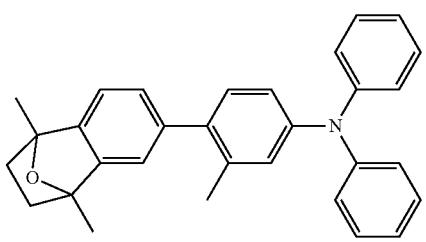
BB-504 + BB-007
BB-1104

-continued
BB-1105
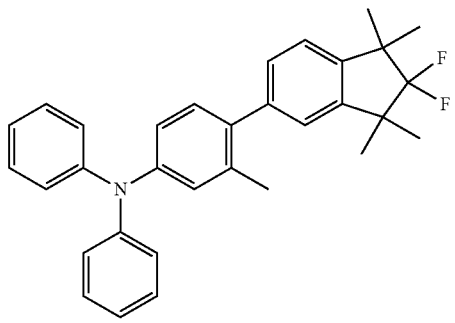
BB-504 + BB-009
BB-1106
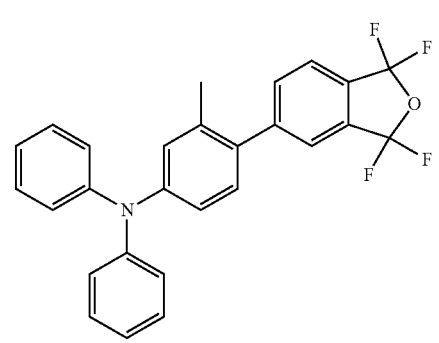
BB-504 + BB-001
BB-1107
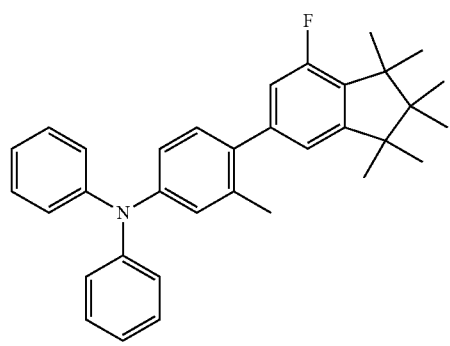
BB-504 + BB-019
BB-1108
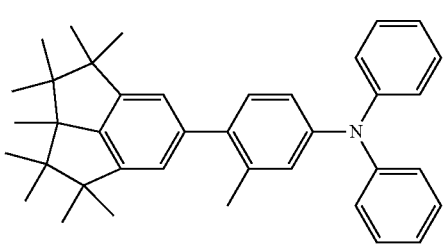
BB-504 + BB-022
-continued
BB-1109
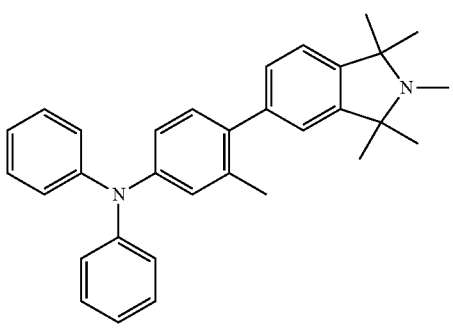
BB-504 + BB-013
BB-1110
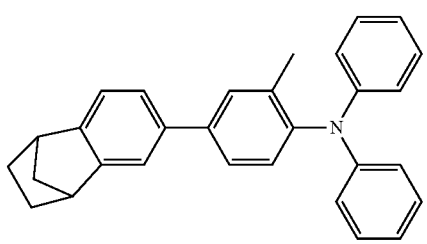
BB-505 + BB-004
BB-1111
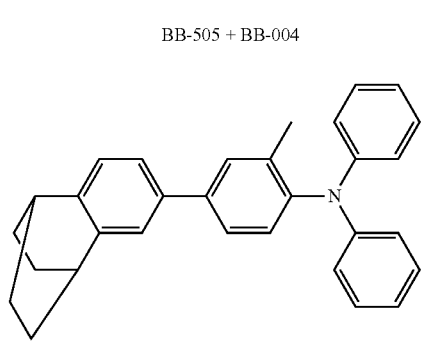
BB-505 + BB-005
BB-1112
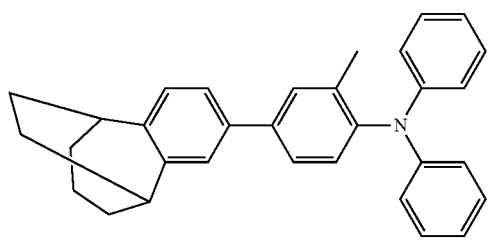
BB-505 + BB-010
BB-1113
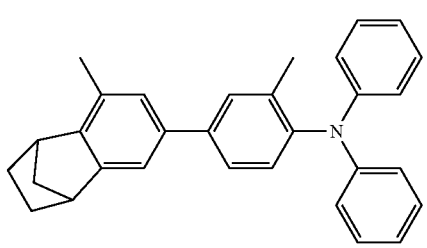
BB-505 + BB-006

179
-continued
BB-1114
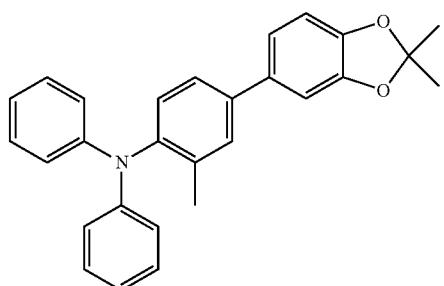
BB-505 + BB-002
BB-1115
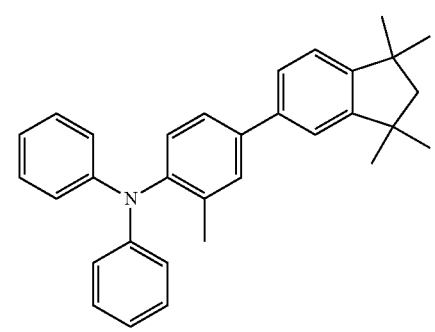
BB-505 + BB-012
BB-1116
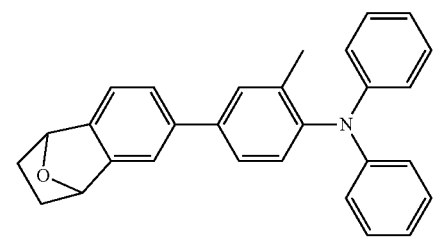
BB-505 + BB-003
BB-1117
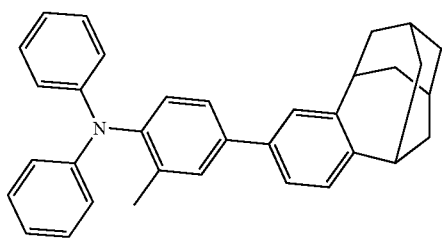
BB-505 + BB-017
180
-continued
BB-1118
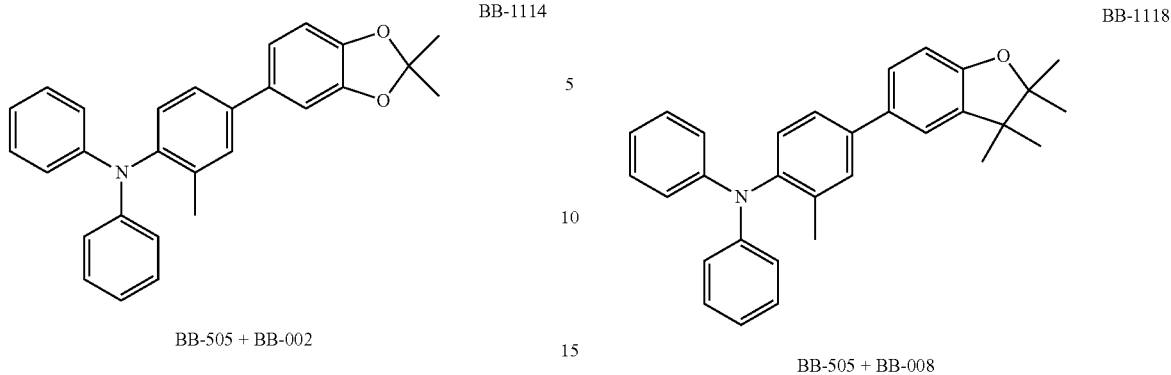
BB-505 + BB-008
BB-1119
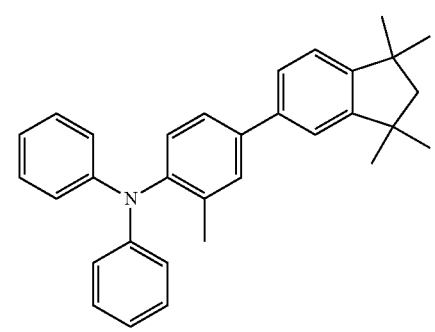
BB-505 + BB-020
BB-1120
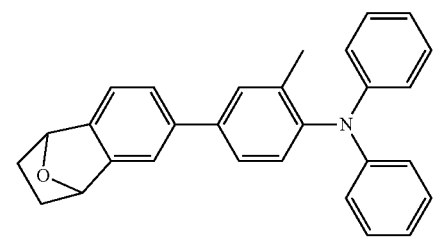
BB-505 + BB-018
BB-1121
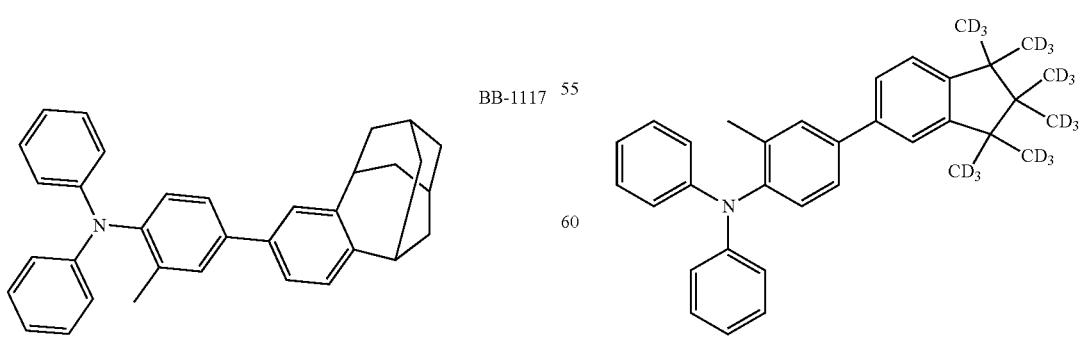
BB-505 + BB-016

-continued
BB-1122
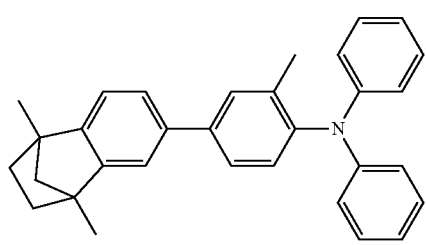
BB-505 + BB-011
BB-1123
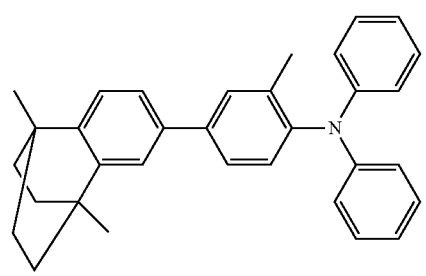
BB-505 + BB-014
BB-1124
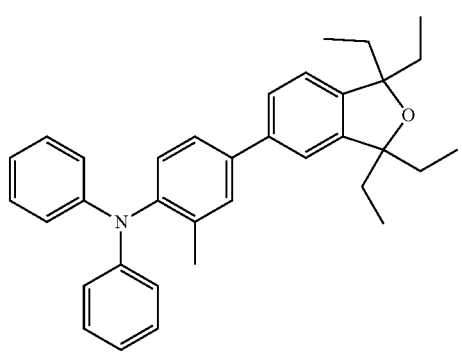
BB-505 + BB-021
BB-1125
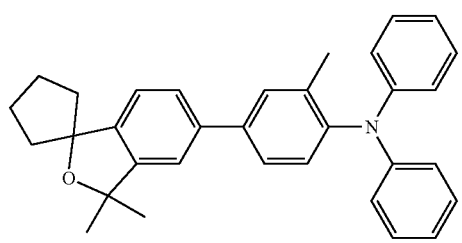
BB-505 + BB-015
-continued
BB-1126
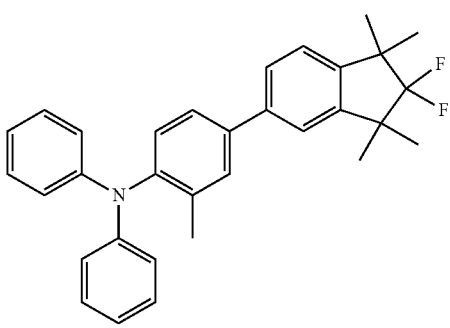
BB-505 + BB-007
BB-1127
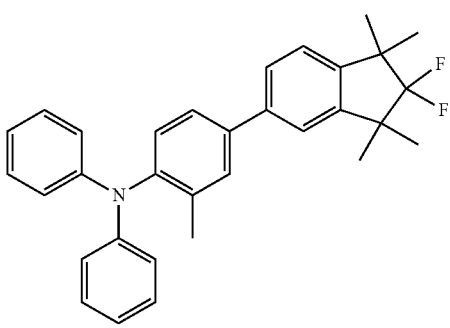
BB-505 + BB-009
BB-1128
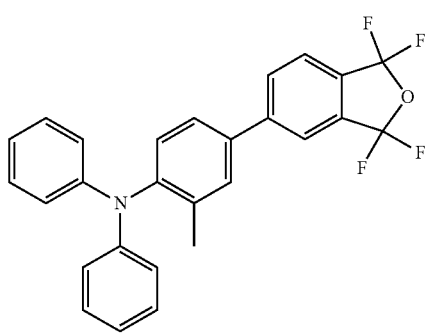
BB-505 + BB-001
BB-1129
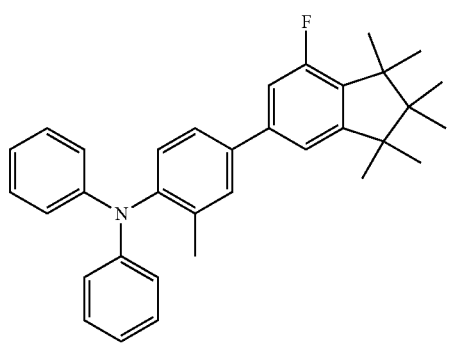
BB-505 + BB-019

-continued
BB-1130
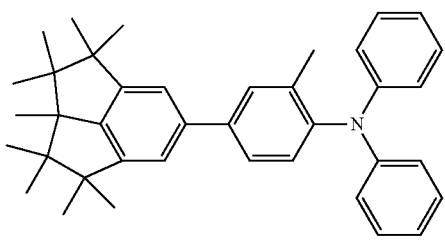
BB-505 + BB-022
BB-1131
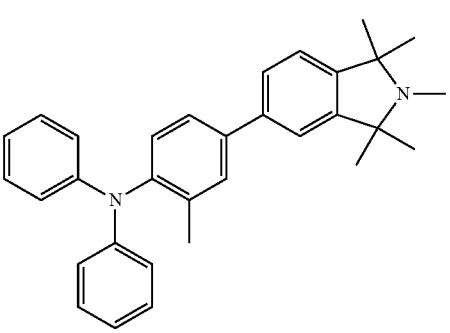
BB-505 + BB-013
BB-1132
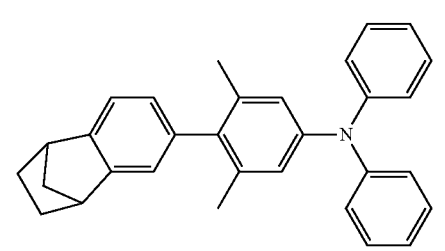
BB-506 + BB-004
BB-1133
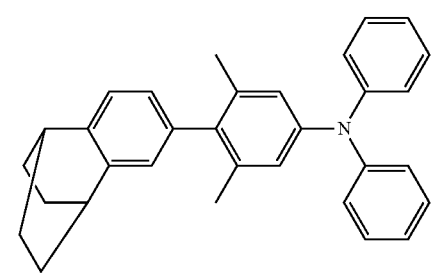
BB-506 + BB-005
BB-1134
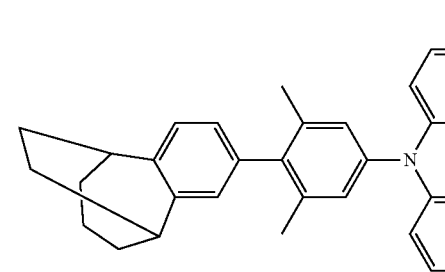
BB-506 + BB-010
-continued
BB-1135
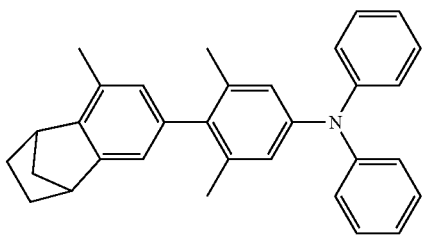
BB-506 + BB-006
BB-1136
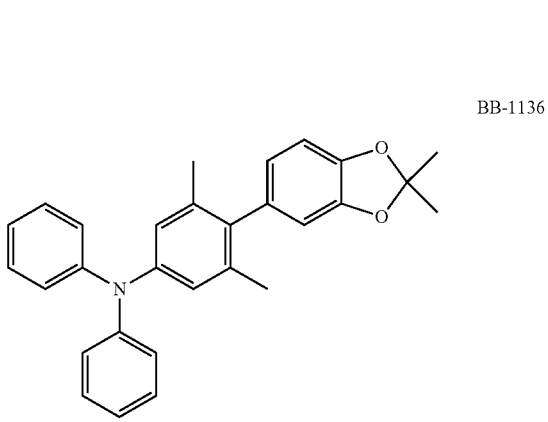
BB-506 + BB-002
BB-1137
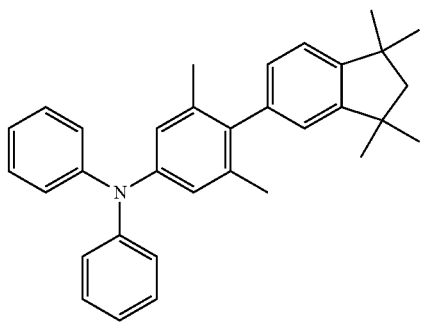
BB-506 + BB-012
BB-1138
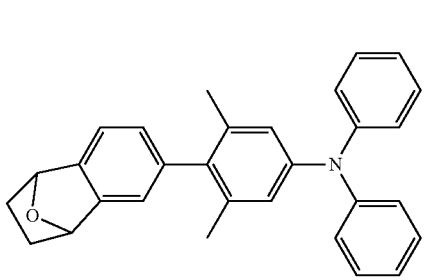
BB-506 + BB-003

BB-1139
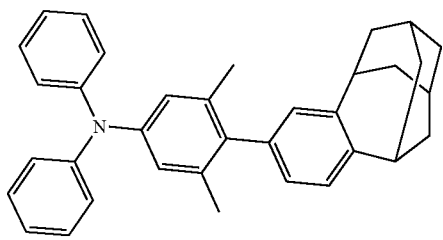
BB-506 + BB-017
BB-1140
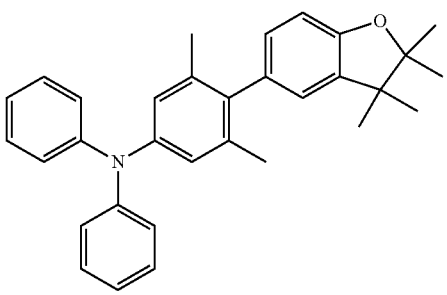
BB-506 + BB-008
BB-1141
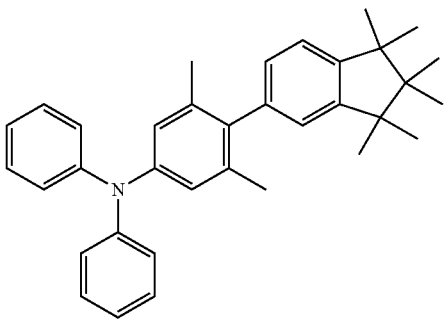
BB-506 + BB-020
BB-1142
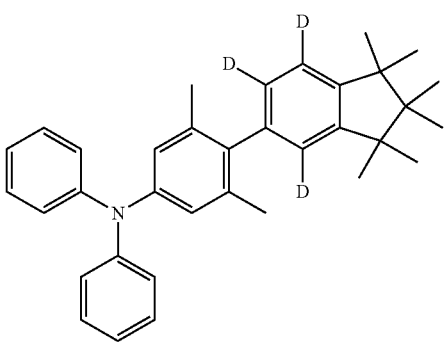
BB-506 + BB-018
BB-1143
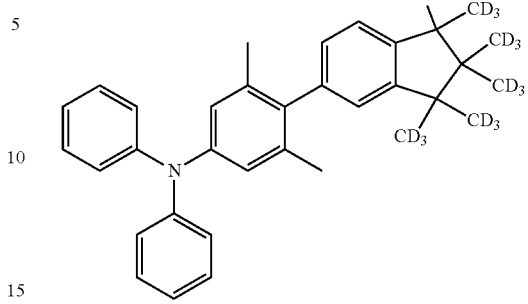
BB-506 + BB-016
BB-1144
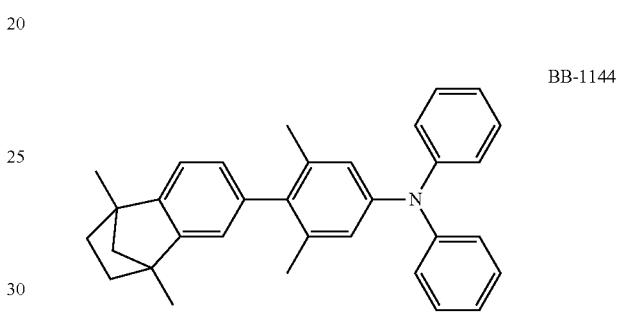
BB-506 + BB-011
BB-1145
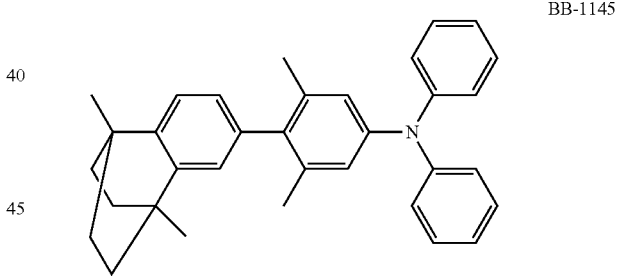
BB-506 + BB-014
BB-1146
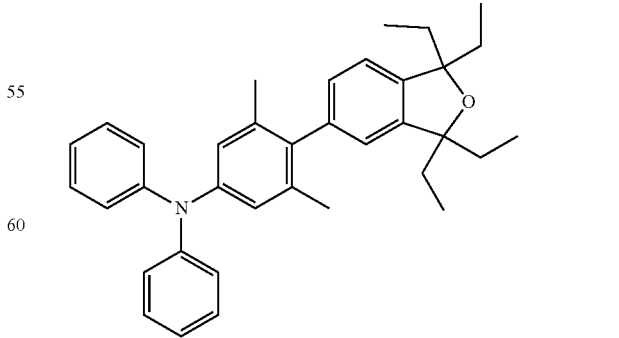
BB-506 + BB-021

-continued
BB-1147
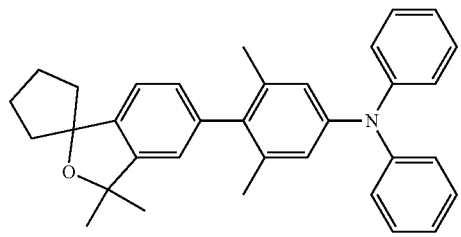
BB-506 + BB-015
BB-1148
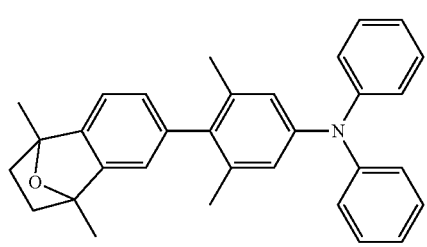
BB-506 + BB-007
BB-1149
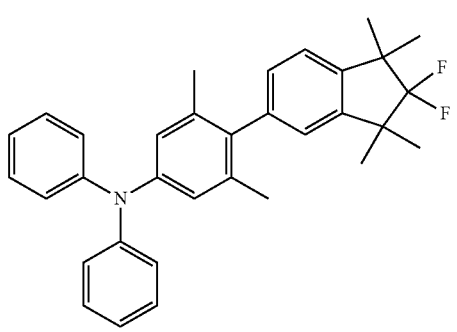
BB-506 + BB-009
BB-1150
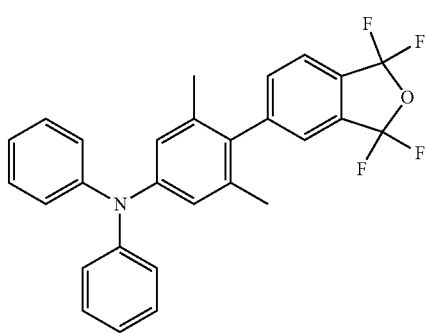
BB-506 + BB-001
-continued
BB-1151
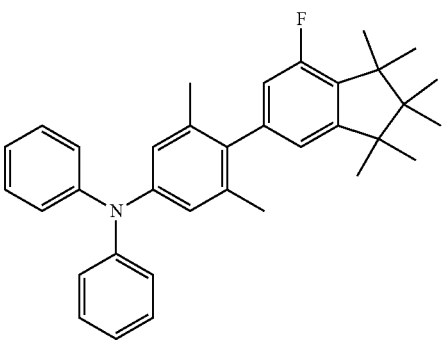
BB-506 + BB-019
BB-1152
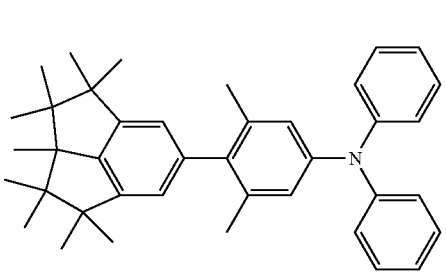
BB-506 + BB-022
BB-1153
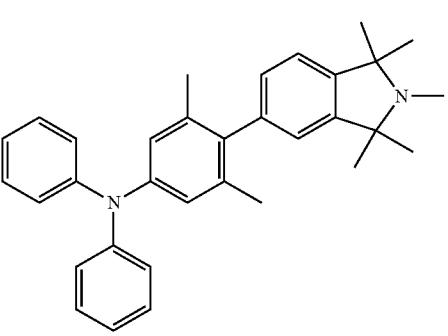
BB-506 + BB-013
BB-1154
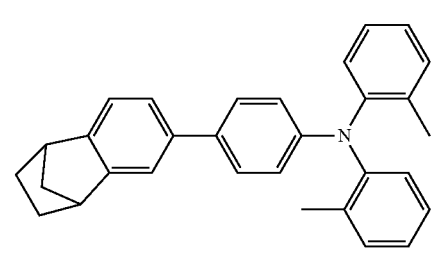
BB-507 + BB-004

BB-1155
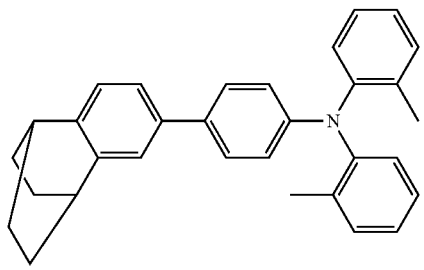
BB-507 + BB-005
BB-1156
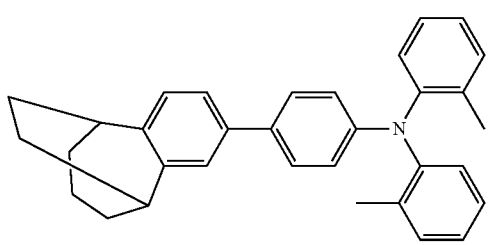
BB-507 + BB-010
BB-1157
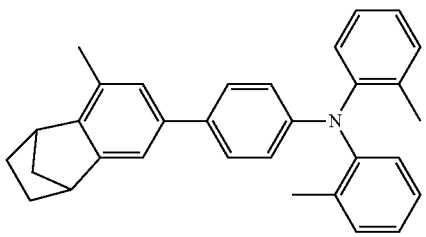
BB-507 + BB-006
BB-1158
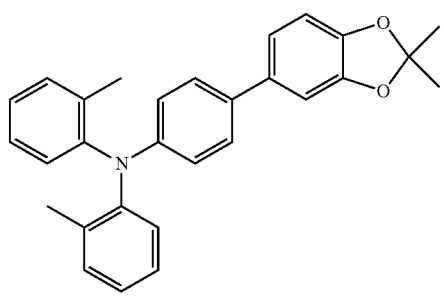
BB-507 + BB-002
BB-1159
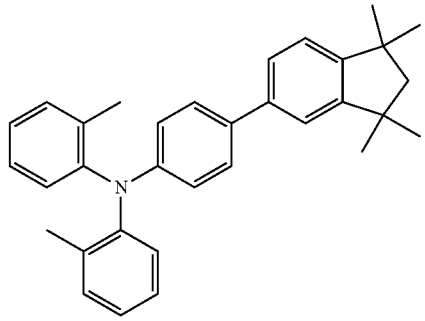
BB-507 + BB-012
BB-1160
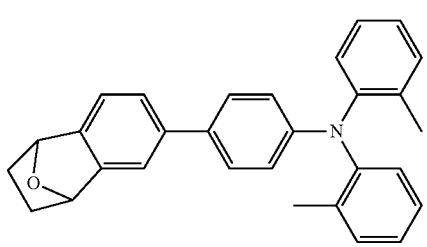
BB-507 + BB-003
BB-1161
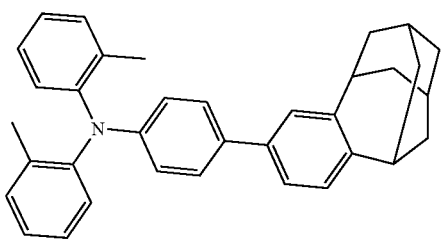
BB-507 + BB-017
BB-1162
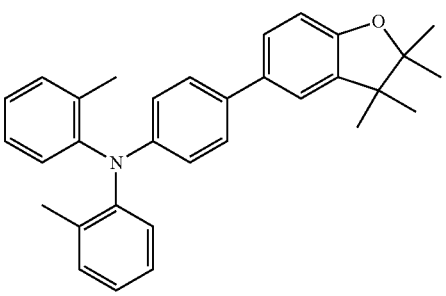
BB-507 + BB-008

BB-1163
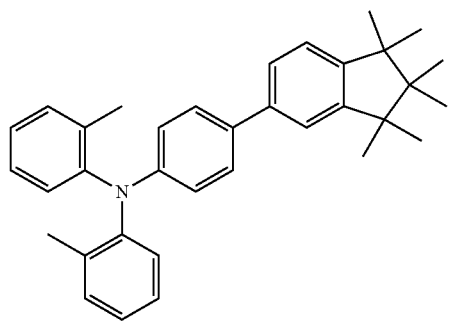
BB-507 + BB-020
BB-1164
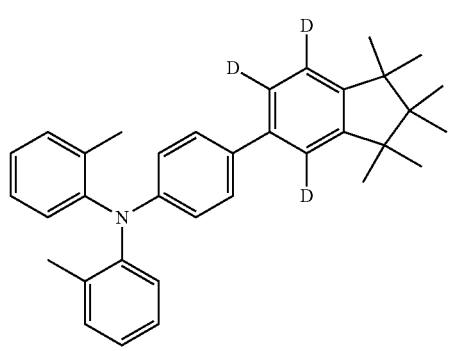
BB-507 + BB-018
BB-1165
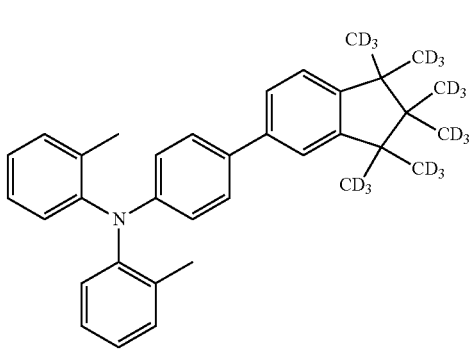
BB-507 + BB-016
BB-1166
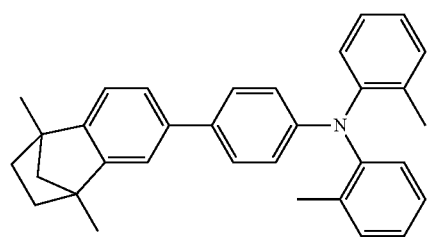
BB-507 + BB-011
BB-1167
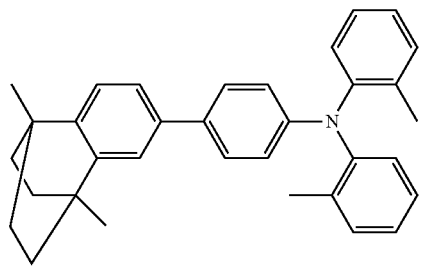
BB-507 + BB-014
BB-1168
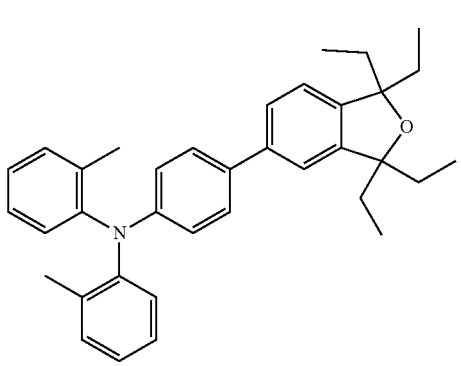
BB-507 + BB-021
BB-1169
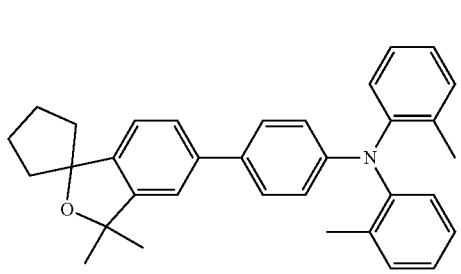
BB-507 + BB-015
BB-1170
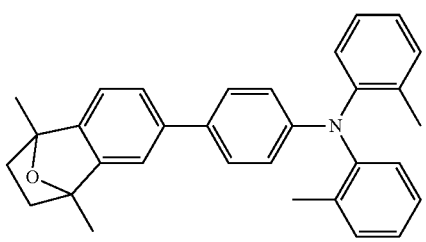
BB-507 + BB-007

BB-1171
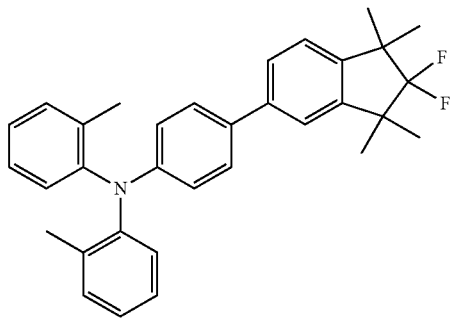
BB-507 + BB-009
BB-1172
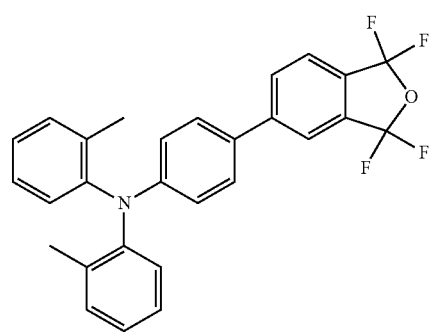
BB-507 + BB-001
BB-1173
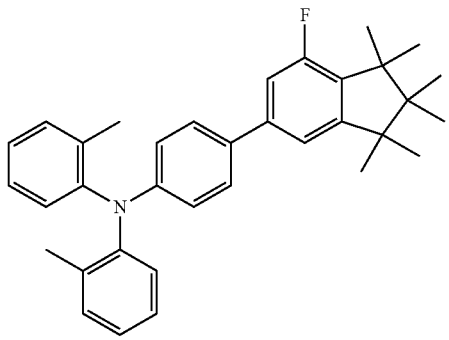
BB-507 + BB-019
BB-1174
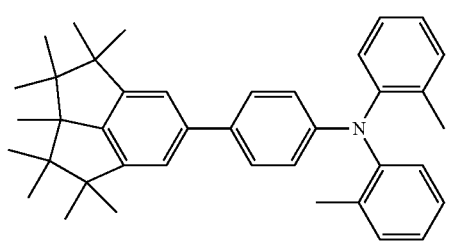
BB-507 + BB-022
BB-1175
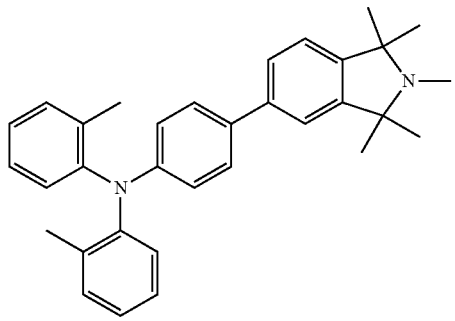
BB-507 + BB-013
BB-1176
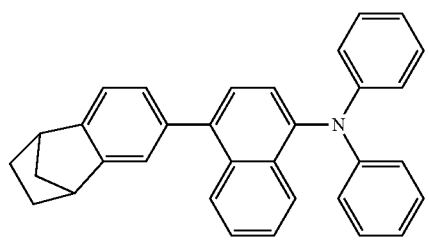
BB-508 + BB-004
BB-1177
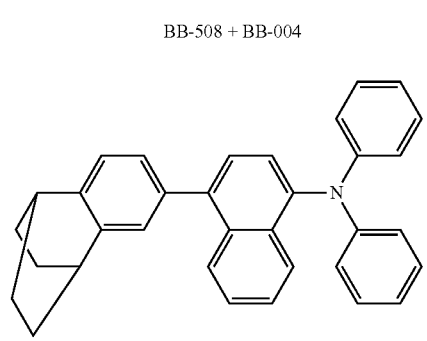
BB-508 + BB-005
BB-1178
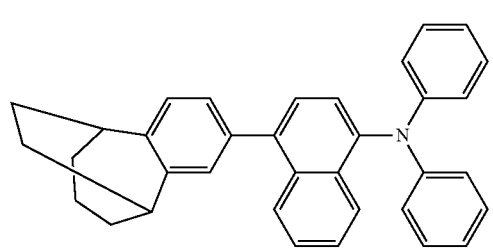
BB-508 + BB-010
BB-1179
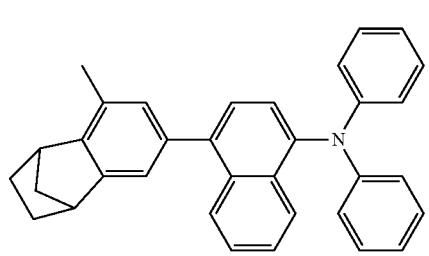
BB-508 + BB-006

195
-continued
BB-1180
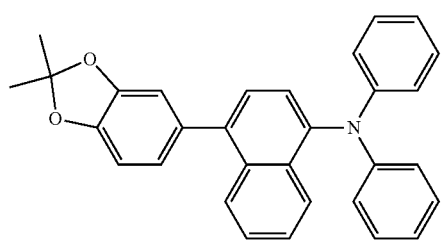
BB-508 + BB-002
BB-1181
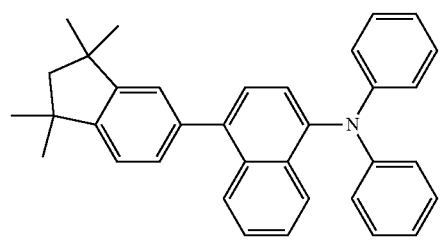
BB-508 + BB-012
BB-1182
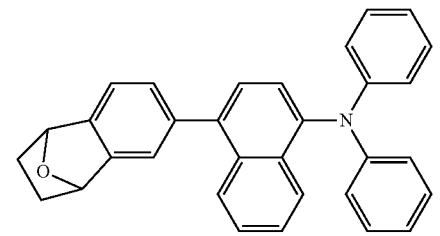
BB-508 + BB-003
BB-1183
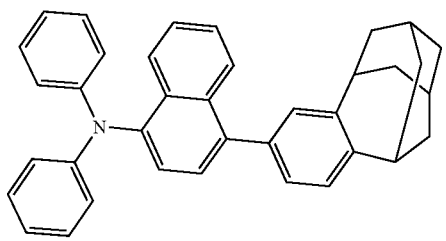
BB-508 + BB-017
BB-1184
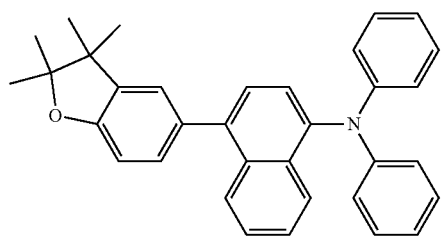
BB-508 + BB-008
196
-continued
BB-1185
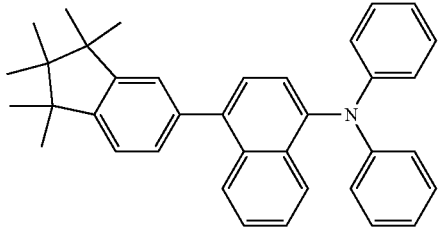
BB-508 + BB-020
BB-1186
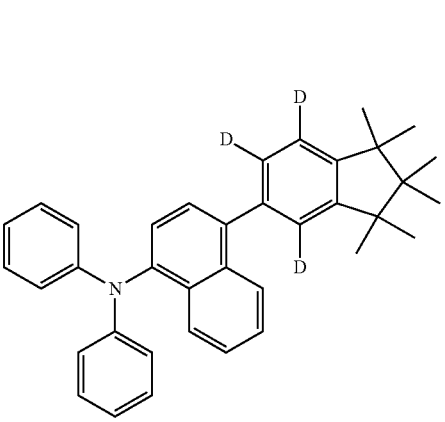
BB-508 + BB-018
BB-1187
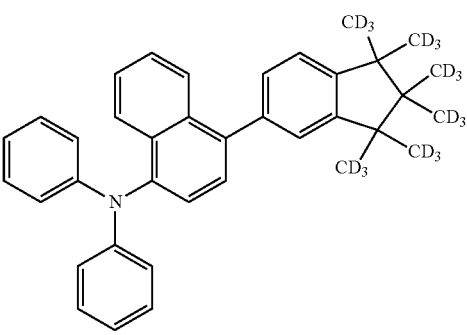
BB-508 + BB-016
BB-1188
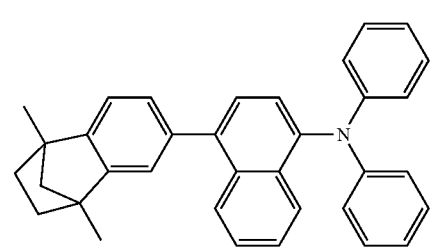
BB-508 + BB-011

-continued
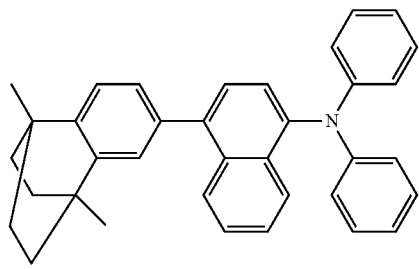
BB-1189
BB-508 + BB-014
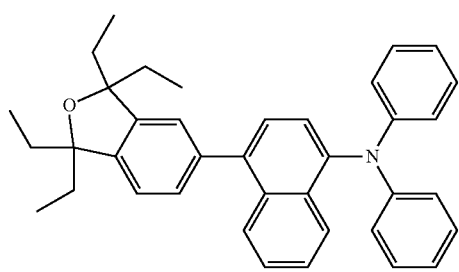
BB-1190
BB-508 + BB-021
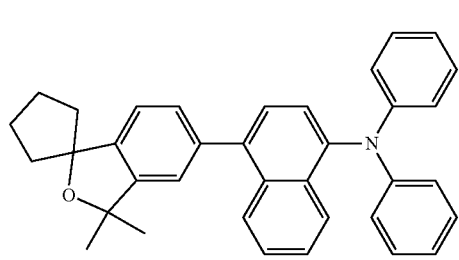
BB-1191
BB-508 + BB-015
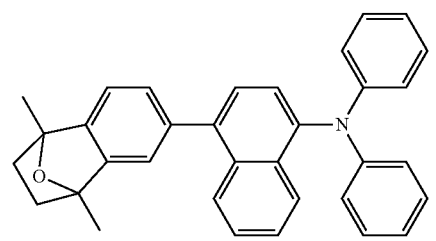
BB-1192
BB-508 + BB-007
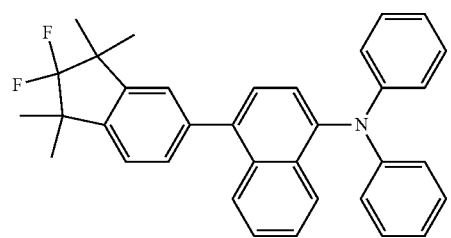
BB-1193
BB-508 + BB-009
-continued
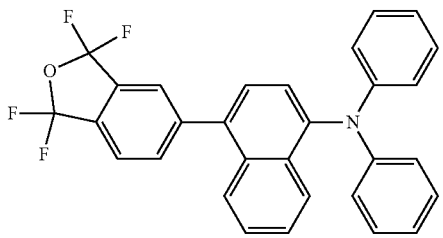
BB-1194
BB-508 + BB-001
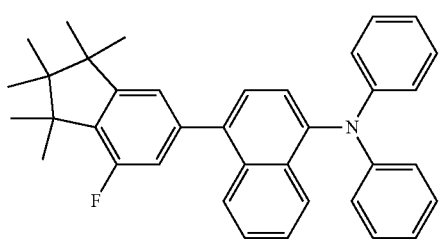
BB-1195
BB-508 + BB-019
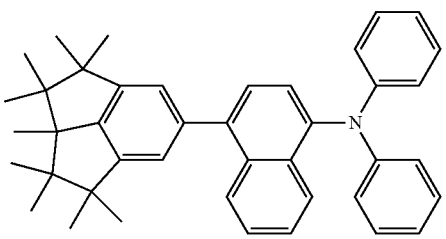
BB-1196
BB-508 + BB-022
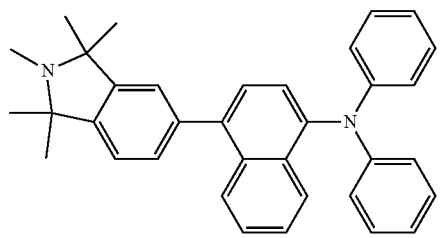
BB-1197
BB-508 + BB-013
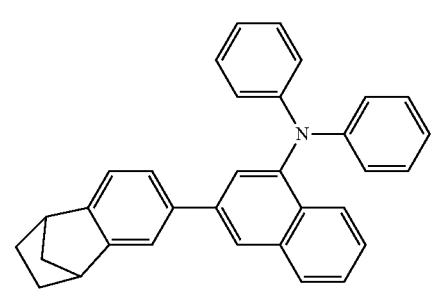
BB-1198
BB-509 + BB-004

-continued
BB-1199
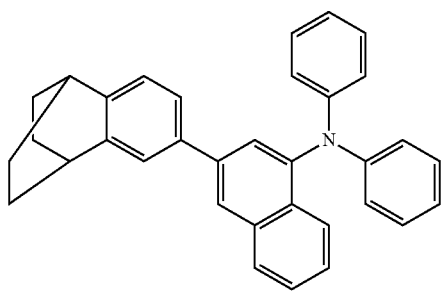
BB-509 + BB-005
BB-1200
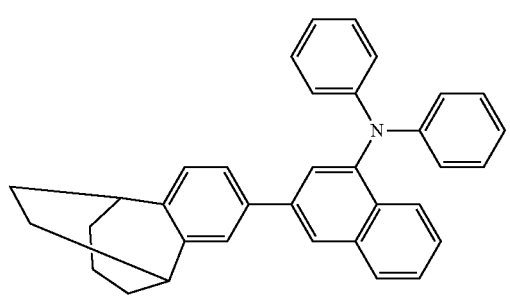
BB-509 + BB-010
BB-1201
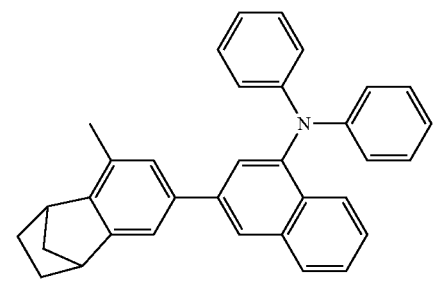
BB-509 + BB-006
BB-1202
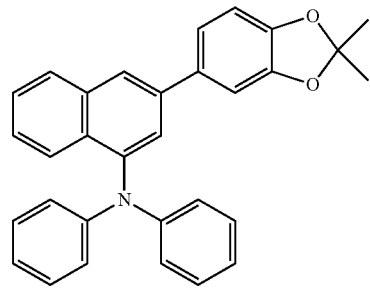
BB-509 + BB-002
-continued
BB-1203
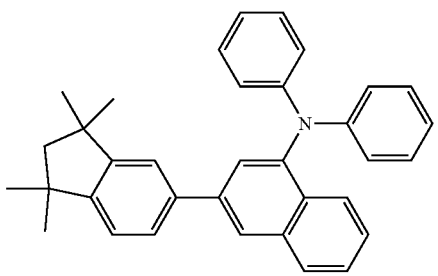
BB-509 + BB-012
BB-1204
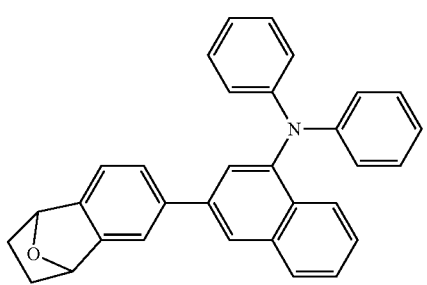
BB-509 + BB-003
BB-1205
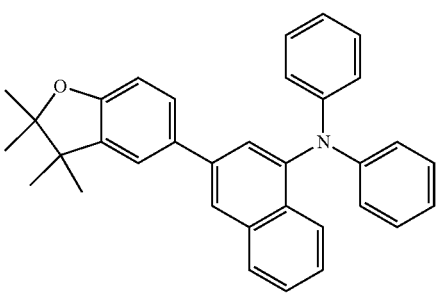
BB-509 + BB-017
BB-1206
BB-509 + BB-008

-continued
BB-1207
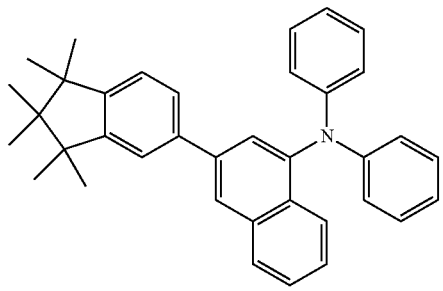
BB-509 + BB-020
BB-1208
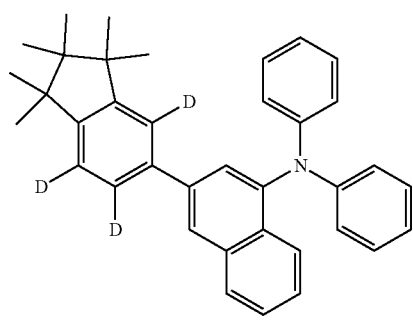
BB-509 + BB-018
BB-1209
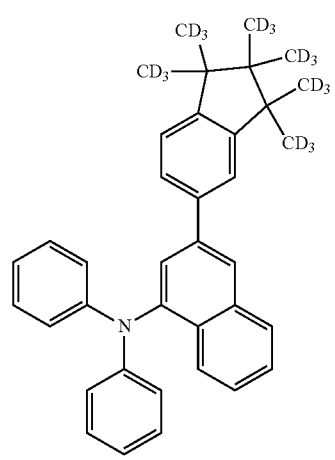
BB-509 + BB-016
BB-1210
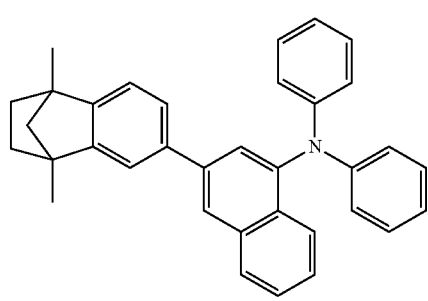
BB-509 + BB-011
-continued
BB-1211
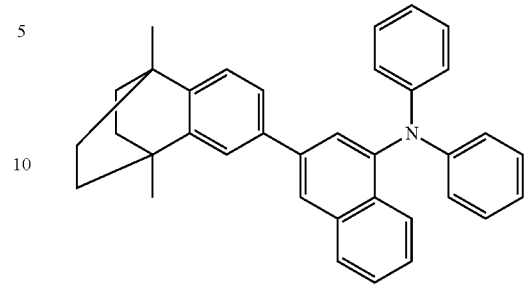
BB-509 + BB-014
BB-1212
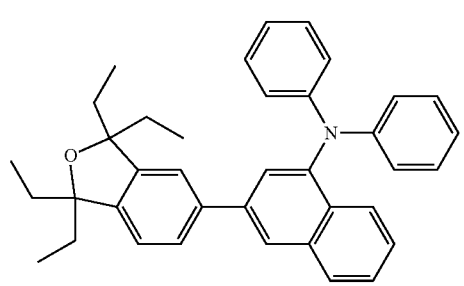
BB-509 + BB-021
BB-1213
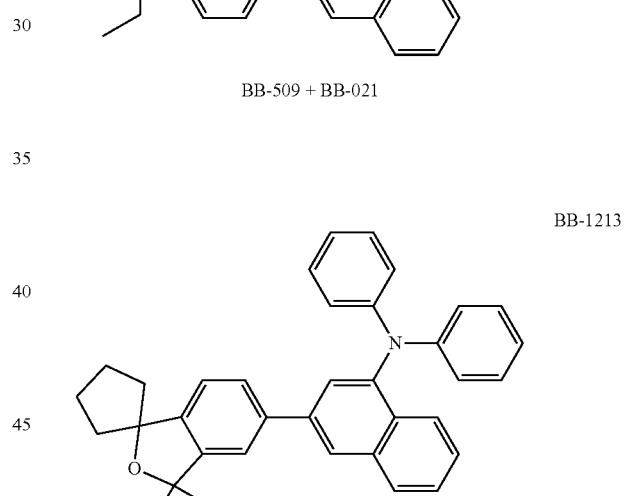
BB-509 + BB-015
BB-1214
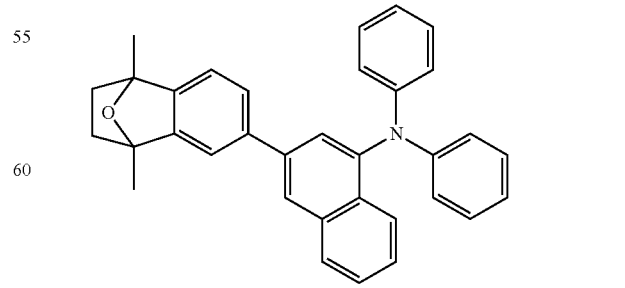
BB-509 + BB-007

-continued
BB-1215
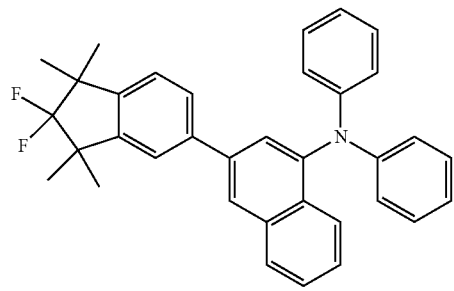
BB-509 + BB-009
BB-1216
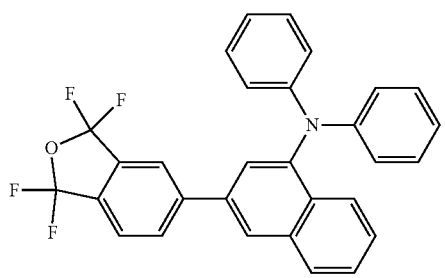
BB-509 + BB-001
BB-1217
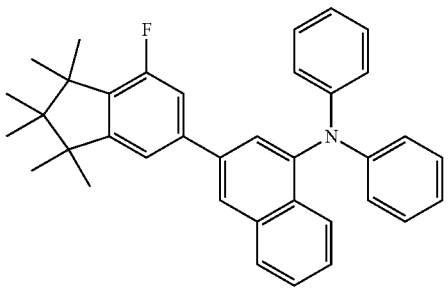
BB-509 + BB-019
BB-1218
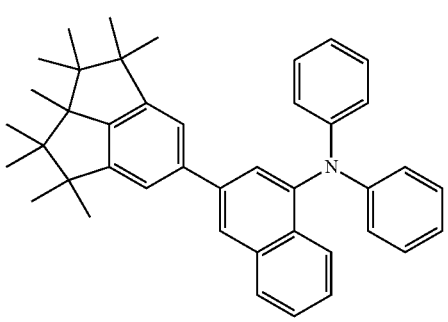
BB-509 + BB-022
-continued
BB-1219
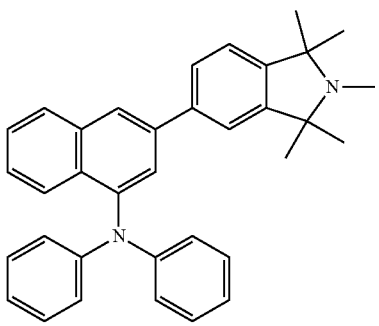
BB-509 + BB-013
BB-1220
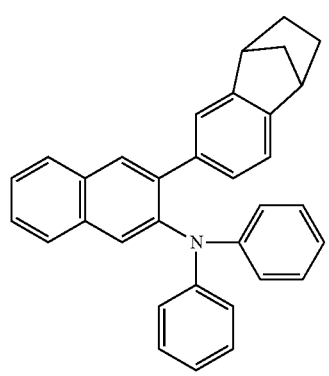
BB-510 + BB-004
BB-1221
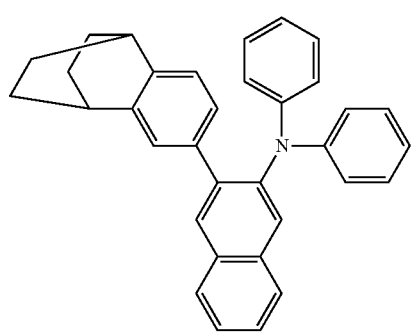
BB-510 + BB-005
BB-1222
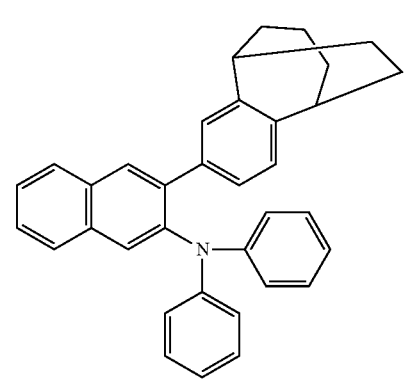
BB-510 + BB-010

BB-1223
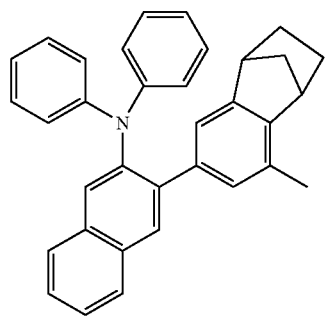
BB-510 + BB-006
BB-1224
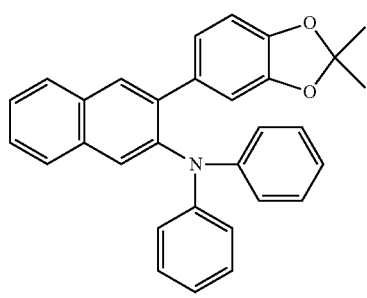
BB-510 + BB-002
BB-1225
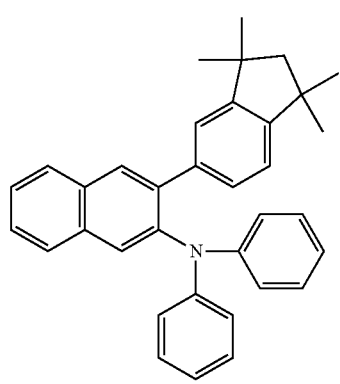
BB-510 + BB-012
BB-1226
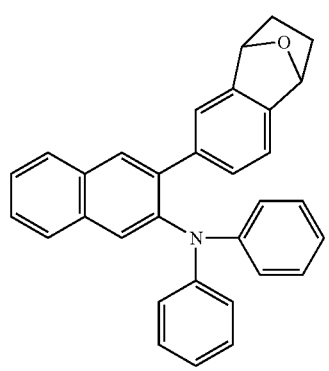
BB-510 + BB-003
BB-1227
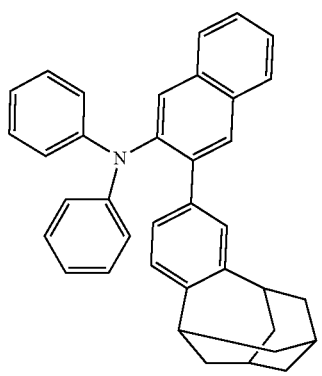
BB-510 + BB-017
BB-1228
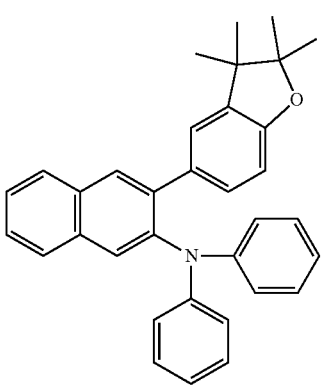
BB-510 + BB-008
BB-1229
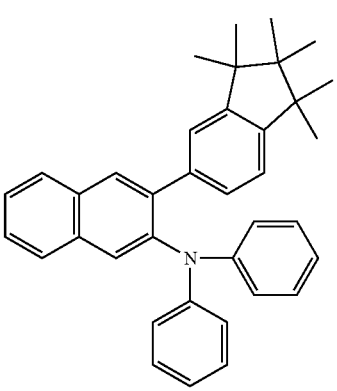
BB-510 + BB-020

207
-continued
BB-1230
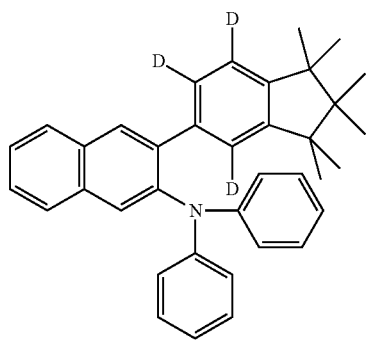
BB-510 + BB-018
BB-1231
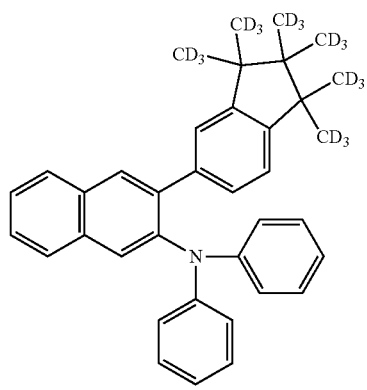
BB-510 + BB-016
BB-1232
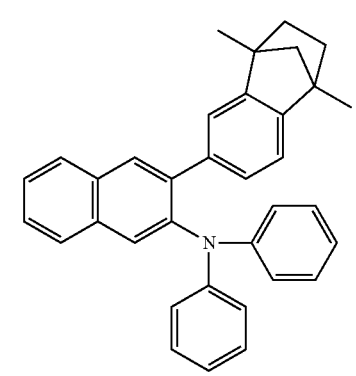
BB-510 + BB-011
208
-continued
BB-1233
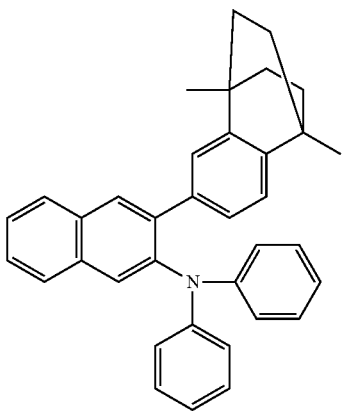
BB-510 + BB-014
BB-1234
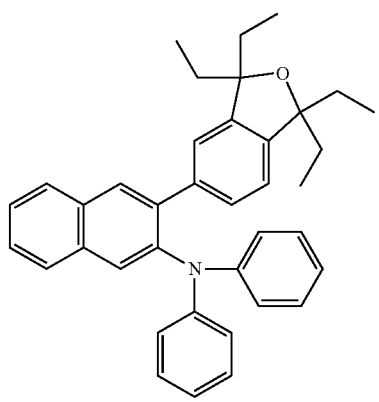
BB-510 + BB-021
BB-1235
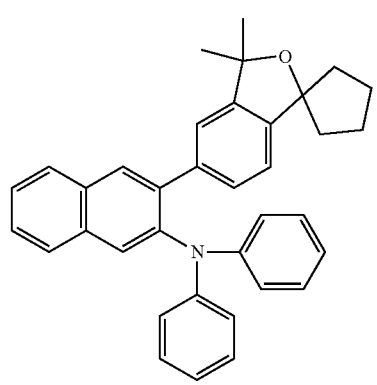
BB-510 + BB-015

BB-1236
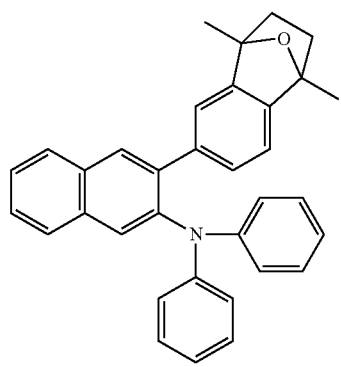
BB-510 + BB-007
BB-1237
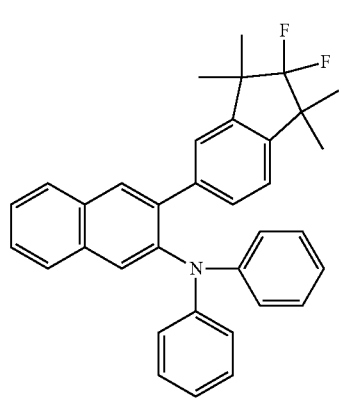
BB-510 + BB-009
BB-1238
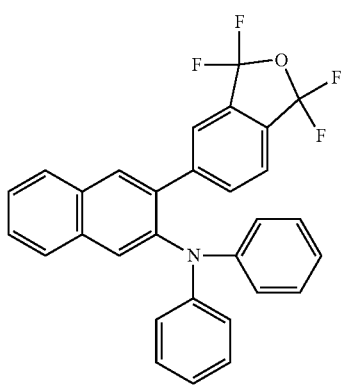
BB-510 + BB-001
BB-1239
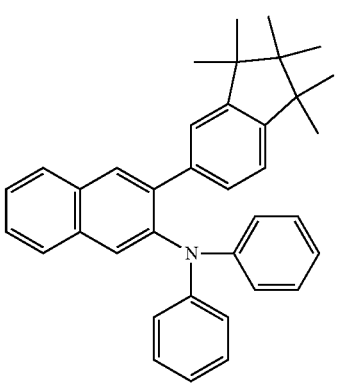
BB-510 + BB-019
BB-1240
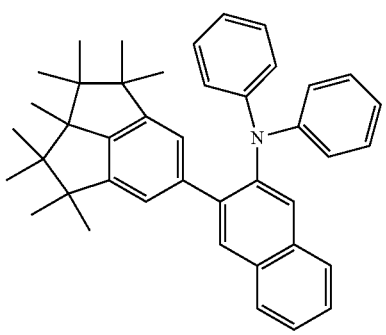
BB-510 + BB-022
BB-1241
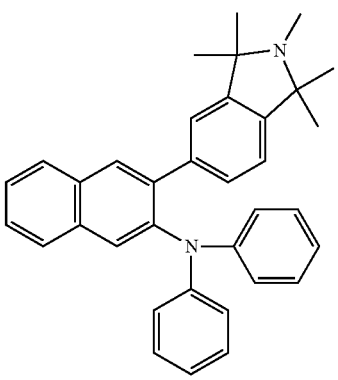
BB-510 + BB-013
BB-1242
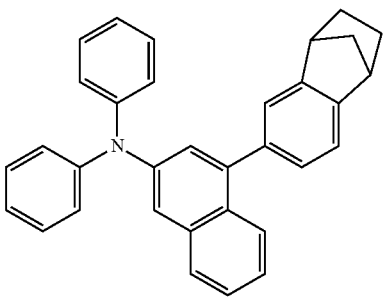
BB-511 + BB-004

211
-continued
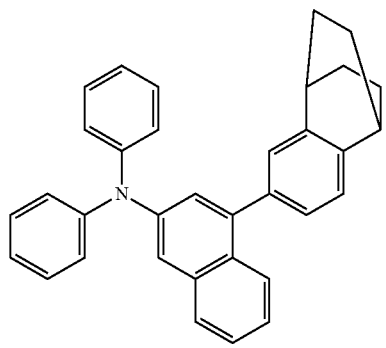
BB-1243
BB-511 + BB-005
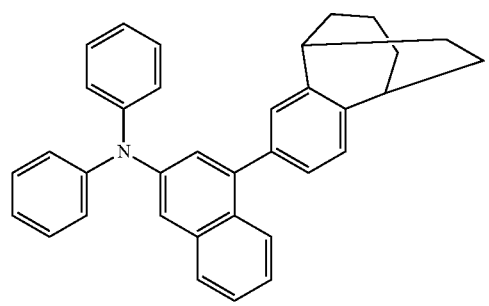
BB-1244
BB-511 + BB-010
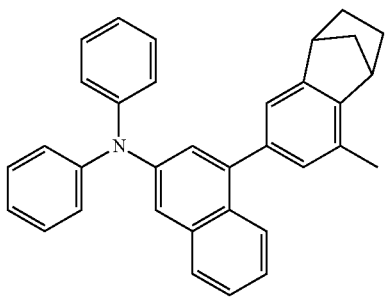
BB-1245
BB-511 + BB-006
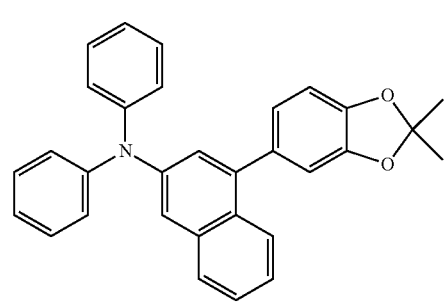
BB-1246
BB-511 + BB-002
212
-continued
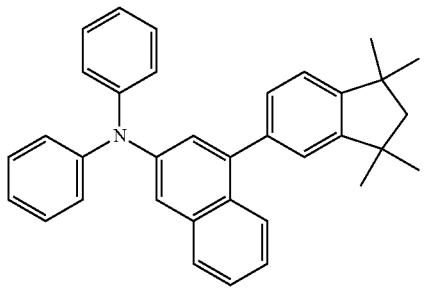
BB-1247
BB-511 + BB-012
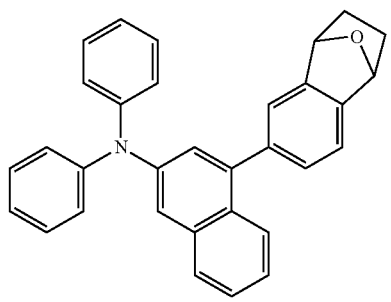
BB-1248
BB-511 + BB-003
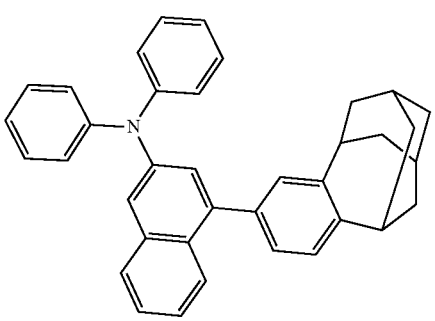
BB-1249
BB-511 + BB-017

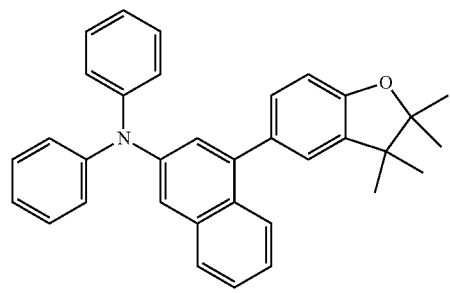
BB-511 + BB-008
BB-1250
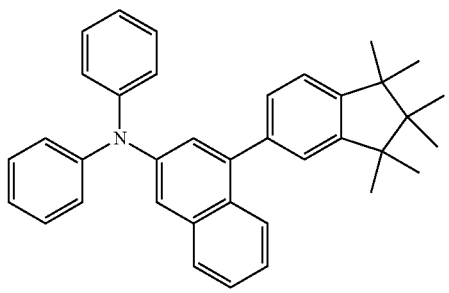
BB-511 + BB-020
BB-1251
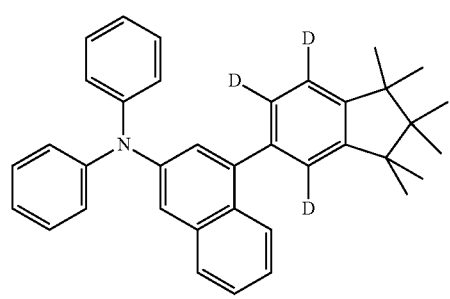
BB-511 + BB-018
BB-1252
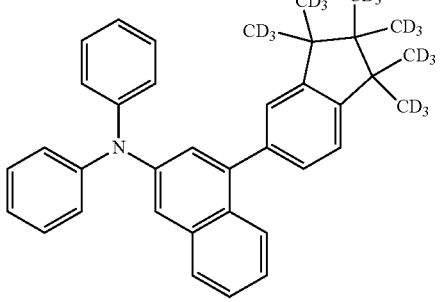
BB-511 + BB-016
BB-1253
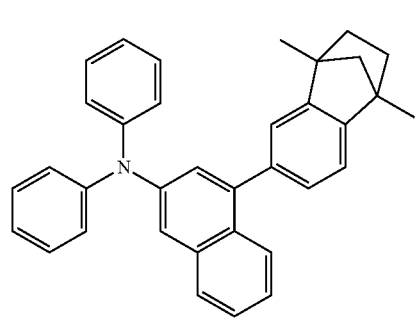
BB-511 + BB-011
BB-1254
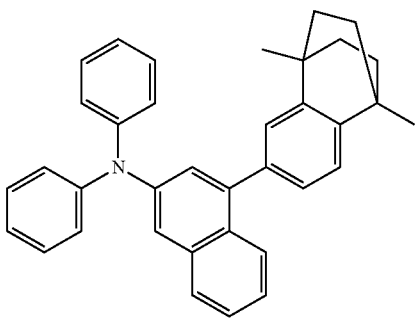
BB-511 + BB-014
BB-1255
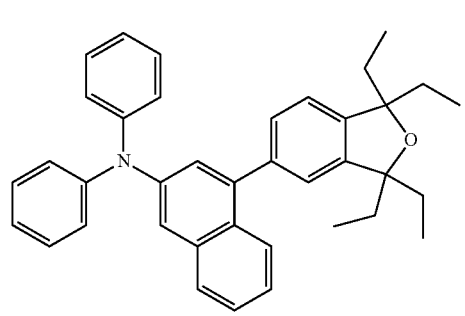
BB-511 + BB-021
BB-1256
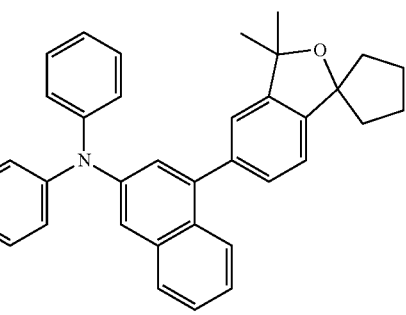
BB-511 + BB-015
BB-1257

-continued
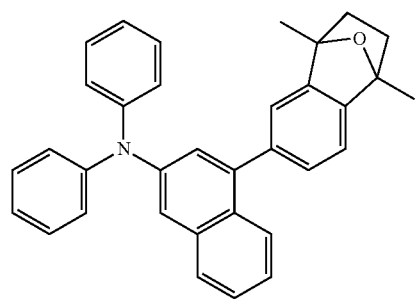
BB-511 + BB-007
BB-1258
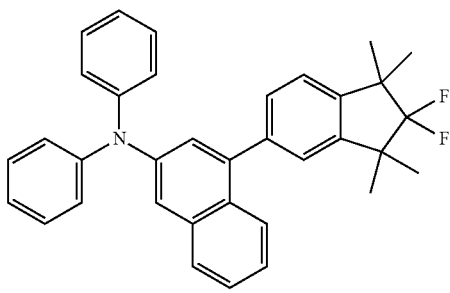
BB-511 + BB-009
BB-1259
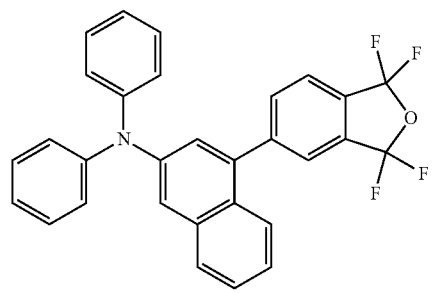
BB-511 + BB-001
BB-1260
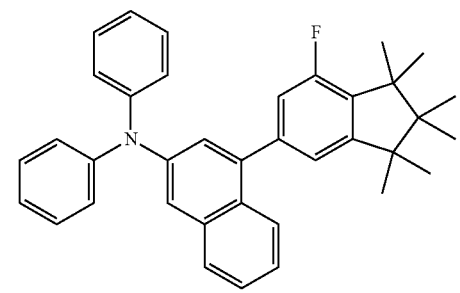
BB-511 + BB-019
BB-1261
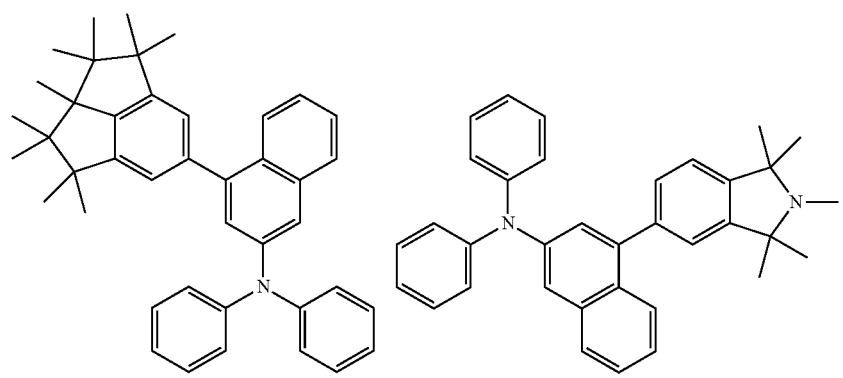
BB-511 + BB-022
BB-1262
BB-511 + BB-013
BB-1263
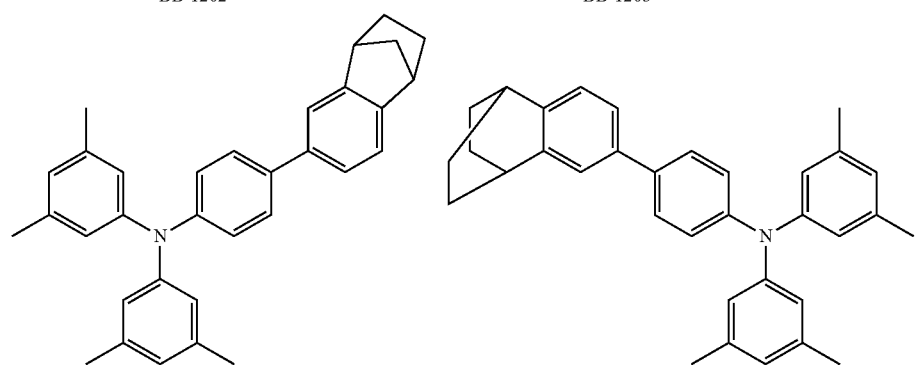
BB-511 + BB-004
BB-1264
BB-512 + BB-005
BB-1265

-continued
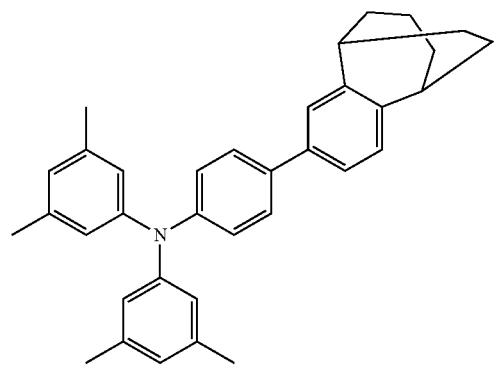
BB-512 + BB-010
BB-1266
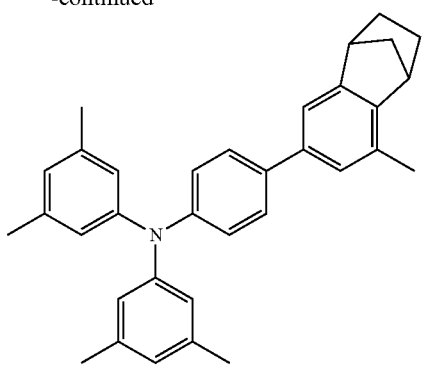
BB-512 + BB-006
BB-1267
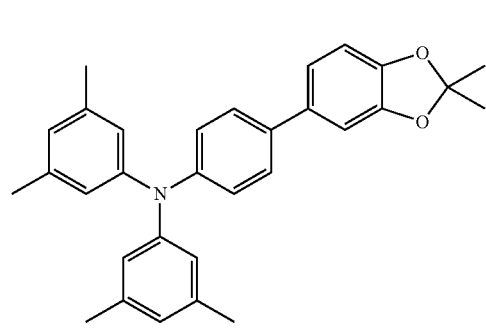
BB-512 + BB-002
BB-1268
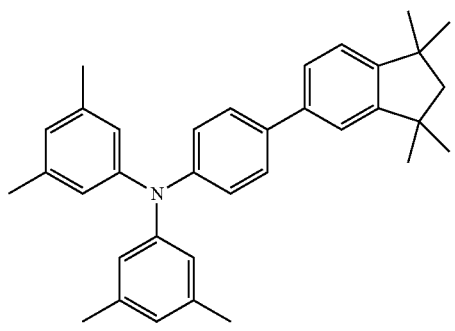
BB-512 + BB-012
BB-1269
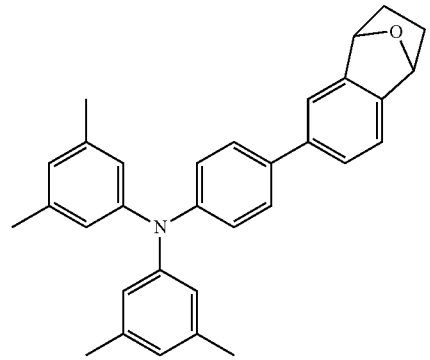
BB-512 + BB-003
BB-1270
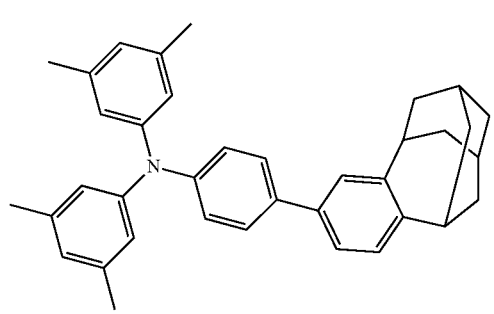
BB-512 + BB-017
BB-1271
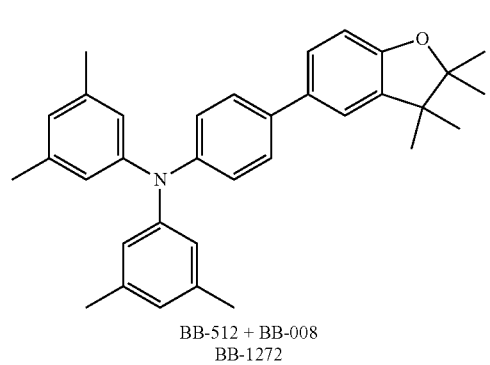
BB-512 + BB-008
BB-1272
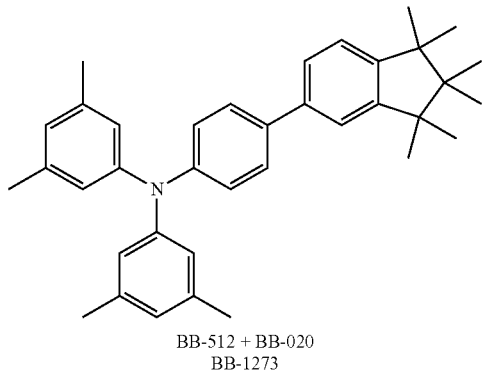
BB-512 + BB-020
BB-1273

-continued
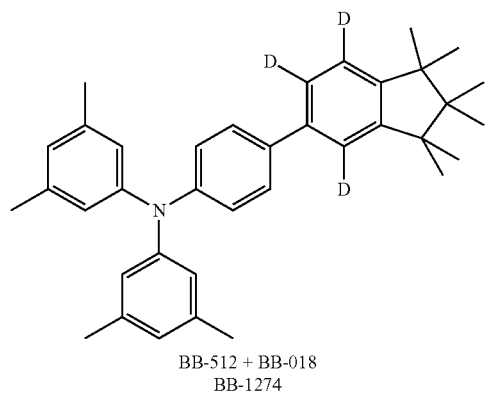
BB-512 + BB-018
BB-1274
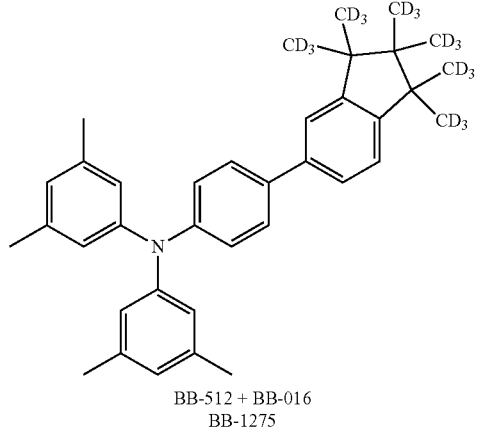
BB-512 + BB-016
BB-1275
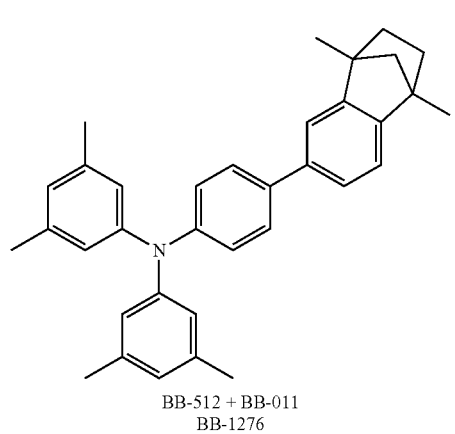
BB-512 + BB-011
BB-1276
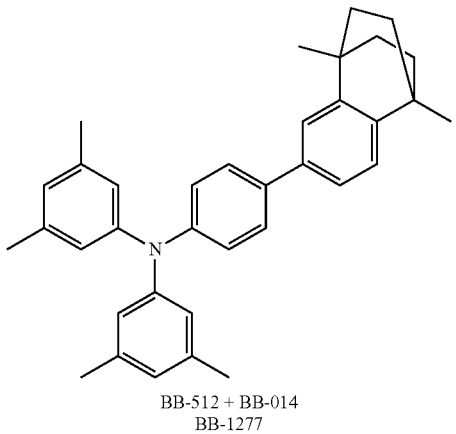
BB-512 + BB-014
BB-1277
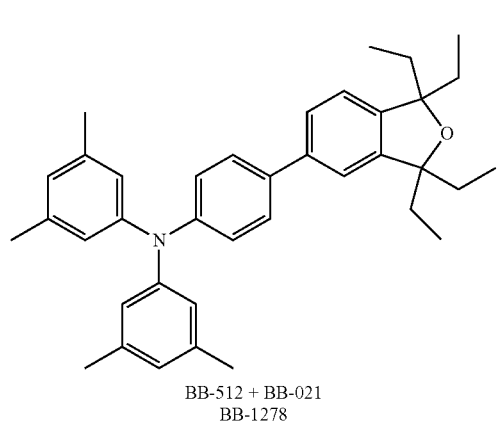
BB-512 + BB-021
BB-1278
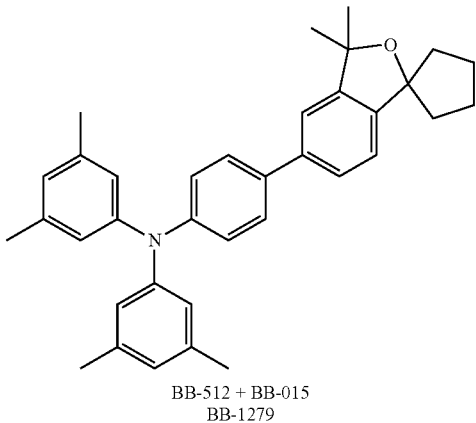
BB-512 + BB-015
BB-1279
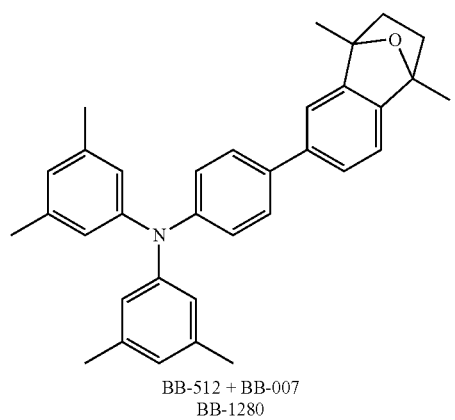
BB-512 + BB-007
BB-1280
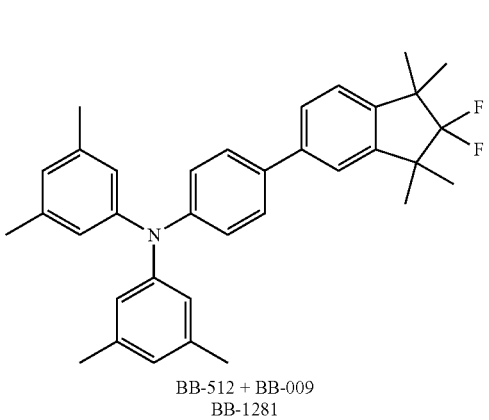
BB-512 + BB-009
BB-1281

-continued
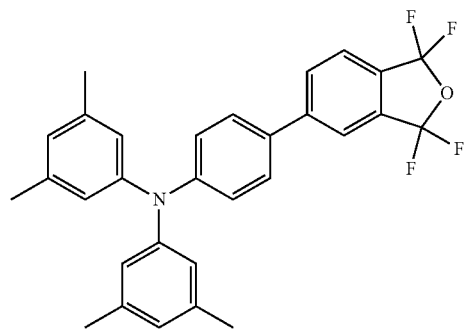
BB-512 + BB-001
BB-1282
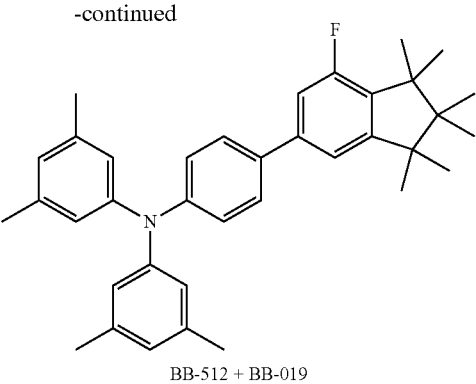
BB-512 + BB-019
BB-1283
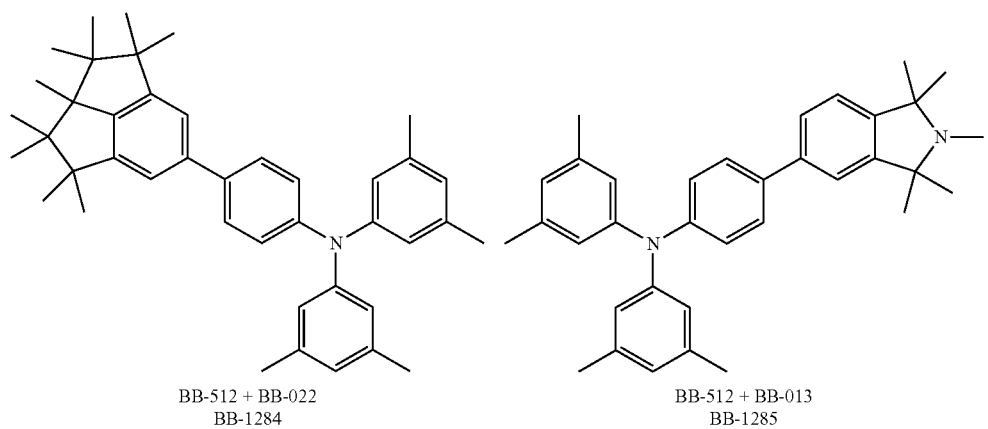
BB-512 + BB-022
BB-1284
BB-512 + BB-013
BB-1285
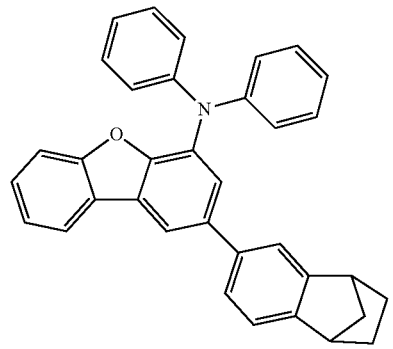
BB-513 + BB-004
BB-1286
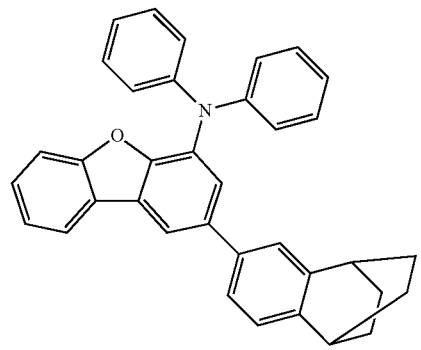
BB-513 + BB-005
BB-1287
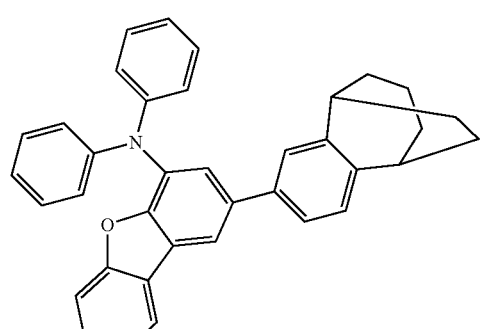
BB-513 + BB-010
BB-1288
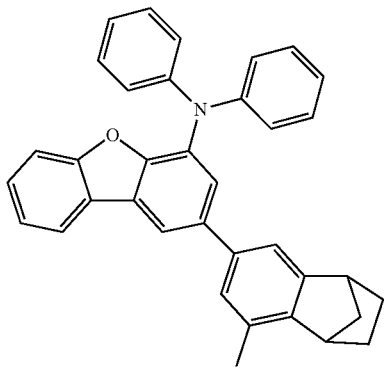
BB-513 + BB-006
BB-1289

-continued
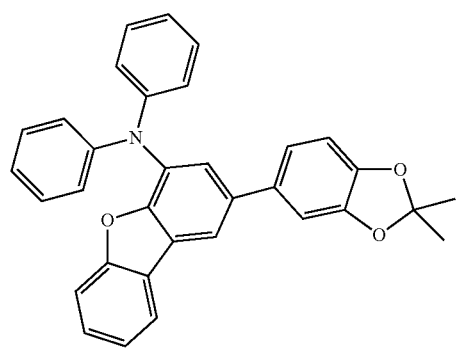
BB-513 + BB-002
BB-1290
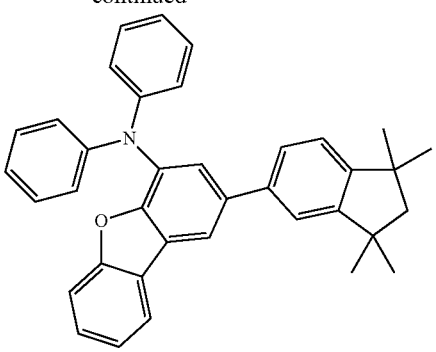
BB-513 + BB-012
BB-1291
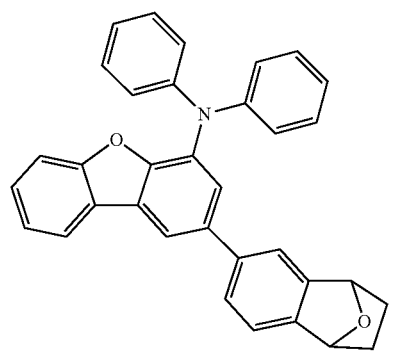
BB-513 + BB-003
BB-1292
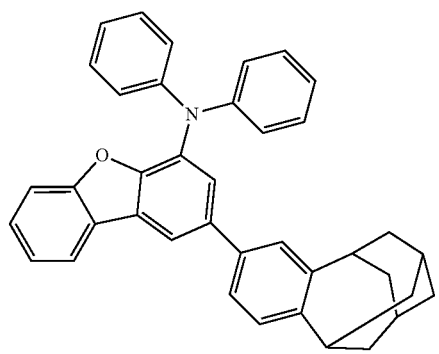
BB-513 + BB-017
BB-1293
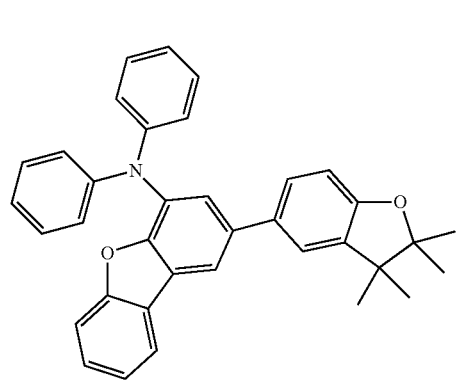
BB-513 + BB-008
BB-1294
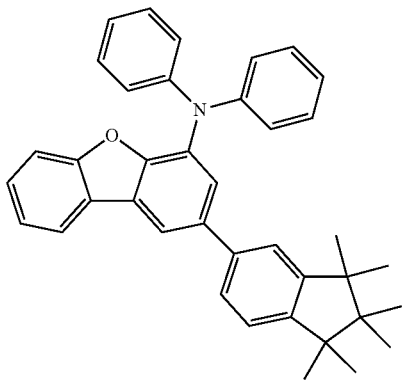
BB-513 + BB-020
BB-1295
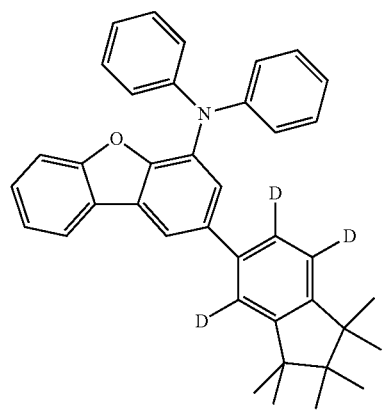
BB-513 + BB-018
BB-1296
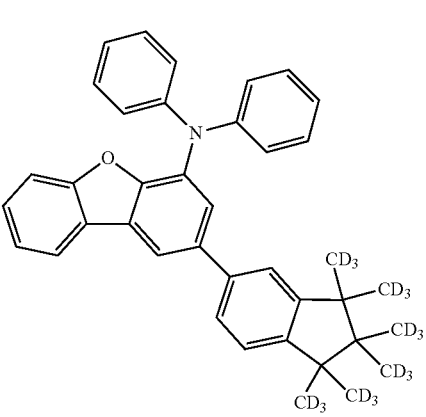
BB-513 + BB-016
BB-1297

-continued
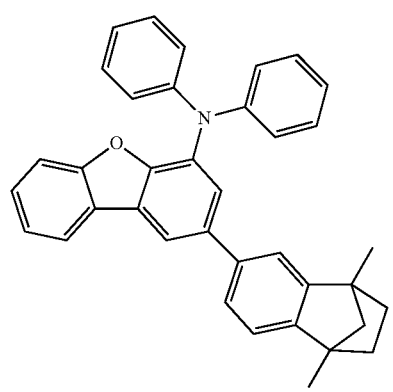
BB-513 + BB-011
BB-1298
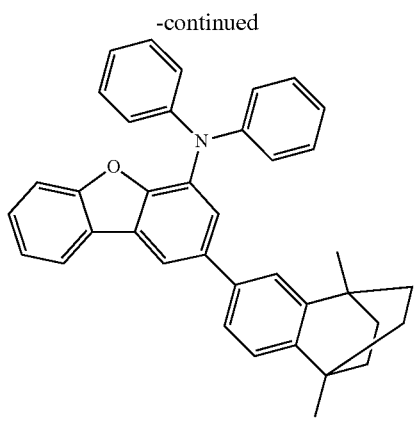
BB-513 + BB-014
BB-1299
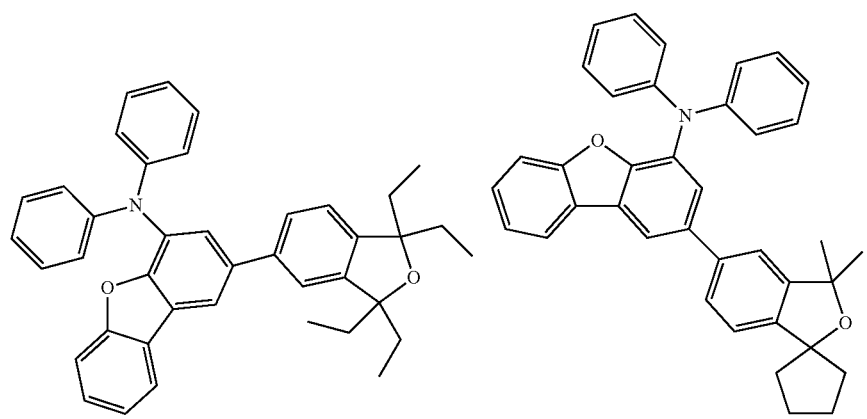
BB-513 + BB-021
BB-1300
BB-513 + BB-015
BB-1301
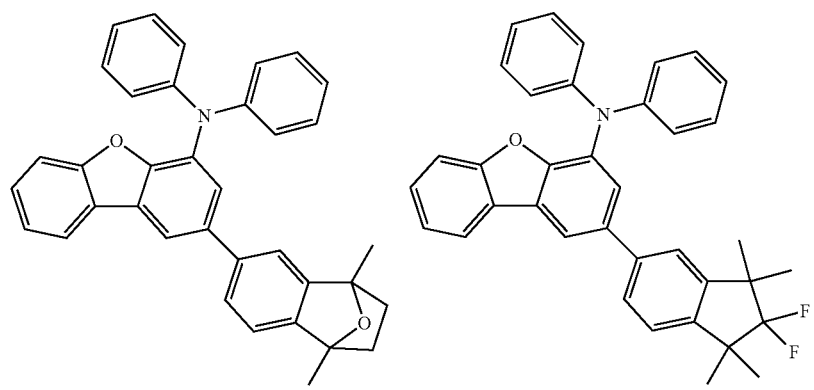
BB-513 + BB-007
BB-1302
BB-513 + BB-009
BB-1303

-continued
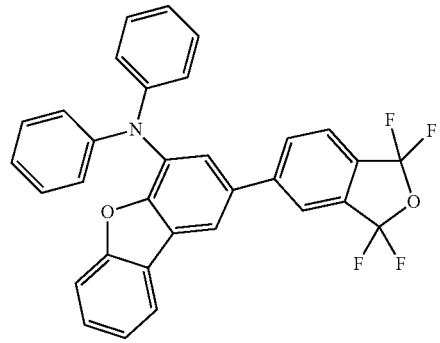
BB-513 + BB-001
BB-1304
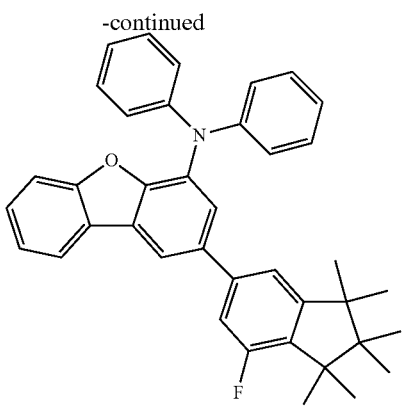
BB-513 + BB-019
BB-1305
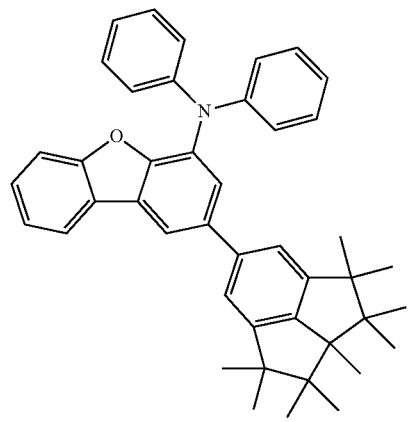
BB-513 + BB-022
BB-1306
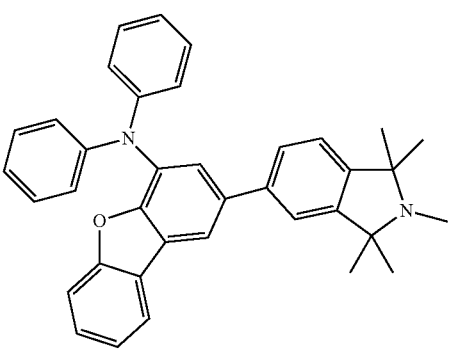
BB-513 + BB-013
BB-1307
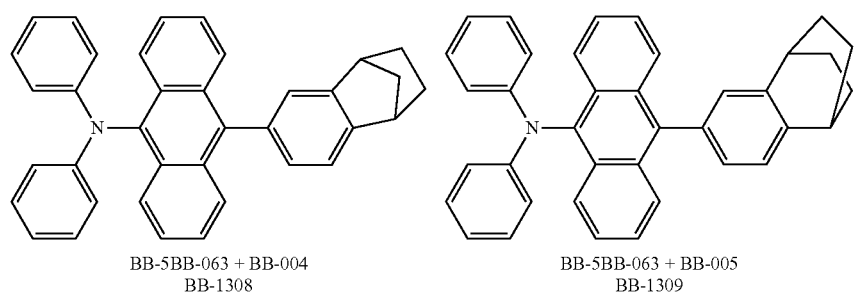
BB-5BB-063 + BB-004
BB-1308
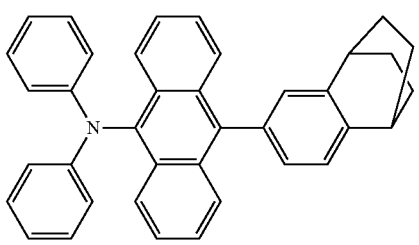
BB-5BB-063 + BB-005
BB-1309
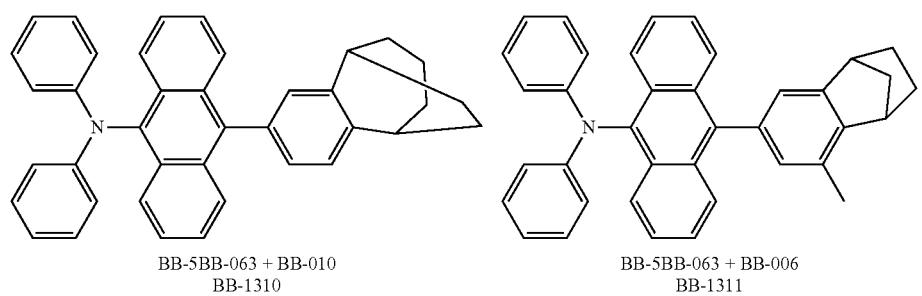
BB-5BB-063 + BB-010
BB-1310
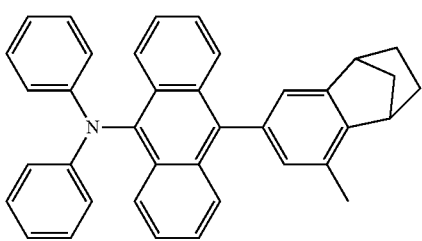
BB-5BB-063 + BB-006
BB-1311

-continued
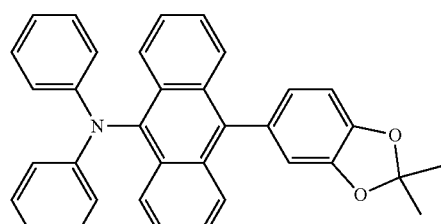
BB-5BB-063 + BB-002
BB-1312
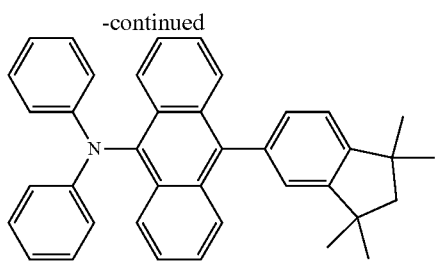
BB-5BB-063 + BB-012
BB-1313
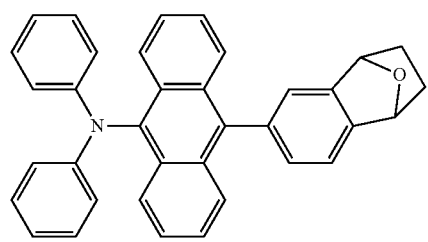
BB-5BB-063 + BB-003
BB-1314
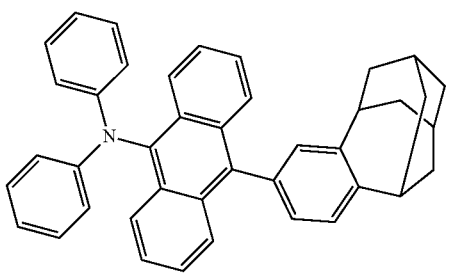
BB-5BB-063 + BB-017
BB-1315
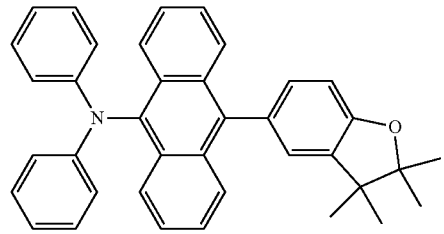
BB-5BB-063 + BB-008
BB-1316
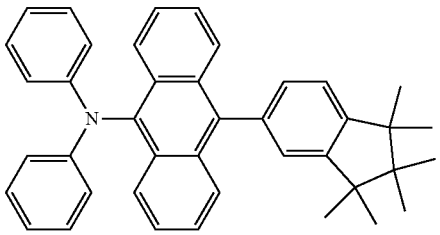
BB-5BB-063 + BB-020
BB-1317
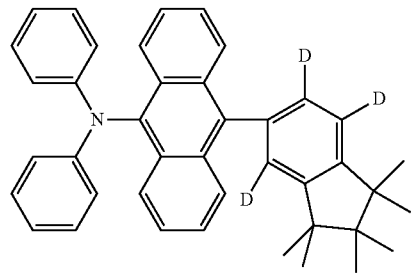
BB-5BB-063 + BB-018
BB-1318
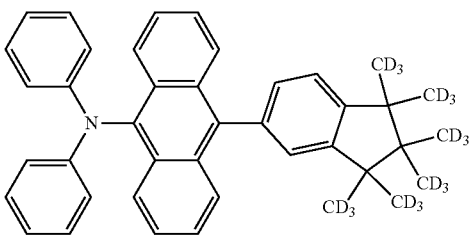
BB-5BB-063 + BB-016
BB-1319
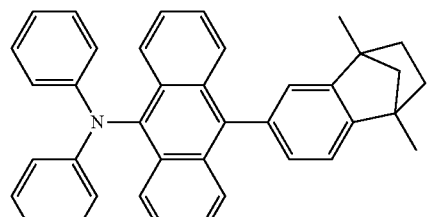
BB-5BB-063 + BB-011
BB-1320
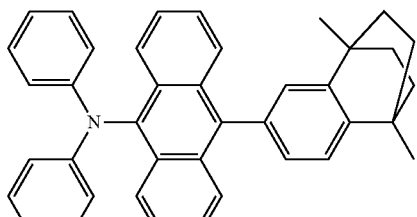
BB-5BB-063 + BB-014
BB-1321

-continued
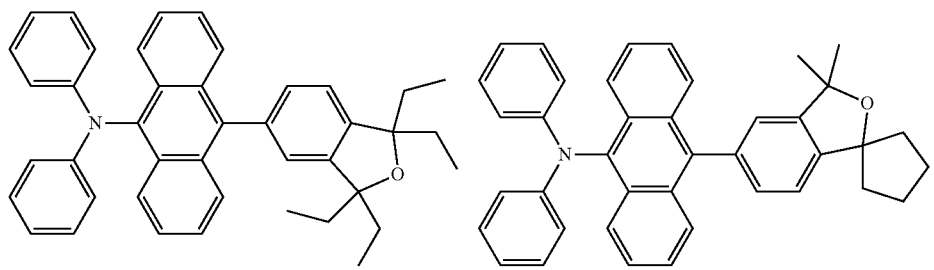
BB-5BB-063 + BB-021
BB-1322
BB-5BB-063 + BB-015
BB-1323
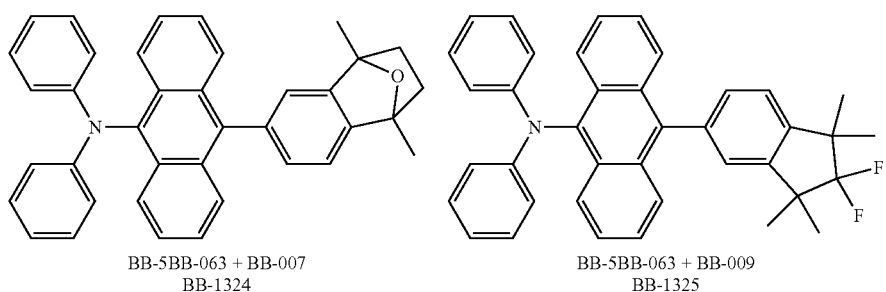
BB-5BB-063 + BB-007
BB-1324
BB-5BB-063 + BB-009
BB-1325
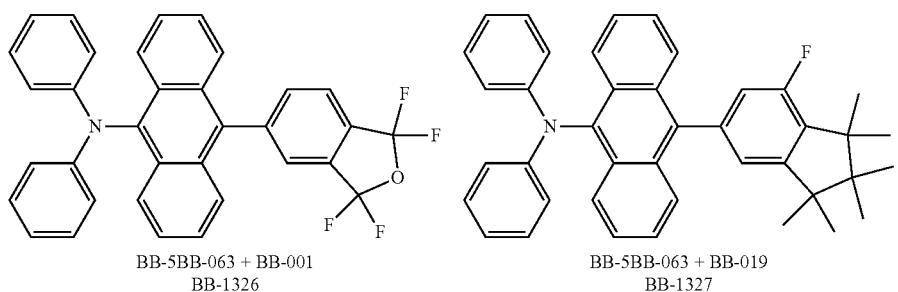
BB-5BB-063 + BB-001
BB-1326
BB-5BB-063 + BB-019
BB-1327
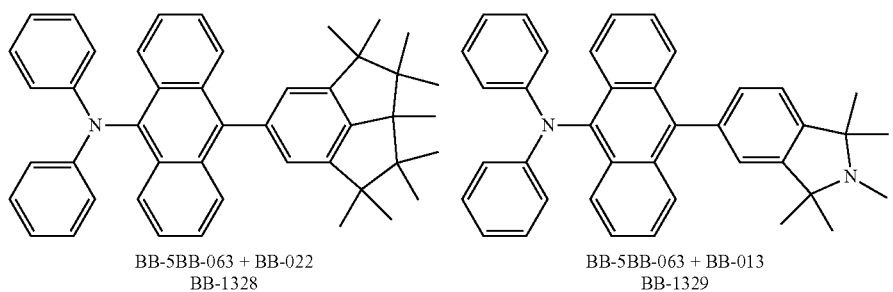
BB-5BB-063 + BB-022
BB-1328
BB-5BB-063 + BB-013
BB-1329
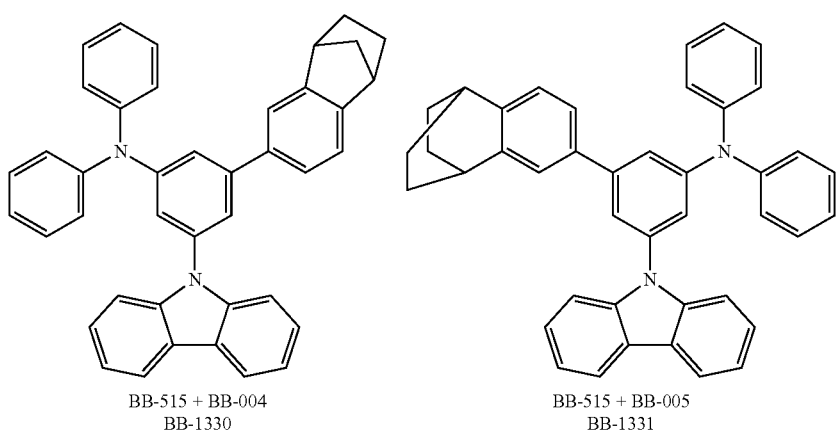
BB-515 + BB-004
BB-1330
BB-515 + BB-005
BB-1331

-continued
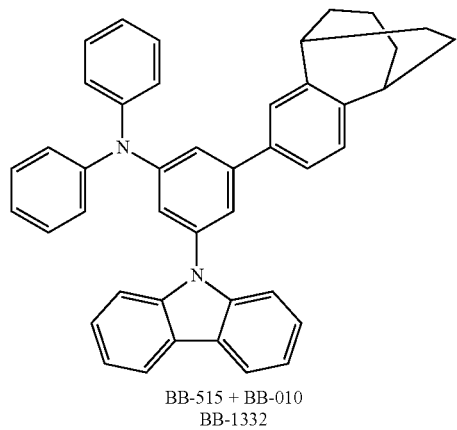
BB-515 + BB-010
BB-1332
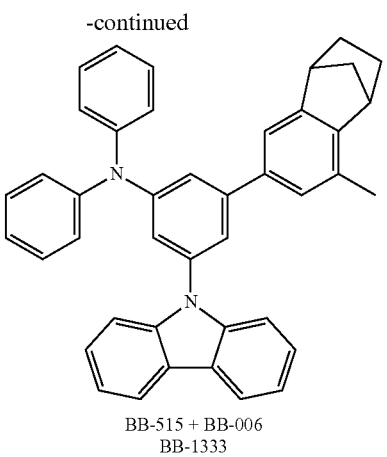
BB-515 + BB-006
BB-1333
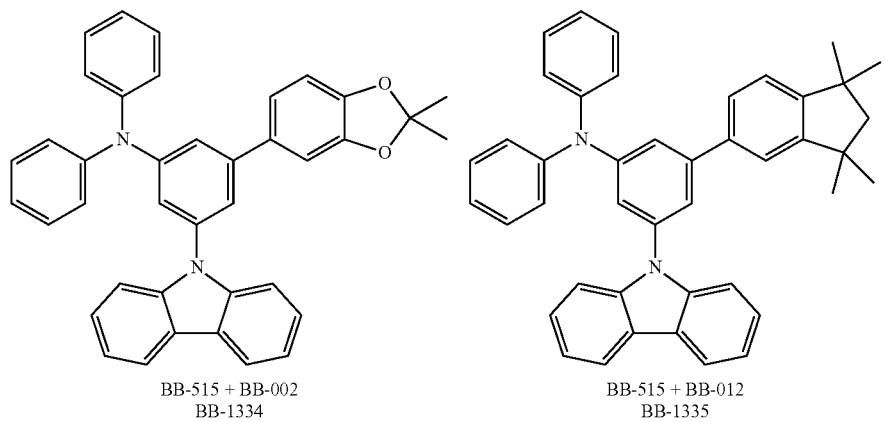
BB-515 + BB-002
BB-1334
BB-515 + BB-012
BB-1335
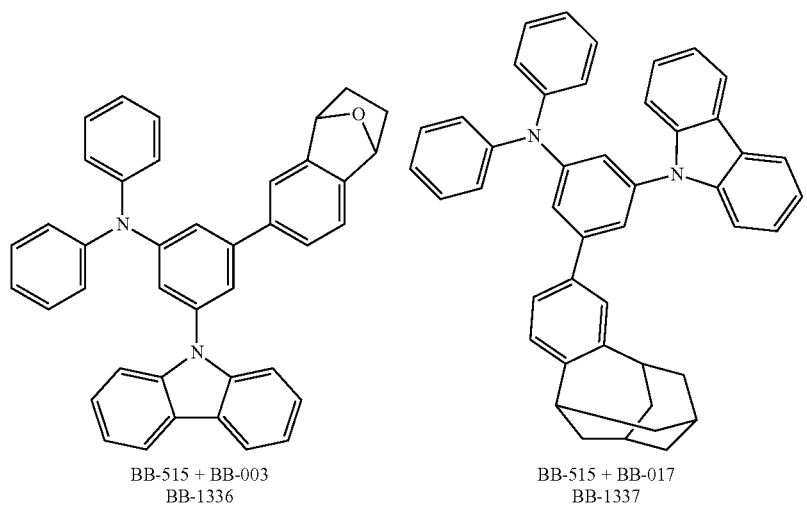
BB-515 + BB-003
BB-1336
BB-515 + BB-017
BB-1337

-continued
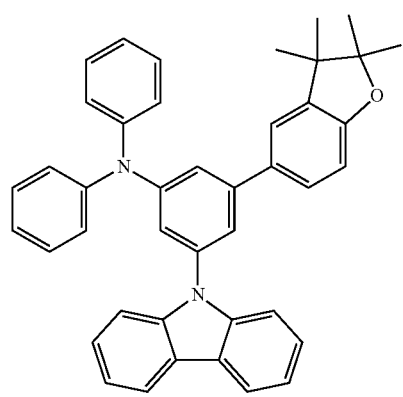
BB-515 + BB-008
BB-1338
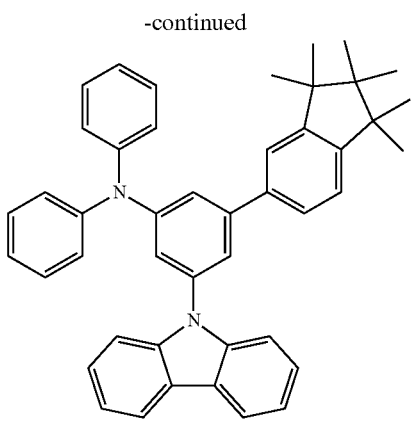
BB-515 + BB-020
BB-1339
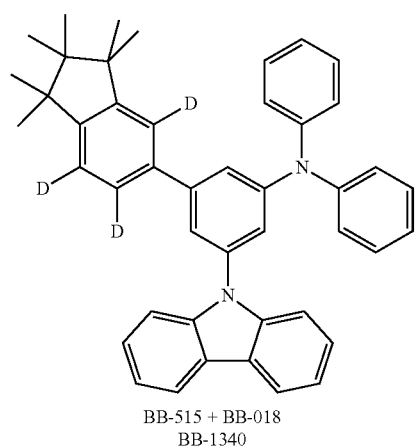
BB-515 + BB-018
BB-1340
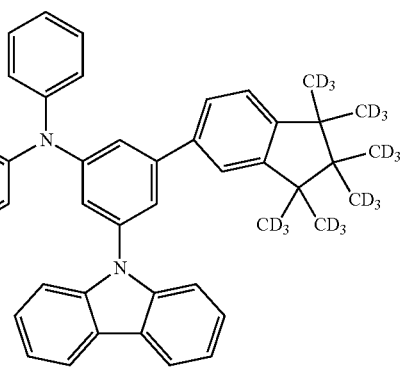
BB-515 + BB-016
BB-1341
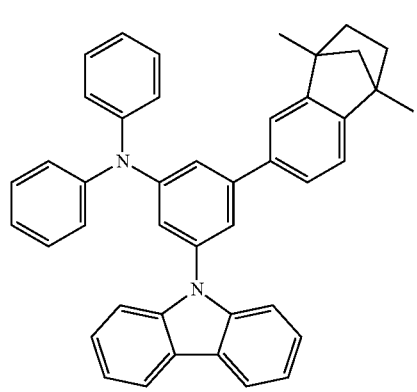
BB-515 + BB-011
BB-1342
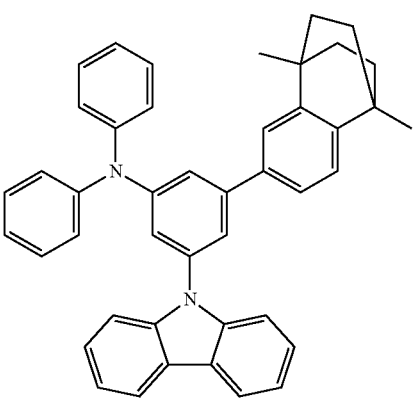
BB-515 + BB-014
BB-1343

-continued
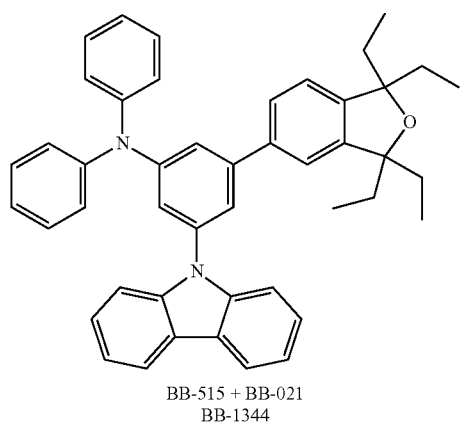
BB-515 + BB-021
BB-1344
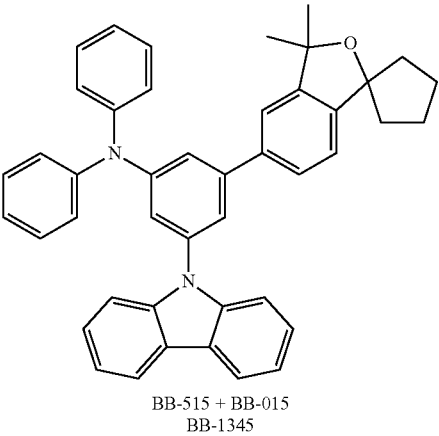
BB-515 + BB-015
BB-1345
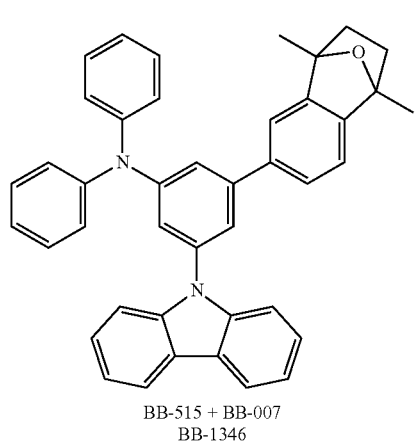
BB-515 + BB-007
BB-1346
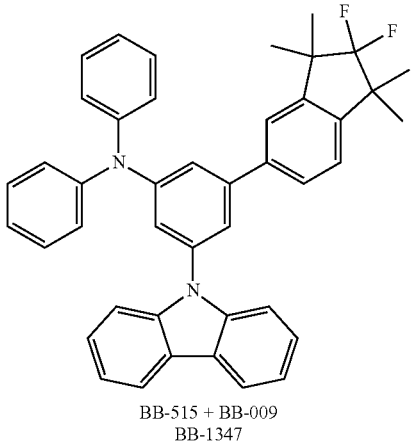
BB-515 + BB-009
BB-1347
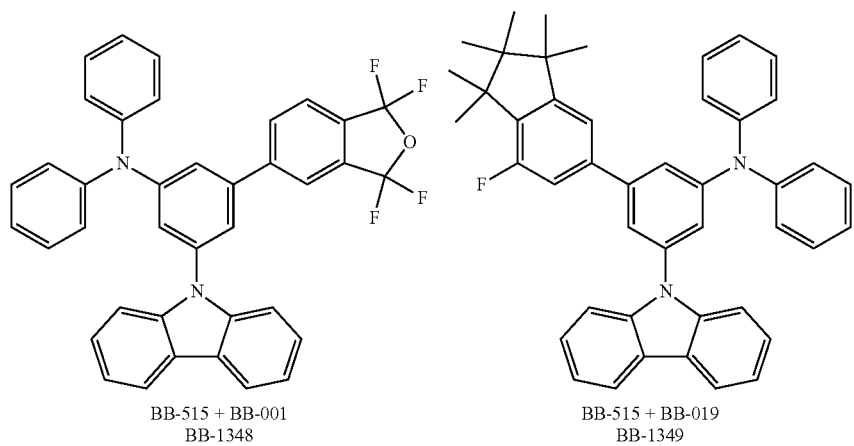
BB-515 + BB-001
BB-1348
BB-515 + BB-019
BB-1349

-continued
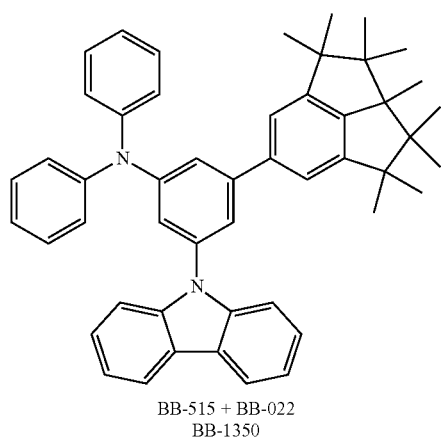
BB-515 + BB-022
BB-1350
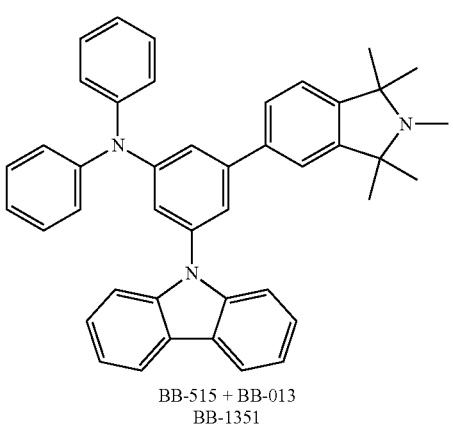
BB-515 + BB-013
BB-1351
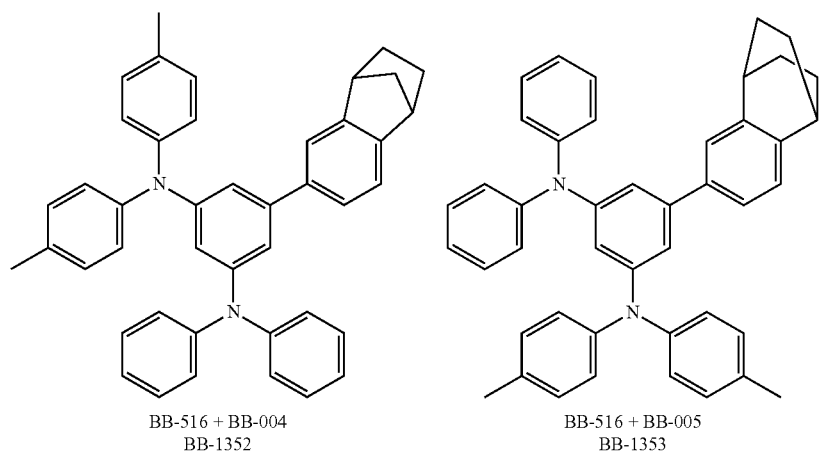
BB-516 + BB-004
BB-1352
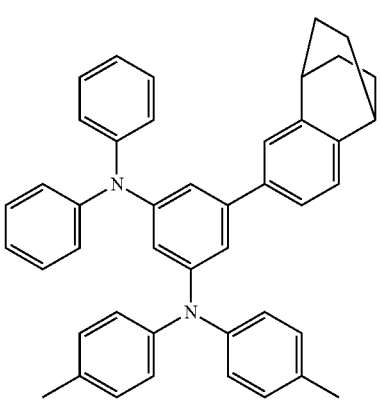
BB-516 + BB-005
BB-1353
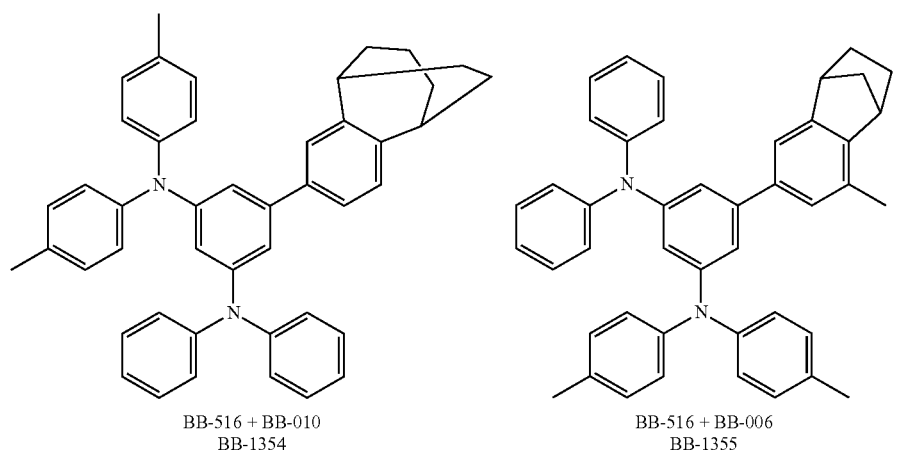
BB-516 + BB-010
BB-1354
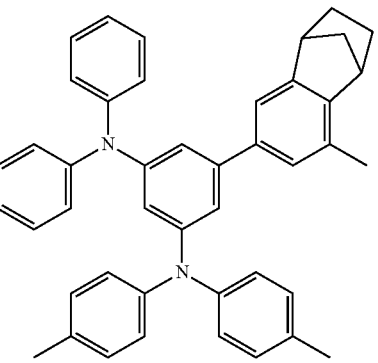
BB-516 + BB-006
BB-1355

-continued
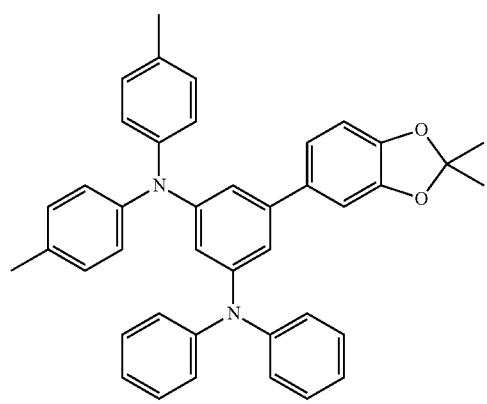
BB-516 + BB-002
BB-1356
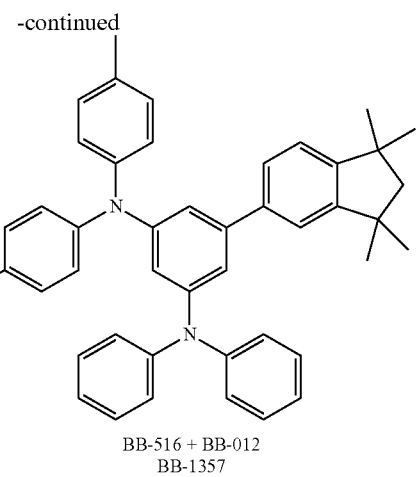
BB-516 + BB-012
BB-1357
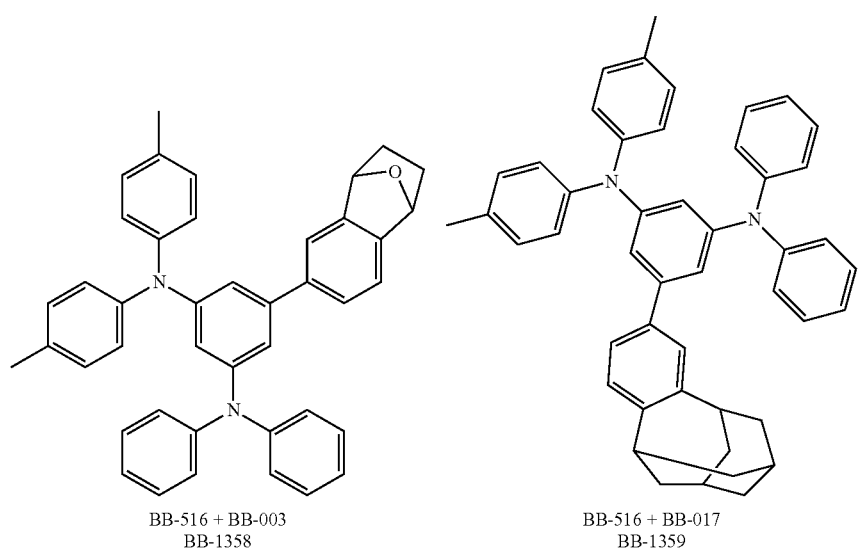
BB-516 + BB-003
BB-1358
BB-516 + BB-017
BB-1359
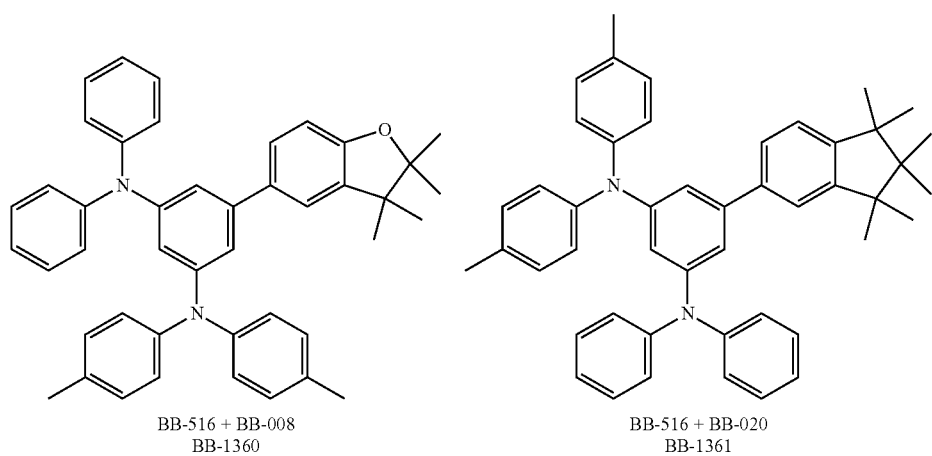
BB-516 + BB-008
BB-1360
BB-516 + BB-020
BB-1361

-continued
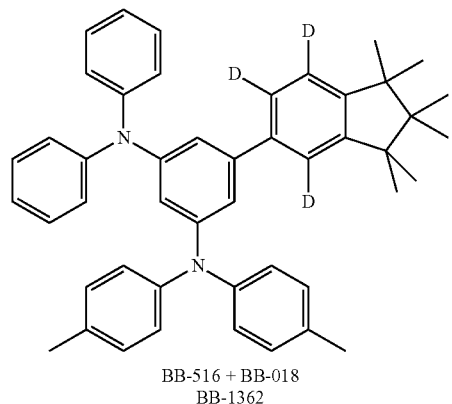
BB-516 + BB-018
BB-1362
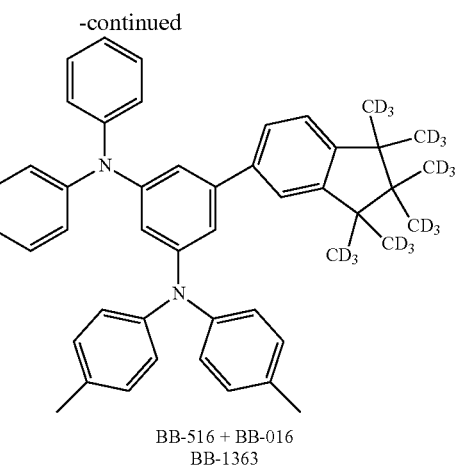
BB-516 + BB-016
BB-1363
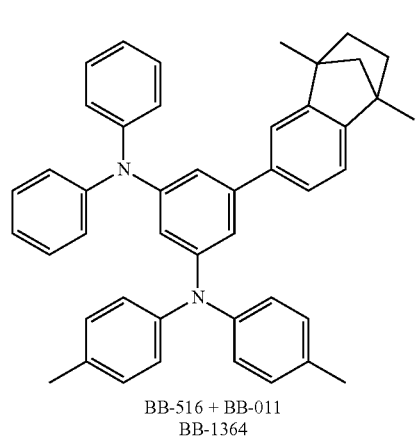
BB-516 + BB-011
BB-1364
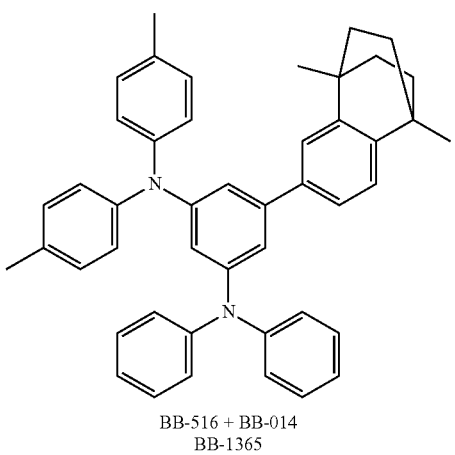
BB-516 + BB-014
BB-1365
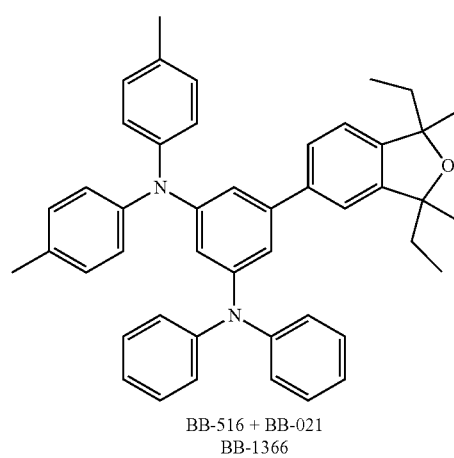
BB-516 + BB-021
BB-1366
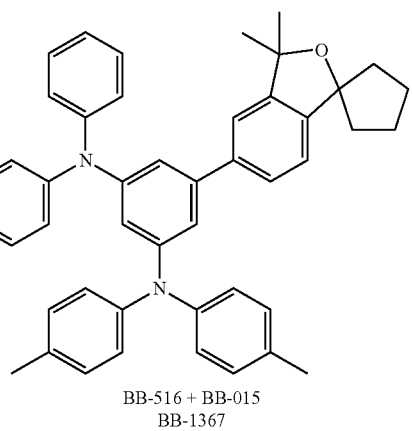
BB-516 + BB-015
BB-1367

-continued
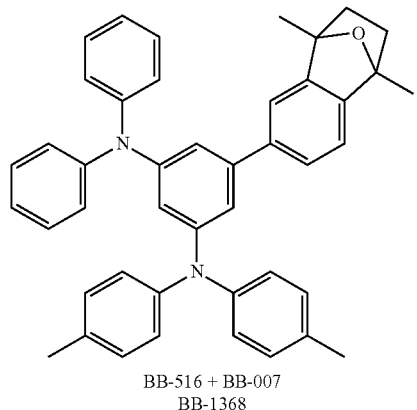
BB-516 + BB-007
BB-1368
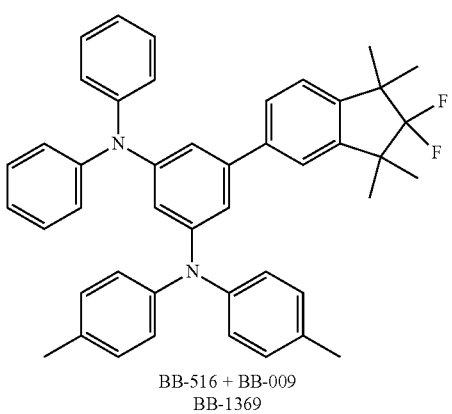
BB-516 + BB-009
BB-1369
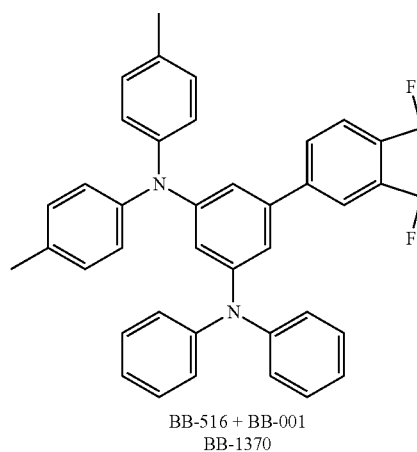
BB-516 + BB-001
BB-1370
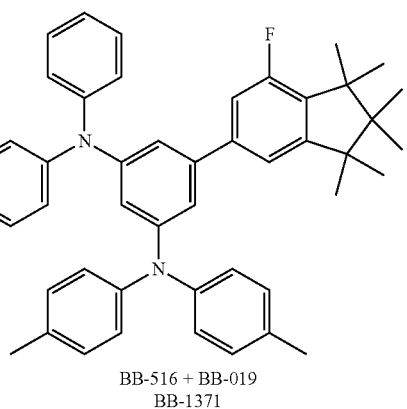
BB-516 + BB-019
BB-1371
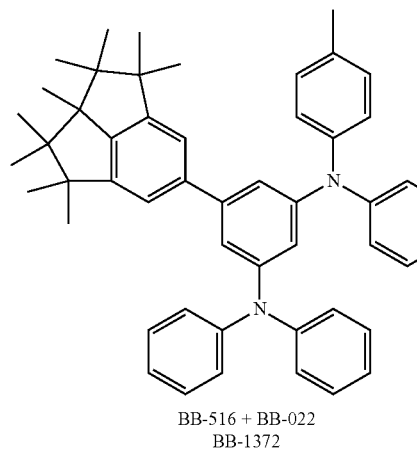
BB-516 + BB-022
BB-1372
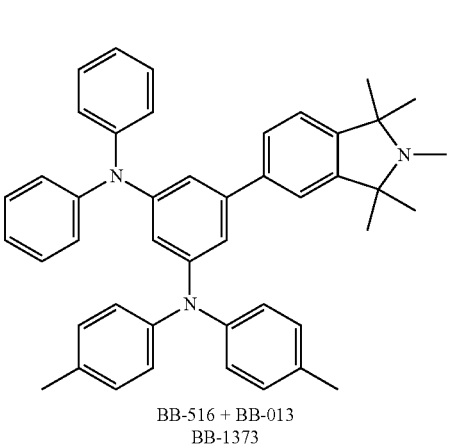
BB-516 + BB-013
BB-1373
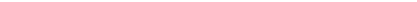
BB-517 + BB-004
BB-1374

-continued
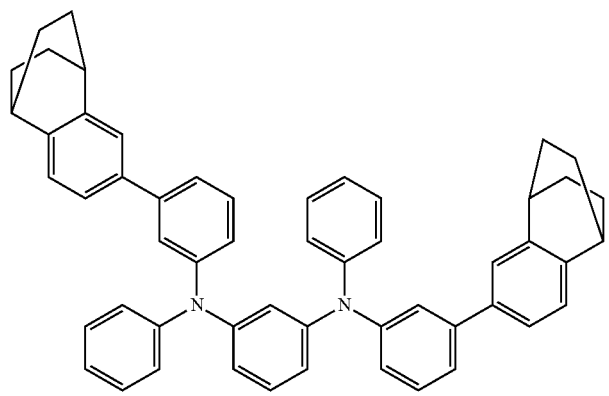
BB-517 + BB-005
BB-1375
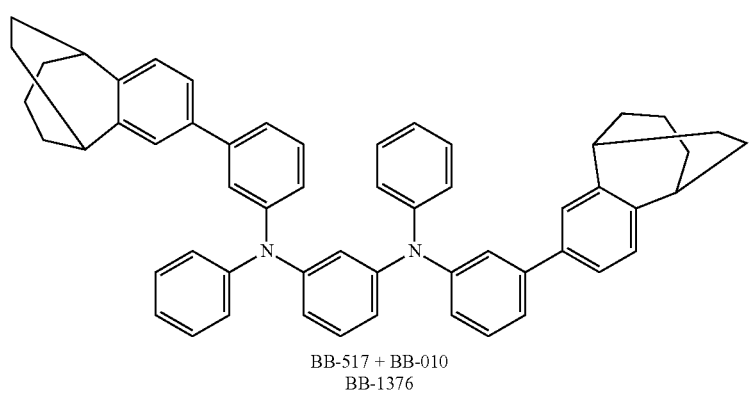
BB-517 + BB-010
BB-1376
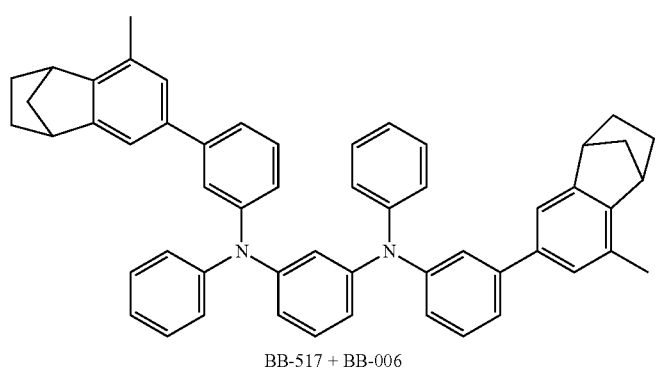
BB-517 + BB-006
BB-1377
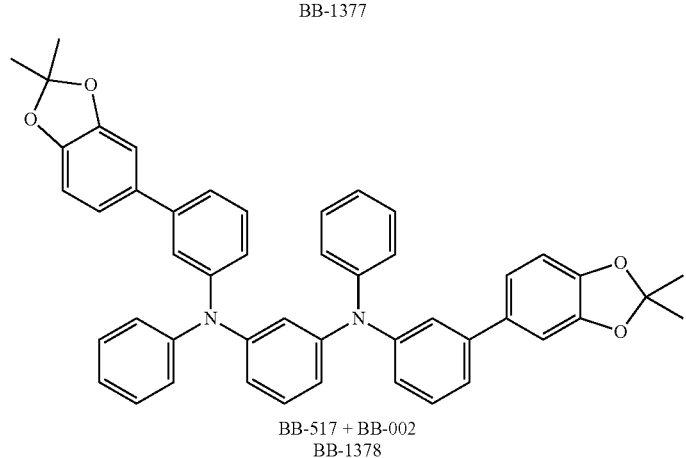
BB-517 + BB-002
BB-1378

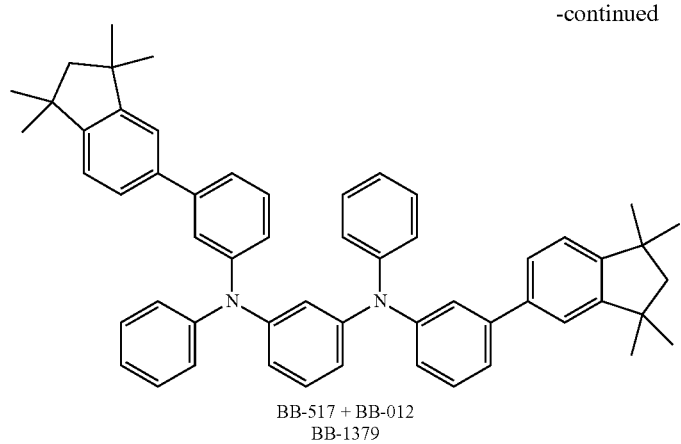
BB-517 + BB-012
BB-1379
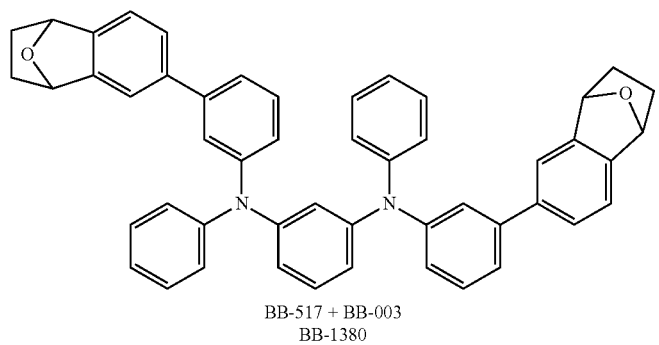
BB-517 + BB-003
BB-1380
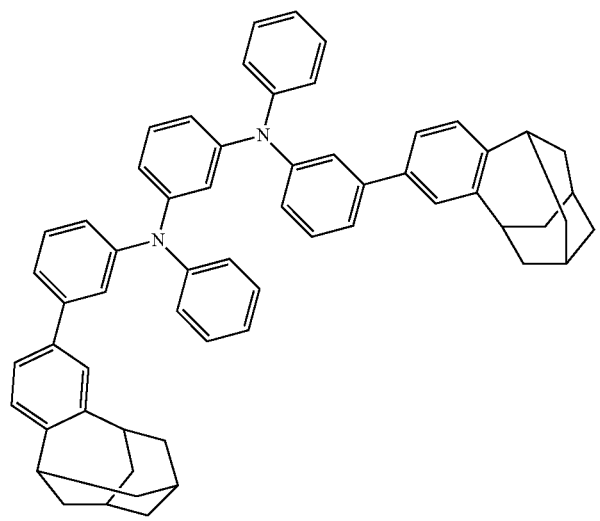
BB-517 + BB-017
BB-1381

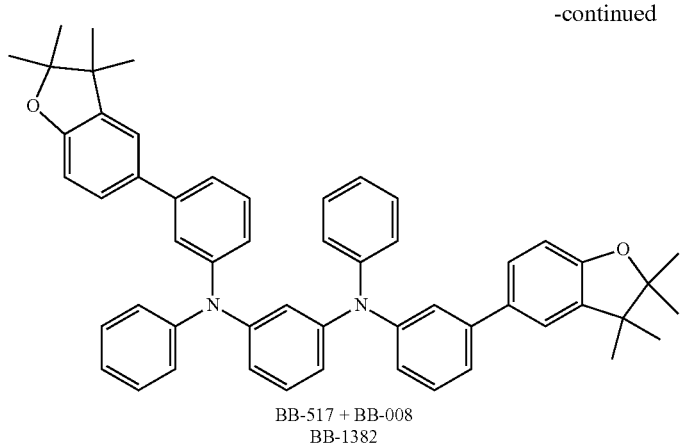
BB-517 + BB-008
BB-1382
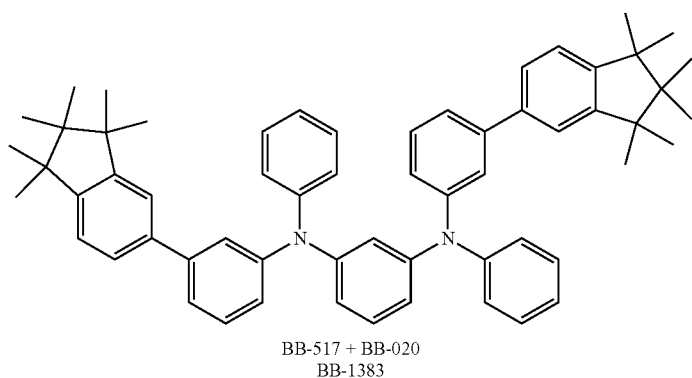
BB-517 + BB-020
BB-1383
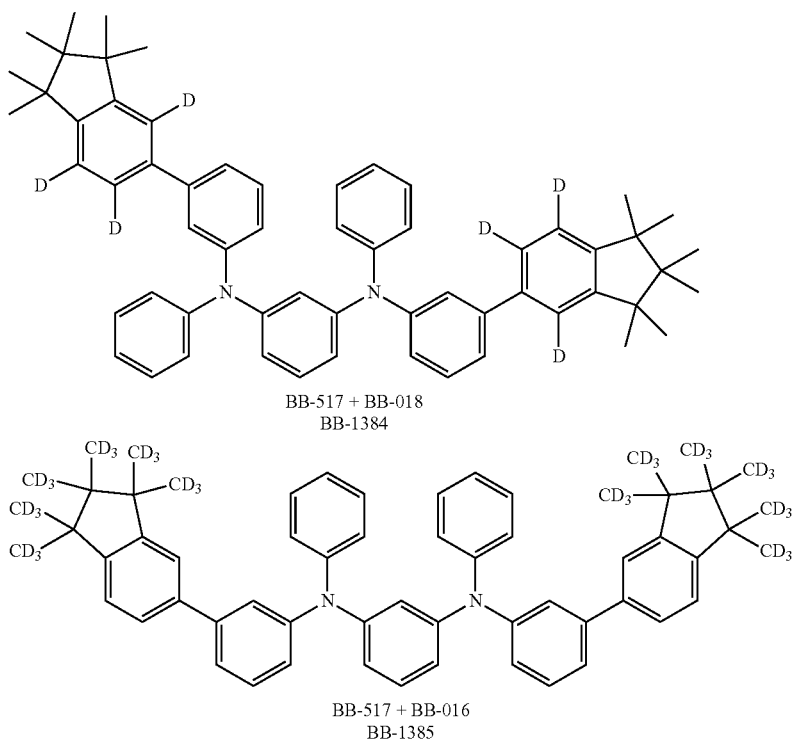
BB-517 + BB-018
BB-1384
BB-517 + BB-016
BB-1385

-continued
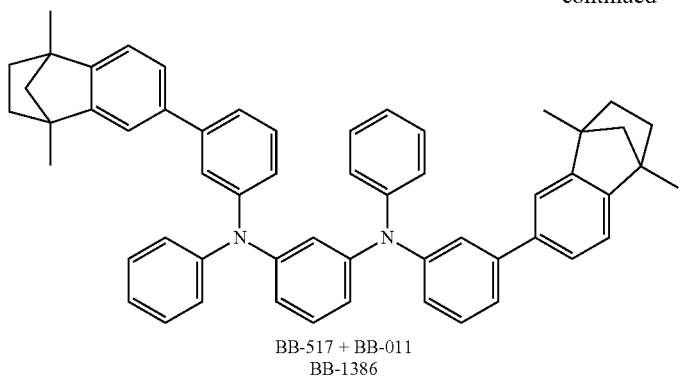
BB-517 + BB-011
BB-1386
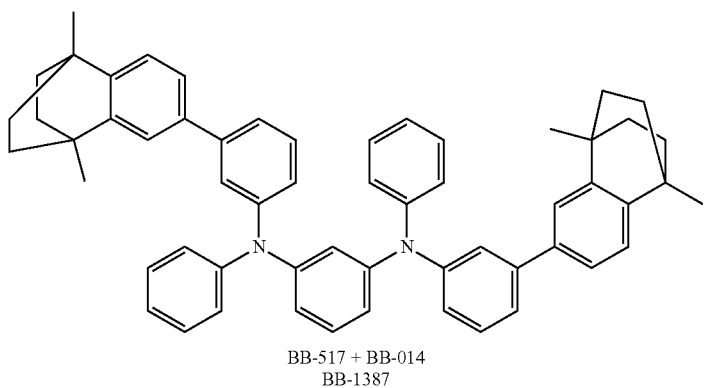
BB-517 + BB-014
BB-1387
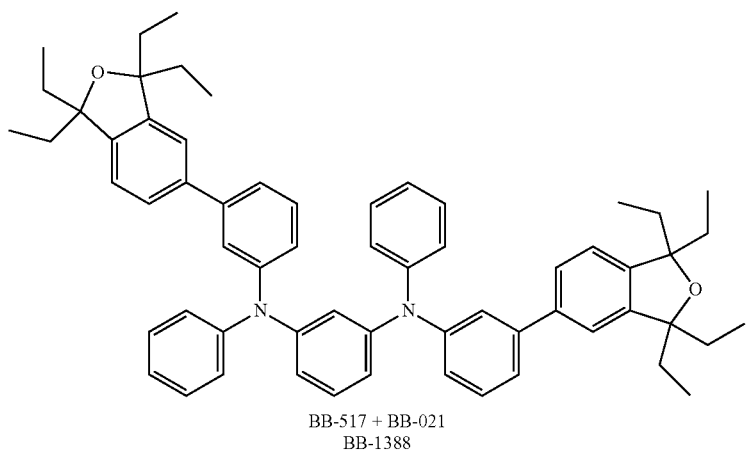
BB-517 + BB-021
BB-1388
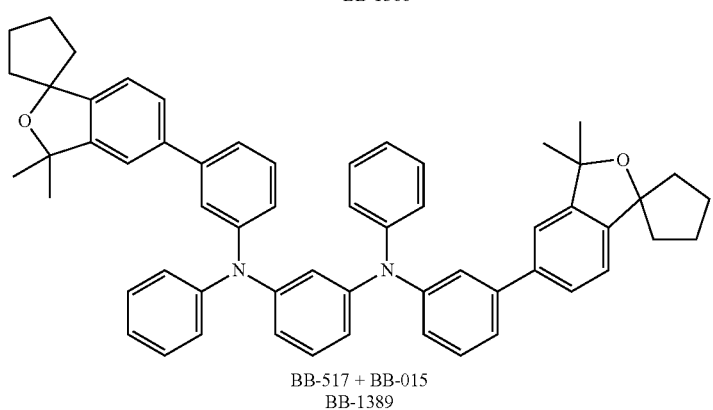
BB-517 + BB-015
BB-1389

-continued
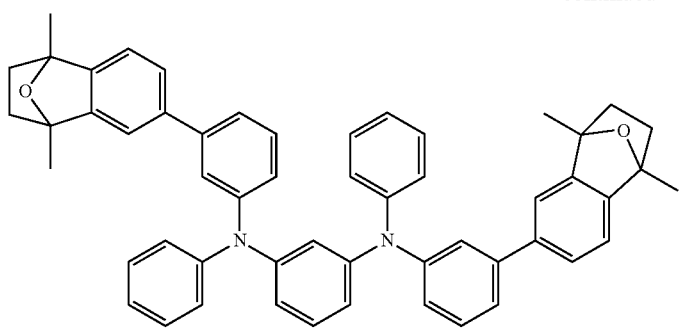
BB-517 + BB-007
BB-1390
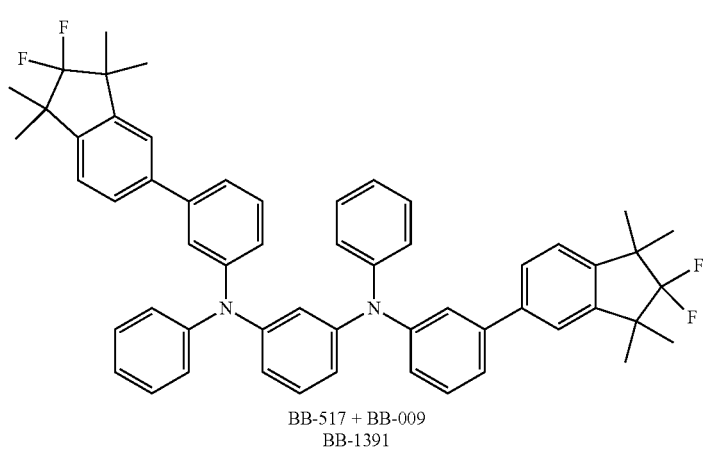
BB-517 + BB-009
BB-1391
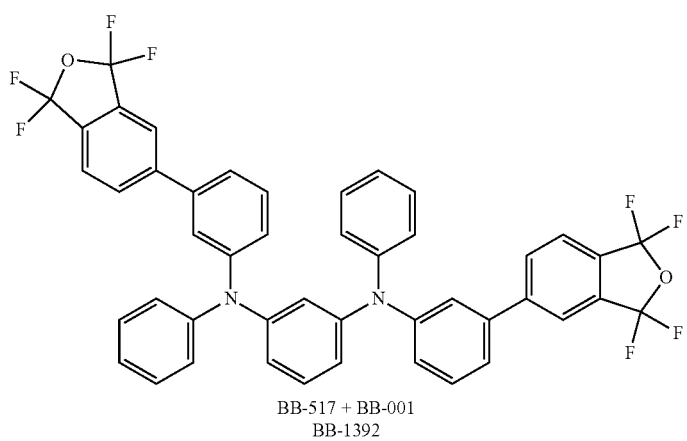
BB-517 + BB-001
BB-1392
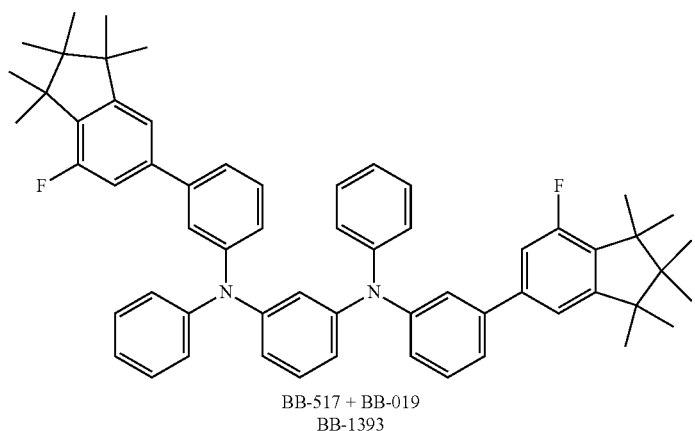
BB-517 + BB-019
BB-1393

-continued
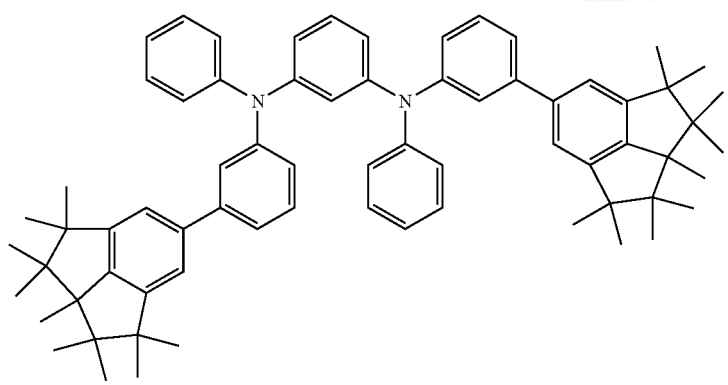
BB-517 + BB-022
BB-1394
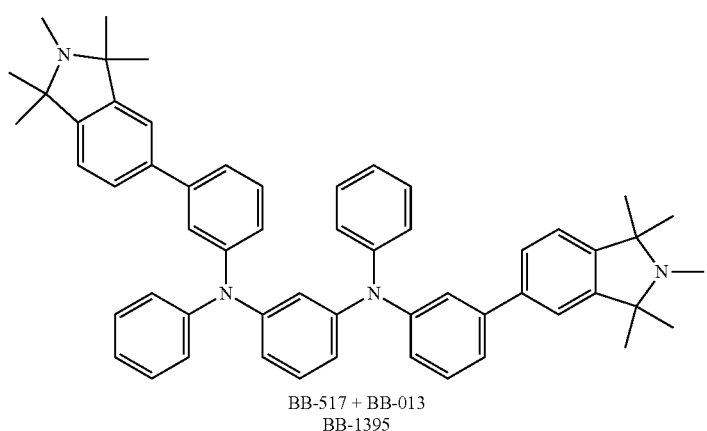
BB-517 + BB-013
BB-1395
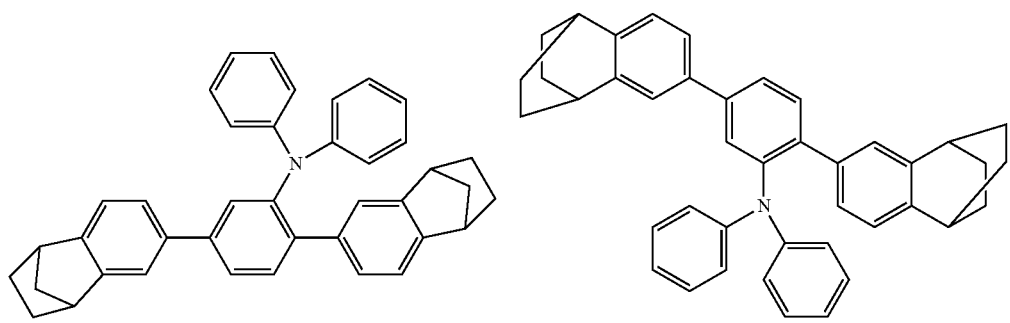
BB-518 + BB-004
BB-1396
BB-518 + BB-005
BB-1397
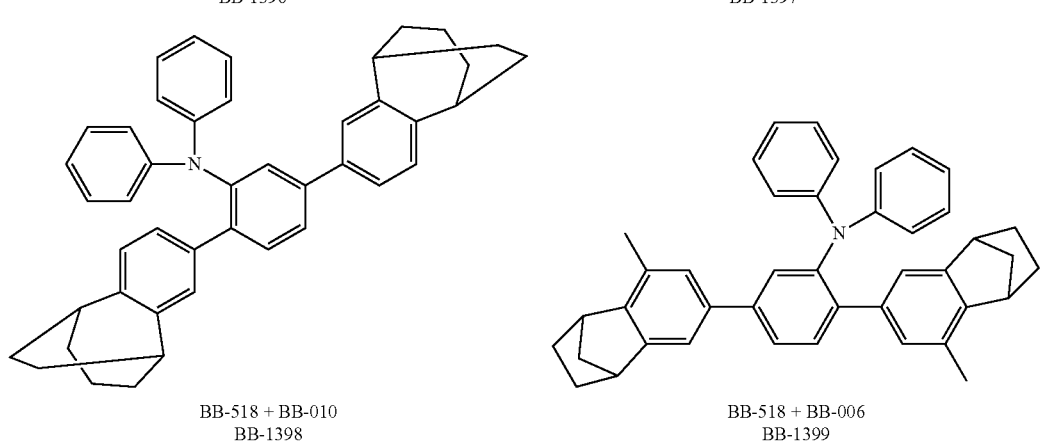
BB-518 + BB-010
BB-1398
BB-518 + BB-006
BB-1399

-continued
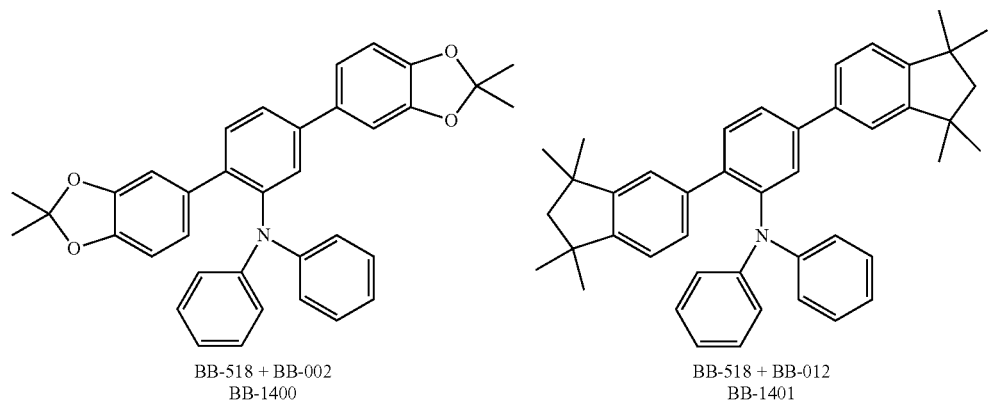
BB-518 + BB-002
BB-1400
BB-518 + BB-012
BB-1401
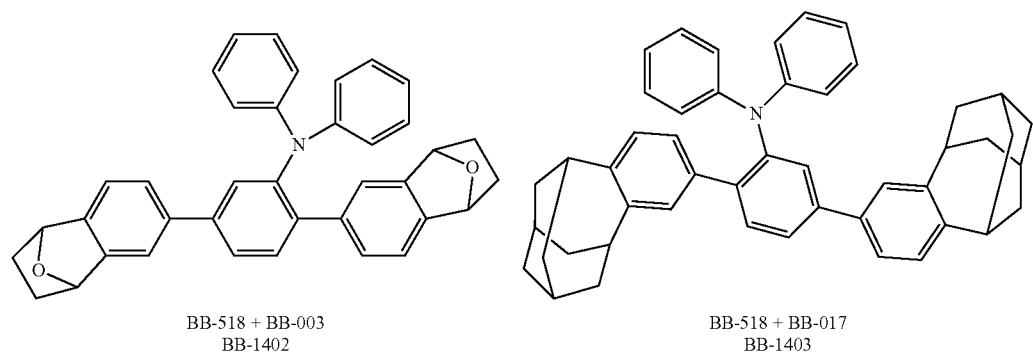
BB-518 + BB-003
BB-1402
BB-518 + BB-017
BB-1403
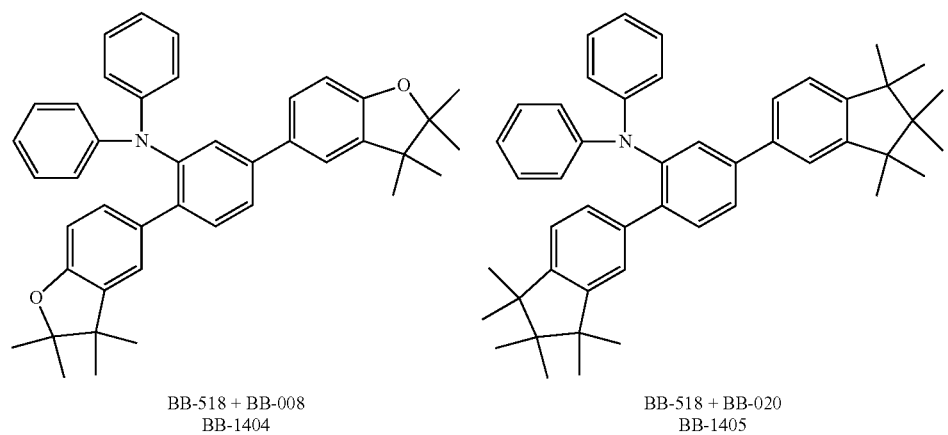
BB-518 + BB-008
BB-1404
BB-518 + BB-020
BB-1405

-continued
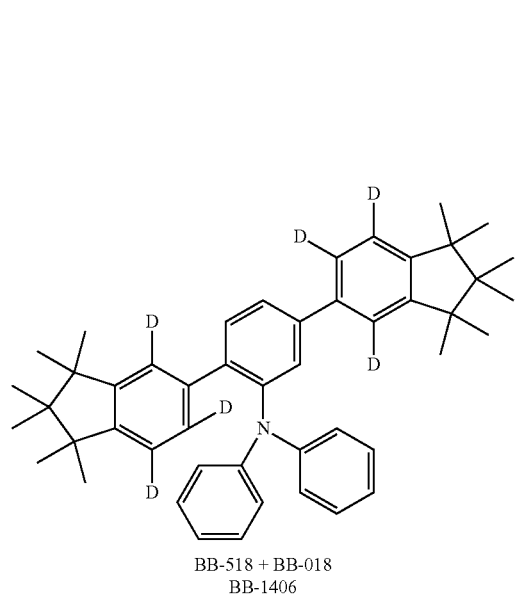
BB-518 + BB-018
BB-1406
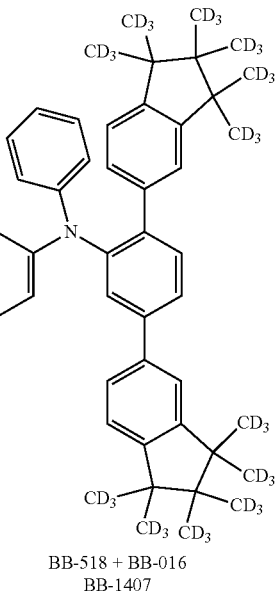
BB-518 + BB-016
BB-1407
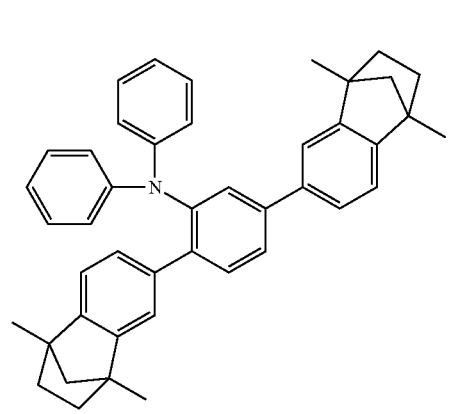
BB-518 + BB-011
BB-1408
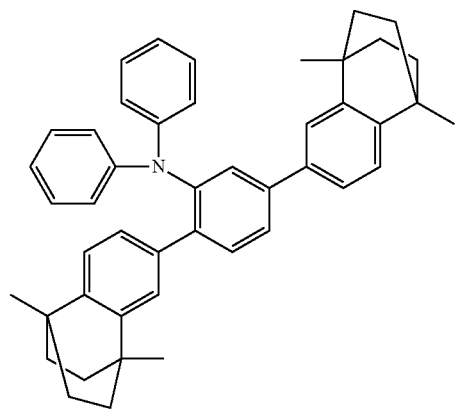
BB-518 + BB-014
BB-1409
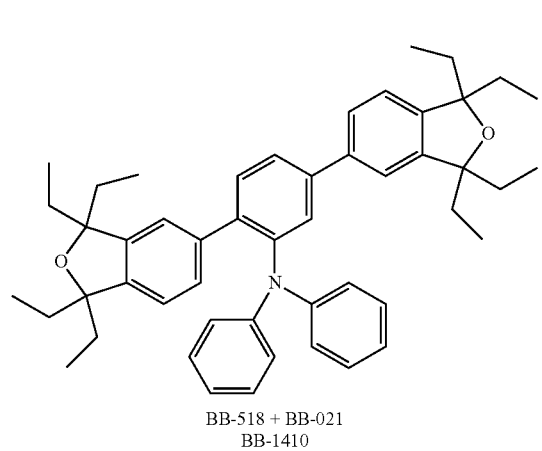
BB-518 + BB-021
BB-1410
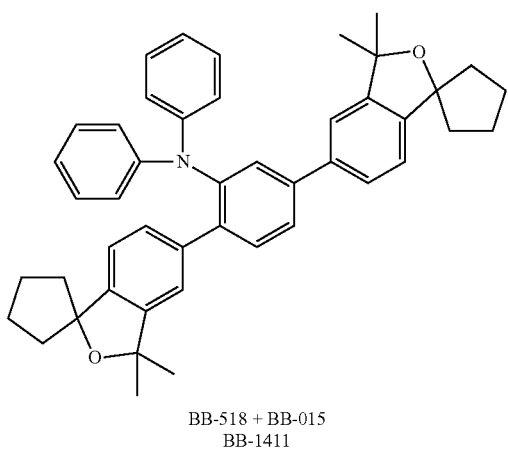
BB-518 + BB-015
BB-1411

-continued
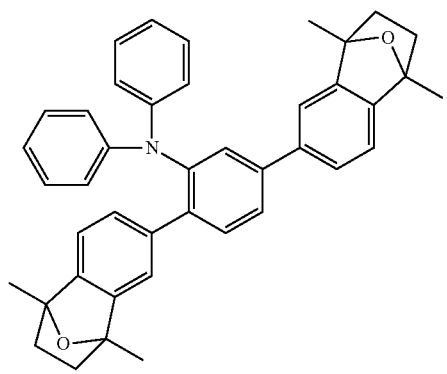
BB-518 + BB-007
BB-1412
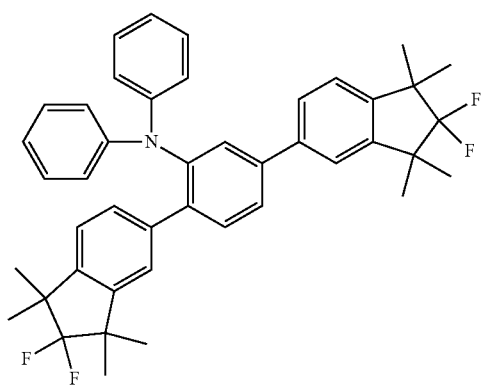
BB-518 + BB-009
BB-1413
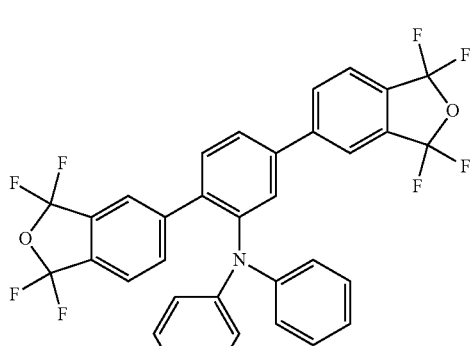
BB-518 + BB-001
BB-1414
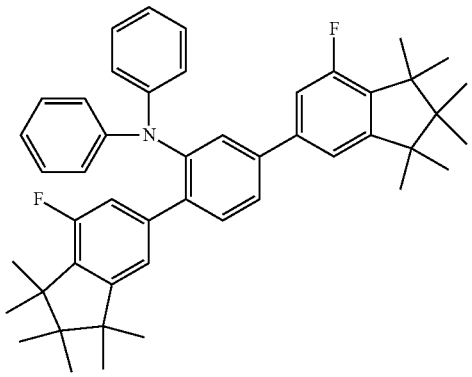
BB-518 + BB-019
BB-1415
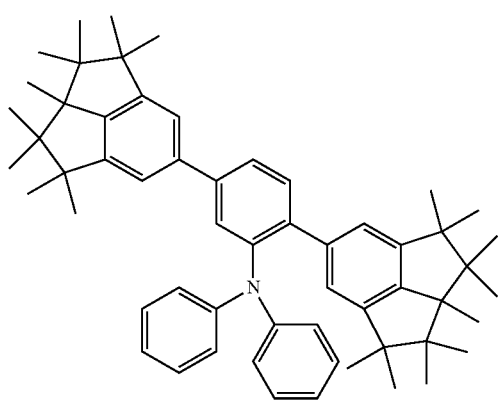
BB-518 + BB-022
BB-1416
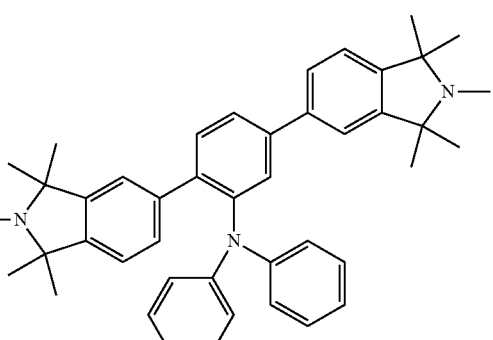
BB-518 + BB-013
BB-1417

-continued
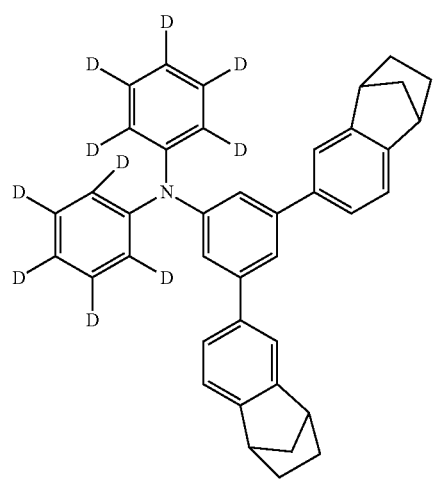
BB-519 + BB-004
BB-1418
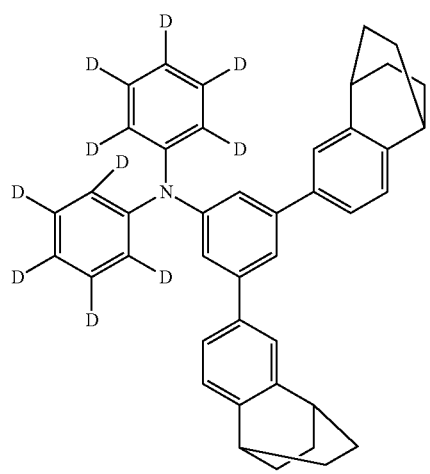
BB-519 + BB-005
BB-1419
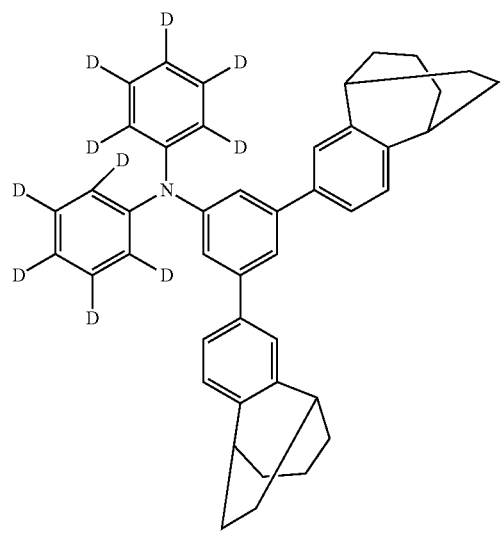
BB-519 + BB-010
BB-1420
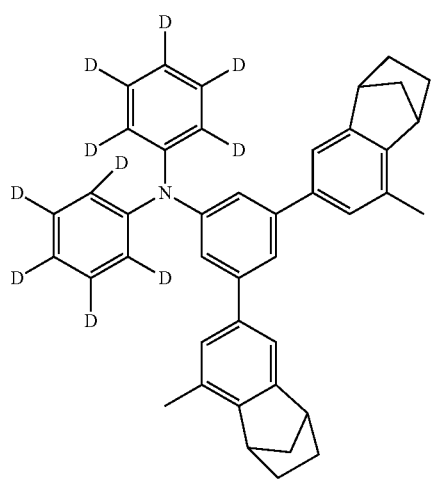
BB-519 + BB-006
BB-1421
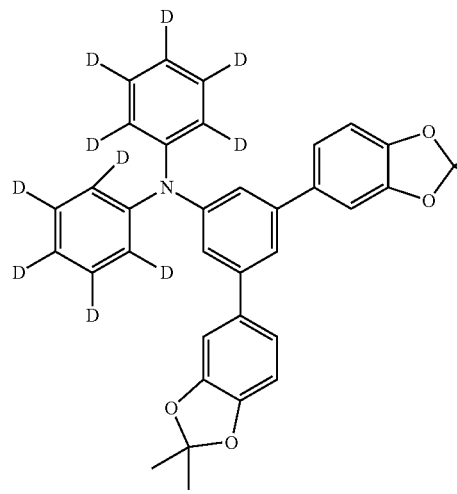
BB-519 + BB-002
BB-1422
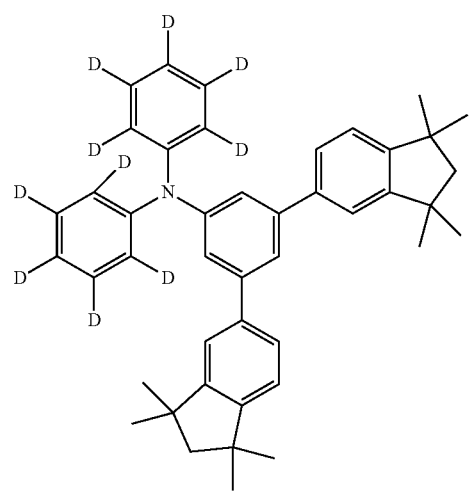
BB-519 + BB-012
BB-1423

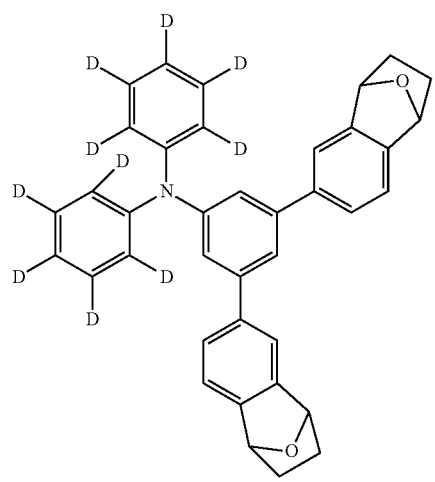
BB-519 + BB-003
BB-1424
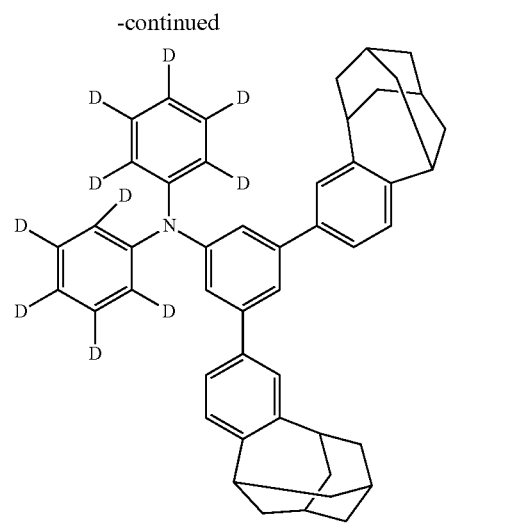
BB-519 + BB-017
BB-1425
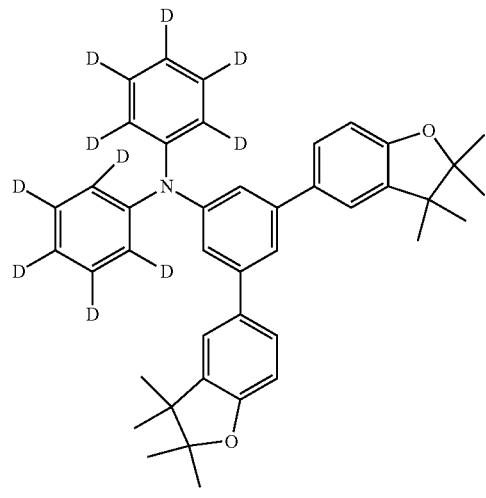
BB-519 + BB-008
BB-1426
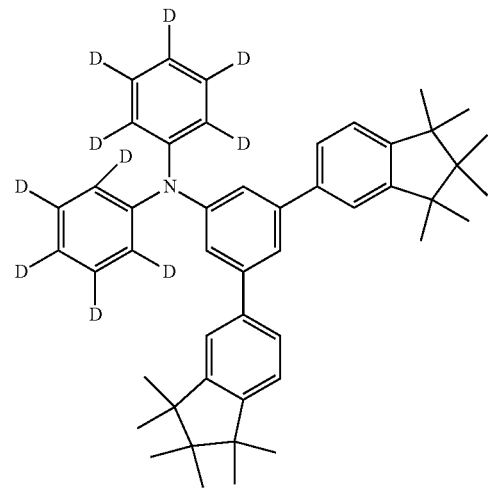
BB-519 + BB-020
BB-1427
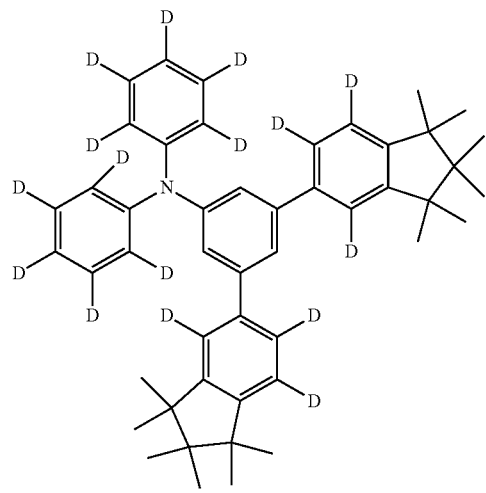
BB-519 + BB-018
BB-1428
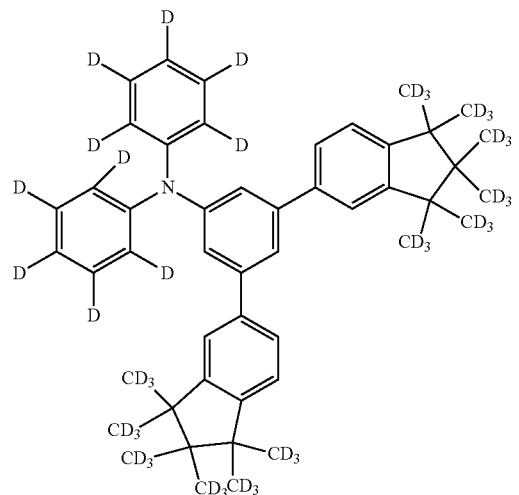
BB-519 + BB-016
BB-1429

-continued
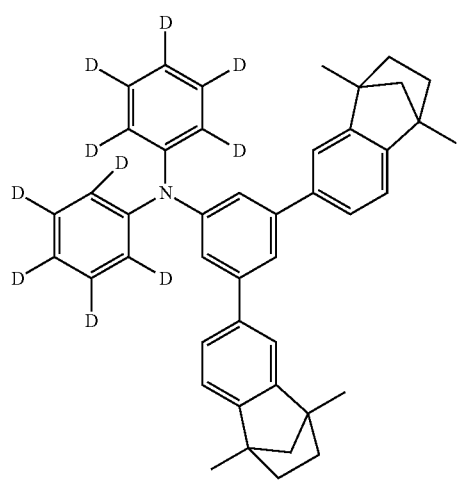
BB-519 + BB-011
BB-1430
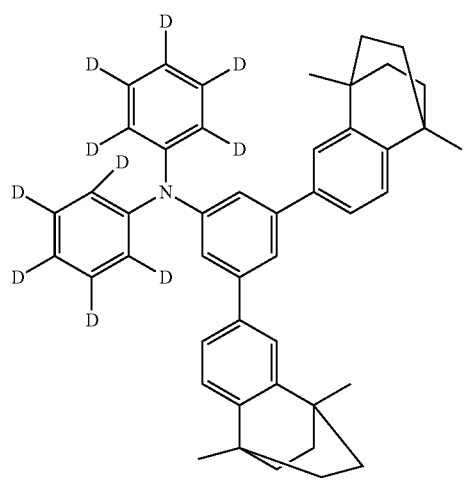
BB-519 + BB-014
BB-1431
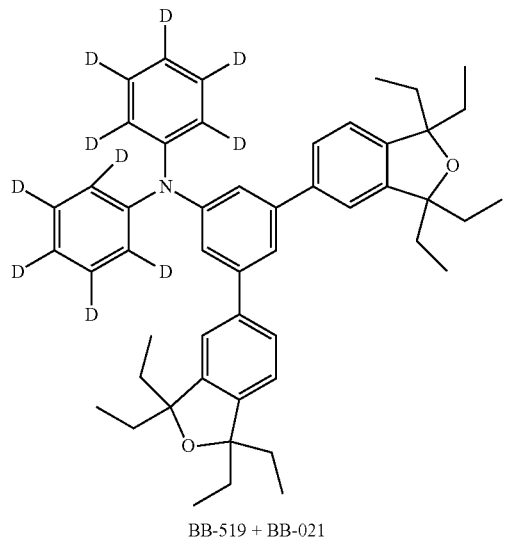
BB-519 + BB-021
BB-1432
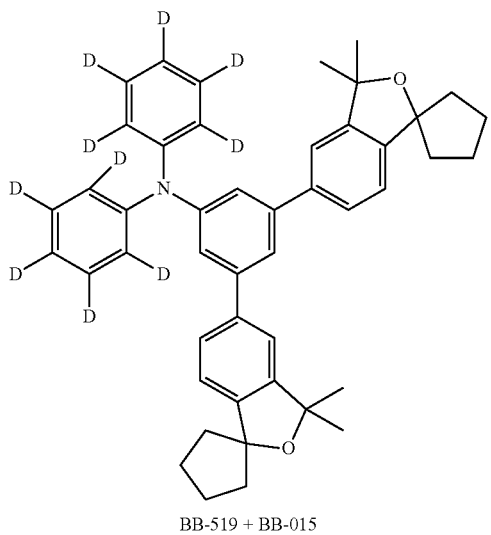
BB-519 + BB-015
BB-1433
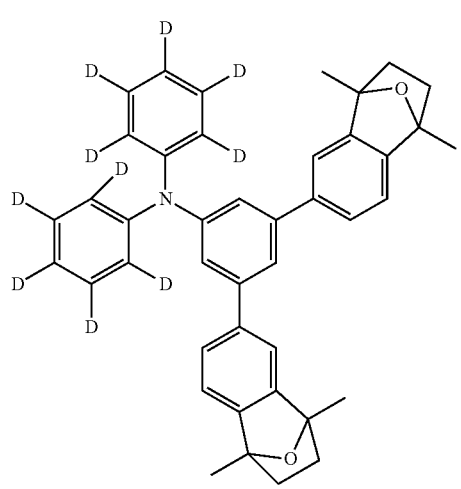
BB-519 + BB-007
BB-1434
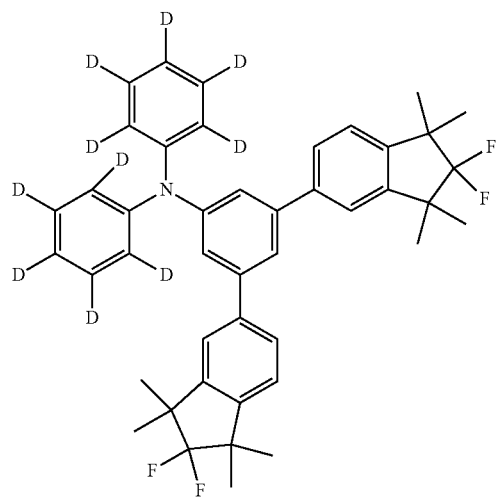
BB-519 + BB-009
BB-1435

-continued
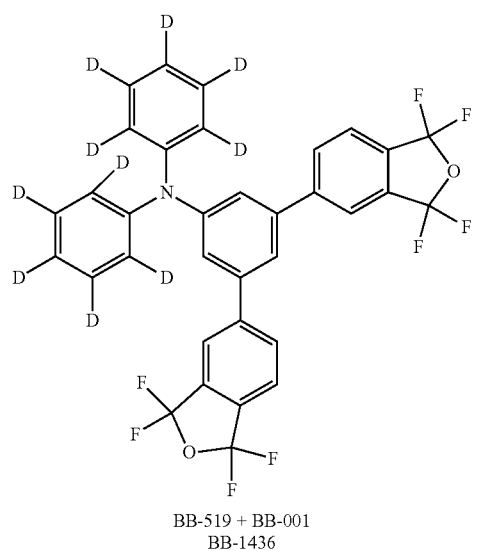
BB-519 + BB-001
BB-1436
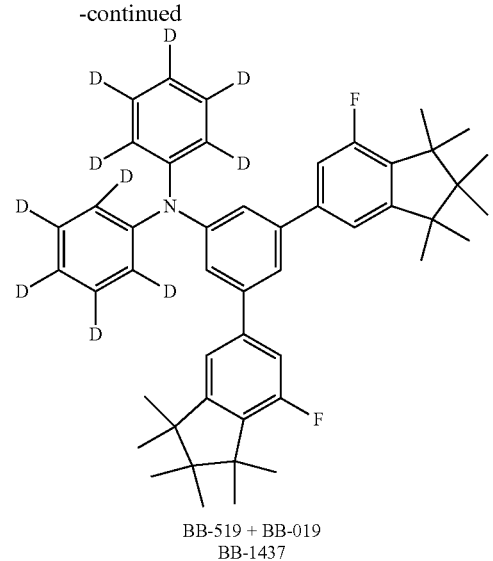
BB-519 + BB-019
BB-1437
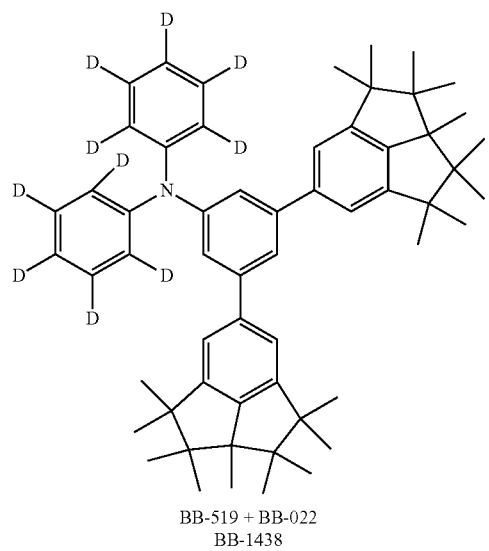
BB-519 + BB-022
BB-1438
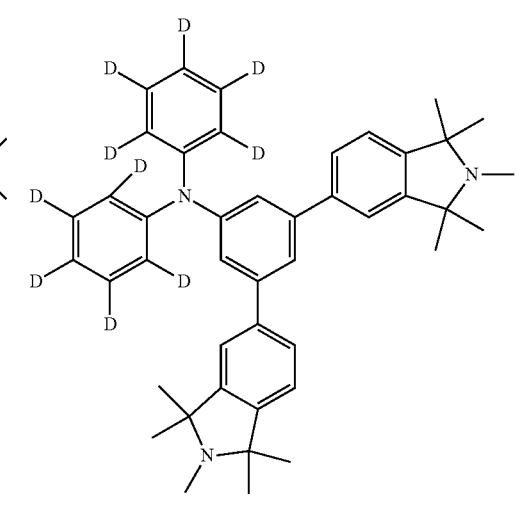
BB-519 + BB-013
BB-1439
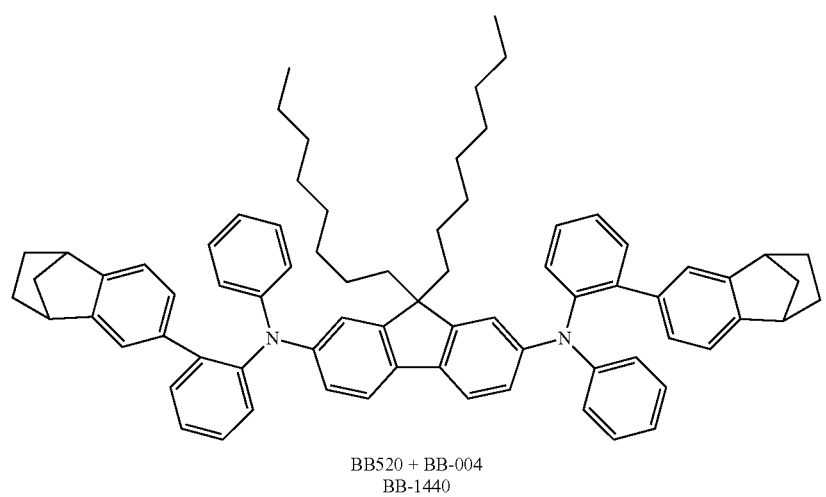
BB520 + BB-004
BB-1440

-continued
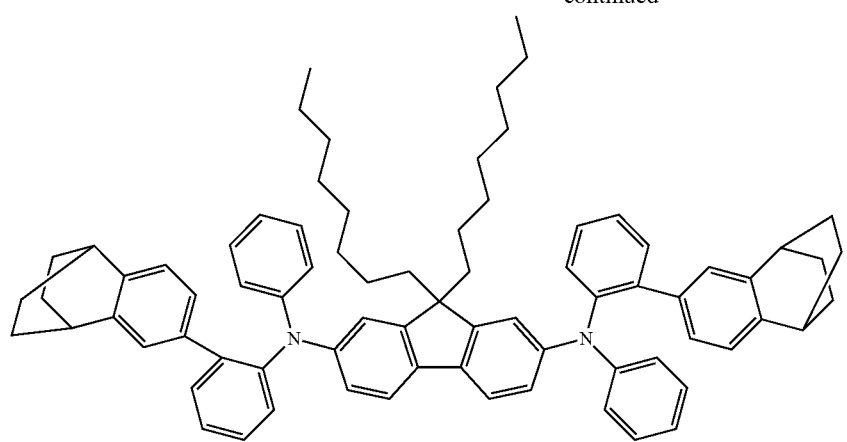
BB520 + BB-005
BB-1441
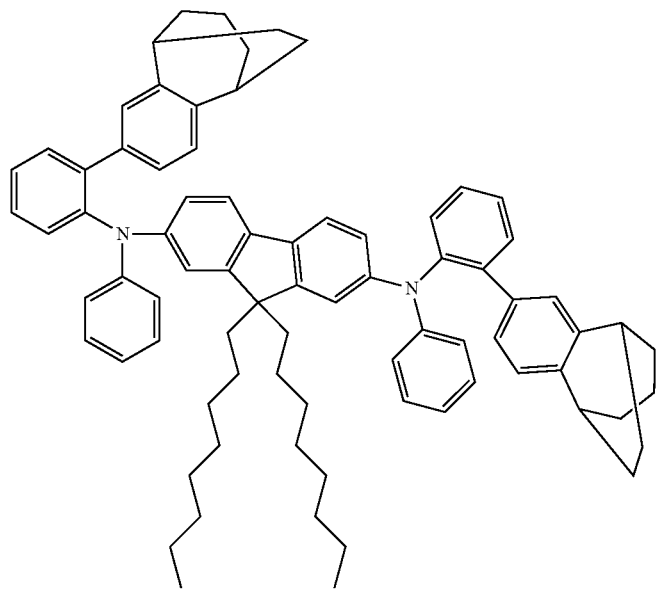
BB520 + BB-010
BB-1442
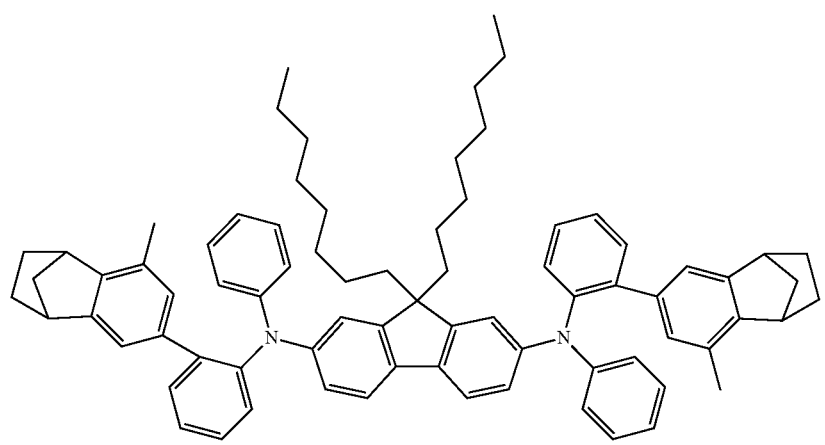
BB520 + BB-006
BB-1443

-continued
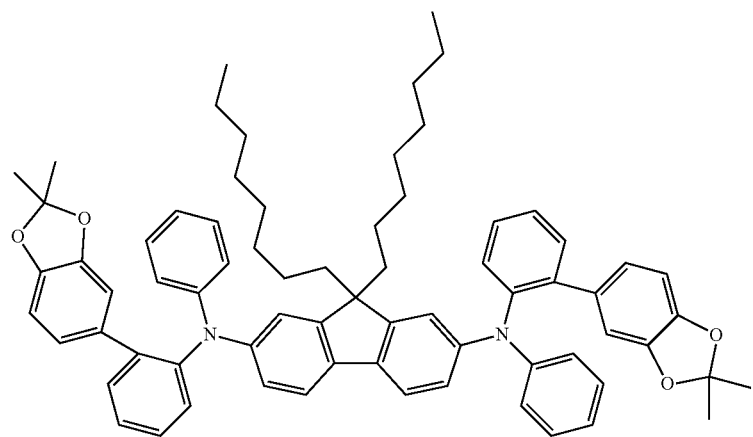
BB520 + BB-002
BB-1444
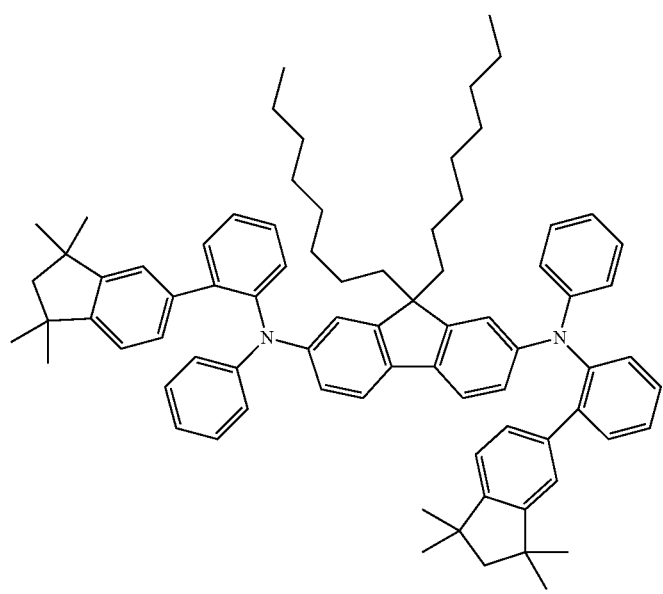
BB520 + BB-012
BB-1445
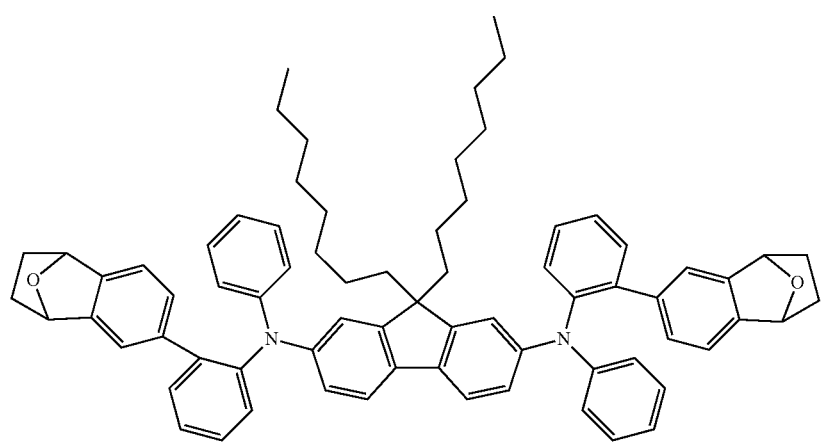
BB520 + BB-003
BB-1446

277 278
-continued
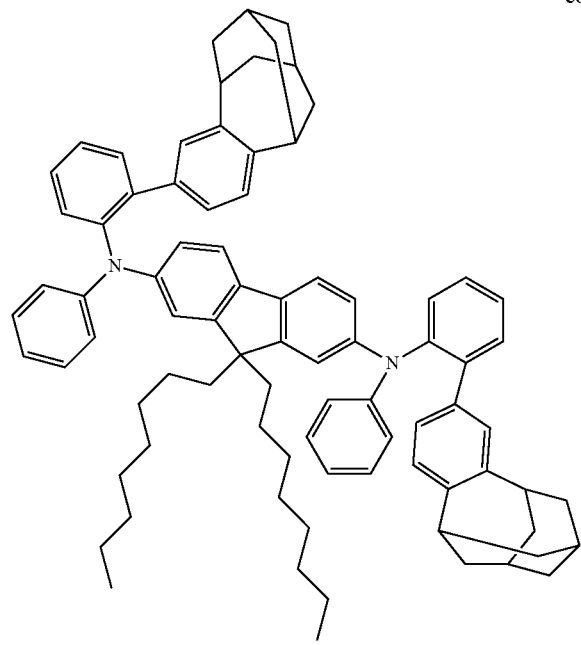
BB520 + BB-017
BB-1447
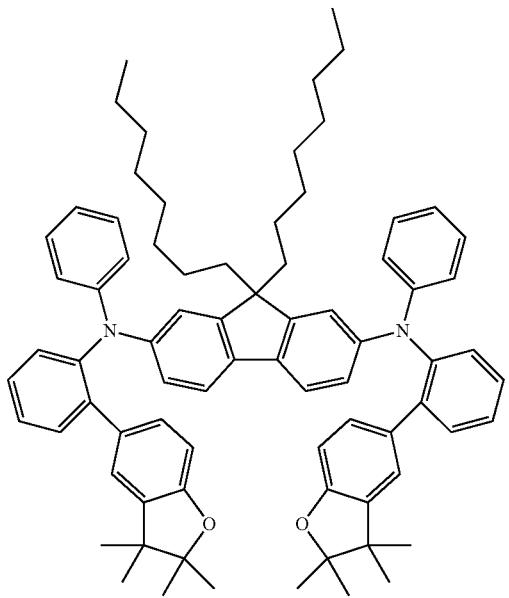
BB520 + BB-008
BB-1448
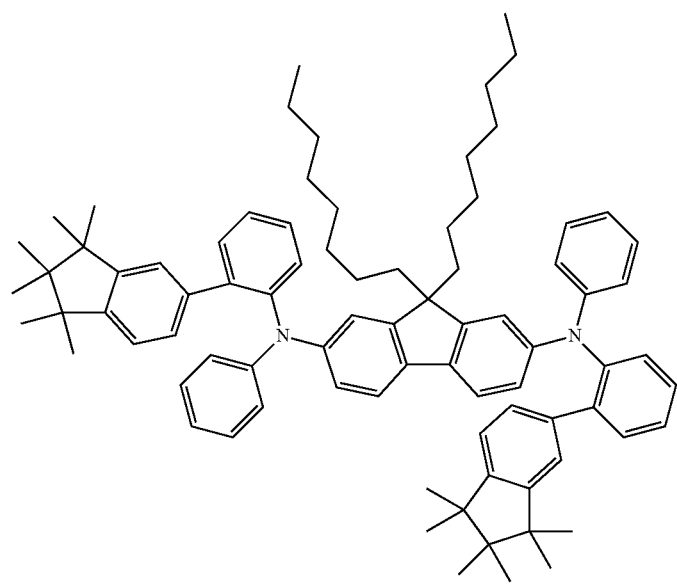
BB520 + BB-020
BB-1449

-continued
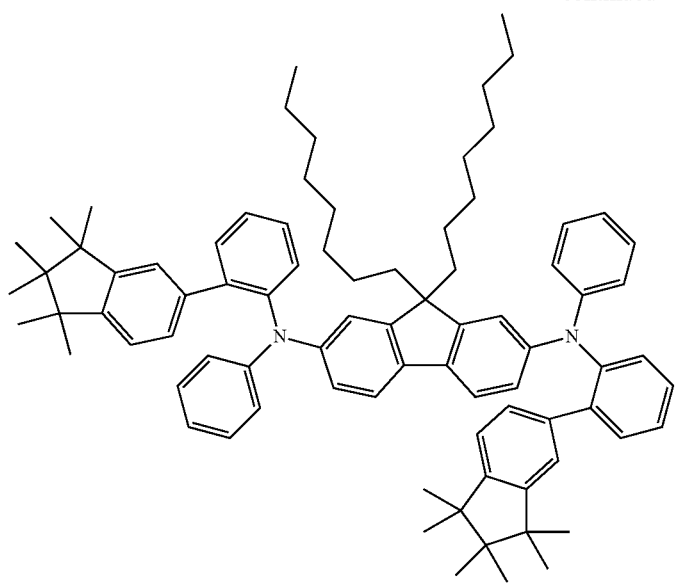
BB520 + BB-016
BB-1450
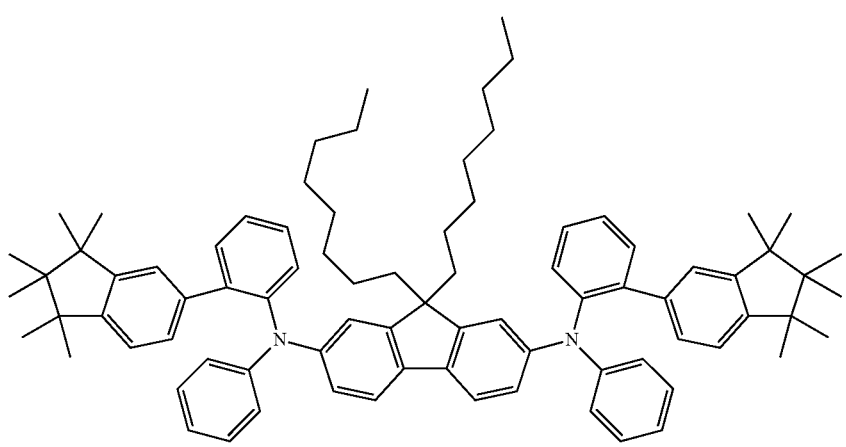
BB520 + BB-018
BB-1451
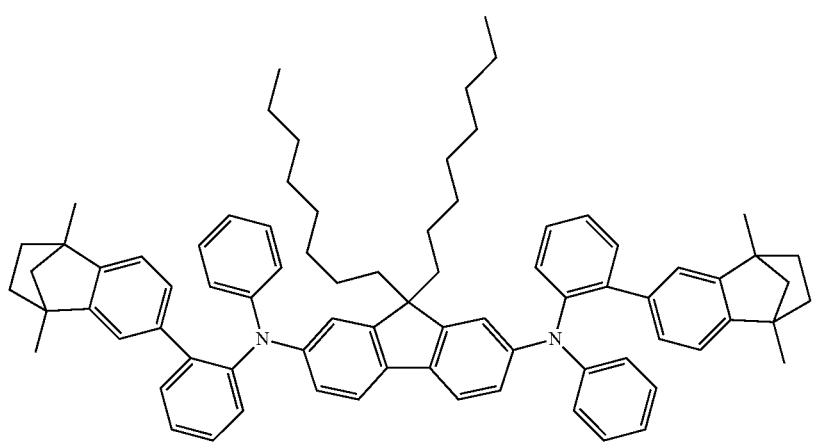
BB520 + BB-011
BB-1452

-continued
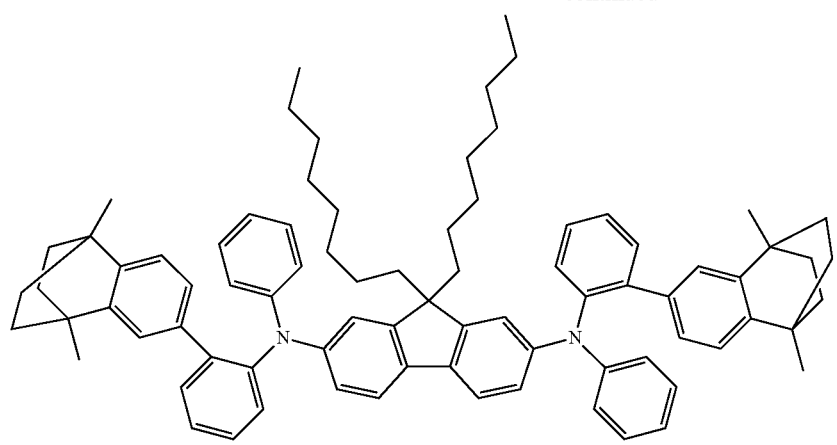
BB520 + BB-014
BB-1453
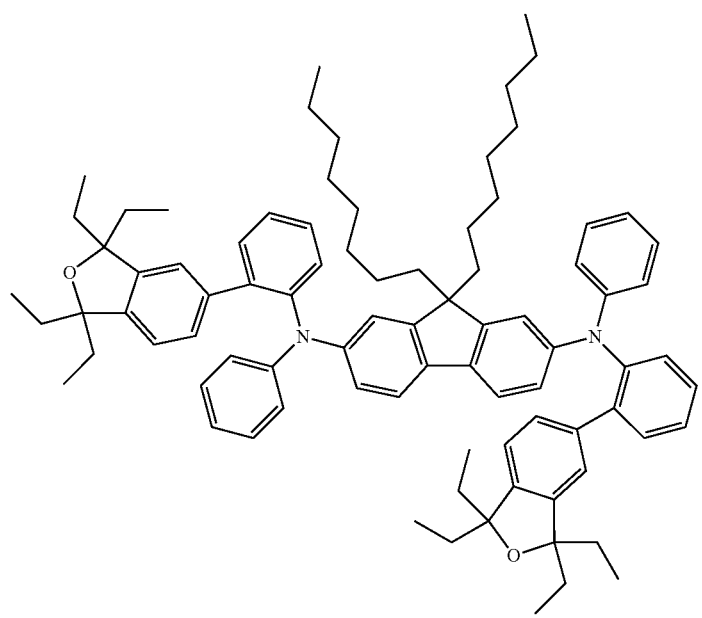
BB520 + BB-021
BB-1454

-continued
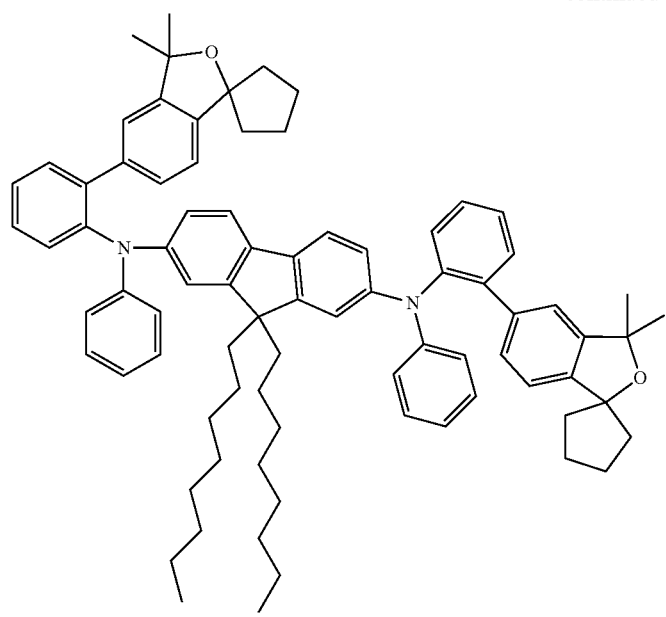
BB520 + BB-015
BB-1455
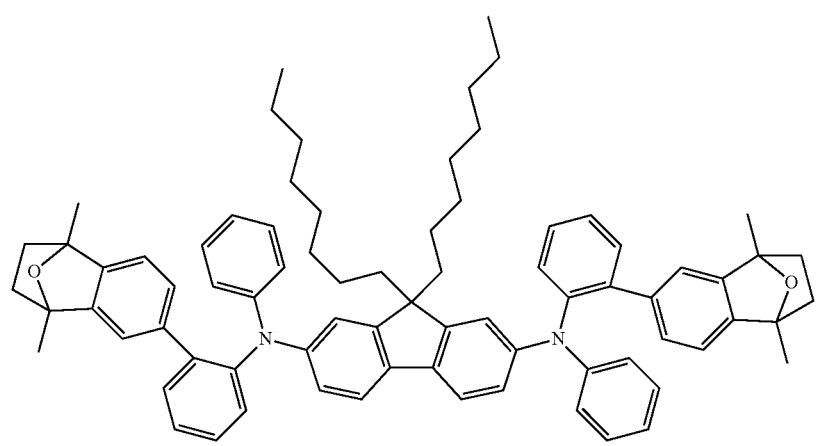
BB520 + BB-007
BB-1456

-continued
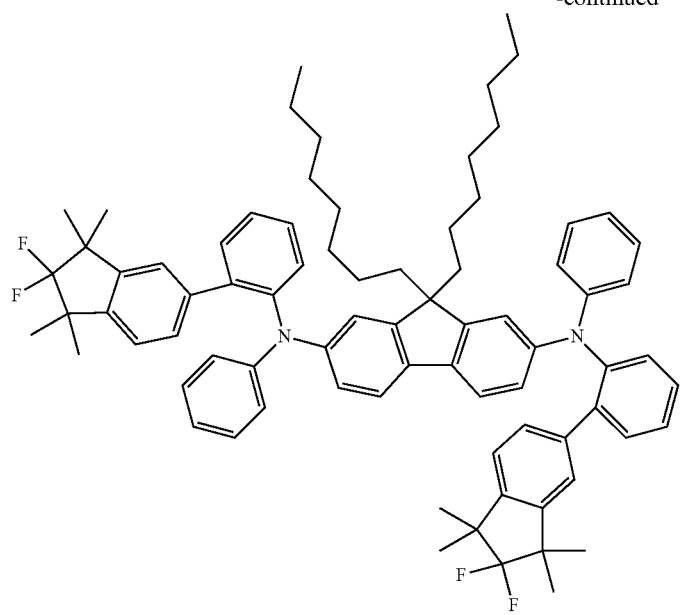
BB520 + BB-015
BB-1457
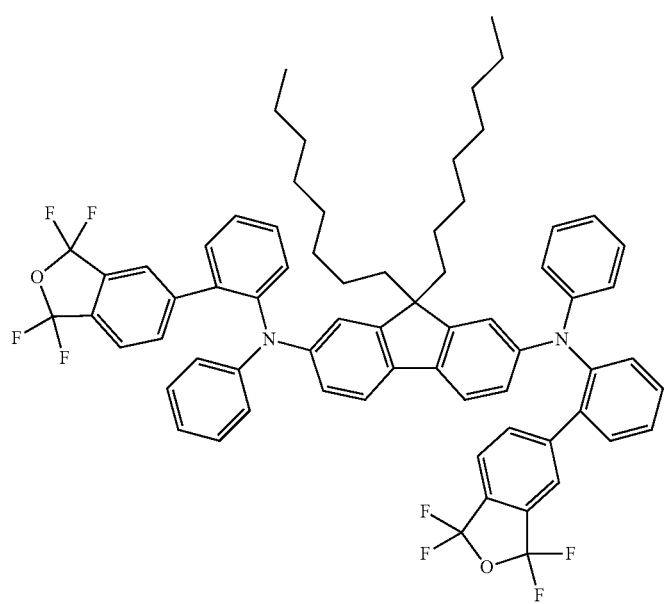
BB520 + BB-001
BB-1458

-continued
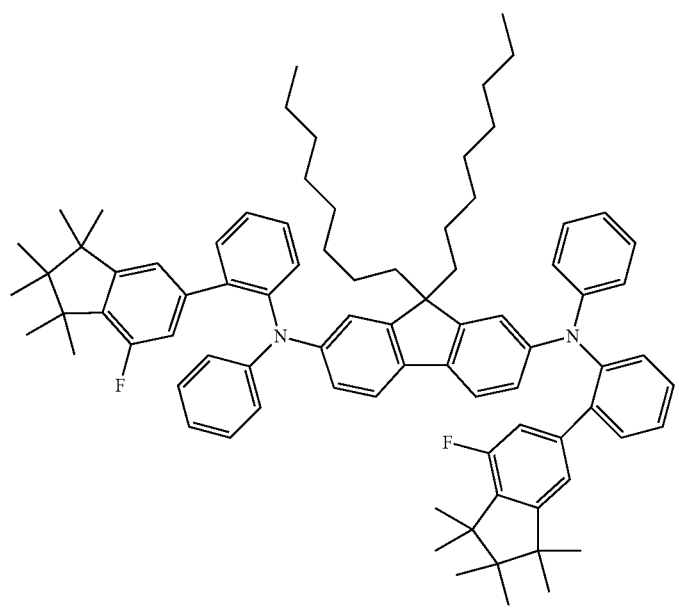
BB520 + BB-019
BB-1459
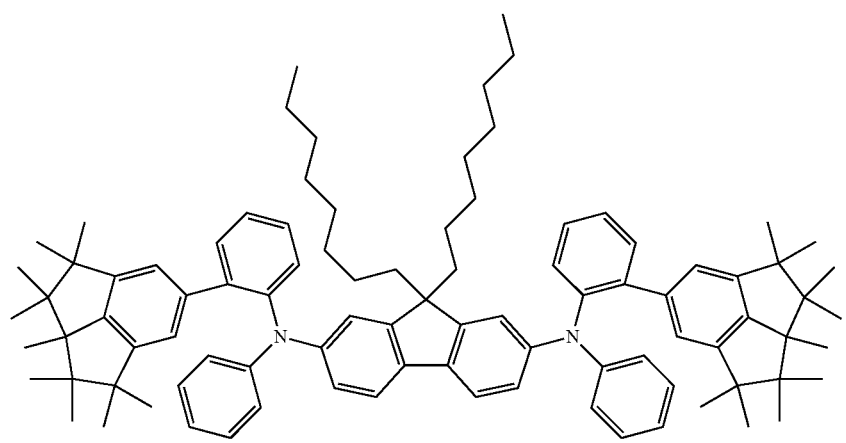
BB520 + BB-022
BB-1460

-continued
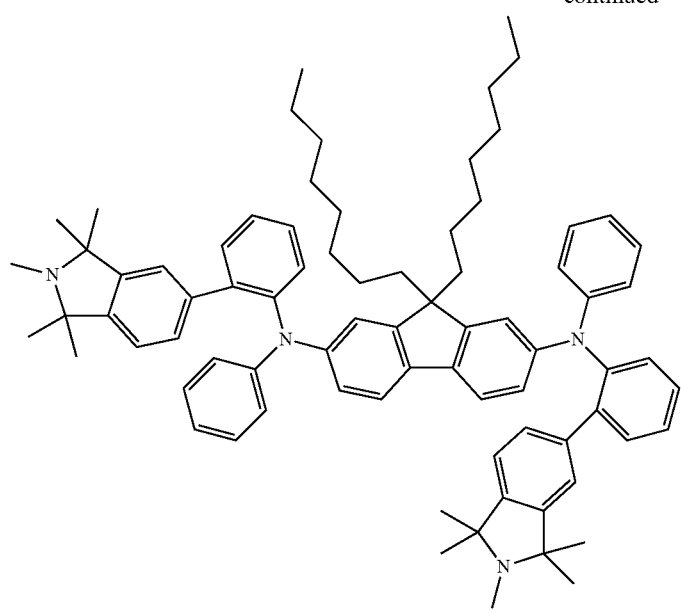
BB520 + BB-013
BB-1461
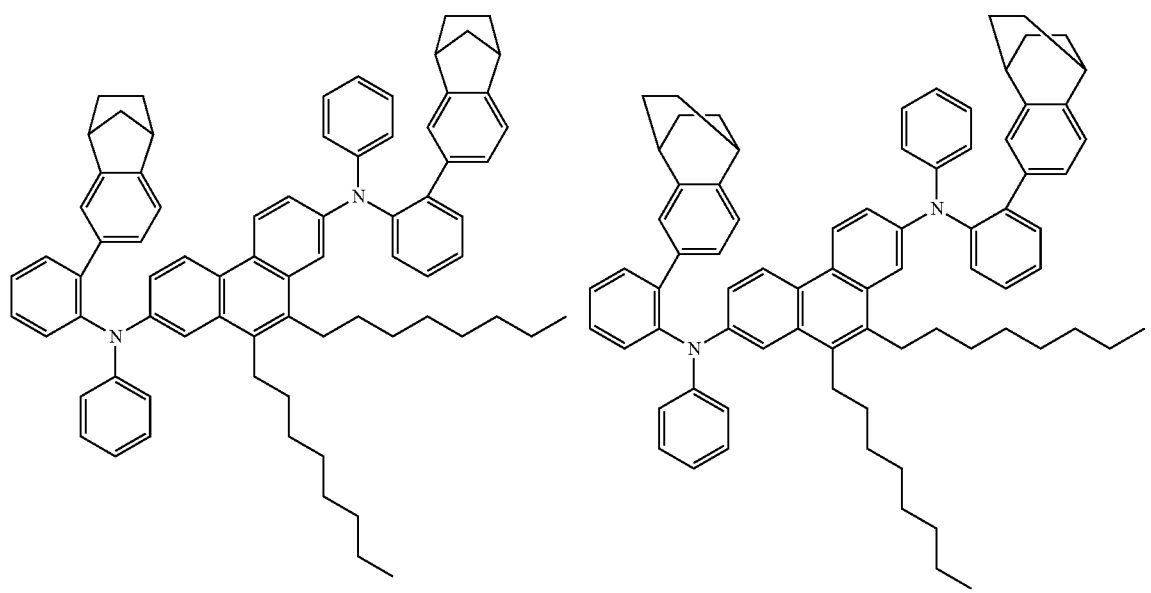
BB521 + BB-004
BB-1462
BB521 + BB-005
BB-1463

-continued
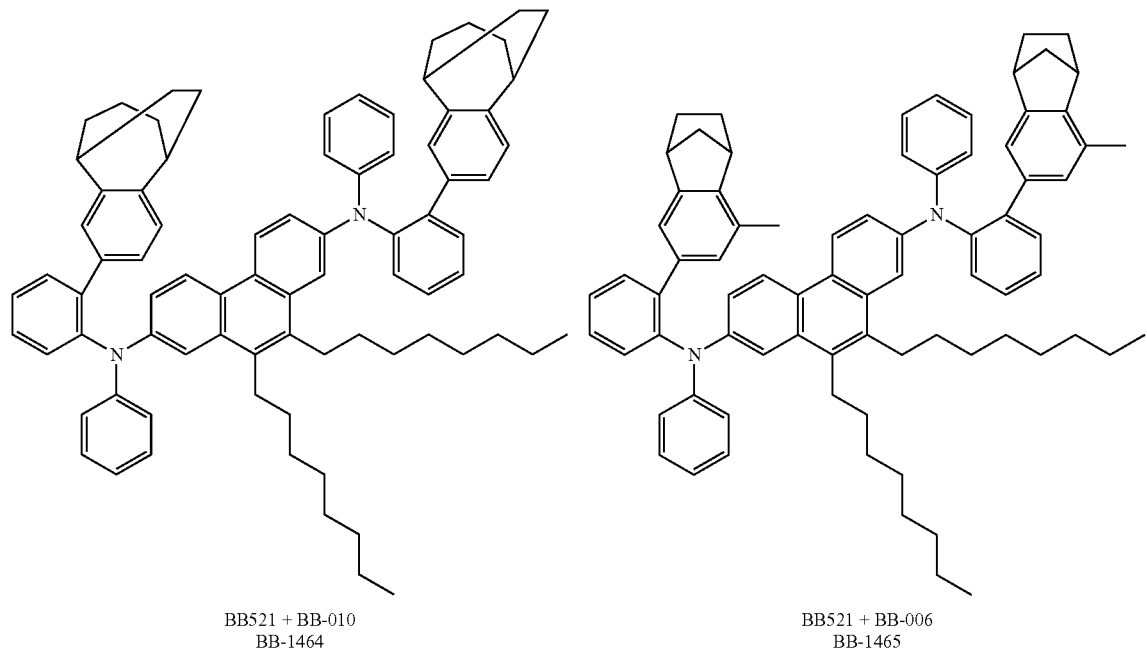
BB521 + BB-010
BB-1464
BB521 + BB-006
BB-1465
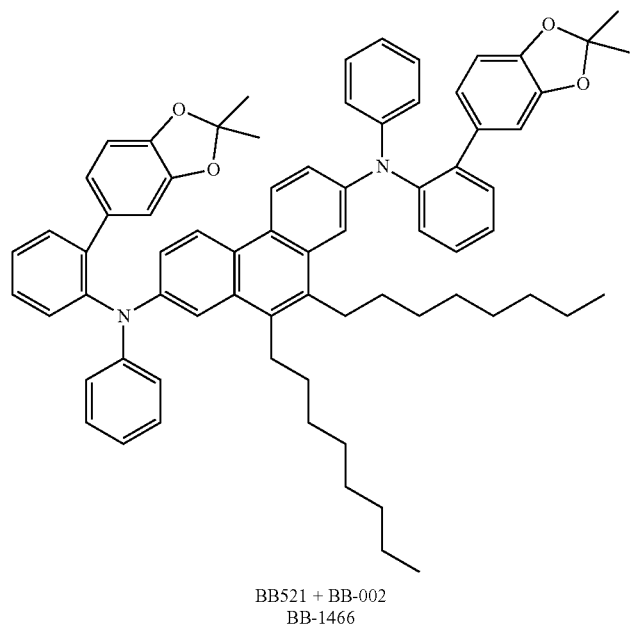
BB521 + BB-002
BB-1466

293
294
-continued
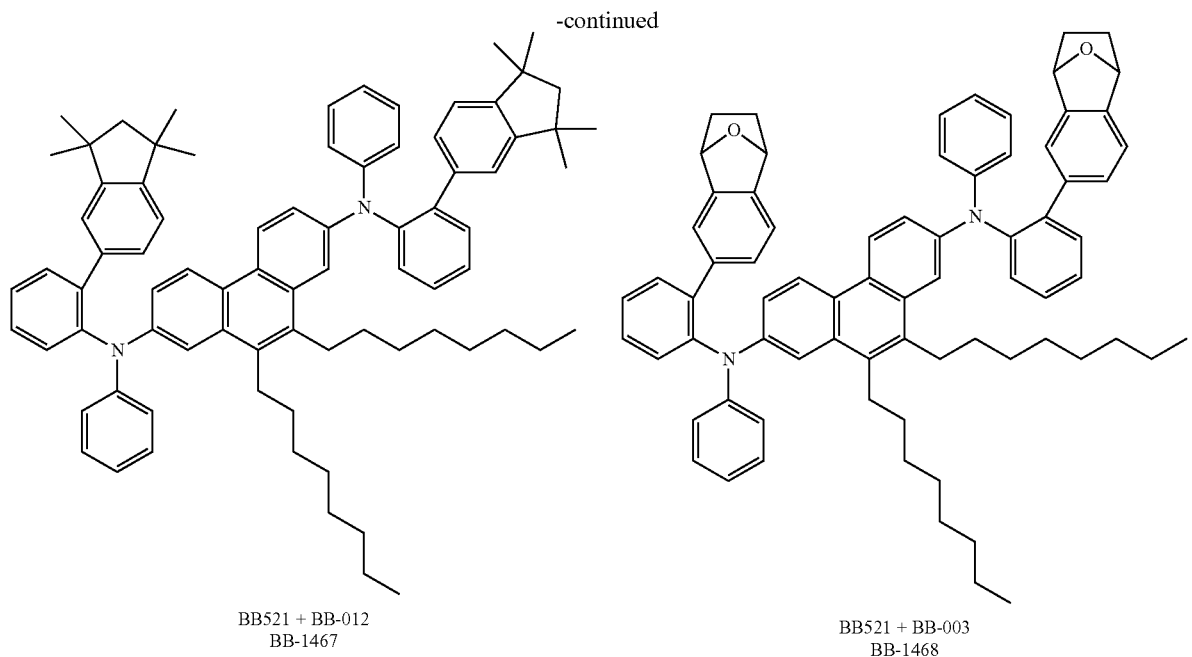
BB521 + BB-012
BB-1467
BB521 + BB-003
BB-1468
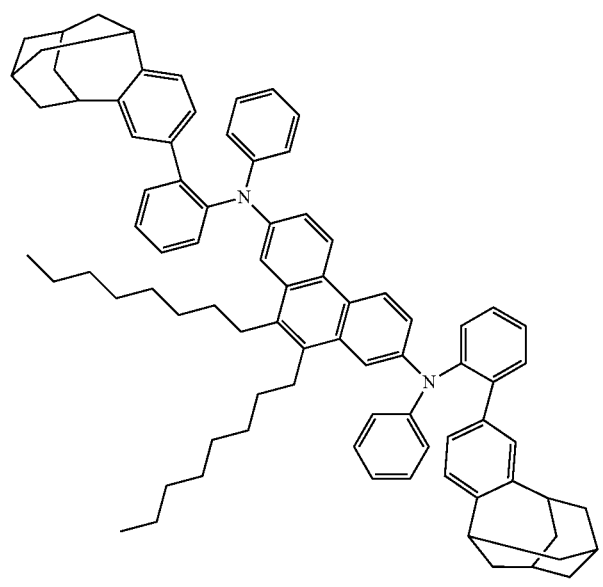
BB521 + BB-017
BB-1469

-continued
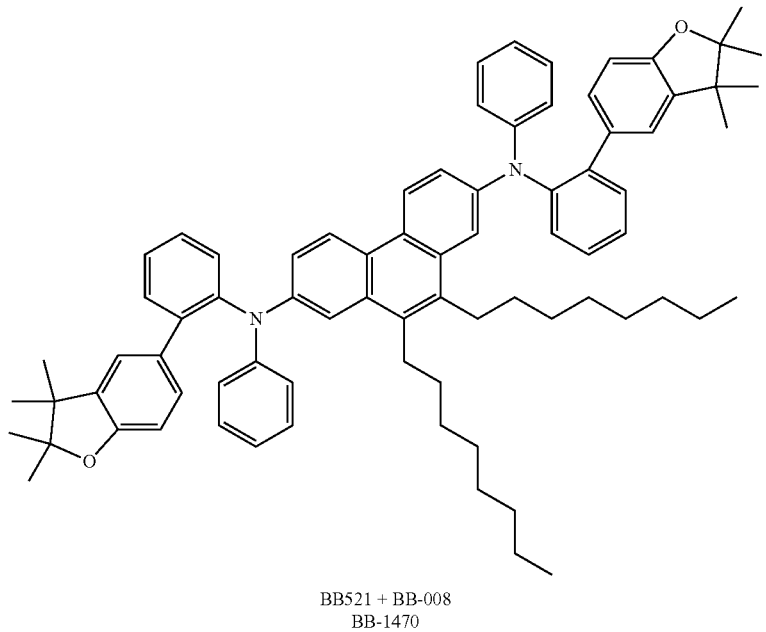
BB521 + BB-008
BB-1470
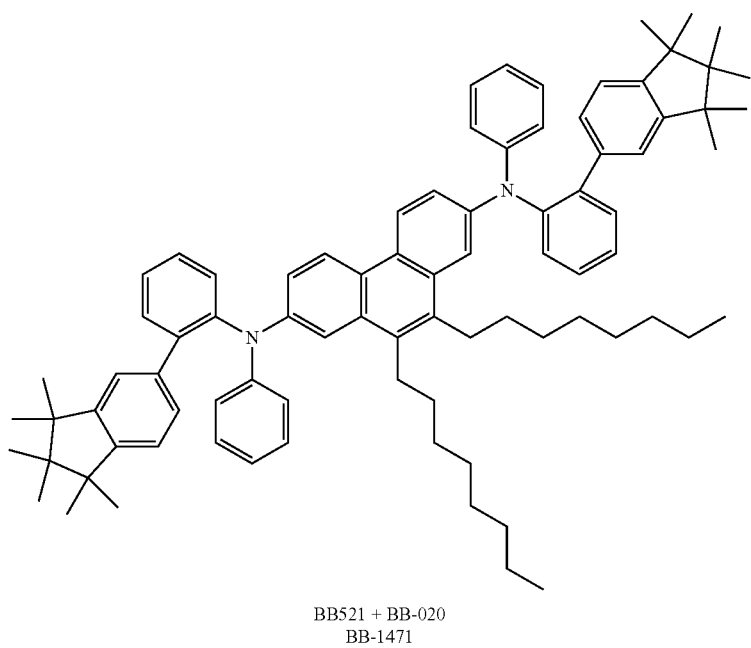
BB521 + BB-020
BB-1471

-continued
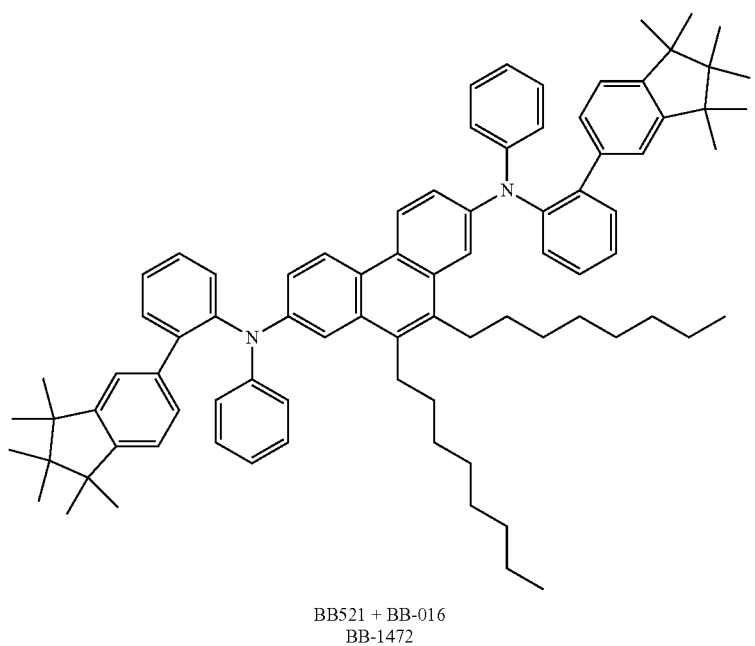
BB521 + BB-016
BB-1472
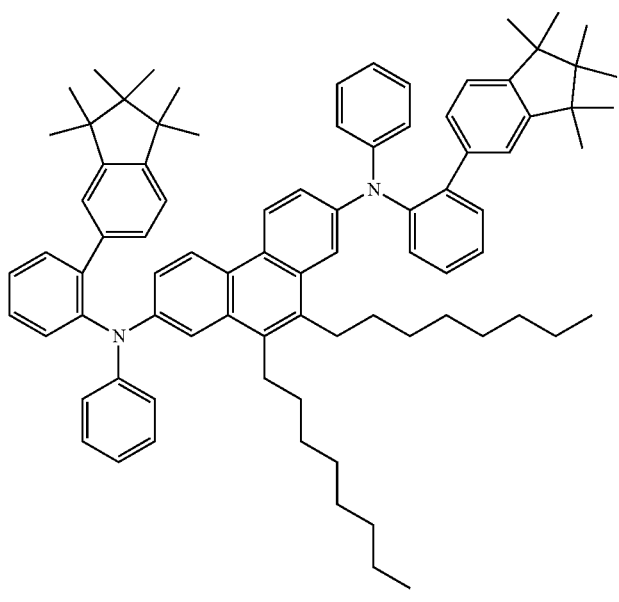
BB521 + BB-018
BB-1473

-continued
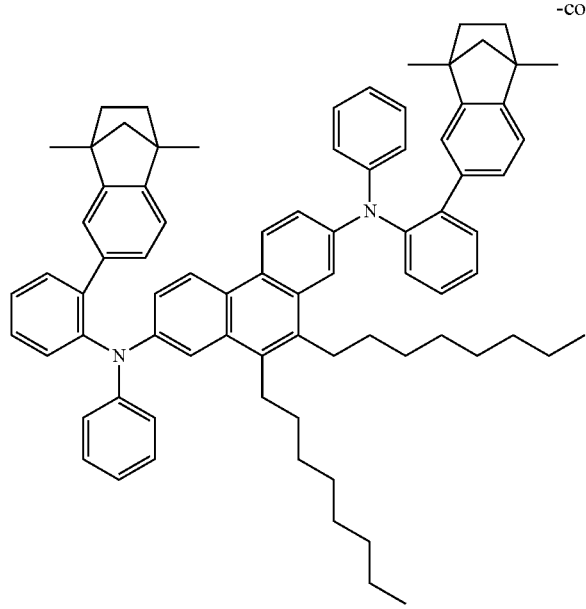
BB521 + BB-011
BB-1474
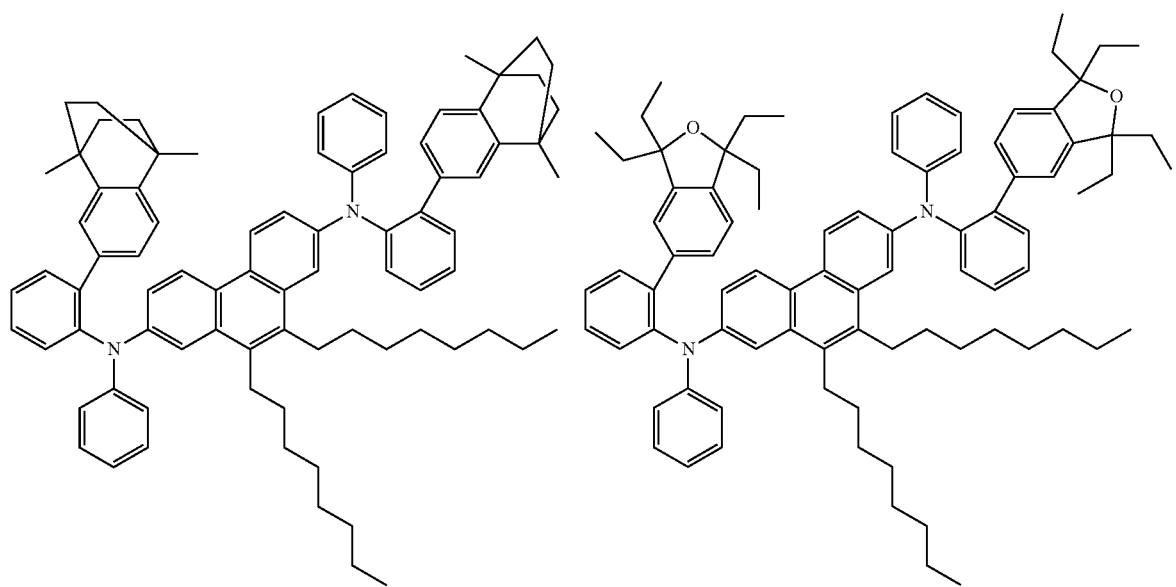
BB521 + BB-014
BB-1475
BB521 + BB-021
BB-1476

-continued
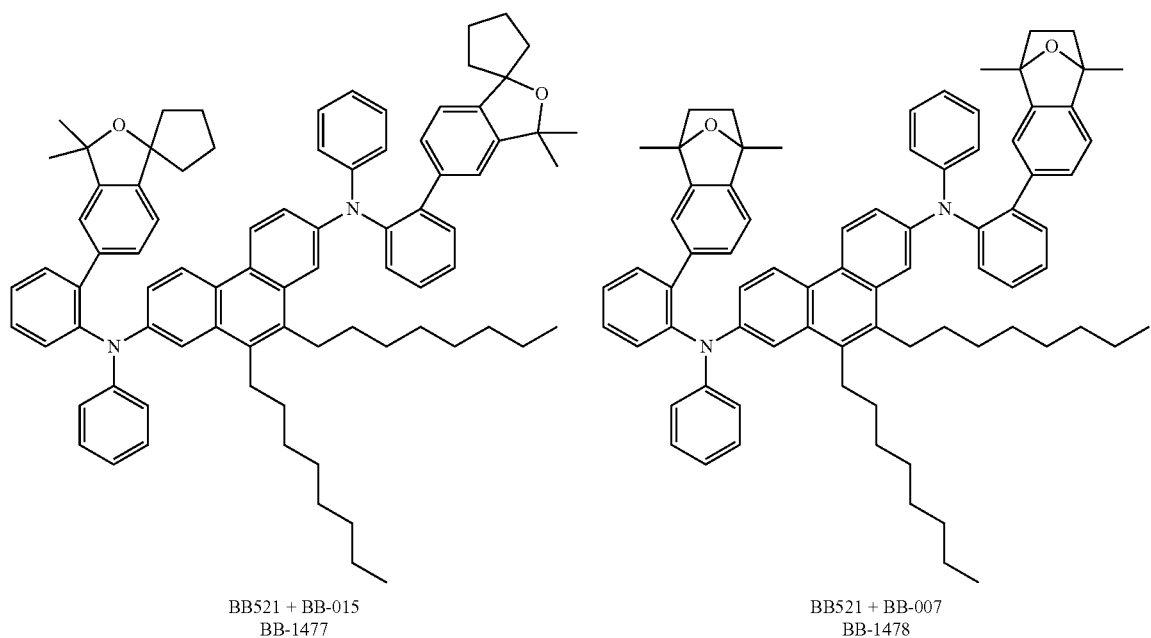
BB521 + BB-015
BB-1477
BB521 + BB-007
BB-1478
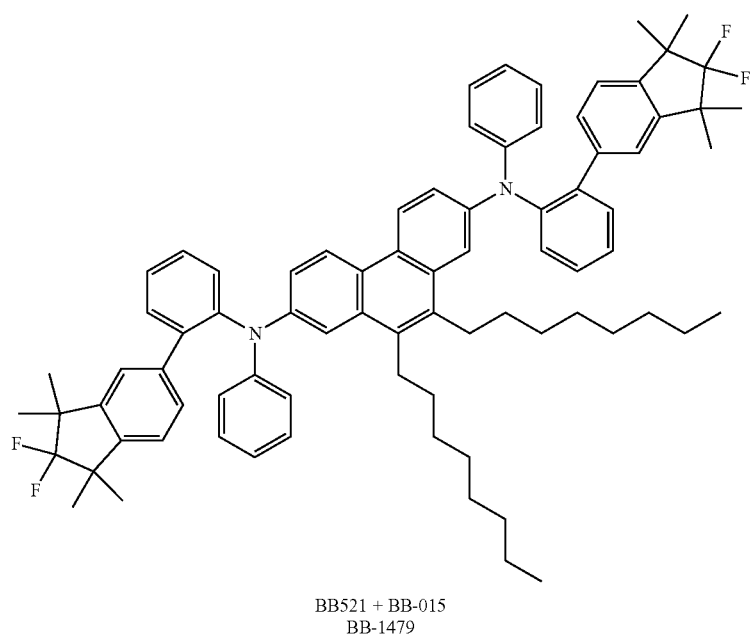
BB521 + BB-015
BB-1479

-continued
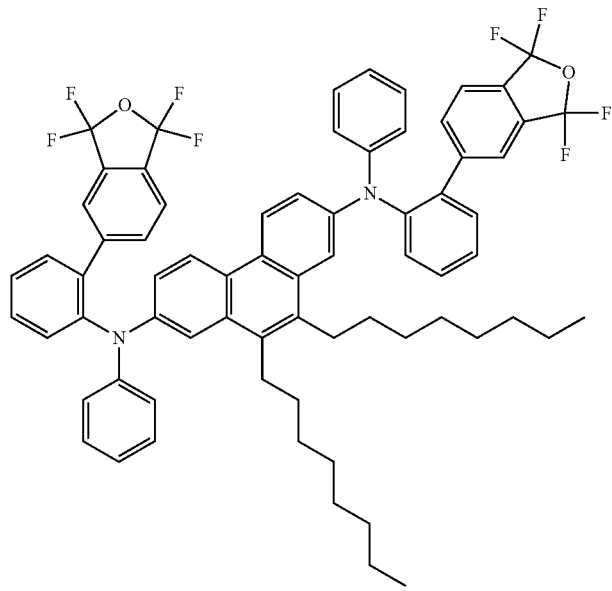
BB521 + BB-001
BB-1480
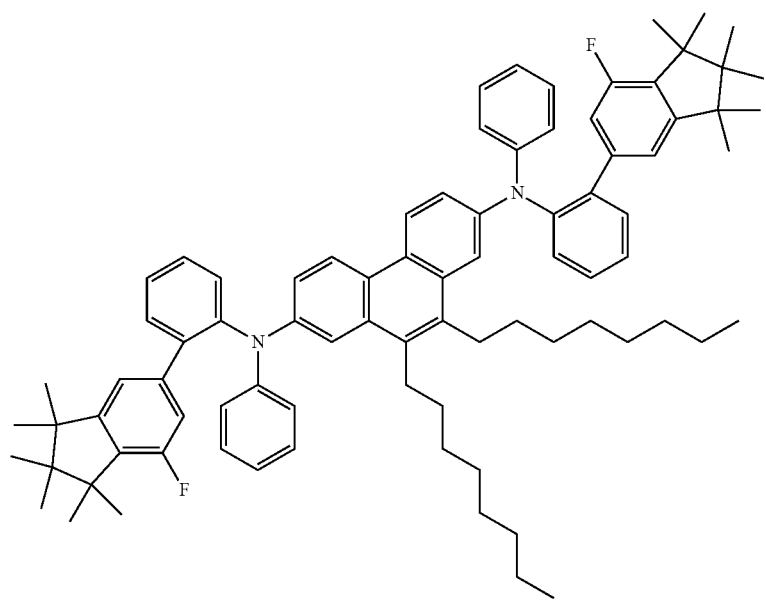
BB521 + BB-019
BB-1481

-continued
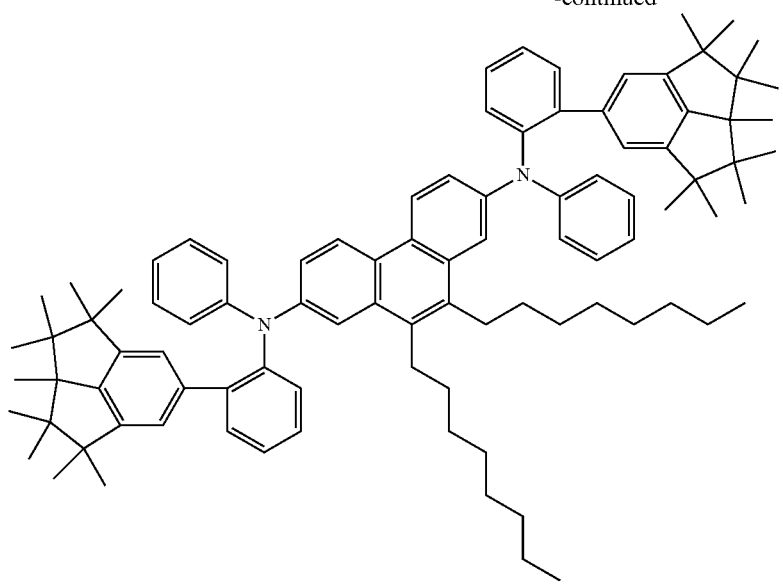
BB521 + BB-022
BB-1482
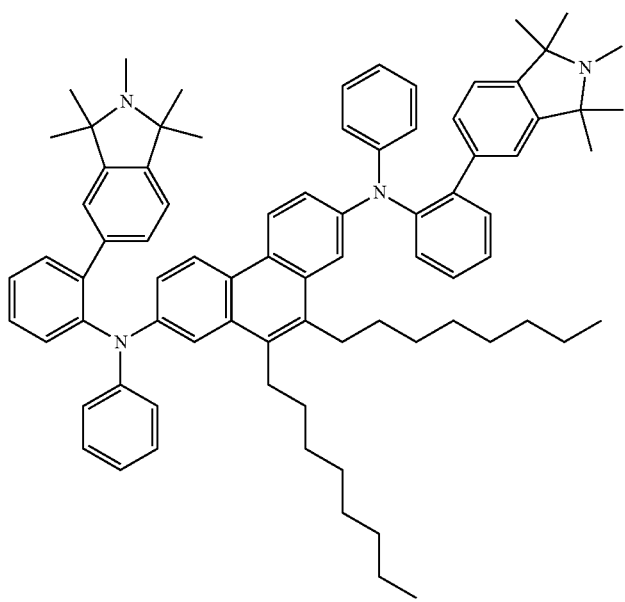
BB521 + BB-013
BB-1483

-continued
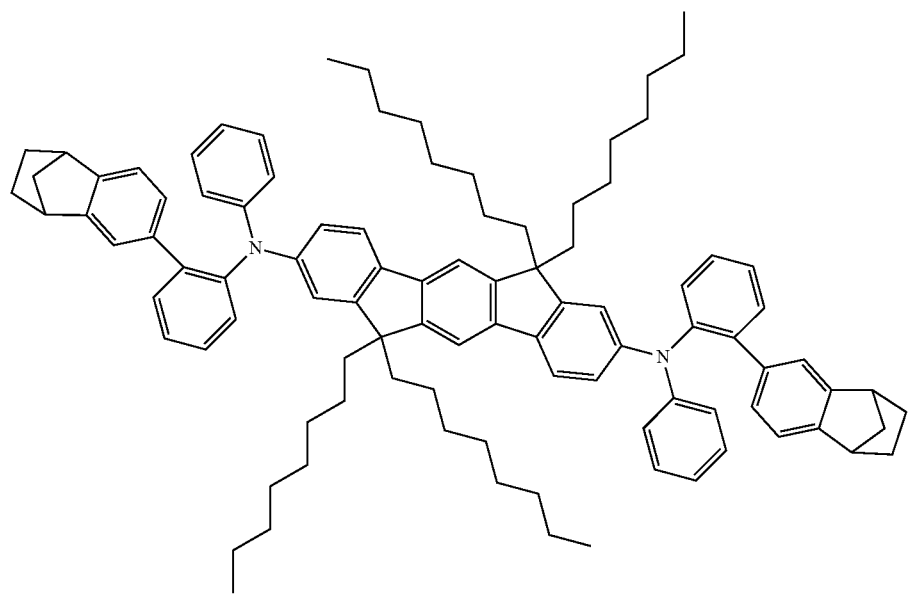
BB522 + BB-004
BB-1484
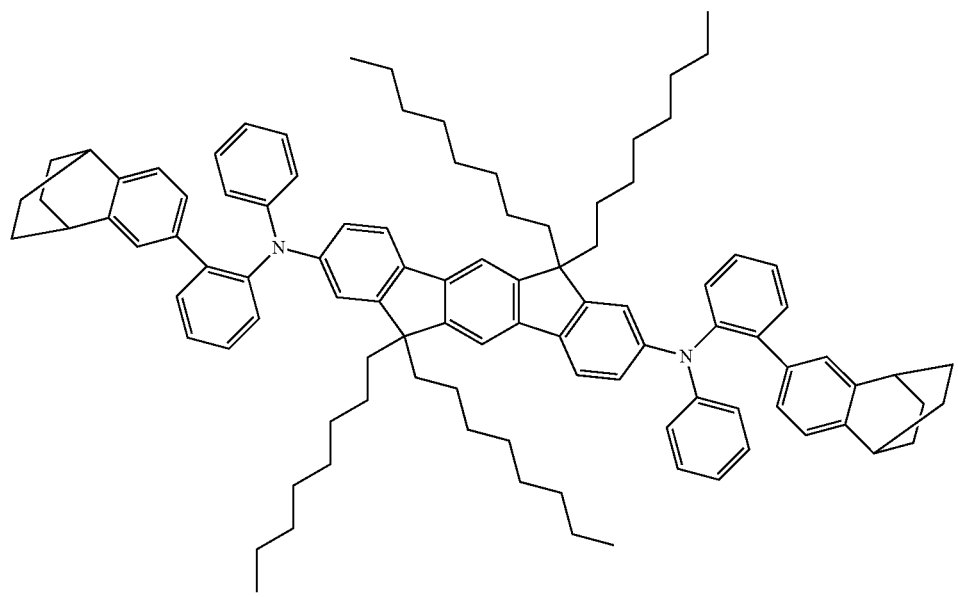
BB522 + BB-005
BB-1485

-continued
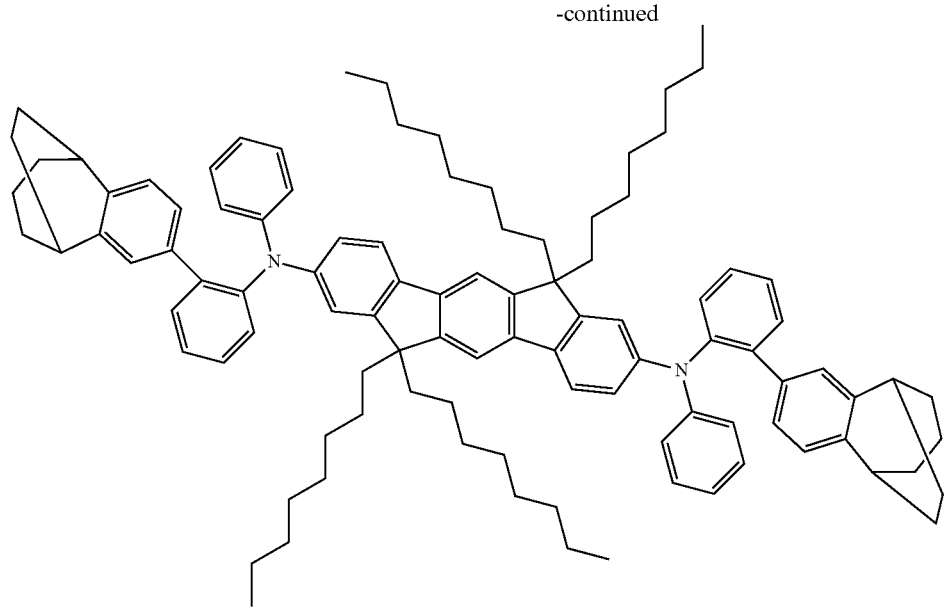
BB522 + BB-010
BB-1486
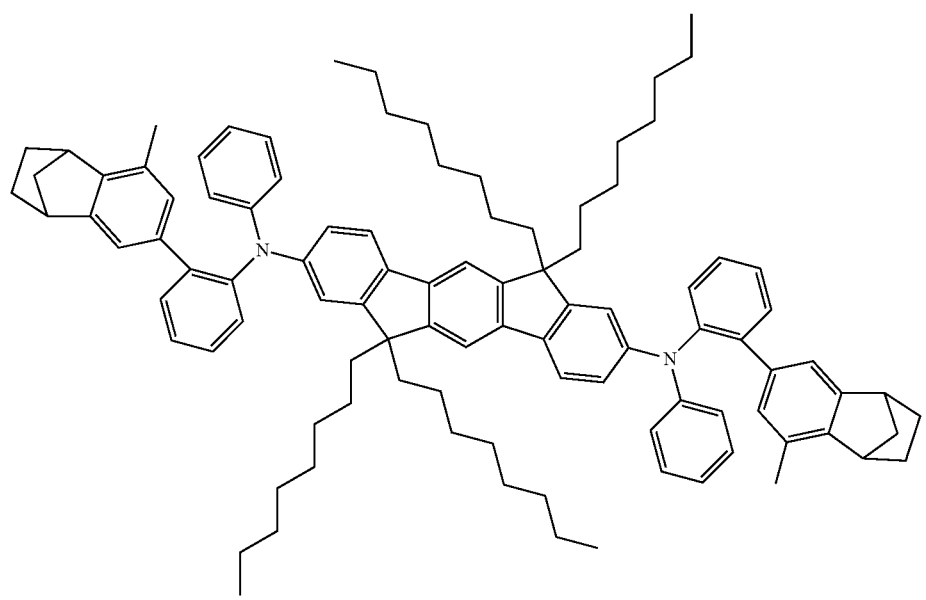
BB522 + BB-006
BB-1487

-continued
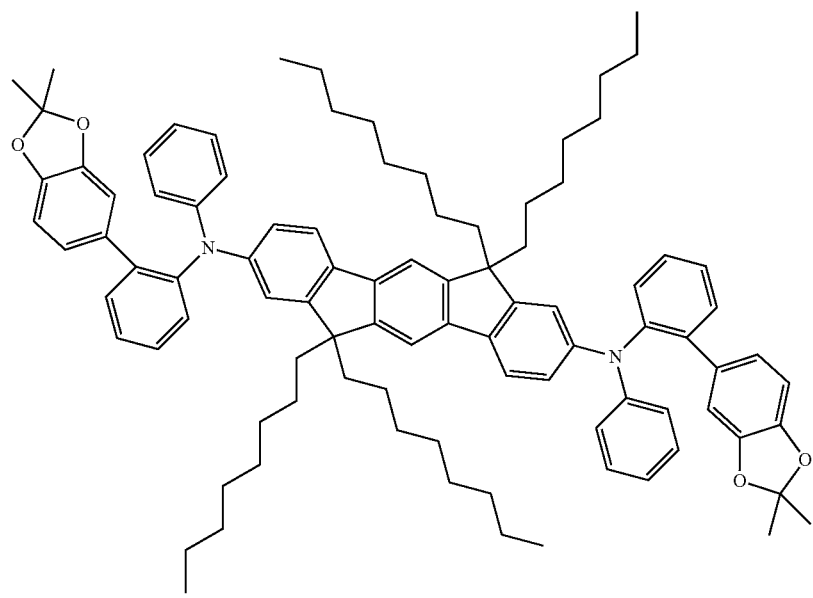
BB522 + BB-002
BB-1488
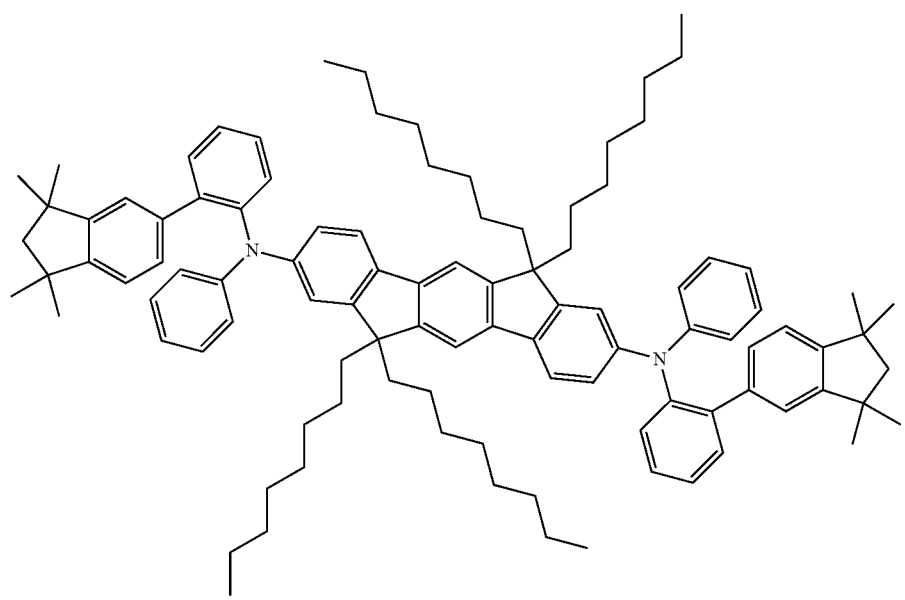
BB522 + BB-012
BB-1489

-continued
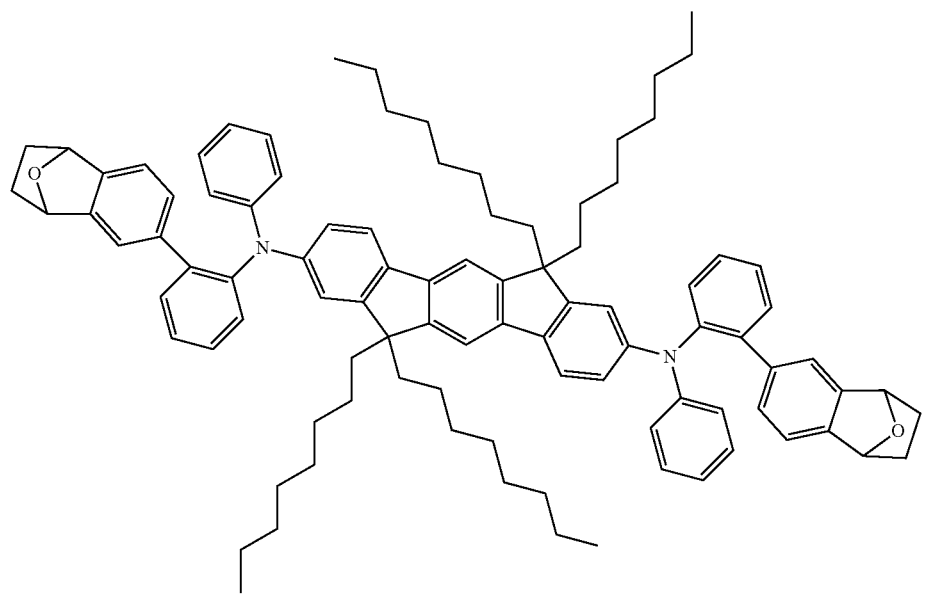
BB522 + BB-003
BB-1490
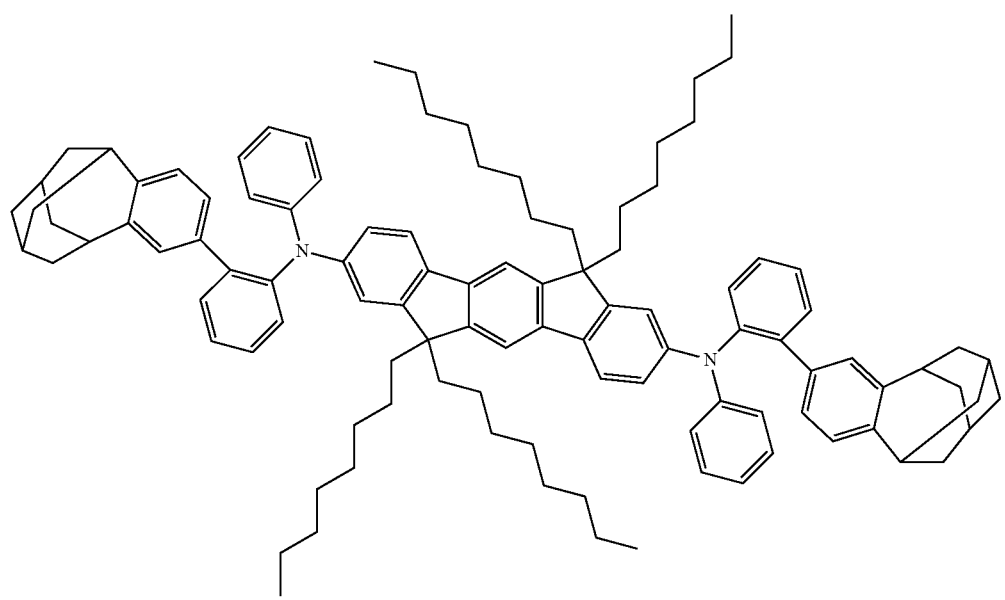
BB522 + BB-017
BB-1491

-continued
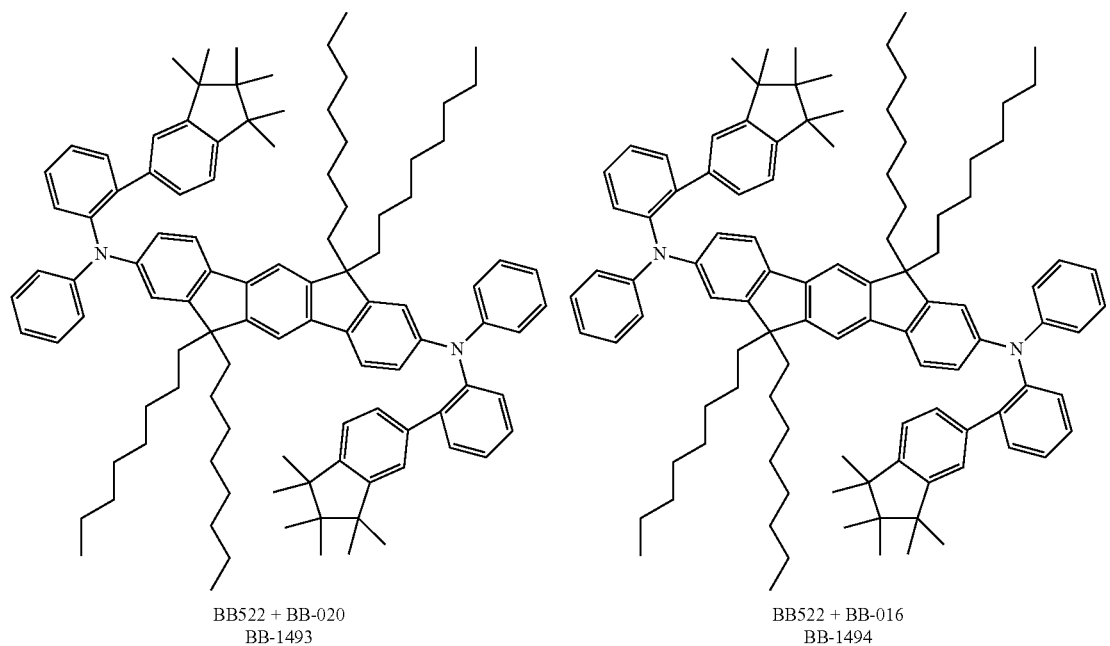
BB522 + BB-020
BB-1493
BB522 + BB-016
BB-1494
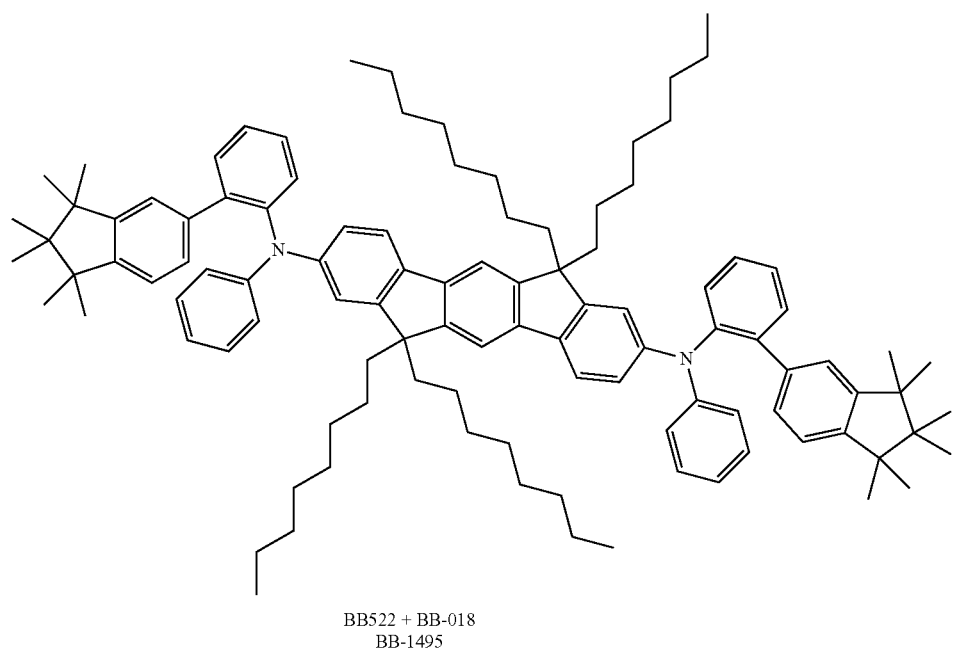
BB522 + BB-018
BB-1495

-continued
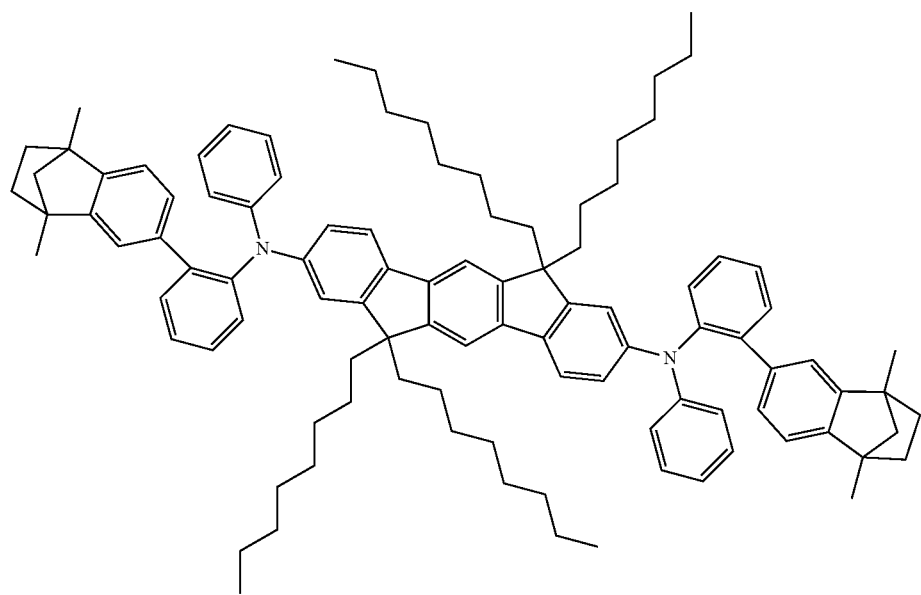
BB522 + BB-011
BB-1496
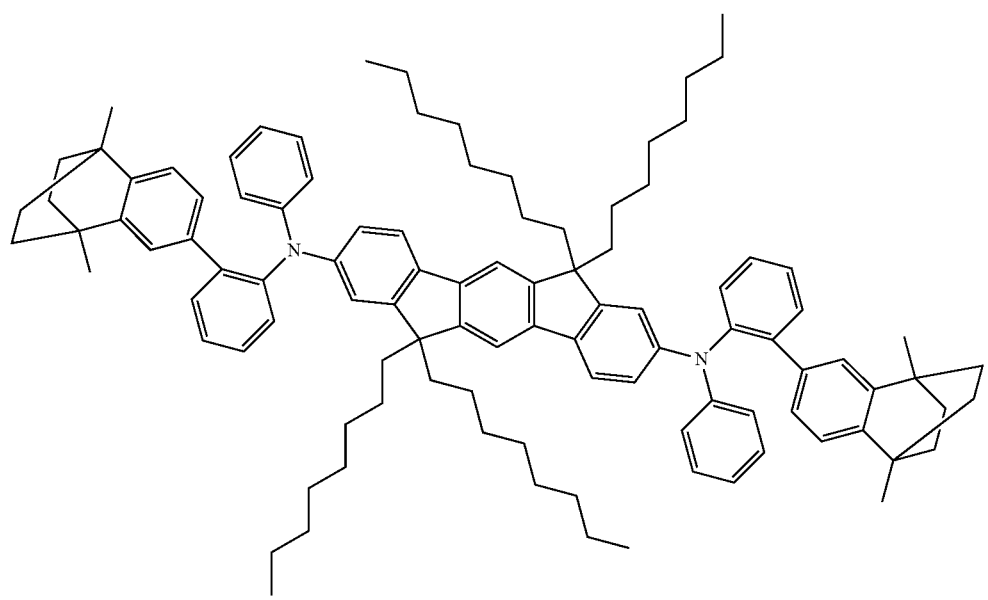
BB522 + BB-014
BB-1497

-continued
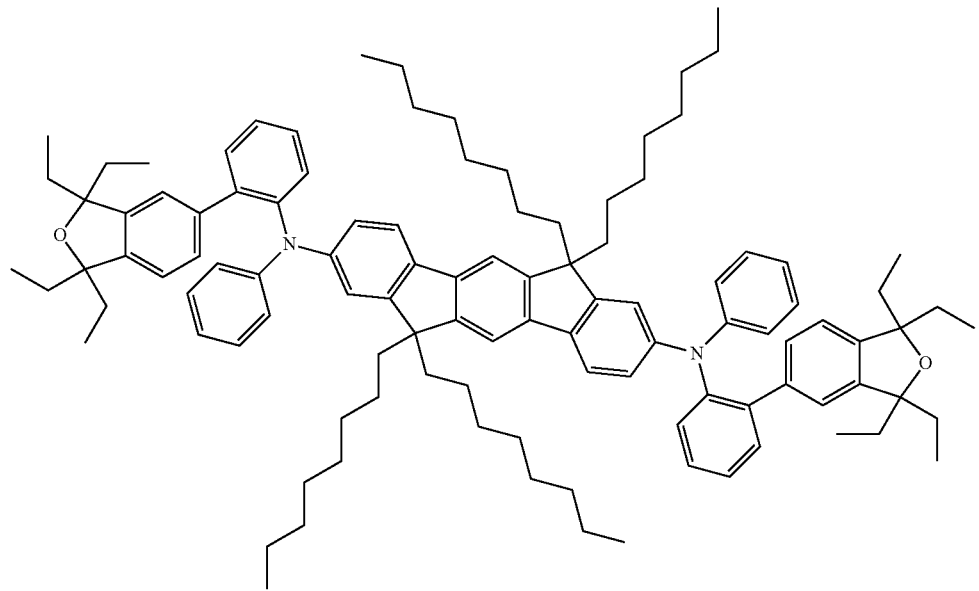
BB522 + BB-021
BB-1498
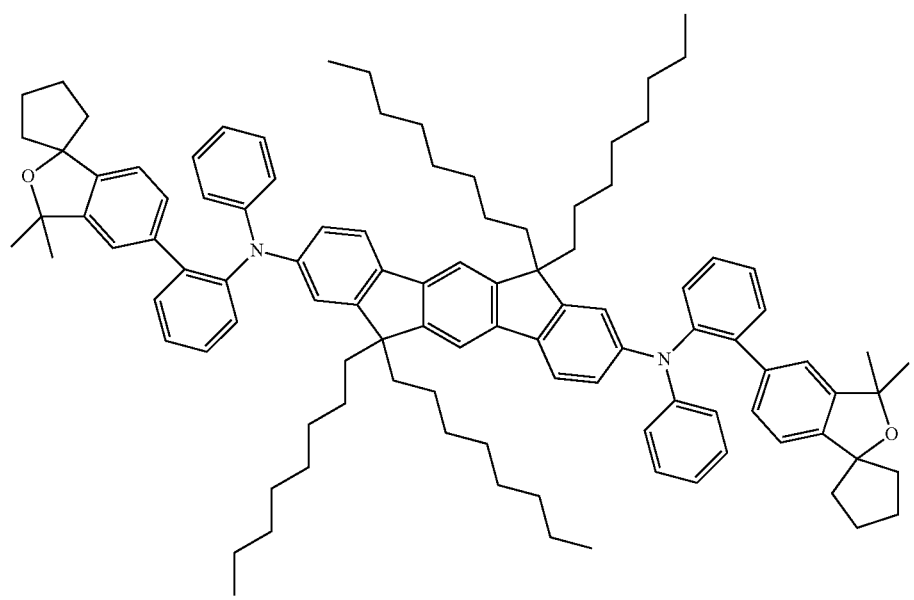
BB522 + BB-015
BB-1499

-continued
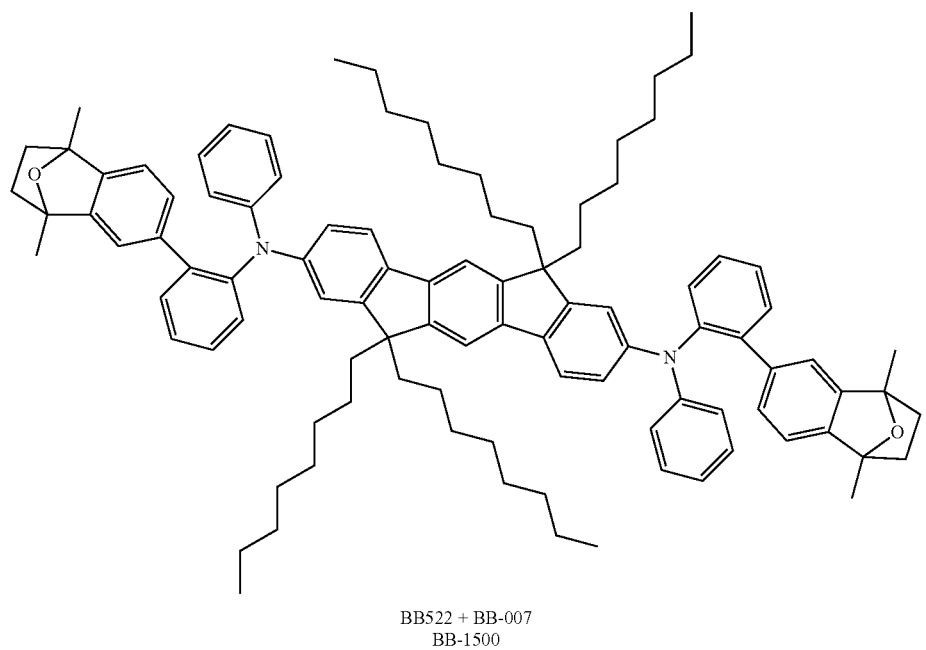
BB522 + BB-007
BB-1500
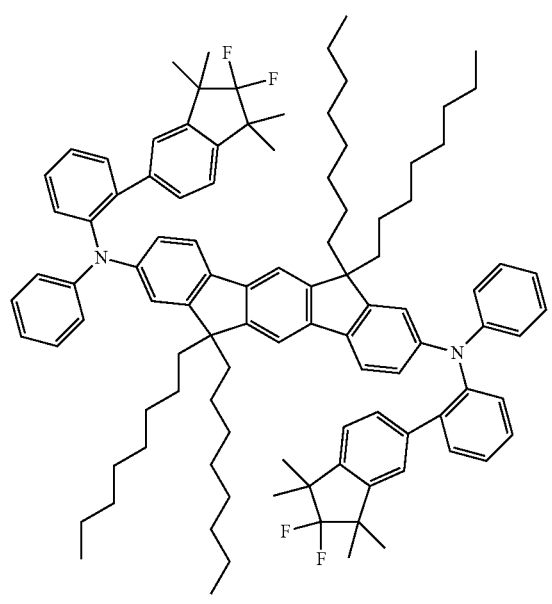
BB522 + BB-015
BB-1501

-continued
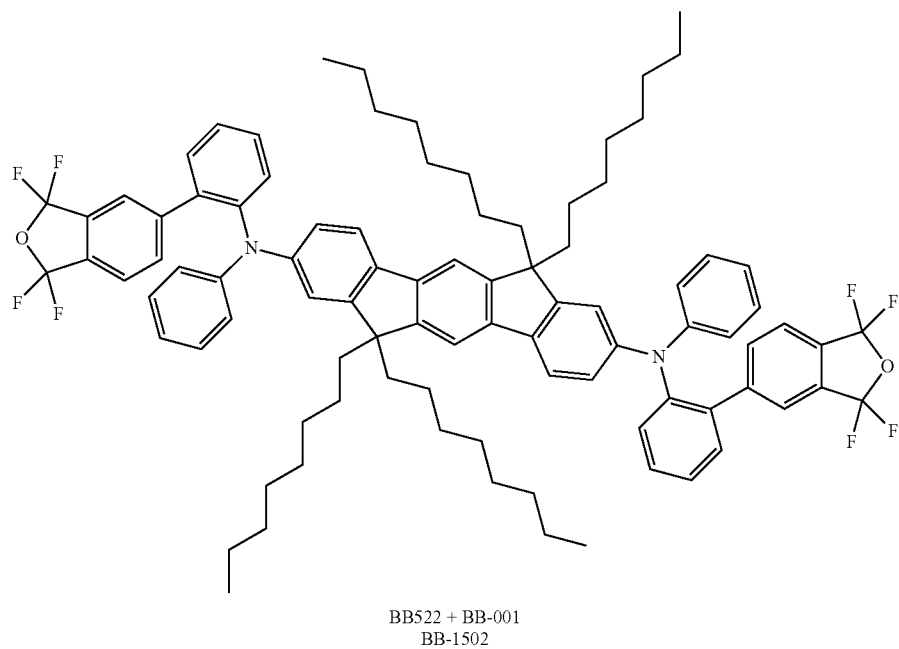
BB522 + BB-001
BB-1502
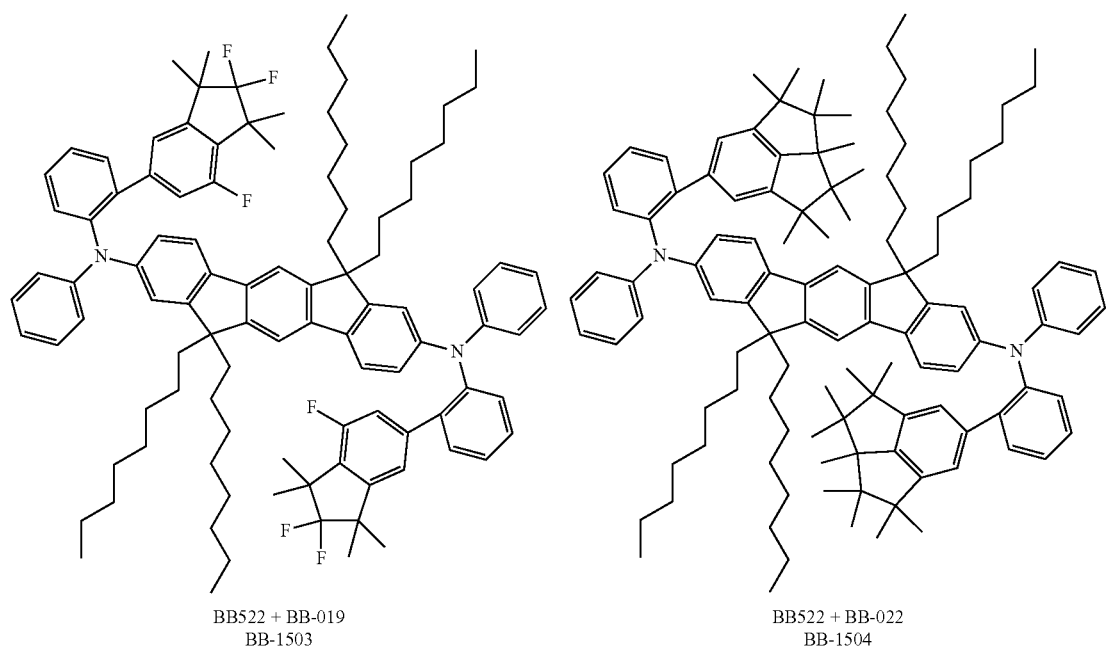
BB522 + BB-019
BB-1503
BB522 + BB-022
BB-1504

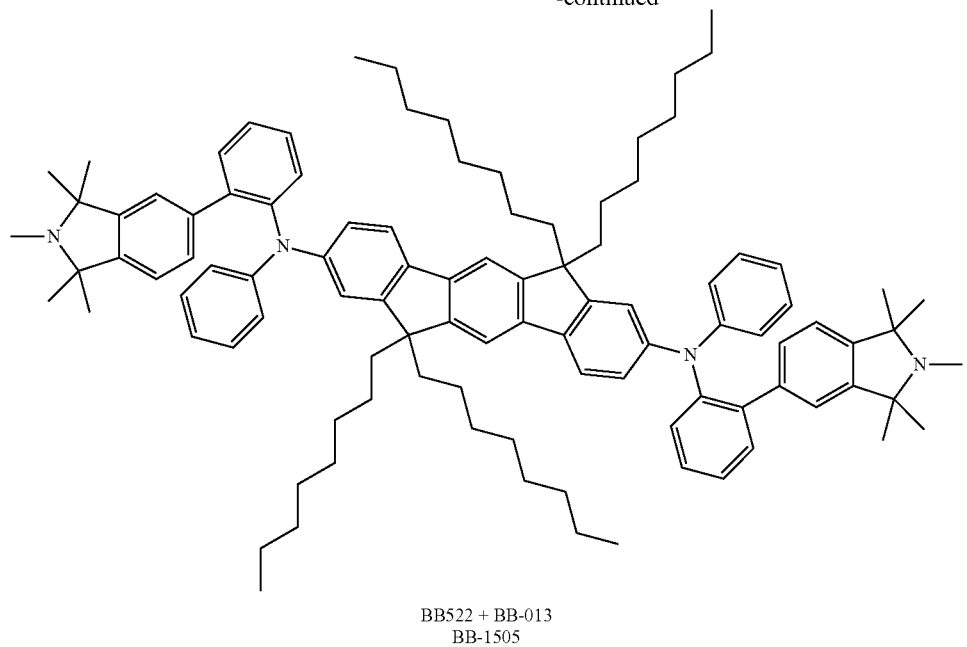

BB522 + BB-013
BB-1505

1-3) Buchwald reaction of the tetralin-analogous building blocks with amine building blocks to give coupling products

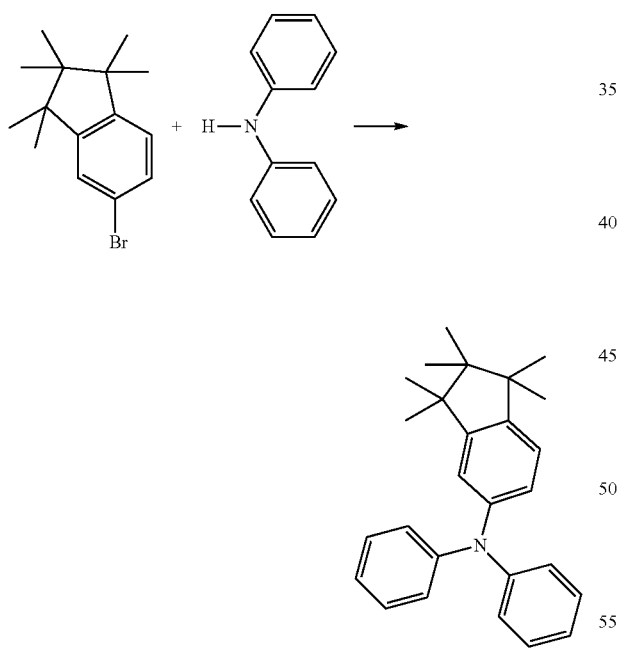

Into a 2 litre four-neck flask with precision glass stirrer, reflux condenser and argon connection are weighed 81 g (288 mmol) of BB-051, 53.61 g (317 mmol, 1.1 eq) of BB-750, 41.5 g (432 mmol, 1.5 eq) of sodium tert-butoxide, 2.36 g (5.76 mmol, 0.02 eq) of 2-dicyclohexylphosphino-2',6'-methoxybiphenyl (SPhos), 647 mg (2.88 mmol, 0.01 eq) of palladium(II) acetate, and 600 ml of toluene, 500 ml of ethanol and 350 ml of water are added. The reaction mixture is boiled under reflux for 48 hours, left to cool, and diluted with 500 ml of water and 500 ml of toluene, and the phases are separated. The organic phase is filtered through neutral alumina and the solvent is removed under reduced pressure. 500 ml of ethanol are added to the residue, which is stirred at 50° C. overnight. The solids are filtered off with suction and dried under reduced pressure. 65.4 g (177 mmol, 61% yield) of a colourless solid BB-2013 are obtained.

The following structures can be obtained by the same method and with similar yields:

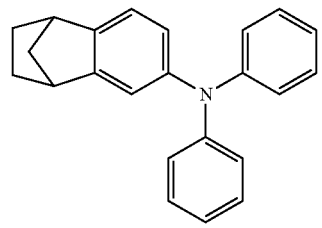

BB-058+BB-750
BB-2001

BB-055+BB-750
BB-2002

-continued
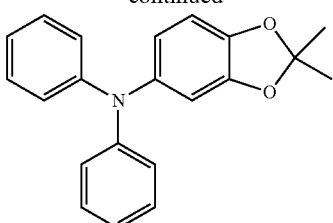
BB-062+BB-750
BB-2003
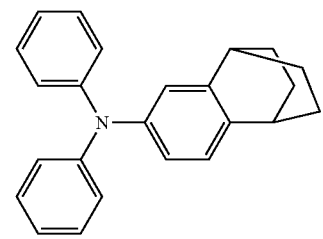
BB-058+BB-750
BB-2004
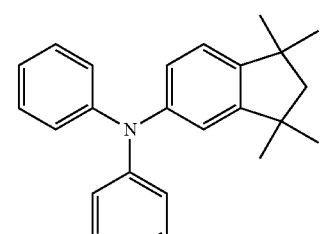
BB-050+BB-750
BB-2005
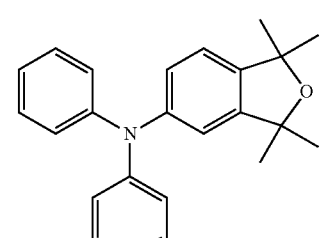
BB-056+BB-750
BB-2006
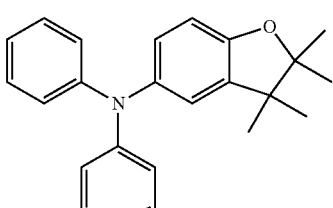
BB-065+BB-750
BB-2007
-continued
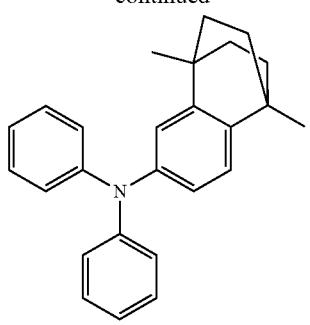
BB-059+BB-750
BB-2008
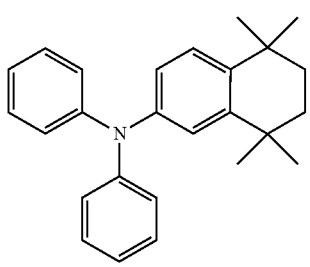
BB-057+BB-750
BB-2009
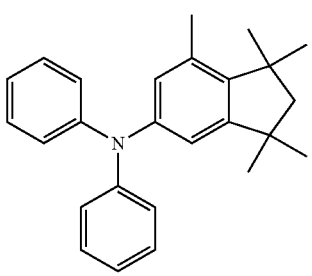
BB-063+BB-750
BB-2010
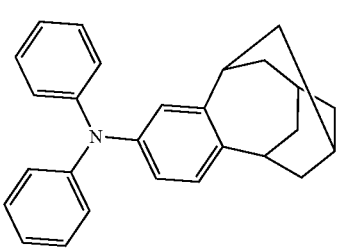
BB-060+BB-750
BB-2011
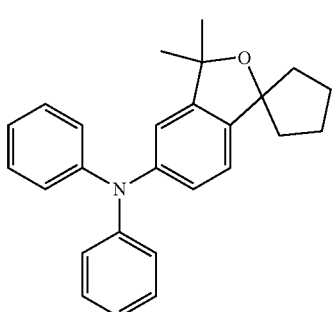
BB-066+BB-750

-continued
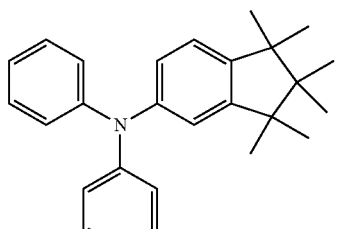
BB-051+BB-750
BB-2013
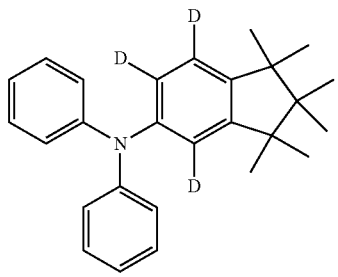
BB-052+BB-750
BB-2014
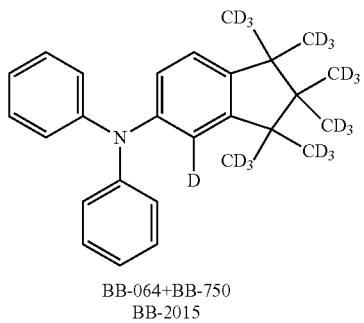
BB-064+BB-750
BB-2015
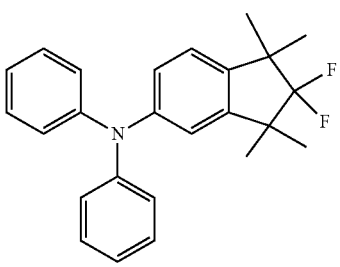
BB-053+BB-750
BB-2016
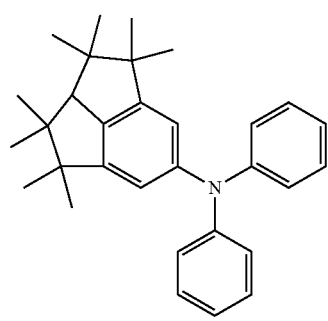
BB-067+BB-750
BB-2017
-continued
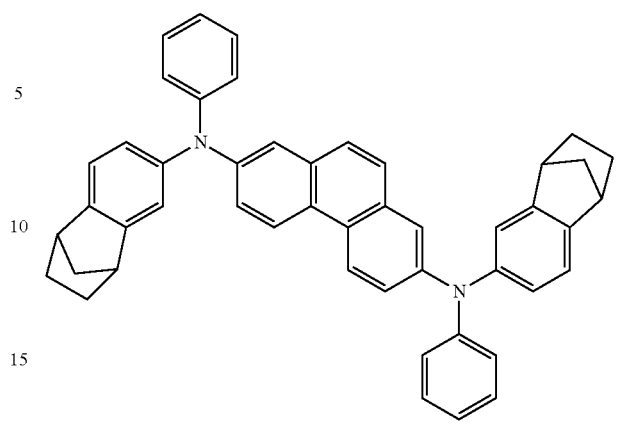
BB-058+BB-751
BB-2019
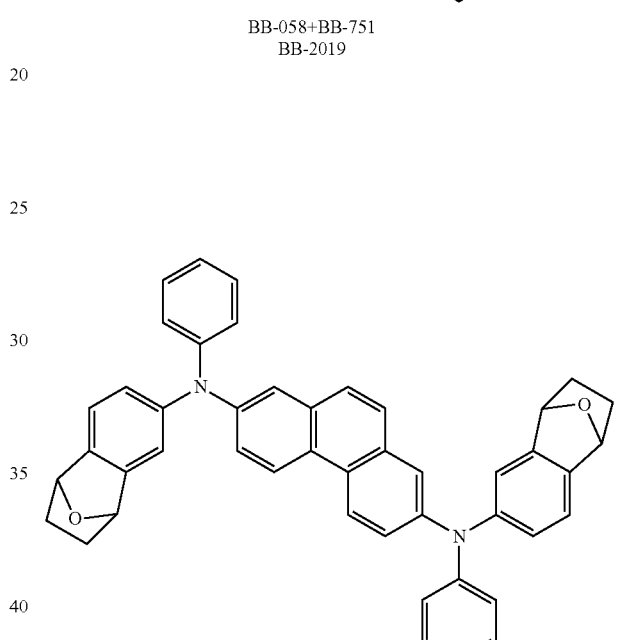
BB-055+BB-751
BB-2020
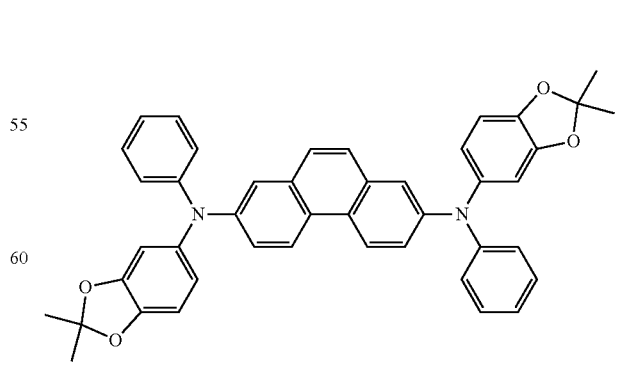
BB-062+BB-751
BB-2021

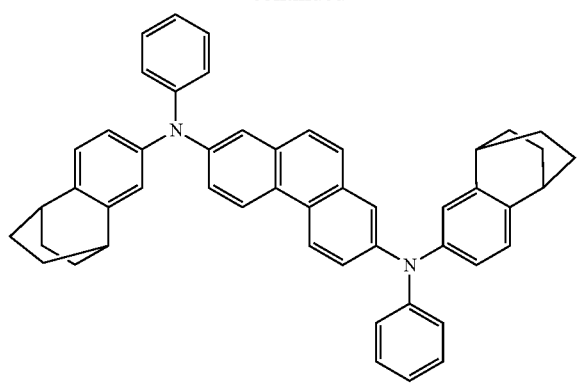
BB-058+BB-751
BB-2022
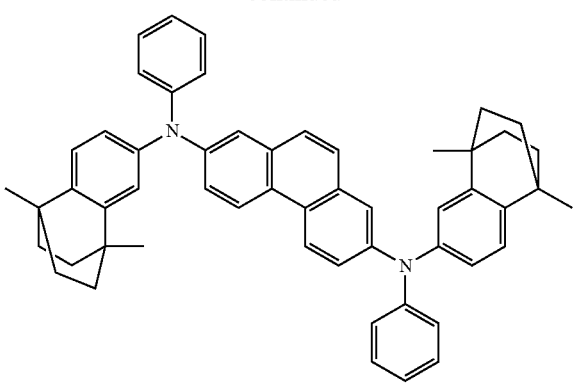
BB-059+BB-751
BB-2026
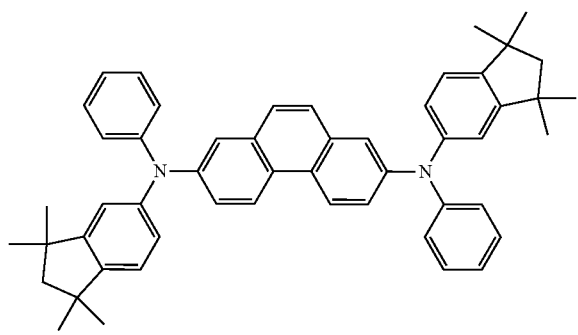
BB-050+BB-751
BB-2023
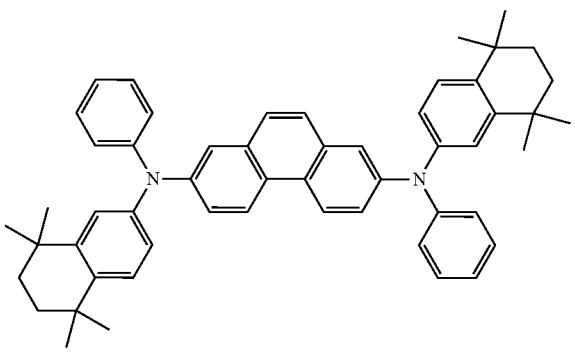
BB-057+BB-751
BB-2027
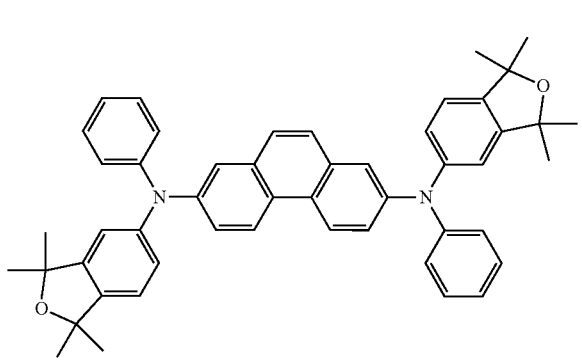
BB-056+BB-751
BB-2024
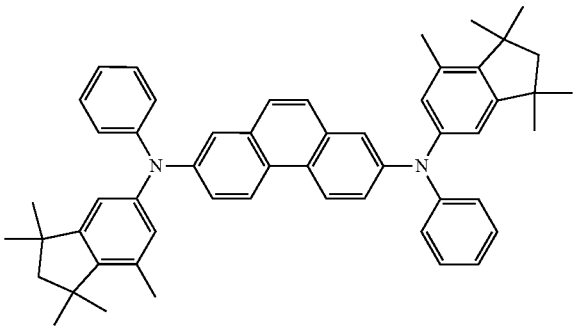
BB-063+BB-751
BB-2028
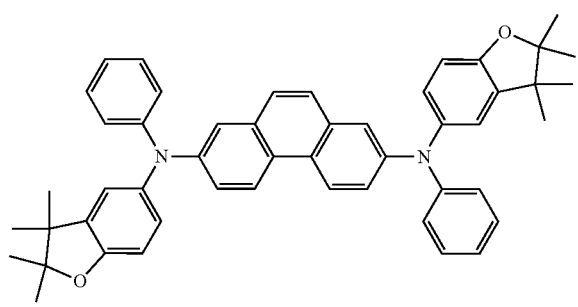
BB-065+BB-751
BB-2025
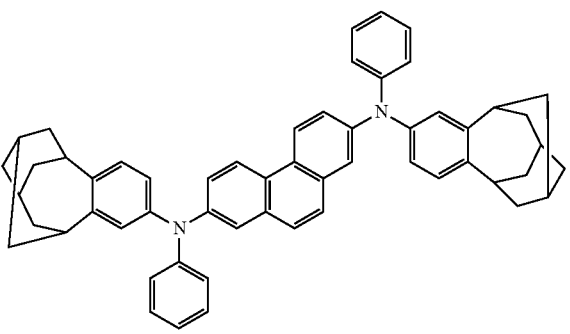
BB-060+BB-751
BB-2029

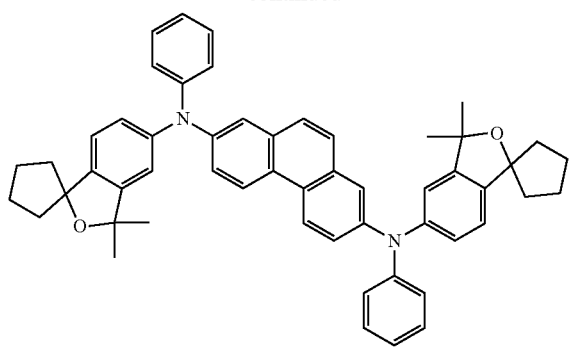
BB-066+BB-751
BB-2030
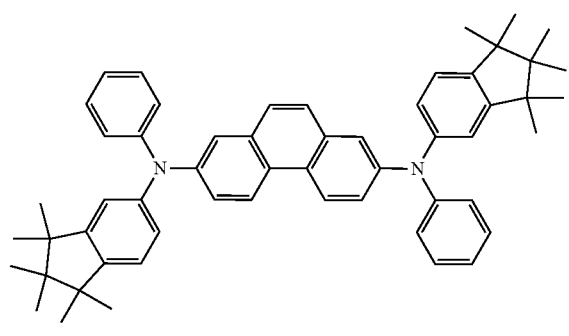
BB-051+BB-751
BB-2031
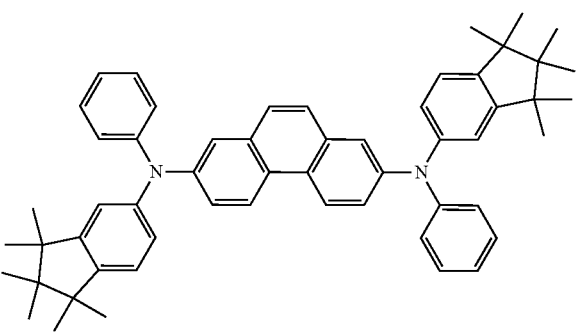
BB-052+BB-751
BB-2032
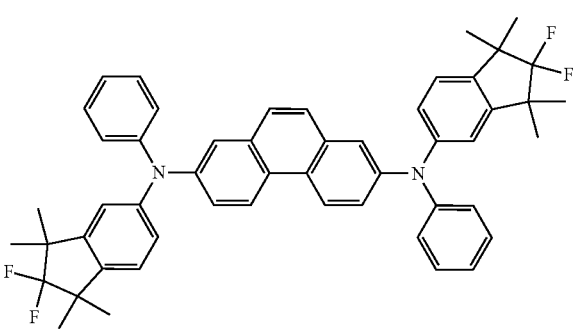
BB-064+BB-751
BB-2033
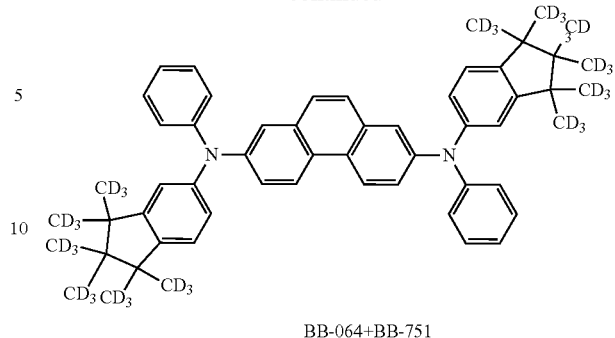
BB-064+BB-751
BB-2033
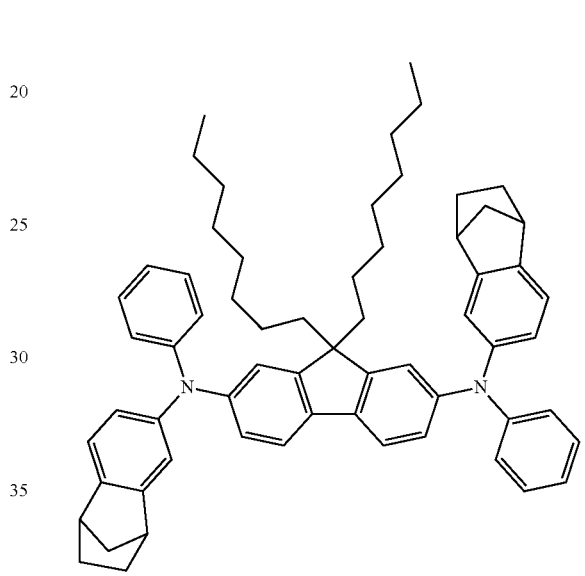
BB-058+BB-752
BB-2036
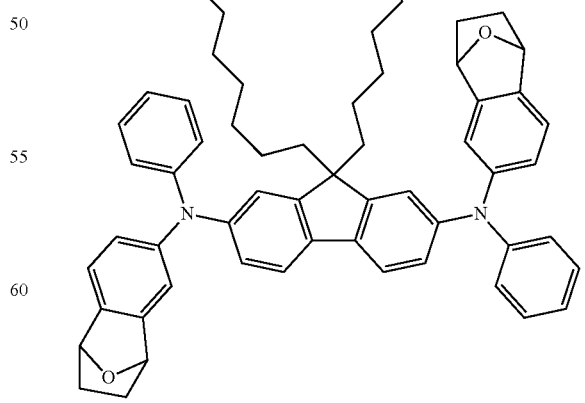
BB-055+BB-752
BB-2037

335
-continued
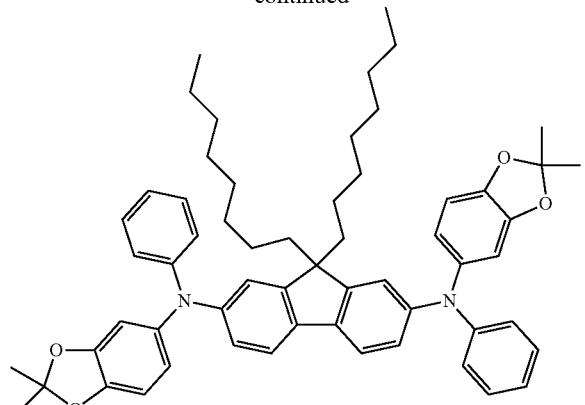
BB-062+BB-752
BB-2038
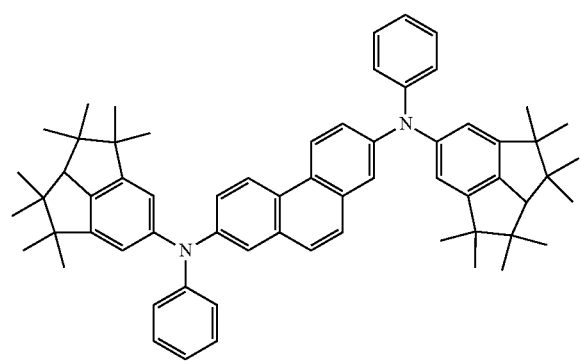
BB-067+BB-751
BB-2039
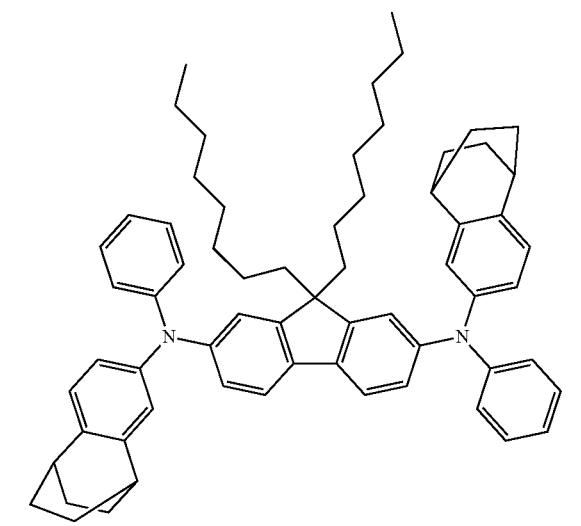
BB-058+BB-752
BB-2040
336
-continued
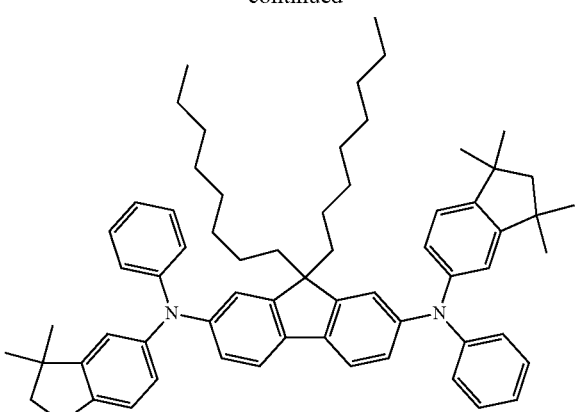
BB-050+BB-752
BB-2041
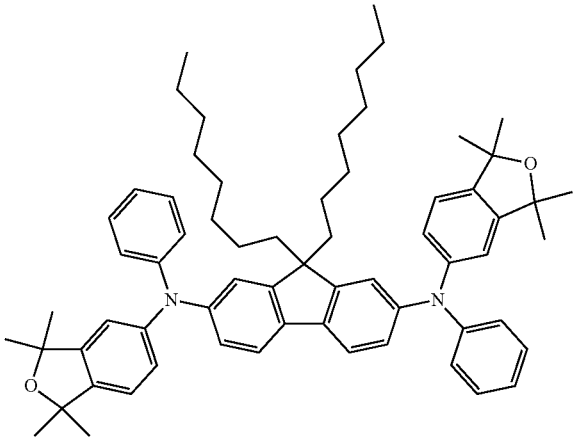
BB-056+BB-752
BB-2042
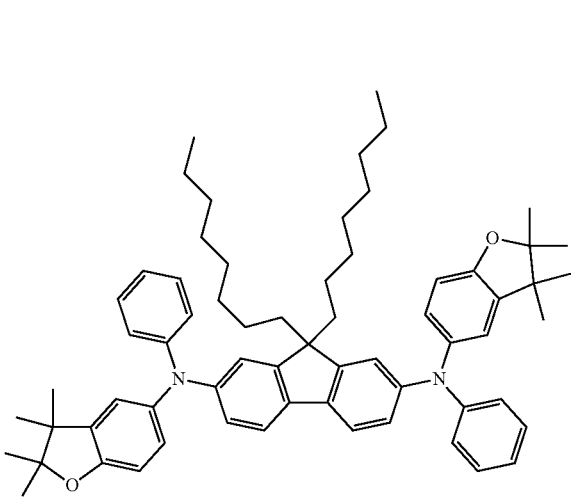
BB-065+BB-752
BB-2043

337
-continued
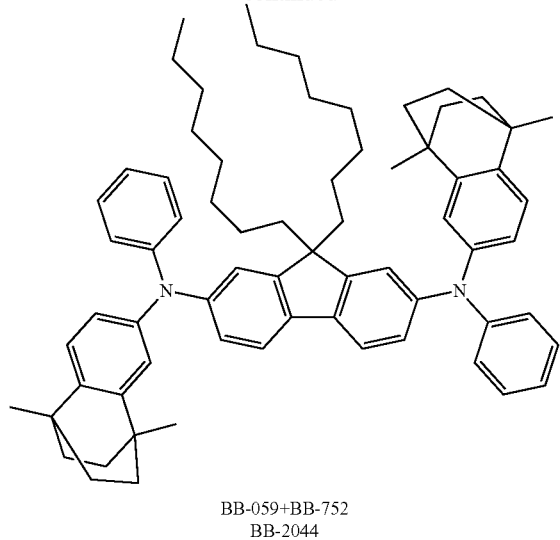
BB-059+BB-752
BB-2044
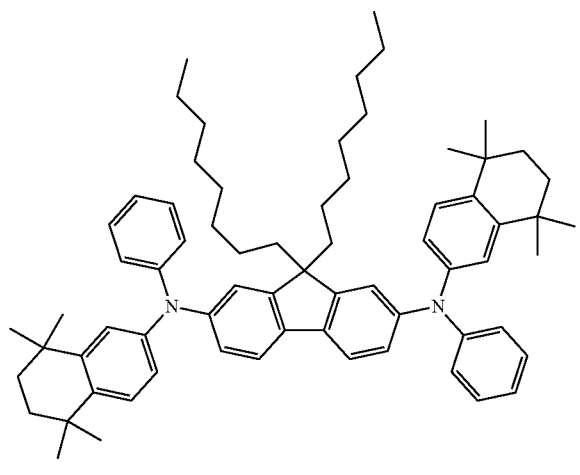
BB-057+BB-752
BB-2045
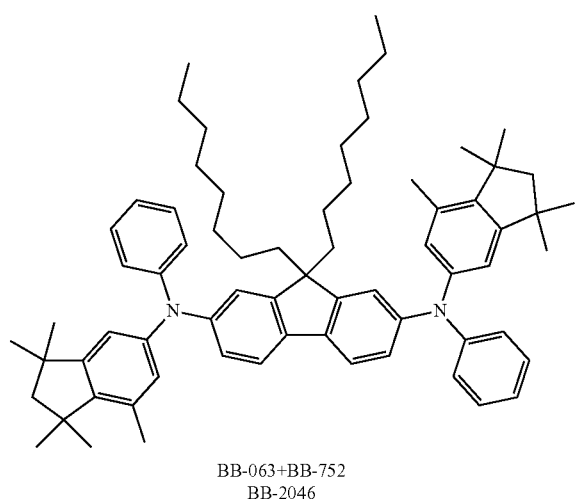
BB-063+BB-752
BB-2046
338
-continued
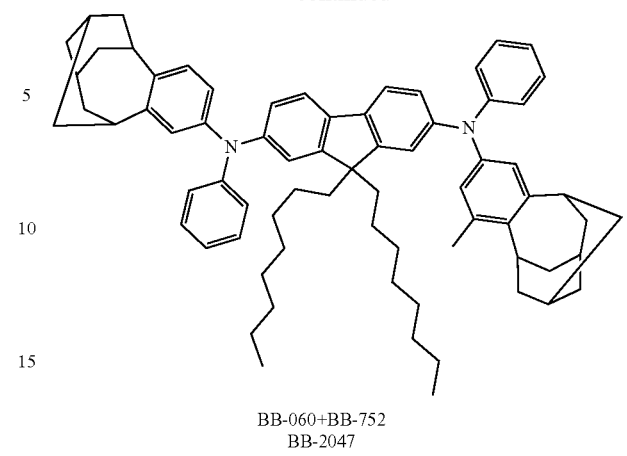
BB-060+BB-752
BB-2047
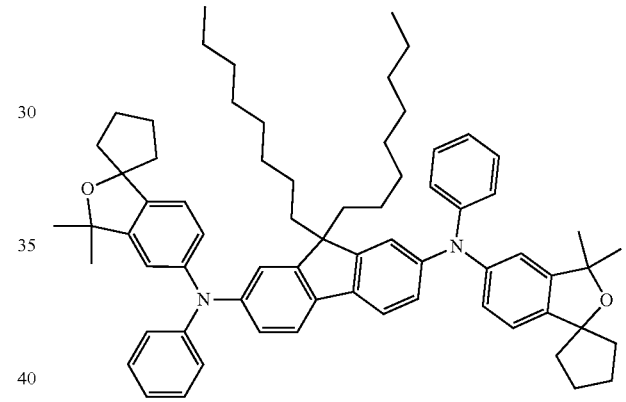
BB-066+BB-752
BB-2048
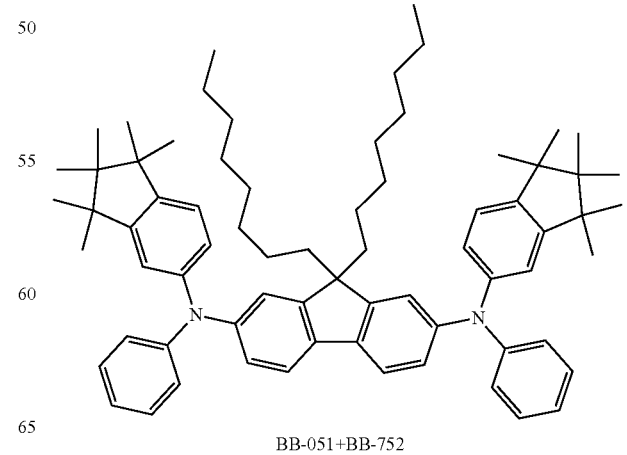
BB-051+BB-752

-continued

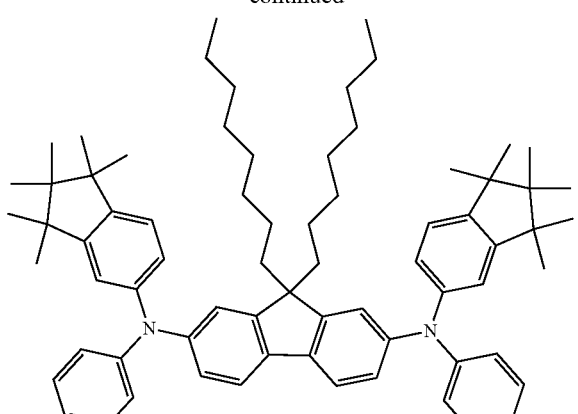

BB-052+BB-752
BB-2049

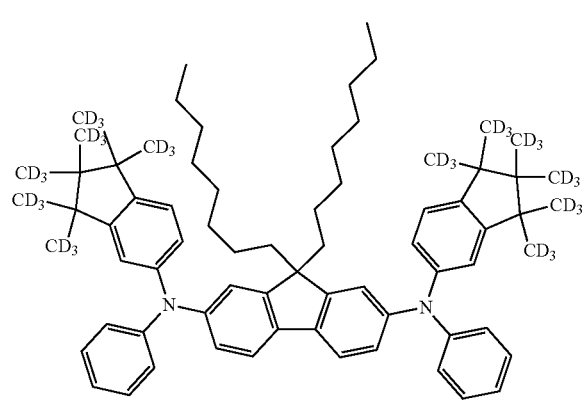

BB-064+BB-752
BB-2050

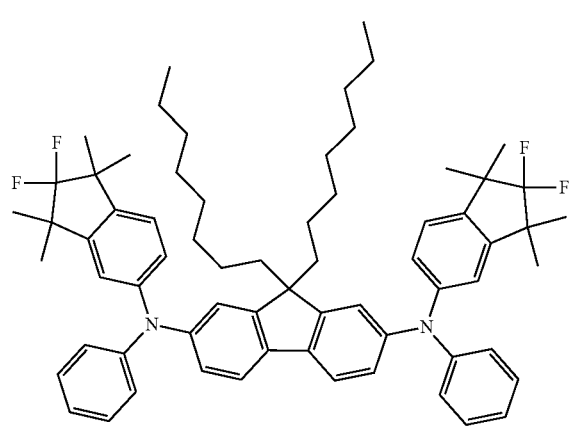

BB-053+BB-752
BB-2051

-continued

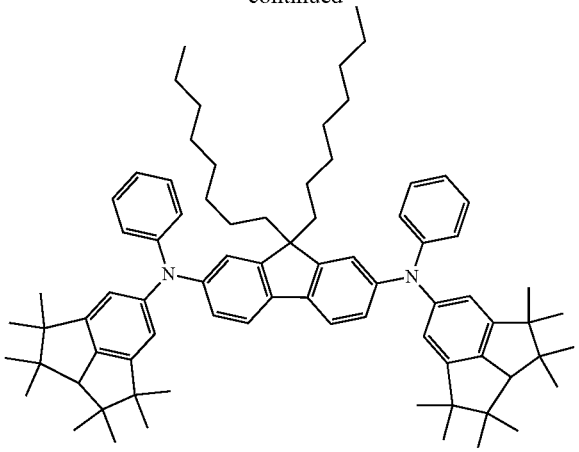

BB-067+BB-752
BB-2052

1-4) Bromination of the coupling products to give the monomer compounds

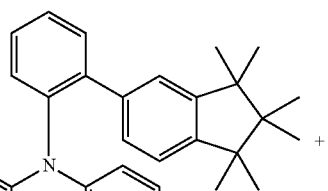
+
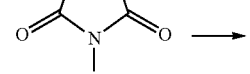
→
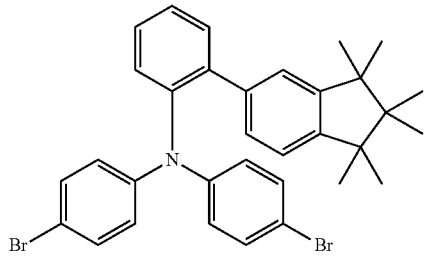

MON-0032 in a 4 litre four-neck flask with a reflux condenser, argon connection, precision glass stirrer and heating bath, 130.4 g (292.6 mmol) of BB-1031 are dissolved in 2500 ml of dichloromethane, 0.5 ml of glacial acetic acid is added, and 104.2 g (585.2 mmol, 2 eq) of N-bromosuccinimide (CAS: 128-08-5) are added in portions. The reaction mixture is stirred at room temperature with exclusion of light for 24 h and extracted with water, and the solvent is removed under reduced pressure. The residue is boiled in 1500 ml of ethanol, and the solids are filtered off with suction and recrystallized repeatedly from methyl ethyl ketone and heptane. 115.9 g (192 mmol, 65.6% yield) of the inventive monomer MON-0032 are obtained as a colourless solid.

The following monomers of the invention can be obtained by the same method and with similar yields:

BB-1000
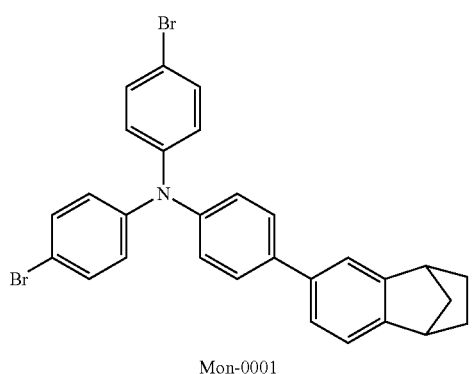
Mon-0001
BB-1001
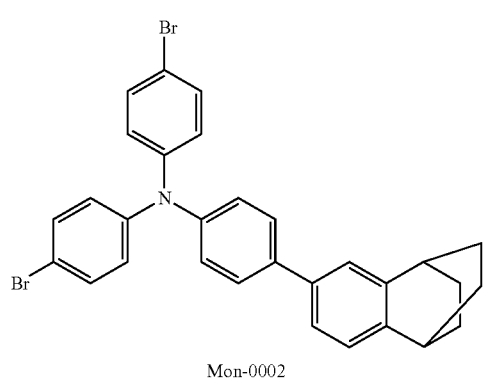
Mon-0002
BB-1002
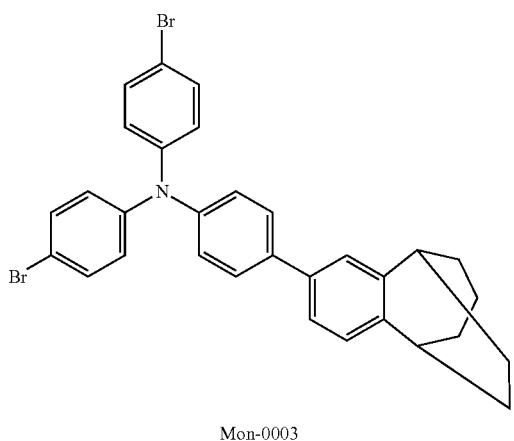
Mon-0003
-continued
BB-1003
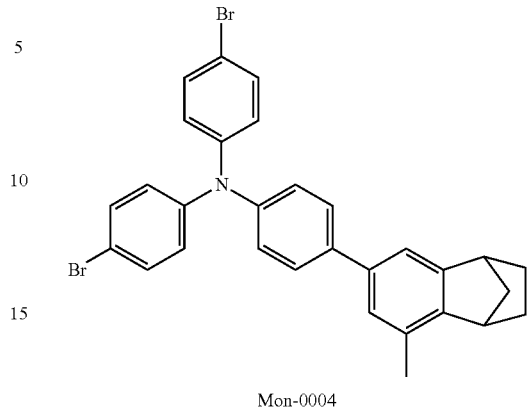
Mon-0004
BB-1004
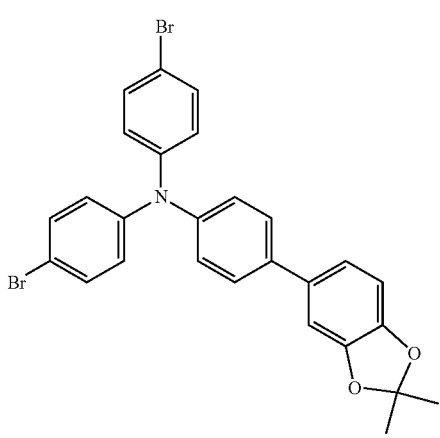
Mon-0005
BB-1005
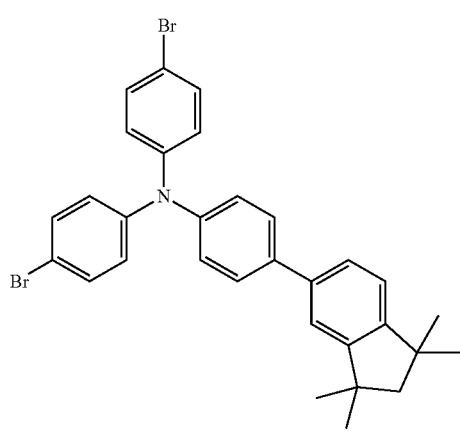
Mon-0006

-continued
BB-1006
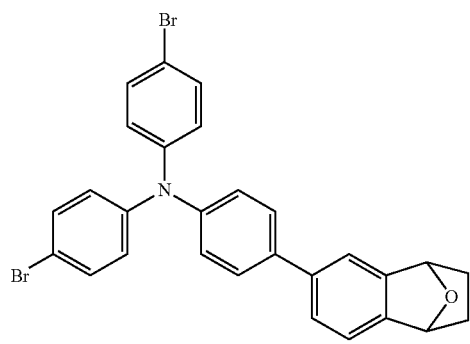
Mon-0007
BB-1007
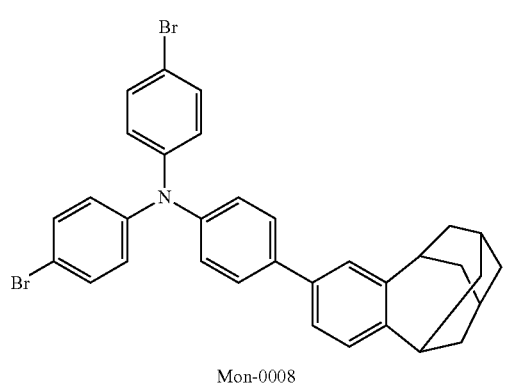
Mon-0008
BB-1008
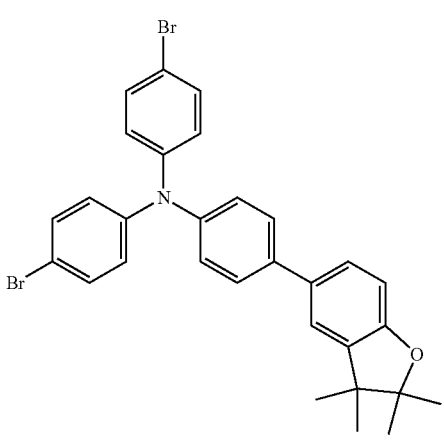
Mon-0009
-continued
BB-1009
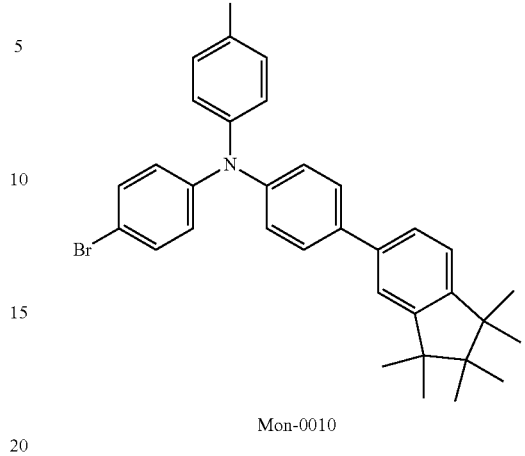
Mon-0010
BB-1010
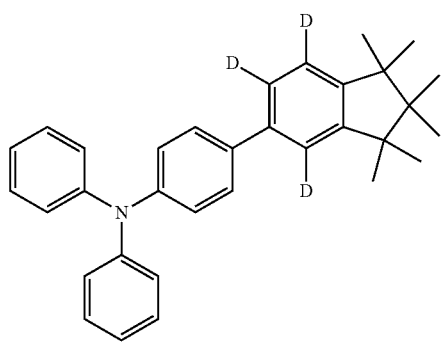
Mon-0011
BB-1011
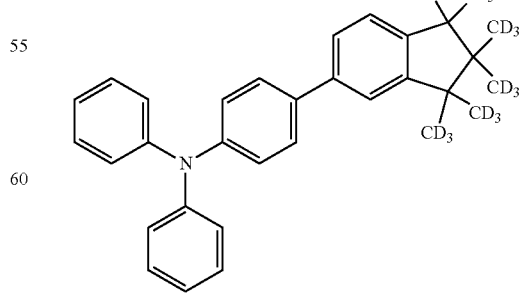
Mon-0012

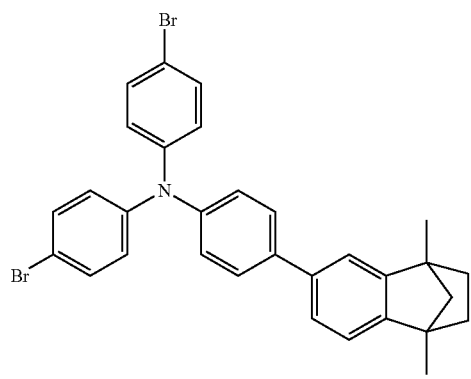
Mon-0013
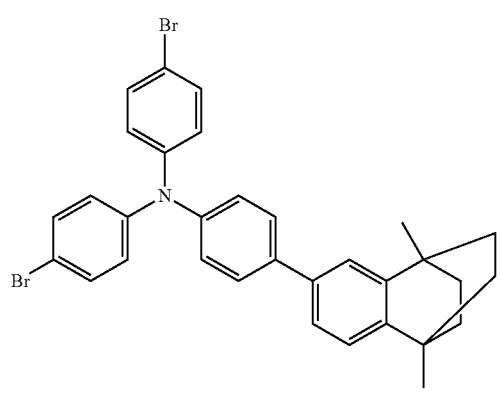
Mon-0014
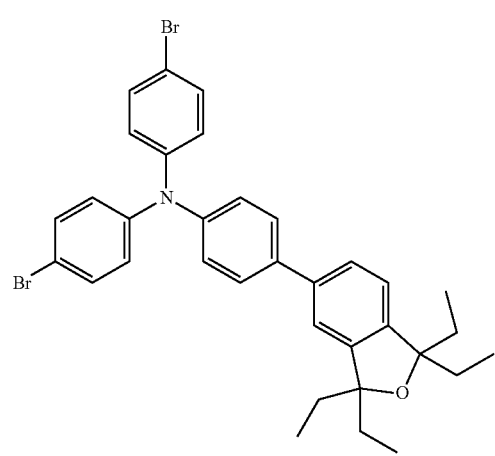
Mon-0015
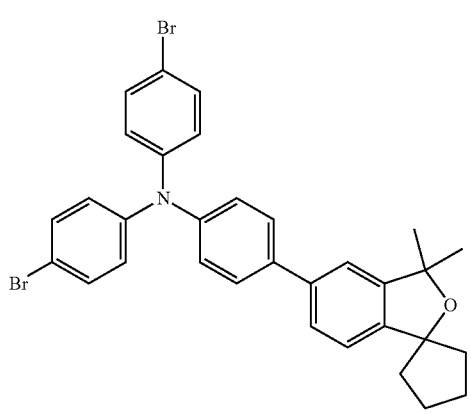
Mon-0016
Mon-0017
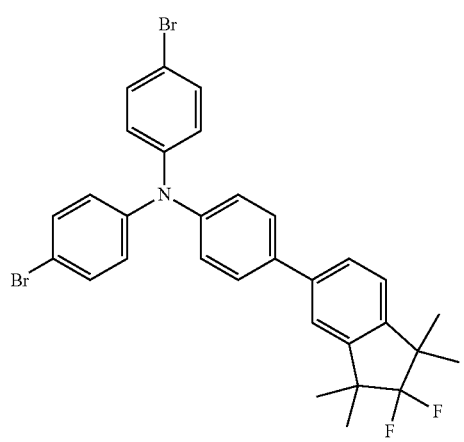
Mon-0018

BB-1018
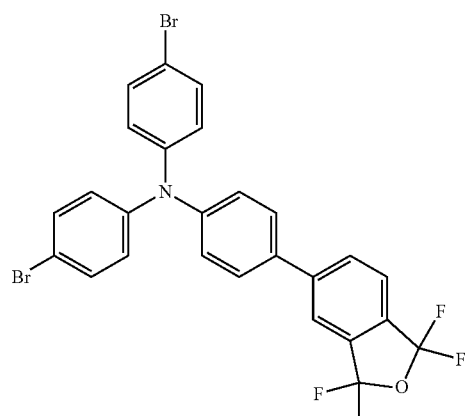
Mon-0019
BB-1019
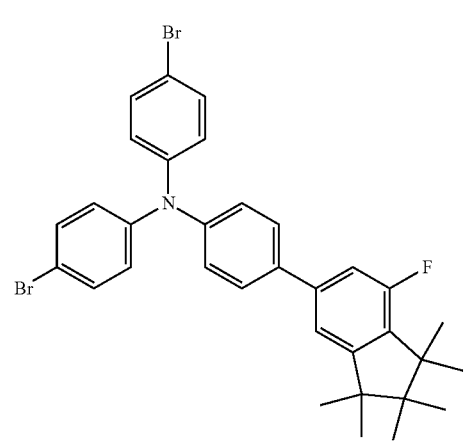
Mon-0020
BB-1020
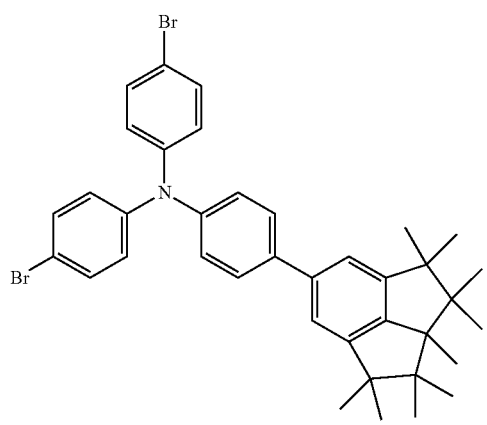
Mon-0021
BB-1021
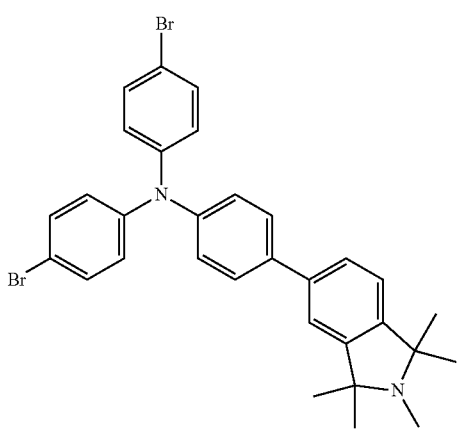
Mon-0022
BB-1022
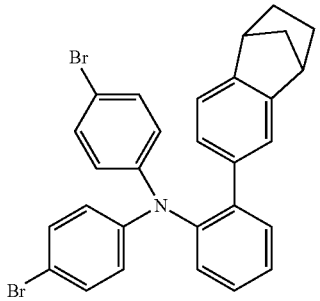
Mon-0023
BB-1023
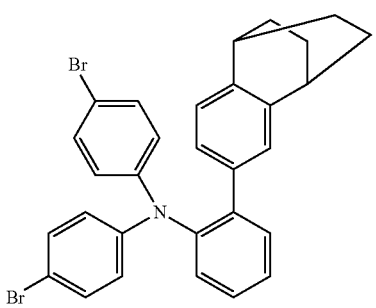
Mon-0024
BB-1024
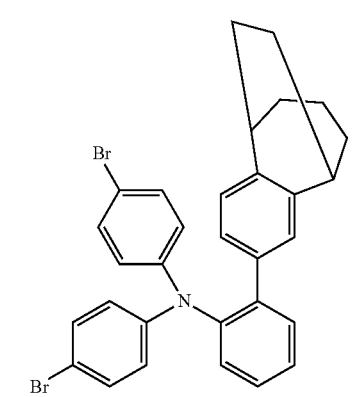
Mon-0025

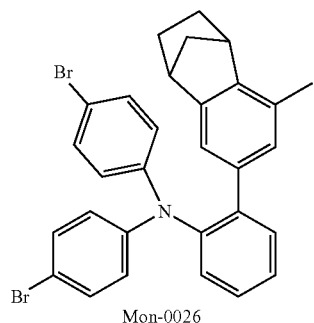
Mon-0026 BB-1025
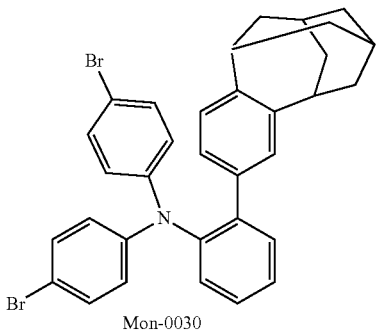
Mon-0030 BB-1029
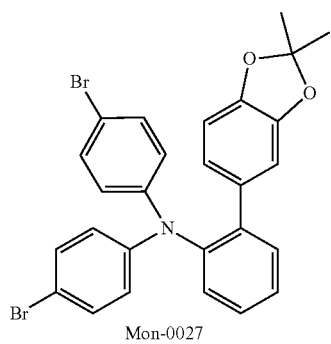
Mon-0027 BB-1026
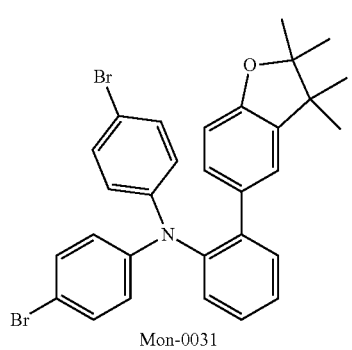
Mon-0031 BB-1030
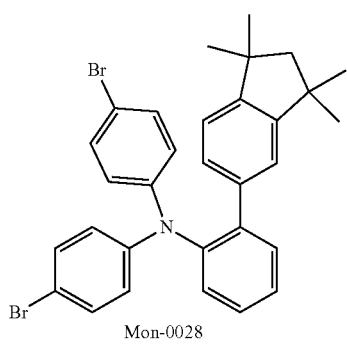
Mon-0028 BB-1027
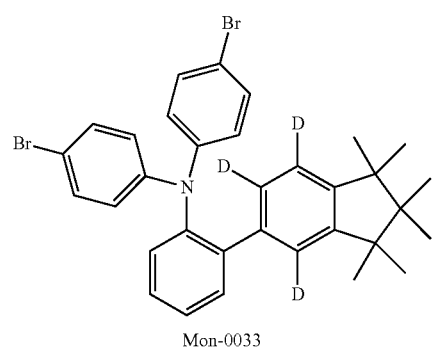
Mon-0033 BB-1032
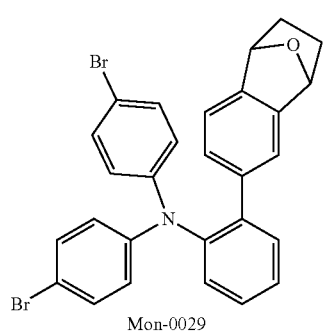
Mon-0029 BB-1028
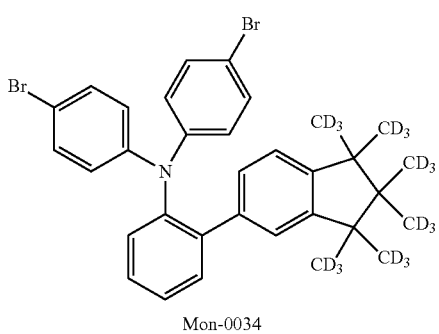
Mon-0034 BB-1033

-continued
BB-1034
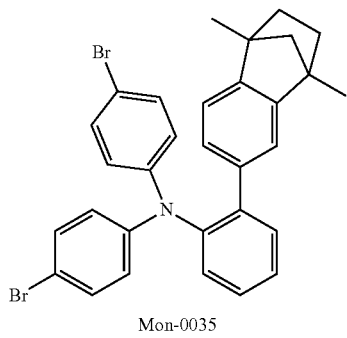
Mon-0035
BB-1035
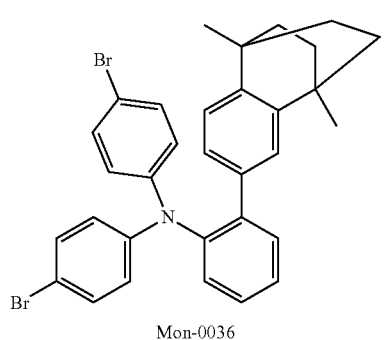
Mon-0036
BB-1036
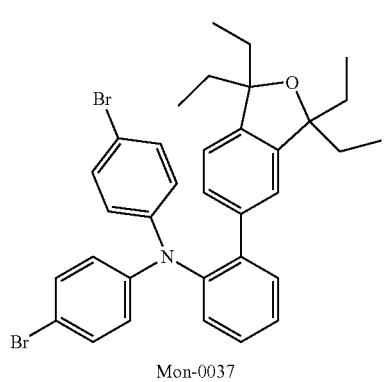
Mon-0037
BB-1037
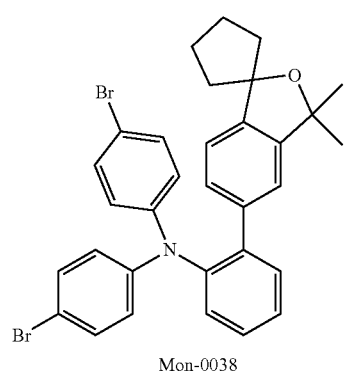
Mon-0038
-continued
BB-1038
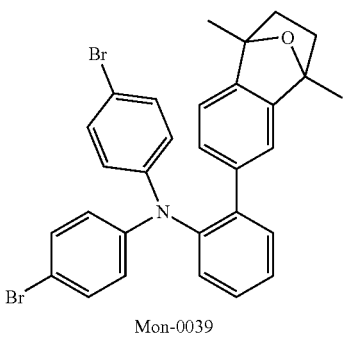
Mon-0039
BB-1039
Mon-0040
BB-1040
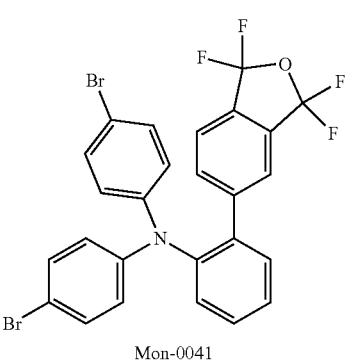
Mon-0041
BB-1041
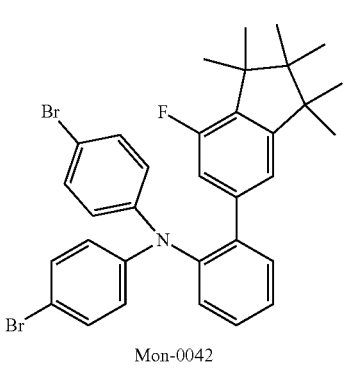
Mon-0042

-continued
BB-1042
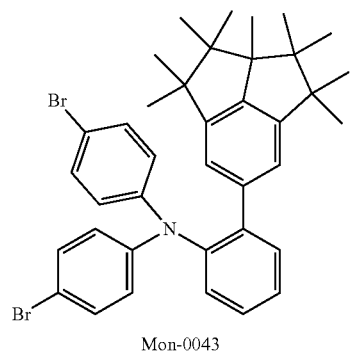
Mon-0043
BB-1043
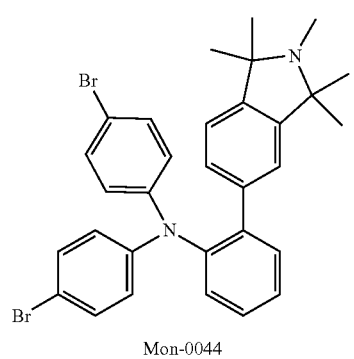
Mon-0044
BB-1044
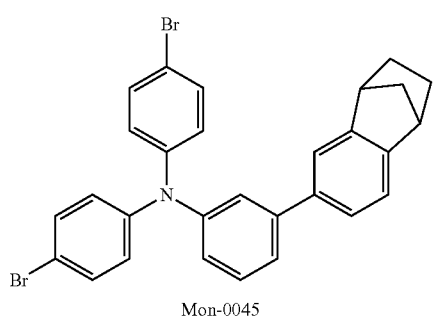
Mon-0045
BB-1045
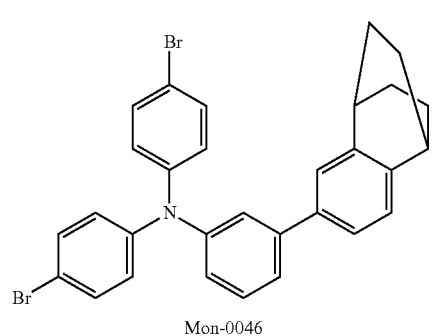
Mon-0046
-continued
BB-1046
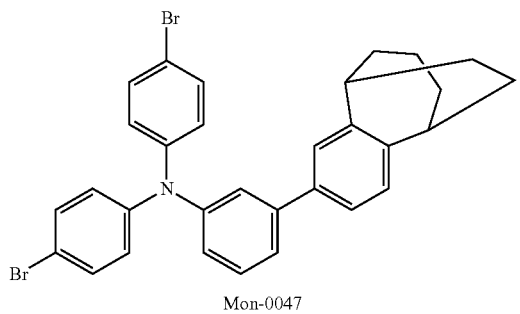
Mon-0047
BB-1047
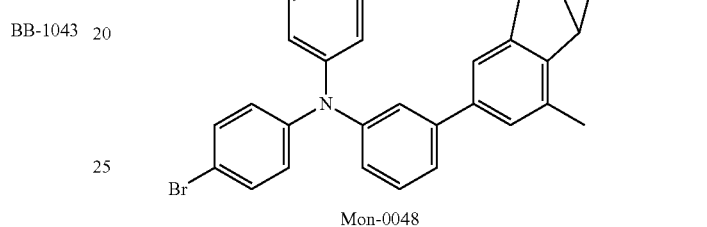
Mon-0048
BB-1048
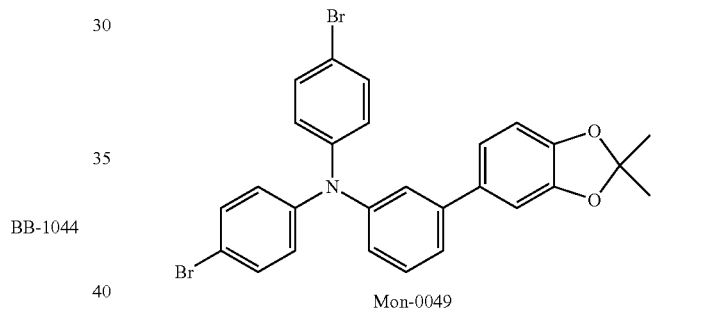
Mon-0049
BB-1049
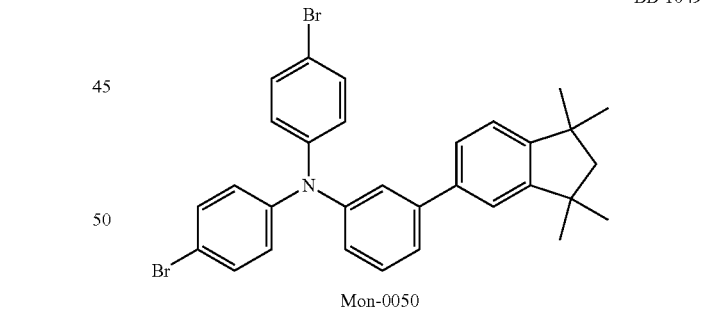
Mon-0050
BB-1050
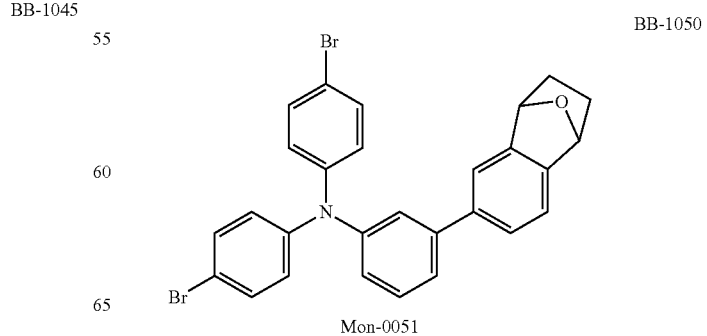
Mon-0051

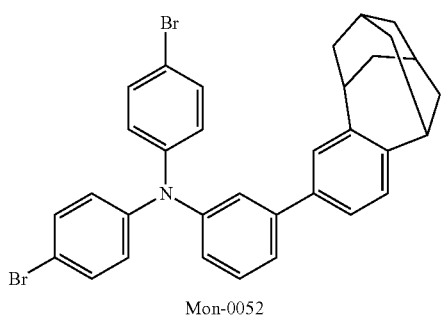
Mon-0052
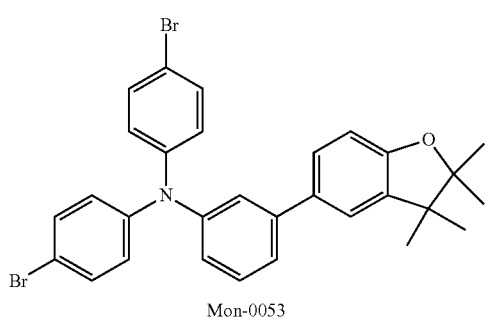
Mon-0053
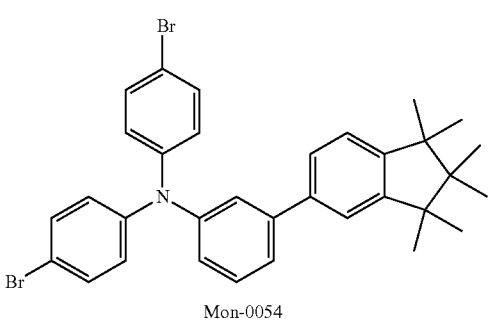
Mon-0054
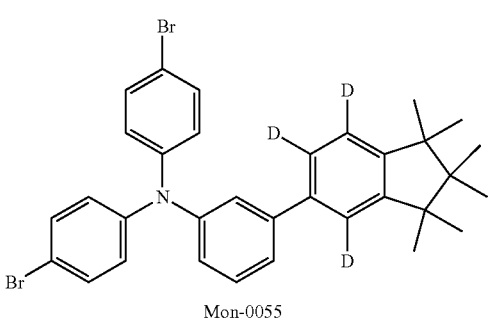
Mon-0055
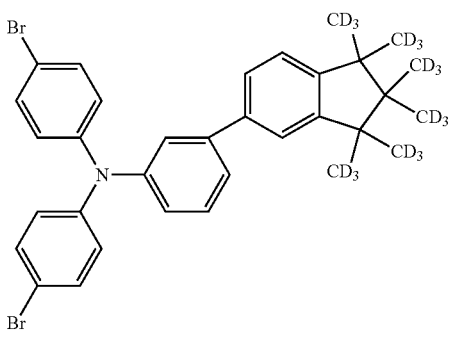
Mon-0056
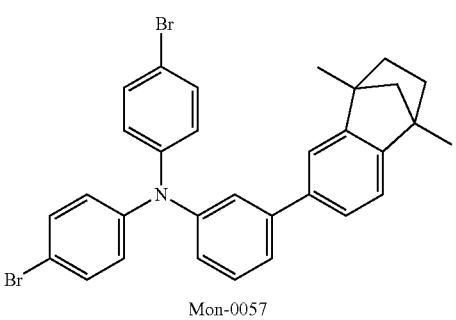
Mon-0057
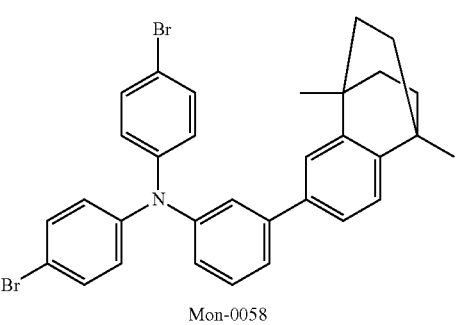
Mon-0058
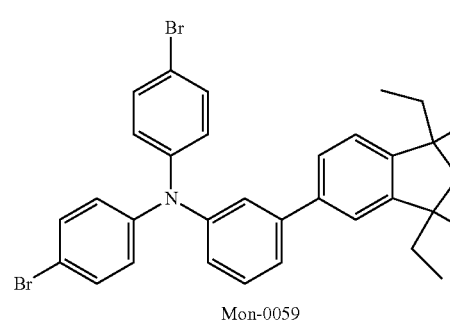
Mon-0059

BB-1059
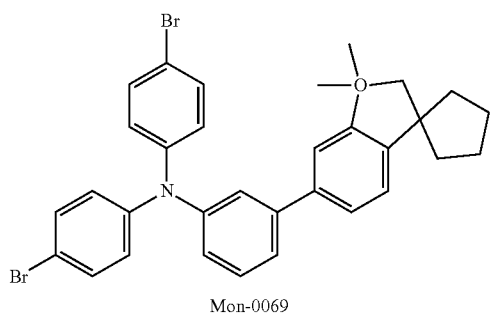
Mon-0069
BB-1060
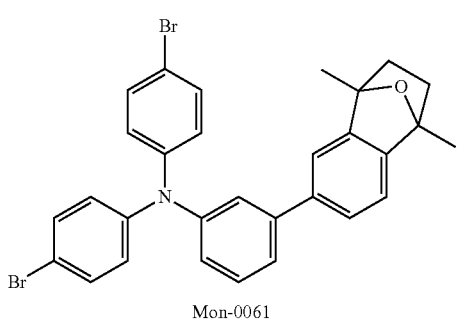
Mon-0061
BB-1061
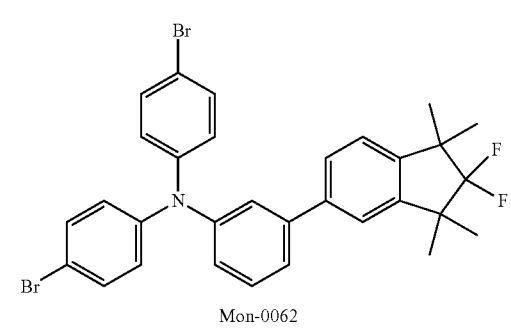
Mon-0062
BB-1062
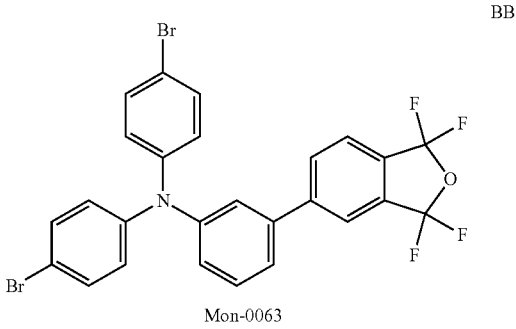
Mon-0063
BB-1063
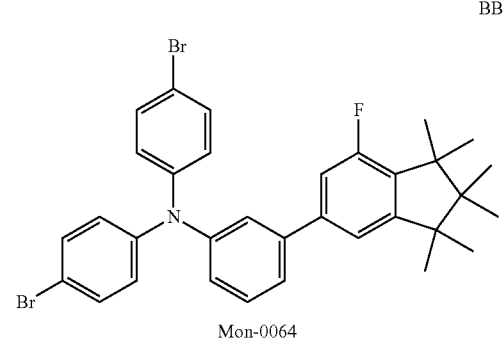
Mon-0064
BB-1064
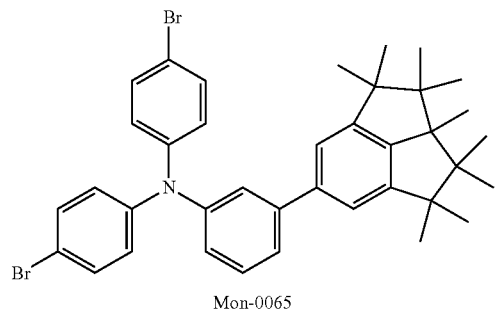
Mon-0065
BB-1065
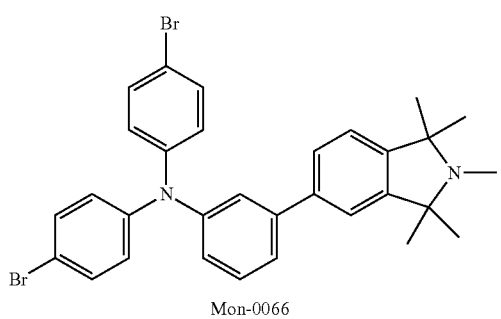
Mon-0066
BB-1066
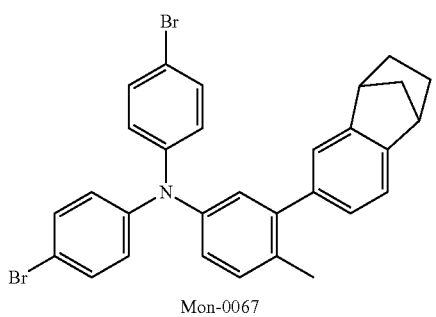
Mon-0067
BB-1067
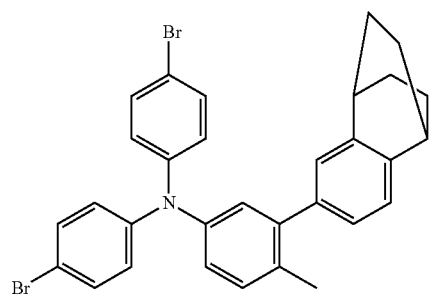
Mon-0068

-continued
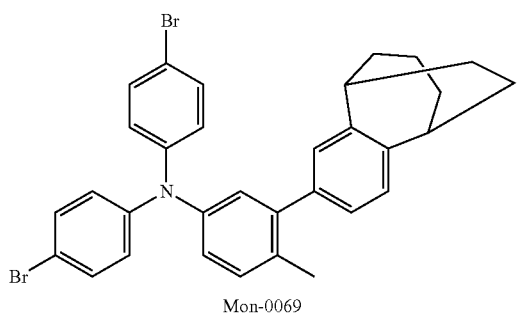
Mon-0069 BB-1068
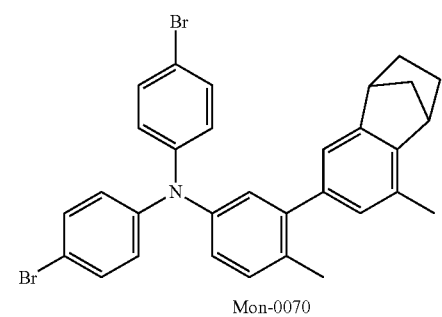
Mon-0070 BB-1069
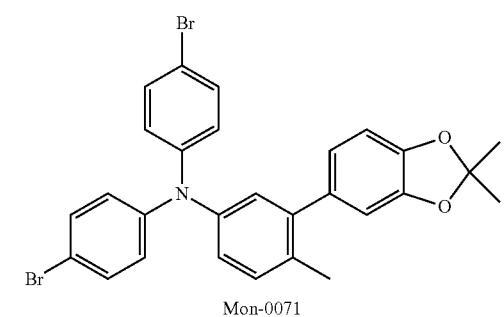
Mon-0071 BB-1070
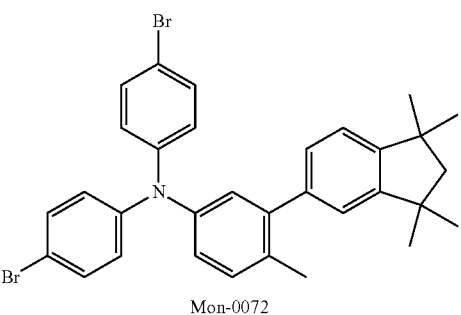
Mon-0072 BB-1071
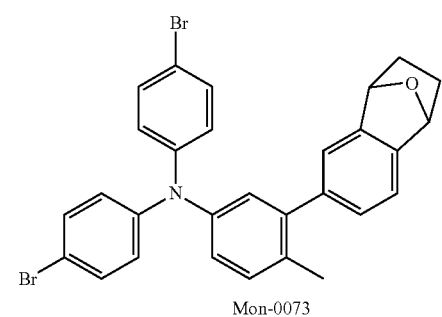
Mon-0073 BB-1072
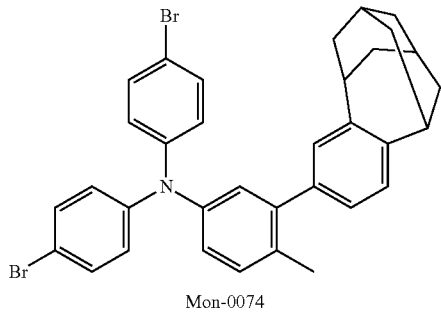
Mon-0074 BB-1073
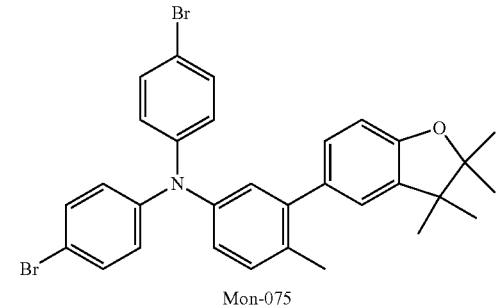
Mon-075 BB-1074
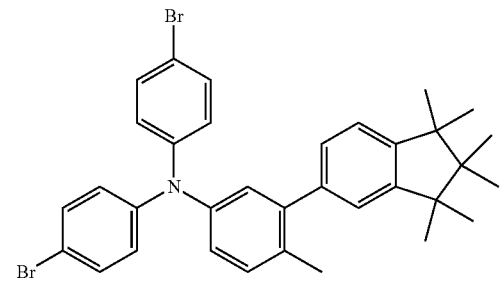
Mon-0076 BB-1075
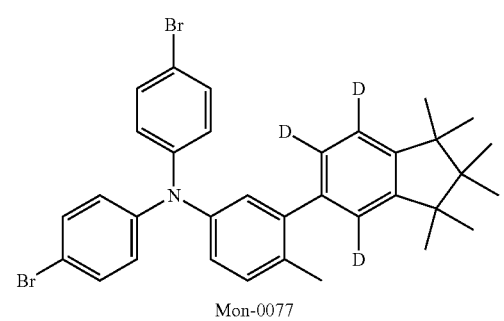
Mon-0077 BB-1076

-continued
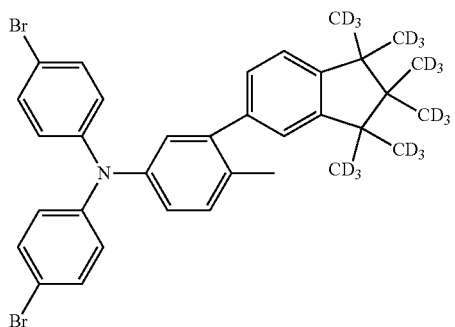
Mon-0078 BB-1077
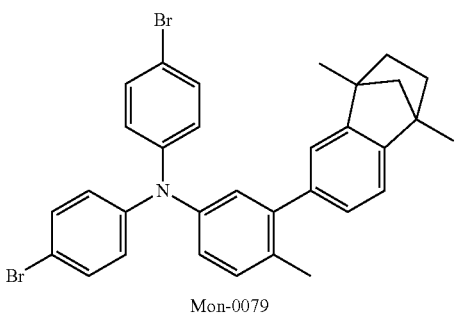
Mon-0079 BB-1078
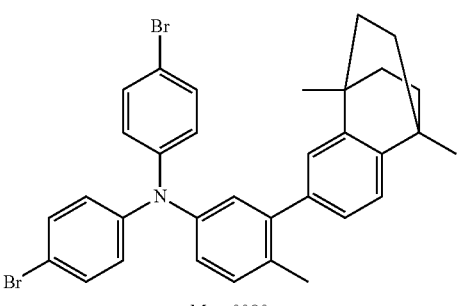
Mon-0080 BB-1079
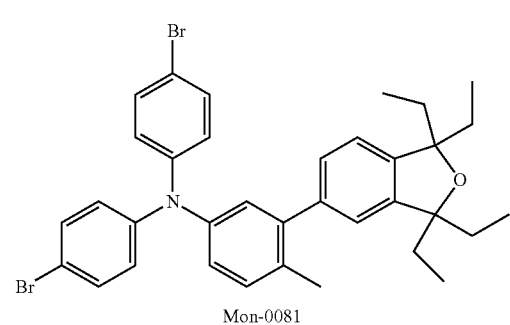
Mon-0081 BB-1080
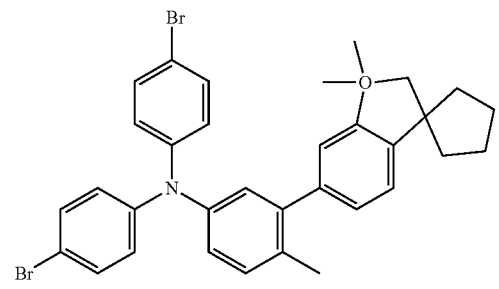
Mon-0082 BB-1081
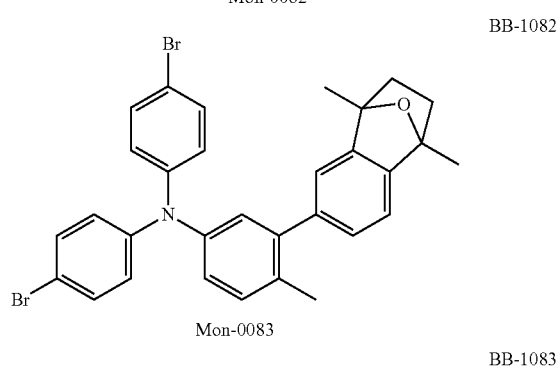
Mon-0083 BB-1082
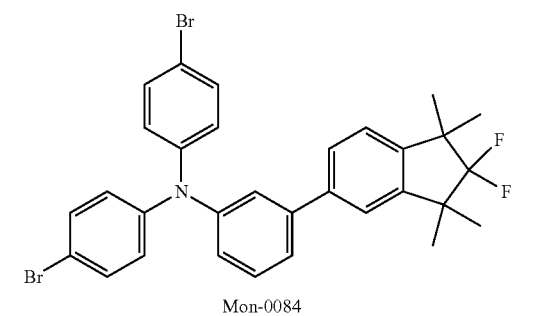
Mon-0084 BB-1083
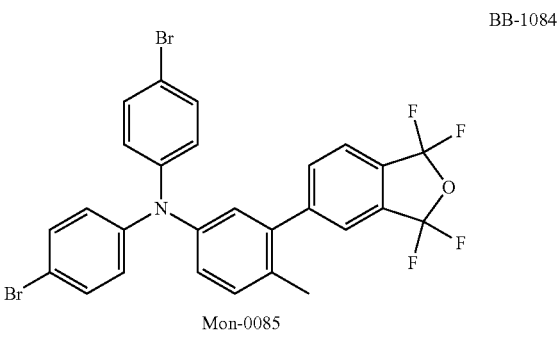
Mon-0085 BB-1084
Mon-0086 BB-1085

-continued
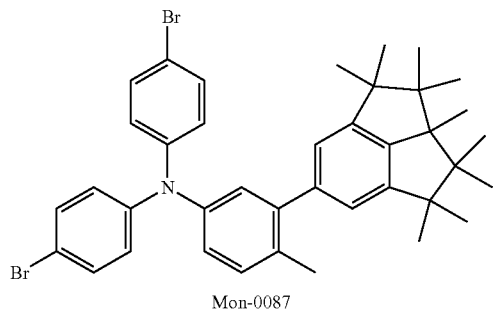
Mon-0087 BB-1086
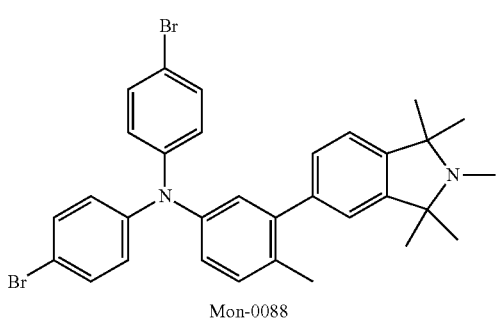
Mon-0088 BB-1087
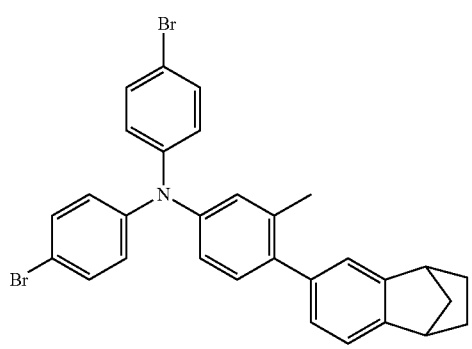
Mon-0089 BB-1088
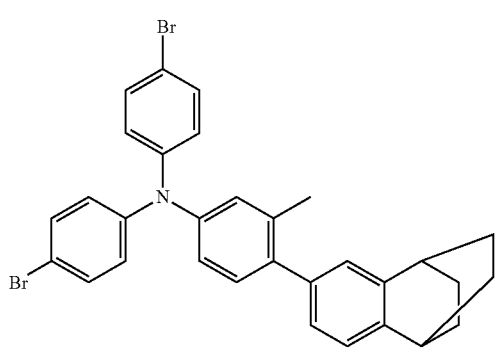
Mon-0090 BB-1089
-continued
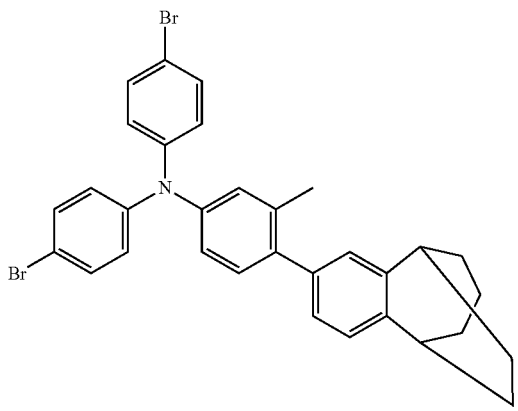
Mon-0091 BB-1090
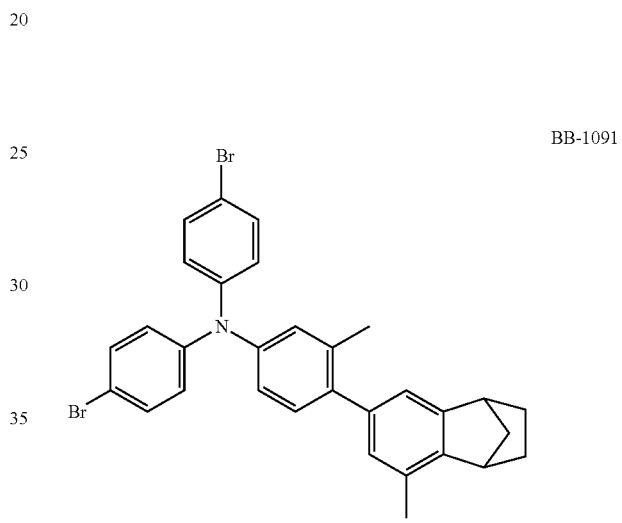
Mon-0092 BB-1091
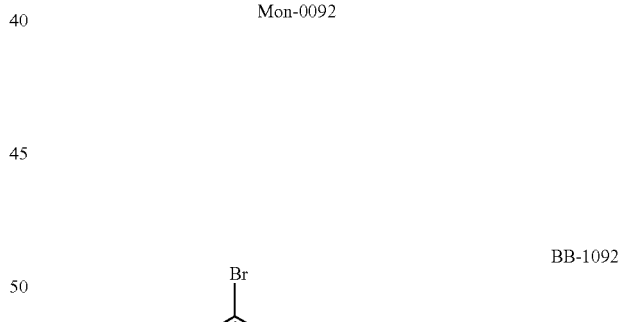
Mon-0093 BB-1092

365
-continued
BB-1093
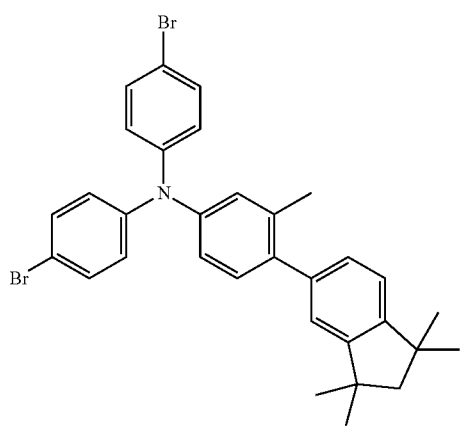
Mon-0094
BB-1094
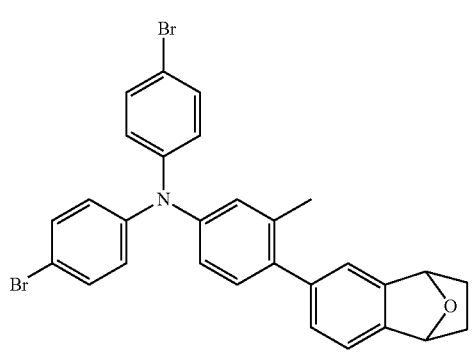
Mon-0095
BB-1095
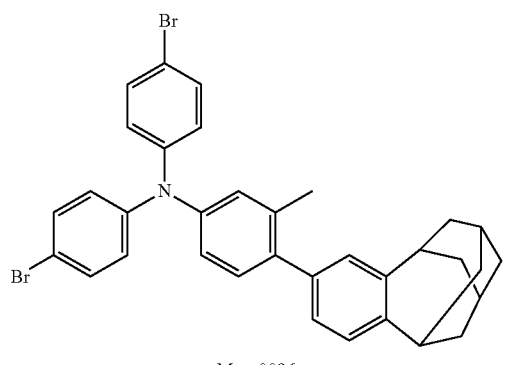
Mon-0096
366
-continued
BB-1096
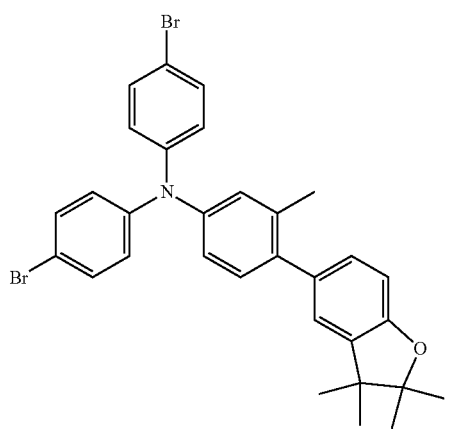
Mon-0097
BB-1097
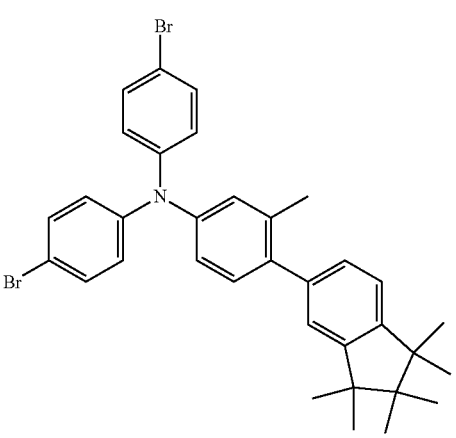
Mon-0098
BB-1098
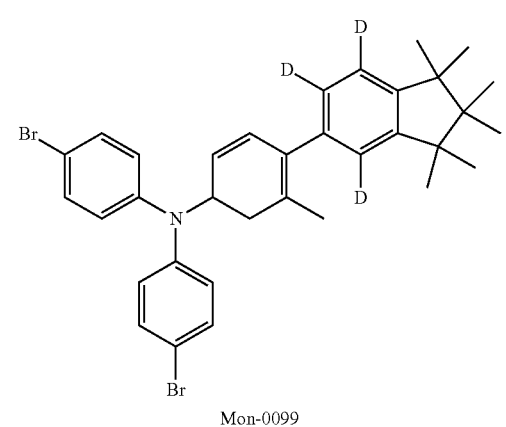
Mon-0099

-continued
BB-1099
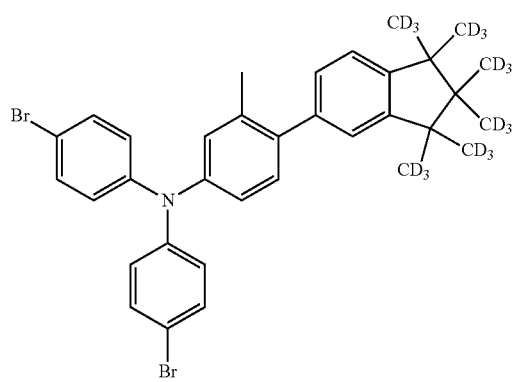
Mon-0100
BB-1100
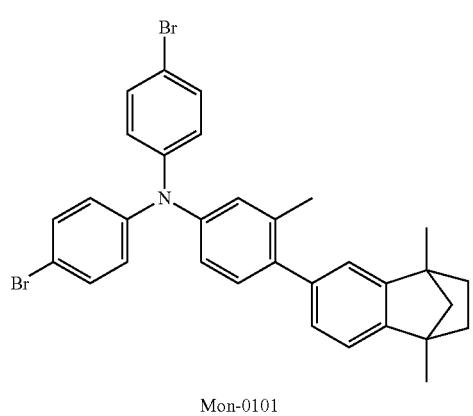
Mon-0101
BB-1101
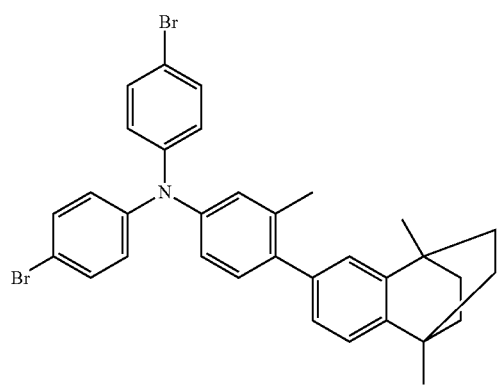
Mon-0102
-continued
BB-1102
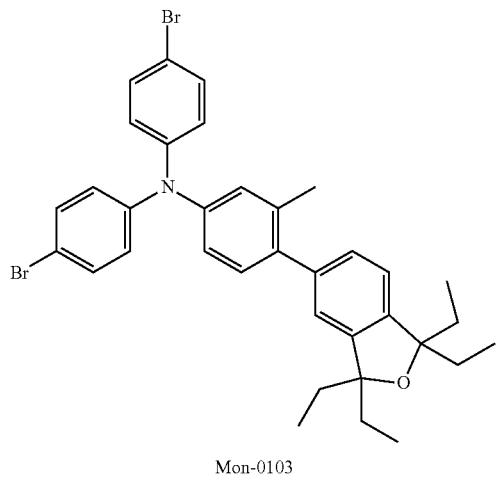
Mon-0103
BB-1103
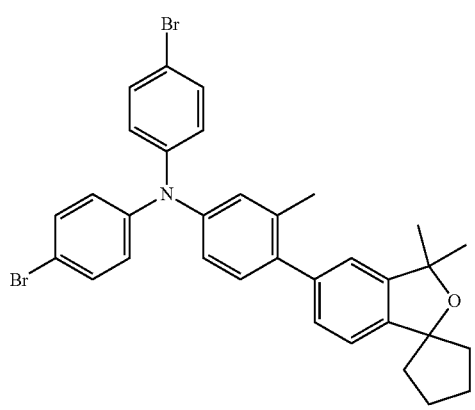
Mon-0104
BB-1104
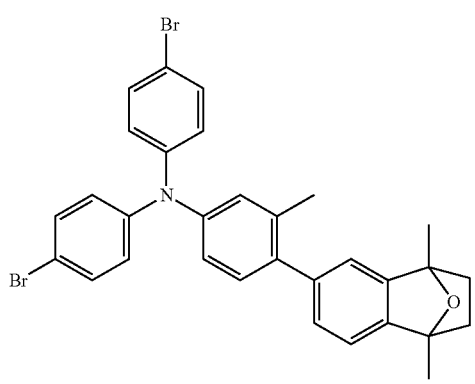
Mon-0105

BB-1105
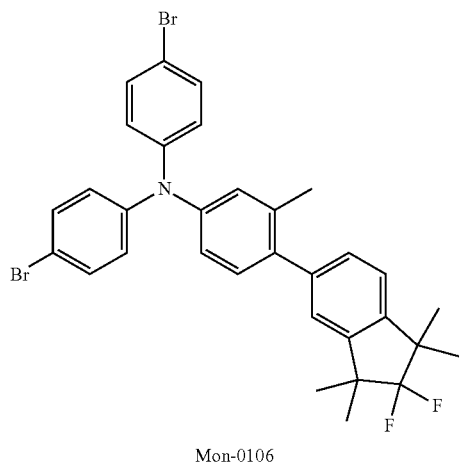
Mon-0106
BB-1106
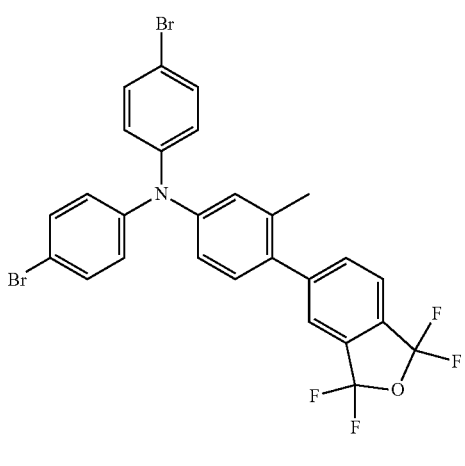
Mon-0107
BB-1107
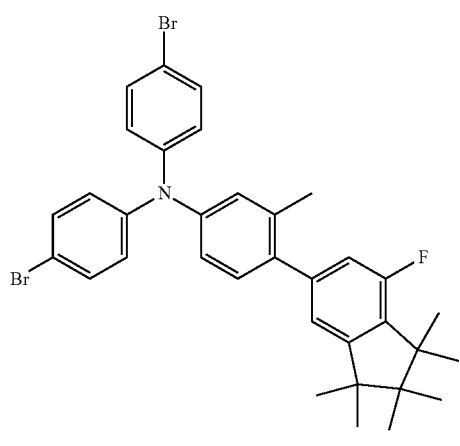
Mon-0108
BB-1108
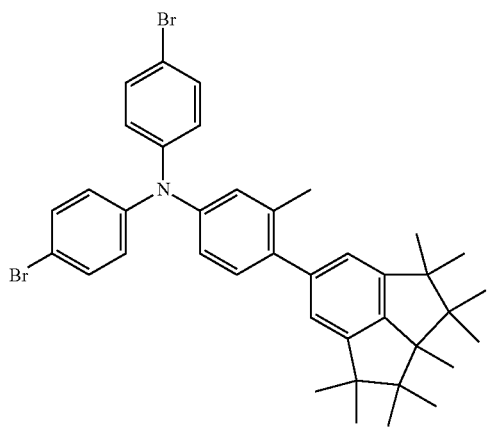
Mon-0109
BB-1109
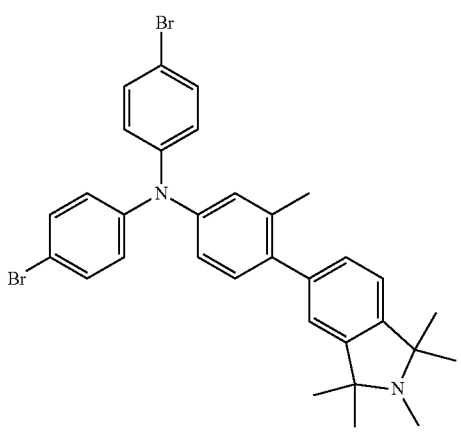
Mon-0110
BB-1110
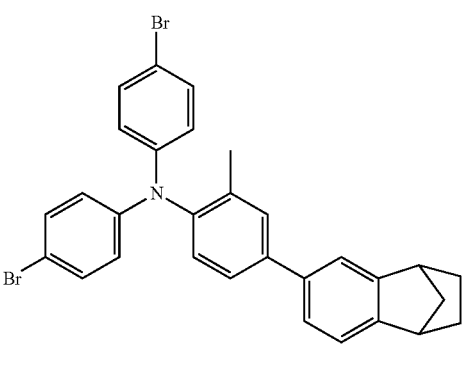
Mon-0111

BB-1111
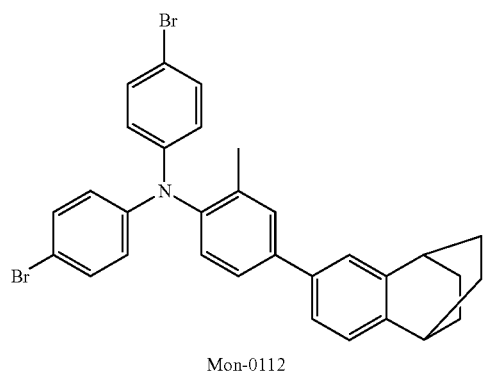
Mon-0112
BB-1112
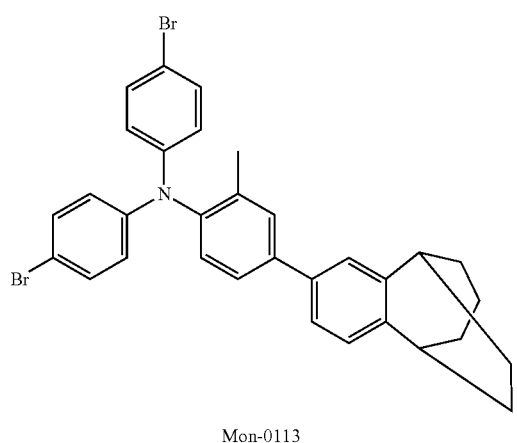
Mon-0113
BB-1113
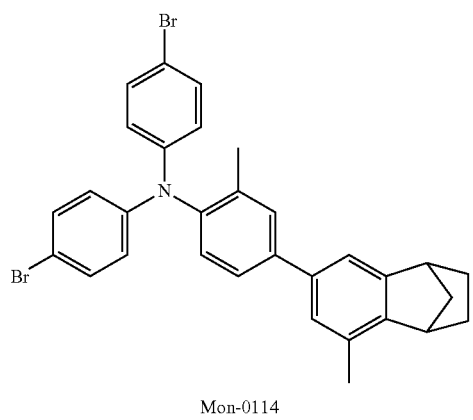
Mon-0114
BB-1114
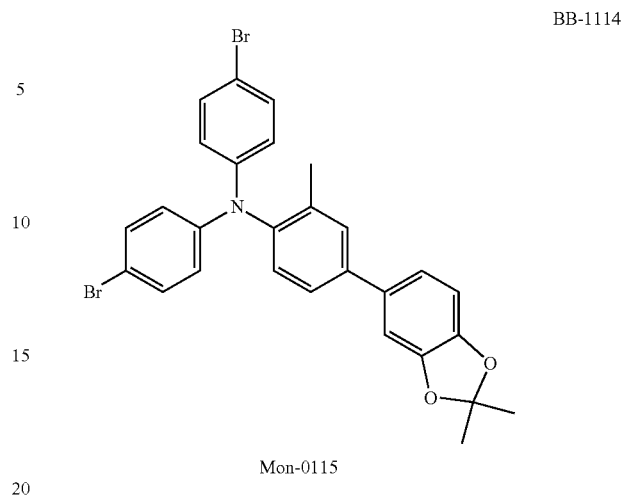
Mon-0115
BB-1115
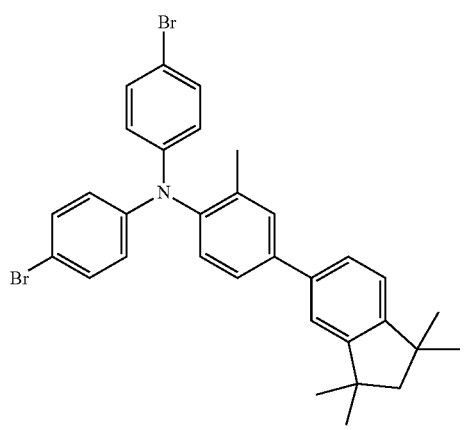
Mon-0116
BB-1116
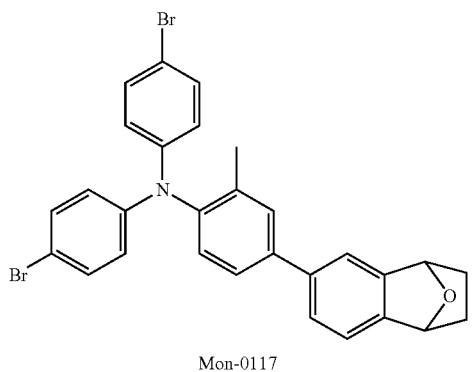
Mon-0117

BB-1117
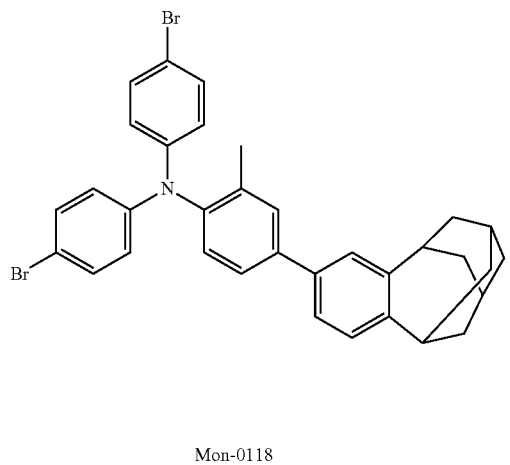
Mon-0118
BB-1118
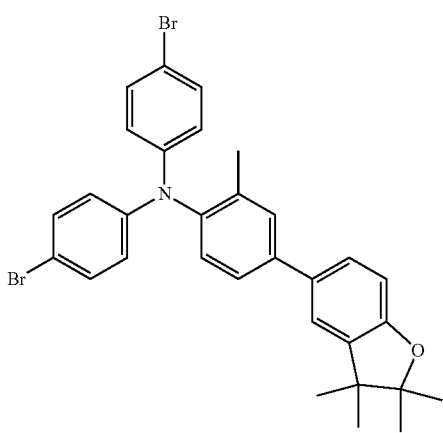
Mon-0119
BB-1119
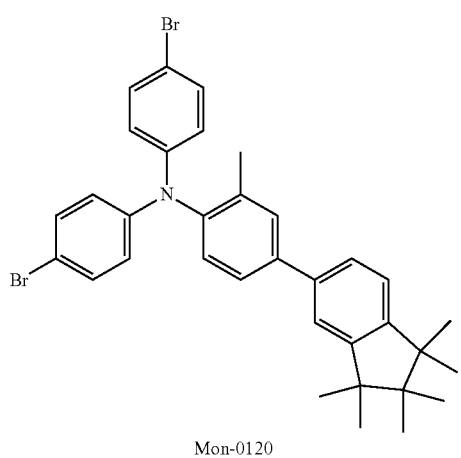
Mon-0120
BB-1120
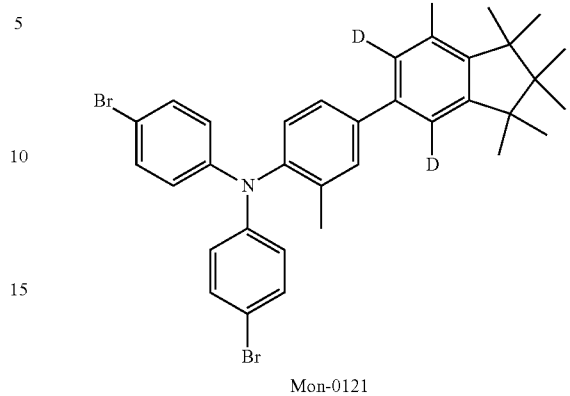
Mon-0121
BB-1121
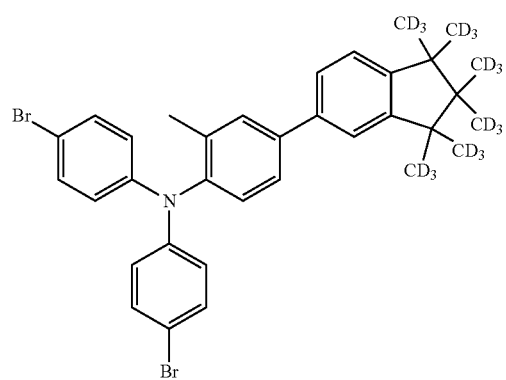
Mon-0122
BB-1122
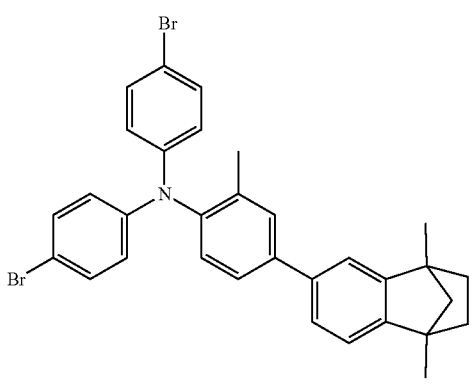
Mon-0123

-continued
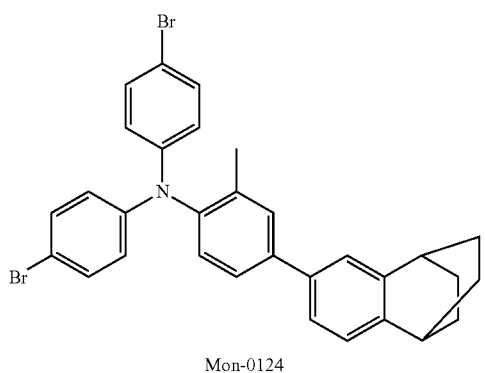
Mon-0124 BB-1123
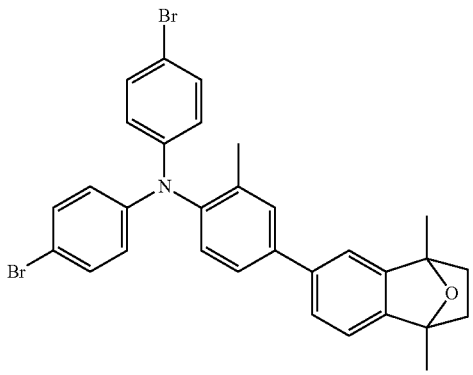
Mon-0127 BB-1126
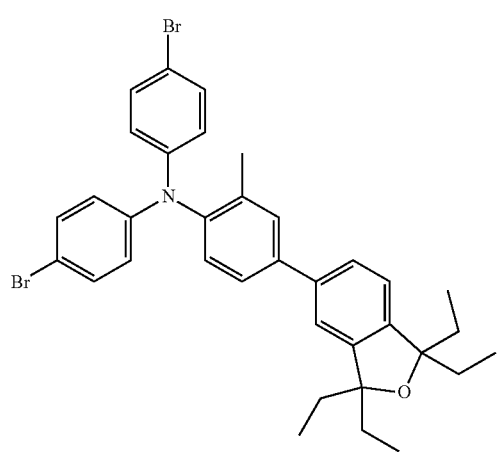
Mon-0125 BB-1124
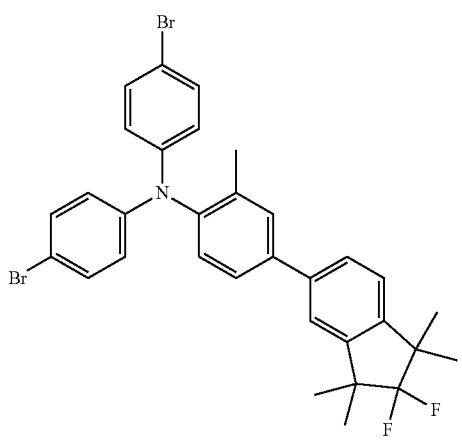
Mon-0128 BB-1127
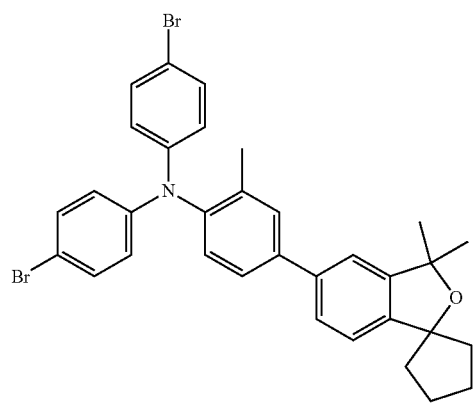
Mon-0126 BB-1125
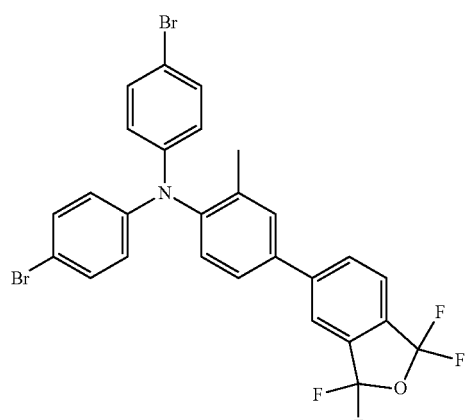
Mon-0129 BB-1128

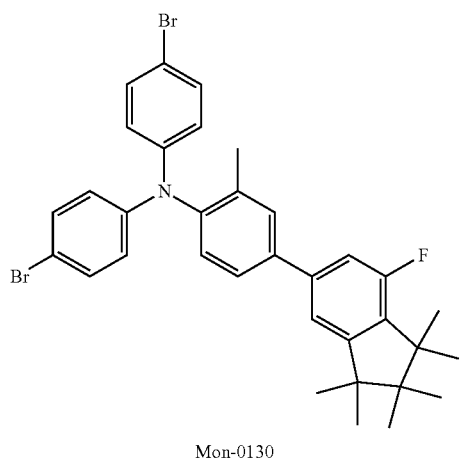
Mon-0130
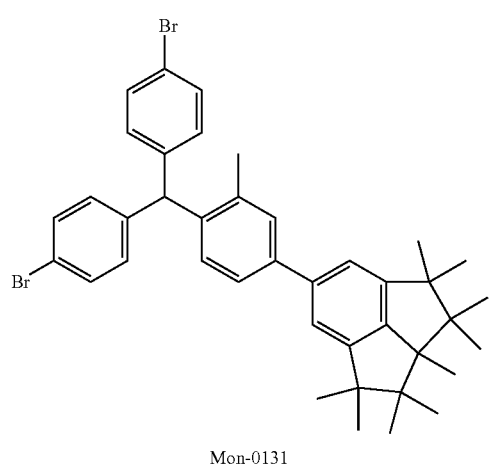
Mon-0131
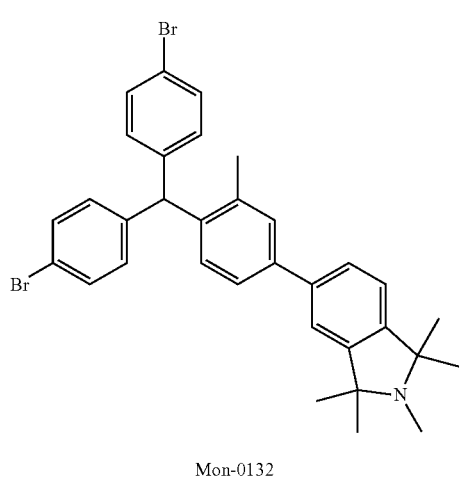
Mon-0132
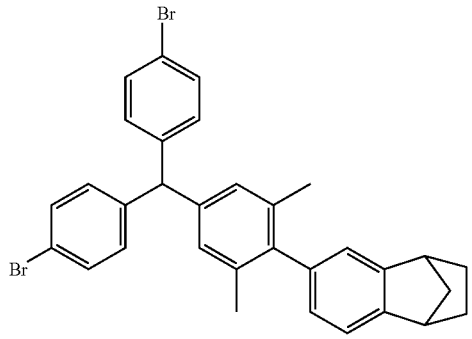
Mon-0133
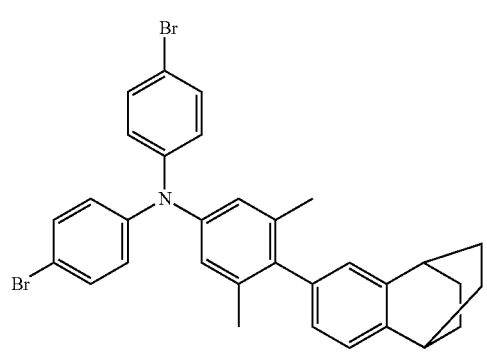
Mon-0134
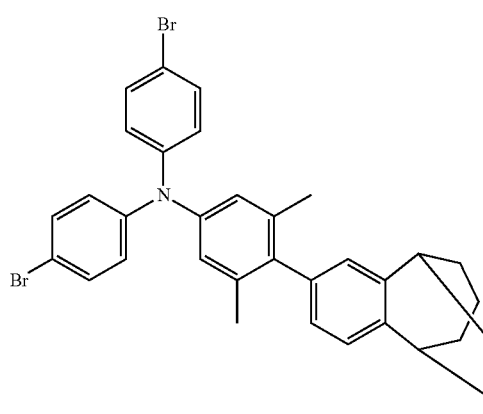
Mon-0135
Mon-0136

BB-1136
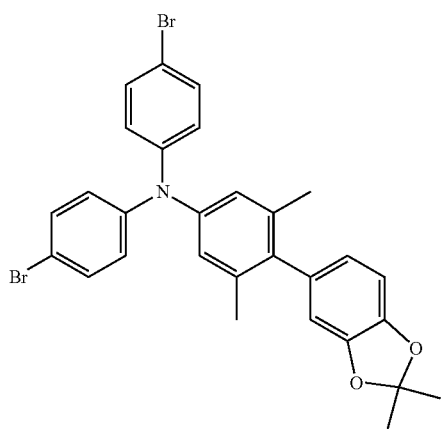
Mon-0137
BB-1137
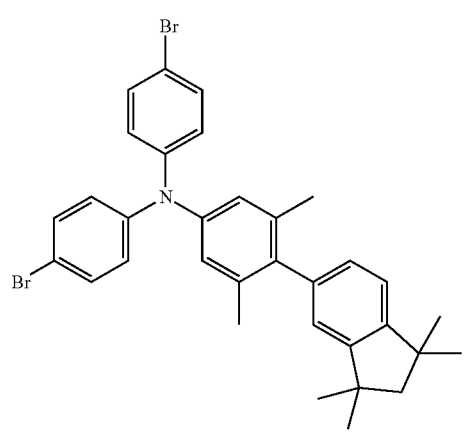
Mon-0138
BB-1138
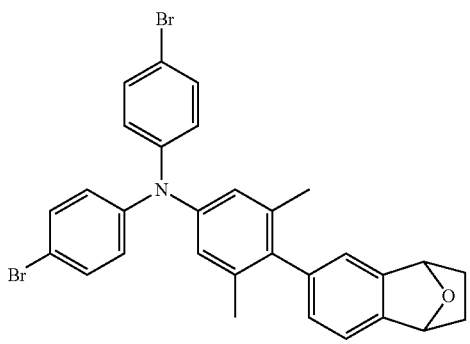
Mon-0139
BB-1139
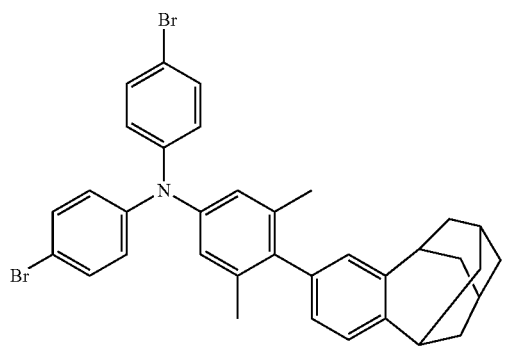
Mon-0140
BB-1140
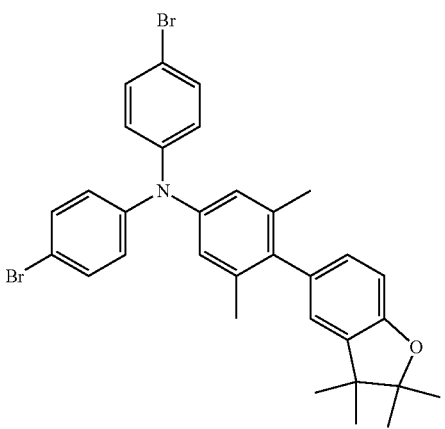
Mon-00141
BB-1141
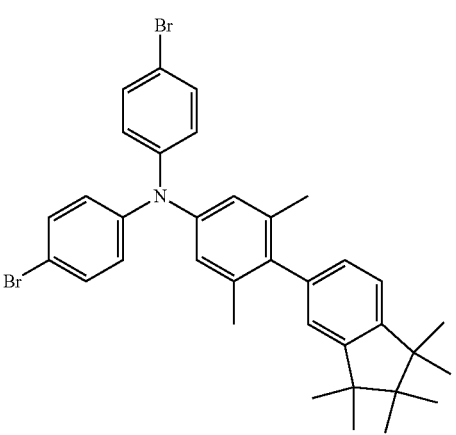
Mon-0142

BB-1142
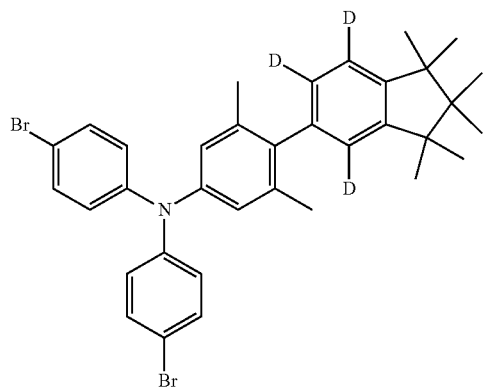
Mon-0143
BB-1143
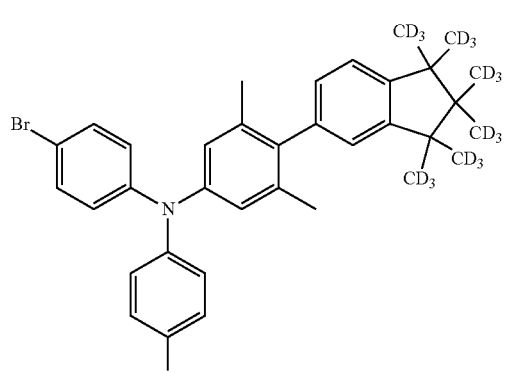
Mon-0144
BB-1144
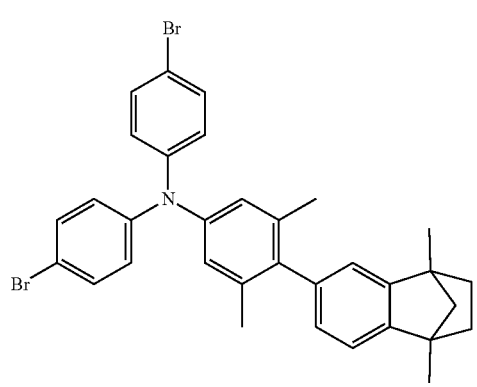
Mon-0145
BB-1145
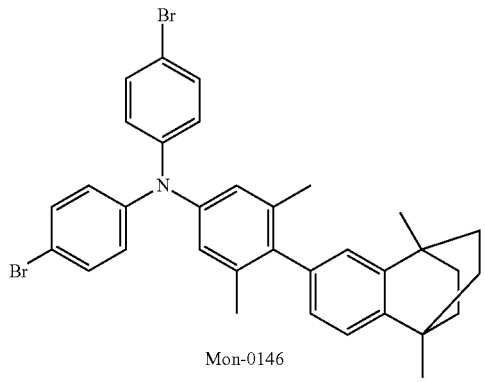
Mon-0146
BB-1146
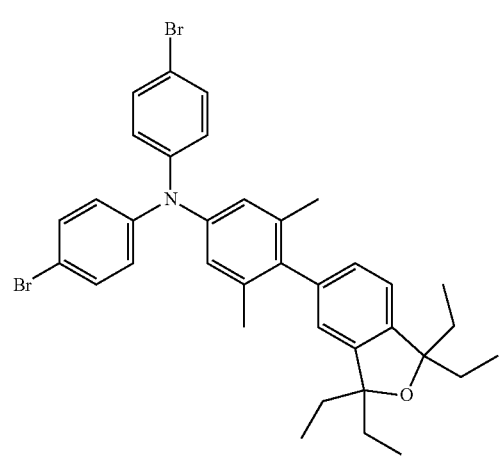
Mon-0147
BB-1147
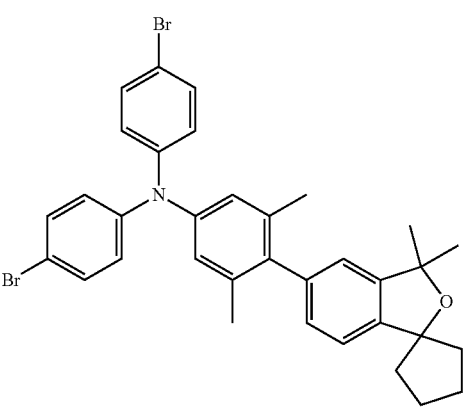
Mon-0148

BB-1148
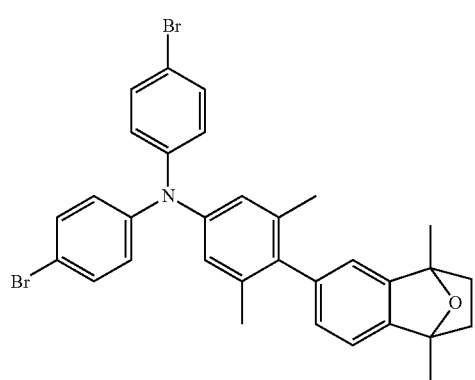
Mon-0149
BB-1149
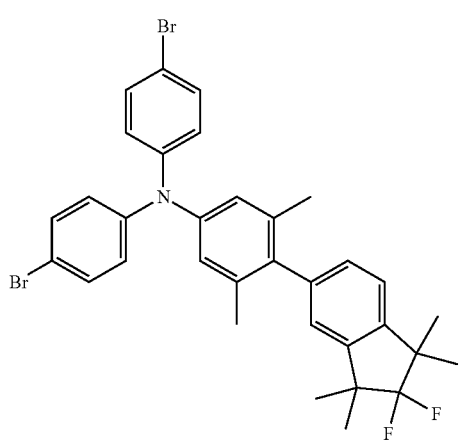
Mon-0150
BB-1150
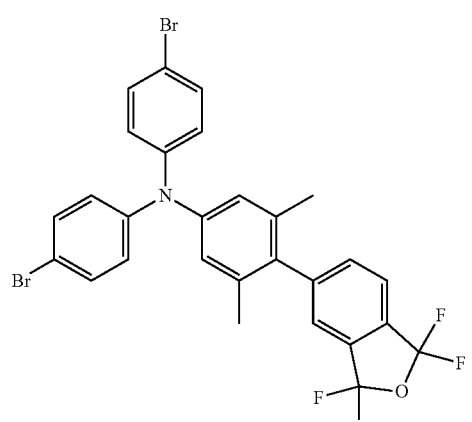
Mon-0151
BB-1151
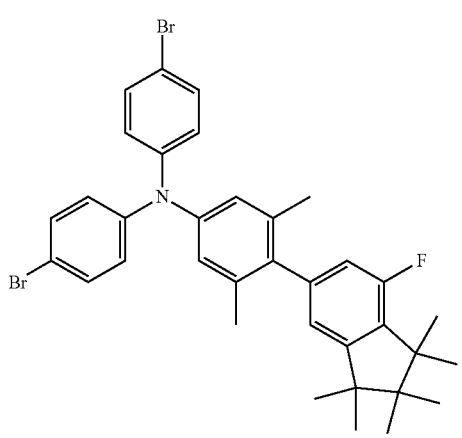
Mon-0152
BB-1152
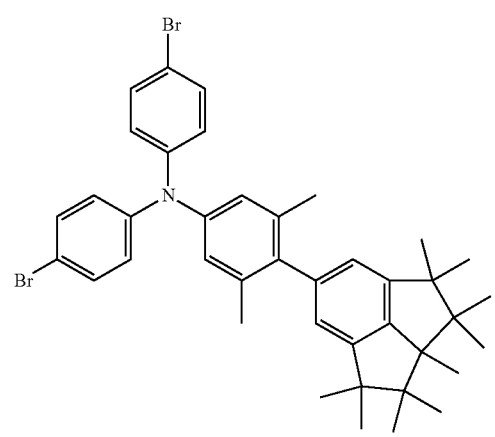
Mon-0153
BB-1153
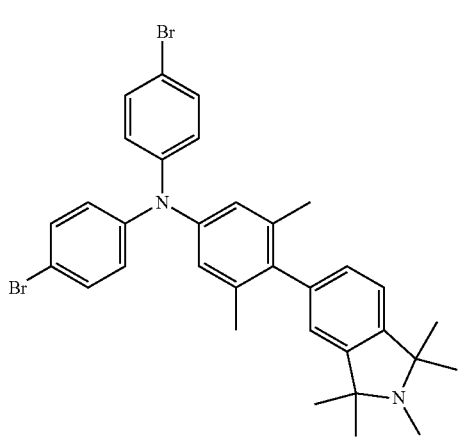
Mon-0154

BB-1154
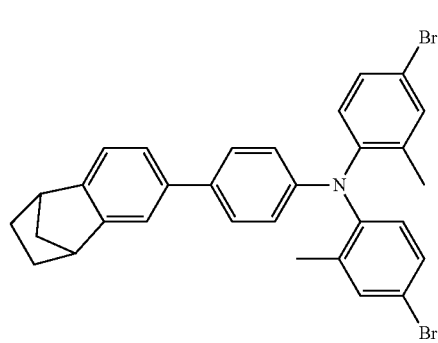
Mon-0155
BB-1155
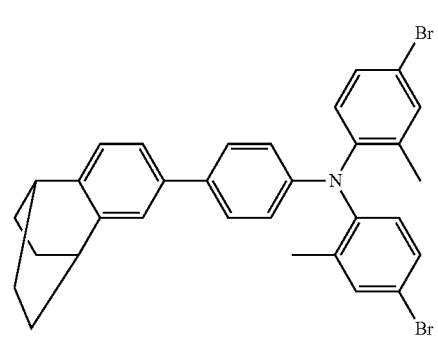
Mon-0156
BB-1156
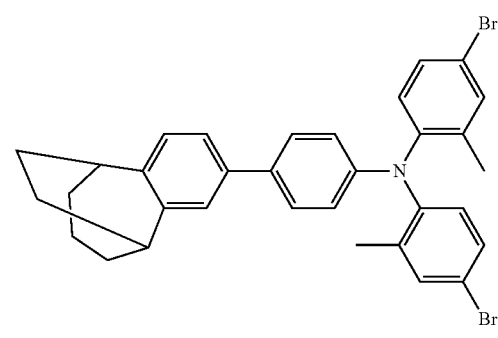
Mon-0157
BB-1157
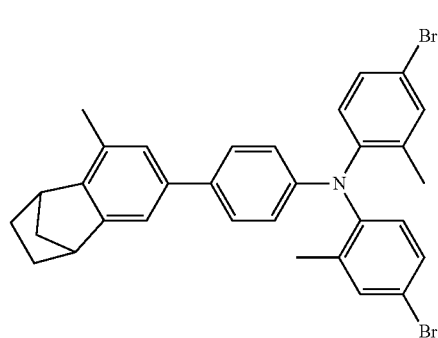
Mon-0158
BB-1158
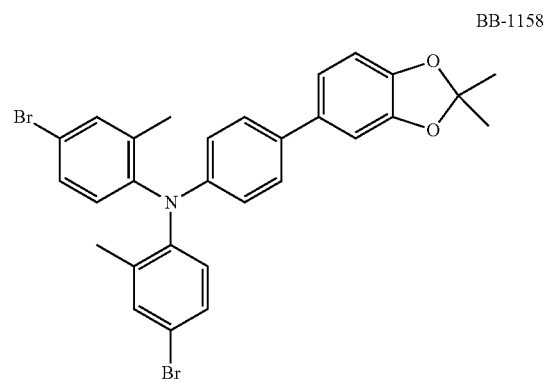
Mon-0159
BB-1159
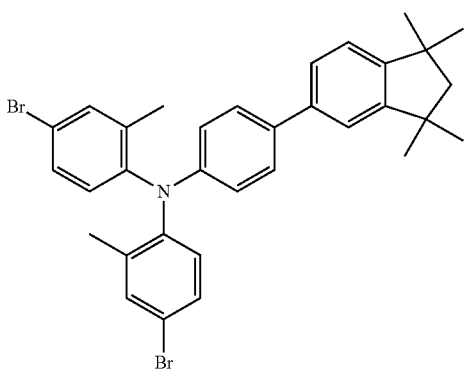
Mon-0160
BB-1160
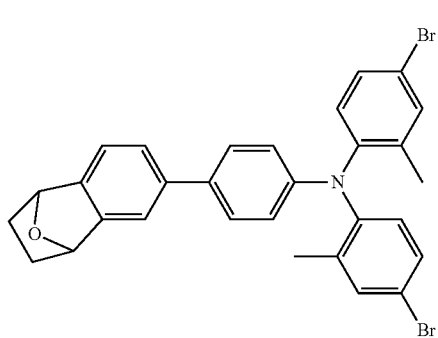
Mon-0161
BB-1161
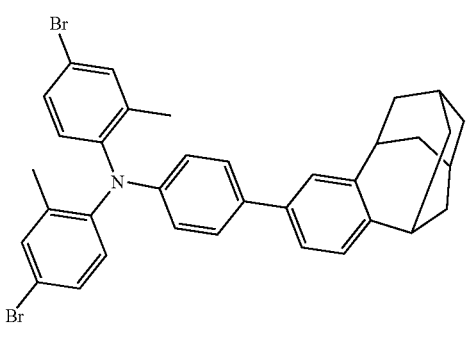
Mon-0162

BB-1162
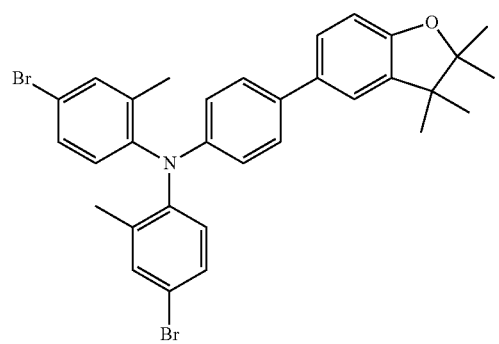
Mon-0163
BB-1163
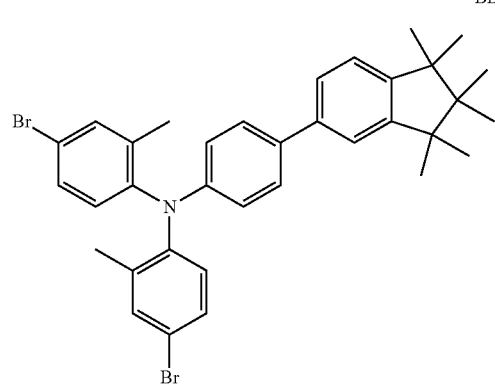
Mon-0164
BB-1164
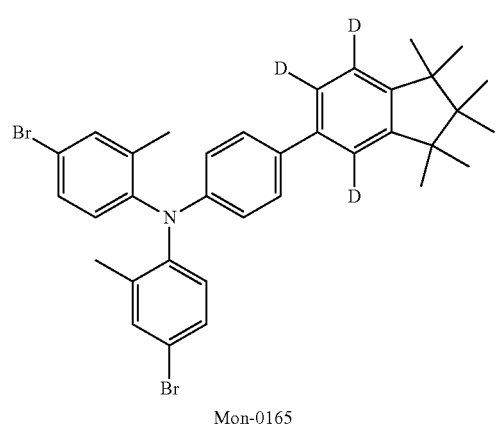
Mon-0165
BB-1165
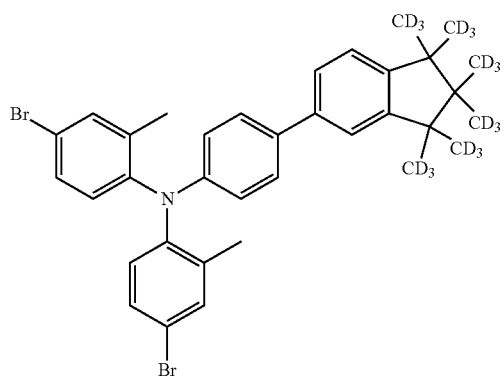
Mon-0166
BB-1166
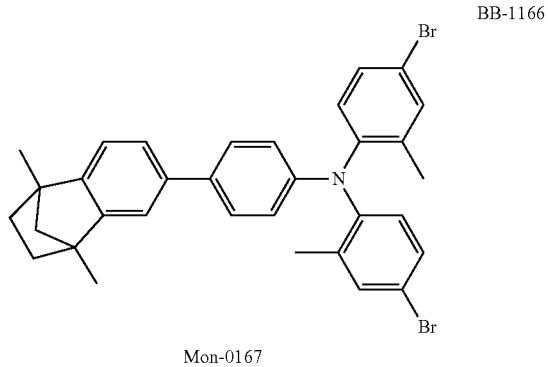
Mon-0167
BB-1167
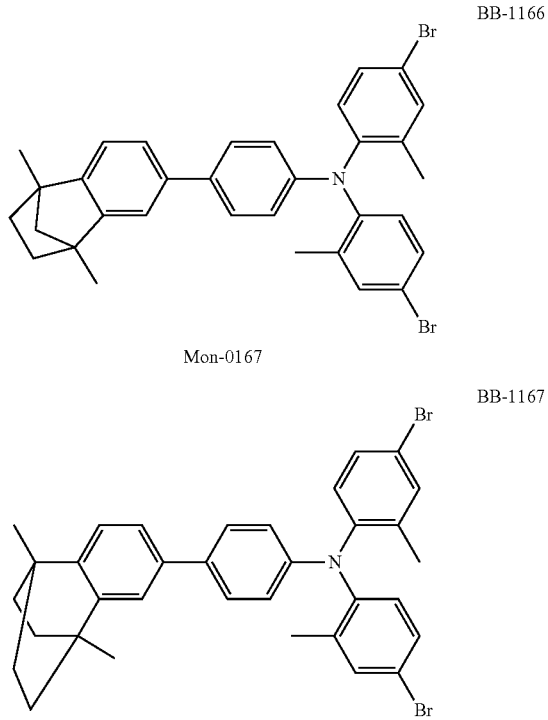
Mon-0168
BB-1168
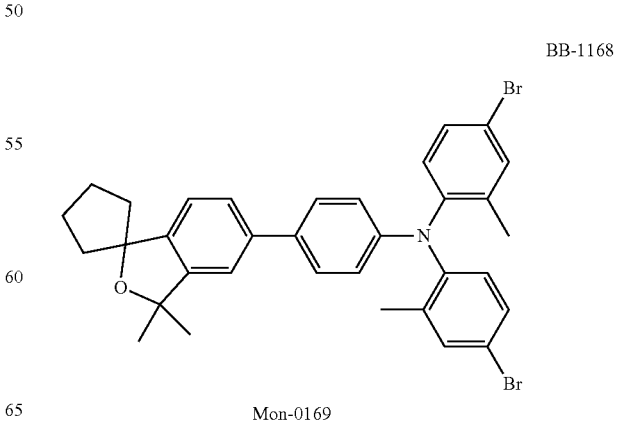
Mon-0169

BB-1169
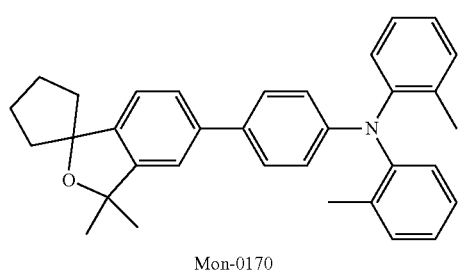
Mon-0170
BB-1170
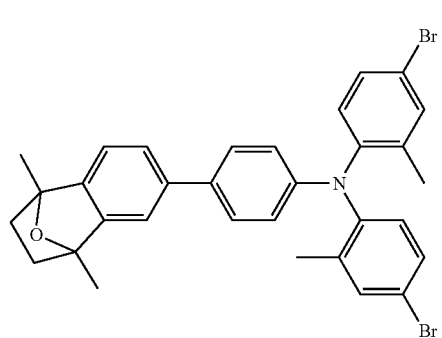
Mon-0171
BB-1171
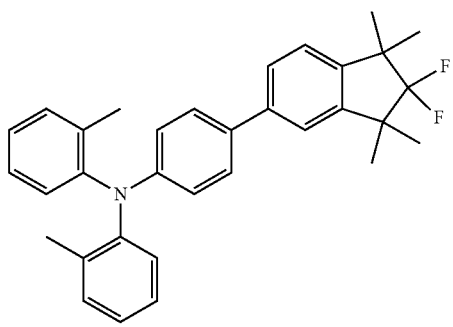
Mon-0172
BB-1172
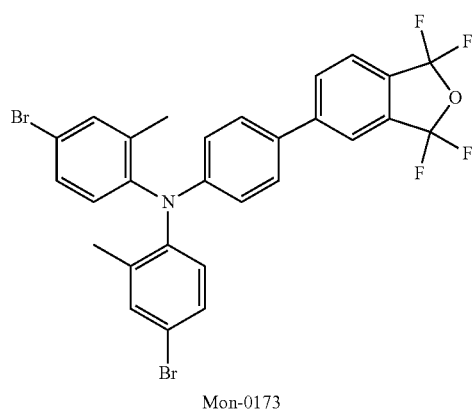
Mon-0173
BB-1173
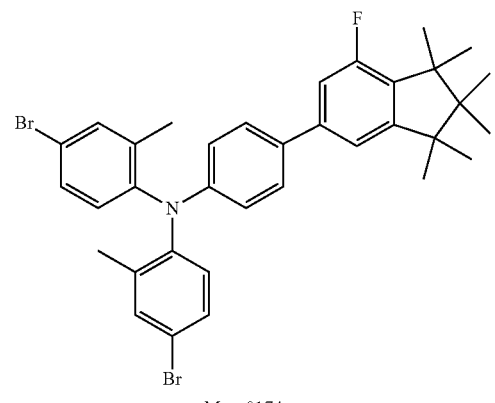
Mon-0174
BB-1174
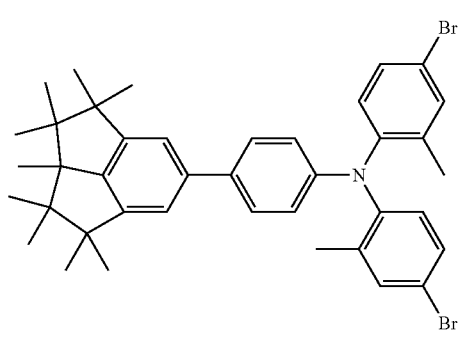
Mon-0175
BB-1175
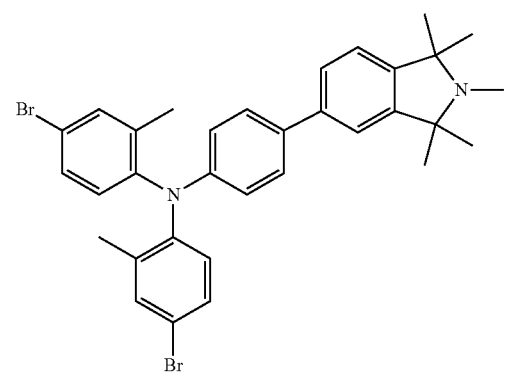
Mon-0176
BB-1176
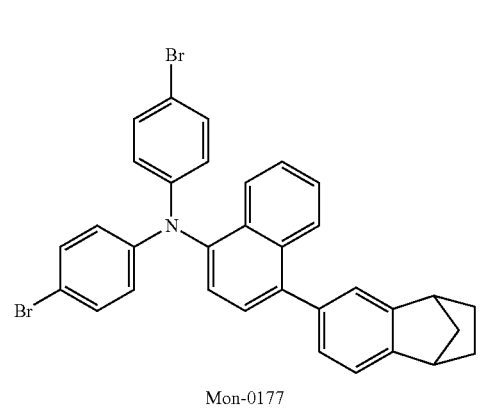
Mon-0177

-continued
BB-1177
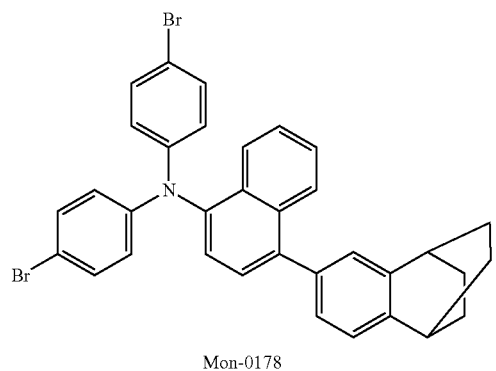
Mon-0178
BB-1178
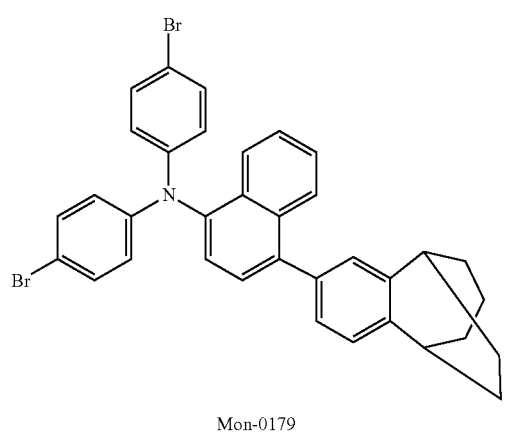
Mon-0179
BB-1179
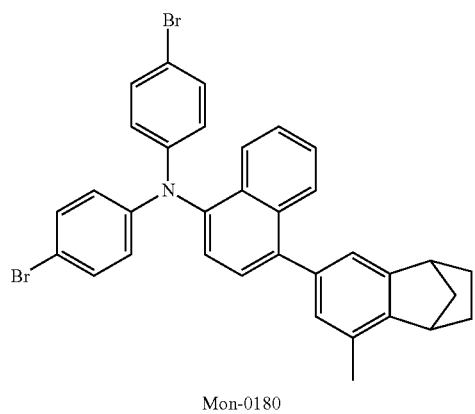
Mon-0180
BB-1180
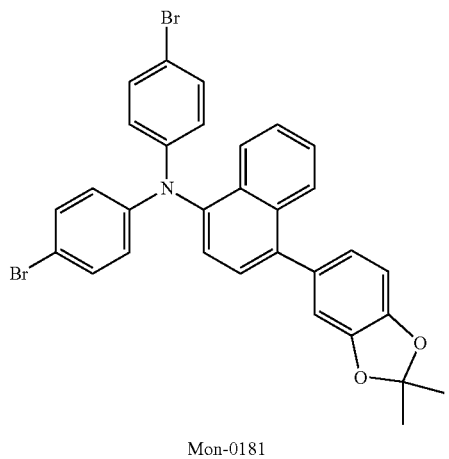
Mon-0181
BB-1181
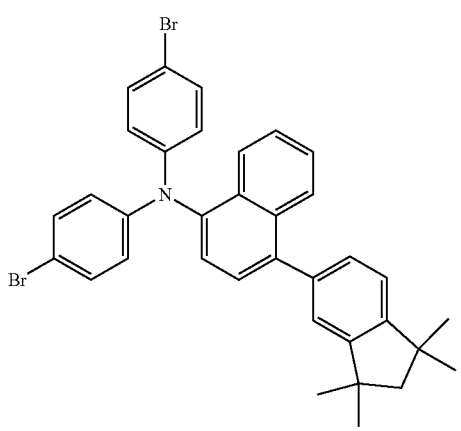
Mon-0182
BB-1182
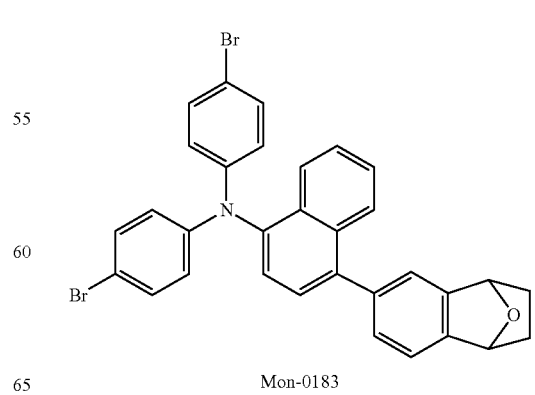
Mon-0183

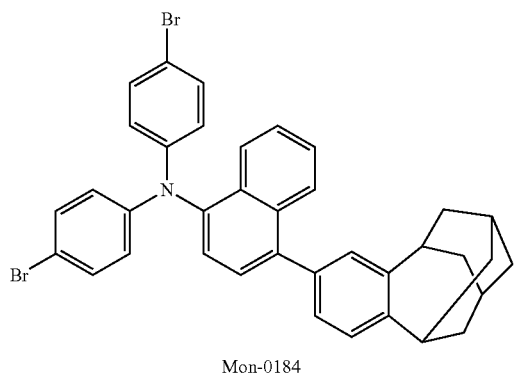
Mon-0184 BB-1183
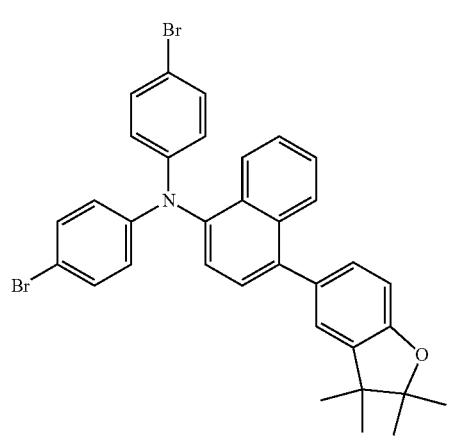
Mon-0185 BB-1184
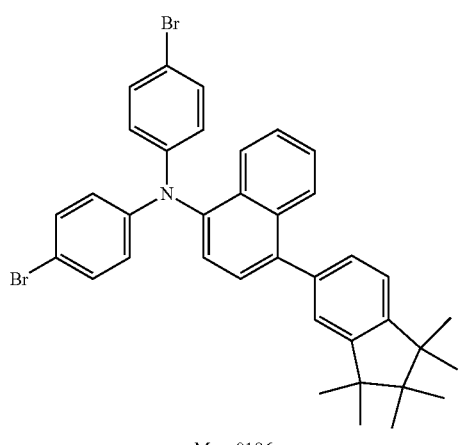
Mon-0186 BB-1185
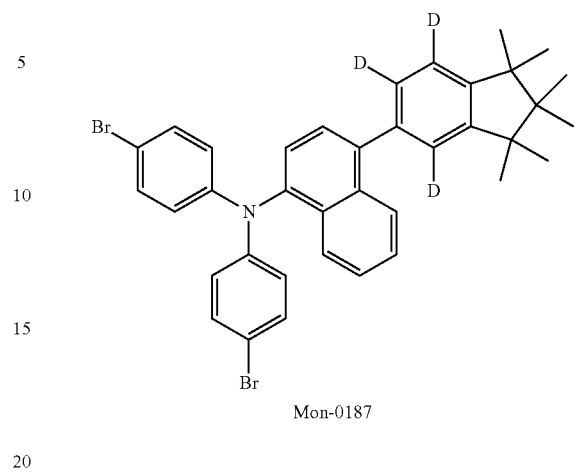
Mon-0187 BB-1186
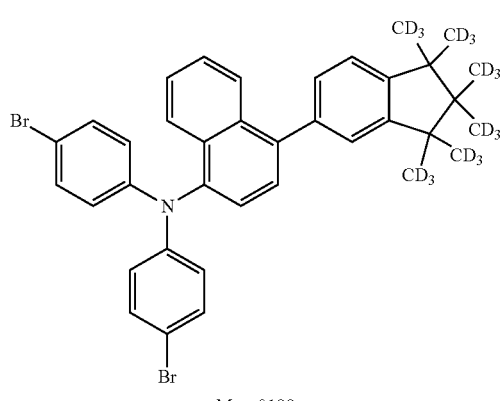
Mon-0188 BB-1187
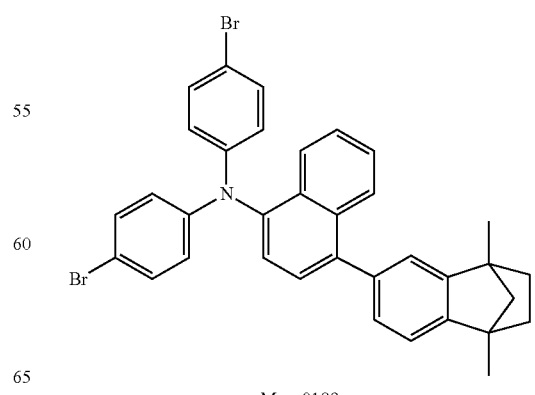
Mon-0189 BB-1188

-continued
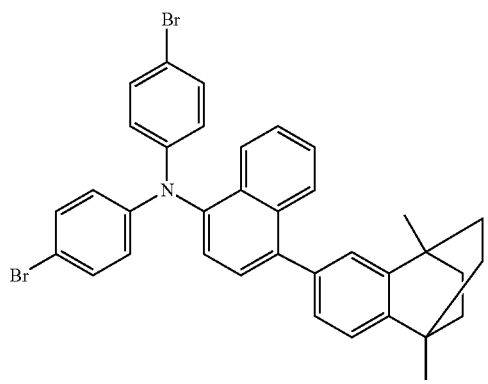
Mon-0190
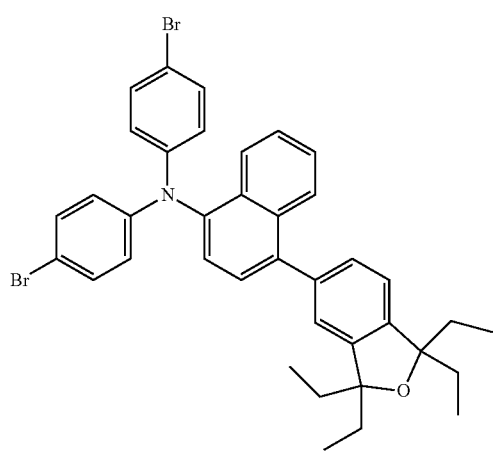
Mon-0191
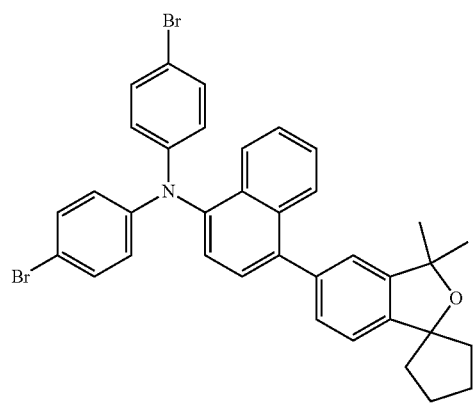
Mon-0192
-continued
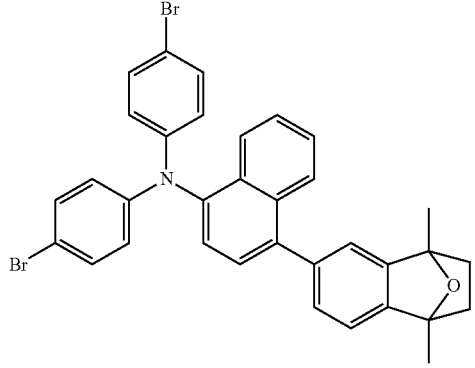
Mon-0193
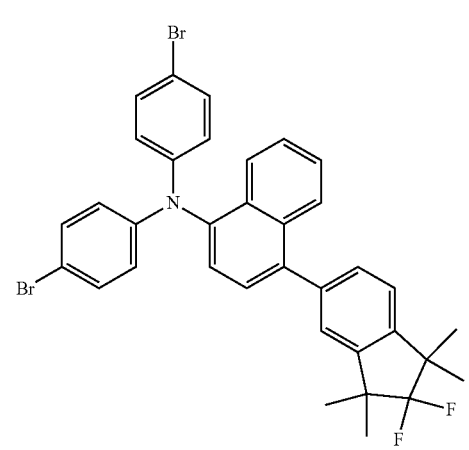
Mon-0194
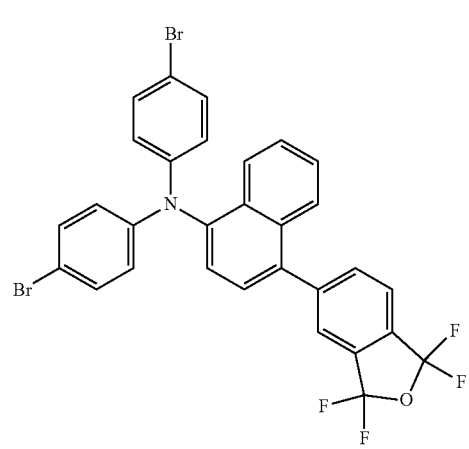
Mon-0195

BB-1195
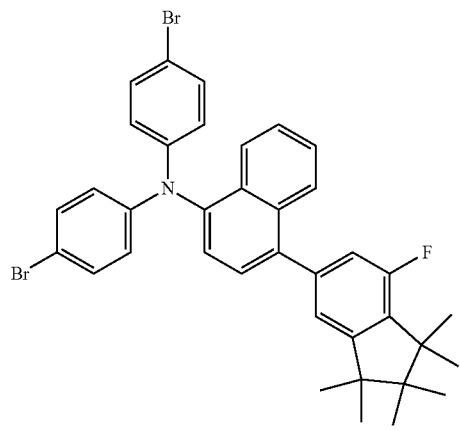
Mon-0196
BB-1196
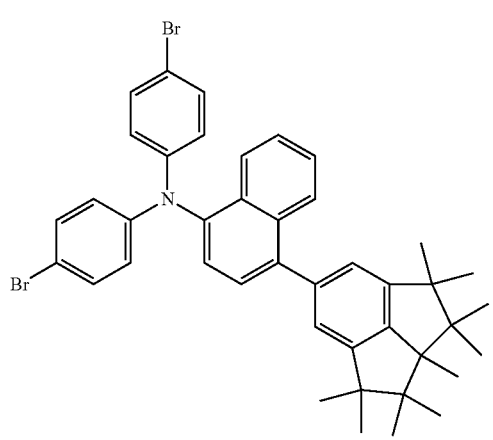
Mon-0197
BB-1197
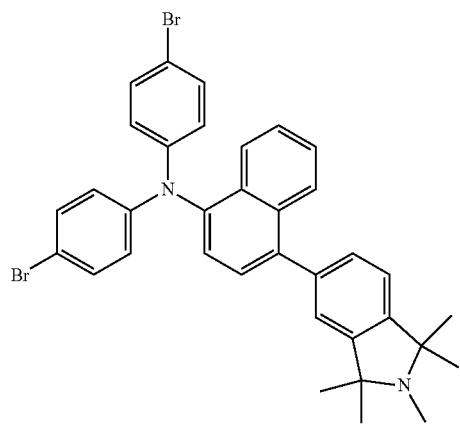
Mon-0198
BB-1198
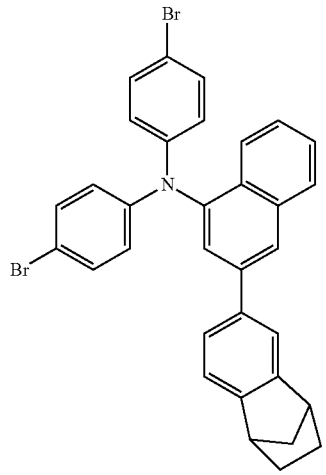
Mon-0199
BB-1199
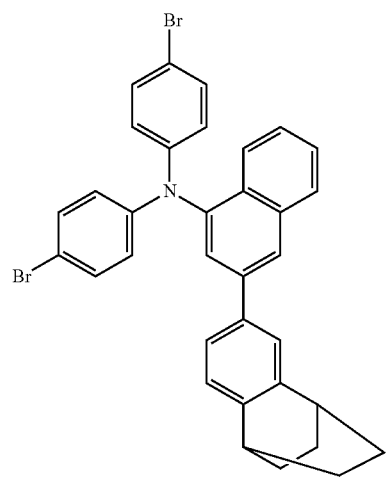
Mon-0200
BB-1200
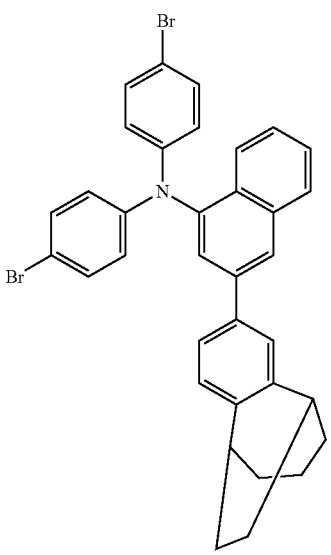
Mon-0201

BB-1201
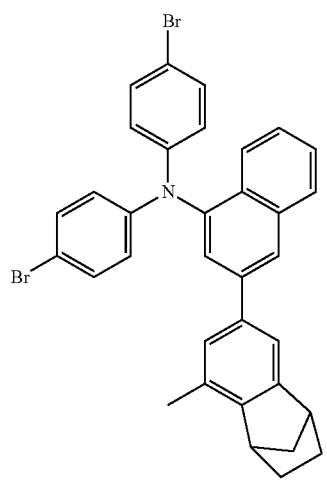
Mon-0202
BB-1202
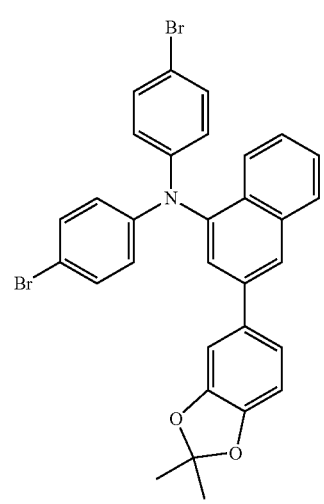
Mon-0203
BB-1203
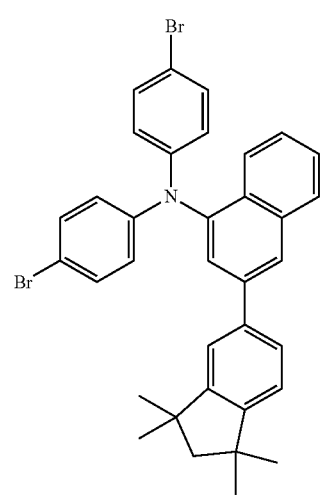
Mon-0204
BB-1204
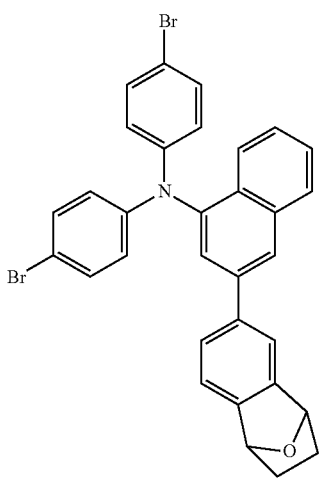
Mon-0205
BB-1205
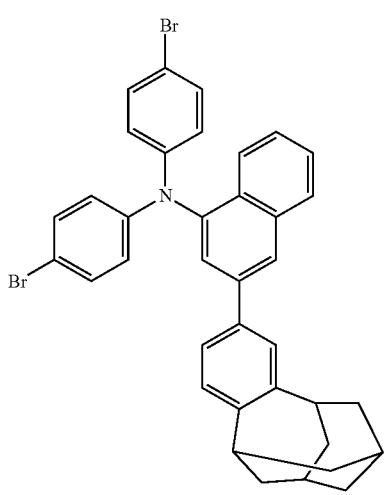
Mon-0206
BB-1206
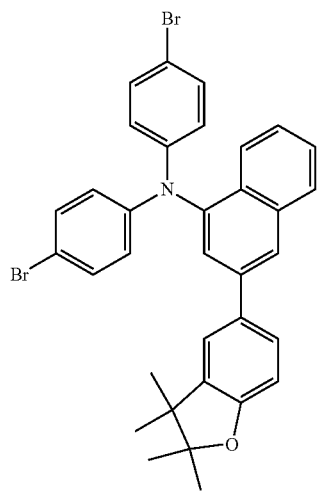
Mon-0207

BB-1207
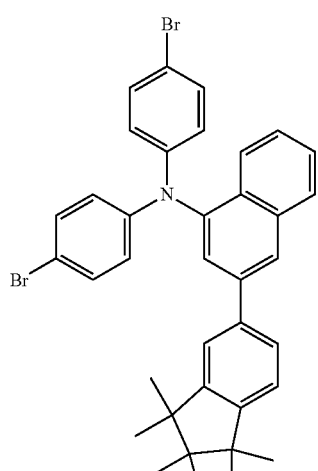
Mon-0208
BB-1210
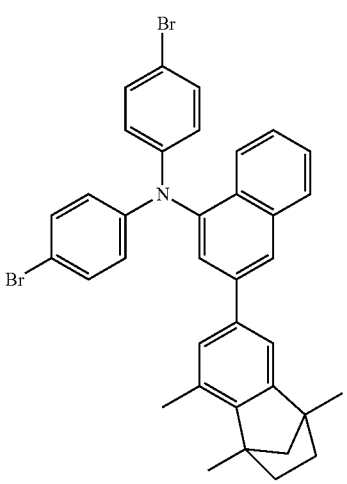
Mon-0211
BB-1208
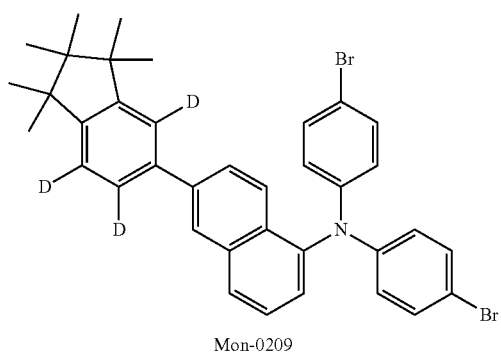
Mon-0209
BB-1211
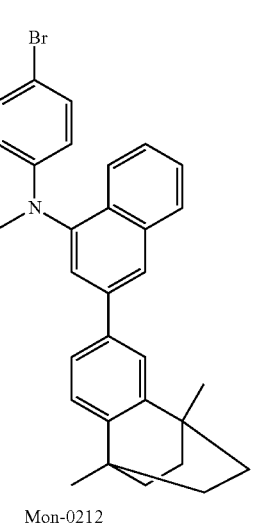
Mon-0212
BB-1209
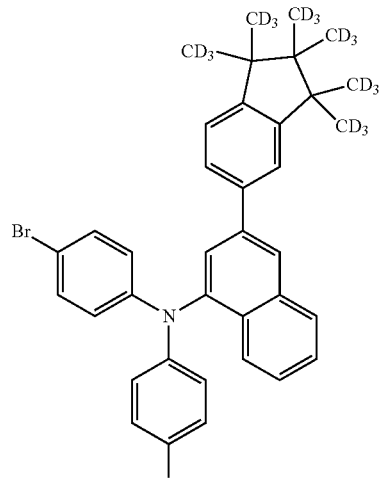
Mon-0210
BB-1212
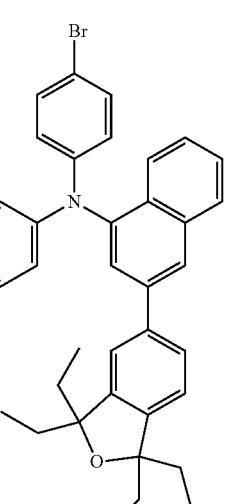
Mon-0213

BB-1213
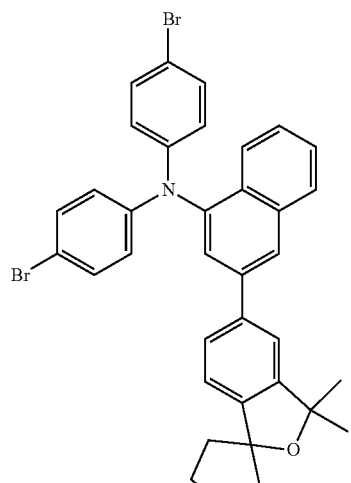
Mon-0214
BB-1214
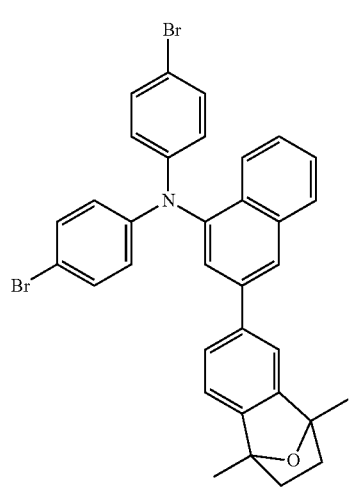
Mon-0215
BB-1215
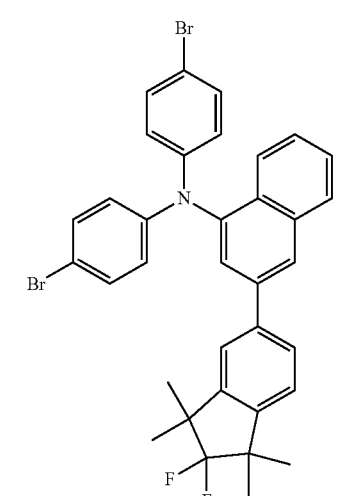
Mon-0216
BB-1216
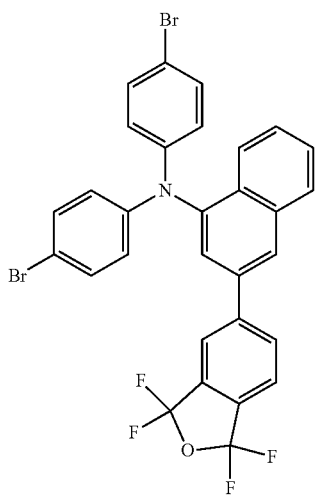
Mon-0217
BB-1217
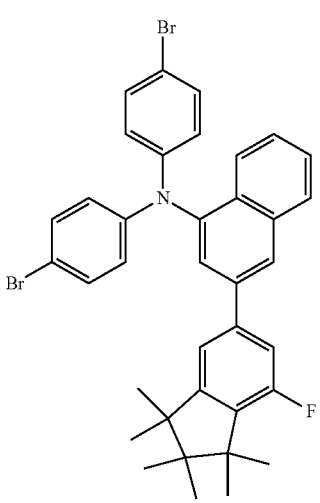
Mon-0218
BB-1218
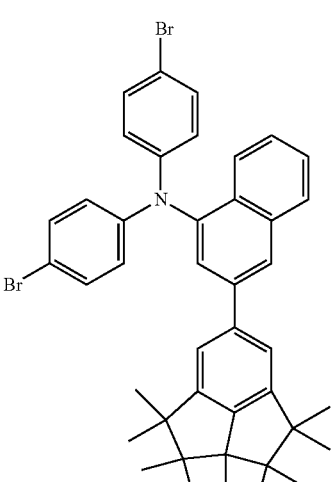
Mon-0219

BB-1219
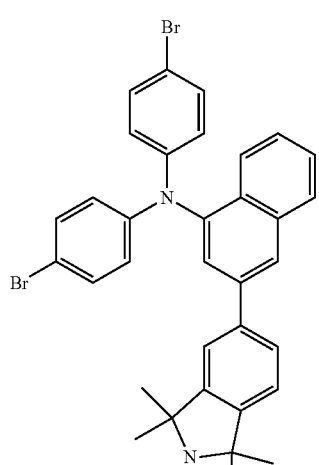
Mon-0220
BB-1220
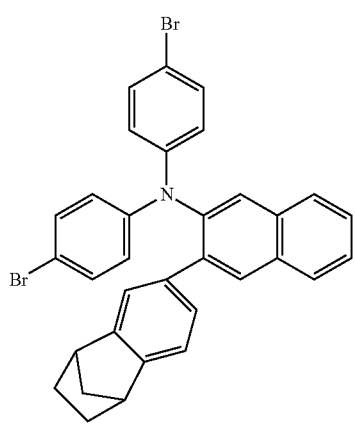
Mon-0221
BB-1221
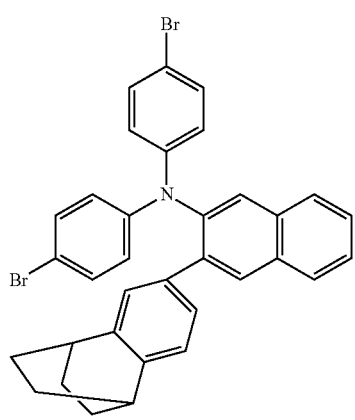
Mon-0222
BB-1222
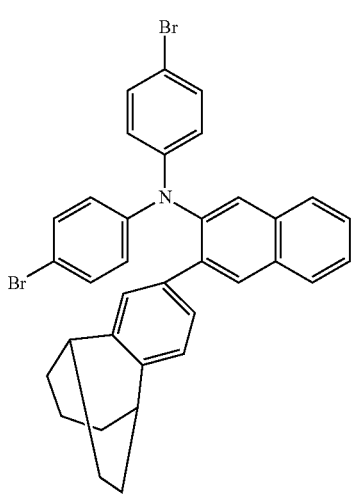
Mon-0223
BB-1223
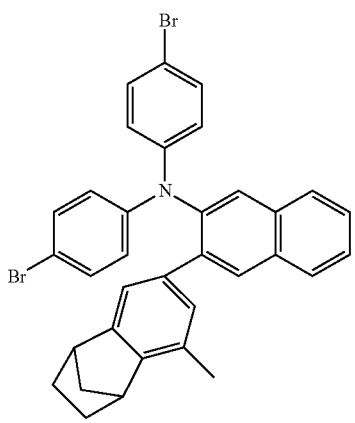
Mon-0224
BB-1224
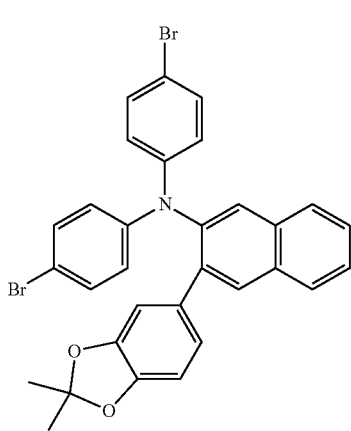
Mon-0225

-continued
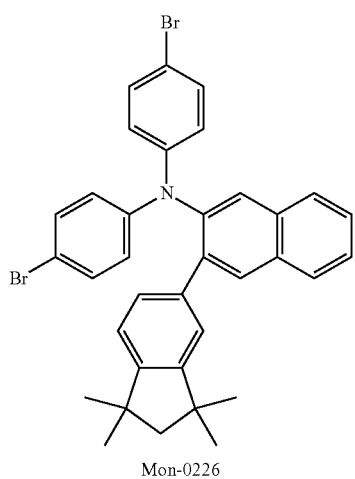
Mon-0226 BB-1225
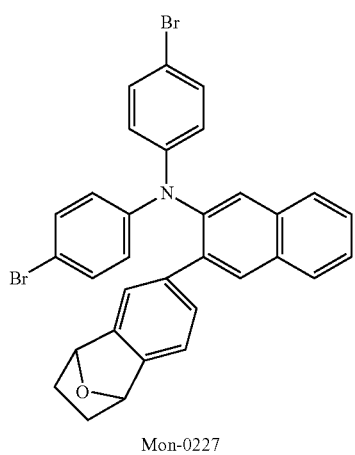
Mon-0227 BB-1226
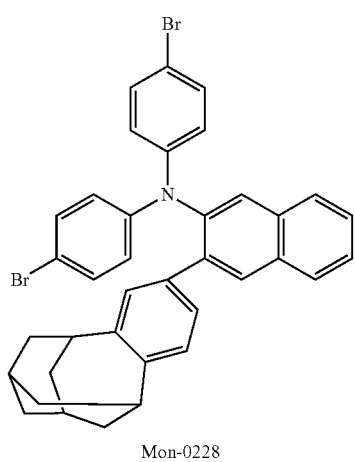
Mon-0228 BB-1227
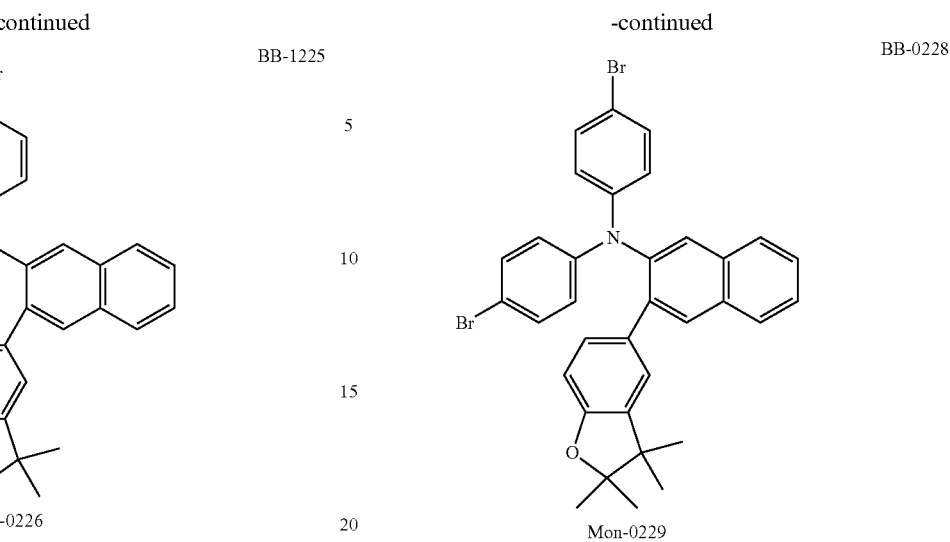
Mon-0229 BB-0228
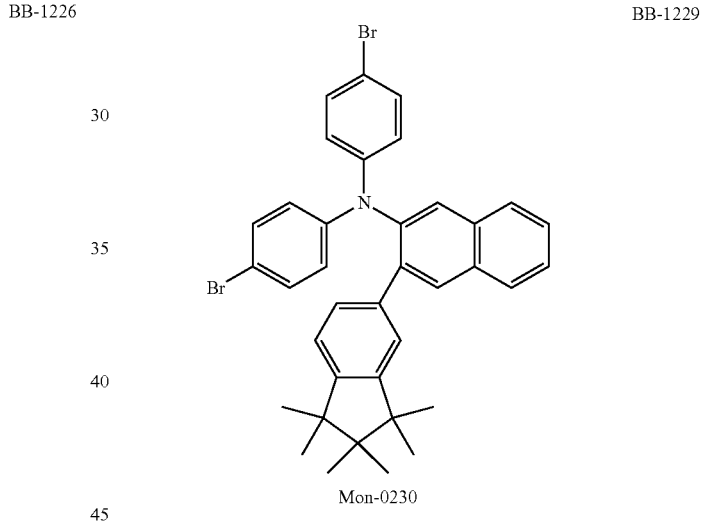
Mon-0230 BB-1229
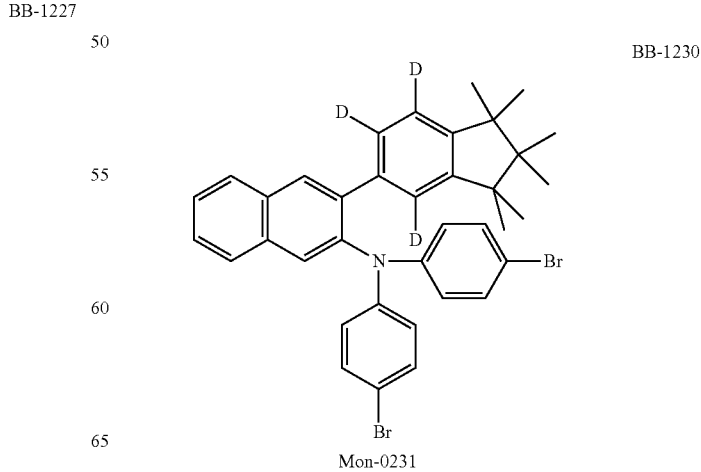
Mon-0231 BB-1230

-continued
BB-1231
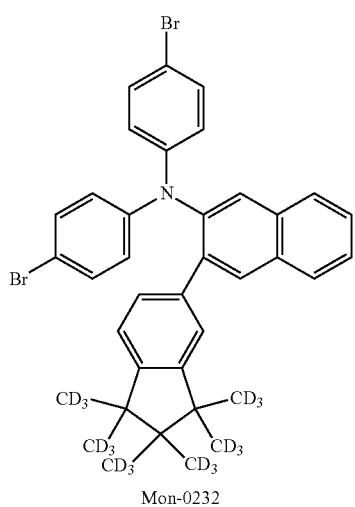
Mon-0232
BB-1232
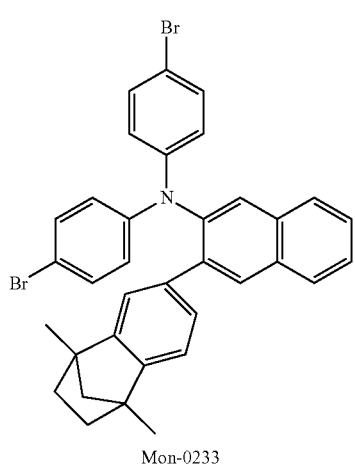
Mon-0233
BB-1233
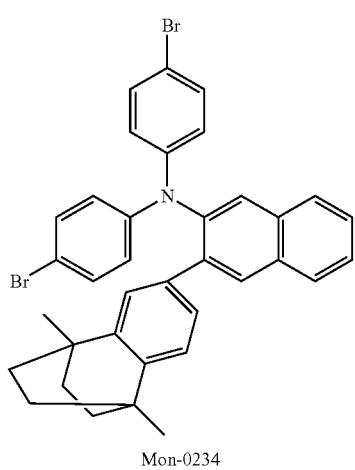
Mon-0234
-continued
BB-1234
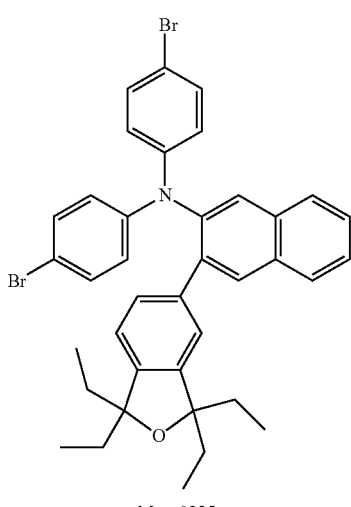
Mon-0235
BB-1235
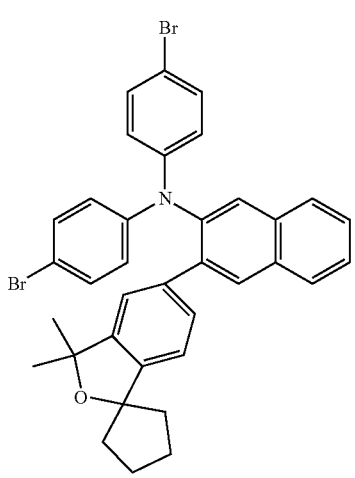
Mon-0236
BB-1236
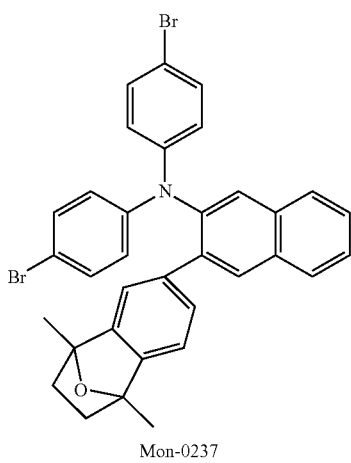
Mon-0237

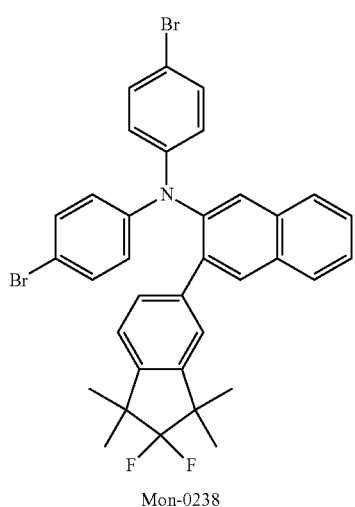
Mon-0238
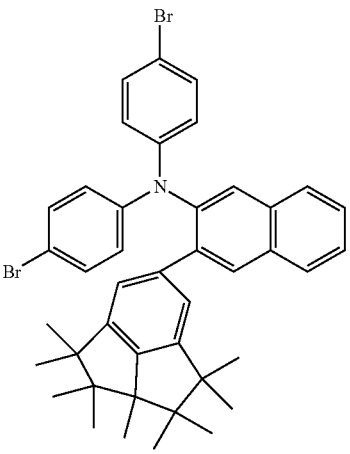
Mon-0241
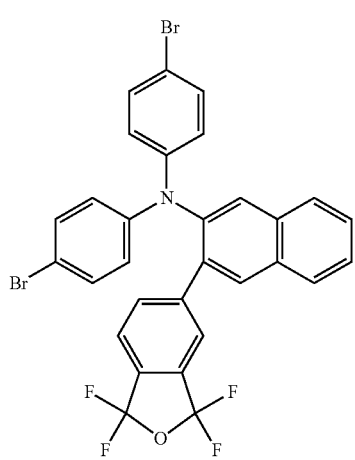
Mon-0239
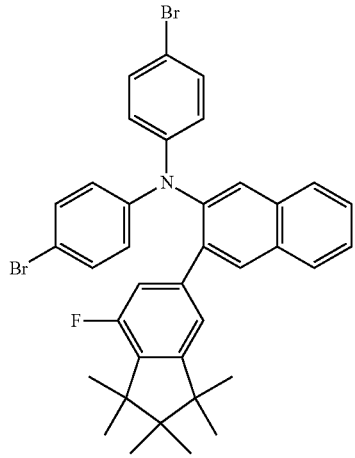
Mon-0240
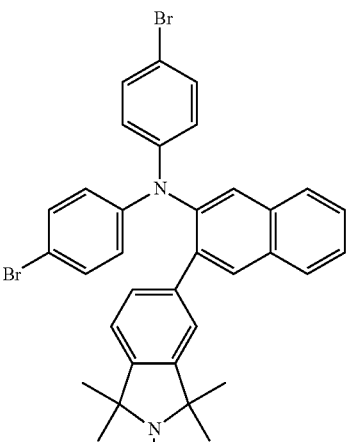
Mon-0242

-continued
BB-1242
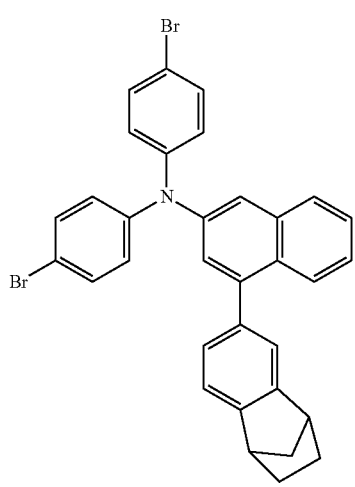
Mon-0243
BB-1244
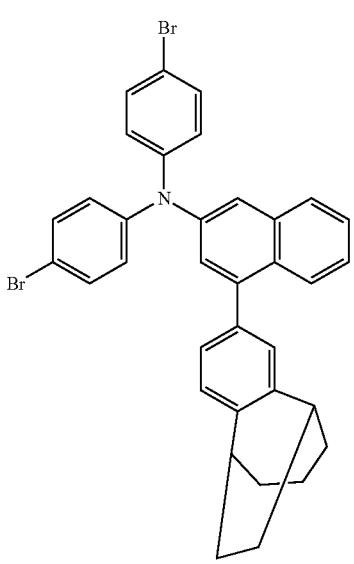
Mon-0245
BB-1243
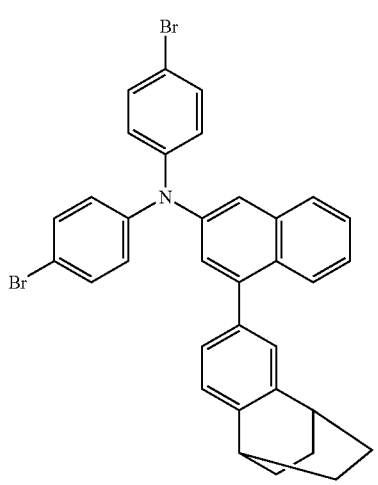
Mon-0244
BB-1245
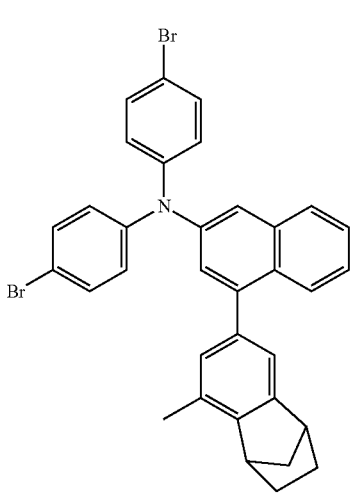
Mon-0246

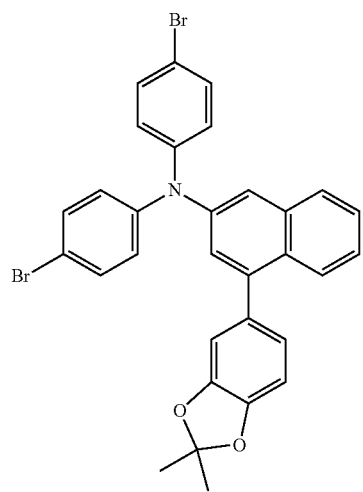
Mon-0247
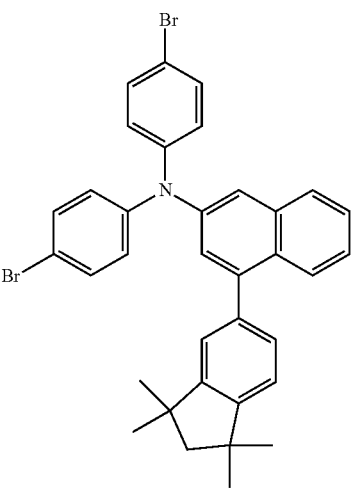
Mon-0248
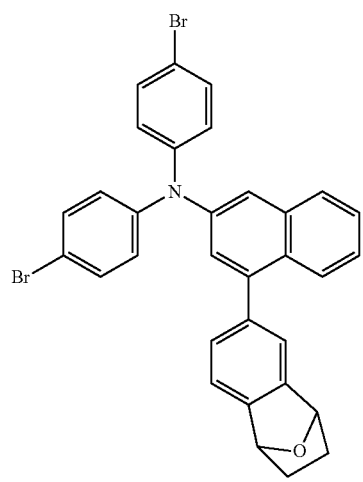
Mon-0249
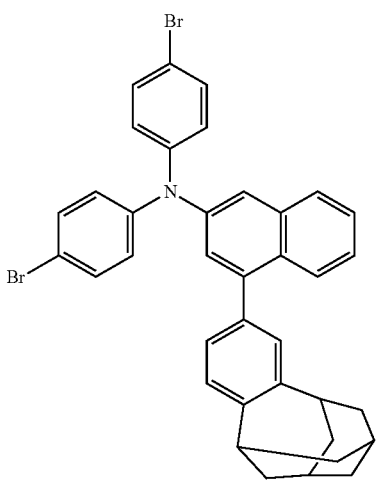
Mon-0250
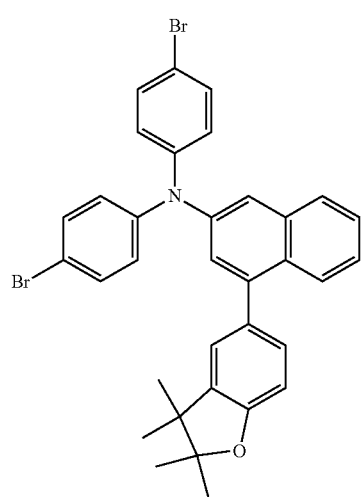
Mon-0251
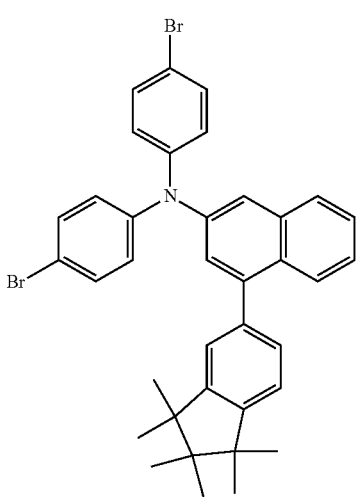
Mon-0252

-continued
BB-1252
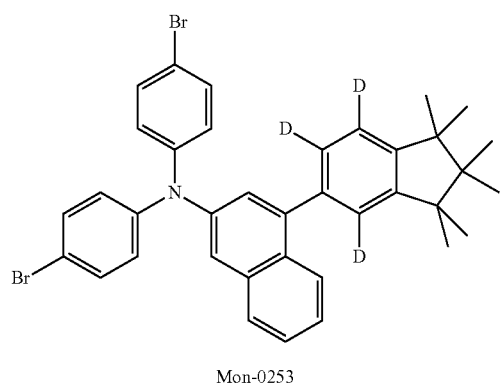
Mon-0253
BB-1253
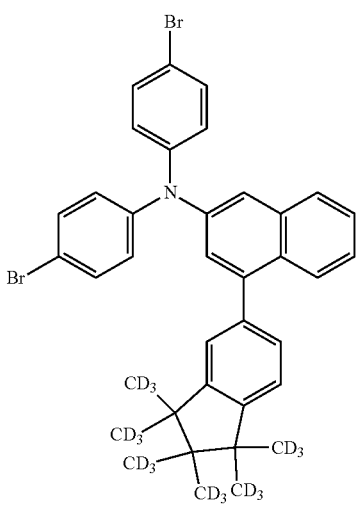
Mon-0254
BB-1254
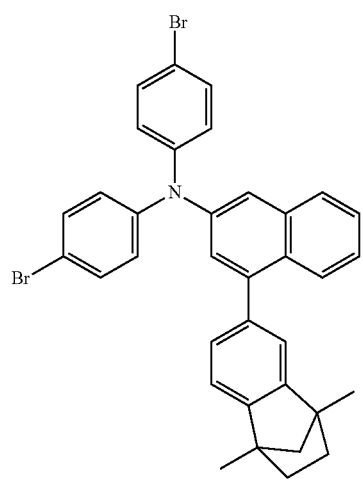
Mon-0255
BB-1255
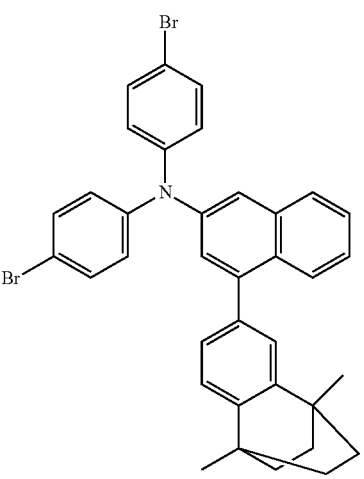
Mon-0256
BB-1256
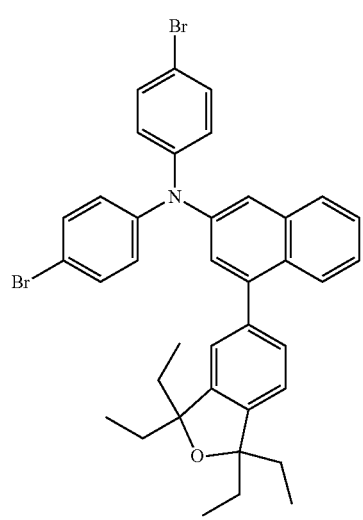
Mon-0257
BB-1257
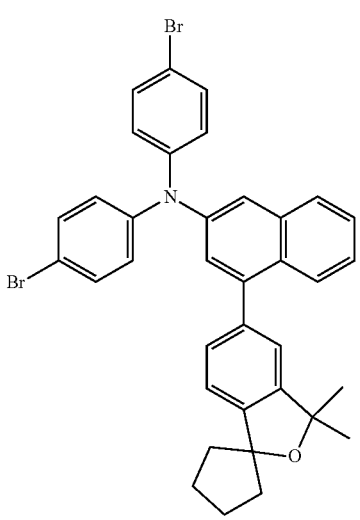
Mon-0258

-continued
| BB-1258 | BB-1259 |
|---|---|
| 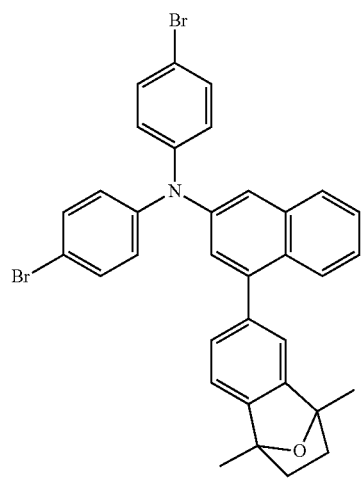 Mon-0259 | 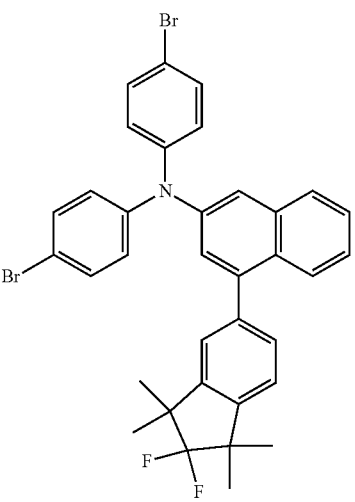 Mon-0260 |
| BB-1260 | BB-1261 |
| 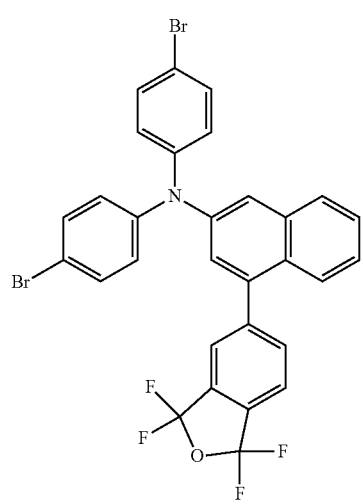 Mon-0261 | 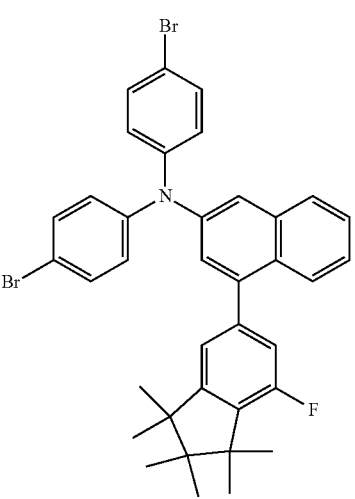 Mon-0262 |
| BB-1262 | BB-1263 |
| 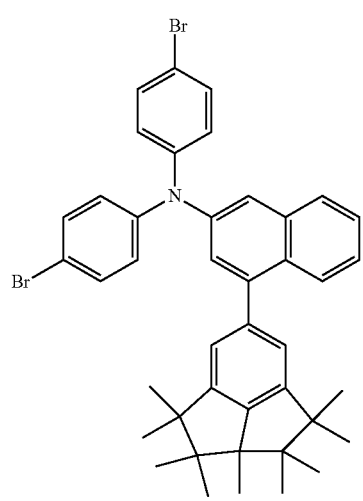 Mon-0263 | 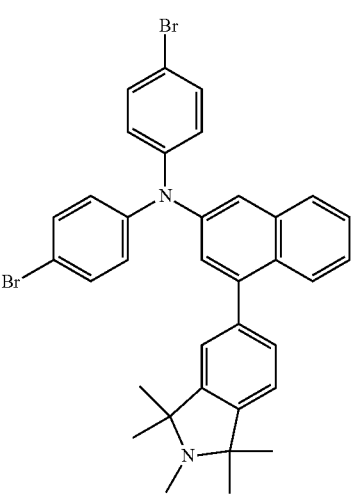 Mon-0264 |

-continued
BB-1264
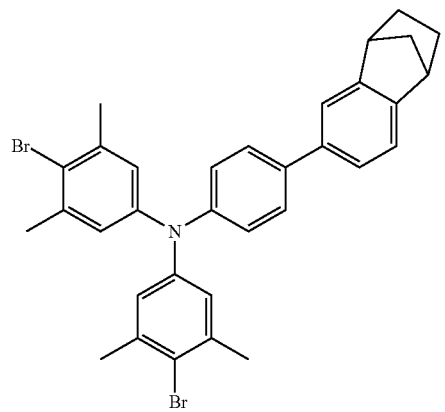
Mon-0265
BB-1265
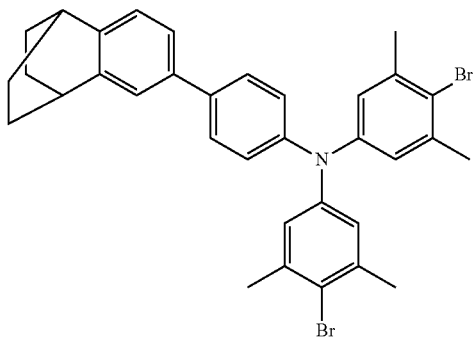
Mon-0266
BB-1266
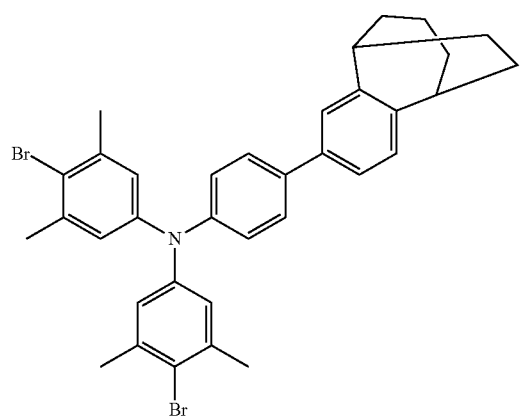
Mon-0267
BB-1267
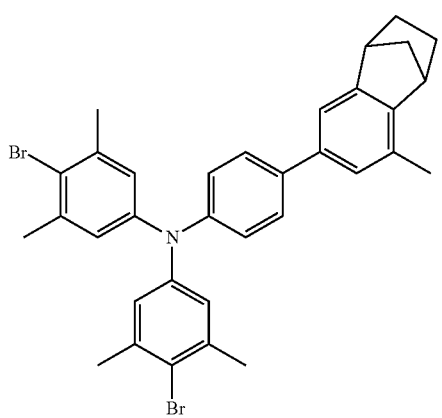
Mon-0268
BB-1268
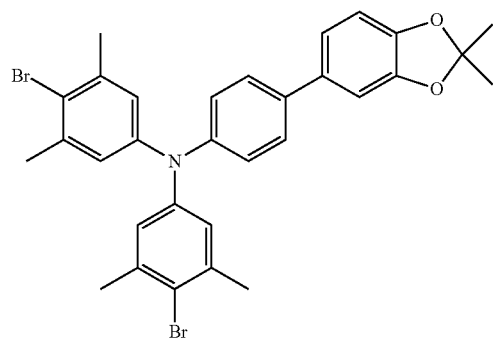
Mon-0269
BB-1269
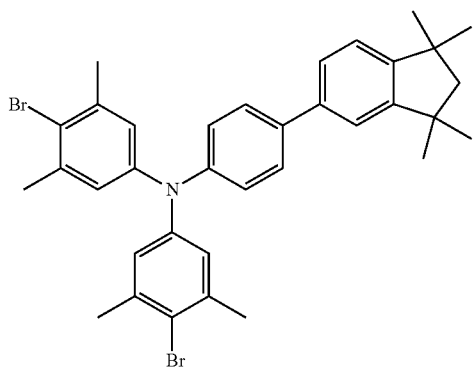
Mon-0270

-continued
BB-1270
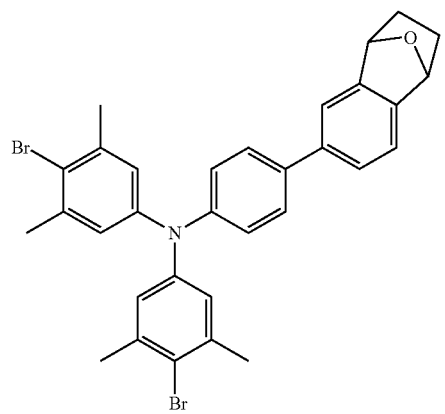
Mon-0271
BB-1271
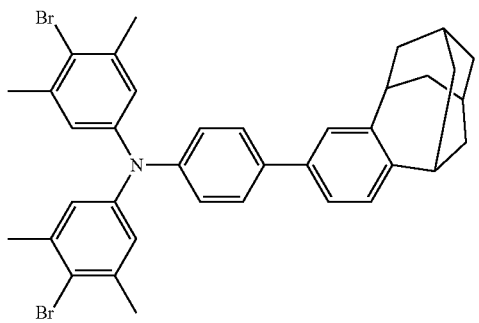
Mon-0272
BB-1272
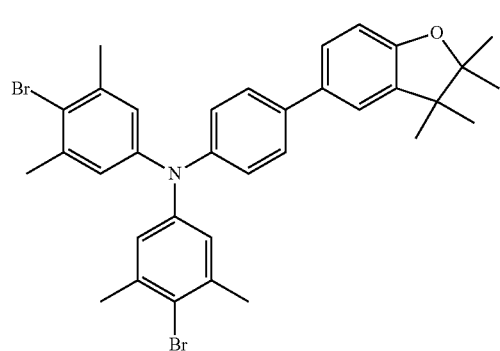
Mon-0273
BB-1273
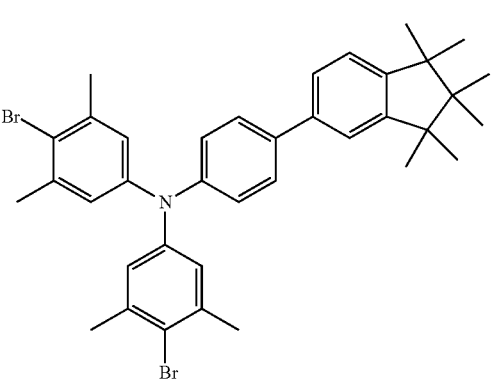
Mon-0274
BB-1274
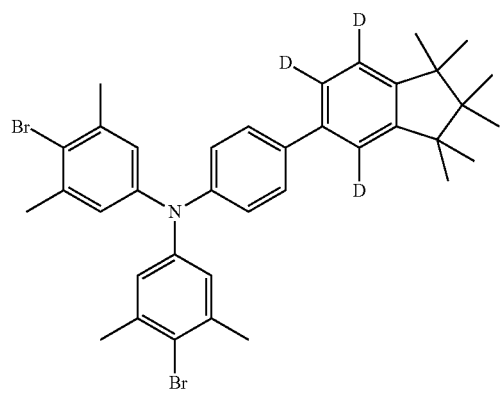
Mon-0275
BB-1275
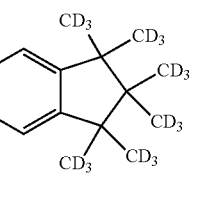
Mon-0276

-continued
BB-1276
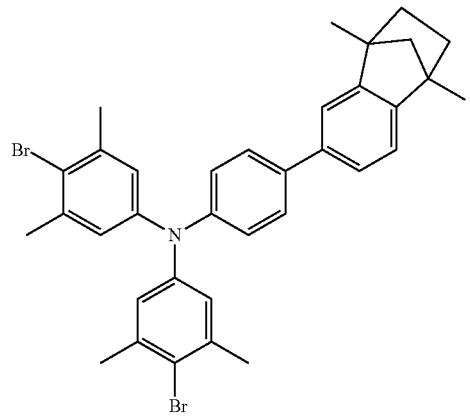
Mon-0277
BB-1277
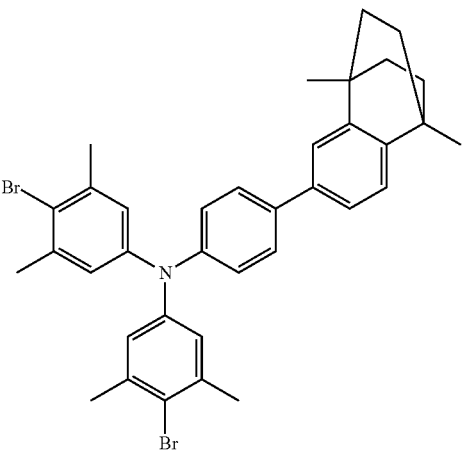
Mon-0278
BB-1278
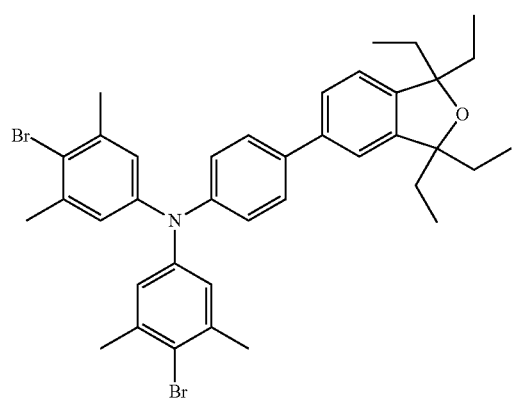
Mon-0279
BB-1279
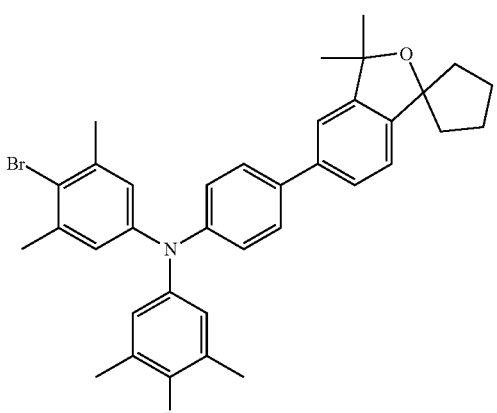
Mon-0280
BB-1280
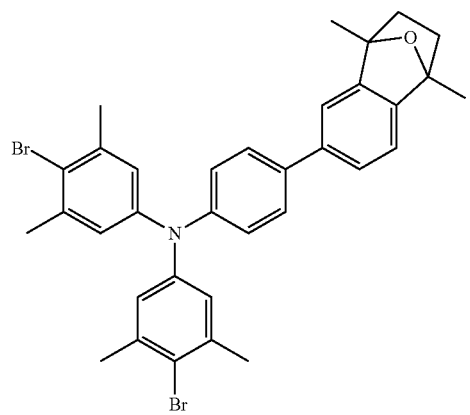
Mon-0281
BB-1281
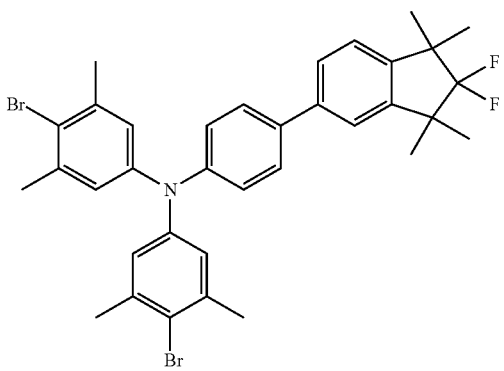
Mon-0282

-continued
BB-1282
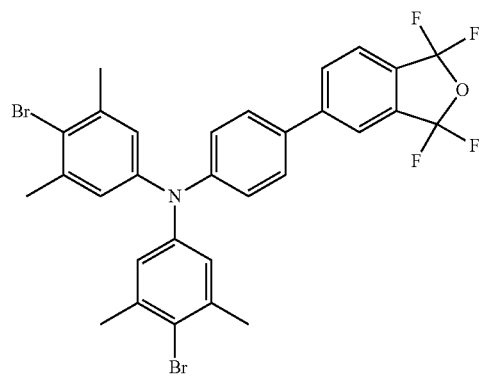
Mon-0283
BB-1283
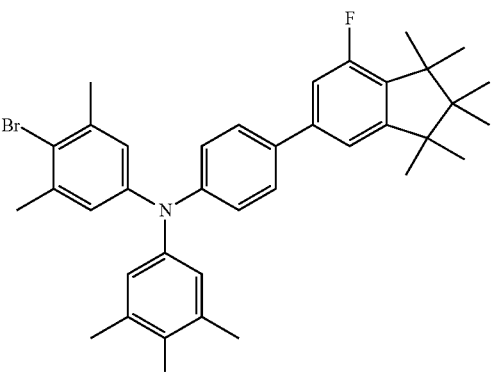
Mon-0284
BB-1284
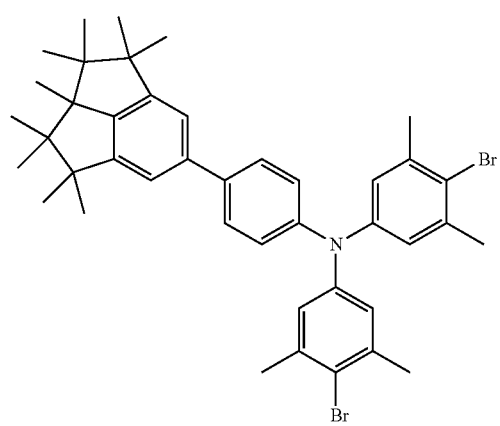
Mon-0285
BB-1285
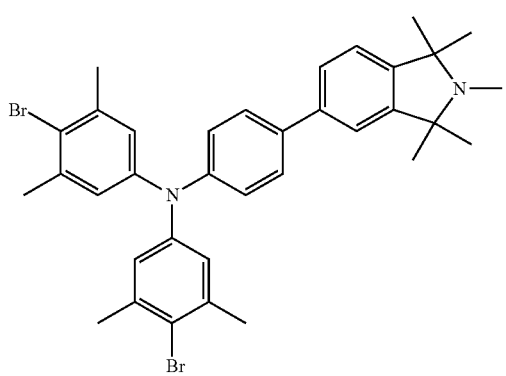
Mon-0286
BB-1286
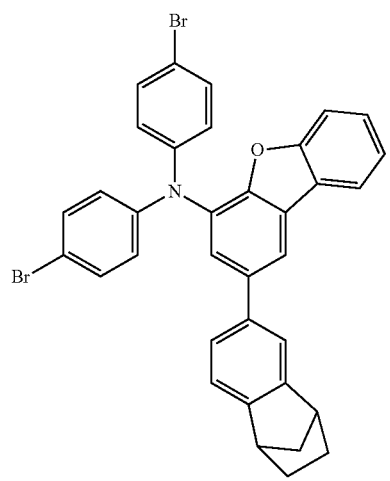
Mon-0287
BB-1287
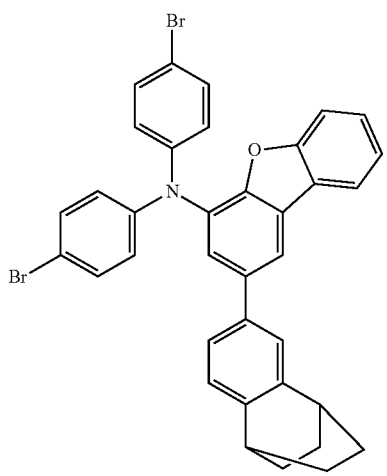
Mon-0288

-continued
BB-1288
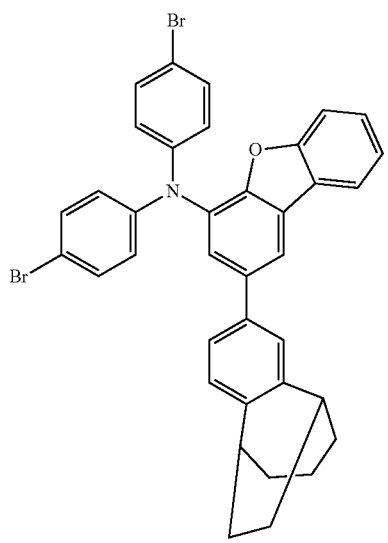
Mon-0289
BB-1290
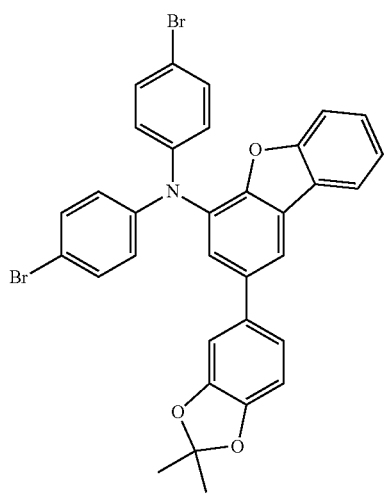
Mon-0291
BB-1292
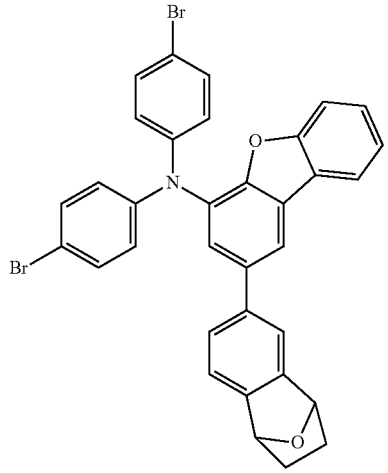
Mon-0293
BB-1289
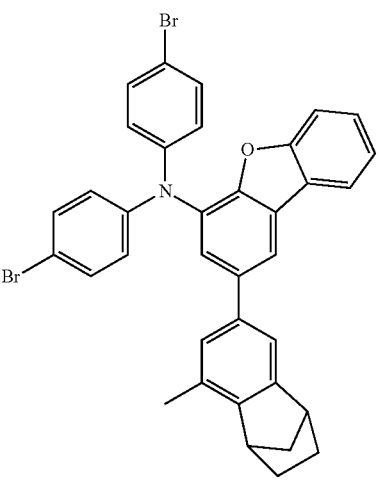
Mon-0290
BB-1291
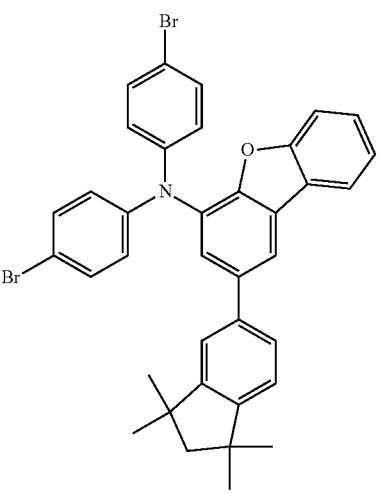
Mon-0292
BB-1293
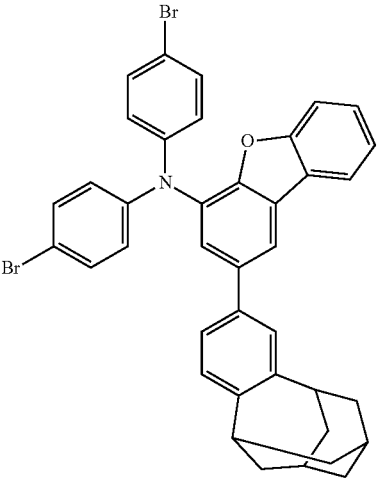
Mon-0294

-continued
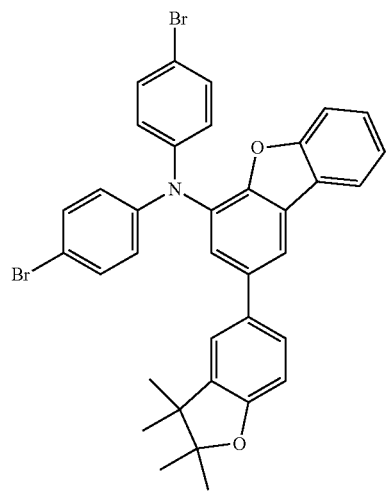
Mon-0295
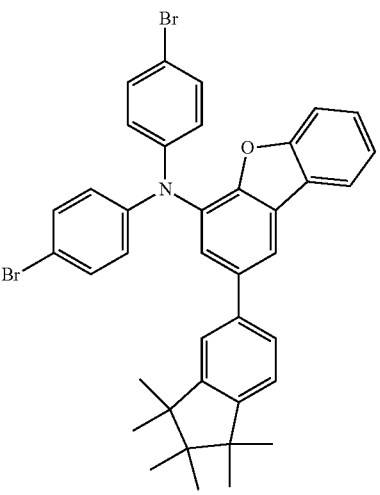
Mon-0296
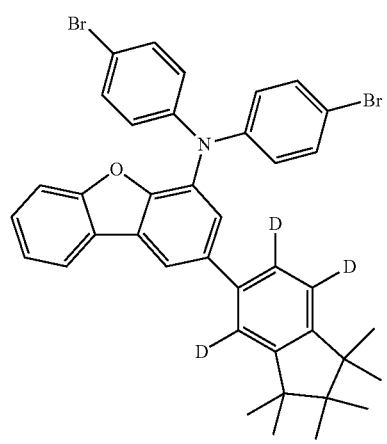
Mon-0297
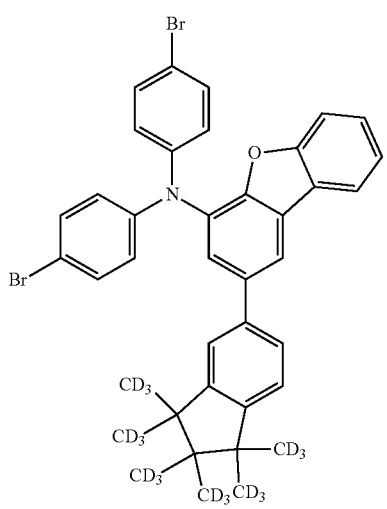
Mon-0298
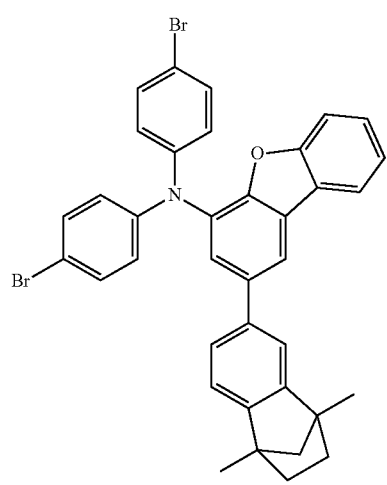
Mon-0299
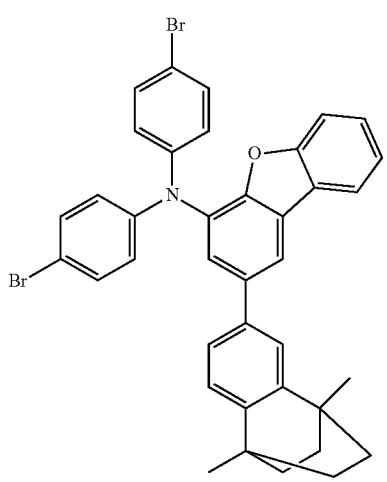
Mon-0300

-continued
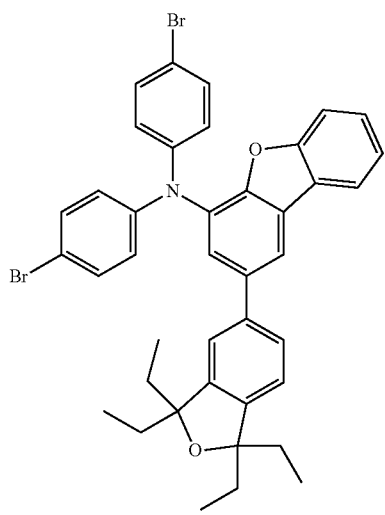
Mon-0301
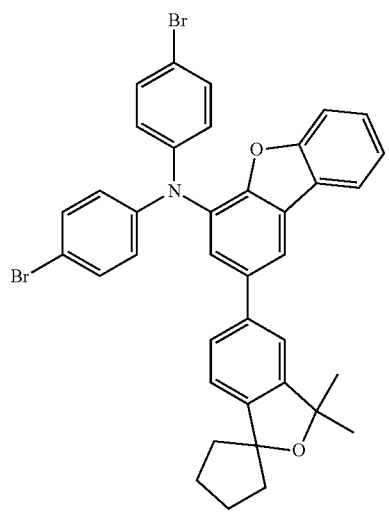
Mon-0302
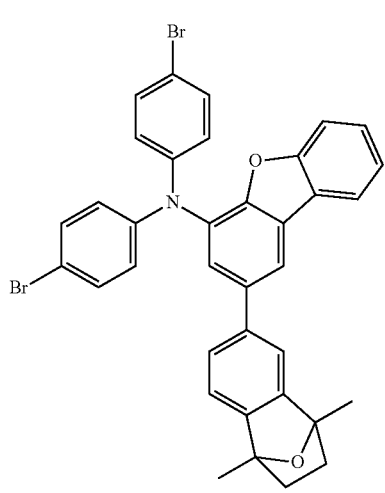
Mon-0303
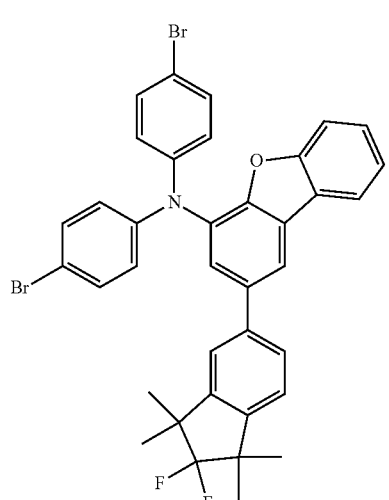
Mon-0304
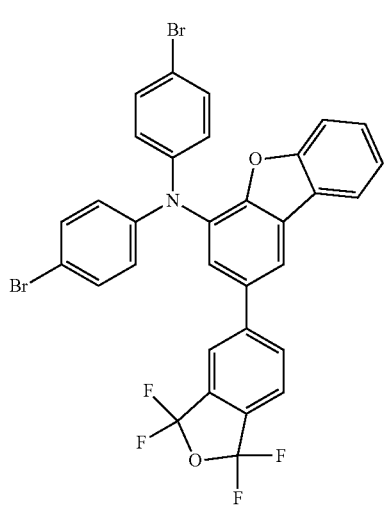
Mon-0305
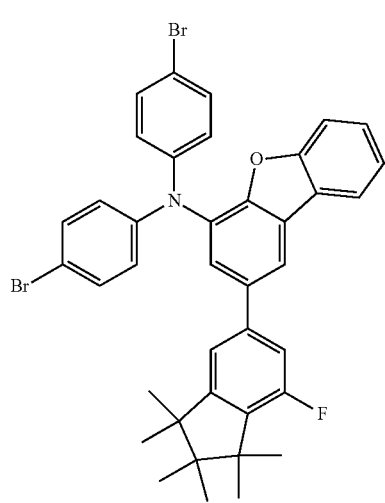
Mon-0306

-continued
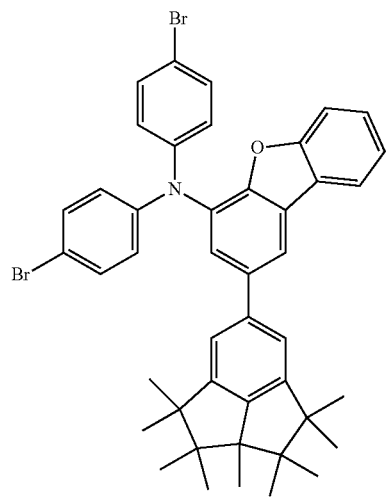
Mon-0307
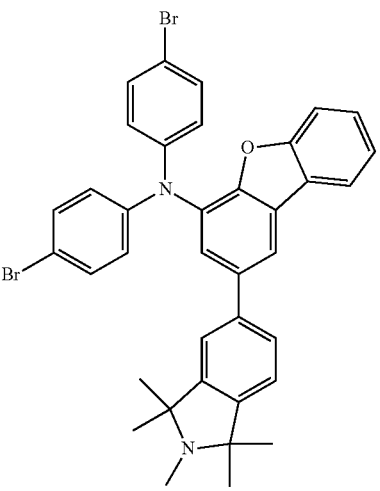
Mon-0308
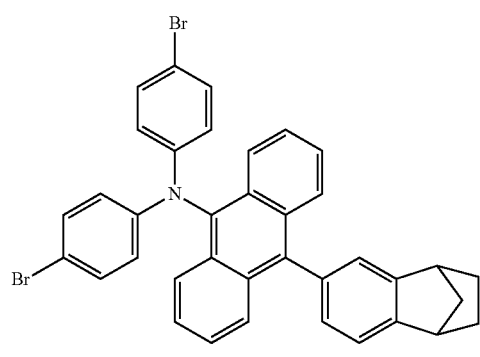
Mon-0309
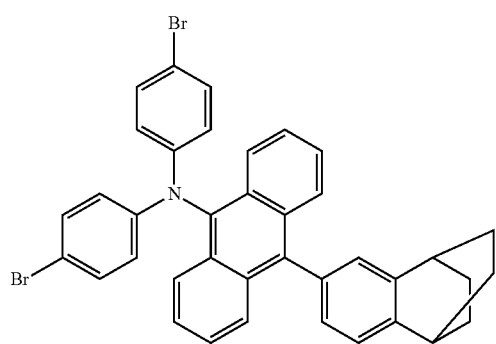
Mon-0310
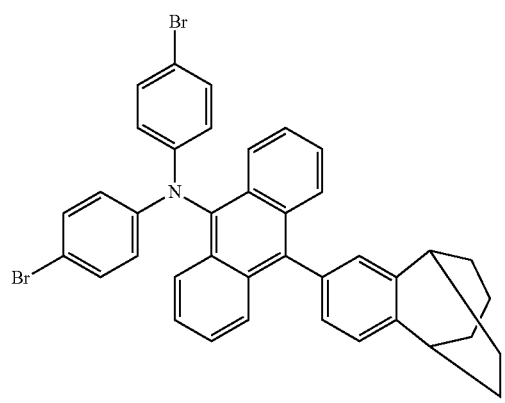
Mon-0311
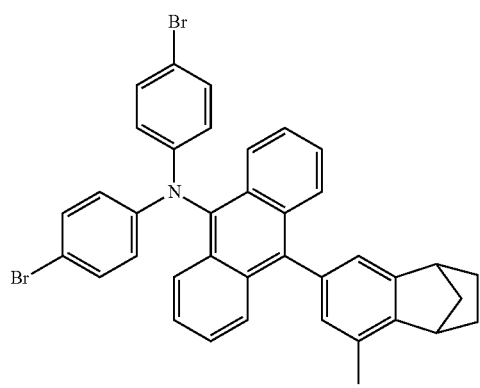
Mon-0312

-continued
BB-1312
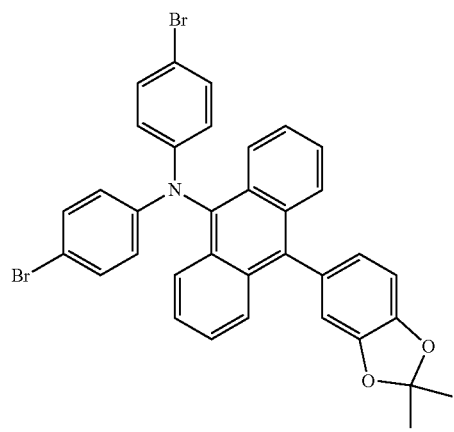
Mon-0313
BB-1313
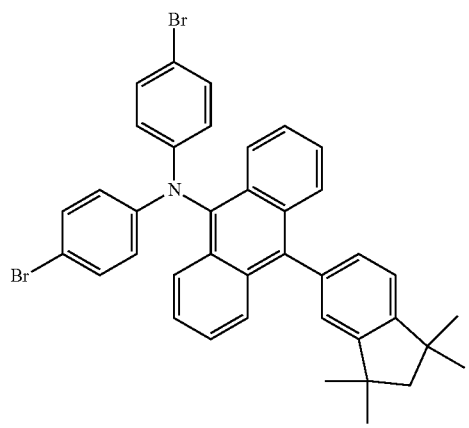
Mon-0314
BB-1314
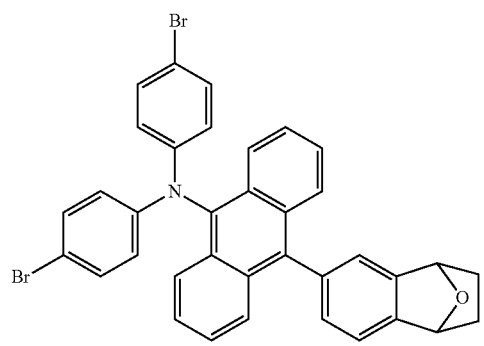
Mon-0315
BB-1315
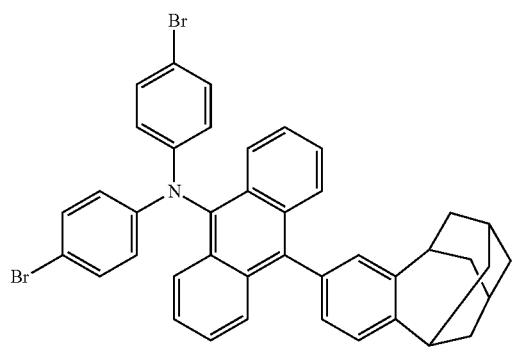
Mon-0316
BB-1316
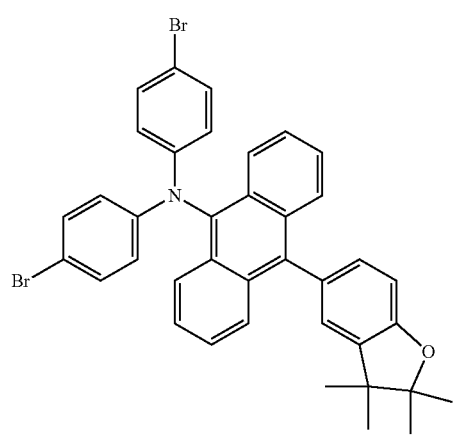
Mon-0317
BB-1317
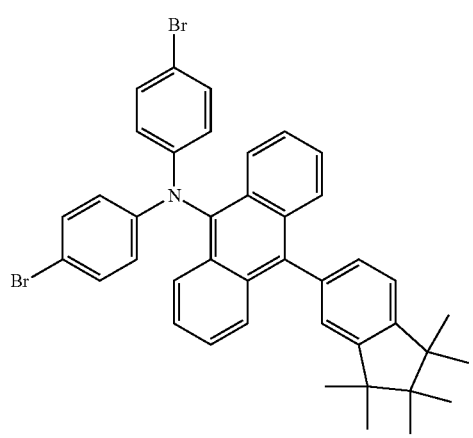
Mon-0318

-continued
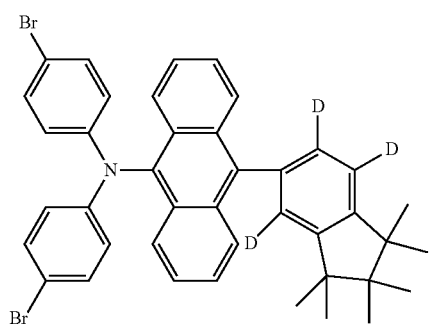
Mon-0319
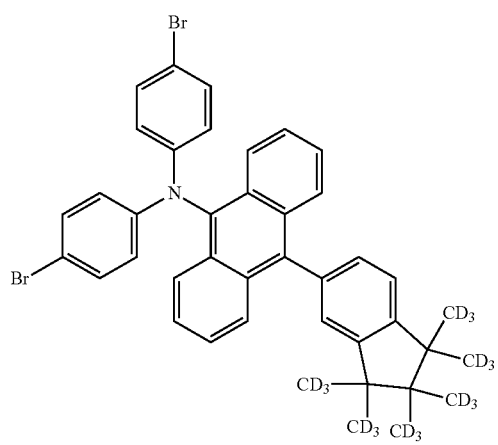
Mon-0320
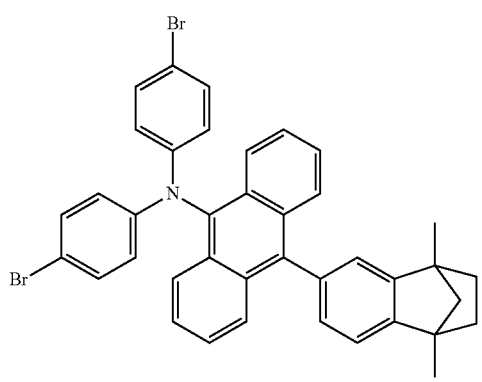
Mon-0321
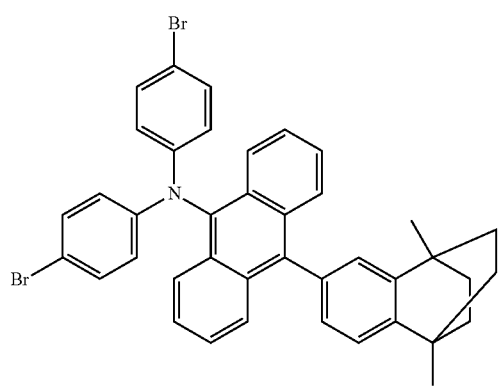
Mon-0322
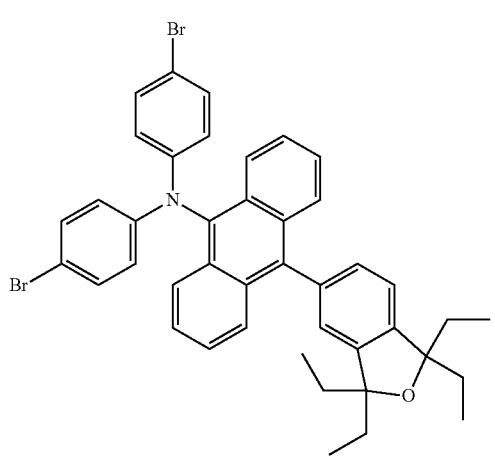
Mon-0323
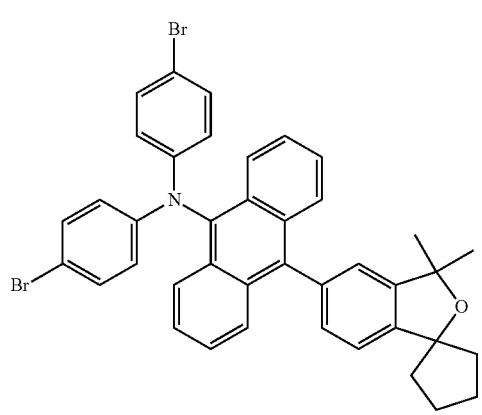
Mon-0324

-continued
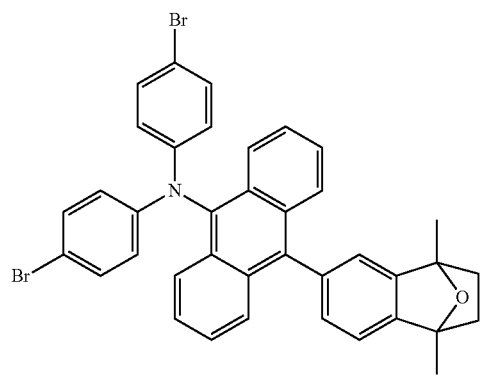
Mon-0325
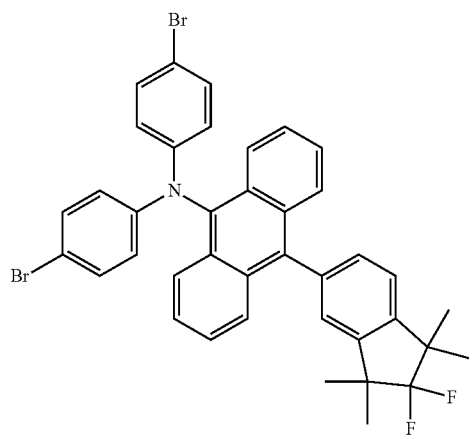
Mon-0326
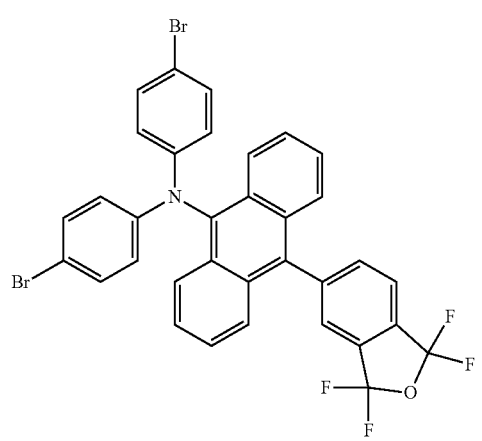
Mon-0327
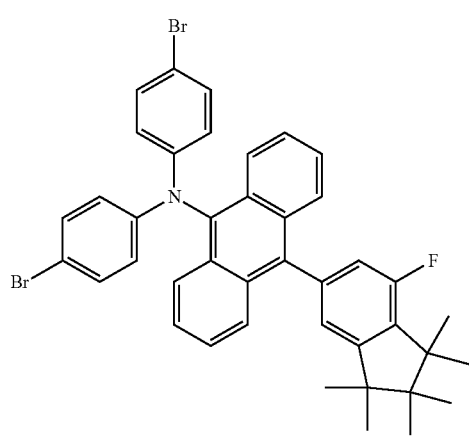
Mon-0328
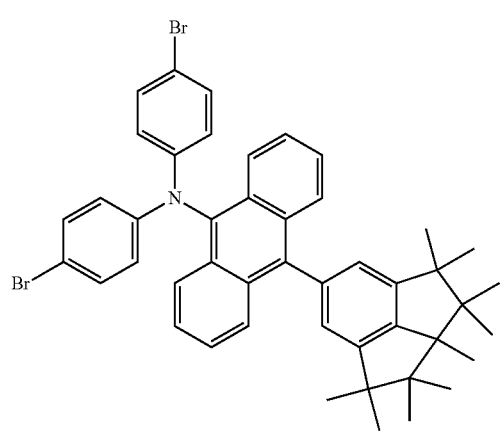
Mon-0329
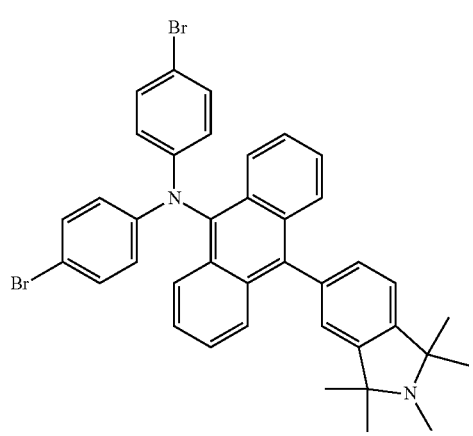
Mon-0330

-continued
BB-1330
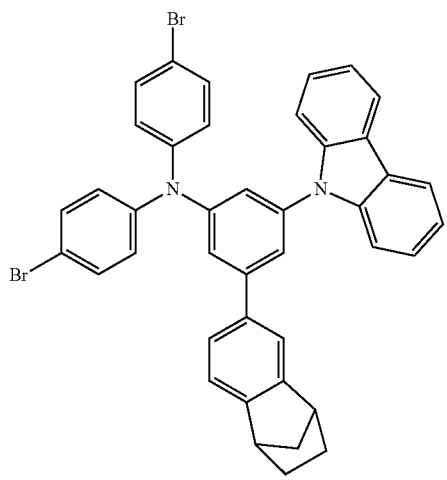
Mon-0331
BB-1331
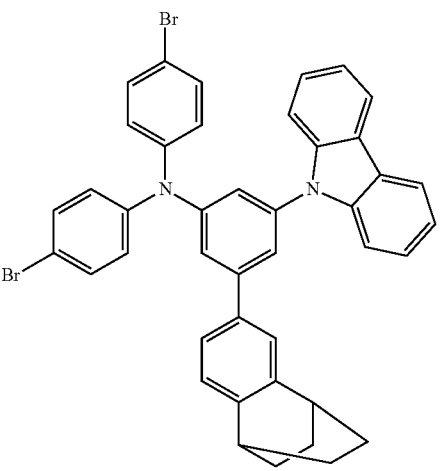
Mon-0332
BB-1332
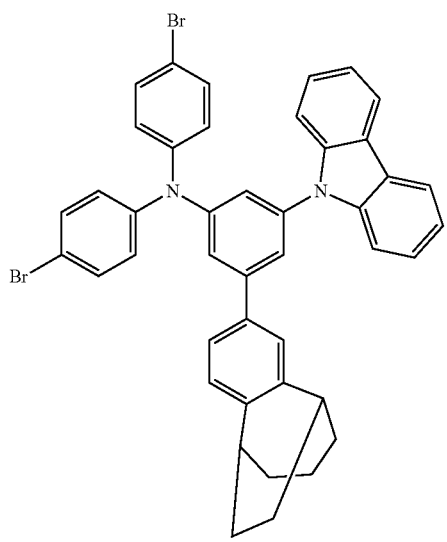
Mon-0333
BB-1333
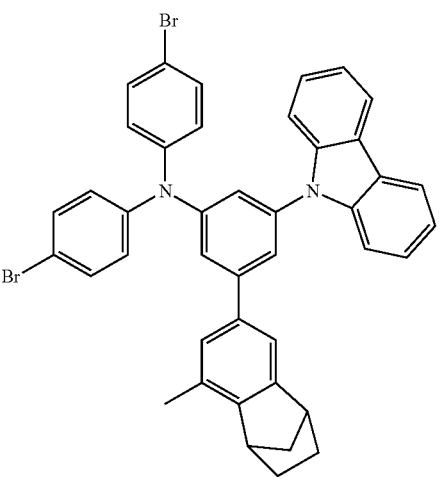
Mon-0334
BB-1334
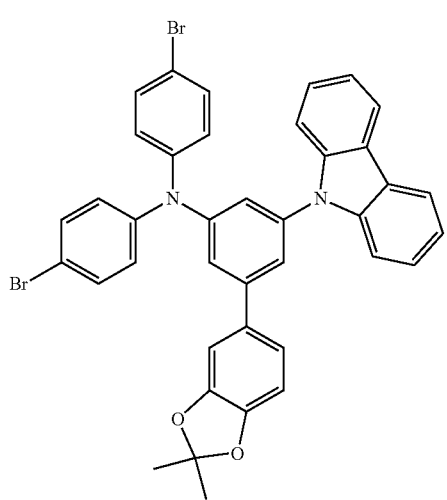
Mon-0335
BB-1335
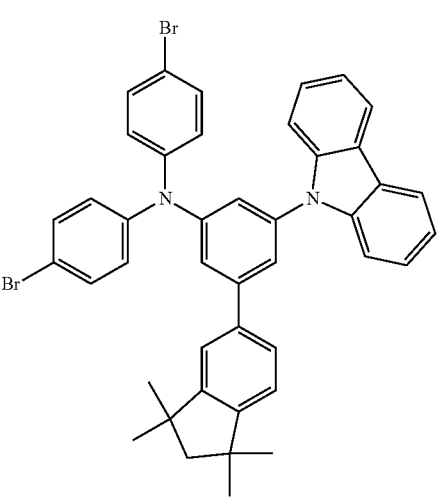
Mon-0336

-continued
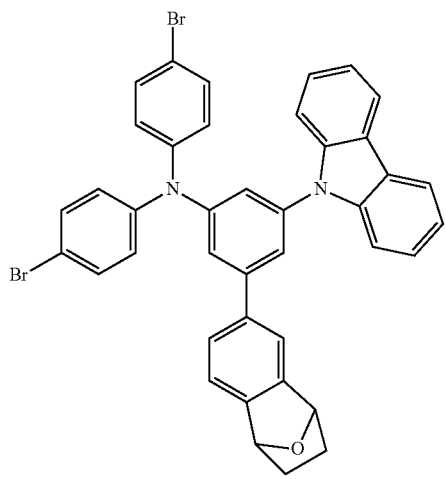
Mon-0337
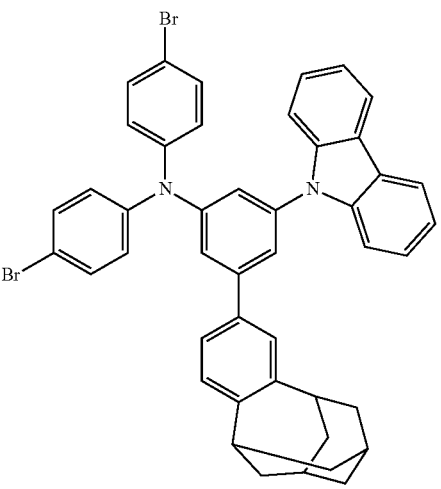
Mon-0338
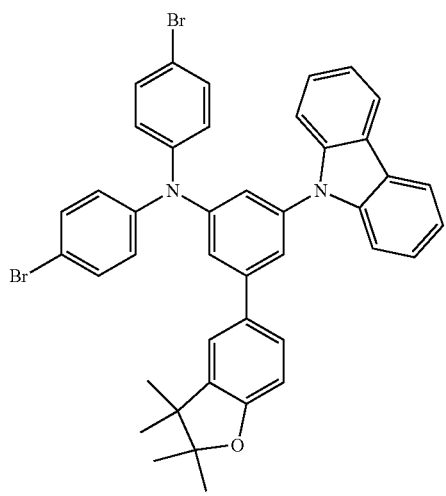
Mon-0339
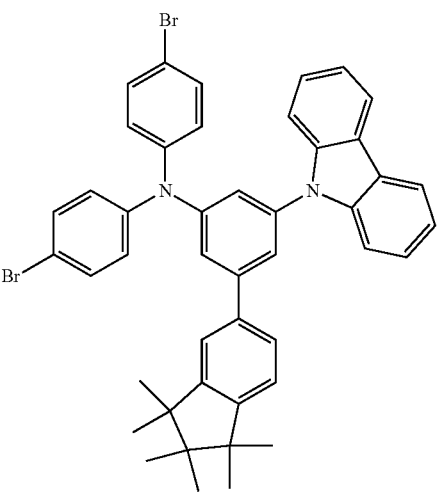
Mon-0340
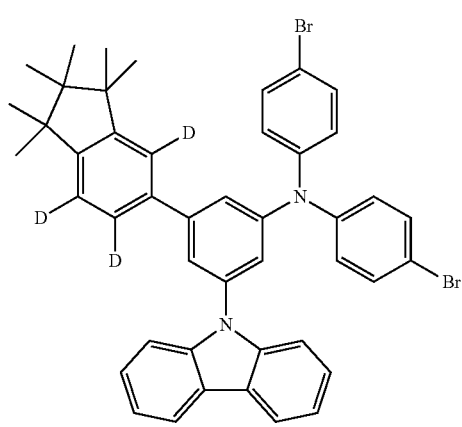
Mon-0341
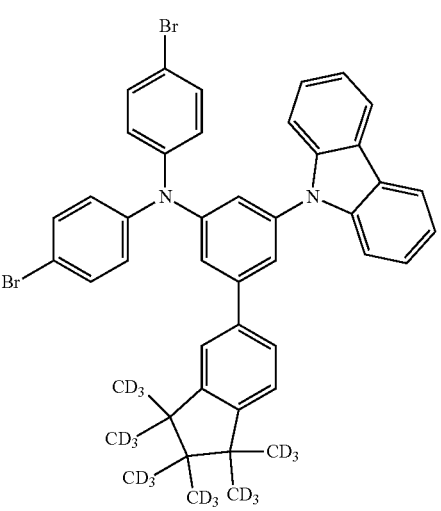
Mon-0342

-continued
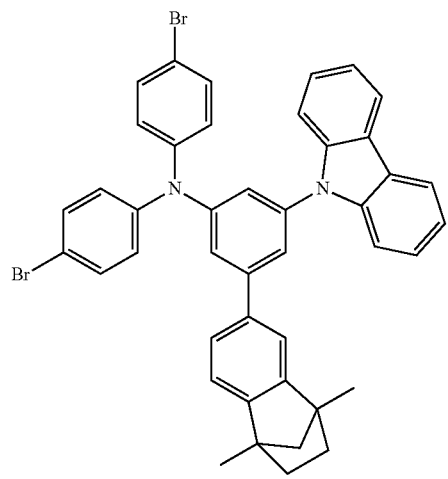
Mon-0343
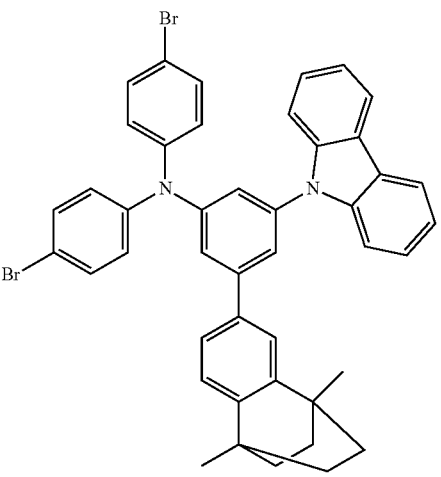
Mon-0344
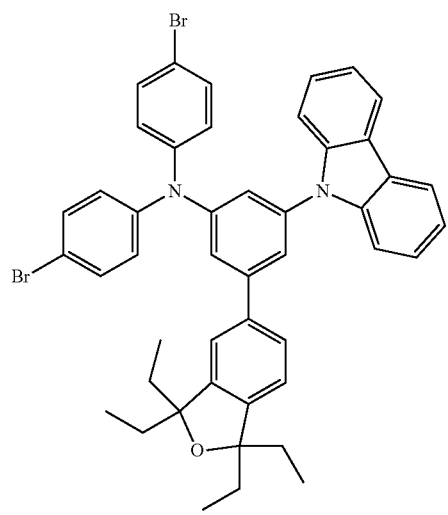
Mon-0345
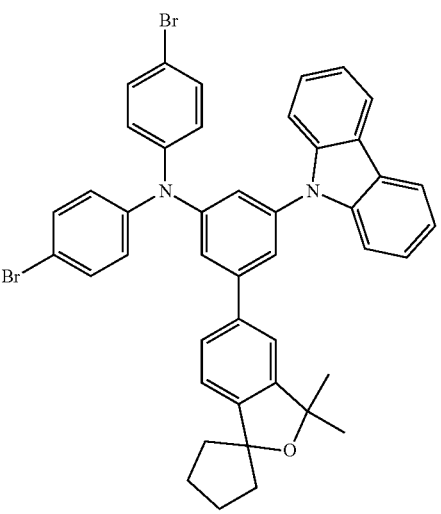
Mon-0346
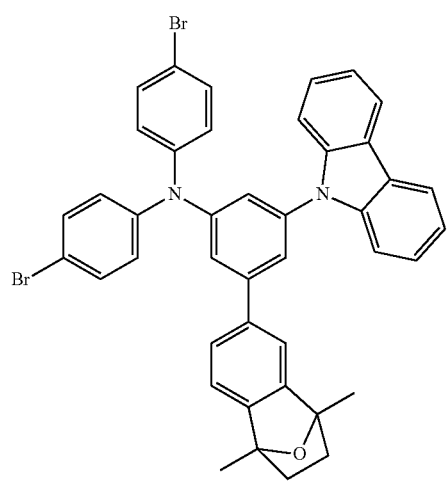
Mon-0347
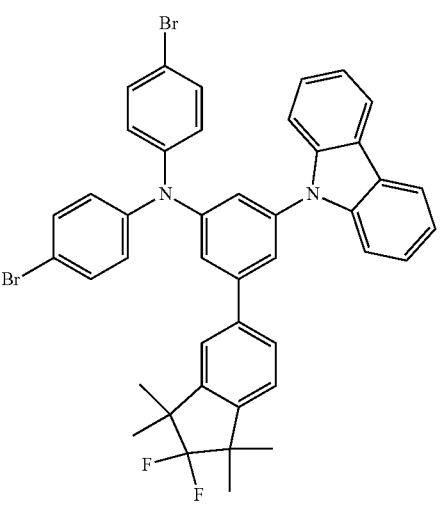
Mon-0348

-continued
BB-1348
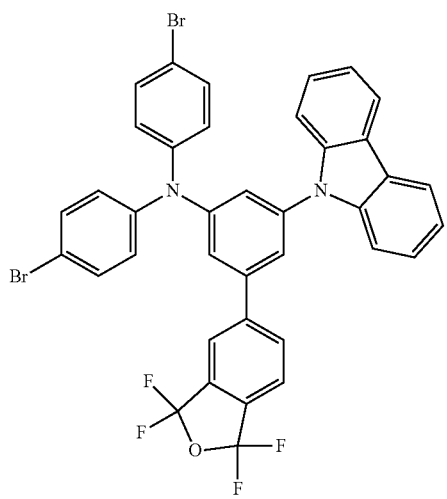
Mon-0349
BB-1349
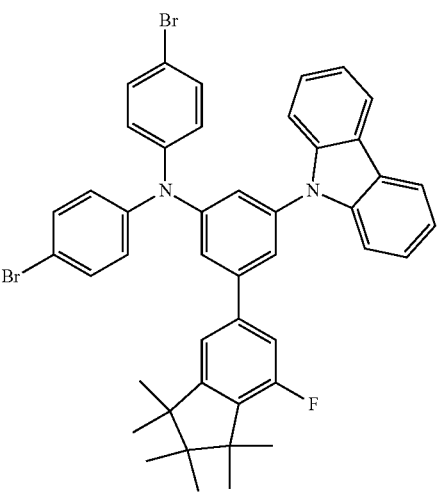
Mon-0350
BB-1350
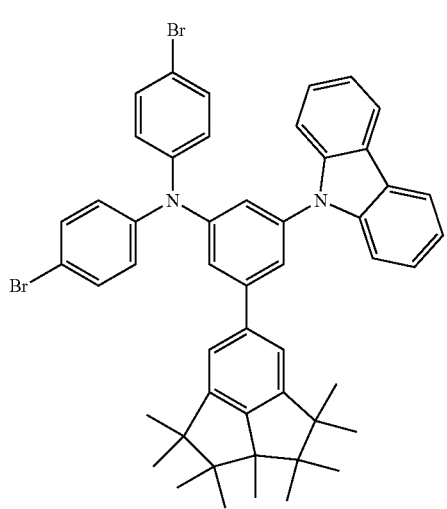
Mon-0351
BB-1351
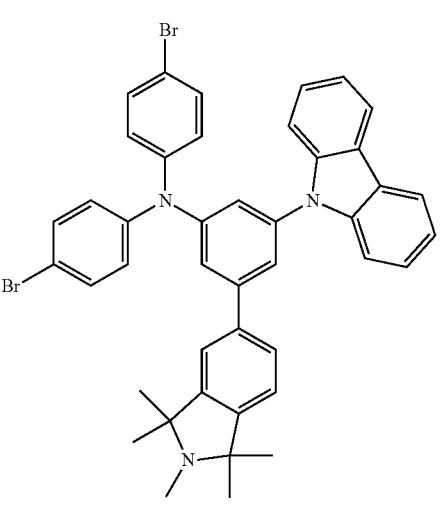
Mon-0352
BB-1352
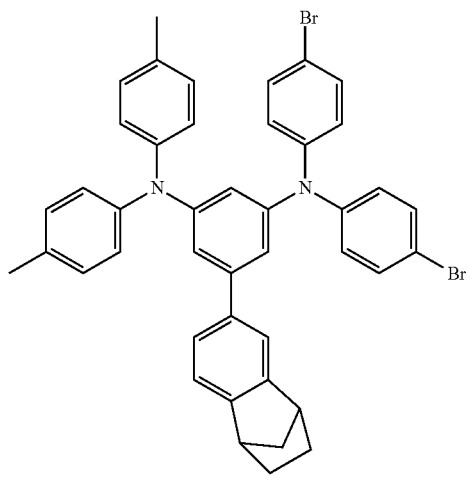
Mon-0353
BB-1353
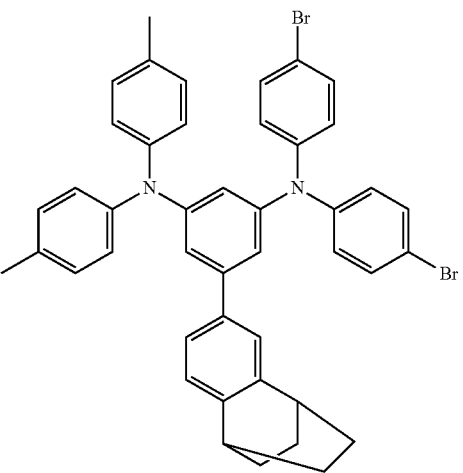
Mon-0354

-continued
BB-1354
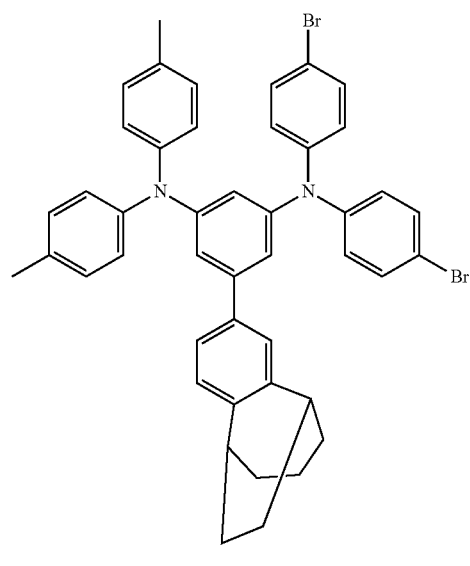
Mon-0355
BB-1355
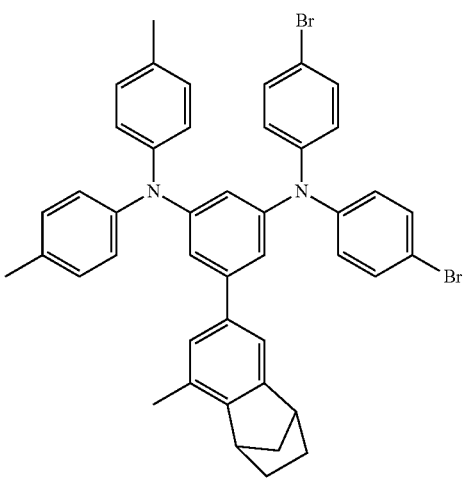
Mon-0356
BB-1356
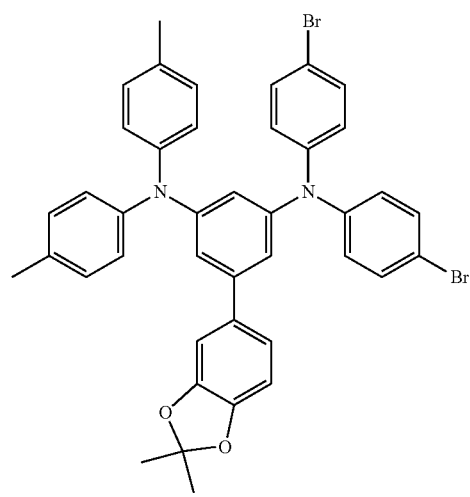
Mon-0357
BB-1357
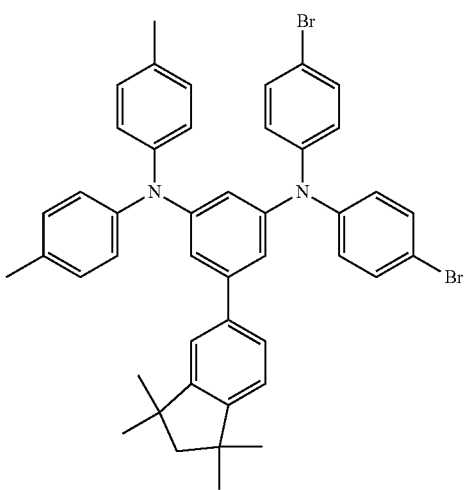
Mon-0358
BB-1358
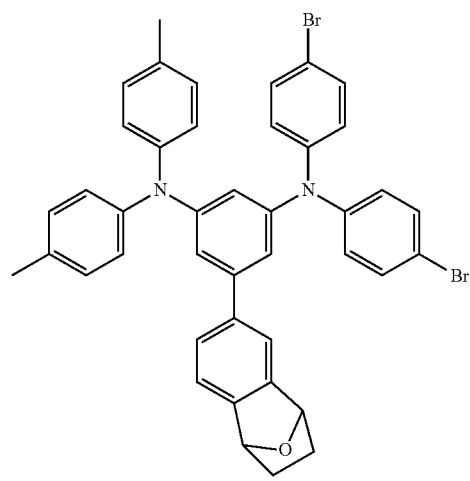
Mon-0359
BB-1359
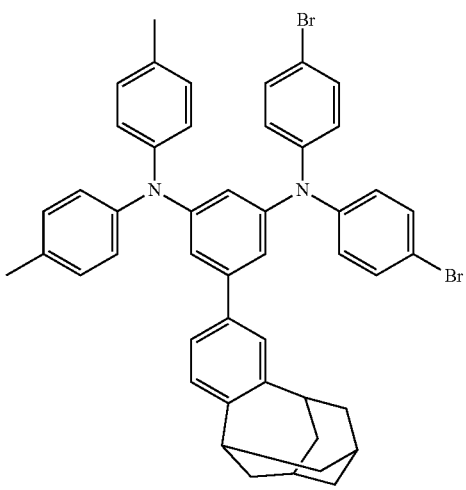
Mon-0360

-continued
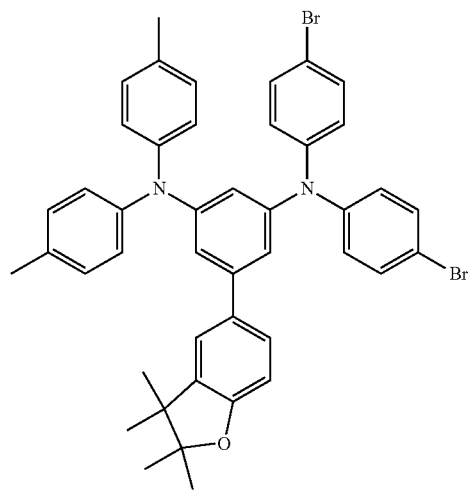
Mon-0361
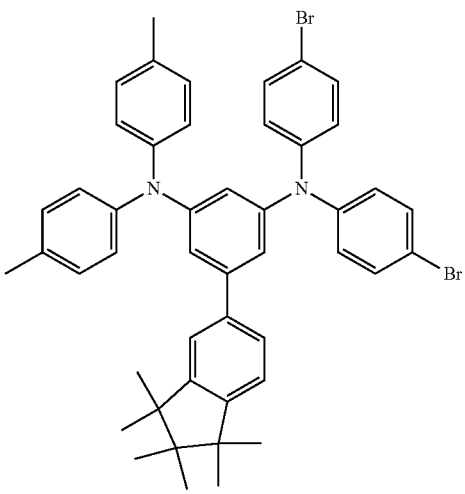
Mon-0362
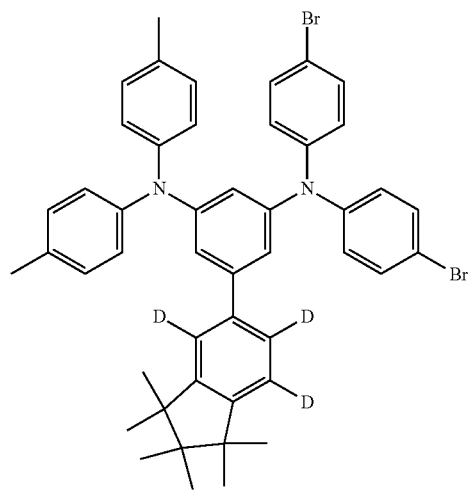
Mon-0363
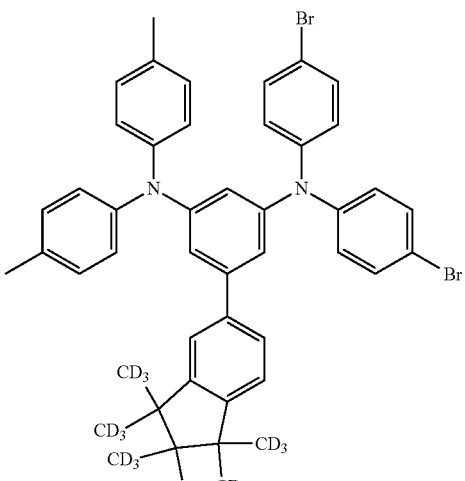
Mon-0364
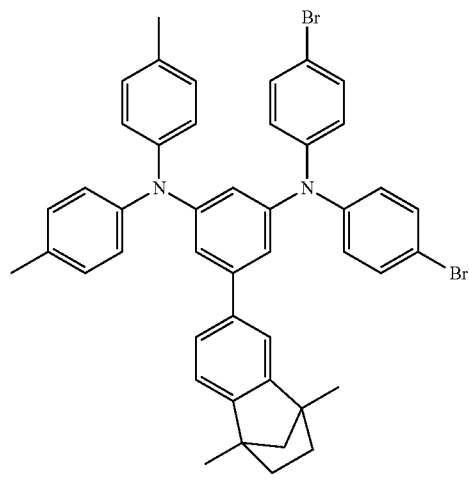
Mon-0365
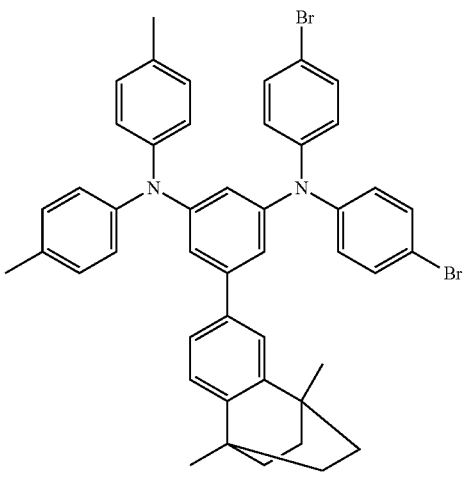
Mon-0366

-continued
BB-1366
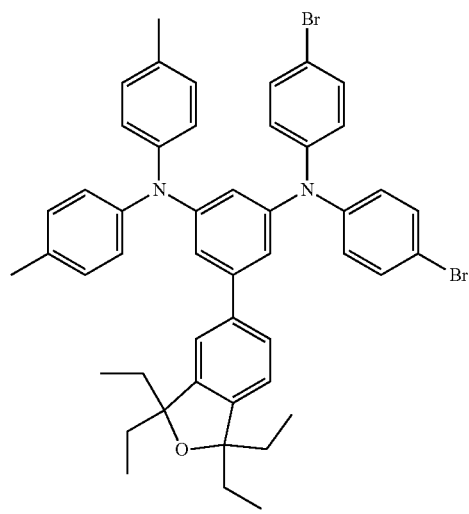
Mon-0367
BB-1367
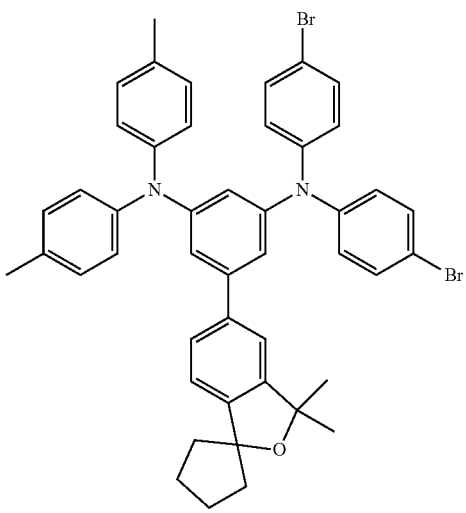
Mon-0368
BB-1368
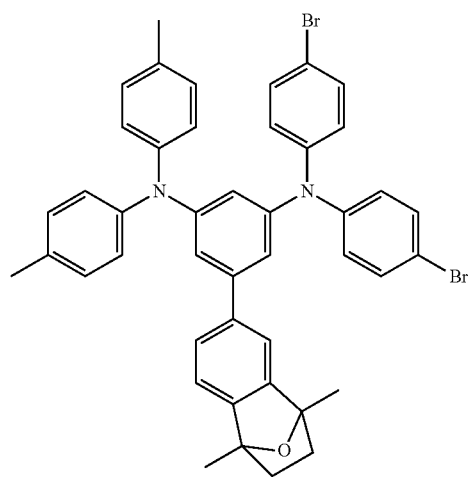
Mon-0369
BB-1369
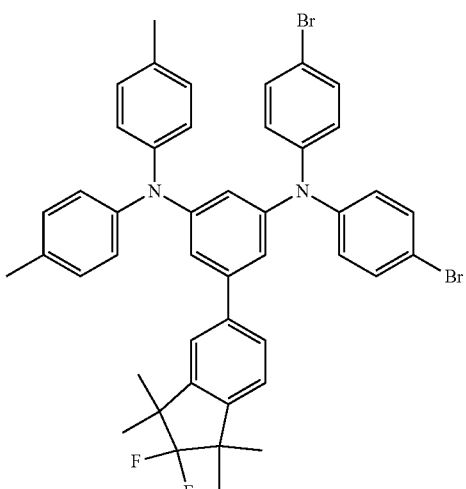
Mon-0370
BB-1370
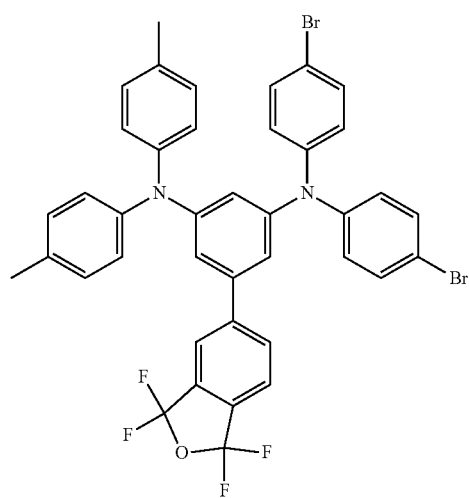
Mon-0371
BB-1371
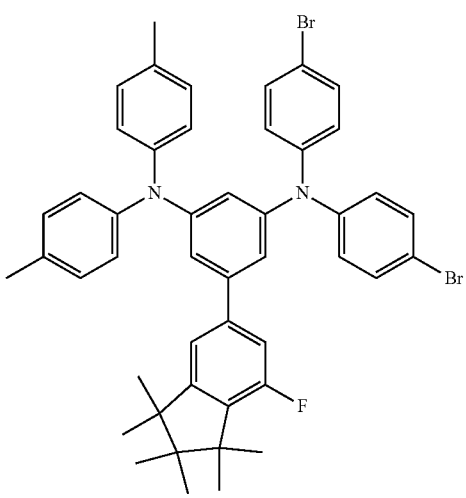
Mon-0372

-continued
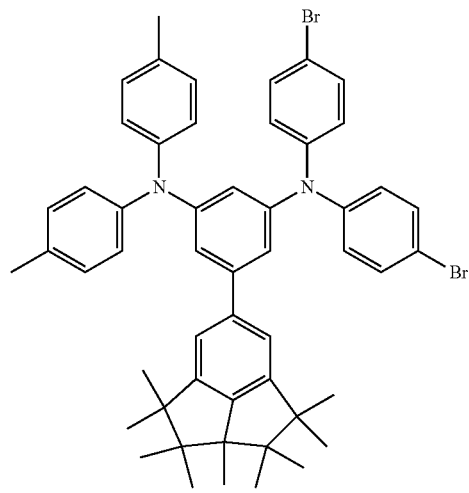
Mon-0373
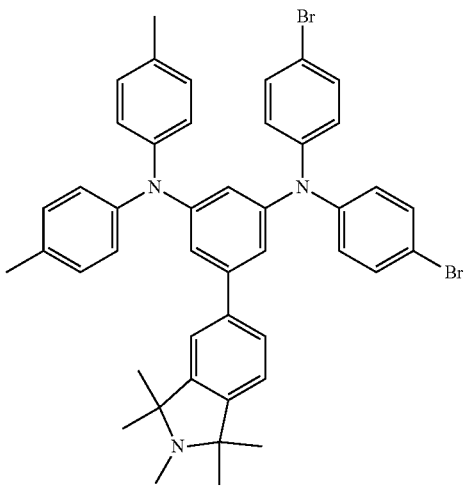
Mon-0374
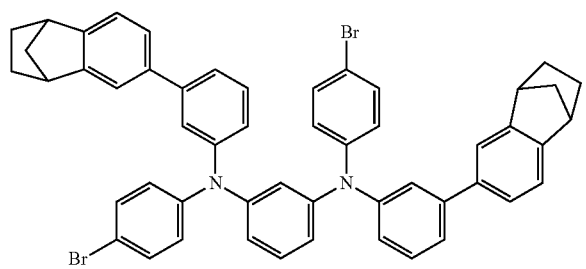
Mon-0375
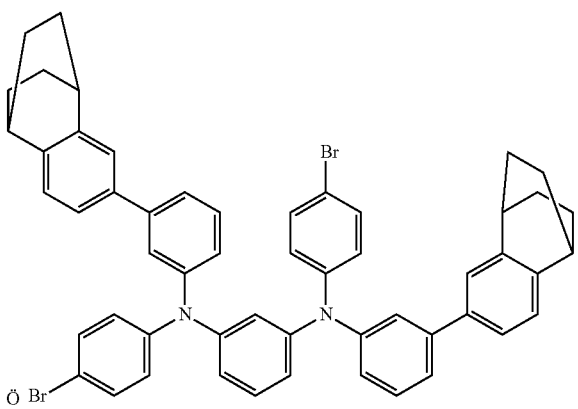
Mon-0376
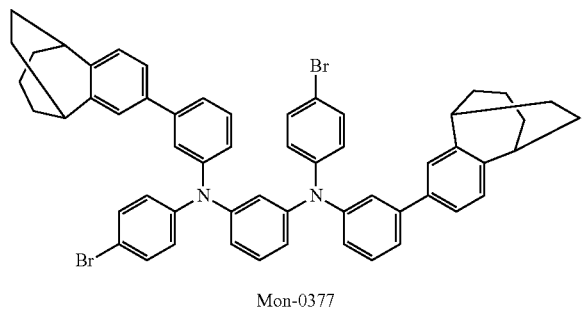
Mon-0377
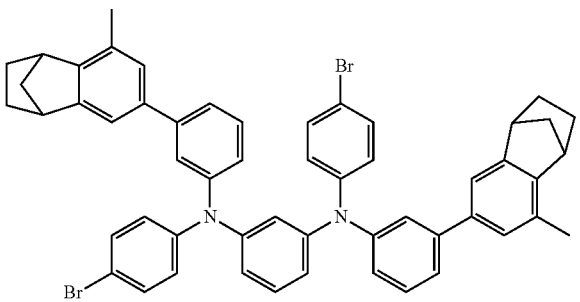
Mon-0378

-continued
BB-1378
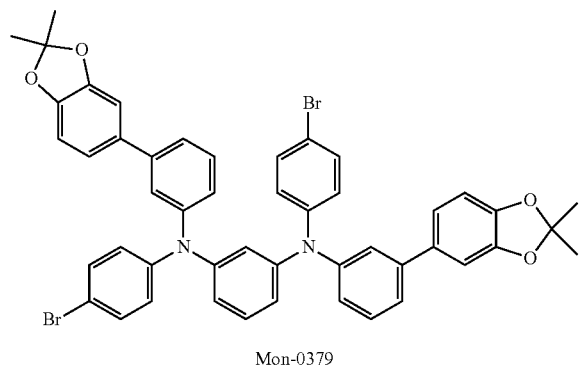
Mon-0379
BB-1379
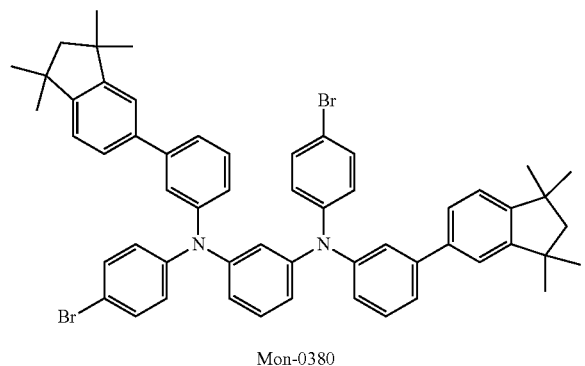
Mon-0380
BB-1380
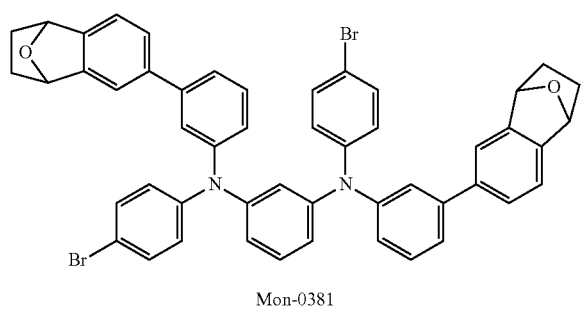
Mon-0381
BB-1381
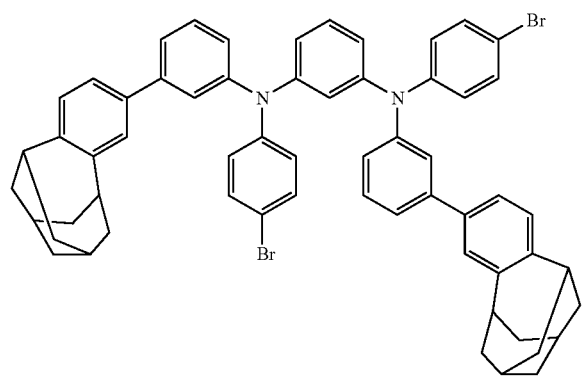
Mon-0382
BB-1382
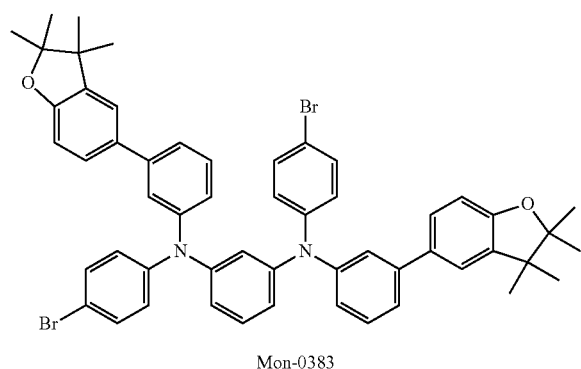
Mon-0383
BB-1383
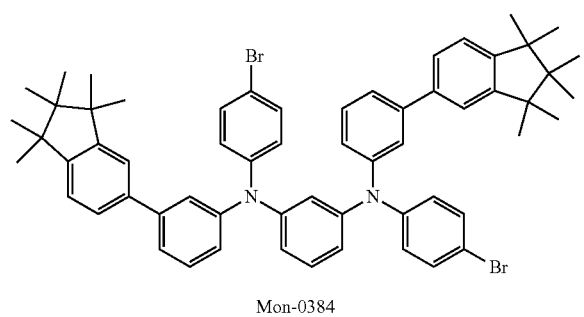
Mon-0384
BB-1384
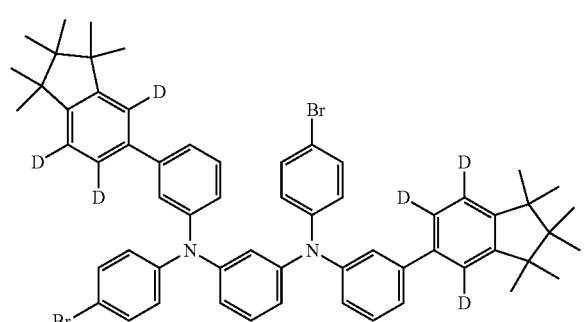
Mon-0385

-continued
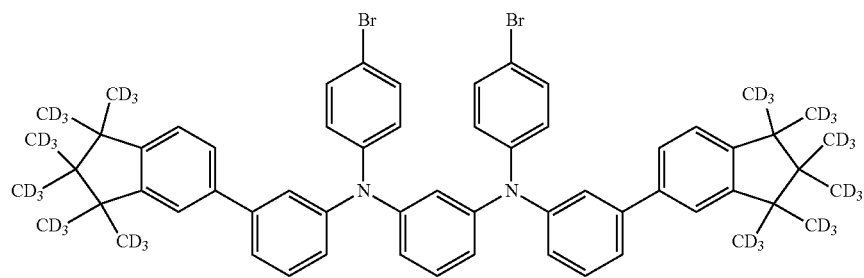
Mon-0386 BB-1385
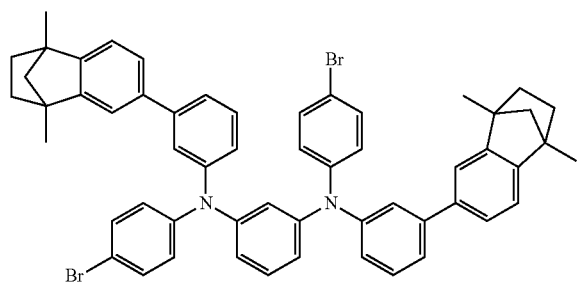
Mon-0387 BB-1386
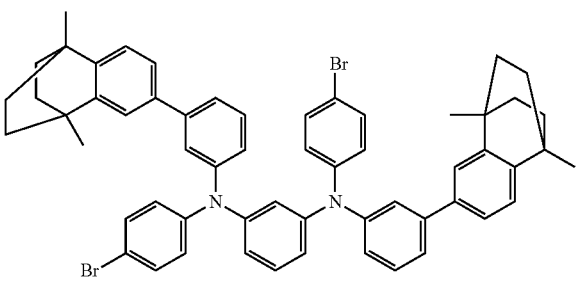
Mon-0388 BB-1387
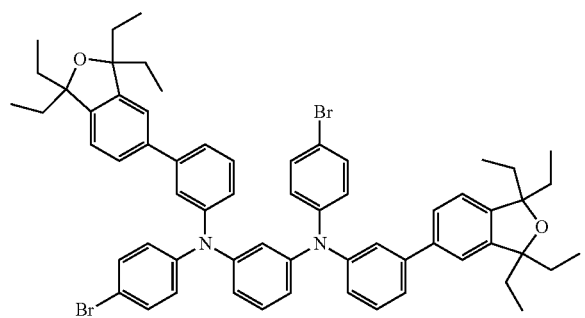
Mon-0389 BB-1388
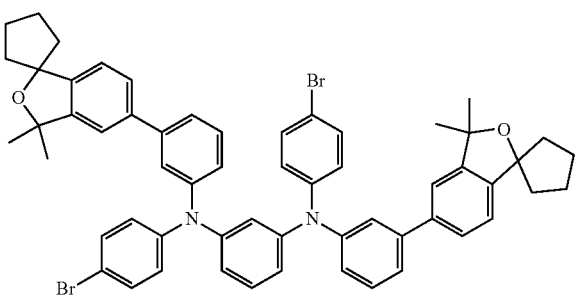
Mon-0390 BB-1389
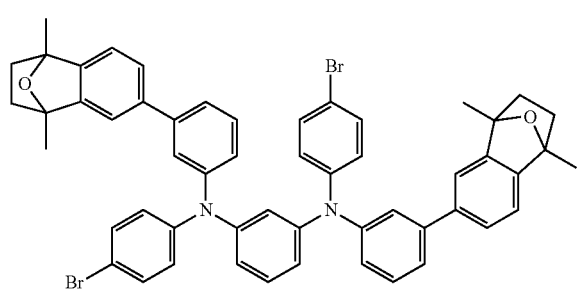
Mon-0391 BB-1390
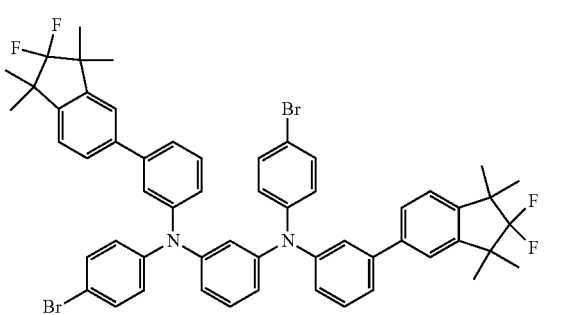
Mon-0392 BB-1391

-continued
BB-1392
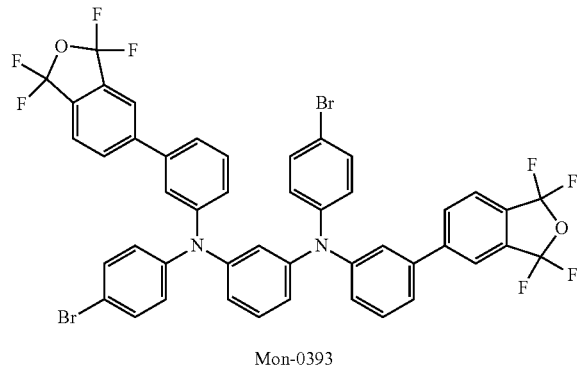
Mon-0393
BB-1393
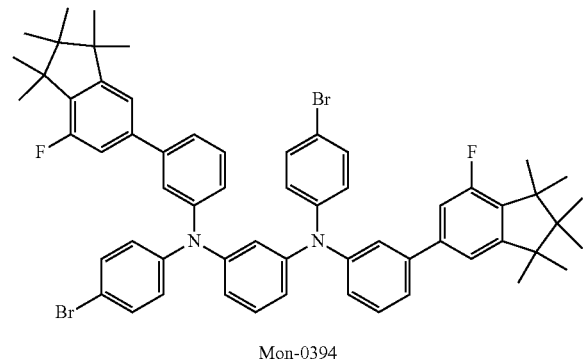
Mon-0394
BB-1394
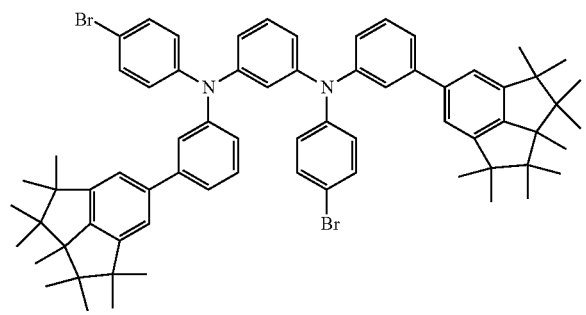
Mon-0395
BB-1395
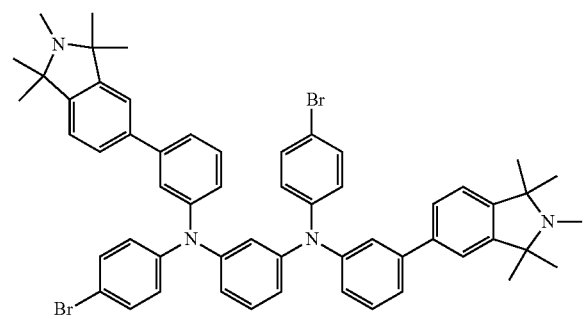
Mon-0396
BB-1396
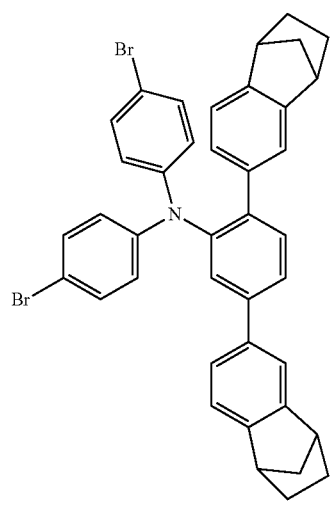
Mon-0397
BB-1397
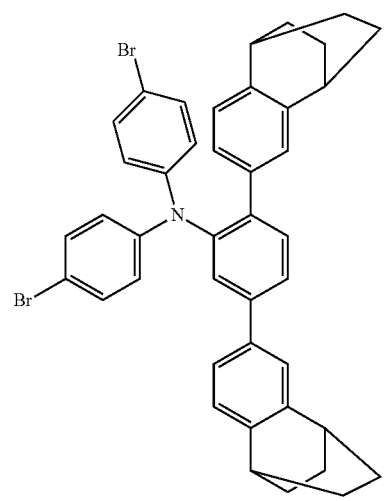
Mon-0398

-continued
BB-1398
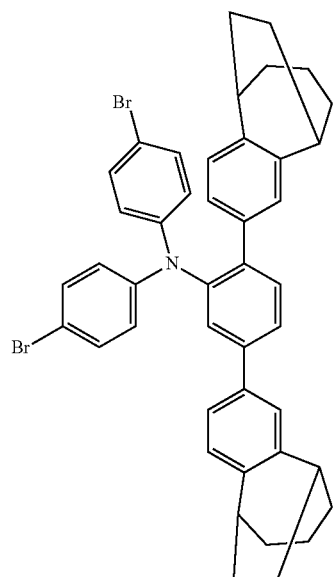
Mon-0399
BB-1399
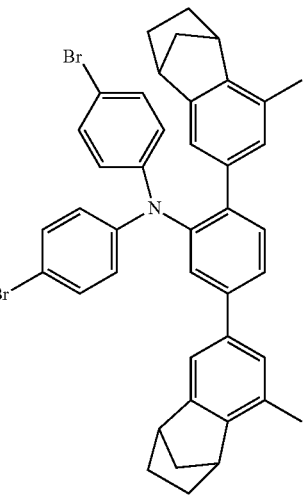
Mon-0400
BB-1400
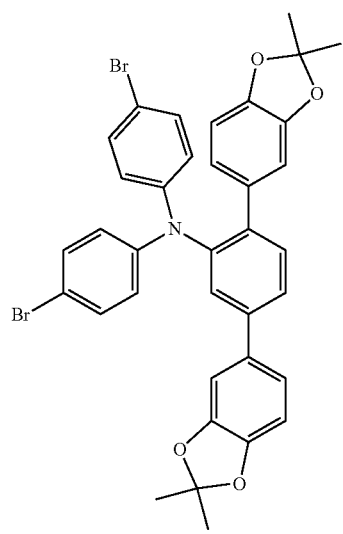
Mon-0401
BB-1401
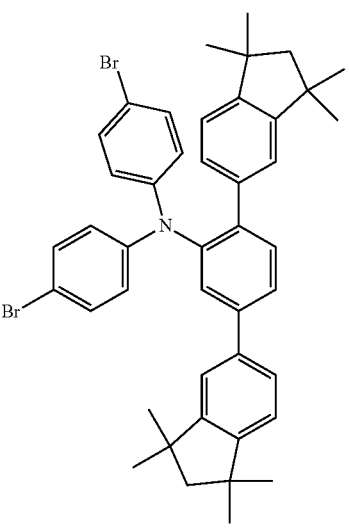
Mon-0402

-continued
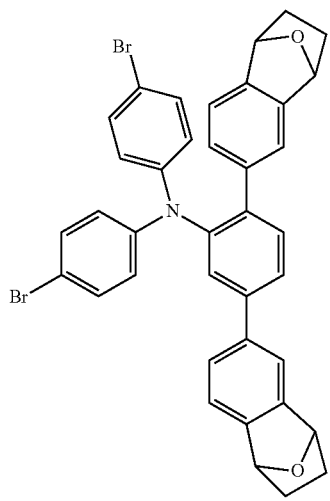
Mon-0403
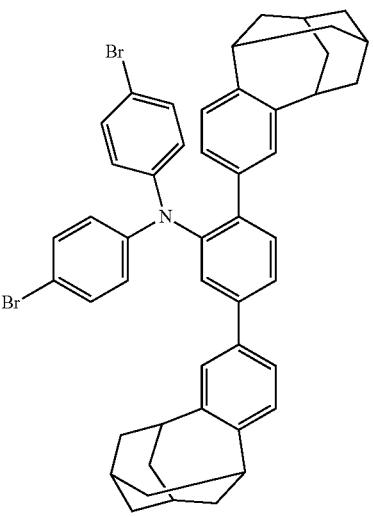
Mon-0404
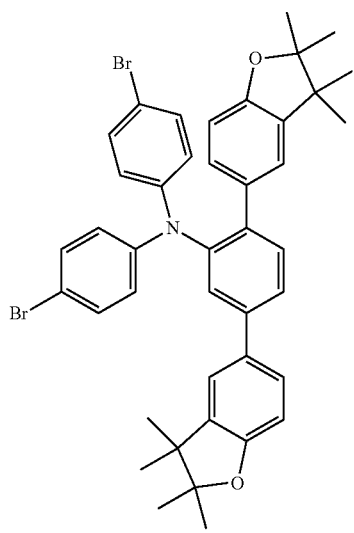
Mon-0405
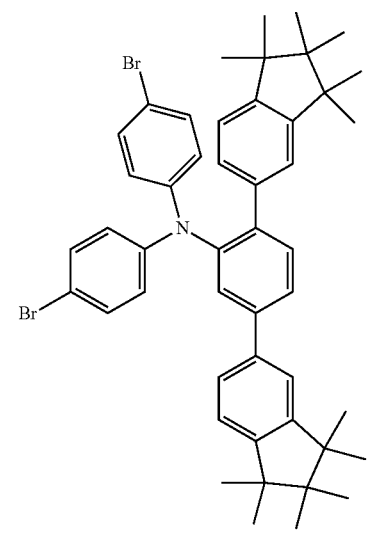
Mon-0406
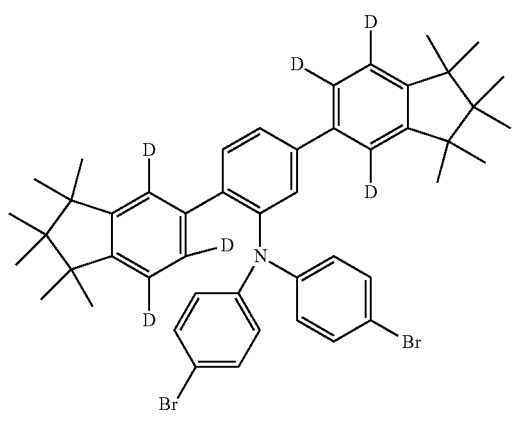
Mon-0407

-continued
BB-1407
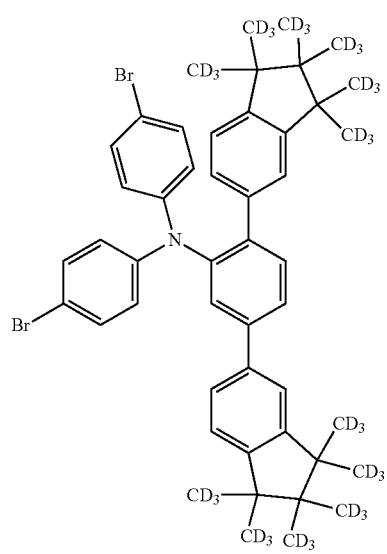
Mon-0408
BB-1408
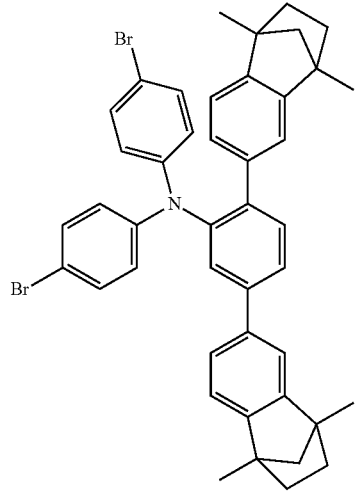
Mon-0409
BB-1409
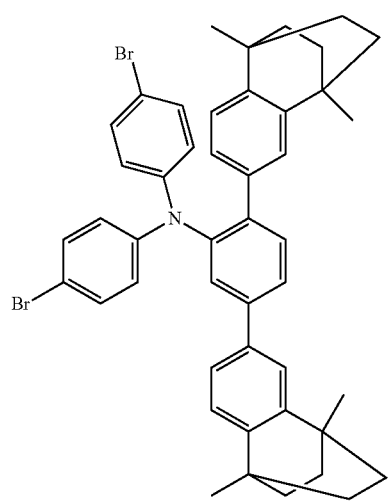
Mon-0410
BB-1410
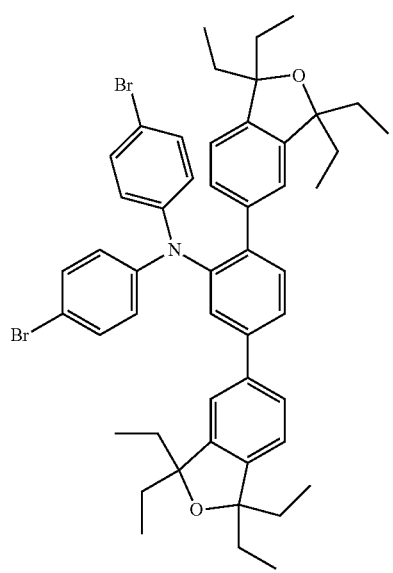
Mon-0411

-continued
BB-1411
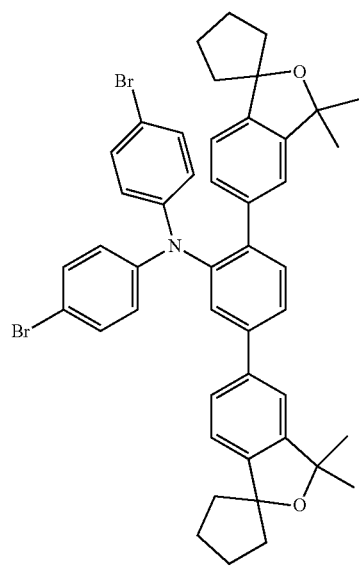
Mon-0412
BB-1412
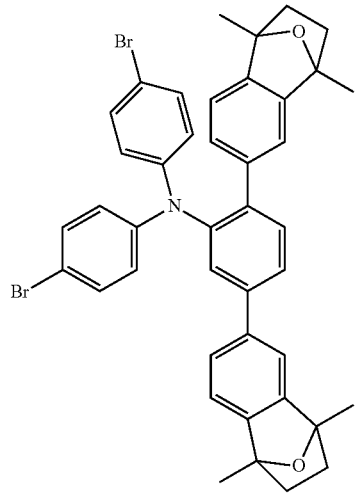
Mon-0413
BB-1413
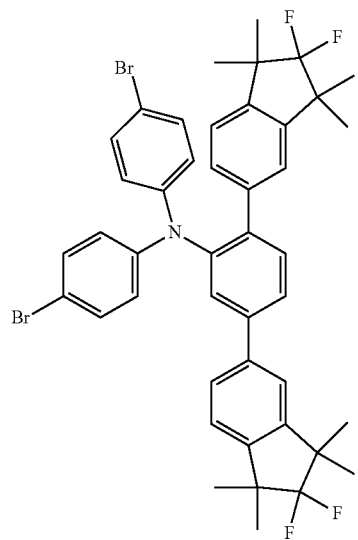
Mon-0414
BB-1414
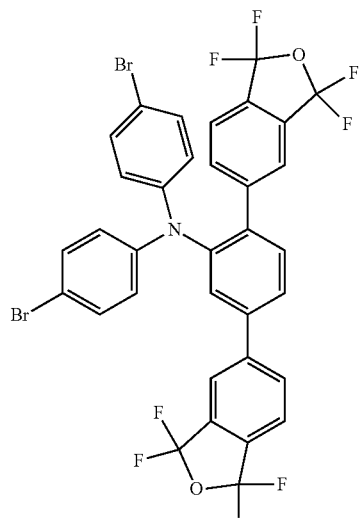
Mon-0415

-continued
BB-1415
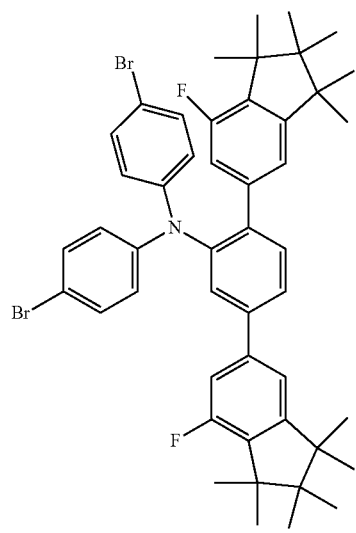
Mon-0416
BB-1416
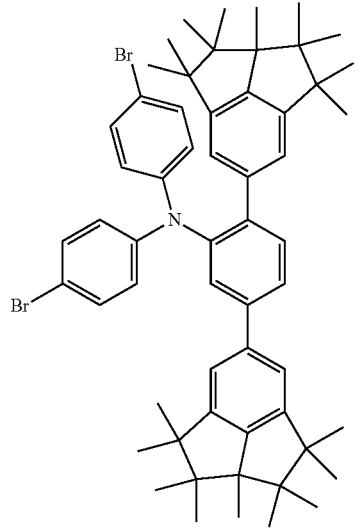
Mon-0417
BB-1417
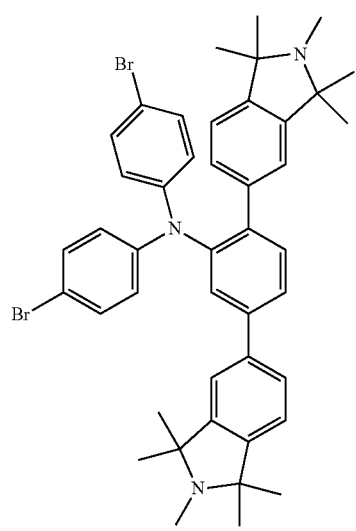
Mon-0418
BB-1418
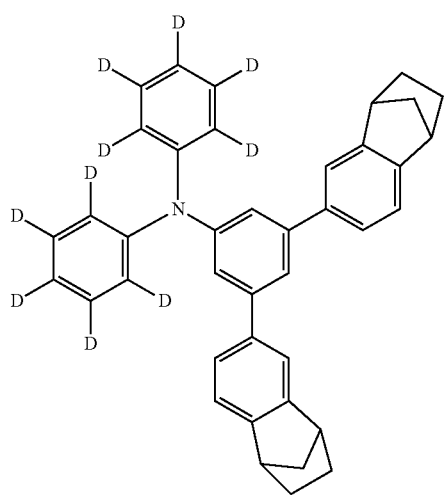
Mon-0419

-continued
BB-1420
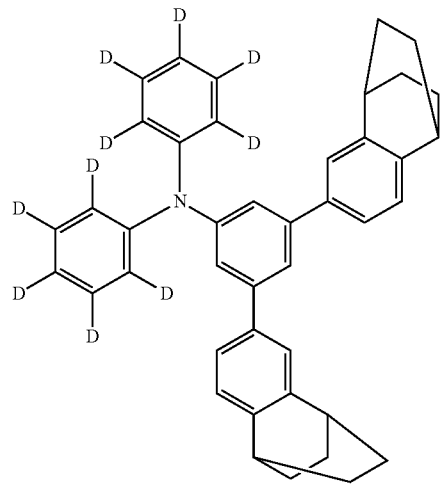
Mon-0421
BB-1421
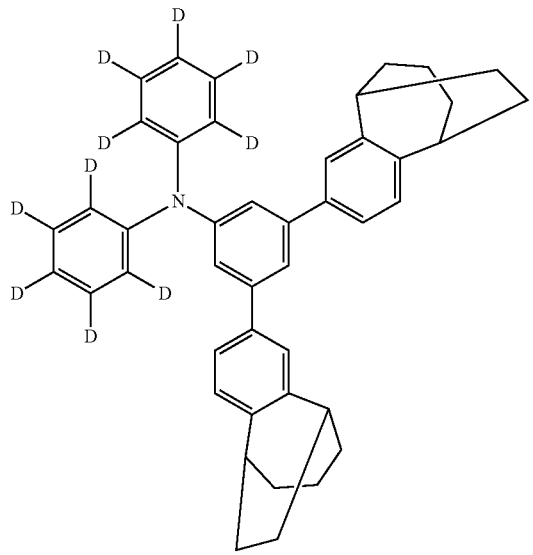
Mon-0422
BB-1422
Mon-0423
BB-1423
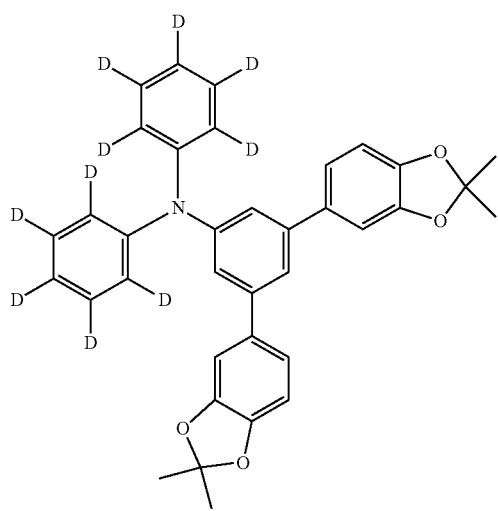
Mon-0424

-continued
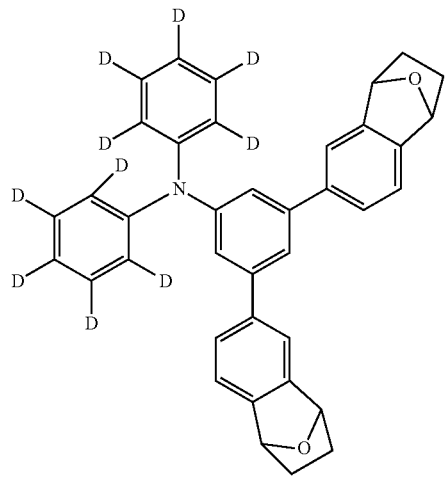
Mon-0425
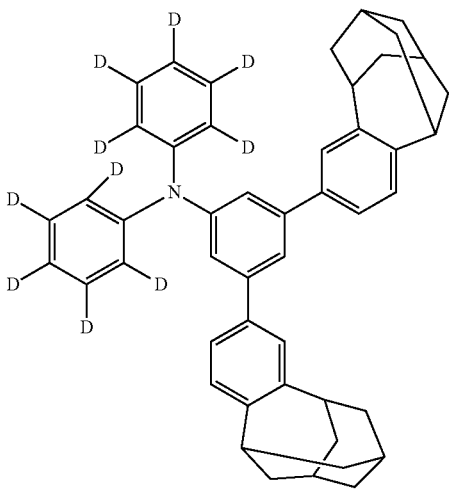
Mon-0426
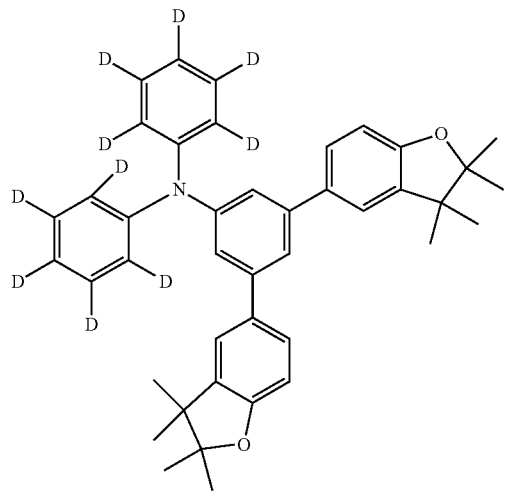
Mon-0427
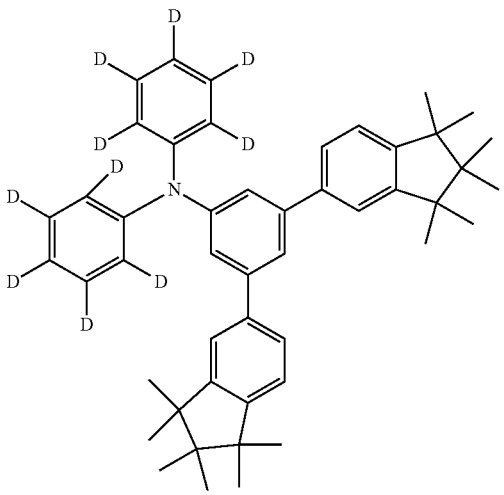
Mon-0428
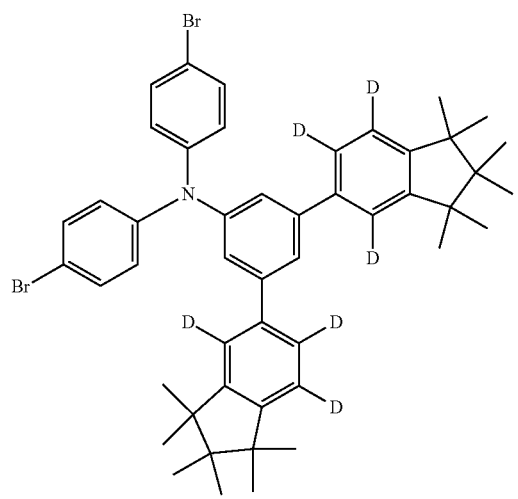
Mon-0429
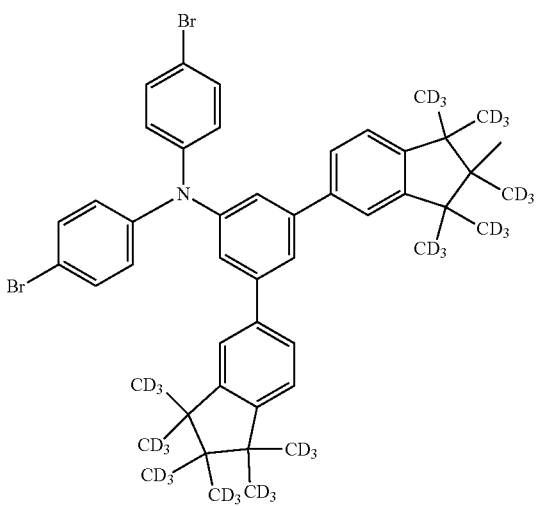
Mon-0430

-continued
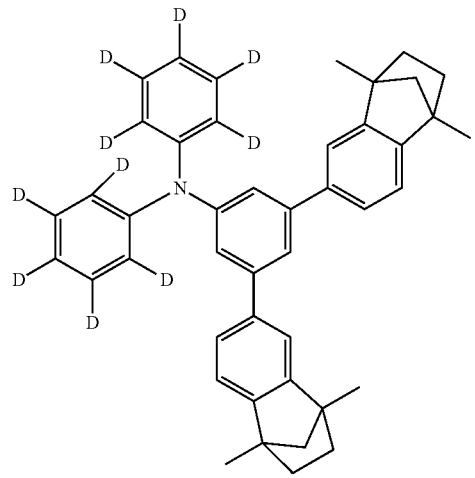
Mon-0431
BB-1430
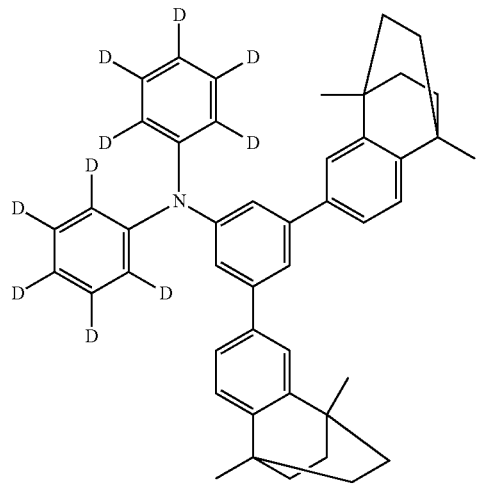
Mon-0432
BB-1431
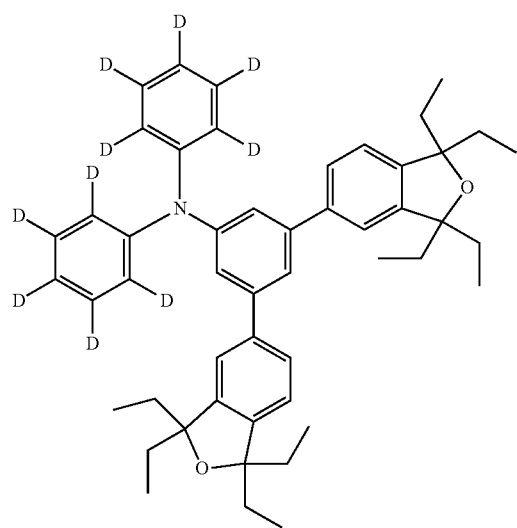
Mon-0433
BB-1432
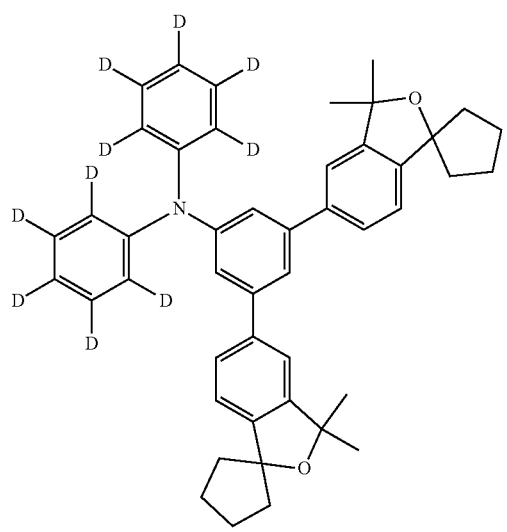
Mon-0434
BB-1433

-continued
BB-1434
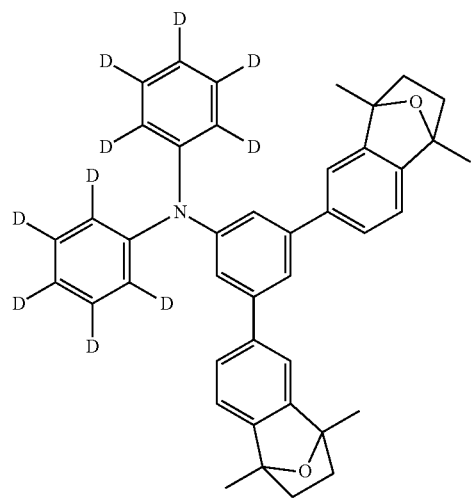
Mon-0435
BB-1435
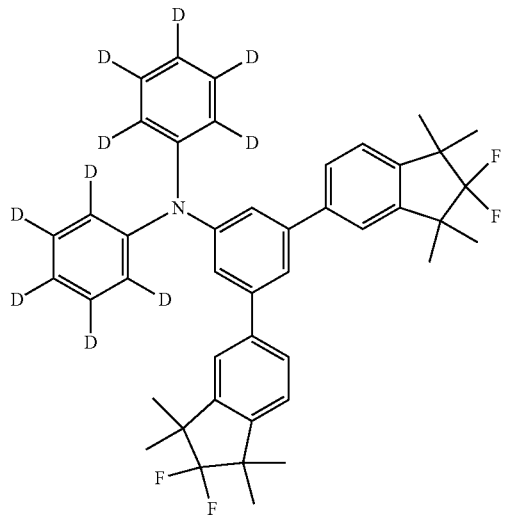
Mon-0436
BB-1436
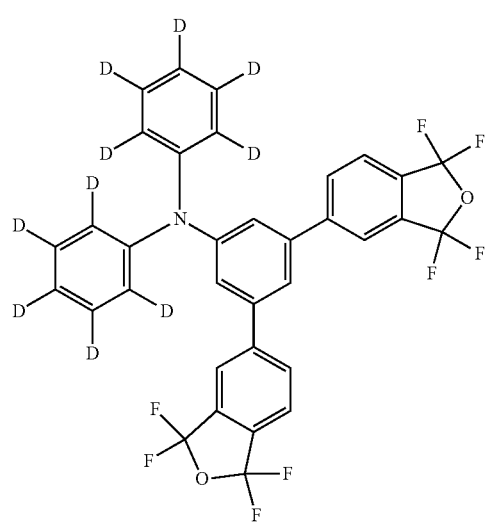
Mon-0437
BB-1437
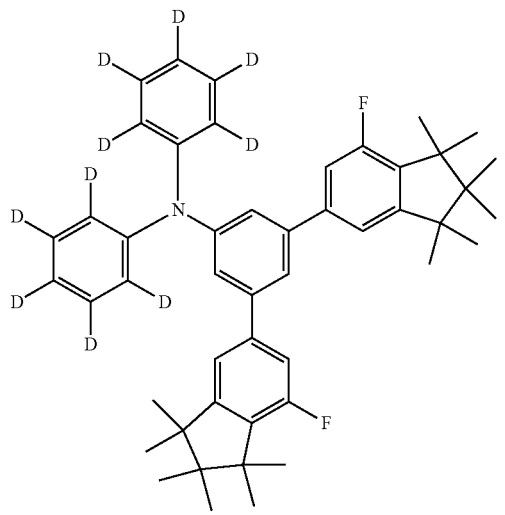
Mon-0438

-continued
BB-1438
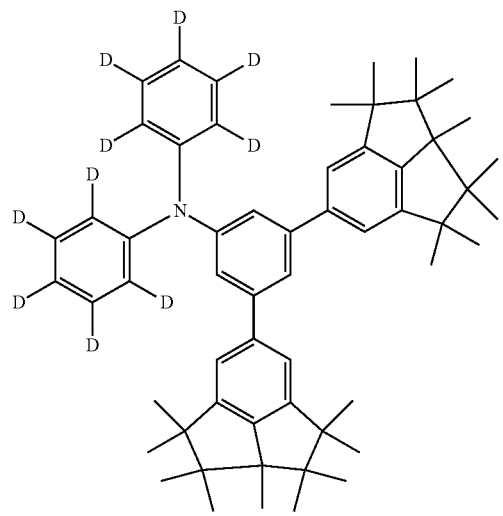
Mon-0439
BB-1439
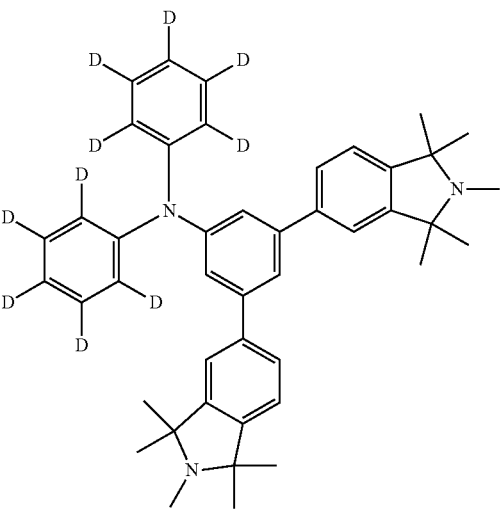
Mon-0440
BB-2001
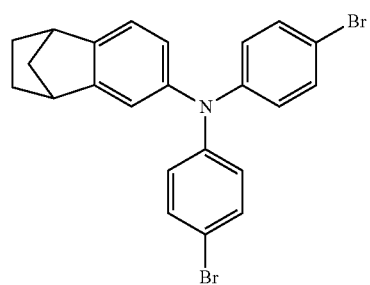
Mon-1001
BB-2002
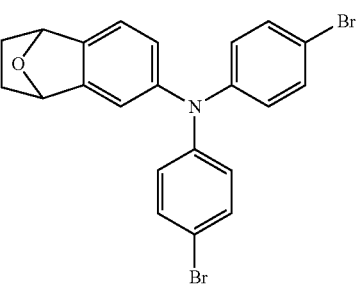
Mon-1002
BB-2003
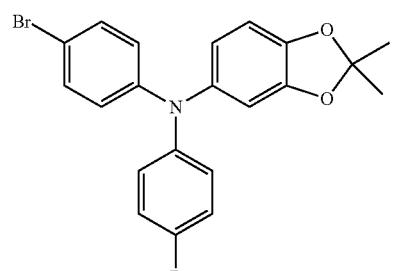
Mon-1003
BB-2004
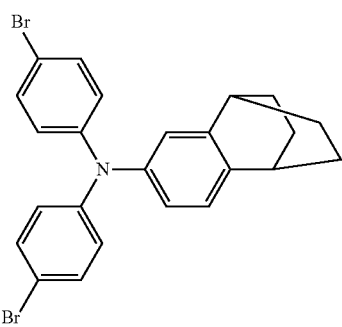
Mon-1004
BB-2005
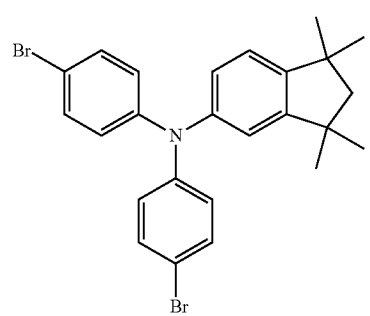
Mon-1005
BB-2006
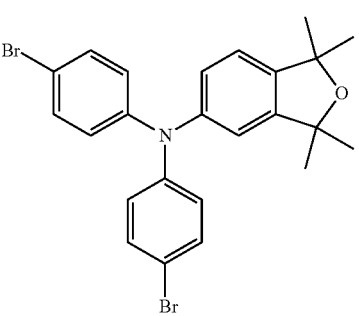
Mon-1006

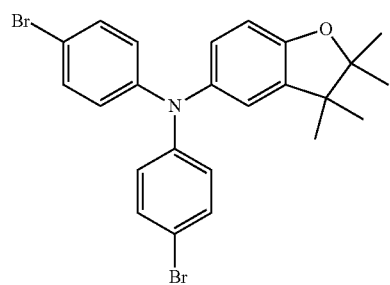
Mon-1007
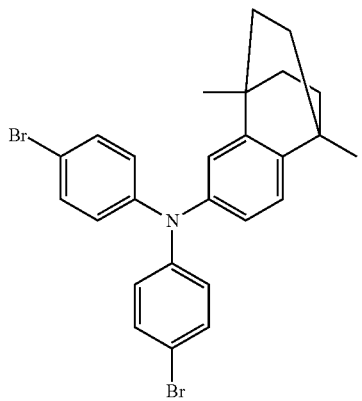
Mon-1008
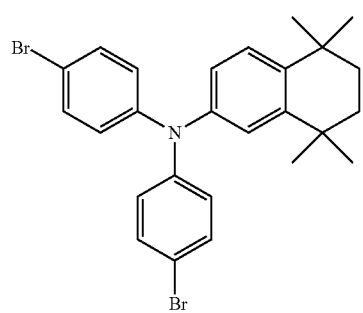
Mon-1009
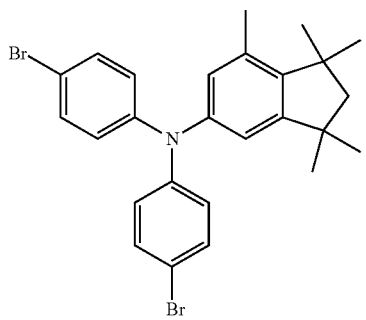
Mon-1010
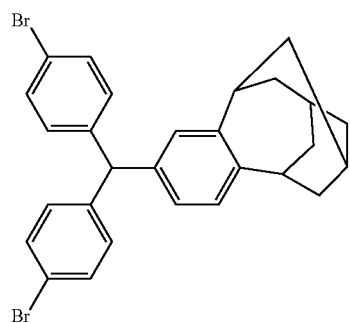
Mon-1011
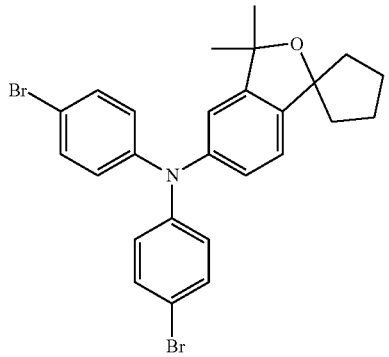
Mon-1012
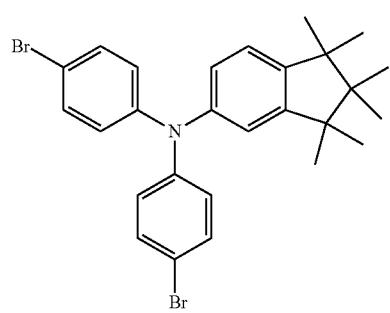
Mon-1013
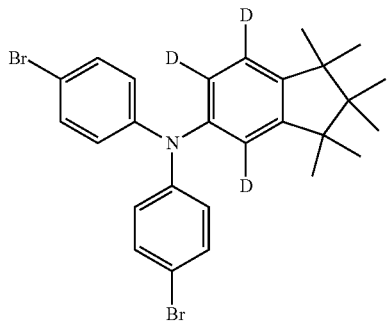
Mon-1014

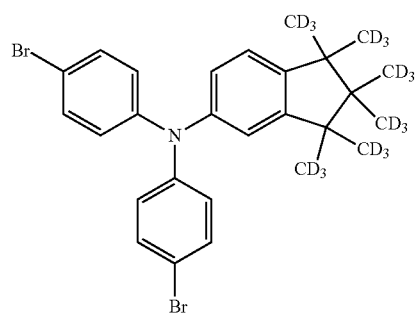
Mon-1015
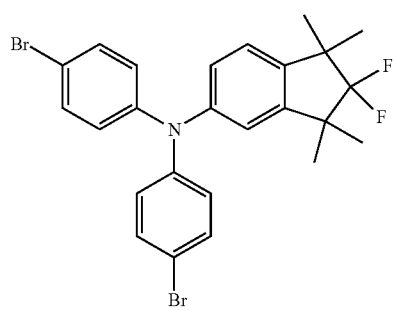
Mon-1016
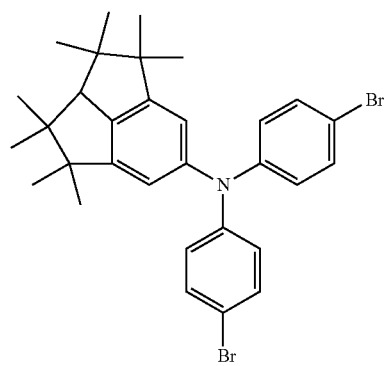
Mon-1017
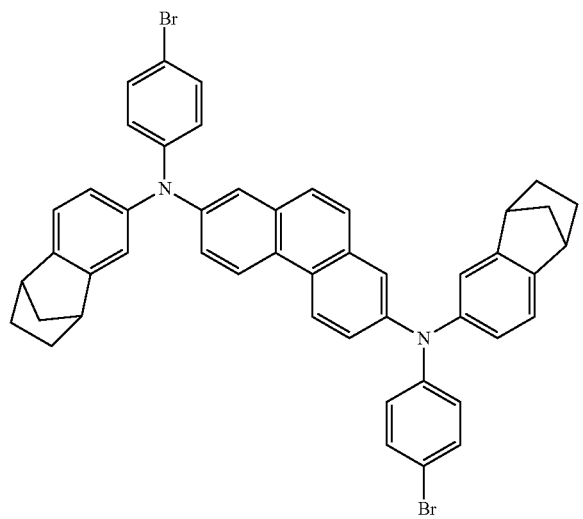
Mon-1019
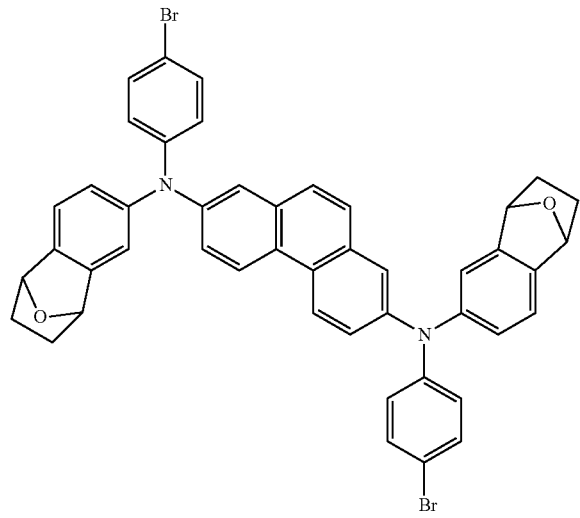
Mon-1020
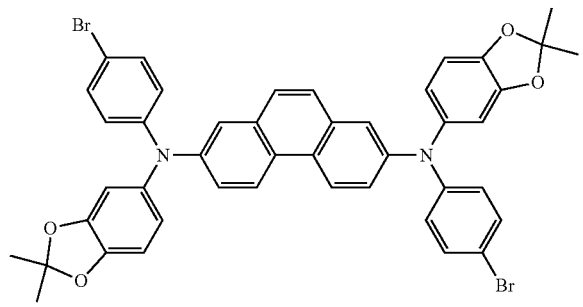
Mon-1021

-continued
BB-2022
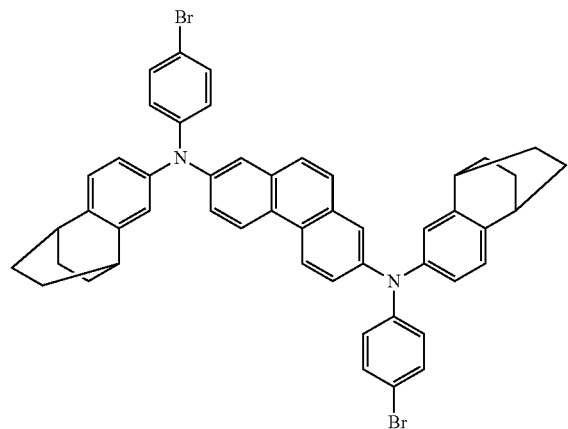
Mon-1022
BB-2023
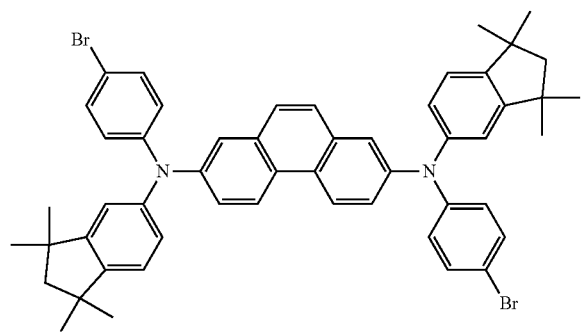
Mon-1023
BB-2024
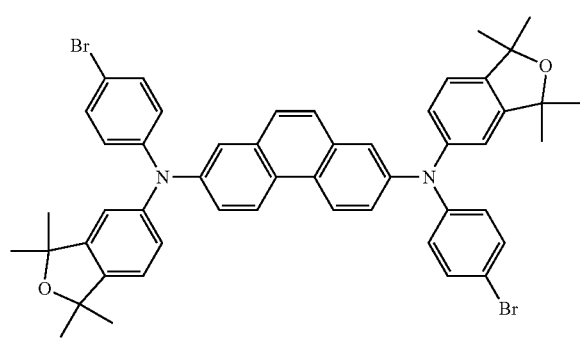
Mon-1024
BB-2025
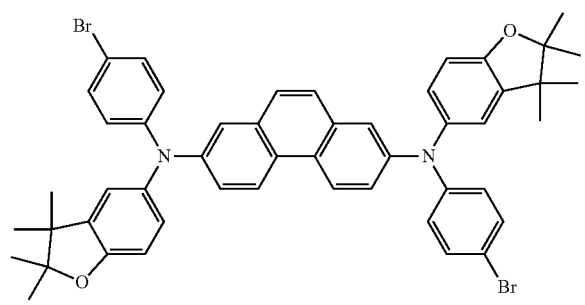
Mon-1025
BB-2026
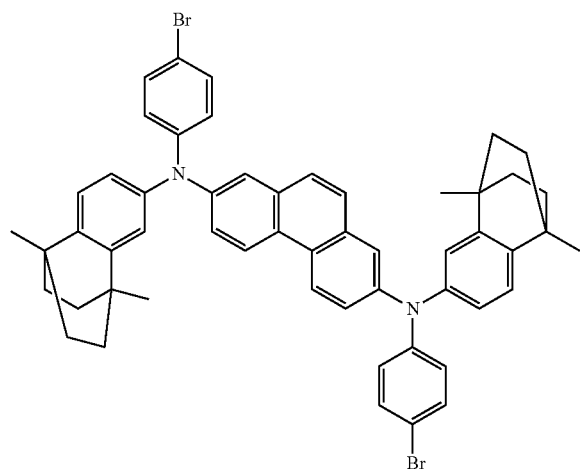
Mon-1026
BB-2027
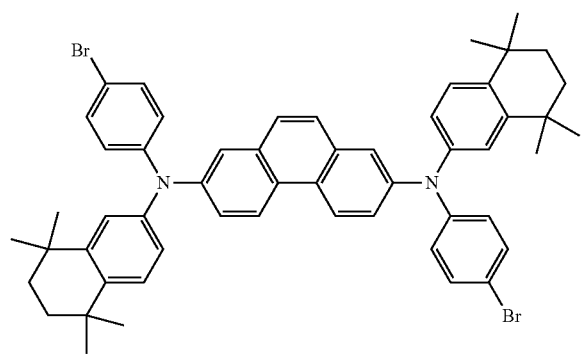
Mon-1027

-continued
BB-2028
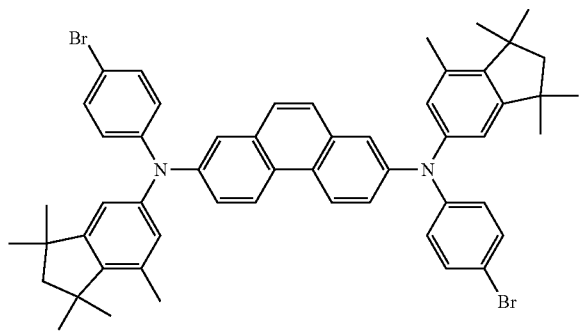
Mon-1028
BB-2029
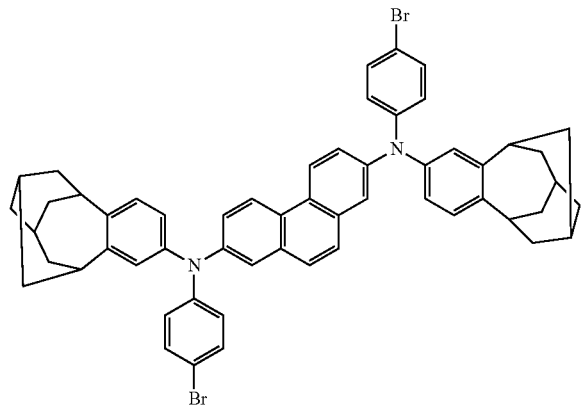
Mon-1029
BB-2030
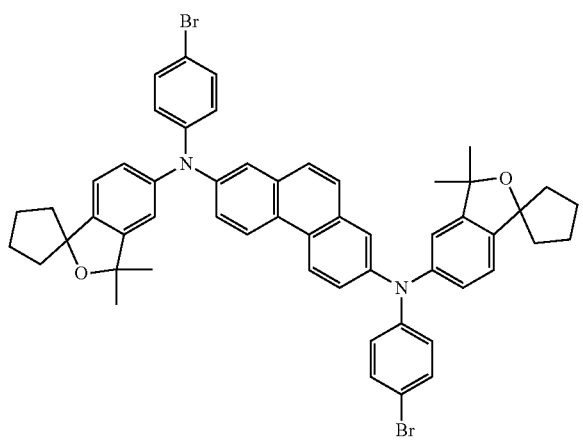
Mon-1030
BB-2031
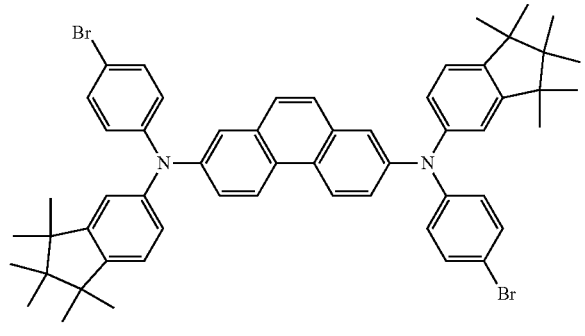
Mon-1031
BB-2032
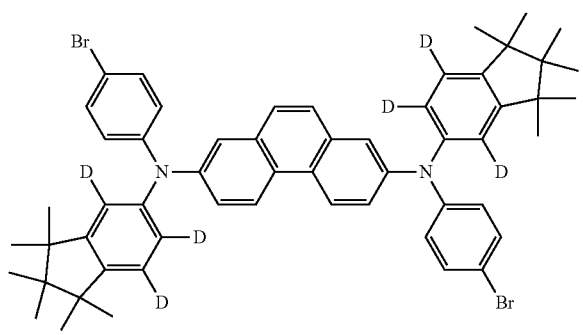
Mon-1032
BB-2033
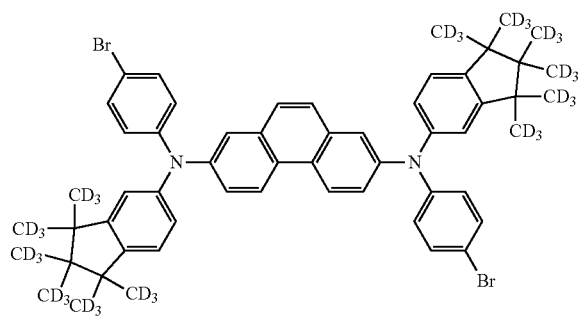
Mon-1033

-continued
BB-2034
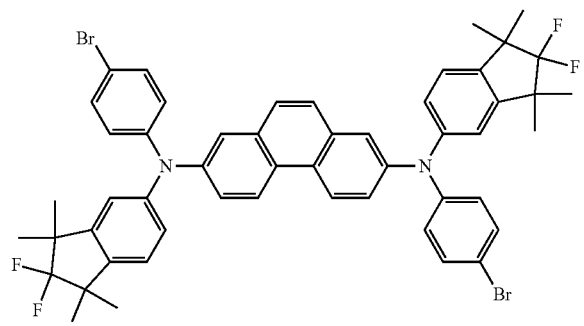
Mon-1034
BB-2036
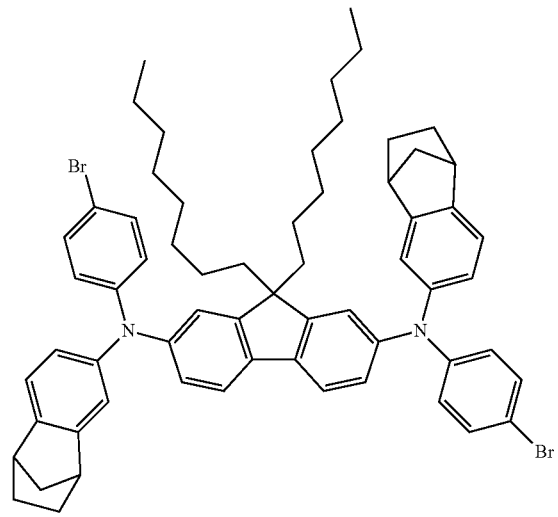
Mon-1036
BB-2037
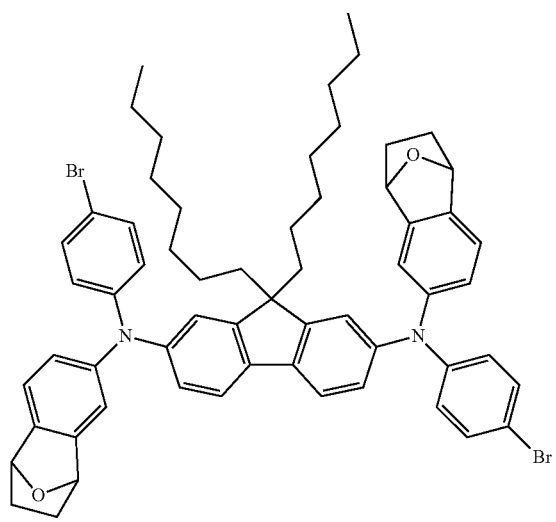
Mon-1037
BB-2038
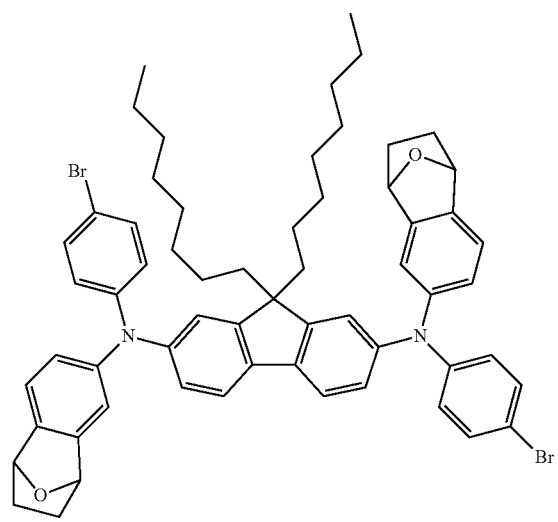
Mon-1038
BB-2039
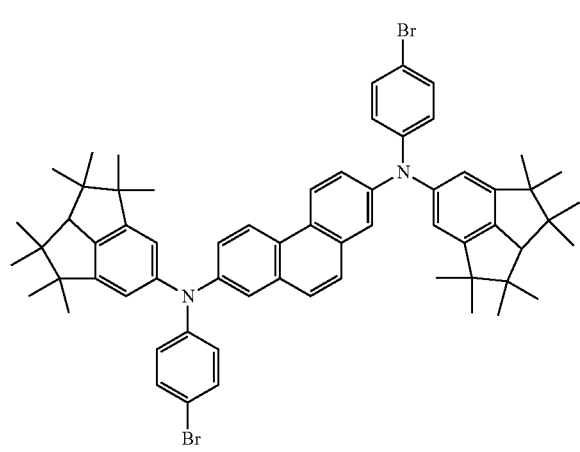
Mon-1039

-continued
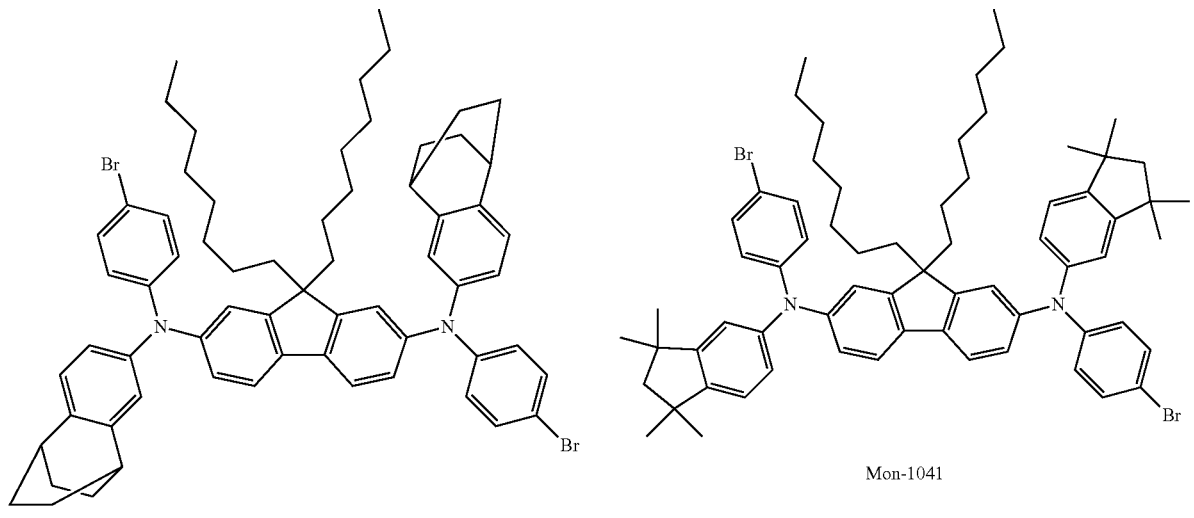
Mon-1040
Mon-1041
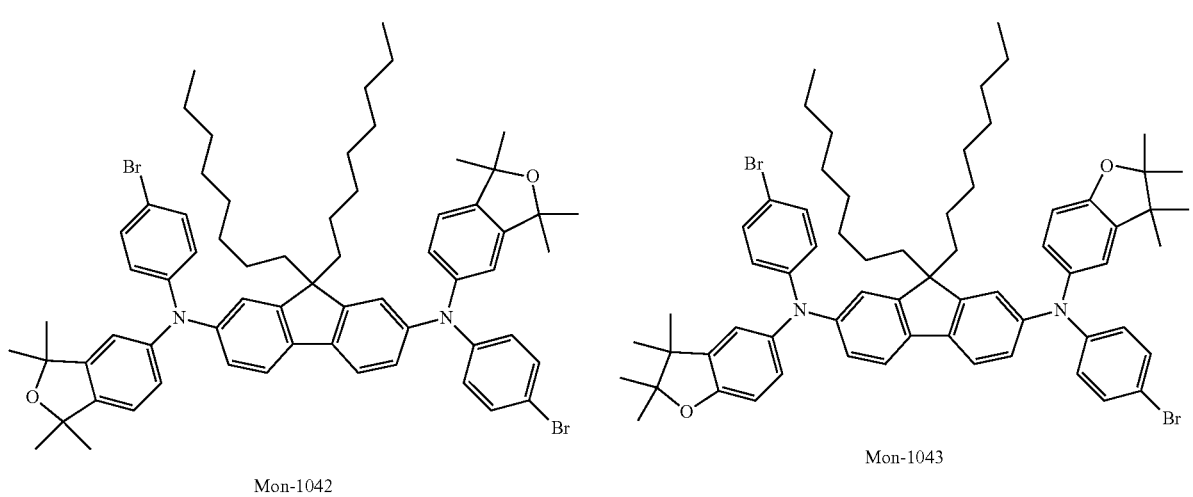
Mon-1042
Mon-1043
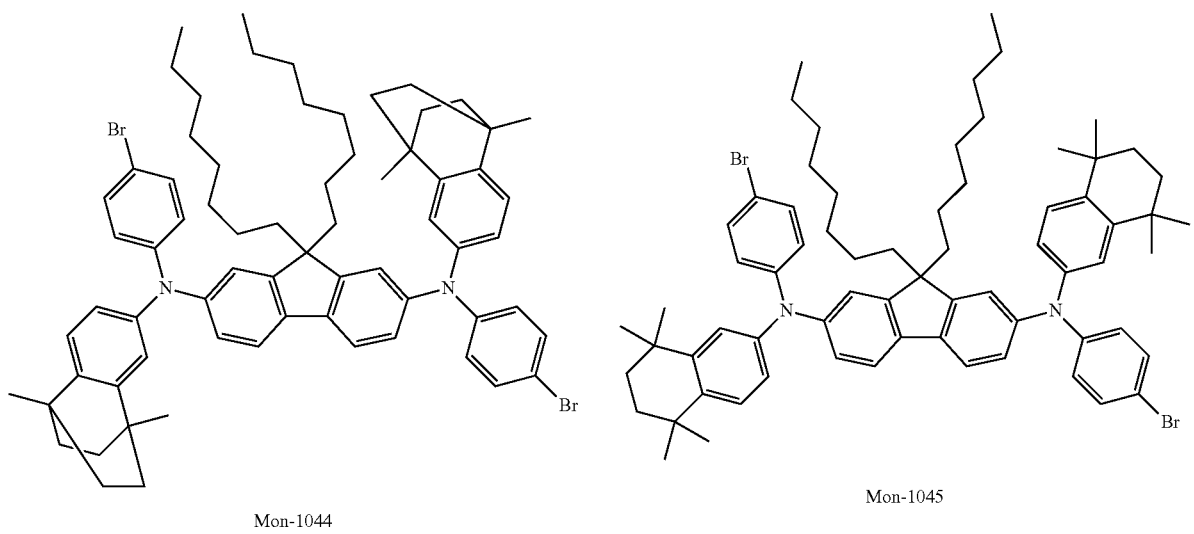
Mon-1044
Mon-1045

-continued
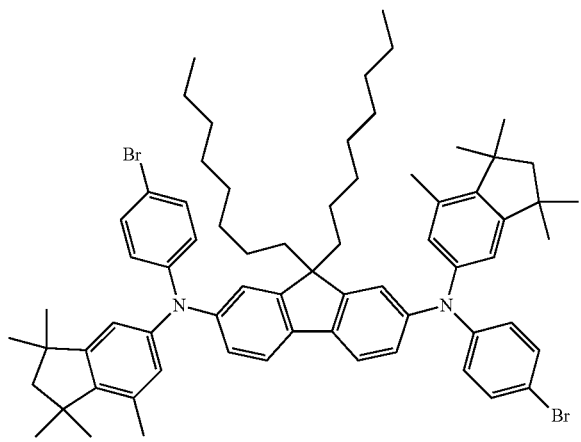
Mon-1046
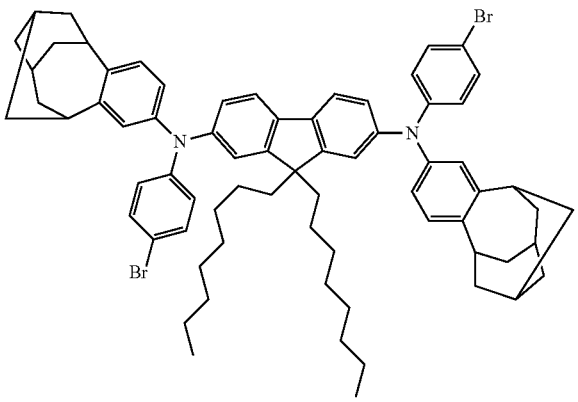
Mon-1047
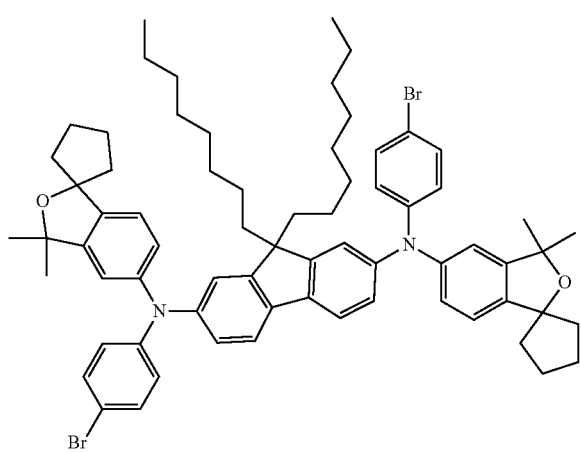
Mon-1048
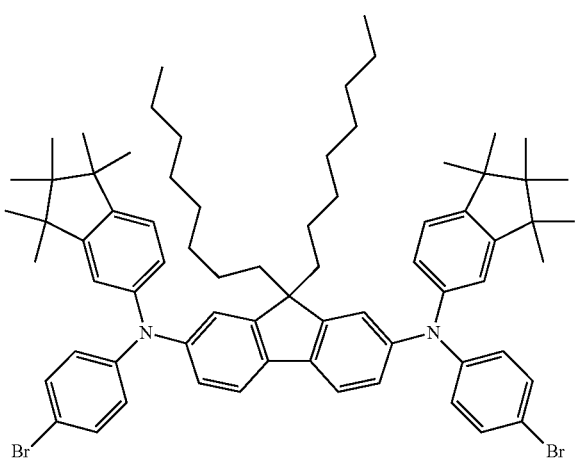
Mon-1049
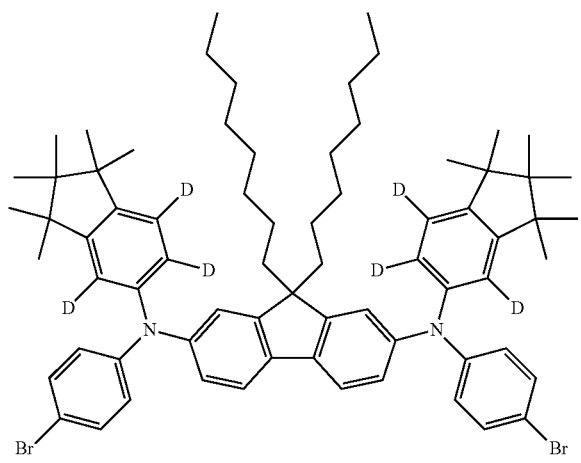
Mon-1050
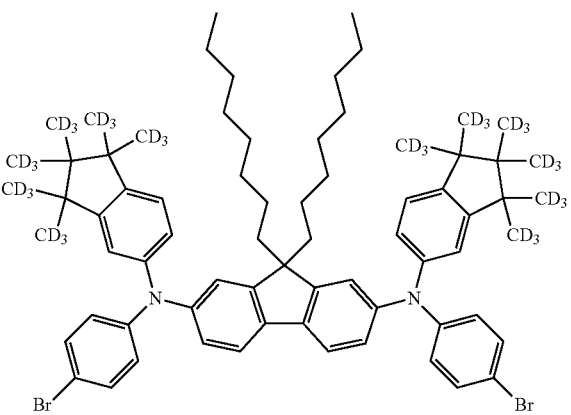
Mon-1051

-continued
BB-2052
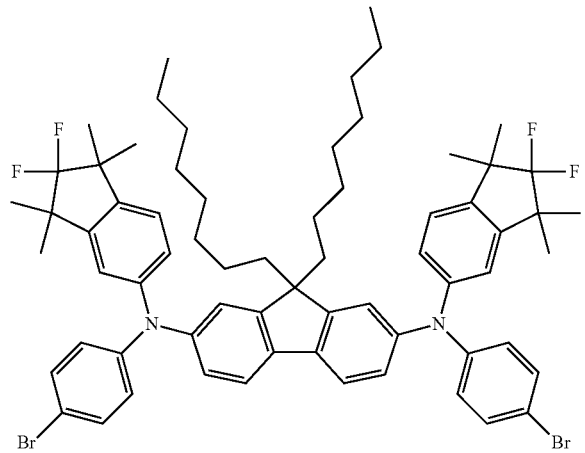
Mon-1052
BB-2053
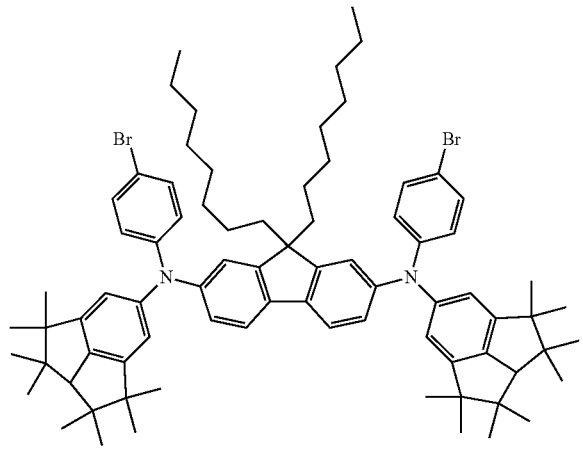
Mon-1053
2) Further Monomers Used:
| Monomer | Structure | Synthesis by publication/CAS number |
|---|---|---|
| MON-01-Br | 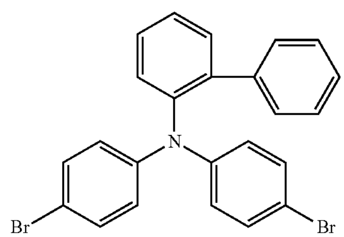 [SMILES: Brc1ccc(N(c2ccc(Br)cc2)c2ccccc2-c2ccccc2)cc1] | WO 2013/156130 |
| MON-01-BE | 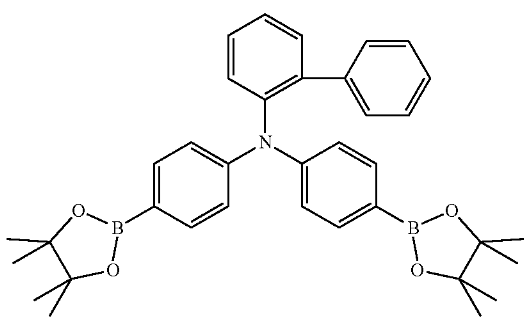 | WO 2013/156130 |
| Mon-02-BE | 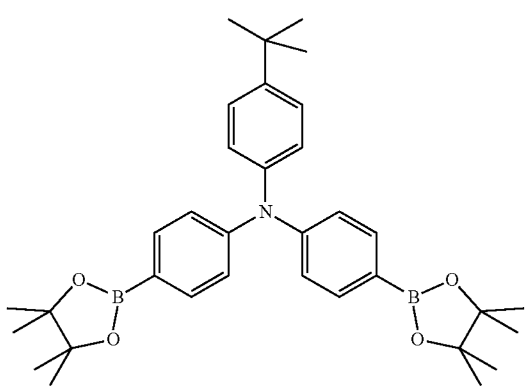 | WO 99/048160 A1 |

-continued

| Monomer | Structure | Synthesis by publication/CAS number |
|---|---|---|
| MON-20-BE | 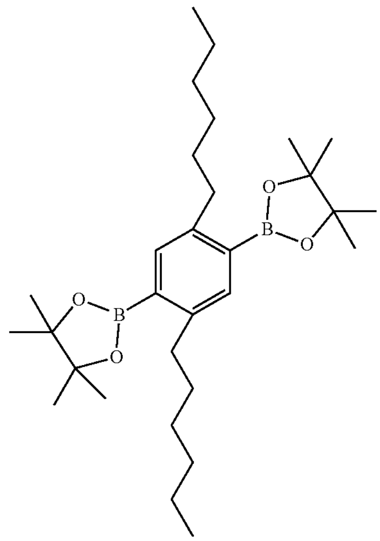 | CAS 374934-77-7 |
| MON-21-BE | 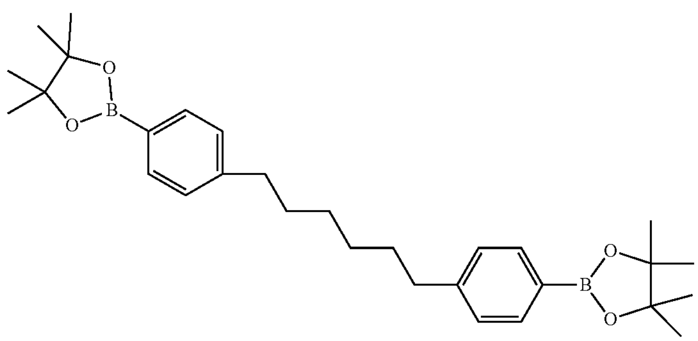 | CAS 1257064-91-7 |
| Mon-22-BE | 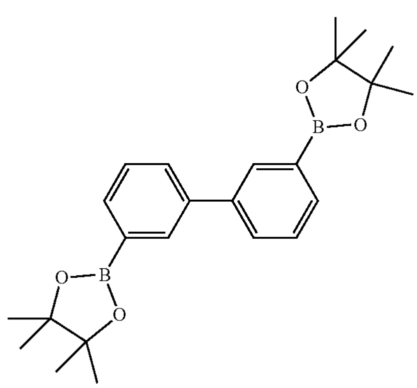 | CAS 850264-92-5 |

-continued
| Monomer | Structure | Synthesis by publication/CAS number |
|---|---|---|
| MON-30-Br | 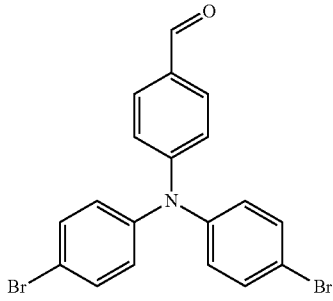 [SMILES: O=Cc1ccc(N(c2ccc(Br)cc2)c2ccc(Br)cc2)cc1] | WO 2010/097155 |
| MON-30-BE | 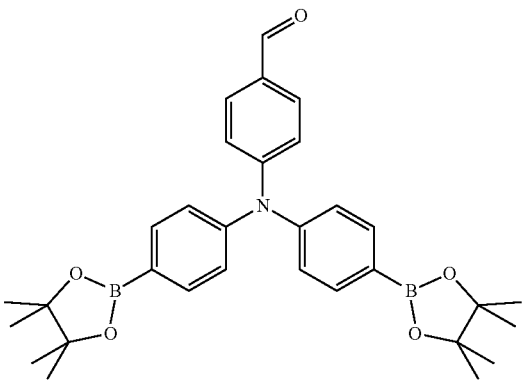 | WO 2010/097155 |
| MON-31-Br | 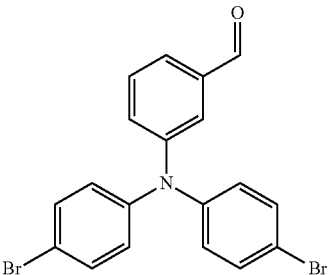 [SMILES: O=Cc1cccc(N(c2ccc(Br)cc2)c2ccc(Br)cc2)c1] | WO 2013/156130 |
| MON-31-BE | 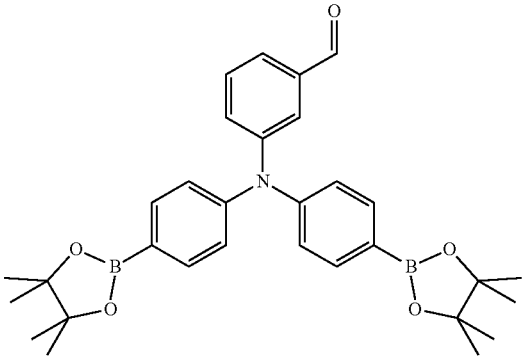 | WO 2013/156130 |

-continued
| Monomer | Structure | Synthesis by publication/CAS number |
|---|---|---|
| MON-32-BE | 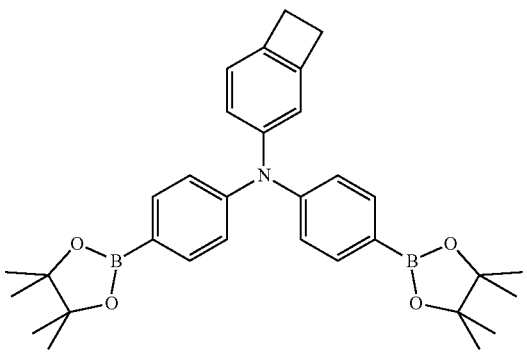 | WO 2009/102027 |
| MON-32-Br | 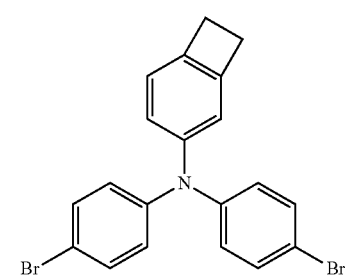 [SMILES: Brc1ccc(N(c2ccc(Br)cc2)c2ccc3c(c2)CC3)cc1] | CAS 852534-20-4 |
| Mon-40-Br | 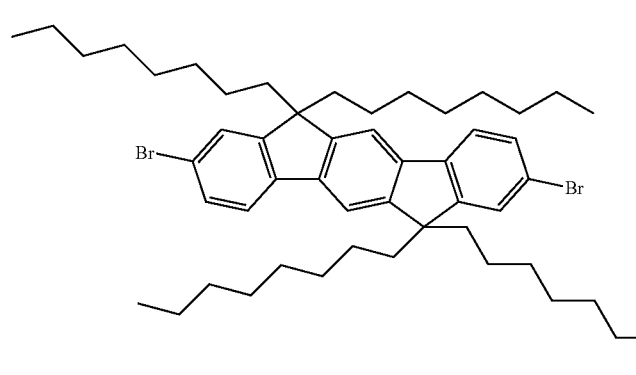 | Macromolecules 2000, 33, 2016-2020 |
| Mon-40-BE | 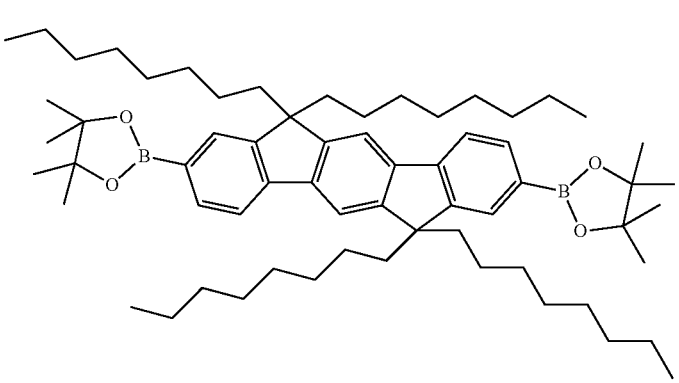 [SMILES: CCCCCCCCC1(CCCCCCCC)c2cc(B3OC(C)(C)C(C)(C)O3)ccc2-c2cc3c(cc21)-c1ccc(B2OC(C)(C)C(C)(C)O2)cc1C3(CCCCCCCC)CCCCCCCC] | CAS 628303-20-8 |

| Monomer | Structure | Synthesis by publication/CAS number |
|---|---|---|
| Mon-41-BE | 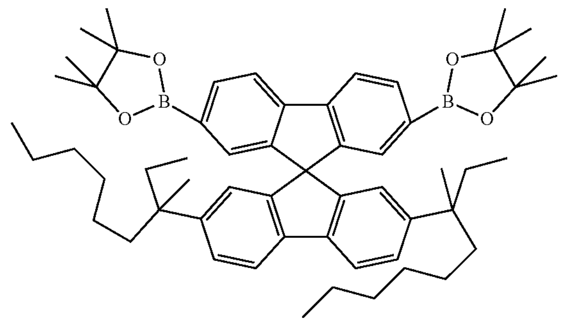 [SMILES: CCCCCCC(C)(CC)c1ccc2c(c1)C1(c3cc(B4OC(C)(C)C(C)(C)O4)ccc3-c3ccc(B4OC(C)(C)C(C)(C)O4)cc31)c1cc(C(C)(CC)CCCCCC)ccc1-2] | WO 2003/020790 |
| Mon-42-BE | 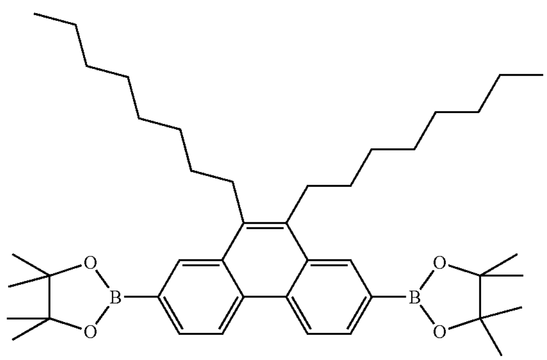 [SMILES: CCCCCCCCc1c(CCCCCCCC)c2cc(B3OC(C)(C)C(C)(C)O3)ccc2c2ccc(B3OC(C)(C)C(C)(C)O3)cc12] | WO 2005/104264 |

3) Synthesis of the Polymers

The comparative polymers V1 and V2 and the inventive polymers Po1 to Po22 are prepared by SUZUKI coupling by the process described in WO 2003/048225 from the monomers disclosed above.

In the preparation of the polymers, the monomers specified below are used in the reaction mixture in the corresponding percentages, as specified below. The polymers V1 and V2 and Po1 to Po22 prepared in this way contain the structural units, after elimination of the leaving groups, in the percentages reported in the table below (percent figures=mol %).

In the case of the polymers which are prepared from monomers having aldehyde groups, the latter are converted to crosslinkable vinyl groups after the polymerization by WITTIG reaction by the process described in WO 2010/097155 (examples with synthesis method on pages 36/37). The polymers listed correspondingly in the table below thus have crosslinkable vinyl groups rather than the aldehyde groups originally present.

The palladium and bromine contents of the polymers are determined by ICP-MS. The values determined are below 10 ppm.

The molecular weights $M_w$ and the polydispersities D are determined by means of gel permeation chromatography (GPC) (model: Agilent HPLC System Series 1100, column: PL-RapidH from Polymer Laboratories; solvent: THF with 0.12% by volume of o-dichlorobenzene; detection: UV and refractive index; temperature: 40° C.). Calibration is effected with polystyrene standards.

Direct Comparisons:

| Polymer | MON A | % | MON B | % | MON C | % | Mw/D |
|---|---|---|---|---|---|---|---|
| V1 | MON-40-Br | 50 | MON-01-BE | 40 | MON-30-BE | 10 | 125 K/2.3 |
| V2 | MON-01-Br | 30 | MON-20-BE | 50 | MON-30-Br | 20 | 65 K/2.7 |
| Po1 | MON-40-BE | 50 | Mon-0032 | 40 | MON-30-Br | 10 | 135 K/2.4 |
| Po2 | Mon-0032 | 30 | MON-20-BE | 50 | MON-30-Br | 20 | 70 K/3.1 |

In addition, the following inventive polymers are prepared using the monomer building blocks Mon-0032, Mon-0033, Mon-0036, Mon-0039, Mon-0042, Mon-0043, Mon-0054, Mon-0084, Mon-0164, Mon-0406, Mon-0410, Mon-0429, Mon-1006, Mon-1013, Mon-1031, Mon-1040, Mon-1041 and Mon-1049 (for structures see table above).

| Polymer | MON A | % | MON B | % | MON C | % | MON D | % | Mw/D |
|---|---|---|---|---|---|---|---|---|---|
| Po3 | MON-40-BE | 50 | Mon-0042 | 40 | MON-30-Br | 10 | | | 150 K/2.3 |
| Po4 | Mon-0054 | 30 | MON-01-BE | 50 | MON-32-BE | 20 | | | 55 K/3.2 |
| Po5 | Mon-0032 | 30 | MON-20-BE | 50 | MON-32-Br | 20 | | | 80 K/4.1 |
| Po6 | MON-041-BE | 40 | Mon-1031 | 50 | MON-31-BE | 20 | | | 180 K/2.5 |
| Po7 | Mon-1013 | 20 | MON-21-BE | 50 | MON-01-Br | 20 | MON-30-Br | 10 | 45 K/3.6 |
| Po8 | MON-40-Br | 25 | MON-22-BE | 50 | Mon-0406 | 25 | | | 120 K/4.5 |
| Po9 | MON-40-BE | 50 | Mon-0429 | 40 | MON-30-Br | 10 | | | 125 K/2.1 |
| Po10 | MON-40-BE | 50 | Mon-0164 | 40 | MON-30-Br | 10 | | | 95 K/2.3 |
| Po11 | MON-41-BE | 50 | Mon-0084 | 40 | MON-032-Br | 10 | | | 90 K/2.6 |
| Po12 | MON-40-BE | 50 | Mon-0036 | 40 | MON-31-Br | 10 | | | 105 K/3.0 |
| Po13 | Mon-1041 | 50 | MON-30-BE | 50 | | | | | 80 K/2.9 |
| Po14 | Mon-1049 | 50 | MON-01-BE | 30 | MON-30-BE | 20 | | | 65 K/2.8 |
| Po15 | Mon-1040 | 50 | MON-02-BE | 30 | MON-32-BE | 20 | | | 55 K/4.2 |
| Po16 | MON-042-BE | 50 | Mon-1006 | 30 | MON-31-Br | 20 | | | 85 K/2.5 |
| Po17 | Mon-0406 | 30 | Mon-0410 | 20 | MON-01-BE | 30 | MON-30-BE | 20 | 50 K/3.1 |
| Po18 | MON-40-BE | 50 | Mon-0043 | 40 | MON-032-Br | 10 | | | 105 K/3.0 |
| Po19 | MON-42-BE | 50 | Mon-0033 | 30 | MON-032-Br | 20 | | | 95 K/2.4 |
| Po20 | MON-041-BE | 40 | Mon-0039 | 50 | MON-30-BE | 10 | | | 75 K/2.6 |
| Po21 | Mon-0032 | 40 | MON-20-BE | 50 | MON-30-Br | 10 | | | 85 K/2.6 |
| Po22 | Mon-0032 | 30 | MON-01-BE | 50 | MON-30-Br | 20 | | | 50 K/3.8 |

B) Examples of Improved Dissolution Characteristics

Concentration of the solutions: 7 mg/ml, solvent: 3-phenoxytoluene

| | V1 | Po1 | V2 | Po2 |
|---|---|---|---|---|
| Time required for complete dissolution (min) | 47 | 38 | 52 | 42 |
| Δ (min) | | 9 | | 10 |

The time before the total amount of polymer has gone into solution is about 20% shorter for the polymers of the invention.

C) Device Examples

The polymers of the invention can be processed from solution. Solution-processed OLEDs are much more easily producible than vacuum-processed OLEDs and nevertheless have good properties.

There are already many descriptions of the production of such solution-based OLEDs in the literature, for example in WO 2004/037887 and WO 2010/097155. The process is matched to the circumstances described hereinafter (variation in layer thickness, materials). The inventive polymers are used in two different layer sequences:

Structure A is as follows:
substrate,
ITO (50 nm),
hole injection layer (HIL) (20 nm),
hole transport layer (HTL) (20 nm),
emission layer (EML) (60 nm),
hole blocker layer (HBL) (10 nm),
electron transport layer (ETL) (40 nm),
cathode (Al) (100 nm).
Structure B is as follows:
substrate,
ITO (50 nm),
hole injection layer (HIL) (20 nm),
hole transport layer (HTL) (20 nm),
emission layer (EML) (30 nm), hole blocker layer (HBL) (10 nm)
electron transport layer (ETL) (40 nm),
cathode (Al) (100 nm).

Substrates used are glass plates coated with structured ITO (indium tin oxide) of thickness 50 nm. The hole injection layer is applied by means of spin-coating in an inert atmosphere. For this purpose, a hole-transporting crosslinkable polymer and a p-doping salt are dissolved in toluene. Corresponding materials have been described in WO 2016/107668, WO 2013/081052 and EP2325190 inter alia. For a resulting layer thickness of 20 nm, a solids content of 6 mg/ml is used. The layer is subsequently baked on a hotplate at 200° C. in an inert gas atmosphere for 30 minutes. The hole transport and emission layers are then applied to these coated glass plates.

The hole transport layers used are the compounds of the invention and comparative compounds, each dissolved in toluene. The solids content of these solutions is 5 mg/ml, since layer thicknesses of 20 nm are to be achieved by means of spin-coating. The layers are spun on in an inert gas atmosphere and baked on a hotplate at 220° C. for 30 minutes.

The emission layer for structure A is composed of the host materials H2 and H3 and the emitting dopant D2. All three materials are present in the emission layer in a proportion by weight of 30% H2, 55% H3 and 15% D2. The mixture for the emission layer is dissolved in toluene. The solids content of this solution is 18 mg/ml, since layer thicknesses of 60 nm are to be achieved by means of spin-coating. The layers are spun on in an inert gas atmosphere and baked at 150° C. for 10 minutes.

The emission layer for structure B is composed of the host material H1 and the emitting dopant D1. The two materials are present in the emission layer in a proportion by weight of 92% H1 and 8% D1. The mixture for the emission layer is dissolved in toluene. The solids content of this solution is 9 mg/ml, since layer thicknesses of 30 nm are to be achieved by means of spin-coating. The layers are spun on in an inert gas atmosphere and baked at 150° C. for 10 minutes.

The materials used in the present case are shown in Table C1.

TABLE C1

Structural formulae of the materials used in the emission layer

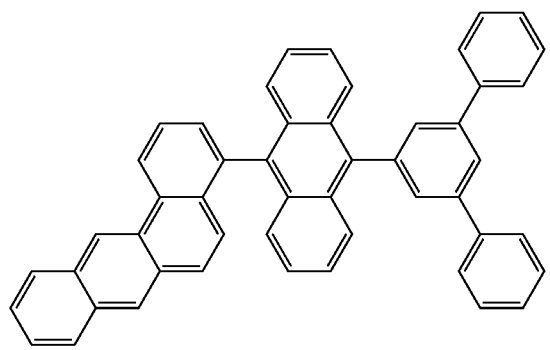 [SMILES: c1ccc(-c2cc(-c3ccccc3)cc(-c3c4ccccc4c(-c4cccc5c4ccc4cc6ccccc6cc45)c4ccccc34)c2)cc1]

H1

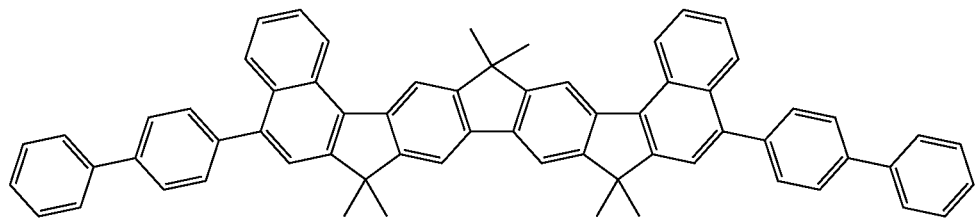 [SMILES: CC1(C)c2cc3c(cc2-c2cc4c(cc21)-c1c(cc(-c2ccc(-c5ccccc5)cc2)c2ccccc12)C4(C)C)C(C)(C)c1cc(-c2ccc(-c4ccccc4)cc2)c2ccccc2c1-3]

D1

TABLE C1-continued
Structural formulae of the materials used in the emission layer
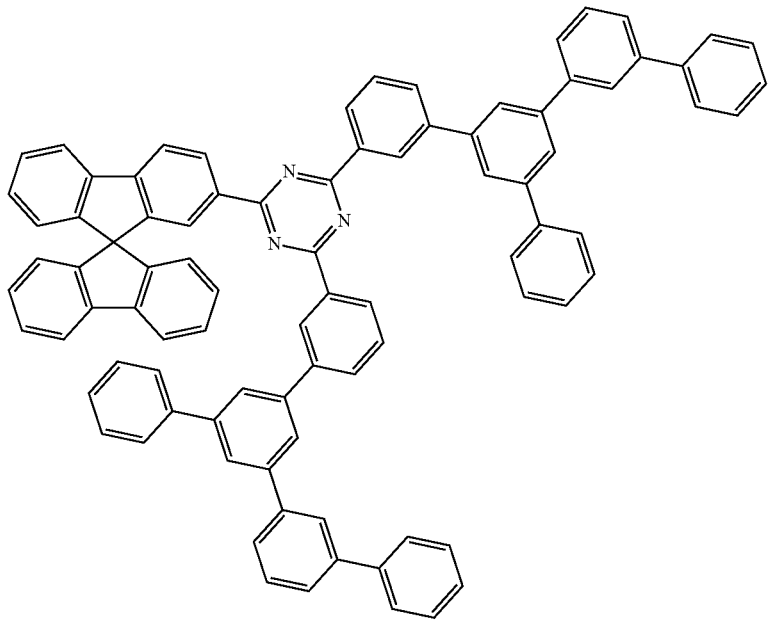 [SMILES: c1ccc(-c2cccc(-c3cc(-c4ccccc4)cc(-c4cccc(-c5nc(-c6cccc(-c7cc(-c8ccccc8)cc(-c8cccc(-c9ccccc9)c8)c7)c6)nc(-c6ccc7c(c6)C6(c8ccccc8-c8ccccc86)c6ccccc6-7)n5)c4)c3)c2)cc1]
H2
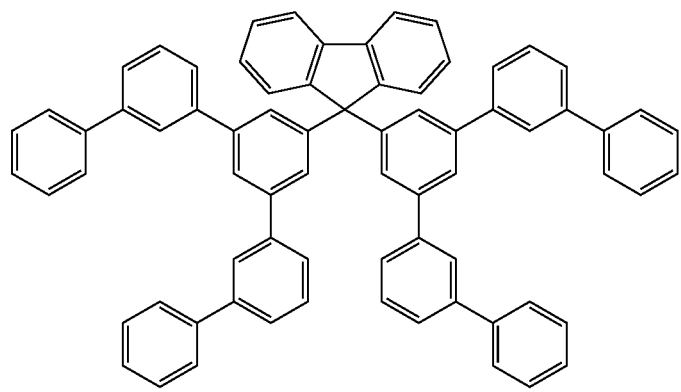 [SMILES: c1ccc(-c2cccc(-c3cc(-c4cccc(-c5ccccc5)c4)cc(C4(c5cc(-c6cccc(-c7ccccc7)c6)cc(-c6cccc(-c7ccccc7)c6)c5)c5ccccc5-c5ccccc54)c3)c2)cc1]
H3
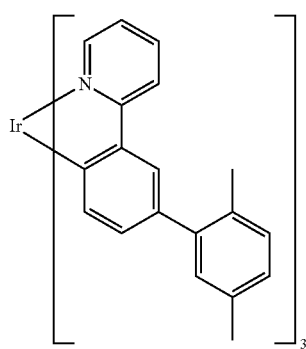
D2

The materials for the hole blocker layer and electron transport layer are applied by thermal vapour deposition in a vacuum chamber and are shown in Table C2. The hole blocker layer consists of ETM1. The electron transport layer consists of the two materials ETM1 and ETM2, which are blended by co-evaporation in a proportion by volume of 50% each.

TABLE C2

HBL and ETL materials used

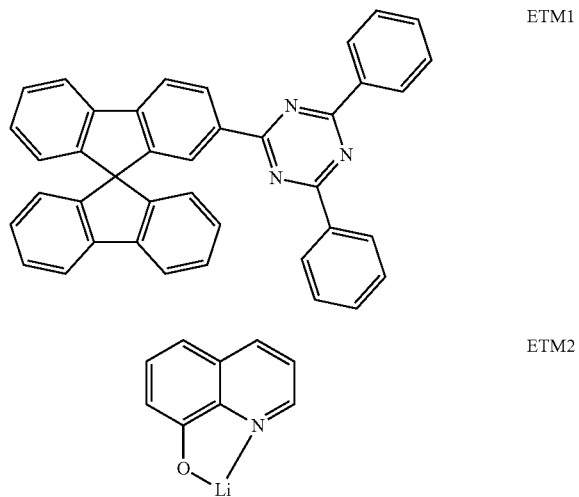

ETM1

ETM2

The cathode is formed by the thermal evaporation of an aluminium layer of thickness 100 nm.

TABLE C3a

Properties of the OLEDs

| Example | HTL polymer | Component structure | Efficiency at 1000 cd/m² % EQE | Voltage at 1000 cd/m² [V] | LD80 at 10 000 cd/m² [h] |
|---|---|---|---|---|---|
| C01 | V1 | A | 18.2 | 4.8 | 552 |
| C03 | Po1 | A | 18.6 | 4.8 | 764 |

TABLE C3b

Properties of the OLEDs

| Example | HTL polymer | Component structure | Efficiency at 1000 cd/m² % EQE | LD80 at 1000 cd/m² [h] |
|---|---|---|---|---|
| C02 | V2 | B | 7.0 | 204 |
| C04 | Po2 | B | 7.1 | 223 |

As shown by the results in Tables C3a and C3b, the polymers of the invention, when used as hole transport layer in green-phosphorescing and blue-fluorescing OLEDs, result in improvements over the prior art, in particular in relation to lifetime, efficiency and voltage.

TABLE C3c

Properties of the OLEDs

| Example | HTL polymer | Component structure | Efficiency at 1000 cd/m² % EQE | Voltage at 1000 cd/m² [V] | LD80 at 10 000 cd/m² [h] | LD80 at 1000 cd/m² [h] |
|---|---|---|---|---|---|---|
| C05 | Po21 | B | 7.5 | — | — | 236 |
| C06 | Po5 | B | 7.6 | — | — | 210 |
| C07 | Po22 | A | 17.7 | 3.2 | 537 | — |

The OLEDs are characterized in a standard manner. For this purpose, the electroluminescence spectra, current-voltage-luminance characteristics (IUL characteristics) assuming Lambertian radiation characteristics and the (operating) lifetime are determined. The IUL characteristics are used to determine parameters, for example the external quantum efficiency (in %) at a particular brightness. LD80 @ 1000 cd/m is the lifetime until the OLED, given a starting brightness of 1000 cd/m, has dropped to 80% of the starting intensity, i.e. to 800 cd/m.

The properties of the different OLEDs are summarized in Tables C3a, C3b and C3c.

Examples C01 and C02 are comparative examples; all the other examples show properties of OLEDs comprising hole transport polymers of the invention. Blue- and green-emitting OLEDs comprising the materials of the invention as HTL are produced.

Table 3c shows the efficiency and lifetime of OLEDs comprising the inventive polymers Po5, Po21 and Po22. The polymers mentioned achieve good results for these parameters.

The further polymers Po3, Po4 and Po6-Po20 too can be used in the same way as shown above to produce blue-fluorescing or green-phosphorescing OLEDs. These also have good properties, especially good lifetime and efficiency.

In addition, it has been found that polymers containing structural units having one or more $R^1$ groups, especially alkyl groups, as substituents on the ring system consisting of the U groups achieve better properties of the OLEDs than polymers containing structural units unsubstituted on the ring system consisting of the U groups.

The invention claimed is:

1. A polymer comprising at least one structural unit of formula (I):

(I)

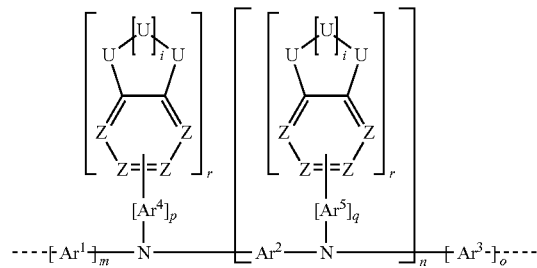

wherein

U is the same or different in each instance and is $C(R^1)_2$, $CR^1=CR^1$, $Si(R^1)_2$, O, or S, wherein the groups $CR^1=CR^1$, O, and S are not bonded directly to one another;

Z is the same or different in each instance and is N or $CR^2$ when no group is bonded thereto, and is C when a group is bonded thereto;

$Ar^1$, $Ar^2$, $Ar^3$, $Ar^4$, and $Ar^5$
are the same or different and are selected from the group consisting of heteroaromatic ring systems, which have 5 to 40 aromatic ring atoms and which are optionally substituted by one or more $R^3$ radicals, and aromatic ring systems which have 6 to 40 aromatic ring atoms and are optionally substituted by one or more $R^3$ radicals;

$R^1$ is the same or different in each instance and is selected from the group consisting of H, D, F, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; wherein the alkyl, alkoxy, alkenyl, and alkynyl groups and the aromatic ring systems and heteroaromatic ring systems are each optionally substituted by one or more $R^4$ radicals; and wherein one or more $CH_2$ groups in the alkyl, alkoxy, alkenyl, and alkynyl groups are optionally replaced by $-R^4C=CR^4-$, $-C\equiv C-$, $Si(R^4)_2$, $C=O$, $C=NR^4$, $-C(=O)O-$, $-C(=O)NR4-$, NR4, $P(=O)(R^4)$, $-O-$, $-S-$, SO, or SO2;

$R^2$ and $R^3$
are the same or different in each instance and are selected from the group consisting of H, D, F, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl, or alkoxy groups having 1 to 20 carbon atoms, branched or cyclic alkyl or alkoxy groups having 3 to 20 carbon atoms, alkenyl, or alkynyl groups having 2 to 20 carbon atoms, aromatic ring systems having 6 to 40 aromatic ring atoms, and heteroaromatic ring systems having 5 to 40 aromatic ring atoms; wherein two or more $R^1$ or $R^2$ or $R^3$ radicals are optionally joined to one another and optionally define a ring; wherein the alkyl, alkoxy, alkenyl, and alkynyl groups and the aromatic ring systems and heteroaromatic ring systems are each optionally substituted by one or more $R^4$ radicals; and wherein one or more $CH_2$ groups in the alkyl, alkoxy, alkenyl, and alkynyl groups are optionally replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, SO, or SO2;

$R^4$ is the same or different in each instance and is selected from the group consisting of H, D, F, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 2 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; wherein two or more $R^4$ radicals are optionally joined to one another and optionally define a ring; wherein the alkyl, alkoxy, alkenyl, and alkynyl groups and the aromatic ring systems and heteroaromatic ring systems are each optionally substituted by one or more $R^5$ radicals; and wherein one or more $CH_2$ groups in the alkyl, alkoxy, alkenyl, and alkynyl groups are optionally replaced by $-R^5C=CR^5-$, $-C\equiv C-$, $Si(R^5)_2$, $C=O$, $C=NR^5$, $-C(=O)O-$, $-C(=O)NR^5-$, $NR^5$, $P(=O)(R^5)$, $-O-$, $-S-$, SO, or SO2;

$R^5$ is the same or different in each instance and is selected from the group consisting of H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^5$ radicals may be joined to one another and may form a ring; and where the alkyl, alkoxy, alkenyl and alkynyl groups, aromatic ring systems and heteroaromatic ring systems mentioned may be substituted by F or CN;

r is 1, 2, or 3 when p is 1, and is 1 when p is 0;
s is 0, 1, 2, or 3 when q is 1, and is 1 when q is 0;
p is 0 or 1; wherein, when p is 0, the groups bonded to the unit between square brackets with index p are bonded directly to one another;
q is 0 or 1; wherein, when q is 0, the groups bonded to the unit between square brackets with index q are bonded directly to one another;
n is 0 or 1, wherein, when n is 0, the groups bonded to the unit between square brackets with index n are bonded directly to one another;
m is 0 or 1, wherein, when m is 0, the groups bonded to the unit between square brackets with index m are bonded directly to one another;
o is 0 or 1, wherein, when o is 0, the groups bonded to the unit between square brackets with index o are bonded directly to one another;
i is the same or different in each instance and is 1, 2, 3, 4, 5, 6, 7, or 8;

wherein at least one U group containing one or more $R^1$ groups selected from the group consisting of straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms is present; wherein the alkyl, alkoxy, alkenyl, and alkynyl groups and the aromatic ring systems and heteroaromatic ring systems are each optionally substituted by one or more $R^4$ radicals; and wherein one or more $CH_2$ groups in the alkyl, alkoxy, alkenyl, and alkynyl groups are optionally replaced by $-R^4C=CR^4-$, $-C\equiv C-$, $Si(R^4)_2$, C=O, C=NR$^4$, —C(=O)O—, —C(=O)NR$^4$—, NR$^4$, P(=O)(R$^4$), —O—, —S—, SO, or SO$_2$.

2. The polymer of claim 1, wherein Ar$^1$, Ar$^2$, Ar$^3$, Ar$^4$, and Ar$^5$ are the same or different in each instance and are selected from the group consisting of benzene, biphenyl, terphenyl, fluorene, naphthalene, phenanthrene, indenofluorene, spirobifluorene, dibenzofuran, dibenzothiophene, carbazole, indenocarbazole, and indolocarbazole, each of which is optionally substituted by one or more R$^1$ radicals.

3. The polymer of claim 1, wherein R$^1$ is the same or different in each instance and is selected from the group consisting of H, D, F, straight-chain alkyl groups having 1 to 10 carbon atoms, and branched alkyl groups having 3 to 10 carbon atoms.

4. The polymer of claim 1, wherein the two U groups directly adjacent to the bridgehead carbon atom are each substituted with an R$^1$ radical selected from the group consisting of F, CN, Si(R$^4$)$_3$, OR$^4$, straight-chain alkyl and alkoxy groups having 1 to 10 carbon atoms, branched alkyl and alkoxy groups having 3 to 10 carbon atoms, and aromatic ring systems having 6 to 20 aromatic ring atoms and wherein the alkyl and alkoxy groups and the aromatic ring systems are each optionally substituted by one or more R$^4$ radicals.

5. The polymer of claim 1, wherein the units:

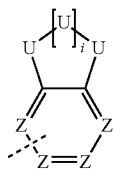

in the structural unit of formula (I) are selected from the group consisting of units of formula (E-1):

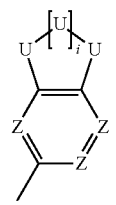

(E-1)

wherein the free bond denotes the bond to the rest of the structural unit of formula (I).

6. The polymer of claim 1, wherein the units:

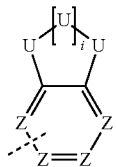

in the structural unit of formula (I) are selected from the group consisting of the following units:

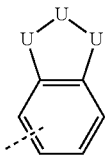

E-a-1

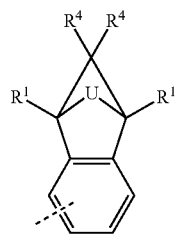

E-a-5

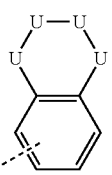

E-b-1

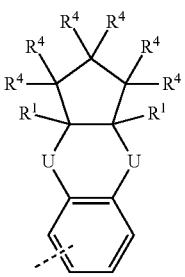

E-b-2

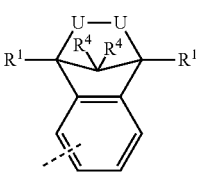

E-b-3

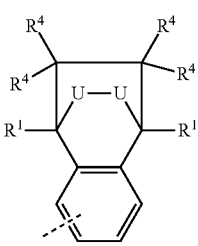

E-b-4

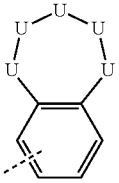

E-c-1

521
-continued

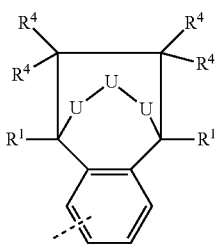
E-c-2 wherein the dotted line denotes the bond to the rest of the structural unit of formula (I).

7. The polymer of claim 1, wherein the structural element corresponds to the formula (I) of any of the formulae (I-1) to (I-6)

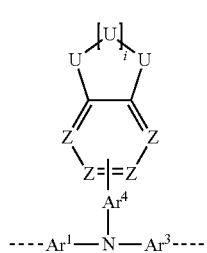
(I-1)

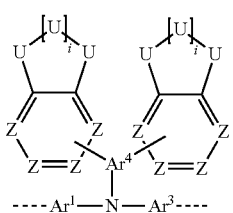
(I-2)

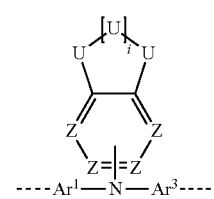
(I-3)

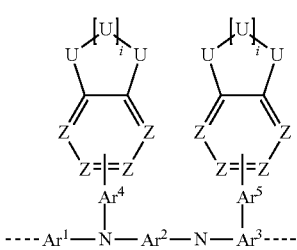
(I-4)

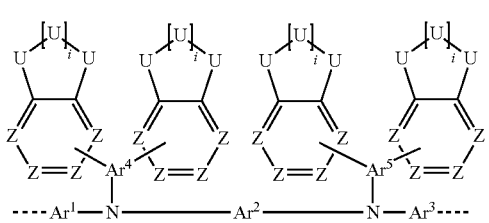
(I-5)

522
-continued

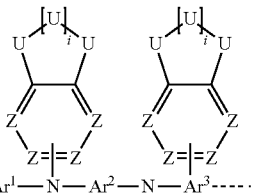
(I-6)

8. The polymer of claim 1, wherein the proportion of structural units of formula (I) in the polymer is in the range of from 30 to 70 mol %, based on 100 mol % of all copolymerizable monomers present as structural units in the polymer.

9. The polymer of claim 1, wherein the polymer comprises at least one structural unit comprising a crosslinkable Q group.

10. The polymer of claim 9, wherein the crosslinkable Q group is selected from the group consisting of the following formulae:

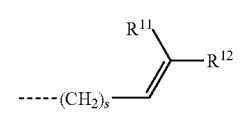
Q1

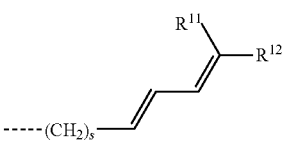
Q2

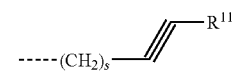
Q3

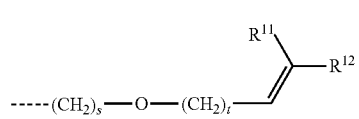
Q4

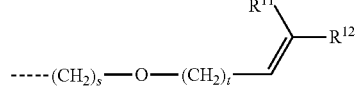
Q5

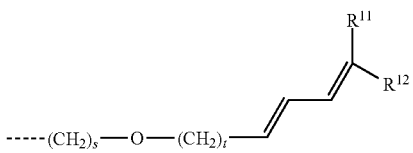
Q6

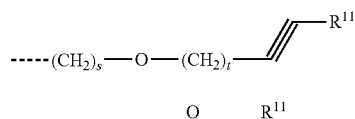
Q7

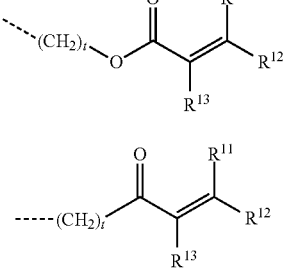
Q8

-continued

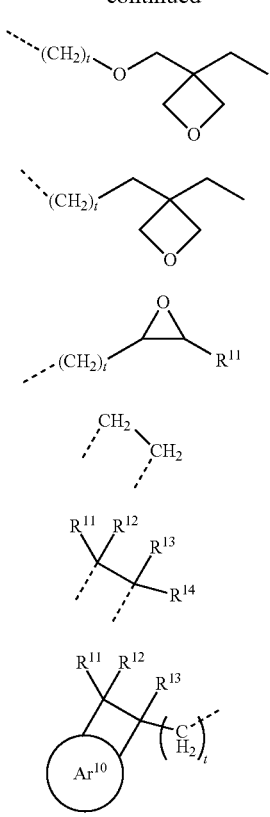

Q9

Q10

Q11

Q12

Q13

Q14 wherein
R$^{11}$, R$^{12}$, R$^{13}$, and R$^{14}$
are the same or different in each instance and are selected from the group consisting of H and straight-chain or branched alkyl groups having 1 to 6 carbon atoms;
s is an integer from 0 to 8;
t is an integer from 1 to 8; and
Ar$^{10}$ is selected from the group consisting of aromatic ring systems which have 6 to 40 aromatic ring atoms and are optionally substituted by one or more R$^{11}$ radicals and heteroaromatic ring systems which have 5 to 40 aromatic ring atoms and are optionally substituted by one or more R$^{11}$ radicals; and
wherein the dotted bond denotes the bond to the rest of the formula.

11. A polymer prepared via the crosslinking reaction of a polymer of claim 9.

12. A mixture comprising one or more polymers of claim 1 and one or more further polymeric, oligomeric, dendritic, and/or low molecular weight substances.

13. A solution comprising one or more polymers of claim 1 and one or more solvents.

14. An electronic device comprising at least one polymer of claim 1.

15. The electronic device of claim 14, wherein the at least one polymer is present in a layer selected from the group consisting of hole-transporting layer, hole injection layer, electron blocker layer, and emitting layer.

16. A process for preparing the polymer of claim 1 comprising conducting a polymerization selected from the group consisting of Suzuki polymerization, Yamamoto polymerization, Stille polymerization, Heck polymerization, Negishi polymerization, Sonogashira polymerization, Hiyama polymerization, and Hartwig-Buchwald.

17. A monomer of formula (M):

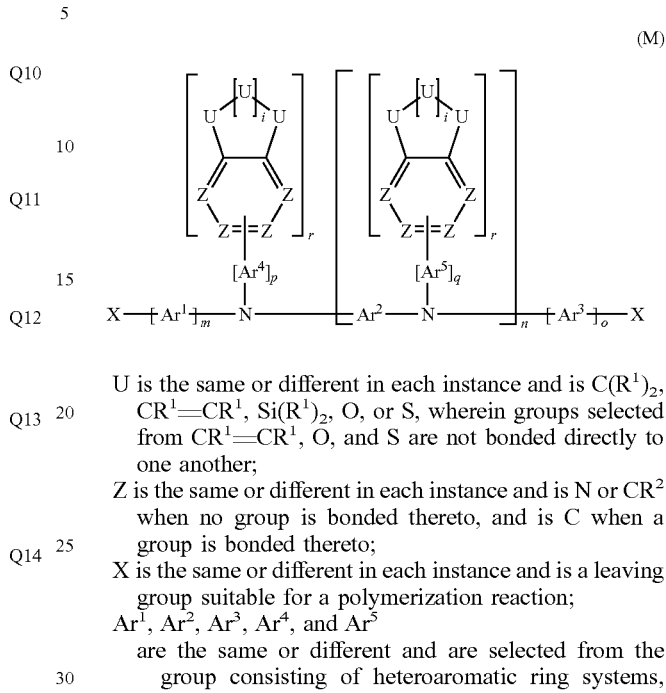

(M)

U is the same or different in each instance and is C(R$^1$)$_2$, CR$^1$=CR$^1$, Si(R$^1$)$_2$, O, or S, wherein groups selected from CR$^1$=CR$^1$, O, and S are not bonded directly to one another;
Z is the same or different in each instance and is N or CR$^2$ when no group is bonded thereto, and is C when a group is bonded thereto;
X is the same or different in each instance and is a leaving group suitable for a polymerization reaction;
Ar$^1$, Ar$^2$, Ar$^3$, Ar$^4$, and Ar$^5$
are the same or different and are selected from the group consisting of heteroaromatic ring systems, which have 5 to 40 aromatic ring atoms and which are optionally substituted by one or more R$^3$ radicals, and aromatic ring systems which have 6 to 40 aromatic ring atoms and are optionally substituted by one or more R$^3$ radicals;
R$^1$ is the same or different in each instance and is selected from the group consisting of H, D, F, C(=O)R$^4$, CN, Si(R$^4$)$_3$, N(R$^4$)$_2$, P(=O)(R$^4$)$_2$, OR$^4$, S(=O)R$^4$, S(=O)$_2$R$^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; wherein the alkyl, alkoxy, alkenyl, and alkynyl groups and the aromatic ring systems and heteroaromatic ring systems are each optionally substituted by one or more R$^4$ radicals; and wherein one or more CH$_2$ groups in the alkyl, alkoxy, alkenyl, and alkynyl groups are optionally replaced by —R$^4$C=CR$^4$—, —C≡C—, Si(R$^4$)$_2$, C=O, C=NR$^4$, —C(=O)O—, —C(=O)NR$^4$—, NR$^4$, P(=O)(R$^4$), —O—, —S—, SO, or SO$_2$;
R and R$^3$
are the same or different in each instance and are selected from the group consisting of H, D, F, C(=O)R$^4$, CN, Si(R$^4$)$_3$, N(R$^4$)$_2$, P(=O)(R$^4$)$_2$, OR$^4$, S(=O)R$^4$, S(=O)$_2$R$^4$, straight-chain alkyl, or alkoxy groups having 1 to 20 carbon atoms, branched or cyclic alkyl or alkoxy groups having 3 to 20 carbon atoms, alkenyl, or alkynyl groups having 2 to 20 carbon atoms, aromatic ring systems having 6 to 40 aromatic ring atoms, and heteroaromatic ring systems having 5 to 40 aromatic ring atoms; wherein two or more R$^1$ or R$^2$ or R$^3$ radicals are optionally joined to one another and optionally define a ring; wherein the alkyl, alkoxy, alkenyl, and alkynyl groups and the aromatic ring systems and heteroaromatic ring systems are each optionally substituted by one or more $R^4$ radicals; and wherein one or more $CH_2$ groups in the alkyl, alkoxy, alkenyl, and alkynyl groups are optionally replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4-O-$, $-S-$, $SO$, or $SO_2$;

$R^4$ is the same or different in each instance and is selected from the group consisting of H, D, F, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; wherein two or more $R^4$ radicals are optionally joined to one another and optionally define a ring; wherein the alkyl, alkoxy, alkenyl, and alkynyl groups and the aromatic ring systems and heteroaromatic ring systems are each optionally substituted by one or more $R^5$ radicals; and wherein one or more $CH_2$ groups in the alkyl, alkoxy, alkenyl, and alkynyl groups are optionally replaced by $-R^5C=CR^5-$, $-C\equiv C-$, $Si(R^5)_2$, $C=O$, $C=NR^5$, $-C(=O)O-$, $-C(=O)NR^5-$, $NR^5$, $P(=O)(R^5)$, $-O-$, $-S-$, $SO$, or $SO_2$;

$R^5$ is the same or different in each instance and is selected from the group consisting of H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^5$ radicals may be joined to one another and may forma ring; and where the alkyl, alkoxy, alkenyl and alkynyl groups, aromatic ring systems and heteroaromatic ring systems mentioned may be substituted by F or CN;

r is 1, 2, or 3 when p is 1, and is 1 when p is 0;

s is 0, 1, 2, or 3 when q is 1, and is 1 when q is 0;

p is 0 or 1; wherein, when p is 0, the groups bonded to the unit between square brackets with index p are bonded directly to one another;

q is 0 or 1; wherein, when q is 0, the groups bonded to the unit between square brackets with index q are bonded directly to one another;

n is 0 or 1, wherein, when n is 0, the groups bonded to the unit between square brackets with index n are bonded directly to one another;

m is 0 or 1, wherein, when m is 0, the groups bonded to the unit between square brackets with index m are bonded directly to one another;

o is 0 or 1, wherein, when o is 0, the groups bonded to the unit between square brackets with index o are bonded directly to one another;

i is the same or different in each instance and is 1, 2, 3, 4, 5, 6, 7, or 8; and wherein at least one U group containing one or more $R^1$ groups selected from the group consisting of straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms is present; wherein two or more $R^1$ or $R^2$ or $R^3$ radicals are optionally joined to one another and optionally define a ring; wherein the alkyl, alkoxy, alkenyl, and alkynyl groups and the aromatic ring systems and heteroaromatic ring systems are each optionally substituted by one or more $R^4$ radicals; and wherein one or more $CH_2$ groups in the alkyl, alkoxy, alkenyl, and alkynyl groups are optionally replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, $SO$, or $SO_2$.

18. The polymer of claim 1, wherein $R^2$ and $R^3$ are the same or different in each instance and are selected from the group consisting of H, D, F, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl, or alkoxy groups having 1 to 20 carbon atoms, branched or cyclic alkyl or alkoxy groups having 3 to 20 carbon atoms, alkenyl, or alkynyl groups having 2 to 20 carbon atoms, aromatic ring systems having 6 to 40 aromatic ring atoms, and heteroaromatic ring systems having 5 to 40 aromatic ring atoms; wherein the alkyl, alkoxy, alkenyl, and alkynyl groups and the aromatic ring systems and heteroaromatic ring systems are each optionally substituted by one or more $R^4$ radicals; and wherein one or more $CH_2$ groups in the alkyl, alkoxy, alkenyl, and alkynyl groups are optionally replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, $SO$, or $SO_2$;

$R^4$ is the same or different in each instance and is selected from the group consisting of H, D, F, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 2 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; wherein the alkyl, alkoxy, alkenyl, and alkynyl groups and the aromatic ring systems and heteroaromatic ring systems are each optionally substituted by one or more $R^5$ radicals; and wherein one or more $CH_2$ groups in the alkyl, alkoxy, alkenyl, and alkynyl groups are optionally replaced by $-R^5C=CR^5-$, $-C\equiv C-$, $Si(R^5)_2$, $C=O$, $C=NR^5$, $-C(=O)O-$, $-C(=O)NR^5-$, $NR^5$, $P(=O)(R^5)$, $-O-$, $-S-$, $SO$, or $SO_2$;

$R^5$ is the same or different in each instance and is selected from the group consisting of H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; and where the alkyl, alkoxy, alkenyl and alkynyl groups, aromatic ring systems and heteroaromatic ring systems mentioned may be substituted by F or CN.

* * * * *